(12) United States Patent
Bentley et al.

(10) Patent No.: US 9,309,243 B2
(45) Date of Patent: Apr. 12, 2016

(54) IMIDAZOPYRIDINE DERIVATIVES AS MODULATORS OF TNF ACTIVITY

(71) Applicant: UCB Biopharma SPRL, Brussels (BE)

(72) Inventors: Jonathan Mark Bentley, Abingdon (GB); Daniel Christopher Brookings, Slough (GB); Julien Alistair Brown, Slough (GB); Thomas Paul Cain, Abingdon (GB); Praful Tulshi Chovatia, Abingdon (GB); Anne Marie Foley, Slough (GB); Ellen Olivia Gallimore, Slough (GB); Laura Jane Gleave, Abingdon (GB); Alexander Heifetz, Abingdon (GB); Helen Tracey Horsley, Slough (GB); Martin Clive Hutchings, Slough (GB); Victoria Elizabeth Jackson, Slough (GB); James Andrew Johnson, Slough (GB); Craig Johnstone, Abingdon (GB); Boris Kroeplien, Slough (GB); Fabien Claude Lecomte, Slough (GB); Deborah Leigh, Abingdon (GB); Martin Alexander Lowe, Slough (GB); James Madden, Abingdon (GB); John Robert Porter, Slough (GB); Joanna Rachel Quincey, Slough (GB); Laura Claire Reed, Abingdon (GB); James Thomas Reuberson, Slough (GB); Anthony John Richardson, Abingdon (GB); Sarah Emily Richardson, Abingdon (GB); Matthew Duncan Selby, Slough (GB); Michael Alan Shaw, Slough (GB); Zhaoning Zhu, Slough (GB)

(73) Assignee: UCB Biopharma SPRL, Brussels (BE)

( * ) Notice: Subject to any disclaimer, the term of this patent is extended or adjusted under 35 U.S.C. 154(b) by 0 days.

(21) Appl. No.: 14/414,287

(22) PCT Filed: Jul. 5, 2013

(86) PCT No.: PCT/EP2013/064331
§ 371 (c)(1),
(2) Date: Jan. 12, 2015

(87) PCT Pub. No.: WO2014/009295
PCT Pub. Date: Jan. 16, 2014

(65) Prior Publication Data
US 2015/0203486 A1 Jul. 23, 2015

(30) Foreign Application Priority Data

Jul. 13, 2012 (GB) .................................. 1212512.6
Dec. 5, 2012 (GB) .................................. 1221920.0

(51) Int. Cl.
C07D 491/02 (2006.01)
C07D 471/04 (2006.01)
C07D 519/00 (2006.01)
A61K 31/437 (2006.01)
A61K 31/496 (2006.01)
(Continued)

(52) U.S. Cl.
CPC ............ C07D 471/04 (2013.01); A61K 31/437 (2013.01); A61K 31/496 (2013.01); A61K 31/506 (2013.01); A61K 31/5377 (2013.01); A61K 31/541 (2013.01); A61K 31/554 (2013.01); A61K 31/5513 (2013.01); C07D 491/107 (2013.01); C07D 519/00 (2013.01)

(58) Field of Classification Search
CPC ...................................................... C07D 471/04
USPC ......................................................... 546/121
See application file for complete search history.

(56) References Cited

U.S. PATENT DOCUMENTS 7,566,725 B2 * 7/2009 Fang et al. .................... 514/300
2010/0075965 A1 * 3/2010 Ni et al. ..................... 514/235.8
(Continued)

FOREIGN PATENT DOCUMENTS

EP        2 070 927 A1    6/2009
WO      03/000682 A1    1/2003
(Continued)

OTHER PUBLICATIONS

Venkatesh et al., J. Pharm. Sci. 89, 145-54 (2000).*
(Continued)

*Primary Examiner* — Nizal Chandrakumar
(74) *Attorney, Agent, or Firm* — McDonnell Boehnen Hulbert & Berghoff LLP

(57) ABSTRACT

A series of imidazo[1,2-a]pyridine derivatives of formula (I), being potent modulators of human TNFa activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

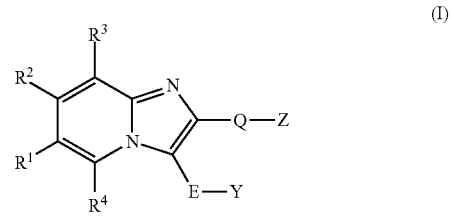

(I)

11 Claims, No Drawings

(51) Int. Cl.
*A61K 31/506* (2006.01)
*A61K 31/5377* (2006.01)
*A61K 31/541* (2006.01)
*A61K 31/5513* (2006.01)
*A61K 31/554* (2006.01)
*C07D 491/107* (2006.01)

(56) References Cited

U.S. PATENT DOCUMENTS

2013/0029964 A1* 1/2013 Aoki et al. ............... 514/210.18
2013/0190332 A1* 7/2013 Ince et al. ................. 514/259.5

FOREIGN PATENT DOCUMENTS

| WO | 2007/113226 A1 | 10/2007 |
| WO | 2008/008539 A2 | 1/2008 |
| WO | 2008/134553 A1 | 11/2008 |
| WO | 2010/116302 A1 | 10/2010 |
| WO | 2011/022439 A1 | 2/2011 |
| WO | 2011/055320 A1 | 5/2011 |
| WO | 2011/123751 A2 | 10/2011 |
| WO | 2012/007345 A2 | 1/2012 |
| WO | 2012/026765 A2 | 3/2012 |
| WO | 2012/116237 A2 | 8/2012 |
| WO | 2013/033070 A1 | 3/2013 |
| WO | 2013/033116 A1 | 3/2013 |

OTHER PUBLICATIONS

Wolff, Burger's medicinal Chemistry and Drug Discovery, vol. 1, Principles and Practice, John Wiley & sons, New York, 1997.*
West, Solid-State Chemistry and Its Applications, 1984, John Wiley & Sons.*
Vishwehwar et al. Journal of Pharmaceutical Sciences, 2006, 95(3), 499-516.*
Al-Tel et al., "Post Groebke-Blackburn multicomponent protocol: Synthesis of new polyfunctional imidazo[1,2-a]pyridine and innidazo[1,2-a]pyrimidine derivatives as potential antimicrobial agents", European Journal of Medicinal Chemistry, 2010, 45(12), 5848-5855, available online Sep. 25, 2010.
Tansey et al., "The TNF superfamily in 2009: new pathways, new indications, and new drugs", Drug Discovery Today, Dec. 2009, 14(23/24), 1082-1088.
Carneiro et al., "Emerging Role for TNF-alpha in Erectile Dysfunction", J. Sexual Medicine, Dec. 2010, vol. 7, 3823-3834.

* cited by examiner

IMIDAZOPYRIDINE DERIVATIVES AS MODULATORS OF TNF ACTIVITY

This application is a U.S. national phase of International Application No. PCT/EP2013/064331 filed on Jul. 5, 2013, which claims priority to Great Britain Patent Application No. 1212512.6 filed on Jul. 13, 2012 and Great Britain Patent Application No. 1221920.0 filed on Dec. 5, 2012.

The present invention relates to a class of fused imidazole derivatives, and to their use in therapy. More particularly, this invention is concerned with pharmacologically active substituted imidazo[1,2-a]pyridine derivatives. These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certulizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

The compounds in accordance with the present invention potently neutralise the activity of TNFα in a commercially available HEK-293 derived reporter cell line known as HEK-Blue™ CD40L. This cell line is a stable transfectant expressing SEAP (secreted alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, the compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound).

The present invention provides a compound of formula (I) or an N-oxide thereof, or a pharmaceutically acceptable salt or solvate thereof, or a glucuronide derivative thereof, or a co-crystal thereof:

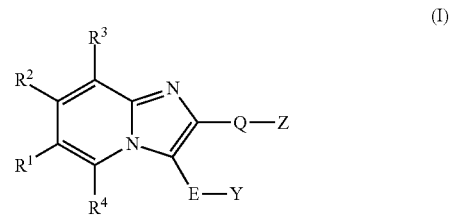

(I)

wherein

E represents a covalent bond; or E represents —O—, —S—, —S(O)—, —S(O)$_2$— or —N(R$^5$)—; or E represents an optionally substituted straight or branched $C_{1-4}$ alkylene chain;

Q represents a covalent bond; or Q represents —O—, —S—, —S(O)—, —S(O)$_2$—, —N(R$^6$)—, —C(O)N(R$^6$)—, —N(R$^6$)C(O)—, —S(O)$_2$N(R$^6$)— or —N(R$^6$)S(O)$_2$—; or Q represents an optionally substituted straight or branched $C_{1-6}$ alkylene chain optionally comprising one, two or three heteroatom-containing linkages independently selected from —O—, —S—, —S(O)—, —S(O)$_2$—, —N(R$^6$)—, —C(O)N(R$^6$)—, —N(R$^6$)C(O)—, —S(O)$_2$N(R$^6$)— and —N(R$^6$)S(O)$_2$—;

Y represents $C_{3-7}$ cycloalkyl, aryl, $C_{3-7}$ heterocycloalkyl or heteroaryl, any of which groups may be optionally substituted by one or more substituents;

Z represents hydrogen, halogen or trifluoromethyl; or Z represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents —Z$^1$-Z$^2$ or —Z$^1$—C(O)—Z$^2$, either of which moieties may be optionally substituted by one or more substituents;

Z$^1$ represents a divalent radical derived from an aryl, $C_{3-7}$ heterocycloalkyl or heteroaryl group;

Z$^2$ represents aryl, $C_{3-7}$ heterocycloalkyl, $C_{3-7}$ heterocycloalkenyl or heteroaryl;

R$^1$, R$^2$, R$^3$ and R$^4$ independently represent hydrogen, halogen, cyano, nitro, hydroxy, trifluoromethyl, trifluoromethoxy, —OR$^a$, —SR$^a$, —SOR$^a$, —SO$_2$R$^a$, —SF$_5$, —NR$^b$R$^c$, —NR$^c$COR$^d$, —NR$^c$CO$_2$R$^d$, —NHCONR$^b$R$^c$, —NR$^c$SO$_2$R$^e$, —N(SO$_2$R$^e$)$_2$, —NHSO$_2$NR$^b$R$^c$, —COR$^d$, —CO$_2$R$^d$, —CONR$^b$R$^c$, —CON(OR$^a$)R$^b$ or —SO$_2$NR$^b$R$^c$; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$) alkyl, $C_{3-7}$ heterocycloalkyl, $C_{3-7}$ heterocycloalkyl($C_{1-6}$) alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$) alkyl-aryl-, heteroaryl($C_{3-7}$)heterocycloalkyl-, ($C_{3-7}$) cycloalkyl-heteroaryl-, ($C_{3-7}$)cycloalkyl($C_{1-6}$)alkyl-heteroaryl-, ($C_{4-7}$)cycloalkenyl-heteroaryl-, ($C_{4-9}$) bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents;

$R^5$ and $R^6$ independently represent hydrogen or $C_{1-6}$ alkyl;

$R^a$ represents $C_{1-6}$ alkyl, aryl, aryl($C_{1-6}$)alkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$) alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

$R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents; and $R^e$ represents $C_{1-6}$ alkyl, aryl or heteroaryl, any of which groups may be optionally substituted by one or more substituents.

The present invention also provides a compound of formula (I) as depicted above or an N-oxide thereof, or a pharmaceutically acceptable salt or solvate thereof, or a co-crystal thereof, wherein $R^1$, $R^2$, $R^3$ and $R^4$ independently represent hydrogen, halogen, cyano, nitro, hydroxy, trifluoromethyl, trifluoromethoxy, $-OR^a$, $-SR^a$, $-SOR^a$, $-SO_2R^a$, $-SF_5$, $-NR^bR^c$, $-NR^cCOR^d$, $-NR^cCO_2R^d$, $-NHCONR^bR^c$, $-NR^cSO_2R^e$, $-N(SO_2R^e)_2$, $-NHSO_2NR^bR^c$, $-COR^d$, $-CO_2R^d$, $-CONR^bR^c$, $-CON(OR^a)R^b$ or $-SO_2NR^bR^c$; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$) alkyl, $C_{3-7}$ heterocycloalkyl, $C_{3-7}$ heterocycloalkyl($C_{1-6}$) alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$) alkyl-aryl-, heteroaryl-($C_{3-7}$)heterocycloalkyl-, ($C_{3-7}$) cycloalkyl-heteroaryl-, ($C_{4-7}$)cycloalkenyl-heteroaryl-, ($C_{3-7}$)heterocyclo alkyl-heteroaryl-, ($C_{3-7}$)heterocycloalkyl ($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents; and E, Q, Y, Z, $R^a$, $R^b$, $R^c$, $R^d$ and $R^e$ are as defined above.

The present invention also provides a compound of formula (I) as depicted above or an N-oxide thereof, or a pharmaceutically acceptable salt or solvate thereof, or a co-crystal thereof, wherein $R^1$, $R^2$, $R^3$ and $R^4$ independently represent hydrogen, halogen, cyano, nitro, hydroxy, trifluoromethyl, trifluoromethoxy, $-OR^a$, $-SR^a$, $-SOR^a$, $-SO_2R^a$, $-SF_5$, $-NR^bR^c$, $-NR^cCOR^d$, $-NR^cCO_2R^d$, $-NHCONR^bR^c$, $-NR^cSO_2R^e$, $-N(SO_2R^e)_2$, $-NHSO_2NR^bR^c$, $-COR^d$, $-CO_2R^d$, $-CONR^bR^c$, $-CON(OR^a)R^b$ or $-SO_2NR^bR^c$; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$) alkyl, $C_{3-7}$ heterocycloalkyl, $C_{3-7}$ heterocycloalkyl($C_{1-6}$) alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$) alkyl-aryl-, heteroaryl($C_{3-7}$)heterocycloalkyl-, ($C_{4-7}$) cycloalkenyl-heteroaryl-, ($C_{3-7}$)heterocycloalkyl-heteroaryl-, ($C_{3-7}$)heterocycloalkyl-($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents; and E, Q, Y, Z, $R^a$, $R^b$, $R^c$, $R^d$ and $R^e$ are as defined above.

The present invention also provides a compound of formula (I) as defined above or an N-oxide thereof, or a pharmaceutically acceptable salt or solvate thereof, or a glucuronide derivative thereof, or a co-crystal thereof, for use in the treatment and/or prevention of disorders for which the administration of a modulator of TNFα function is indicated.

In another aspect, the present invention provides a compound of formula (I) as defined above or an N-oxide thereof, or a pharmaceutically acceptable salt or solvate thereof, or a glucuronide derivative thereof, or a co-crystal thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

In another aspect, the present invention provides a method for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of use in the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; ammonium salts; and salts formed with suitable organic ligands, e.g. quaternary ammonium salts, and meglumine salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

The present invention also includes co-crystals within its scope. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012). Typical examples of co-crystal formers, which may be present in the co-crystal alongside the active pharmaceutical ingredient, include L-ascorbic acid, citric acid, glutaric acid, urea and nicotinamide.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in *Design of Prodrugs*, ed. H. Bundgaard, Elsevier, 1985.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-4}$ alkylene chain" refers to a divalent straight or branched alkylene chain containing 1 to 4 carbon atoms. Typical examples include methylene, ethylene, methylmethylene, ethylmethylene and dimethylmethylene.

Suitable $C_{2-6}$ alkenyl groups include vinyl and allyl.

Suitable $C_{2-6}$ alkynyl groups include ethynyl, propargyl and butynyl.

Suitable $C_{3-7}$ cycloalkyl groups, which may comprise benzo-fused analogues thereof, include cyclopropyl, cyclobutyl, benzocyclobutenyl, cyclopentyl, indanyl, cyclohexyl and cycloheptyl.

Suitable $C_{4-7}$ cycloalkenyl groups include cyclobutenyl, cyclopentenyl, cyclohexenyl and cycloheptenyl.

Typical bicycloalkyl groups include bicyclo[3.1.0]hexanyl, bicyclo[4.1.0]heptanyl and bicyclo[2.2.2]octanyl.

Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include azetidinyl, tetrahydrofuranyl, dihydrobenzofuranyl, pyrrolidinyl, indolinyl, oxazolidinyl, thiazolidinyl, imidazolidinyl, tetrahydropyranyl, chromanyl, tetrahydrothiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl, thiomorpholinyl, diazepanyl, thiadiazepanyl and azocanyl. Additional values include oxetanyl, dihydrobenzothienyl, isoindolinyl, isothiazolidinyl, hexahydro-[1,2,5]thiadiazolo[2,3---α]pyrazinyl, azepanyl and oxazepanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, imidazolinyl, dihydropyranyl, dihydrothiopyranyl and 1,2,3,6-tetrahydropyridinyl.

Typical heterobicycloalkyl groups include 3-azabicyclo[3.1.0]hexanyl, 2-oxa-5-azabicyclo[2.2.1]heptanyl, quinuclidinyl, 2-oxa-5-azabicyclo[2.2.2]octanyl, 8-azabicyclo[3.2.1]octanyl, 3,8-diazabicyclo[3.2.1]octanyl and 3,9-diazabicyclo[4.2.1]nonanyl. Additional values include 6-azabicyclo[3.2.0]heptanyl, 3-azabicyclo[3.1.1]heptanyl, 3-azabicyclo[4.1.0]heptanyl, 2-oxabicyclo[2.2.2]octanyl, 3-azabicyclo[3.2.1]octanyl, 3-oxa-8-azabicyclo[3.2.1]octanyl, 3,6-diazabicyclo[3.2.2]nonanyl and 3-oxa-7-azabicyclo[3.3.1]-nonanyl.

Suitable spiroheterocycloalkyl groups include 2-azaspiro[3.3]heptanyl, 2-oxa-6-azaspiro[3.3]heptanyl, 2-oxa-6-azaspiro[3.4]octanyl, 2-oxa-6-azaspiro[3.5]nonanyl and 2-oxa-7-azaspiro[3.5]nonanyl. Additional values include 5-azaspiro[2.3]hexanyl, 5-azaspiro[2.4]heptanyl, 7-oxa-2-azaspiro[3.5]nonanyl and 2,4,8-triazaspiro[4.5]decanyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups. Additional values include thieno[2,3-c]pyrazolyl, thieno[3,4-b][1,4]dioxinyl, pyrrolo[3,4-b]pyridinyl and imidazo[2,1-b]thiazolyl.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto (CH$_2$C=O)⇌enol (CH=CHOH) tautomers or amide (NHC=O)⇌hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1$H, $^2$H (deuterium) or $^3$H (tritium) atom, preferably $^1$H. Similarly, by way of example, each individual carbon atom present in formula (I), or in the formulae depicted hereinafter, may be present as a $^{12}$C, $^{13}$C or $^{14}$C atom, preferably $^{12}$C.

In one aspect, the present invention provides a compound of formula (I) as depicted above or an N-oxide thereof, or a pharmaceutically acceptable salt or solvate thereof, or a glucuronide derivative thereof, or a co-crystal thereof, wherein Q represents —O—, —S—, —S(O)—, —S(O)$_2$—, —N(R$^6$)—, —C(O)N(R$^6$)—, —N(R$^6$)C(O)—, —S(O)$_2$N(R$^6$)— or —N(R$^6$)S(O)$_2$—; or Q represents an optionally substituted straight or branched C$_{1-6}$ alkylene chain optionally comprising one, two or three heteroatom-containing linkages independently selected from —O—, —S—, —S(O)—, —S(O)$_2$—, —N(R$^6$)—, —C(O)N(R$^6$)—, —N(R$^6$)C(O)—, —S(O)$_2$N(R$^6$)— and —N(R$^6$)S(O)$_2$—;

Z represents C$_{3-7}$ cycloalkyl, aryl, C$_{3-7}$ heterocycloalkyl, C$_{3-7}$ heterocycloalkenyl or heteroaryl, any of which groups may be optionally substituted by one or more substituents; or Z represents —Z$^1$-Z$^2$ or —Z$^1$—C(O)—Z$^2$, either of which moieties may be optionally substituted by one or more substituents; and E, Y, R$^1$, R$^2$, R$^3$, R$^4$, R$^6$, Z$^1$ and Z$^2$ are as defined above.

In another aspect, the present invention provides a compound of formula (I) as depicted above or an N-oxide thereof, or a pharmaceutically acceptable salt or solvate thereof, or a glucuronide derivative thereof, or a co-crystal thereof, wherein R$^1$ represents halogen or cyano; or C$_{1-6}$ alkyl, C$_{2-6}$ alkenyl, C$_{2-6}$ alkynyl, C$_{3-7}$ cycloalkyl, C$_{4-7}$ cycloalkenyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, C$_{3-7}$ heterocycloalkenyl, C$_{4-9}$ heterobicycloalkyl, heteroaryl, heteroaryl(C$_{1-6}$)alkyl, (C$_{3-7}$)heterocycloalkyl(C$_{1-6}$)alkyl-aryl-, heteroaryl(C$_{3-7}$)heterocycloalkyl-, (C$_{3-7}$)cycloalkyl-heteroaryl-, (C$_{3-7}$)cycloalkyl-(C$_{1-6}$)alkyl-heteroaryl-, (C$_{4-7}$)cycloalkenyl-heteroaryl-, (C$_{4-9}$)bicycloalkyl-heteroaryl-, (C$_{3-7}$)heterocycloalkyl-heteroaryl-, (C$_{3-7}$)heterocycloalkyl(C$_{1-6}$)alkyl-heteroaryl-, (C$_{3-7}$)heterocycloalkenyl-heteroaryl-, (C$_{4-9}$)heterobicycloalkyl-heteroaryl- or (C$_{4-9}$)spiroheterocycloalkyl-heteroaryl-, any of which groups may be optionally substituted by one or more substituents; and E, Q, Y, Z, R$^2$, R$^3$ and R$^4$ are as defined above.

In another aspect, the present invention provides a compound of formula (I) as depicted above or an N-oxide thereof, or a pharmaceutically acceptable salt or solvate thereof, or a co-crystal thereof, wherein R$^1$ represents halogen or cyano; or C$_{1-6}$ alkyl, C$_{2-6}$ alkenyl, C$_{2-6}$ alkynyl, C$_{3-7}$ cycloalkyl, C$_{4-7}$ cycloalkenyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, C$_{3-7}$ heterocycloalkenyl, C$_{4-9}$ heterobicycloalkyl, heteroaryl, heteroaryl(C$_{1-6}$)alkyl, (C$_{3-7}$)heterocycloalkyl(C$_{1-6}$)alkyl-aryl-, heteroaryl(C$_{3-7}$)heterocycloalkyl-, (C$_{3-7}$)cycloalkyl-heteroaryl-, (C$_{4-7}$)cycloalkenyl-heteroaryl-, (C$_{3-7}$)heterocycloalkyl-heteroaryl-, (C$_{3-7}$)heterocycloalkyl(C$_{1-6}$)alkyl-heteroaryl-, (C$_{3-7}$)heterocycloalkenyl-heteroaryl-, (C$_{4-9}$)heterobicycloalkyl-heteroaryl- or (C$_{4-9}$)spiroheterocycloalkyl-heteroaryl-, any of which groups may be optionally substituted by one or more substituents; and E, Q, Y, Z, R$^2$, R$^3$ and R$^4$ are as defined above.

In another aspect, the present invention provides a compound of formula (I) as depicted above or an N-oxide thereof, or a pharmaceutically acceptable salt or solvate thereof, or a co-crystal thereof, wherein R$^1$ represents halogen or cyano; or C$_{1-6}$ alkyl, C$_{2-6}$ alkenyl, C$_{2-6}$ alkynyl, C$_{3-7}$ cycloalkyl, C$_{4-7}$ cycloalkenyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, C$_{3-7}$ heterocycloalkenyl, C$_{4-9}$ heterobicycloalkyl, heteroaryl, heteroaryl(C$_{1-6}$)alkyl, (C$_{3-7}$)heterocycloalkyl(C$_{1-6}$)alkyl-aryl-, heteroaryl(C$_{3-7}$)heterocycloalkyl-, (C$_{3-7}$)cycloalkyl-heteroaryl-, (C$_{3-7}$)heterocycloalkyl-heteroaryl-, (C$_{3-7}$)heterocycloalkyl(C$_{1-6}$)alkyl-heteroaryl-, (C$_{3-7}$)heterocycloalkenyl-heteroaryl-, (C$_{4-9}$)heterobicycloalkyl-heteroaryl- or (C$_{4-9}$)spiroheterocycloalkyl-heteroaryl-, any of which groups may be optionally substituted by one or more substituents; and E, Q, Y, Z, R$^2$, R$^3$ and R$^4$ are as defined above.

Where the compounds in accordance with the invention comprise an optionally substituted straight or branched alkylene chain, typical values thereof include methylene (—CH$_2$—), (methyl)methylene, ethylene (—CH$_2$CH$_2$—), (ethyl)methylene, (dimethyl)-methylene, (methyl)ethylene, propylene (—CH$_2$CH$_2$CH$_2$—), (propyl)methylene and (dimethyl)ethylene, any of which chains may be optionally substituted by one or more substituents. Suitably, such chains are unsubstituted, monosubstituted or disubstituted. Typically, such chains are unsubstituted or monosubstituted. In one embodiment, such chains are unsubstituted. In another embodiment, such chains are monosubstituted. In a further embodiment, such chains are disubstituted.

Examples of typical substituents on the alkylene chain which may be present in a compound in accordance with the invention include halogen, trifluoromethyl, oxo, hydroxy, C$_{1-6}$ alkoxy, trifluoromethoxy, amino, C$_{1-6}$ alkylamino, di(C$_{1-6}$)alkylamino, carboxy, tetrazolyl, aminocarbonyl, C$_{1-6}$ alkylaminocarbonyl and di(C$_{1-6}$)alkylaminocarbonyl. Additional examples include cyano, carboxy(C$_{1-6}$)alkoxy, C$_{2-6}$ alkylcarbonylamino and benzyloxycarbonyl.

Examples of suitable substituents on the alkylene chain which may be present in a compound in accordance with the invention include halogen, trifluoromethyl, hydroxy, C$_{1-6}$ alkoxy, amino, carboxy and tetrazolyl. Additional examples include cyano, carboxy-(C$_{1-6}$)alkoxy, C$_{2-6}$ alkylcarbonylamino and benzyloxycarbonyl.

Specific examples of suitable substituents on the alkylene chain which may be present in a compound in accordance with the invention include fluoro, trifluoromethyl, hydroxy, methoxy, amino, carboxy and tetrazolyl. Additional examples include cyano, carboxymethoxy, acetylamino and benzyloxycarbonyl.

In a first embodiment, E represents a covalent bond, whereby the integer Y is attached directly to the imidaz[1,2-a]pyridine nucleus.

In a second embodiment, E represents —O—, —S—, —S(O)—, —S(O)$_2$— or —N(R$^5$)—. In a first aspect of that embodiment, E represents —O—. In a second aspect of that embodiment, E represents —S—. In a third aspect of that embodiment, E represents —S(O)—. In a fourth aspect of that embodiment, E represents —S(O)$_2$—. In a fifth aspect of that embodiment, E represents —N(R$^5$)—.

In a third embodiment, E represents an optionally substituted straight or branched $C_{1-4}$ alkylene chain. In a first aspect of that embodiment, E represents an optionally substituted methylene (—$CH_2$—) linkage. In a second aspect of that embodiment, E represents an optionally substituted (methyl) methylene linkage. In a third aspect of that embodiment, E represents an optionally substituted (ethyl)methylene linkage.

Generally, E represents a covalent bond; or E represents —$N(R^5)$—; or E represents an optionally substituted straight or branched $C_{1-4}$ alkylene chain.

Typically, E represents —$N(R^5)$—; or E represents an optionally substituted straight or branched $C_{1-4}$ alkylene chain.

Suitably, E represents a covalent bond; or E represents —$N(R^5)$—; or E represents methylene (—$CH_2$—), (methyl) methylene or (ethyl)methylene, any of which groups may be optionally substituted by one or more substituents.

Generally, E represents —$N(R^5)$—; or E represents methylene (—$CH_2$—) or (ethyl)methylene, either of which groups may be optionally substituted by one or more substituents.

Appositely, E represents —$N(R^5)$—, or optionally substituted methylene.

Selected examples of typical substituents on the linkage represented by E include halogen, trifluoromethyl, hydroxy, $C_{1-6}$ alkoxy, trifluoromethoxy, amino, $C_{1-6}$ alkylamino, di($C_{1-6}$)alkylamino, carboxy and tetrazolyl. Additional examples include carboxy($C_{1-6}$)-alkoxy, $C_{2-6}$ alkylcarbonylamino and benzyloxycarbonyl.

Selected examples of suitable substituents on the linkage represented by E include hydroxy, $C_{1-6}$ alkoxy, carboxy ($C_{1-6}$)alkoxy, amino, $C_{2-6}$ alkylcarbonylamino, carboxy and benzyloxycarbonyl.

Specific examples of typical substituents on the linkage represented by E include fluoro, trifluoromethyl, hydroxy, methoxy, trifluoromethoxy, amino, methylamino, dimethylamino, carboxy and tetrazolyl. Additional examples include carboxymethoxy, acetylamino and benzyloxycarbonyl.

Specific examples of suitable substituents on the linkage represented by E include hydroxy, methoxy, carboxymethoxy, amino, acetylamino, carboxy and benzyloxycarbonyl.

A particular example of a typical substituent on E is hydroxy.

Typical values of E include —$N(R^5)$—, —$CH_2$—, —$CH(OH)$—, —$CH(CH_3)$— and —$CH(CH_2CH_3)$—; or E may represent a covalent bond.

Selected values of E include —$N(R^5)$—, —$CH_2$—, —$CH(OH)$—, —$CH(OCH_3)$—, —$CH(OCH_2CO_2H)$—, —$CH(NH_2)$—, —$CH(NHCOCH_3)$—, —$CH(CO_2H)$—, —$CH(CO_2benzyl)$-, —$CH(CH_3)$— and —$C(CH_3)(OH)$—.

Suitable values of E include —$N(R^5)$—, —$CH_2$— and —$CH(OH)$—. In one embodiment, E represents —$N(R^5)$—. In another embodiment, E represents —$CH_2$—. In a further embodiment, E represents —$CH(OH)$—.

In another embodiment, E represents —$CH(OCH_3)$—.

In another embodiment, E represents —$CH(NH_2)$—.

In an additional embodiment, E represents —$CH(CH_3)$—. In a particular aspect of that embodiment, the —$CH(CH_3)$— linkage represented by E is in the (S) stereochemical configuration.

In a further embodiment, E represents —$C(CH_3)(OH)$—.

In a first embodiment, Q represents a covalent bond, whereby the integer Z is attached directly to the imidazo[1,2-a]pyridine nucleus.

In a second embodiment, Q represents —O—, —S—, —$S(O)$—, —$S(O)_2$—, —$N(R^6)$—, —$C(O)N(R^6)$—, —$N(R^6)C(O)$—, —$S(O)_2N(R^6)$— or —$N(R^6)S(O)_2$—. In a first aspect of that embodiment, Q represents —O—. In a second aspect of that embodiment, Q represents —S—. In a third aspect of that embodiment, Q represents —$S(O)$—. In a fourth aspect of that embodiment, Q represents —$S(O)_2$—. In a fifth aspect of that embodiment, Q represents —$N(R^6)$—. In a sixth aspect of that embodiment, Q represents —$C(O)N(R^6)$—. In a seventh aspect of that embodiment, Q represents —$N(R^6)C(O)$—. In an eighth aspect of that embodiment, Q represents —$S(O)_2N(R^6)$—. In a ninth aspect of that embodiment, Q represents —$N(R^6)S(O)_2$—.

In a third embodiment, Q represents an optionally substituted straight or branched $C_{1-6}$ alkylene chain optionally comprising one, two or three heteroatom-containing linkages independently selected from —O—, —S—, —$S(O)$—, —$S(O)_2$—, —$N(R^6)$—, —$C(O)N(R^6)$—, —$N(R^6)C(O)$—, —$S(O)_2N(R^6)$— and —$N(R^6)S(O)_2$—. In a first aspect of that embodiment, Q represents an optionally substituted straight or branched $C_{1-6}$ alkylene chain. In a second aspect of that embodiment, Q represents an optionally substituted straight or branched $C_{1-6}$ alkylene chain comprising one heteroatom-containing linkage independently selected from —O—, —S—, —$S(O)$—, —$S(O)_2$—, —$N(R^6)$—, —$C(O)N(R^6)$—, —$N(R^6)C(O)$—, —$S(O)_2N(R^6)$— and —$N(R^6)S(O)_2$—. In a third aspect of that embodiment, Q represents an optionally substituted straight or branched $C_{1-6}$ alkylene chain comprising two heteroatom-containing linkages independently selected from —O—, —S—, —$S(O)$—, —$S(O)_2$—, —$N(R^6)$—, —$C(O)N(R^6)$—, —$N(R^6)C(O)$—, —$S(O)_2N(R^6)$— and —$N(R^6)S(O)_2$—. In a fourth aspect of that embodiment, Q represents an optionally substituted straight or branched $C_{1-6}$ alkylene chain comprising three heteroatom-containing linkages independently selected from —O—, —S—, —$S(O)$—, —$S(O)_2$—, —$N(R^6)$—, —$C(O)N(R^6)$—, —$N(R^6)C(O)$—, —$S(O)_2N(R^6)$— and —$N(R^6)S(O)_2$—. In a fifth aspect of that embodiment, Q represents an optionally substituted straight or branched $C_{1-6}$ alkylene chain comprising one, two or three heteroatom-containing linkages independently selected from —O—, —S—, —$N(R^6)$—, —$C(O)N(R^6)$— and —$N(R^6)C(O)$—.

Typically, Q represents a covalent bond; or Q represents —$S(O)$— or —$S(O)_2$—; or Q represents an optionally substituted straight or branched $C_{1-6}$ alkylene chain optionally comprising one or two heteroatom-containing linkages selected from —O—, —S—, —$N(R^6)$—, —$C(O)N(R^6)$—, and —$N(R^6)C(O)$—.

Selected examples of typical substituents on the linkage represented by Q include halogen, trifluoromethyl, hydroxy, $C_{1-6}$ alkoxy and amino. An additional example is cyano.

Selected examples of suitable substituents on the linkage represented by Q include cyano, hydroxy and $C_{1-6}$ alkoxy.

Specific examples of typical substituents on the linkage represented by Q include fluoro, trifluoromethyl, hydroxy, methoxy and amino. An additional example is cyano.

Specific examples of suitable substituents on the linkage represented by Q include cyano, hydroxy and methoxy.

Suitably, Q represents a covalent bond; or Q represents —$S(O)$— or —$S(O)_2$—; or Q represents —$CH_2$—, —$CH(F)$—, —$CF_2$—, —$CH(CH_3)$—, —$CH(OH)$—, —$CH(OCH_3)$—, —$CH(NH_2)$—, —$CH_2CH_2$—, —$CH(OH)CH_2$—, —$CH(OH)CF_2$—, —$CH(OCH_3)CH_2$—, —$CH_2O$—, —$CH(CH_3)O$—, —$C(CH_3)_2O$—, —$CH(CH_2CH_3)O$—, —$CH(CF_3)O$—, —$CH_2S$—, —$CH_2N(R^6)$—, —$CH_2CH_2CH_2$—, —$CH(OH)CH_2CH_2$—, —$CH(OCH_3)CH_2CH_2$—, —$CH_2CH_2O$—, —$CH_2OCH_2$—, —$CH_2OCH(F)$—, —$CH_2OCF_2$—, —$CH_2OCH(CH_3)$—, —$CH(CH_3)OCH_2$—, —$CH_2OC(CH_3)_2$—, —C(CH$_3$)$_2$OCH$_2$—, —CH$_2$SCH$_2$—, —CH$_2$CH$_2$N(R$^6$)—, —CH$_2$N(R$^6$)CH$_2$—, —CH$_2$CH$_2$OCH$_2$—, —CH$_2$CH$_2$N(R$^6$)C(O)—, —CH$_2$OCH$_2$CH$_2$—, —CH$_2$OCH$_2$CF$_2$—, —CH$_2$OCH$_2$CH(CH$_3$)—, —CH$_2$OCH(CH$_3$)CH$_2$—, —CH$_2$OC(CH$_3$)$_2$CH$_2$—, —CH$_2$OCH$_2$CH(CH$_3$)CH$_2$—, —CH$_2$OCH$_2$CH$_2$O—, —CH$_2$OCH$_2$C(O)N(R$^6$)— or —CH$_2$OCH$_2$CH$_2$OCH$_2$—. Additional values include —N(R$^5$)—, —CH(CN)—, —CH(CH$_2$OH)—, —CH$_2$S(O)—, —CH$_2$S(O)$_2$—, —CH$_2$S(O)CH$_2$—, —CH$_2$S(O)$_2$CH$_2$— and —CH$_2$N(R$^5$)C(O)—.

Appositely, Q represents a covalent bond; or Q represents —CH$_2$—, —CH(CN)—, —CH(OH)—, —CH(OCH$_3$)—, —CH$_2$O—, —CH$_2$N(R$^6$)— or —CH$_2$OCH$_2$—.

Particular values of Q include —CH$_2$—, —CH(OH)—, —CH$_2$O—, —CH$_2$S— and —CH$_2$OCH$_2$—. In a first embodiment, Q represents —CH$_2$—. In a second embodiment, Q represents —CH(OH)—. In a third embodiment, Q represents —CH$_2$O—. In a fourth embodiment, Q represents —CH$_2$S—. In a fifth embodiment, Q represents —CH$_2$OCH$_2$—.

Generally, Y represents C$_{3-7}$ cycloalkyl, aryl or heteroaryl, any of which groups may be optionally substituted by one or more substituents.

Typically, Y represents aryl or heteroaryl, either of which groups may be optionally substituted by one or more substituents.

In a first embodiment, Y represents optionally substituted C$_{3-7}$ cycloalkyl. In one aspect of that embodiment, Y represents unsubstituted C$_{3-7}$ cycloalkyl. In another aspect of that embodiment, Y represents monosubstituted C$_{3-7}$ cycloalkyl. In a further aspect of that embodiment, Y represents disubstituted C$_{3-7}$ cycloalkyl.

In a second embodiment, Y represents optionally substituted aryl. In one aspect of that embodiment, Y represents unsubstituted aryl. In another aspect of that embodiment, Y represents monosubstituted aryl. In a further aspect of that embodiment, Y represents disubstituted aryl.

In a third embodiment, Y represents optionally substituted C$_{3-7}$ heterocycloalkyl. In one aspect of that embodiment, Y represents unsubstituted C$_{3-7}$ heterocycloalkyl. In another aspect of that embodiment, Y represents monosubstituted C$_{3-7}$ heterocycloalkyl.

In a further aspect of that embodiment, Y represents disubstituted C$_{3-7}$ heterocycloalkyl. In a fourth embodiment, Y represents optionally substituted heteroaryl. In one aspect of that embodiment, Y represents unsubstituted heteroaryl. In another aspect of that embodiment, Y represents monosubstituted heteroaryl. In a further aspect of that embodiment, Y represents disubstituted heteroaryl.

Suitably, Y represents benzocyclobutenyl, phenyl, thienyl, thiazolyl or pyridinyl, any of which groups may be optionally substituted by one or more substituents.

Appropriately, Y represents phenyl, thienyl or thiazolyl, any of which groups may be optionally substituted by one or more substituents.

Appositely, Y represents phenyl, which may be optionally substituted by one or more substituents.

Examples of optional substituents which may be present on the moiety Y include one, two or three substituents independently selected from halogen, cyano, nitro, C$_{1-6}$ alkyl, trifluoromethyl, hydroxy, C$_{1-6}$ alkoxy, difluoromethoxy, trifluoromethoxy, C$_{1-6}$ alkylthio, C$_{1-6}$ alkylsulfinyl, C$_{1-6}$ alkylsulfonyl, amino, C$_{1-6}$ alkylamino, di(C$_{1-6}$)alkylamino, arylamino, C$_{2-6}$ alkylcarbonylamino, C$_{1-6}$ alkylsulfonylamino, formyl, C$_{2-6}$ alkylcarbonyl, C$_{3-6}$ cycloalkylcarbonyl, C$_{3-6}$ heterocycloalkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, aminosulfonyl, C$_{1-6}$ alkylaminosulfonyl and di(C$_{1-6}$)alkylaminosulfonyl. An additional example is (C$_{1-6}$) alkylsulfonyloxy.

Selected examples of optional substituents on the moiety Y include halogen, C$_{1-6}$ alkyl, difluoromethoxy and (C$_{1-6}$)alkylsulfonyloxy.

Typical examples of optional substituents on the moiety Y include halogen, C$_{1-6}$ alkyl and difluoromethoxy.

Examples of particular substituents on the moiety Y include fluoro, chloro, bromo, cyano, nitro, methyl, isopropyl, trifluoromethyl, hydroxy, methoxy, difluoromethoxy, trifluoromethoxy, methylthio, methylsulfinyl, methylsulfonyl, amino, methylamino, tert-butylamino, dimethylamino, phenylamino, acetylamino, methylsulfonylamino, formyl, acetyl, cyclopropylcarbonyl, azetidinylcarbonyl, pyrrolidinylcarbonyl, piperidinyl-carbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl. An additional example is methylsulfonyloxy.

Selected examples of particular substituents on the moiety Y include fluoro, chloro, methyl, difluoromethoxy and methylsulfonyloxy.

Typical examples of particular substituents on the moiety Y include chloro, methyl and difluoromethoxy.

Typical values of Y include benzocyclobutenyl, phenyl, fluorophenyl (including 2-fluorophenyl, 3-fluorophenyl and 4-fluorophenyl), chlorophenyl (including 2-chlorophenyl, 3-chlorophenyl and 4-chlorophenyl), difluorophenyl (including 2,6-difluorophenyl), (chloro)(fluoro)phenyl (including 5-chloro-2-fluorophenyl and 2-chloro-5-fluorophenyl), dichlorophenyl (including 2,5-dichlorophenyl and 2,6-dichlorophenyl), methylphenyl (including 4-methylphenyl), dimethylphenyl (including 2,5-dimethylphenyl and 2,6-dimethylphenyl), (trifluoromethyl)phenyl [including 2-(trifluoromethyl)phenyl], (chloro)(trifluoromethyl)phenyl [including 5-chloro-2-(trifluoromethyl)phenyl], (methyl)-(trifluoromethyl)phenyl [including 2-methyl-5-(trifluoromethyl)phenyl], bis(trifluoromethyl)phenyl [including 2,5-bis(trifluoromethyl)phenyl], methoxyphenyl (including 2-methoxyphenyl), (difluoromethoxy)phenyl [including 2-(difluoromethoxy)phenyl and 3-(difluoromethoxy) phenyl], (difluoromethoxy)(fluoro)phenyl [including 2-(difluoromethoxy)-5-fluorophenyl and 5-(difluoromethoxy)-2-fluorophenyl], (chloro)(difluoromethoxy)phenyl [including 5-chloro-2-(difluoromethoxy) phenyl and 6-chloro-2-(difluoromethoxy)phenyl], (trifluoromethoxy)phenyl [including 2-(trifluoromethoxy)-phenyl], (amino)(chloro)phenyl (including 5-amino-2-chlorophenyl), methylthienyl (including 3-methylthien-2-yl), methylthiazolyl (including 2-methyl-1,3-thiazol-4-yl), (chloro)(methyl)thiazolyl (including 5-chloro-2-methyl-1,3-thiazol-4-yl), dimethylthiazolyl (including 2,4-dimethyl-1,3-thiazol-5-yl) and pyridinyl (including pyridin-3-yl and pyridin-4-yl). An additional value is methylsulfonyloxyphenyl.

Selected values of Y include dichlorophenyl, dimethylphenyl, (difluoromethoxy)-phenyl, (difluoromethoxy)(fluoro) phenyl, methylsulfonyloxyphenyl, methylthienyl and dimethylthiazolyl.

Suitable values of Y include dichlorophenyl, dimethylphenyl, (difluoromethoxy)-phenyl, methylthienyl and dimethylthiazolyl.

In one embodiment, Y represents 2,5-dichlorophenyl.

In another embodiment, Y represents 2,5-dimethylphenyl.

In a particular embodiment, Y represents 2-(difluoromethoxy)phenyl.

In another embodiment, Y represents (difluoromethoxy)(fluoro)phenyl.

In another embodiment, Y represents 3-methylthien-2-yl.

In another embodiment, Y represents 2,4-dimethyl-1,3-thiazol-5-yl.

In one embodiment, Z represents hydrogen.

In another embodiment, Z is other than hydrogen.

In a selected embodiment, Z represents hydrogen; or Z represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents —$Z^1$-$Z^2$ or —$Z^1$—C(O)—$Z^2$, either of which moieties may be optionally substituted by one or more substituents.

In a further embodiment, Z represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents —$Z^1$-$Z^2$ or —Z—C(O)—$Z^2$, either of which moieties may be optionally substituted by one or more substituents.

Suitably, Z represents hydrogen; or Z represents $C_{1-6}$ alkyl, aryl or heteroaryl, any of which groups may be optionally substituted by one or more substituents; or Z represents —$Z^1$-$Z^2$, which moiety may be optionally substituted by one or more substituents.

Typically, Z represents hydrogen, fluoro or trifluoromethyl; or Z represents methyl, ethyl, n-propyl, isopropyl, n-butyl, sec-butyl, isobutyl, tert-butyl, cyclopropyl, cyclobutyl, cyclopentyl, cyclohexyl, phenyl, tetrahydrofuranyl, pyrrolidinyl, indolinyl, tetrahydropyranyl, piperidinyl, 1,2,3,4-tetrahydroquinolinyl, morpholinyl, azocanyl, thiazolinyl, furyl, thienyl, pyrazolyl, 4,5,6,7-tetrahydroindazolyl, benzoxazolyl, isoxazolyl, thiazolyl, benzothiazolyl, imidazolyl, benzimidazolyl, [1,2,4]triazolo[1,5-a]-pyrimidinyl, tetrazolyl, pyridinyl, quinolinyl, isoquinolinyl, phthalazinyl, pyrimidinyl or pyrazinyl, any of which groups may be optionally substituted by one or more substituents; or Z represents —$Z^1$-$Z^2$ or —Z—C(O)—$Z^2$, either of which moieties may be optionally substituted by one or more substituents.

Appositely, Z represents hydrogen; or Z represents methyl, phenyl or pyridinyl, any of which groups may be optionally substituted by one or more substituents; or Z represents —$Z^1$-$Z^2$, which moiety may be optionally substituted by one or more substituents.

The moiety $Z^1$ represents a divalent radical derived from an aryl, $C_{3-7}$ heterocycloalkyl or heteroaryl group, any of which groups may be optionally substituted by one or more substituents. Typically, the moiety $Z^1$ represents a divalent radical derived from a phenyl, pyrrolidinyl, piperazinyl, pyrazolyl, thiazolyl, triazolyl, tetrazolyl or pyridinyl group, any of which groups may be optionally substituted by one or more substituents. Typical values of the moiety $Z^1$ include the groups of formula (Za), (Zb), (Zc), (Zd), (Ze), (Zf), (Zg), (Zh) and (Zj):

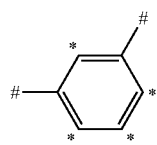
(Za)

-continued

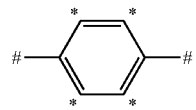
(Zb)

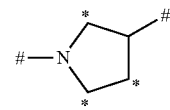
(Zc)

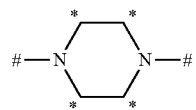
(Zd)

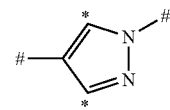
(Ze)

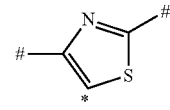
(Zf)

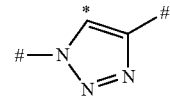
(Zg)

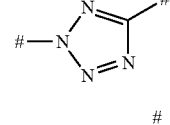
(Zh)

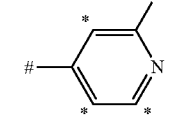
(Zj)

wherein
the symbols # represent the points of attachment of the moiety $Z^1$ to the remainder of the molecule; and
the asterisks (*) represent the site of attachment of optional substituents.

Additional values of the moiety $Z^1$ include the group of formula (Zk):

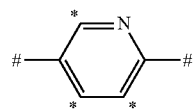
(Zk)

wherein
and * are as defined above.

Particular values of the moiety $Z^1$ include the groups of formula (Za), (Zc), (Ze), (Zf), (Zg), (Zh) and (Zj) as depicted above.

The moiety $Z^2$ represents aryl, $C_{3-7}$ heterocycloalkyl, $C_{3-7}$ heterocycloalkenyl or heteroaryl, any of which groups may be optionally substituted by one or more substituents. Typically, $Z^2$ represents phenyl, pyrrolidinyl, oxazolidinyl, imidazolidinyl, morpholinyl, imidazolinyl, thiazolyl, imidazolyl, tetrazolyl or pyridinyl, any of which groups may be optionally substituted by one or more substituents.

Examples of optional substituents which may be present on the moiety Z, $Z^1$ or $Z^2$ include one, two or three substituents independently selected from halogen, cyano, nitro, $C_{1-6}$ alkyl, trifluoromethyl, oxo, hydroxy, hydroxy($C_{1-6}$)alkyl, $C_{1-6}$ alkoxy, difluoromethoxy, trifluoromethoxy, $C_{1-3}$ alkylenedioxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, di($C_{1-6}$)alkylamino($C_{1-6}$)alkyl, $C_{2-6}$ alkylcarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl, aminocarbonylamino and hydrazinocarbonyl.

Typical examples of optional substituents on the moiety Z, $Z^1$ or $Z^2$ include halogen, cyano, nitro, $C_{1-6}$ alkyl, trifluoromethyl, oxo, hydroxy, hydroxy($C_{1-6}$)alkyl, $C_{1-6}$ alkoxy, difluoromethoxy, trifluoromethoxy, $C_{1-3}$ alkylenedioxy, $C_{1-6}$ alkylsulfonyl, amino, di($C_{1-6}$)alkylamino, di($C_{1-6}$)alkylamino($C_{1-6}$)alkyl, $C_{2-6}$ alkylcarbonylamino, $C_{1-6}$ alkylsulfonylamino, formyl, carboxy, $C_{2-6}$ alkoxycarbonyl, aminocarbonyl, $C_{1-6}$ alkylaminocarbonyl, di($C_{1-6}$)alkylaminocarbonyl, aminocarbonylamino and hydrazinocarbonyl.

Selected examples of optional substituents on the moiety Z, $Z^1$ or $Z^2$ include oxo and $C_{1-6}$ alkylsulfonyl.

Examples of particular substituents on the moiety Z, $Z^1$ or $Z^2$ include fluoro, chloro, bromo, cyano, nitro, methyl, ethyl, isopropyl, trifluoromethyl, oxo, hydroxy, hydroxymethyl, methoxy, difluoromethoxy, trifluoromethoxy, methylenedioxy, methylthio, methylsulfinyl, methylsulfonyl, amino, methylamino, tert-butylamino, dimethylamino, dimethylaminomethyl, dimethylaminoethyl, acetylamino, methylsulfonylamino, formyl, acetyl, carboxy, methoxycarbonyl, tert-butoxycarbonyl, aminocarbonyl, methylaminocarbonyl, dimethylaminocarbonyl, aminosulfonyl, methylaminosulfonyl, dimethylaminosulfonyl, aminocarbonylamino and hydrazinocarbonyl.

Typical examples of particular substituents on the moiety Z, $Z^1$ or $Z^2$ include fluoro, chloro, bromo, cyano, nitro, methyl, ethyl, trifluoromethyl, oxo, hydroxy, hydroxymethyl, methoxy, difluoromethoxy, trifluoromethoxy, methylenedioxy, methylsulfonyl, amino, dimethylamino, dimethylaminomethyl, dimethylaminoethyl, acetylamino, methylsulfonylamino, formyl, carboxy, methoxycarbonyl, tert-butoxycarbonyl, aminocarbonyl, methylaminocarbonyl, dimethylaminocarbonyl, aminocarbonylamino and hydrazinocarbonyl.

Selected examples of optional substituents on the moiety Z, $Z^1$ or $Z^2$ include oxo and methylsulfonyl.

Typical values of $Z^2$ include phenyl, hydroxyphenyl, oxopyrrolidinyl, dioxo-pyrrolidinyl, (hydroxy)(oxo)pyrrolidinyl, (amino)(oxo)pyrrolidinyl, (oxo)oxazolidinyl, oxoimidazolidinyl, morpholinyl, imidazolinyl, methylthiazolyl, formylthiazolyl, imidazolyl, tetrazolyl and pyridinyl.

Selected values of $Z^2$ include oxopyrrolidinyl and (oxo)oxazolidinyl. In one embodiment, $Z^2$ represents oxopyrrolidinyl. In another embodiment, $Z^2$ represents (oxo)oxazolidinyl.

Typical values of Z include hydrogen, fluoro, trifluoromethyl, methyl, ethyl, n-propyl, isopropyl, isobutyl, tert-butyl, cyclopropyl, cyclopentyl, cyclohexyl, oxocyclohexyl, phenyl, bromophenyl, cyanophenyl, nitrophenyl, methoxyphenyl, difluoromethoxyphenyl, trifluoromethoxyphenyl, methylenedioxyphenyl, methylsulfonylphenyl, dimethylaminophenyl, acetylaminophenyl, methylsulfonylaminophenyl, carboxyphenyl, aminocarbonylphenyl, methylaminocarbonylphenyl, dimethylaminocarbonylphenyl, aminocarbonylaminophenyl, tetrahydrofuranyl, oxopyrrolidinyl, dimethylamino-pyrrolidinyl, tert-butoxycarbonylpyrrolidinyl, indolinyl, tetrahydropyranyl, piperidinyl, ethylpiperidinyl, tert-butoxycarbonylpiperidinyl, aminocarbonylpiperidinyl, 2-oxo-3,4-dihydroquinolinyl, morpholinyl, azocanyl, oxothiazolinyl, furyl, hydroxymethylfuryl, thienyl, methylpyrazolyl, dimethylpyrazolyl, 4,5,6,7-tetrahydroindazolyl, benzoxazolyl, methylisoxazolyl, dimethylisoxazolyl, methylthiazolyl, aminothiazolyl, benzothiazolyl, methylbenzothiazolyl, aminobenzothiazolyl, imidazolyl, methylimidazolyl, methyl-benzimidazolyl, dimethyl[1,2,4]triazolo[1,5-a]pyrimidinyl, dimethylaminoethyltetrazolyl, pyridinyl, fluoropyridinyl, chloropyridinyl, cyanopyridinyl, methylpyridinyl, (cyano)-(methyl)pyridinyl, trifluoromethylpyridinyl, oxopyridinyl, methoxypyridinyl, dimethyl-aminomethylpyridinyl, acetylaminopyridinyl, carboxypyridinyl, methoxycarbonyl-pyridinyl, aminocarbonylpyridinyl, (aminocarbonyl)(fluoro)pyridinyl, methylamino-carbonylpyridinyl, dimethylaminocarbonylpyridinyl, hydrazinocarbonylpyridinyl, quinolinyl, isoquinolinyl, (methyl)(oxo)phthalazinyl, pyrimidinyl, pyrazinyl, oxopyrrolidinylphenyl, dioxopyrrolidinylphenyl, (hydroxy)(oxo)pyrrolidinylphenyl, (amino)(oxo)pyrrolidinylphenyl, (oxo)oxazolidinylphenyl, oxoimidazolidinylphenyl, imidazolinylphenyl, methylthiazolylphenyl, formylthiazolylphenyl, imidazolylphenyl, tetrazolylphenyl, phenylpyrrolidinyl, hydroxyphenylpiperazinyl, (methyl)(phenyl)-pyrazolyl, oxoimidazolidinylthiazolyl, hydroxyphenyltriazolyl, morpholinyltetrazolyl, oxopyrrolidinylpyridinyl, (oxo)oxazolidinylpyridinyl, oxoimidazolidinylpyridinyl, pyridinylthiazolyl, pyridinyltetrazolyl and morpholinylcarbonylphenyl. Additionally, Z may represent methylsulfonylpyridinyl.

Particular values of Z include hydrogen, methyl, methylsulfonylphenyl, pyridinyl, oxopyrrolidinylphenyl, (hydroxy)(oxo)pyrrolidinylphenyl and (oxo)oxazolidinylphenyl. Additionally, Z may represent methylsulfonylpyridinyl. In a first embodiment, Z represents hydrogen. In a second embodiment, Z represents methyl. In a third embodiment, Z represents methylsulfonylphenyl. In one aspect of that embodiment, Z represents 3-(methylsulfonyl)phenyl. In another aspect of that embodiment, Z represents 4-(methylsulfonyl)phenyl. In a fourth embodiment, Z represents pyridinyl. In one aspect of that embodiment, Z represents pyridin-4-yl. In a fifth embodiment, Z represents oxopyrrolidinylphenyl. In one aspect of that embodiment, Z represents 3-(2-oxopyrrolidin-1-yl)phenyl. In a sixth embodiment, Z represents (hydroxy)(oxo)pyrrolidinylphenyl. In one aspect of that embodiment, Z represents 3-(3-hydroxy-2-oxopyrrolidin-1-yl)phenyl. In another aspect of that embodiment, Z represents 3-(4-hydroxy-2-oxopyrrolidin-1-yl)phenyl. In a seventh embodiment, Z represents (oxo)oxazolidinylphenyl. In one aspect of that embodiment, Z represents 3-(2-oxo-oxazolidin-3-yl)phenyl. In an eighth embodiment, Z represents methylsulfonylpyridinyl.

In general, $R^1$, $R^2$, $R^3$ and $R^4$ independently represent hydrogen, halogen, cyano, nitro, hydroxy, trifluoromethyl, trifluoromethoxy, —$OR^a$, —$SR^a$, —$SOR^a$, —$SO_2R^a$, —$SF_5$, —$NR^bR^c$, —$NR^cCOR^d$, —$NR^cCO_2R^d$, —$NHCONR^bR^c$, —$NR^cSO_2R^e$, —$N(SO_2R^e)_2$, —$NHSO_2NR^bR^c$, —$COR^d$, —$CO_2R^d$, —$CONR^bR^c$, —$CON(OR^a)R^b$ or —$SO_2NR^bR^c$; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)

alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{3-7}$)cycloalkyl-heteroaryl-, ($C_{4-7}$)cycloalkenyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

Generally, $R^1$, $R^2$, $R^3$ and $R^4$ independently represent hydrogen, halogen, cyano, nitro, hydroxy, trifluoromethyl, trifluoromethoxy, $-OR^a$, $-SR^a$, $-SOR^a$, $-SO_2R^a$, $-SF_5$, $-NR^bR^c$, $-NR^cCOR^d$, $-NR^cCO_2R^d$, $-NHCONR^bR^c$, $-NR^cSO_2R^e$, $-N(SO_2R^e)_2$, $-NHSO_2NR^bR^c$, $-COR^d$, $-CO_2R^d$, $-CONR^bR^c$, $-CON(OR^a)R^b$ or $-SO_2NR^bR^c$; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{4-7}$)cycloalkenyl-heteroaryl-, ($C_{3-7}$)heterocycloalkyl-heteroaryl-, ($C_{3-7}$)heterocycloalkyl-($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

Suitably, $R^1$, $R^2$, $R^3$ and $R^4$ independently represent hydrogen, halogen, cyano, trifluoromethyl or $-CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, ($C_{3-7}$)cycloalkyl-heteroaryl-, ($C_{4-7}$)cycloalkenyl-heteroaryl-, ($C_{3-7}$)heterocycloalkyl-heteroaryl-, ($C_{4-9}$)heterobicycloalkyl-heteroaryl- or ($C_{4-9}$) spiroheterocycloalkyl-heteroaryl-, any of which groups may be optionally substituted by one or more substituents. Additionally, $R^1$, $R^2$, $R^3$ and $R^4$ may independently represent ($C_{3-7}$)cycloalkyl($C_{1-6}$)alkyl-heteroaryl- or ($C_{4-9}$)bicycloalkyl-heteroaryl-, either of which groups may be optionally substituted by one or more substituents.

Typically, $R^1$, $R^2$, $R^3$ and $R^4$ independently represent hydrogen, halogen, cyano, trifluoromethyl or $-CO_2R^d$; or $C_{1-6}$ alkyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl-($C_{3-7}$)heterocycloalkyl-, ($C_{4-7}$)cycloalkenyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$) spiroheterocycloalkyl-heteroaryl-, any of which groups may be optionally substituted by one or more substituents.

Examples of optional substituents which may be present on $R^1$, $R^2$, $R^3$ or $R^4$ include one, two or three substituents independently selected from halogen, cyano, cyano($C_{1-6}$)alkyl, nitro, $C_{1-6}$ alkyl, trifluoromethyl, trifluoroethyl, $C_{2-6}$ alkenyl, hydroxy, $C_{1-6}$ alkoxy, difluoromethoxy, trifluoromethoxy, trifluoroethoxy, $C_{1-3}$ alkylenedioxy, $C_{1-6}$ alkoxy($C_{1-6}$)alkyl, $C_{1-6}$ alkylthio, $C_{1-6}$ alkylsulphonyl, ($C_{1-6}$)alkylsulphonyl($C_{1-6}$)alkyl, oxo, amino, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]amino, $C_{2-6}$ alkylcarbonylamino, $C_{2-6}$ alkoxycarbonylamino, $C_{1-6}$ alkylaminocarbonylamino, $C_{1-6}$ alkylsulphonylamino, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, a carboxylic acid isostere or prodrug moiety $\Omega$, aminocarbonyl, $C_{1-6}$ alkylaminocarbonyl, di($C_{1-6}$)alkylaminocarbonyl, aminosulphonyl and di($C_{1-6}$)alkylaminosulphonyl. Additional examples include bis[($C_{1-6}$)alkylsulphonyl]amino, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino and $-(C_{1-6})$alkyl-$\Omega$, in which $\Omega$ is as defined herein. Additional examples include halo($C_{1-6}$)-alkyl, nitro($C_{1-6}$)alkyl, difluoromethyl, difluoroethyl, hydroxy($C_{1-6}$)alkyl, carboxy($C_{3-7}$)-cycloalkyloxy, $C_{1-6}$ alkylsulphinyl, amino($C_{1-6}$)alkyl, hydroxy($C_{1-6}$)alkylamino, $C_{1-6}$ alkoxyamino, [($C_{1-6}$)alkoxy](hydroxy)($C_{1-6}$)alkylamino, [($C_{1-6}$)alkylthio](hydroxy)($C_{1-6}$)-alkylamino, di($C_{1-6}$)alkylamino($C_{1-6}$)alkylamino, N-[di($C_{1-6}$)alkylamino ($C_{1-6}$)alkyl]-N-[hydroxy($C_{1-6}$)alkyl]amino, hydroxy($C_{1-6}$) alkyl($C_{3-7}$)cycloalkylamino, (hydroxy)[($C_{3-7}$)-cycloalkyl($C_{1-6}$)alkyl]amino, ($C_{3-7}$)heterocycloalkyl($C_{1-6}$)alkylamino, oxo($C_{3-7}$)-heterocycloalkyl($C_{1-6}$)alkylamino, ($C_{1-6}$)alkylheteroarylamino, heteroaryl($C_{1-6}$)alkylamino, ($C_{1-6}$)alkylheteroaryl($C_{1-6}$)alkylamino, N—[($C_{1-6}$)alkyl]-N—[($C_{2-6}$)alkylcarbonyl]amino, ($C_{2-6}$)alkylcarbonylamino($C_{1-6}$)alkyl, $C_{3-6}$ alkenylcarbonylamino, bis[($C_{3-6}$)alkenylcarbonyl]amino, N—[($C_{1-6}$)alkyl]-N—[($C_{3-7}$)cycloalkylcarbonyl]amino, $C_{2-6}$ alkoxycarbonyl-($C_{1-6}$)alkylamino, N—[($C_{1-6}$)alkyl]-N—[($C_{1-6}$)alkylsulphonyl]amino, ($C_{3-7}$)cycloalkylcarbonyl, phenylcarbonyl, ($C_{2-6}$)alkylcarbonyloxy($C_{1-6}$)alkyl, morpholinyl($C_{1-6}$)alkoxycarbonyl, $C_{2-6}$ alkoxycarbonylmethylidenyl, hydroxy($C_{1-6}$)alkylaminocarbonyl, aminocarbonyl ($C_{1-6}$)alkyl and $C_{1-6}$ alkoxyaminocarbonyl.

By the expression "carboxylic acid isostere or prodrug moiety" is meant any functional group, structurally distinct from a carboxylic acid moiety, that will be recognised by a biological system as being similar to, and thus capable of mimicking, a carboxylic acid moiety, or will be readily convertible by a biological system in vivo into a carboxylic acid moiety. A synopsis of some common carboxylic acid isosteres is presented by N. A. Meanwell in *J. Med. Chem.*, 2011, 54, 2529-2591 (cf. in particular FIGS. 25 and 26). Typical examples of suitable carboxylic acid isostere or prodrug moieties represented by $\Omega$ include the functional groups of formula (i) to (xli):

(i)

(ii)

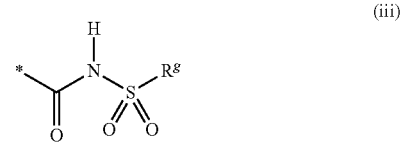

(iii)

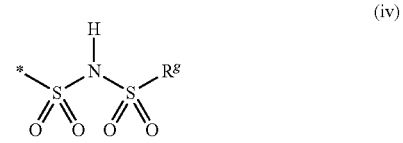

(iv)

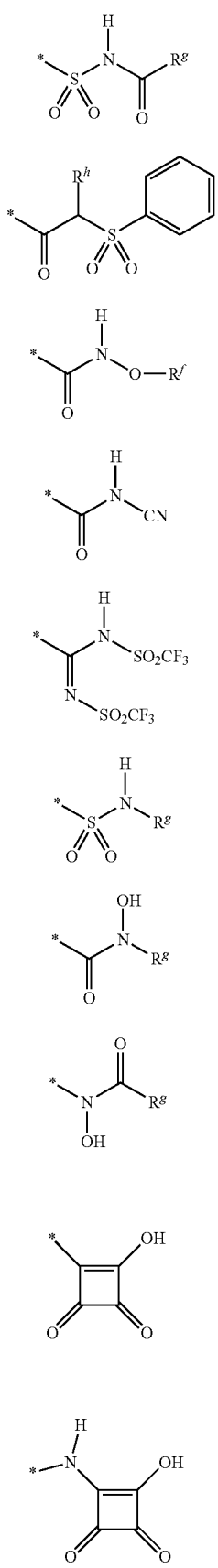
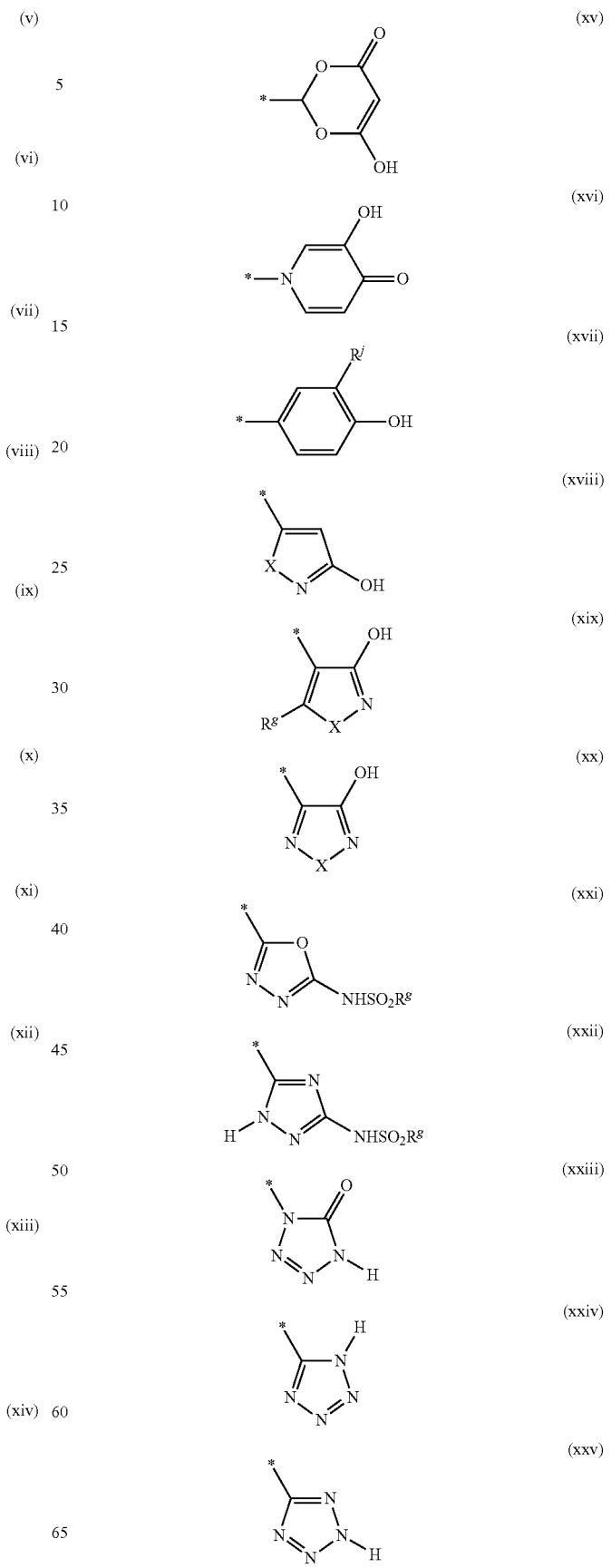

-continued

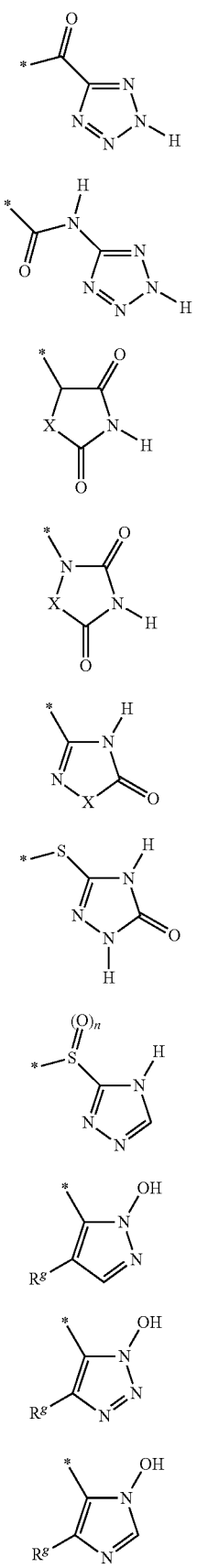

(xxvi)
(xxvii)
(xxviii)
(xxix)
(xxx)
(xxxi)
(xxxii)
(xxxiii)
(xxxiv)
(xxxv)

-continued

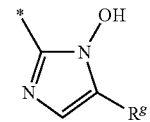
(xxxvi)

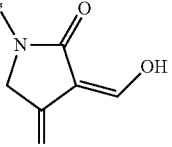
(xxxvii)

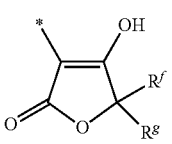
(xxxviii)

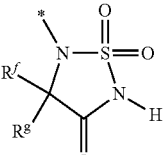
(xxxix)

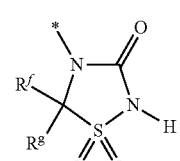
(xl)

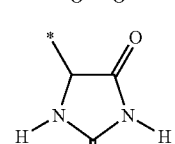
(xli)

wherein
the asterisk (*) represents the site of attachment to the remainder of the molecule;
n is zero, 1 or 2;
X represents oxygen or sulphur;
$R^f$ represents hydrogen, $C_{1-6}$ alkyl or —CH$_2$CH(OH)CH$_2$OH;
$R^g$ represents $C_{1-6}$ alkyl, trifluoromethyl, —CH$_2$CH$_2$F, —CH$_2$CHF$_2$, —CH$_2$CF$_3$ or —CF$_2$CF$_3$;
$R^h$ represents hydrogen, cyano or —CO$_2$R$^d$, in which R$^d$ is as defined above; and
$R^j$ represents hydrogen or halogen.

In one embodiment, n is zero. In another embodiment, n is 1. In a further embodiment, n is 2.

In one embodiment, X represents oxygen. In another embodiment, X represents sulphur.

In one embodiment, $R^f$ represents hydrogen. In another embodiment, $R^f$ represents $C_{1-6}$ alkyl, especially methyl. In a further embodiment, $R^f$ is —CH$_2$CH(OH)CH$_2$OH.

In one embodiment, $R^g$ represents $C_{1-6}$ alkyl, especially methyl. In another embodiment, $R^g$ represents trifluoromethyl, —CH$_2$CH$_2$F, —CH$_2$CHF$_2$, —CH$_2$CF$_3$ or —CF$_2$CF$_3$. In a first aspect of that embodiment, $R^g$ represents trifluoromethyl. In a second aspect of that embodiment, $R^g$ represents —CH$_2$CH$_2$F. In a third aspect of that embodiment, $R^g$ represents —CH$_2$CHF$_2$. In a fourth aspect of that embodiment, R$^g$ represents —CH$_2$CF$_3$. In a fifth aspect of that embodiment, R$^g$ represents —CF$_2$CF$_3$.

In one embodiment, R$^h$ is hydrogen. In another embodiment, R$^h$ represents cyano. In a further embodiment, R$^h$ represents —CO$_2$R$^d$, especially methoxycarbonyl.

In one embodiment, R$^j$ represents hydrogen. In another embodiment, R$^j$ represents halogen, especially chloro.

In a selected embodiment, Ω represents tetrazolyl, especially a C-linked tetrazolyl moiety of formula (xxiv) or (xxv) as depicted above, in particular a group of formula (xxiv) as depicted above.

In another embodiment, Ω represents C$_{1-6}$ alkylsulphonylaminocarbonyl, i.e. a moiety of formula (iii) as depicted above wherein R$^g$ represents C$_{1-6}$ alkyl.

In another embodiment, Ω represents C$_{1-6}$ alkylaminosulphonyl, i.e. a moiety of formula (x) as depicted above wherein R$^g$ represents C$_{1-6}$ alkyl.

In a further embodiment, Ω represents (C$_{1-6}$)alkylcarbonylaminosulphonyl, i.e. a moiety of formula (v) as depicted above wherein R$^g$ represents C$_{1-6}$ alkyl.

Additional examples of suitable carboxylic acid isostere or prodrug moieties represented by Ω include the functional group of formula (xlii):

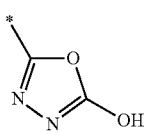

(xlii)

wherein the asterisk (*) represents the site of attachment to the remainder of the molecule.

Suitable examples of optional substituents which may be present on R$^1$, R$^2$, R$^3$ or R$^4$ include one, two or three substituents independently selected from C$_{1-6}$ alkyl, hydroxy, C$_{1-6}$ alkoxy, C$_{1-6}$ alkylsulphonyl, oxo, amino, C$_{1-6}$ alkylsulphonylamino, bis[(C$_{1-6}$)alkylsulphonyl]amino, N—[(C$_{1-6}$)alkyl]-N-[carboxy(C$_{1-6}$)alkyl]amino, carboxy(C$_{3-7}$)cycloalkylamino, carboxy(C$_{3-7}$)cycloalkyl(C$_{1-6}$)alkylamino, C$_{2-6}$ alkylcarbonyl, carboxy, carboxy-(C$_{1-6}$)alkyl, C$_{2-6}$ alkoxycarbonyl, C$_{2-6}$ alkoxycarbonyl(C$_{1-6}$)alkyl, a carboxylic acid isostere or prodrug moiety Ω as defined herein, —(C$_{1-6}$)alkyl-Ω, and aminosulphonyl. Additional examples include halogen, halo(C$_{1-6}$)alkyl, cyano, nitro(C$_{1-6}$)alkyl, trifluoromethyl, hydroxy(C$_{1-6}$)alkyl, carboxy(C$_{3-7}$)cycloalkyloxy, C$_{1-6}$ alkylthio, amino(C$_{1-6}$)alkyl, C$_{1-6}$ alkylamino, (C$_{2-6}$)alkylcarbonylamino(C$_{1-6}$)alkyl, N—[(C$_{1-6}$)alkyl]-N—[(C$_{1-6}$)alkylsulphonyl]-amino, formyl, (C$_{2-6}$)alkylcarbonyloxy(C$_{1-6}$) alkyl, morpholinyl(C$_{1-6}$)alkoxycarbonyl, C$_{2-6}$ alkoxycarbonylmethylidenyl and C$_{1-6}$ alkoxyaminocarbonyl.

Typical examples of optional substituents which may be present on R$^1$, R$^2$, R$^3$ or R$^4$ include one, two or three substituents independently selected from C$_{1-6}$ alkyl, hydroxy, C$_{1-6}$ alkoxy, oxo, amino, C$_{1-6}$ alkylsulphonylamino, carboxy and C$_{2-6}$ alkoxycarbonyl.

Examples of particular substituents on R$^1$, R$^2$, R$^3$ or R$^4$ include fluoro, chloro, bromo, cyano, cyanoethyl, nitro, methyl, ethyl, tert-butyl, trifluoromethyl, trifluoroethyl, ethenyl, hydroxy, methoxy, isopropoxy, difluoromethoxy, trifluoromethoxy, trifluoroethoxy, methylenedioxy, ethylenedioxy, methoxymethyl, methylthio, methylsulphonyl, methylsulphonylethyl, oxo, amino, methylamino, dimethylamino, methoxyethylamino, N-(hydroxyethyl)-N-(methyl)amino, acetylamino, methoxycarbonylamino, ethoxycarbonylamino, ethylaminocarbonylamino, butylaminocarbonylamino, methylsulphonylamino, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolyl, aminocarbonyl, methylaminocarbonyl, dimethylaminocarbonyl, methylsulphonylaminocarbonyl, aminosulphonyl, methylaminosulphonyl and dimethylaminosulphonyl. Additional examples include bis(methylsulphonyl)amino, N-(carboxyethyl)-N-(methyl)amino, carboxycyclopentylamino, carboxycyclopropylmethylamino, methoxycarbonylmethyl, tetrazolylmethyl and acetylaminosulphonyl. Additional examples include fluoromethyl, fluoroisopropyl, nitromethyl, isopropyl, isobutyl, difluoromethyl, difluoroethyl, hydroxymethyl, hydroxyisopropyl, methoxyethyl, carboxycyclobutyloxy, methylsulphinyl, aminomethyl, aminoisopropyl, ethylamino, hydroxyethylamino, hydroxypropylamino, (hydroxy)(methyl)propylamino, (hydroxy)(methoxy)(methyl)propylamino, (hydroxy)-(methylthio)butylamino, dimethylaminoethylamino, (dimethylamino)(methyl)propylamino, N-(dimethylaminoethyl)-N-(hydroxyethyl)amino, hydroxymethylcyclopentyl-amino, hydroxycyclobutylmethylamino, (cyclopropyl)(hydroxy)propylamino, morpholinylethylamino, oxopyrrolidinylmethylamino, ethyloxadiazolylamino, methyl-thiadiazolylamino, thiazolylmethylamino, thiazolylethylamino, pyrimidinylmethylamino, methylpyrazolylmethylamino, N-acetyl-N-methylamino, N-isopropylcarbonyl-N-methylamino, acetylaminomethyl, ethenylcarbonylamino, bis(ethenylcarbonyl)amino, N-cyclopropylcarbonyl-N-methylamino, N-(carboxymethyl)-N-methylamino, tert-butoxycarbonylamino, methoxycarbonylethylamino, N-methyl-N-(methylsulphonyl)amino, isopropylcarbonyl, cyclobutylcarbonyl, phenylcarbonyl, acetoxyisopropyl, n-butoxycarbonyl, morpholinylethoxycarbonyl, ethoxycarbonylmethylidenyl, hydroxyoxadiazolyl, hydroxyethylaminocarbonyl and methoxyaminocarbonyl.

Suitable examples of particular substituents on R$^1$, R$^2$, R$^3$ or R$^4$ include methyl, hydroxy, methoxy, methylsulphonyl, oxo, amino, methylsulphonylamino, bis(methylsulphonyl)amino, N-(carboxyethyl)-N-(methyl)amino, carboxycyclopentylamino, carboxycyclopropylmethylamino, acetyl, carboxy, carboxyethyl, methoxycarbonyl, ethoxycarbonyl, tert-butoxycarbonyl, methoxycarbonylmethyl, ethoxycarbonylethyl, tetrazolyl, tetrazolylmethyl, aminosulphonyl and acetylaminosulphonyl. Additional examples include fluoro, chloro, fluoromethyl, fluoroisopropyl, cyano, nitromethyl, ethyl, isopropyl, trifluoromethyl, hydroxymethyl, hydroxyisopropyl, carboxycyclobutyloxy, methylthio, aminomethyl, aminoisopropyl, methylamino, acetylaminomethyl, N-methyl-N-(methylsulphonyl)amino, formyl, acetoxyisopropyl, carboxymethyl, n-butoxycarbonyl, ethoxycarbonylmethyl, morpholinylethoxycarbonyl, ethoxycarbonylmethylidenyl, hydroxyoxadiazolyl, methoxyaminocarbonyl and methylsulphonylaminocarbonyl.

Typical examples of particular substituents on R$^1$, R$^2$, R$^3$ or R$^4$ include methyl, hydroxy, methoxy, oxo, amino, methylsulphonylamino, carboxy, methoxycarbonyl and tert-butoxycarbonyl.

Typically, R$^1$ represents hydrogen, halogen, cyano or —CO$_2$R$^d$; or C$_{1-6}$ alkyl, aryl, C$_{3-7}$ heterocycloalkyl, C$_{3-7}$ heterocycloalkenyl, heteroaryl, (C$_{3-7}$)heterocycloalkyl-(C$_{1-6}$) alkyl-aryl-, heteroaryl(C$_{3-7}$)heterocycloalkyl-, (C$_{4-7}$)cycloalkenyl-heteroaryl-, (C$_{3-7}$)heterocycloalkyl-heteroaryl-, (C$_{3-7}$)heterocycloalkyl(C$_{1-6}$)alkyl-heteroaryl-, (C$_{3-7}$)heterocycloalkenyl-heteroaryl-, (C$_{4-9}$)heterobicycloalkyl-heteroaryl- or $(C_{4-9})$spiroheterocycloalkyl-heteroaryl-, any of which groups may be optionally substituted by one or more substituents. Additionally, $R^1$ may represent $C_{2-6}$ alkynyl or $(C_{3-7})$cycloalkyl-heteroaryl-, either of which groups may be optionally substituted by one or more substituents. Additionally, $R^1$ may represent $(C_{3-7})$cycloalkyl$(C_{1-6})$alkyl-heteroaryl- or $(C_{4-9})$bicycloalkyl-heteroaryl-, either of which groups may be optionally substituted by one or more substituents.

Suitably, $R^1$ represents halogen, cyano or $-CO_2R^d$; or $C_{1-6}$ alkyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{4-7})$cycloalkenyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents. Additionally, $R^1$ may represent $C_{2-6}$ alkynyl or $(C_{3-7})$cycloalkyl-heteroaryl-, either of which groups may be optionally substituted by one or more substituents. Additionally, $R^1$ may represent $(C_{3-7})$cycloalkyl$(C_{1-6})$alkyl-heteroaryl- or $(C_{4-9})$bicycloalkyl-heteroaryl-, either of which groups may be optionally substituted by one or more substituents.

Generally, $R^1$ represents halogen or cyano; or $C_{1-6}$ alkyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl $(C_{3-7})$heterocycloalkyl-, $(C_{4-7})$cycloalkenyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents. Additionally, $R^1$ may represent $C_{2-6}$ alkynyl or $(C_{3-7})$cycloalkyl-heteroaryl-, either of which groups may be optionally substituted by one or more substituents. Additionally, $R^1$ may represent $(C_{3-7})$cycloalkyl$(C_{1-6})$alkyl-heteroaryl- or $(C_{4-9})$bicycloalkyl-heteroaryl-, either of which groups may be optionally substituted by one or more substituents.

More generally, $R^1$ represents halogen or cyano; or $C_{1-6}$ alkyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$heterocycloalkyl-heteroaryl-, $(C_{3-7})$heterocycloalkyl$(C_{1-6})$alkyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents. Additionally, $R^1$ may represent $C_{2-6}$ alkynyl, $(C_{3-7})$cycloalkyl-heteroaryl- or $(C_{4-7})$cycloalkenyl-heteroaryl-, any of which groups may be optionally substituted by one or more substituents. Additionally, $R^1$ may represent $(C_{3-7})$cycloalkyl$(C_{1-6})$alkyl-heteroaryl- or $(C_{4-9})$bicycloalkyl-heteroaryl-, either of which groups may be optionally substituted by one or more substituents.

Still more generally, $R^1$ represents $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$cycloalkyl-heteroaryl-, $(C_{4-7})$-cycloalkenyl-heteroaryl-, $(C_{3-7})$heterocycloalkyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents. Additionally, $R^1$ may represent $(C_{3-7})$cycloalkyl$(C_{1-6})$alkyl-heteroaryl- or $(C_{4-9})$bicycloalkyl-heteroaryl-, either of which groups may be optionally substituted by one or more substituents.

Even more generally, $R^1$ represents $C_{1-6}$ alkyl, $C_{3-7}$ heterocycloalkenyl, heteroaryl, $(C_{3-7})$heterocycloalkyl-heteroaryl- or $(C_{4-9})$heterobicycloalkyl-heteroaryl-, any of which groups may be optionally substituted by one or more substituents.

In a first embodiment, $R^1$ represents hydrogen.

In a second embodiment, $R^1$ represents halogen. In one aspect of that embodiment, $R^1$ represents bromo.

In a third embodiment, $R^1$ represents cyano.

In a fourth embodiment, $R^1$ represents $-CO_2R^d$.

In a fifth embodiment, $R^1$ represents optionally substituted $C_{1-6}$ alkyl. In one aspect of that embodiment, $R^1$ represents optionally substituted ethyl.

In a sixth embodiment, $R^1$ represents optionally substituted $C_{2-6}$ alkynyl. In one aspect of that embodiment, $R^1$ represents optionally substituted butynyl.

In a seventh embodiment, $R^1$ represents optionally substituted aryl. In one aspect of that embodiment, $R^1$ represents optionally substituted phenyl.

In an eighth embodiment, $R^1$ represents optionally substituted $C_{3-7}$ heterocycloalkyl.

In a ninth embodiment, $R^1$ represents optionally substituted $C_{3-7}$ heterocycloalkenyl.

In a tenth embodiment, $R^1$ represents optionally substituted heteroaryl. In selected aspects of that embodiment, $R^1$ represents benzofuryl, thienyl, indolyl, pyrazolyl, indazolyl, isoxazolyl, imidazolyl, pyridinyl, quinolinyl, pyridazinyl, pyrimidinyl or pyrazinyl, any of which groups may be optionally substituted by one or more substituents. In a further aspect, $R^1$ represents optionally substituted thiazolyl.

In an eleventh embodiment, $R^1$ represents optionally substituted $(C_{3-7})$-heterocycloalkyl$(C_{1-6})$alkyl-aryl-. In a first aspect of that embodiment, $R^1$ represents optionally substituted pyrrolidinylmethylphenyl-. In a second aspect of that embodiment, $R^1$ represents optionally substituted piperazinylmethylphenyl-.

In a twelfth embodiment, $R^1$ represents optionally substituted heteroaryl$(C_{3-7})$-heterocycloalkyl-. In one aspect of that embodiment, $R^1$ represents optionally substituted pyridinylpiperazinyl-.

In a thirteenth embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclohexylpyridinyl-. In a third aspect of that embodiment, $R^1$ represents optionally substituted cyclopropylpyrimidinyl-. In a fourth aspect of that embodiment, $R^1$ represents optionally substituted cyclobutylpyrimidinyl-. In a fifth aspect of that embodiment, $R^1$ represents optionally substituted cyclopentylpyrimidinyl-. In a sixth aspect of that embodiment, $R^1$ represents optionally substituted cyclohexylpyrimidinyl-. In a seventh aspect of that embodiment, $R^1$ represents optionally substituted cyclohexylpyrazinyl-.

In a fourteenth embodiment, $R^1$ represents optionally substituted $(C_{4-7})$-cycloalkenyl-heteroaryl-.

In a fifteenth embodiment, $R^1$ represents optionally substituted $(C_{3-7})$-heterocycloalkyl-heteroaryl-. In a first aspect of that embodiment, $R^1$ represents optionally substituted pyrrolidinylpyridinyl-. In a second aspect of that embodiment, $R^1$ represents optionally substituted tetrahydropyranylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinylpyridinyl-. In a seventh aspect of that embodiment, $R^1$ represents optionally substituted diazepanylpyridinyl-. In an eighth aspect of that embodiment, R¹ represents optionally substituted oxetanylpyrimidinyl-. In a ninth aspect of that embodiment, R¹ represents optionally substituted azetidinylpyrimidinyl-. In a tenth aspect of that embodiment, R¹ represents optionally substituted tetrahydrofuranylpyrimidinyl-. In an eleventh aspect of that embodiment, R¹ represents optionally substituted pyrrolidinylpyrimidinyl-. In a twelfth aspect of that embodiment, R¹ represents optionally substituted tetrahydropyranylpyrimidinyl-. In a thirteenth aspect of that embodiment, R¹ represents optionally substituted piperidinylpyrimidinyl-. In a fourteenth aspect of that embodiment, R represents optionally substituted piperazinylpyrimidinyl-. In a fifteenth aspect of that embodiment, R¹ represents optionally substituted morpholinylpyrimidinyl-. In a sixteenth aspect of that embodiment, R¹ represents optionally substituted thiomorpholinylpyrimidinyl-. In a seventeenth aspect of that embodiment, R¹ represents optionally substituted azepanylpyrimidinyl-. In an eighteenth aspect of that embodiment, R represents optionally substituted oxazepanylpyrimidinyl-. In a nineteenth aspect of that embodiment, R¹ represents optionally substituted diazepanylpyrimidinyl-. In a twentieth aspect of that embodiment, R¹ represents optionally substituted thiadiazepanylpyrimidinyl-. In a twenty-first aspect of that embodiment, R¹ represents optionally substituted piperidinylpyrazinyl-.

In a sixteenth embodiment, R¹ represents optionally substituted $(C_{3-7})$-heterocycloalkyl$(C_{1-6})$alkyl-heteroaryl-. In a first aspect of that embodiment, R¹ represents optionally substituted morpholinylmethylthienyl-. In a second aspect of that embodiment, R¹ represents optionally substituted morpholinylethylpyrazolyl-.

In a seventeenth embodiment, R¹ represents optionally substituted $(C_{3-7})$-heterocycloalkenyl-heteroaryl-.

In an eighteenth embodiment, R¹ represents optionally substituted $(C_{4-9})$-heterobicycloalkyl-heteroaryl-.

In a nineteenth embodiment, R¹ represents optionally substituted $(C_{4-9})$-spiroheterocycloalkyl-heteroaryl-.

In a twentieth embodiment, R¹ represents optionally substituted $(C_{3-7})$cycloalkyl-$(C_{1-6})$alkyl-heteroaryl-. In one aspect of that embodiment, R¹ represents optionally substituted cyclohexylmethylpyrimidinyl-.

In a twenty-first embodiment, R¹ represents optionally substituted $(C_{4-9})$-bicycloalkyl-heteroaryl-.

Appositely, R¹ represents hydrogen, bromo, cyano or —CO₂R^d; or ethyl, phenyl, piperidinyl, piperazinyl, morpholinyl, 1,2,3,6-tetrahydropyridinyl, benzofuryl, thienyl, indolyl, pyrazolyl, indazolyl, isoxazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, pyrrolidinylpyridinyl, piperidinylpyridinyl, piperazinylpyridinyl, morpholinylpyridinyl, thiomorpholinylpyridinyl, diazepanylpyridinyl, pyrrolidinylpyrimidinyl, piperidinylpyrimidinyl, piperazinylpyrimidinyl, morpholinylpyrimidinyl, thiomorpholinylpyrimidinyl, diazepanylpyrimidinyl, thiadiazepanylpyrimidinyl, morpholinylmethylthienyl, morpholinylethylpyrazolyl, 2-oxa-5-azabicyclo[2.2.1]-heptanylpyrimidinyl, 2-oxa-6-azaspiro[3.3]heptanylpyrimidinyl, 2-oxa-6-azaspiro[3.4]-octanylpyrimidinyl, 2-oxa-6-azaspiro[3.5]nonanylpyrimidinyl or 2-oxa-7-azaspiro[3.5]-nonanylpyrimidinyl, any of which groups may be optionally substituted by one or more substituents. Additionally, R¹ may represent butynyl, cyclohexylpyrimidinyl, cyclohexenylpyrimidinyl, azetidinylpyrimidinyl, 3-azabicyclo[3.1.0]hexanylpyrimidinyl or 2-azaspiro[3.3]heptanylpyrimidinyl, any of which groups may be optionally substituted by one or more substituents. Additionally, R¹ may represent pyrrolidinyl, thiazolyl, cyclohexylpyrazolyl, cyclohexylpyridinyl, cyclopropylpyrimidinyl, cyclobutylpyrimidinyl, cyclopentylpyrimidinyl, cyclohexylpyrazinyl, cyclohexylmethylpyrimidinyl, cyclohexenylpyridinyl, bicyclo[3.1.0]hexanylpyridinyl, bicyclo[3.1.0]hexanylpyrimidinyl, bicyclo[4.1.0]heptanylpyrimidinyl, bicyclo[2.2.2]octanylpyrimidinyl, tetrahydropyranylpyridinyl, oxetanylpyrimidinyl, tetrahydrofuranylpyrimidinyl, tetrahydropyranylpyrimidinyl, hexahydro-[1,2,5]thiadiazolo[2,3-a]pyrazinylpyrimidinyl, azepanylpyrimidinyl, oxazepanylpyrimidinyl, piperidinylpyrazinyl, 3-azabicyclo[3.1.0]-hexanylpyridinyl, 3-azabicyclo[3.1.0]hexanylpyridazinyl, 3-azabicyclo[3.1.1]heptanylpyrimidinyl, 3-azabicyclo[4.1.0]heptanylpyrimidinyl, 2-oxabicyclo[2.2.2]octanylpyrimidinyl, 3-azabicyclo[3.2.1]octanylpyrimidinyl, 8-azabicyclo[3.2.1]octanylpyrimidinyl, 3-oxa-8-azabicyclo[3.2.1]octanylpyrimidinyl, 3,6-diazabicyclo[3.2.2]-nonanylpyrimidinyl, 3-oxa-7-azabicyclo[3.3.1]nonanylpyrimidinyl, 5-azaspiro[2.3]-hexanylpyrimidinyl, 5-azaspiro[2.4]heptanylpyrimidinyl or 2,4,8-triazaspiro[4.5]decanylpyrimidinyl, any of which groups may be optionally substituted by one or more substituents.

Appropriately, R¹ represents ethyl, butynyl, phenyl, morpholinyl, 1,2,3,6-tetrahydropyridinyl, pyrazolyl, pyridinyl, pyrimidinyl, cyclohexylpyrimidinyl, cyclohexenylpyrimidinyl, piperazinylpyridinyl, morpholinylpyridinyl, azetidinylpyrimidinyl, pyrrolidinylpyrimidinyl, piperidinylpyrimidinyl, piperazinylpyrimidinyl, morpholinylpyrimidinyl, thiomorpholinylpyrimidinyl, diazepanylpyrimidinyl, thiadiazepanylpyrimidinyl, 3-azabicyclo[3.1.0]hexanylpyrimidinyl, 2-oxa-5-azabicyclo-[2.2.1]heptanylpyrimidinyl or 2-azaspiro[3.3]heptanylpyrimidinyl, any of which groups may be optionally substituted by one or more substituents. Additionally, R¹ may represent pyrrolidinyl, piperidinyl, isoxazolyl, thiazolyl, imidazolyl, cyclohexylpyrazolyl, cyclohexylpyridinyl, cyclopropylpyrimidinyl, cyclobutylpyrimidinyl, cyclopentylpyrimidinyl, cyclohexylpyrazinyl, cyclohexylmethylpyrimidinyl, cyclohexenylpyridinyl, bicyclo[3.1.0]hexanylpyridinyl, bicyclo[3.1.0]hexanylpyrimidinyl, bicyclo[4.1.0]-heptanylpyrimidinyl, bicyclo[2.2.2]octanylpyrimidinyl, tetrahydropyranylpyridinyl, piperidinylpyridinyl, oxetanylpyrimidinyl, tetrahydrofuranylpyrimidinyl, tetrahydropyranylpyrimidinyl, hexahydro-[1,2,5]thiadiazolo[2,3-a]pyrazinylpyrimidinyl, azepanylpyrimidinyl, oxazepanylpyrimidinyl, piperidinylpyrazinyl, 3-azabicyclo[3.1.0]-hexanylpyridinyl, 3-azabicyclo[3.1.0]hexanylpyridazinyl, 3-azabicyclo[3.1.1]heptanylpyrimidinyl, 3-azabicyclo[4.1.0]heptanylpyrimidinyl, 2-oxabicyclo[2.2.2]octanylpyrimidinyl, 3-azabicyclo[3.2.1]octanylpyrimidinyl, 8-azabicyclo[3.2.1]octanylpyrimidinyl, 3-oxa-8-azabicyclo[3.2.1]octanylpyrimidinyl, 3,6-diazabicyclo[3.2.2]-nonanylpyrimidinyl, 3-oxa-7-azabicyclo[3.3.1]nonanylpyrimidinyl, 5-azaspiro[2.3]-hexanylpyrimidinyl, 5-azaspiro[2.4]heptanylpyrimidinyl or 2,4,8-triazaspiro[4.5]decanylpyrimidinyl, any of which groups may be optionally substituted by one or more substituents.

Illustratively, R¹ represents ethyl, 1,2,3,6-tetrahydropyridinyl, pyrazolyl, pyridinyl, piperazinylpyridinyl, morpholinylpyridinyl, piperidinylpyrimidinyl, piperazinylpyrimidinyl, morpholinylpyrimidinyl, thiomorpholinylpyrimidinyl, diazepanylpyrimidinyl, thiadiazepanylpyrimidinyl or 2-oxa-5-azabicyclo[2.2.1]heptanylpyrimidinyl, any of which groups may be optionally substituted by one or more substituents.

Typical examples of optional substituents on R¹ include one, two or three substituents independently selected from halogen, cyano, cyano$(C_{1-6})$alkyl, $C_{1-6}$ alkyl, trifluoromethyl, trifluoroethyl, $C_{2-6}$ alkenyl, hydroxy, $C_{1-6}$ alkoxy, trifluoroethoxy, $C_{1-6}$ alkylsulphonyl, $(C_{1-6})$alkylsulphonyl$(C_{1-6})$alkyl, oxo, amino, di$(C_{1-6})$alkylamino, $(C_{1-6})$alkoxy$(C_{1-6})$alkylamino, N—[$(C_{1-6})$alkyl]-N-[hydroxy$(C_{1-6})$alkyl]amino, $C_{1-6}$ alkylsulphonylamino, $C_{2-6}$ alkylcarbonyl, carboxy, carboxy$(C_{1-6})$alkyl, $C_{2-6}$ alkoxycarbonyl, $C_{2-6}$ alkoxycarbonyl$(C_{1-6})$alkyl, a carboxylic acid isostere or prodrug moiety Ω as defined herein, and aminocarbonyl. Additional examples include bis[$(C_{1-6})$alkylsulphonyl]amino, N—[$(C_{1-6})$alkyl]-N-[carboxy$(C_{1-6})$alkyl]amino, carboxy$(C_{3-7})$cycloalkylamino, carboxy$(C_{3-7})$cycloalkyl$(C_{1-6})$alkylamino, —$(C_{1-6})$alkyl-Ω, in which Ω is as defined herein, and aminosulphonyl. Additional examples include halo$(C_{1-6})$alkyl, nitro$(C_{1-6})$alkyl, hydroxy$(C_{1-6})$alkyl, carboxy$(C_{3-7})$cycloalkyloxy, $C_{1-6}$ alkylthio, amino$(C_{1-6})$alkyl, $C_{1-6}$ alkylamino, $(C_{2-6})$alkylcarbonylamino$(C_{1-6})$alkyl, N—[$(C_{1-6})$alkyl]-N—[$(C_{1-6})$alkylsulphonyl]-amino, formyl, $(C_{2-6})$alkylcarbonyloxy$(C_{1-6})$alkyl, morpholinyl$(C_{1-6})$alkoxycarbonyl, $C_{2-6}$ alkoxycarbonylmethylidenyl and $C_{1-6}$ alkoxyaminocarbonyl.

Particular examples of optional substituents on $R^1$ include one, two or three substituents independently selected from $C_{1-6}$ alkyl, hydroxy, $C_{1-6}$ alkoxy, $C_{1-6}$ alkylsulphonyl, oxo, amino, N—[$(C_{1-6})$alkyl]-N-[carboxy$(C_{1-6})$alkyl]amino, carboxy-$(C_{3-7})$cycloalkylamino, carboxy$(C_{3-7})$cycloalkyl$(C_{1-6})$alkylamino, $C_{1-6}$ alkylsulphonylamino, bis[$(C_{1-6})$alkylsulphonyl]amino, $C_{2-6}$ alkylcarbonyl, carboxy, carboxy$(C_{1-6})$alkyl, $C_{2-6}$ alkoxycarbonyl, $C_{2-6}$ alkoxycarbonyl$(C_{1-6})$alkyl, a carboxylic acid isostere or prodrug moiety Ω as defined herein, —$(C_{1-6})$alkyl-Ω, and aminosulphonyl. Additional examples include halogen, halo$(C_{1-6})$alkyl, cyano, nitro$(C_{1-6})$alkyl, trifluoromethyl, hydroxy$(C_{1-6})$-alkyl, carboxy$(C_{3-7})$cycloalkyloxy, $C_{1-6}$ alkylthio, amino$(C_{1-6})$alkyl, $C_{1-6}$ alkylamino, $(C_{2-6})$alkylcarbonylamino$(C_{1-6})$alkyl, N—[$(C_{1-6})$alkyl]-N—[$(C_{1-6})$alkylsulphonyl]amino, formyl, $(C_{2-6})$alkylcarbonyloxy$(C_{1-6})$alkyl, morpholinyl$(C_{1-6})$alkoxycarbonyl, $C_{2-6}$ alkoxycarbonylmethylidenyl and $C_{1-6}$ alkoxyaminocarbonyl.

Suitable examples of optional substituents on $R^1$ include one, two or three substituents independently selected from $C_{1-6}$ alkyl, hydroxy, $C_{1-6}$ alkoxy, oxo, amino, $C_{1-6}$ alkylsulphonylamino, carboxy and $C_{2-6}$ alkoxycarbonyl.

Typical examples of particular substituents on $R^1$ include one, two or three substituents independently selected from fluoro, chloro, cyano, cyanoethyl, methyl, trifluoromethyl, trifluoroethyl, ethenyl, hydroxy, methoxy, isopropoxy, trifluoromethoxy, methylsulphonyl, methylsulphonylethyl, oxo, amino, dimethylamino, methoxyethylamino, N-(hydroxyethyl)-N-(methyl)amino, methylsulphonylamino, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolyl, aminocarbonyl and methylsulphonylaminocarbonyl. Additional examples include bis(methylsulphonyl)amino, N-(carboxyethyl)-N-(ethyl)amino, carboxycyclopentylamino, carboxycyclopropylmethylamino, methoxycarbonylmethyl, tetrazolylmethyl, aminosulphonyl and acetylaminosulphonyl. Additional examples include fluoromethyl, fluoroisopropyl, nitromethyl, ethyl, isopropyl, hydroxymethyl, hydroxyisopropyl, carboxycyclobutyloxy, methylthio, aminomethyl, aminoisopropyl, methylamino, acetylaminomethyl, N-methyl-N-(methylsulphonyl)amino, formyl, acetoxyisopropyl, n-butoxycarbonyl, morpholinylethoxycarbonyl, ethoxycarbonylmethylidenyl, hydroxyoxadiazolyl and methoxyaminocarbonyl.

Representative examples of particular substituents on $R^1$ include one, two or three substituents independently selected from methyl, hydroxy, methoxy, methylsulphonyl, oxo, amino, methylsulphonylamino, bis(methylsulphonyl)amino, N-(carboxyethyl)-N-(ethyl)amino, carboxycyclopentylamino, carboxycyclopropylmethylamino, acetyl, carboxy, carboxyethyl, methoxycarbonyl, ethoxycarbonyl, tert-butoxycarbonyl, methoxycarbonylmethyl, ethoxycarbonylethyl, tetrazolyl, tetrazolylmethyl, aminosulphonyl and acetylaminosulphonyl. Additional examples include fluoro, chloro, fluoromethyl, fluoroisopropyl, cyano, nitromethyl, ethyl, isopropyl, trifluoromethyl, hydroxymethyl, hydroxyisopropyl, carboxycyclobutyloxy, methylthio, aminomethyl, aminoisopropyl, methylamino, acetylaminomethyl, N-methyl-N-(methylsulphonyl)amino, formyl, acetoxyisopropyl, carboxymethyl, n-butoxycarbonyl, morpholinylethoxycarbonyl, ethoxycarbonylmethylidenyl, hydroxyoxadiazolyl, methoxyaminocarbonyl and methylsulphonylaminocarbonyl.

Suitable examples of particular substituents on $R^1$ include one, two or three substituents independently selected from methyl, hydroxy, methoxy, oxo, amino, methylsulphonylamino, carboxy, methoxycarbonyl and tert-butoxycarbonyl.

In a particular embodiment, $R^1$ is substituted by hydroxy $(C_{1-6})$alkyl. In one aspect of that embodiment, $R^1$ is substituted by hydroxyisopropyl, especially 2-hydroxyprop-2-yl.

Selected values of $R^1$ include hydrogen, bromo, cyano, —$CO_2R^d$, methoxycarbonylethyl, ethoxycarbonylethyl, chlorophenyl, hydroxyphenyl, acetylphenyl, aminocarbonylphenyl, oxopiperidinyl, methylsulphonylpiperazinyl, morpholinyl, tert-butoxycarbonyl-1,2,3,6-tetrahydropyridinyl, benzofuryl, thienyl, indolyl, pyrazolyl, methylpyrazolyl, dimethylpyrazolyl, methylindazolyl, dimethylisoxazolyl, methylimidazolyl, pyridinyl, fluoropyridinyl, cyanopyridinyl, methylpyridinyl, (cyano)(methyl)pyridinyl, dimethylpyridinyl, trifluoromethylpyridinyl, ethenylpyridinyl, methoxypyridinyl, (methoxy)-(methyl)pyridinyl, isopropoxypyridinyl, trifluoroethoxypyridinyl, (methyl)(trifluoroethoxy)pyridinyl, oxopyridinyl, (methyl)(oxo)pyridinyl, (dimethyl)(oxo)pyridinyl, aminopyridinyl, dimethylaminopyridinyl, methoxyethylaminopyridinyl, N-(hydroxyethyl)-N-(methyl)aminopyridinyl, methylsulphonylaminopyridinyl, carboxypyridinyl, quinolinyl, hydroxypyridazinyl, pyrimidinyl, methoxypyrimidinyl, oxopyrimidinyl, aminopyrimidinyl, dimethylaminopyrimidinyl, methoxyethylaminopyrimidinyl, hydroxypyrazinyl, pyrrolidinylmethylphenyl, piperazinylmethylphenyl, pyridinylpiperazinyl, pyrrolidinylpyridinyl, hydroxypyrrolidinylpyridinyl, piperidinylpyridinyl, acetylpiperidinylpyridinyl, piperazinylpyridinyl, (methyl)(piperazinyl)-pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)-(methyl)pyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, hydroxypyrrolidinylpyrimidinyl, carboxypiperidinylpyrimidinyl, piperazinylpyrimidinyl, methylsulphonylpiperazinylpyrimidinyl, oxopiperazinylpyrimidinyl, tert-butoxycarbonylpiperazinylpyrimidinyl, morpholinylpyrimidinyl, thiomorpholinylpyrimidinyl, dioxothiomorpholinylpyrimidinyl, oxodiazepanylpyrimidinyl, dioxothiadiazepanylpyrimidinyl, morpholinylmethylthienyl, morpholinylethylpyrazolyl, 2-oxa-5-azabicyclo[2.2.1]heptanylpyrimidinyl, 2-oxa-6-azaspiro[3.3]heptanylpyrimidinyl, 2-oxa-6-azaspiro[3.4]octanylpyrimidinyl, 2-oxa-6-azaspiro[3.5]

nonanylpyrimidinyl and 2-oxa-7-azaspiro[3.5]nonanylpyrimidinyl. Additional values include hydroxybutynyl, aminosulphonylphenyl, acetylaminosulphonylphenyl, methylsulphonyl-1,2,3,6-tetrahydropyridinyl, acetyl-1,2,3,6-tetrahydropyridinyl, methoxycarbonylmethyl-1,2,3,6-tetrahydropyridinyl, [bis(methylsulphonyl)amino]pyridinyl, N-(carboxyethyl)-N-(methyl)aminopyrimidinyl, carboxycyclopentylaminopyrimidinyl, carboxycyclopropylmethylaminopyrimidinyl, ethoxycarbonylethylpyrimidinyl, carboxycyclohexylpyrimidinyl, carboxycyclohexenylpyrimidinyl, ethoxycarbonylcyclohexenylpyrimidinyl, carboxyazetidinylpyrimidinyl, carboxypyrrolidinylpyrimidinyl, (carboxy)(methyl)piperidinylpyrimidinyl, ethoxycarbonylpiperidinylpyrimidinyl, (methoxycarbonyl)(methyl)piperidinylpyrimidinyl, (ethoxycarbonyl)(methyl)piperidinylpyrimidinyl, tetrazolylpiperidinylpyrimidinyl, carboxyethylpiperazinylpyrimidinyl, tetrazolylmethylpiperazinylpyrimidinyl, carboxymorpholinylpyrimidinyl, carboxy-3-azabicyclo[3.1.0]hexanylpyrimidinyl, ethoxycarbonyl-3-azabicyclo[3.1.0]hexanylpyrimidinyl and carboxy-2-azaspiro[3.3]heptanylpyrimidinyl. Additional values include methylsulphonylphenyl, aminomethylphenyl, aminoisopropylphenyl, acetylaminomethylphenyl, methoxycarbonylphenyl, (methoxycarbonyl)(methyl)pyrrolidinyl, ethoxycarbonylpiperidinyl, (methyl)[N-methyl-N-(methylsulfonyl)]pyrazolyl, hydroxyisopropylthiazolyl, dimethylimidazolyl, hydroxyisopropylpyridinyl, methylsulphonylpyridinyl, methylaminopyridinyl, fluoroisopropylpyrimidinyl, hydroxyisopropylpyrimidinyl, carboxycyclobutyloxypyrimidinyl, methylthiopyrimidinyl, methylsulphonylpyrimidinyl, acetoxyisopropylpyrimidinyl, hydroxyisopropylpyrazinyl, carboxycyclohexylpyrazolyl, carboxycyclohexylpyridinyl, fluoromethylcyclopropylpyrimidinyl, acetylaminomethylcyclopropylpyrimidinyl, hydroxycyclobutylpyrimidinyl, carboxycyclopentylpyrimidinyl, (carboxy)(methyl)cyclohexylpyrimidinyl, (carboxy)(hydroxy)cyclohexylpyrimidinyl, carboxymethylcyclohexylpyrimidinyl, ethoxycarbonylcyclohexylpyrimidinyl, (methoxycarbonyl)(methyl)cyclohexylpyrimidinyl, (ethoxycarbonyl)(methyl)cyclohexylpyrimidinyl, carboxycyclohexylpyrazinyl, carboxycyclohexylmethylpyrimidinyl, carboxycyclohexenylpyrimidinyl, carboxybicyclo[3.1.0]hexanylpyrimidinyl, carboxybicyclo-[3.1.0]hexanylpyrimidinyl, ethoxycarbonylbicyclo[3.1.0]hexanylpyrimidinyl, carboxybicyclo[4.1.0]heptanylpyrimidinyl, carboxybicyclo[2.2.2]octanylpyrimidinyl, hydroxytetrahydropyranylpyridinyl, (carboxy)(methyl)piperidinylpyridinyl, [(carboxy)-(methyl)piperidinyl](fluoro)pyridinyl, [(carboxy)(methyl)piperidinyl](chloro)pyridinyl, fluorooxetanylpyrimidinyl, hydroxyoxetanylpyrimidinyl, hydroxyazetidinylpyrimidinyl, (hydroxy)(methyl)azetidinylpyrimidinyl, (tert-butoxycarbonyl)(hydroxy)azetidinylpyrimidinyl, tetrazolylazetidinylpyrimidinyl, hydroxytetrahydrofuranylpyrimidinyl, (carboxy)(methyl)pyrrolidinylpyrimidinyl, carboxymethylpyrrolidinylpyrimidinyl, ethoxycarbonylpyrrolidinylpyrimidinyl, fluorotetrahydropyranylpyrimidinyl, hydroxytetrahydropyranylpyrimidinyl, difluoropiperidinylpyrimidinyl, (cyano)(methyl)-piperidinylpyrimidinyl, (hydroxy)(nitromethyl)piperidinylpyrimidinyl, (hydroxy)-(methyl)piperidinylpyrimidinyl, (hydroxy)(trifluoromethyl)piperidinylpyrimidinyl, (hydroxymethyl)(methyl)piperidinylpyrimidinyl, methylsulphonylpiperidinylpyrimidinyl, oxopiperidinylpyrimidinyl, (formyl)(methyl)piperidinylpyrimidinyl, (carboxy)(fluoro)-piperidinylpyrimidinyl, (carboxy)(ethyl)piperidinylpyrimidinyl, (carboxy)-(trifluoromethyl)piperidinylpyrimidinyl, (carboxy)(hydroxy)piperidinylpyrimidinyl, (carboxy)(hydroxymethyl)piperidinylpyrimidinyl, (carboxy)(methoxy)piperidinylpyrimidinyl, (amino)(carboxy)piperidinylpyrimidinyl, carboxymethylpiperidinylpyrimidinyl, methoxycarbonylpiperidinylpyrimidinyl, (ethoxycarbonyl)(fluoro)-piperidinylpyrimidinyl, (ethyl)(methoxycarbonyl)piperidinylpyrimidinyl, (isopropyl)-(methoxycarbonyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinylpyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, hydroxyoxadiazolylpiperidinylpyrimidinyl, methoxyaminocarbonylpiperidinylpyrimidinyl, methylsulphonylaminocarbonylpiperidinylpyrimidinyl, aminosulphonylpiperidinylpyrimidinyl, acetylaminosulphonylpiperidinylpyrimidinyl, carboxypiperazinylpyrimidinyl, trioxohexahydro-[1,2,5]thiadiazolo[2,3-a]pyrazinylpyrimidinyl, dimethylmorpholinylpyrimidinyl, hydroxymethylmorpholinylpyrimidinyl, (carboxy)(methyl)morpholinylpyrimidinyl, carboxymethylmorpholinylpyrimidinyl, carboxyazepanylpyrimidinyl, carboxyoxazepanylpyrimidinyl, (oxodiazepanyl)-(trifluoromethyl)pyrimidinyl, (oxodiazepanyl)(methoxy)pyrimidinyl, (methyl)(oxo)-diazepanylpyrimidinyl, hydroxyoxetanylpyrazinyl, (carboxy)(methyl)piperidinylpyrazinyl, (ethoxycarbonyl)(methyl)piperidinylpyrazinyl, carboxy-3-azabicyclo[3.1.0]-hexanylpyridinyl, carboxy-3-azabicyclo[4.1.0]heptanylpyridinyl, carboxy-3-azabicyclo-[3.1.0]hexanylpyridazinyl, (carboxy)(methyl)-3-azabicyclo[3.1.0]hexanylpyrimidinyl, methoxycarbonyl-3-azabicyclo[3.1.0]hexanylpyrimidinyl, carboxy-2-oxa-5-azabicyclo-[2.2.1]heptanylpyrimidinyl, carboxy-3-azabicyclo[3.1.1]heptanylpyrimidinyl, carboxy-3-azabicyclo[4.1.0]heptanylpyrimidinyl, methoxycarbonyl-3-azabicyclo[4.1.0]heptanylpyrimidinyl, ethoxycarbonyl-3-azabicyclo[4.1.0]heptanylpyrimidinyl, (hydroxy)(methyl)-(oxo)-2-oxabicyclo[2.2.2]octanylpyrimidinyl, carboxy-3-azabicyclo[3.2.1]octanylpyrimidinyl, methoxycarbonyl-3-azabicyclo[3.2.1]octanylpyrimidinyl, oxo-8-azabicyclo-[3.2.1]octanylpyrimidinyl, ethoxycarbonylmethylidenyl-8-azabicyclo[3.2.1]octanylpyrimidinyl, 3-oxa-8-azabicyclo[3.2.1]octanylpyrimidinyl, oxo-3,6-diazabicyclo[3.2.2]-nonanylpyrimidinyl, carboxy-3-oxa-7-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro[2.4]heptanylpyrimidinyl and (dioxo)(methyl)-2,4,8-triazaspiro[4.5]-decanylpyrimidinyl.

Definitive values of $R^1$ include hydrogen, bromo, ethoxycarbonylethyl, hydroxybutynyl, methylsulfonylphenyl, aminomethylphenyl, aminoisopropylphenyl, acetylaminomethylphenyl, methoxycarbonylphenyl, aminosulphonylphenyl, acetylaminosulphonylphenyl, (methoxycarbonyl)(methyl)pyrrolidinyl, ethoxycarbonylpiperidinyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, methylpyrazolyl, (methyl)[N-methyl-N-(methylsulfonyl)]pyrazolyl, dimethylisoxazolyl, hydroxyisopropylthiazolyl, dimethylimidazolyl, hydroxyisopropylpyridinyl, methoxypyridinyl, (methoxy)(methyl)pyridinyl, methylsulphonylpyridinyl, oxopyridinyl, (methyl)

(oxo)pyridinyl, aminopyridinyl, methylaminopyridinyl, methylsulphonylaminopyridinyl, [bis(methylsulphonyl)amino]-pyridinyl, carboxypyridinyl, fluoroisopropylpyrimidinyl, hydroxyisopropylpyrimidinyl, carboxycyclobutyloxypyrimidinyl, methylthiopyrimidinyl, methylsulphonylpyrimidinyl, N-(carboxyethyl)-N-(methyl)aminopyrimidinyl, carboxycyclopentylaminopyrimidinyl, carboxycyclopropylmethylaminopyrimidinyl, acetoxyisopropylpyrimidinyl, ethoxycarbonylethylpyrimidinyl, hydroxyisopropylpyrazinyl, carboxycyclohexylpyrazolyl, carboxycyclohexylpyridinyl, fluoromethylcyclopropylpyrimidinyl, acetyl-aminomethylcyclopropylpyrimidinyl, hydroxycyclobutylpyrimidinyl, carboxycyclopentylpyrimidinyl, carboxycyclohexylpyrimidinyl, (carboxy)(methyl)cyclohexylpyrimidinyl, (carboxy)(hydroxy)cyclohexylpyrimidinyl, carboxymethylcyclohexylpyrimidinyl, ethoxycarbonylcyclohexylpyrimidinyl, (methoxycarbonyl)(methyl)-cyclohexylpyrimidinyl, (ethoxycarbonyl)(methyl)cyclohexylpyrimidinyl, carboxycyclohexylpyrazinyl, carboxycyclohexylmethylpyrimidinyl, carboxycyclohexenylpyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexanylpyrimidinyl, ethoxycarbonylbicyclo[3.1.0]hexanylpyrimidinyl, carboxybicyclo[4.1.0]heptanylpyrimidinyl, carboxybicyclo[2.2.2]octanylpyrimidinyl, hydroxytetrahydropyranylpyridinyl, piperidinylpyridinyl, (carboxy)(methyl)piperidinylpyridinyl, [(carboxy)-(methyl)piperidinyl](fluoro)pyridinyl, [(carboxy)(methyl)piperidinyl](chloro)pyridinyl, piperazinylpyridinyl, morpholinylpyridinyl, fluorooxetanylpyrimidinyl, hydroxyoxetanylpyrimidinyl, hydroxyazetidinylpyrimidinyl, (hydroxy)(methyl)azetidinylpyrimidinyl, carboxyazetidinylpyrimidinyl, (tert-butoxycarbonyl)(hydroxy)azetidinylpyrimidinyl, tetrazolylazetidinylpyrimidinyl, hydroxytetrahydrofuranylpyrimidinyl, carboxypyrrolidinylpyrimidinyl, (carboxy)(methyl)pyrrolidinylpyrimidinyl, carboxymethylpyrrolidinylpyrimidinyl, ethoxycarbonylpyrrolidinylpyrimidinyl, fluorotetrahydropyranylpyrimidinyl, hydroxytetrahydropyranylpyrimidinyl, difluoropiperidinylpyrimidinyl, (cyano)(methyl)piperidinylpyrimidinyl, (hydroxy)(nitromethyl)piperidinylpyrimidinyl, (hydroxy)(methyl)piperidinylpyrimidinyl, (hydroxy)(trifluoromethyl)-piperidinylpyrimidinyl, (hydroxymethyl)(methyl)piperidinylpyrimidinyl, methylsulphonylpiperidinylpyrimidinyl, oxopiperidinylpyrimidinyl, (formyl)(methyl)-piperidinylpyrimidinyl, carboxypiperidinylpyrimidinyl, (carboxy)(fluoro)piperidinylpyrimidinyl, (carboxy)(methyl)piperidinylpyrimidinyl, (carboxy)(ethyl)piperidinylpyrimidinyl, (carboxy)(trifluoromethyl)piperidinylpyrimidinyl, (carboxy)(hydroxy)-piperidinylpyrimidinyl, (carboxy)(hydroxymethyl)piperidinylpyrimidinyl, (carboxy)-(methoxy)piperidinylpyrimidinyl, (amino)(carboxy)piperidinylpyrimidinyl, carboxymethylpiperidinylpyrimidinyl, methoxycarbonylpiperidinylpyrimidinyl, ethoxycarbonylpiperidinylpyrimidinyl, (ethoxycarbonyl)(fluoro)piperidinylpyrimidinyl, (methoxycarbonyl)(methyl)piperidinylpyrimidinyl, (ethyl)(methoxycarbonyl)piperidinylpyrimidinyl, (isopropyl)(methoxycarbonyl)piperidinylpyrimidinyl, (ethoxycarbonyl)-(methyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinylpyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, hydroxyoxadiazolylpiperidinylpyrimidinyl, tetrazolylpiperidinylpyrimidinyl, methoxyaminocarbonylpiperidinylpyrimidinyl, methylsulphonylaminocarbonylpiperidinylpyrimidinyl, aminosulphonylpiperidinylpyrimidinyl, acetylaminosulphonylpiperidinylpyrimidinyl, piperazinylpyrimidinyl, oxopiperazinylpyrimidinyl, methylsulfonylpiperazinylpyrimidinyl, carboxypiperazinylpyrimidinyl, carboxyethylpiperazinylpyrimidinyl, tert-butoxycarbonylpiperazinylpyrimidinyl, tetrazolylmethyl-piperazinylpyridinyl, trioxohexahydro-[1,2,5]thiadiazolo[2,3-a]pyrazinylpyrimidinyl, morpholinylpyrimidinyl, dimethylmorpholinylpyrimidinyl, hydroxymethylmorpholinylpyrimidinyl, carboxymorpholinylpyrimidinyl, (carboxy)(methyl)morpholinylpyrimidinyl, carboxymethylmorpholinylpyrimidinyl, dioxothiomorpholinylpyrimidinyl, carboxyazepanylpyrimidinyl, carboxyoxazepanylpyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxothiadiazepanylpyrimidinyl, hydroxyoxetanylpyrazinyl, (carboxy)(methyl)piperidinylpyrazinyl, (ethoxycarbonyl)(methyl)piperidinylpyrazinyl, carboxy-3-azabicyclo[3.1.0]hexanylpyridinyl, carboxy-3-azabicyclo[4.1.0]-heptanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanylpyrimidinyl, 2-oxa-5-azabicyclo[2.2.1]heptanylpyrimidinyl, carboxy-2-oxa-5-azabicyclo[2.2.1]heptanylpyrimidinyl, carboxy-3-azabicyclo[3.1.1]-heptanylpyrimidinyl, carboxy-3-azabicyclo[4.1.0]heptanylpyrimidinyl, methoxycarbonyl-3-azabicyclo[4.1.0]heptanylpyrimidinyl, ethoxycarbonyl-3-azabicyclo[4.1.0]heptanylpyrimidinyl, (hydroxy)(methyl)(oxo)-2-oxabicyclo[2.2.2]octanylpyrimidinyl, carboxy-3-azabicyclo[3.2.1]octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8-azabicyclo[3.2.1]octanylpyrimidinyl, 3-oxa-8-azabicyclo[3.2.1]octanylpyrimidinyl, oxo-3,6-diazabicyclo[3.2.2]nonanylpyrimidinyl, carboxy-3-oxa-7-azabicyclo[3.3.1]nonanylpyrimidinyl, carboxy-5-azaspiro[2.3]hexanylpyrimidinyl, (carboxy)(methyl)-5-azaspiro-[2.3]hexanylpyrimidinyl, carboxy-5-azaspiro[2.4]heptanylpyrimidinyl, carboxy-2-azaspiro[3.3]heptanylpyrimidinyl and (dioxo)(methyl)-2,4,8-triazaspiro[4.5]decanylpyrimidinyl.

Particular values of $R^1$ include ethoxycarbonylethyl, hydroxybutynyl, aminosulphonylphenyl, acetylaminosulphonylphenyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, methylpyrazolyl, methoxypyridinyl, (methoxy)(methyl)pyridinyl, oxopyridinyl, (methyl)(oxo)-pyridinyl, aminopyridinyl, methylsulphonylaminopyridinyl, [bis(methylsulphonyl)-amino]pyridinyl, N-(carboxyethyl)-N-(methyl)aminopyrimidinyl, carboxycyclopentylaminopyrimidinyl, carboxycyclopropylmethylaminopyrimidinyl, ethoxycarbonylethylpyrimidinyl, carboxycyclohexylpyrimidinyl, carboxycyclohexenylpyrimidinyl, ethoxycarbonylcyclohexenylpyrimidinyl, piperazinylpyridinyl, morpholinylpyridinyl, carboxyazetidinylpyrimidinyl, carboxypyrrolidinylpyrimidinyl, carboxypiperidinylpyrimidinyl, (carboxy)(methyl)piperidinylpyrimidinyl, ethoxycarbonylpiperidinylpyrimidinyl, (methoxycarbonyl)(methyl)piperidinylpyrimidinyl, (ethoxycarbonyl)-(methyl)piperidinylpyrimidinyl, tetrazolylpiperidinylpyrimidinyl, piperazinylpyrimidinyl, oxopiperazinylpyrimidinyl, carboxyethylpiperazinylpyrimidinyl, tetrazolylmethyl-piperazinylpyridinyl, morpholinylpyrimidinyl, carboxymorpholinylpyrimidinyl, dioxothiomorpholinylpyrimidinyl, oxodiazepanylpyrimidinyl, dioxothiadiazepanylpyrimidinyl, carboxy-3-azabicyclo[3.1.0]hexanylpyrimidinyl, ethoxycarbonyl-3-azabicyclo[3.1.0]hexanylpyrimidinyl, 2-oxa-5-azabicyclo[2.2.1]heptanylpyrimidinyl and carboxy-2-azaspiro[3.3]heptanylpyrimidinyl.

Illustrative values of $R^1$ include methoxycarbonylethyl, tert-butoxycarbonyl-1,2,3,6-tetrahydropyridinyl, methylpyrazolyl, methoxypyridinyl, (methoxy)(methyl)-pyridinyl, oxopyridinyl, (methyl)(oxo)pyridinyl, aminopyridinyl, methylsulphonylaminopyridinyl, piperazinylpyridinyl, morpholinylpyridinyl, carboxypiperidinylpyrimidinyl, piperazinylpyrimidinyl, oxopiperazinylpyrimidinyl, morpholinylpyrimidinyl, dioxothiomorpholinylpyrimidinyl, oxodiazepanylpyrimidinyl, dioxothiadiazepanylpyrimidinyl and 2-oxa-5-azabicyclo[2.2.1]heptanylpyrimidinyl.

Typically, $R^2$ represents hydrogen, halogen, trifluoromethyl or optionally substituted $C_{1-6}$ alkyl. Additionally, $R^2$ may represent —$OR^a$.

Typical examples of optional substituents on $R^2$ include $C_{2-6}$ alkoxycarbonyl.

Typical examples of particular substituents on $R^2$ include ethoxycarbonyl.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents trifluoromethyl. In a fourth embodiment, $R^2$ represents optionally substituted $C_{1-6}$ alkyl. In one aspect of that embodiment, $R^2$ represents unsubstituted methyl. In another aspect of that embodiment, $R^2$ represents unsubstituted ethyl. In a further aspect of that embodiment, $R^2$ represents monosubstituted methyl or monosubstituted ethyl. In a fifth embodiment, $R^2$ represents —$OR^a$.

Typical values of $R^2$ include hydrogen, fluoro, trifluoromethyl, methyl and ethoxycarbonylethyl. Additional values include chloro and —$OR^a$.

Suitable values of $R^2$ include hydrogen, fluoro, trifluoromethyl and methyl. Additional values include chloro and —$OR^a$.

Typically, $R^3$ represents hydrogen, halogen or $C_{1-6}$ alkyl.

In a first embodiment, $R^3$ represents hydrogen. In a second embodiment, $R^3$ represents halogen. In one aspect of that embodiment, $R^3$ represents fluoro. In a third embodiment, $R^3$ represents $C_{1-6}$ alkyl. In one aspect of that embodiment, $R^3$ represents methyl. In another aspect of that embodiment, $R^3$ represents ethyl.

In a particular embodiment, $R^4$ represents hydrogen.

Suitably, $R^5$ represents hydrogen or methyl.

In a first embodiment, $R^5$ represents hydrogen. In a second embodiment, $R^5$ represents $C_{1-6}$ alkyl, especially methyl.

Suitably, $R^6$ represents hydrogen, methyl or ethyl.

In a first embodiment, $R^6$ represents hydrogen. In a second embodiment, $R^6$ represents $C_{1-6}$ alkyl, especially methyl or ethyl. In one aspect of that embodiment, $R^6$ represents methyl. In another aspect of that embodiment, $R^6$ represents ethyl.

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolylpropyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$)alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylaminoethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl.

Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, amino azetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxooxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

One sub-class of compounds according to the invention is represented by the compounds of formula (IIA) and N-oxides thereof, and pharmaceutically acceptable salts and solvates thereof, and glucuronide derivatives thereof, and co-crystals thereof:

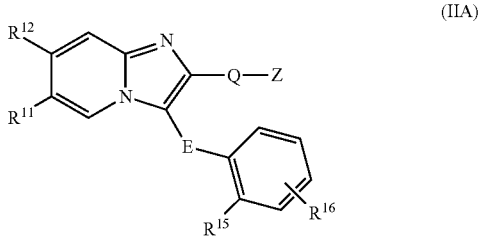

(IIA)

wherein $R^{11}$ represents halogen or cyano; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl $(C_{3-7})$heterocycloalkyl-, $(C_{3-7})$cycloalkyl-heteroaryl-, $(C_{3-7})$cycloalkyl-$(C_{1-6})$alkyl-heteroaryl-, $(C_{4-7})$cycloalkenyl-heteroaryl-, $(C_{4-9})$ bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents;

$R^{12}$ represents hydrogen, halogen, trifluoromethyl or optionally substituted $C_{1-6}$ alkyl;

$R^{15}$ and $R^{16}$ independently represent hydrogen, halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di$(C_{1-6})$alkylamino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di$(C_{1-6})$alkylaminocarbonyl, aminosulfonyl, $C_{1-6}$ alkylaminosulfonyl or di$(C_{1-6})$alkylaminosulfonyl; and E, Q and Z are as defined above.

The present invention also provides a compound of formula (IIA) as depicted above or an N-oxide thereof, or a pharmaceutically acceptable salt or solvate thereof, or a co-crystal thereof, wherein $R^{11}$ represents halogen or cyano; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl $(C_{3-7})$heterocycloalkyl-, $(C_{3-7})$cycloalkyl-heteroaryl-, $(C_{4-7})$cycloalkenyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents; and E, Q, Z, $R^{12}$, $R^{15}$ and $R^{16}$ are as defined above.

The present invention also provides a compound of formula (IIA) as depicted above or an N-oxide thereof, or a pharmaceutically acceptable salt or solvate thereof, or a co-crystal thereof, wherein $R^{11}$ represents halogen or cyano; or $C_{1-6}$ alkyl, aryl, $C_{3-7}$ heterocycloalkyl, $C_{3-7}$ heterocycloalkenyl, heteroaryl, $(C_{3-7})$ heterocycloalkyl$(C_{1-6})$alkyl-aryl-, heteroaryl-$(C_{3-7})$heterocycloalkyl-, $(C_{4-7})$cycloalkenyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$ heterobicycloalkyl-heteroaryl- or $(C_{4-9})$ spiroheterocycloalkyl-heteroaryl-, any of which groups may be optionally substituted by one or more substituents; and E, Q, Z, $R^{12}$, $R^{15}$ and $R^{16}$ are as defined above.

Aptly, $R^{11}$ represents halogen or cyano; or $C_{1-6}$ alkyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl-$(C_{3-7})$ heterocycloalkyl-, $(C_{3-7})$heterocycloalkyl-heteroaryl-, $(C_{3-7})$ heterocycloalkyl-$(C_{1-6})$alkyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents. Additionally, $R^{11}$ may represent $C_{2-6}$ alkynyl, $(C_{3-7})$cycloalkyl-heteroaryl- or $(C_{4-7})$cycloalkenyl-heteroaryl-, any of which groups may be optionally substituted by one or more substituents. Additionally, $R^{11}$ may represent $(C_{3-7})$cycloalkyl$(C_{1-6})$alkyl-heteroaryl- or $(C_{4-9})$ bicycloalkyl-heteroaryl-, either of which groups may be optionally substituted by one or more substituents.

Examples of optional substituents which may be present on $R^{11}$ include one, two or three substituents independently selected from halogen, cyano, cyano$(C_{1-6})$alkyl, nitro, $C_{1-6}$ alkyl, trifluoromethyl, trifluoroethyl, $C_{2-6}$ alkenyl, hydroxy, $C_{1-6}$ alkoxy, difluoromethoxy, trifluoromethoxy, trifluoroethoxy, $C_{1-3}$ alkylenedioxy, $C_{1-6}$ alkoxy$(C_{1-6})$alkyl, $C_{1-6}$ alkylthio, $C_{1-6}$ alkylsulphonyl, $(C_{1-6})$alkylsulphonyl$(C_{1-6})$alkyl, oxo, amino, $C_{1-6}$ alkylamino, di$(C_{1-6})$alkylamino, $(C_{1-6})$ alkoxy$(C_{1-6})$alkylamino, N—[$(C_{1-6})$alkyl]-N-[hydroxy$(C_{1-6})$alkyl]-amino, $C_{2-6}$ alkylcarbonylamino, $C_{2-6}$ alkoxycarbonylamino, $C_{1-6}$ alkylaminocarbonylamino, $C_{1-6}$ alkylsulphonylamino, formyl, $C_{2-6}$ alkylcarbonyl, carboxy, carboxy$(C_{1-6})$alkyl, $C_{2-6}$ alkoxycarbonyl, $C_{2-6}$ alkoxycarbonyl$(C_{1-6})$alkyl, a carboxylic acid isostere or prodrug moiety Ω as defined herein, aminocarbonyl, $C_{1-6}$ alkylaminocarbonyl, di$(C_{1-6})$alkylaminocarbonyl, aminosulphonyl and di$(C_{1-6})$ alkylaminosulphonyl. Additional examples include bis[$(C_{1-6})$alkylsulphonyl]amino, N—[$(C_{1-6})$alkyl]-N-[carboxy$(C_{1-6})$alkyl]amino, carboxy-$(C_{3-7})$cycloalkylamino, carboxy$(C_{3-7})$cycloalkyl$(C_{1-6})$alkylamino and —$(C_{1-6})$ alkyl-Ω, in which Ω is as defined herein. Additional examples include halo$(C_{1-6})$alkyl, nitro$(C_{1-6})$-alkyl, difluoromethyl, difluoroethyl, hydroxy$(C_{1-6})$alkyl, carboxy$(C_{3-7})$cycloalkyloxy, $C_{1-6}$ alkylsulphinyl, amino$(C_{1-6})$alkyl, hydroxy$(C_{1-6})$ alkylamino, $C_{1-6}$ alkoxyamino, [$(C_{1-6})$-alkoxy](hydroxy)$(C_{1-6})$alkylamino, [$(C_{1-6})$alkylthio](hydroxy)$(C_{1-6})$ alkylamino, di$(C_{1-6})$-alkylamino$(C_{1-6})$alkylamino, N-[di$(C_{1-6})$alkylamino$(C_{1-6})$alkyl]-N-[hydroxy$(C_{1-6})$alkyl]-amino, hydroxy$(C_{1-6})$alkyl$(C_{3-7})$cycloalkylamino, (hydroxy) [$(C_{3-7})$cycloalkyl$(C_{1-6})$alkyl]-amino, $(C_{3-7})$heterocycloalkyl $(C_{1-6})$alkylamino, oxo$(C_{3-7})$heterocycloalkyl$(C_{1-6})$ alkylamino, $(C_{1-6})$alkylheteroarylamino, heteroaryl$(C_{1-6})$ alkylamino, $(C_{1-6})$alkylheteroaryl$(C_{1-6})$alkylamino, N—[$(C_{1-6})$alkyl]-N—[$(C_{2-6})$alkylcarbonyl]amino, $(C_{2-6})$ alkylcarbonylamino$(C_{1-6})$alkyl, $C_{3-6}$ alkenylcarbonylamino, bis[$(C_{3-6})$alkenylcarbonyl]amino, N—[$(C_{1-6})$alkyl]-N—[$(C_{3-7})$-cycloalkylcarbonyl]amino, $C_{2-6}$ alkoxycarbonyl $(C_{1-6})$alkylamino, N—[$(C_{1-6})$alkyl]-N—[$(C_{1-6})$-alkylsulphonyl]amino, $C_{1-6}$ alkylsulphonylamino($C_{1-6}$)alkyl, ($C_{3-7}$) cycloalkylcarbonyl, phenylcarbonyl, ($C_{2-6}$)alkylcarbonyloxy ($C_{1-6}$)alkyl, morpholinyl($C_{1-6}$)alkoxycarbonyl, $C_{2-6}$ alkoxycarbonylmethylidenyl, hydroxy($C_{1-6}$)alkylaminocarbonyl, aminocarbonyl($C_{1-6}$)alkyl and $C_{1-6}$ alkoxyaminocarbonyl.

Examples of particular substituents on $R^{11}$ include fluoro, chloro, bromo, cyano, cyanoethyl, nitro, methyl, ethyl, tert-butyl, trifluoromethyl, trifluoroethyl, ethenyl, hydroxy, methoxy, isopropoxy, difluoromethoxy, trifluoromethoxy, trifluoroethoxy, methylenedioxy, ethylenedioxy, methoxymethyl, methylthio, methylsulphonyl, methylsulphonylethyl, oxo, amino, methylamino, dimethylamino, methoxyethylamino, N-(hydroxyethyl)-N-(methyl)amino, acetylamino, methoxycarbonylamino, ethoxycarbonylamino, ethylaminocarbonylamino, butylaminocarbonylamino, methylsulphonylamino, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolyl, aminocarbonyl, methylaminocarbonyl, dimethylaminocarbonyl, methylsulphonylaminocarbonyl, aminosulphonyl, methylaminosulphonyl and dimethylaminosulphonyl. Additional examples include bis(methylsulphonyl)amino, N-(carboxyethyl)-N-(methyl)amino, carboxycyclopentylamino, carboxycyclopropylmethylamino, methoxycarbonylmethyl, tetrazolylmethyl and acetylaminosulphonyl. Additional examples include fluoromethyl, fluoroisopropyl, nitromethyl, isopropyl, isobutyl, difluoromethyl, difluoroethyl, hydroxymethyl, hydroxyisopropyl, methoxyethyl, carboxycyclobutyloxy, methylsulphinyl, aminomethyl, aminoisopropyl, ethylamino, hydroxyethylamino, hydroxypropylamino, (hydroxy)(methyl)propylamino, (hydroxy)(methoxy)(methyl)propylamino, (hydroxy)-(methylthio)butylamino, dimethylaminoethylamino, (dimethylamino)(methyl)propylamino, N-(dimethylaminoethyl)-N-(hydroxyethyl)amino, hydroxymethylcyclopentyl-amino, hydroxycyclobutylmethylamino, (cyclopropyl)(hydroxy)propylamino, morpholinylethylamino, oxopyrrolidinylmethylamino, ethyloxadiazolylamino, methyl-thiadiazolylamino, thiazolylmethylamino, thiazolylethylamino, pyrimidinylmethylamino, methylpyrazolylmethylamino, N-acetyl-N-methylamino, N-isopropylcarbonyl-N-methylamino, acetylaminomethyl, ethenylcarbonylamino, bis(ethenylcarbonyl) amino, N-cyclopropylcarbonyl-N-methylamino, N-(carboxymethyl)-N-methylamino, tert-butoxycarbonylamino, methoxycarbonylethylamino, N-methyl-N-(methylsulphonyl)amino, isopropylcarbonyl, cyclobutylcarbonyl, phenylcarbonyl, acetoxyisopropyl, n-butoxycarbonyl, morpholinylethoxycarbonyl, ethoxycarbonylmethylidenyl, hydroxyoxadiazolyl, hydroxyethylaminocarbonyl and methoxyaminocarbonyl.

Generally, $R^{11}$ represents $C_{1-6}$ alkyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl-($C_{3-7}$)heterocycloalkyl-, ($C_{4-7}$)cycloalkenyl-heteroaryl-, ($C_{3-7}$) heterocycloalkyl-heteroaryl-, ($C_{3-7}$)heterocycloalkyl($C_{1-6}$) alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents. Additionally, $R^{11}$ may represent $C_{2-6}$ alkynyl or ($C_{3-7}$)cycloalkyl-heteroaryl-, either of which groups may be optionally substituted by one or more substituents. Additionally, $R^{11}$ may represent ($C_{3-7}$) cycloalkyl($C_{1-6}$)alkyl-heteroaryl- or ($C_{4-9}$) bicycloalkyl-heteroaryl-, either of which groups may be optionally substituted by one or more substituents.

More generally, $R^{11}$ represents $C_{1-6}$ alkyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl-($C_{3-7}$)heterocycloalkyl-, ($C_{3-7}$)heterocycloalkyl-heteroaryl-, ($C_{3-7}$) heterocycloalkyl-($C_{1-6}$)alkyl-heteroaryl-, ($C_{4-9}$) heterobicycloalkyl-heteroaryl- or ($C_{4-9}$)spiroheterocycloalkyl-heteroaryl-, any of which groups may be optionally substituted by one or more substituents. Additionally, $R^{11}$ may represent $C_{2-6}$ alkynyl, ($C_{3-7}$)cycloalkyl-heteroaryl- or ($C_{4-7}$)cycloalkenyl-heteroaryl-, any of which groups may be optionally substituted by one or more substituents. Additionally, $R^{11}$ may represent ($C_{3-7}$)cycloalkyl($C_{1-6}$) alkyl-heteroaryl- or ($C_{4-9}$) bicycloalkyl-heteroaryl-, either of which groups may be optionally substituted by one or more substituents.

Still more generally, $R^{11}$ represents $C_{1-6}$ alkyl, $C_{2-6}$ alkynyl, aryl, $C_{3-7}$ heterocycloalkyl, $C_{3-7}$ heterocycloalkenyl, heteroaryl, ($C_{3-7}$)cycloalkyl-heteroaryl-, ($C_{4-7}$)-cycloalkenyl-heteroaryl-, ($C_{3-7}$)heterocycloalkyl-heteroaryl-, ($C_{4-9}$) heterobicycloalkyl-heteroaryl- or ($C_{4-9}$) spiroheterocycloalkyl-heteroaryl-, any of which groups may be optionally substituted by one or more substituents. Additionally, $R^{11}$ may represent ($C_{3-7}$)cycloalkyl($C_{1-6}$)alkyl-heteroaryl- or ($C_{4-9}$) bicycloalkyl-heteroaryl-, either of which groups may be optionally substituted by one or more substituents.

Even more generally, $R^{11}$ represents $C_{1-6}$ alkyl, $C_{3-7}$ heterocycloalkenyl, heteroaryl, ($C_{3-7}$)heterocycloalkyl-heteroaryl- or ($C_{4-9}$)heterobicycloalkyl-heteroaryl-, any of which groups may be optionally substituted by one or more substituents.

In a first embodiment, $R^{11}$ represents halogen. In one aspect of that embodiment, $R^{11}$ represents bromo.

In a second embodiment, $R^{11}$ represents cyano.

In a third embodiment, $R^{11}$ represents optionally substituted $C_{1-6}$ alkyl. In one aspect of that embodiment, $R^{11}$ represents optionally substituted ethyl.

In a fourth embodiment, $R^{11}$ represents optionally substituted $C_{2-6}$ alkynyl. In one aspect of that embodiment, $R^{11}$ represents optionally substituted butynyl.

In a fifth embodiment, $R^{11}$ represents optionally substituted aryl. In one aspect of that embodiment, $R^{11}$ represents optionally substituted phenyl.

In a sixth embodiment, $R^{11}$ represents optionally substituted $C_{3-7}$ heterocycloalkyl.

In a seventh embodiment, $R^{11}$ represents optionally substituted $C_{3-7}$ heterocycloalkenyl.

In an eighth embodiment, $R^{11}$ represents optionally substituted heteroaryl. In selected aspects of that embodiment, $R^{11}$ represents benzofuryl, thienyl, indolyl, pyrazolyl, indazolyl, isoxazolyl, imidazolyl, pyridinyl, quinolinyl, pyridazinyl, pyrimidinyl or pyrazinyl, any of which groups may be optionally substituted by one or more substituents. In a further aspect, $R^{11}$ represents optionally substituted thiazolyl.

In a ninth embodiment, $R^{11}$ represents optionally substituted ($C_{3-7}$)-heterocycloalkyl($C_{1-6}$)alkyl-aryl-. In a first aspect of that embodiment, $R^{11}$ represents optionally substituted pyrrolidinylmethylphenyl-. In a second aspect of that embodiment, $R^{11}$ represents optionally substituted piperazinylmethylphenyl-.

In a tenth embodiment, $R^{11}$ represents optionally substituted heteroaryl($C_{3-7}$)-heterocycloalkyl-. In one aspect of that embodiment, $R^{11}$ represents optionally substituted pyridinylpiperazinyl-.

In an eleventh embodiment, $R^{11}$ represents optionally substituted ($C_{3-7}$)cycloalkyl-heteroaryl-. In a first aspect of that embodiment, $R^{11}$ represents optionally substituted cyclohexylpyrazolyl-. In a second aspect of that embodiment, $R^{11}$ represents optionally substituted cyclohexylpyridinyl-. In a third aspect of that embodiment, $R^{11}$ represents optionally substituted cyclopropylpyrimidinyl-. In a fourth aspect of that embodiment, $R^{11}$ represents optionally substituted cyclobutylpyrimidinyl-. In a fifth aspect of that embodiment, $R^{11}$ represents optionally substituted cyclopentylpyrimidinyl-. In a sixth aspect of that embodiment, $R^{11}$ represents optionally substituted cyclohexylpyrimidinyl-. In a seventh aspect of that embodiment, $R^{11}$ represents optionally substituted cyclohexylpyrazinyl-.

In a twelfth embodiment, $R^{11}$ represents optionally substituted $(C_{4-7})$cycloalkenyl-heteroaryl-.

In a thirteenth embodiment, $R^{11}$ represents optionally substituted $(C_{3-7})$-heterocycloalkyl-heteroaryl-. In a first aspect of that embodiment, $R^{11}$ represents optionally substituted pyrrolidinylpyridinyl-. In a second aspect of that embodiment, $R^{11}$ represents optionally substituted tetrahydropyranylpyridinyl-. In a third aspect of that embodiment, $R^{11}$ represents optionally substituted piperidinylpyridinyl-. In a fourth aspect of that embodiment, $R^{11}$ represents optionally substituted piperazinylpyridinyl-. In a fifth aspect of that embodiment, $R^{11}$ represents optionally substituted morpholinylpyridinyl-. In a sixth aspect of that embodiment, $R^{11}$ represents optionally substituted thiomorpholinylpyridinyl-. In a seventh aspect of that embodiment, $R^{11}$ represents optionally substituted diazepanylpyridinyl-. In an eighth aspect of that embodiment, $R^{11}$ represents optionally substituted oxetanylpyrimidinyl-. In a ninth aspect of that embodiment, $R^{11}$ represents optionally substituted azetidinylpyrimidinyl-. In a tenth aspect of that embodiment, $R^{11}$ represents optionally substituted tetrahydrofuranylpyrimidinyl-. In an eleventh aspect of that embodiment, $R^{11}$ represents optionally substituted pyrrolidinylpyrimidinyl-. In a twelfth aspect of that embodiment, $R^{11}$ represents optionally substituted tetrahydropyranylpyrimidinyl-. In a thirteenth aspect of that embodiment, $R^{11}$ represents optionally substituted piperidinylpyrimidinyl-. In a fourteenth aspect of that embodiment, $R^{11}$ represents optionally substituted piperazinylpyrimidinyl-. In a fifteenth aspect of that embodiment, $R^{11}$ represents optionally substituted morpholinylpyrimidinyl-. In a sixteenth aspect of that embodiment, $R^{11}$ represents optionally substituted thiomorpholinylpyrimidinyl-. In a seventeenth aspect of that embodiment, $R^{11}$ represents optionally substituted azepanylpyrimidinyl-. In an eighteenth aspect of that embodiment, $R^{11}$ represents optionally substituted oxazepanylpyrimidinyl-. In a nineteenth aspect of that embodiment, $R^{11}$ represents optionally substituted diazepanylpyrimidinyl-. In a twentieth aspect of that embodiment, $R^{11}$ represents optionally substituted thiadiazepanylpyrimidinyl-. In a twenty-first aspect of that embodiment, $R^{11}$ represents optionally substituted piperidinylpyrazinyl-.

In a fourteenth embodiment, $R^{11}$ represents optionally substituted $(C_{3-7})$-heterocycloalkyl$(C_{1-6})$alkyl-heteroaryl-. In a first aspect of that embodiment, $R^{11}$ represents optionally substituted morpholinylmethylthienyl-. In a second aspect of that embodiment, $R^{11}$ represents optionally substituted morpholinylethylpyrazolyl-.

In a fifteenth embodiment, $R^{11}$ represents optionally substituted $(C_{3-7})$-heterocycloalkenyl-heteroaryl-.

In a sixteenth embodiment, $R^{11}$ represents optionally substituted $(C_{4-9})$-heterobicycloalkyl-heteroaryl-.

In a seventeenth embodiment, $R^{11}$ represents optionally substituted $(C_{4-9})$-spiroheterocycloalkyl-heteroaryl-.

In an eighteenth embodiment, $R^{11}$ represents optionally substituted $(C_{3-7})$-cycloalkyl$(C_{1-6})$alkyl-heteroaryl-. In one aspect of that embodiment, $R^{11}$ represents optionally substituted cyclohexylmethylpyrimidinyl-.

In a nineteenth embodiment, $R^{11}$ represents optionally substituted $(C_{4-9})$-bicycloalkyl-heteroaryl-.

Appositely, $R^{11}$ represents bromo or cyano; or ethyl, phenyl, piperidinyl, piperazinyl, morpholinyl, 1,2,3,6-tetrahydropyridinyl, benzofuryl, thienyl, indolyl, pyrazolyl, indazolyl, isoxazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, pyrrolidinylpyridinyl, piperidinylpyridinyl, piperazinylpyridinyl, morpholinylpyridinyl, thiomorpholinylpyridinyl, diazepanylpyridinyl, pyrrolidinylpyrimidinyl, piperidinylpyrimidinyl, piperazinylpyrimidinyl, morpholinylpyrimidinyl, thiomorpholinylpyrimidinyl, diazepanylpyrimidinyl, thiadiazepanylpyrimidinyl, morpholinylmethylthienyl, morpholinylethylpyrazolyl, 2-oxa-5-azabicyclo[2.2.1]-heptanylpyrimidinyl, 2-oxa-6-azaspiro[3.3]heptanylpyrimidinyl, 2-oxa-6-azaspiro[3.4]-octanylpyrimidinyl, 2-oxa-6-azaspiro[3.5]nonanylpyrimidinyl or 2-oxa-7-azaspiro[3.5]-nonanylpyrimidinyl, any of which groups may be optionally substituted by one or more substituents. Additionally, $R^{11}$ may represent butynyl, cyclohexylpyrimidinyl, cyclohexenylpyrimidinyl, azetidinylpyrimidinyl, 3-azabicyclo[3.1.0]hexanylpyrimidinyl or 2-azaspiro[3.3]heptanylpyrimidinyl, any of which groups may be optionally substituted by one or more substituents. Additionally, $R^{11}$ may represent pyrrolidinyl, thiazolyl, cyclohexylpyrazolyl, cyclohexylpyridinyl, cyclopropylpyrimidinyl, cyclobutylpyrimidinyl, cyclopentylpyrimidinyl, cyclohexylpyrazinyl, cyclohexylmethylpyrimidinyl, cyclohexenylpyridinyl, bicyclo[3.1.0]hexanylpyridinyl, bicyclo[3.1.0]hexanylpyrimidinyl, bicyclo[4.1.0]heptanylpyrimidinyl, bicyclo[2.2.2]octanylpyrimidinyl, tetrahydropyranylpyridinyl, oxetanylpyrimidinyl, tetrahydrofuranylpyrimidinyl, tetrahydropyranylpyrimidinyl, hexahydro-[1,2,5]thiadiazolo[2,3-a]pyrazinylpyrimidinyl, azepanylpyrimidinyl, oxazepanylpyrimidinyl, piperidinylpyrazinyl, 3-azabicyclo[3.1.0]-hexanylpyridinyl, 3-azabicyclo[3.1.0]hexanylpyridazinyl, 3-azabicyclo[3.1.1]heptanylpyrimidinyl, 3-azabicyclo[4.1.0]heptanylpyrimidinyl, 2-oxabicyclo[2.2.2]octanylpyrimidinyl, 3-azabicyclo[3.2.1]octanylpyrimidinyl, 8-azabicyclo[3.2.1]octanylpyrimidinyl, 3-oxa-8-azabicyclo[3.2.1]octanylpyrimidinyl, 3,6-diazabicyclo[3.2.2]-nonanylpyrimidinyl, 3-oxa-7-azabicyclo[3.3.1]nonanylpyrimidinyl, 5-azaspiro[2.3]-hexanylpyrimidinyl, 5-azaspiro[2.4]heptanylpyrimidinyl or 2,4,8-triazaspiro[4.5]decanylpyrimidinyl, any of which groups may be optionally substituted by one or more substituents.

Appropriately, $R^{11}$ represents ethyl, butynyl, phenyl, morpholinyl, 1,2,3,6-tetrahydropyridinyl, pyrazolyl, pyridinyl, pyrimidinyl, cyclohexylpyrimidinyl, cyclohexenylpyrimidinyl, piperazinylpyridinyl, morpholinylpyridinyl, azetidinylpyrimidinyl, pyrrolidinylpyrimidinyl, piperidinylpyrimidinyl, piperazinylpyrimidinyl, morpholinylpyrimidinyl, thiomorpholinylpyrimidinyl, diazepanylpyrimidinyl, thiadiazepanylpyrimidinyl, 3-azabicyclo[3.1.0]hexanylpyrimidinyl, 2-oxa-5-azabicyclo-[2.2.1]heptanylpyrimidinyl or 2-azaspiro[3.3]heptanylpyrimidinyl, any of which groups may be optionally substituted by one or more substituents. Additionally, $R^{11}$ may represent pyrrolidinyl, piperidinyl, isoxazolyl, thiazolyl, imidazolyl, cyclohexylpyrazolyl, cyclohexylpyridinyl, cyclopropylpyrimidinyl, cyclobutylpyrimidinyl, cyclopentylpyrimidinyl, cyclohexylpyrazinyl, cyclohexylmethylpyrimidinyl, cyclohexenylpyridinyl, bicyclo[3.1.0]hexanylpyridinyl, bicyclo[3.1.0]hexanylpyrimidinyl, bicyclo[4.1.0]-heptanylpyrimidinyl, bicyclo[2.2.2]octanylpyrimidinyl, tetrahydropyranylpyridinyl, piperidinylpyridinyl, oxetanylpyrimidinyl, tetrahydrofuranylpyrimidinyl, tetrahydropyranylpyrimidinyl, hexahydro-[1,2,5]thiadiazolo[2,3-a]pyrazinylpyrimidinyl, azepanylpyrimidinyl, oxazepanylpyrimidinyl, piperidinylpyrazinyl, 3-azabicyclo[3.1.0]-hexanylpyridinyl, 3-azabicyclo[3.1.0]hexanylpyridazinyl, 3-azabicyclo[3.1.1]heptanylpyrimidinyl, 3-azabicyclo[4.1.0]heptanylpyrimidinyl, 2-oxabicyclo[2.2.2]octanylpyrimidinyl, 3-azabicyclo[3.2.1]octanylpyrimidinyl, 8-azabicyclo[3.2.1]octanylpyrimidinyl, 3-oxa-8-azabicyclo[3.2.1]octanylpyrimidinyl, 3,6-diazabicyclo[3.2.2]-nonanylpyrimidinyl, 3-oxa-7-azabicyclo[3.3.1]nonanylpyrimidinyl, 5-azaspiro[2.3]-hexanylpyrimidinyl, 5-azaspiro[2.4]heptanylpyrimidinyl or 2,4,8-triazaspiro[4.5]decanylpyrimidinyl, any of which groups may be optionally substituted by one or more substituents.

Illustratively, $R^{11}$ represents ethyl, 1,2,3,6-tetrahydropyridinyl, pyrazolyl, pyridinyl, piperazinylpyridinyl, morpholinylpyridinyl, piperidinylpyrimidinyl, piperazinylpyrimidinyl, morpholinylpyrimidinyl, thiomorpholinylpyrimidinyl, diazepanylpyrimidinyl, thiadiazepanylpyrimidinyl or 2-oxa-5-azabicyclo[2.2.1]heptanylpyrimidinyl, any of which groups may be optionally substituted by one or more substituents.

Typical examples of optional substituents on $R^{11}$ include one, two or three substituents independently selected from halogen, cyano, cyano($C_{1-6}$)alkyl, $C_{1-6}$ alkyl, trifluoromethyl, trifluoroethyl, $C_{2-6}$ alkenyl, hydroxy, $C_{1-6}$ alkoxy, trifluoroethoxy, $C_{1-6}$ alkylsulphonyl, $(C_{1-6})$alkylsulphonyl$(C_{1-6})$alkyl, oxo, amino, di($C_{1-6}$)alkylamino, $(C_{1-6})$alkoxy$(C_{1-6})$alkylamino, N—[($C_{1-6}$)alkyl]-N-[hydroxy($C_{1-6}$)alkyl]amino, $C_{1-6}$ alkylsulphonylamino, $C_{2-6}$ alkylcarbonyl, carboxy, carboxy($C_{1-6}$)alkyl, $C_{2-6}$ alkoxycarbonyl, $C_{2-6}$ alkoxycarbonyl$(C_{1-6})$alkyl, a carboxylic acid isostere or prodrug moiety Ω as defined herein, and aminocarbonyl. Additional examples include bis[($C_{1-6}$)alkylsulphonyl]amino, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, —($C_{1-6}$)alkyl-Ω, in which Ω is as defined herein, and aminosulphonyl. Additional examples include halo($C_{1-6}$)alkyl, nitro($C_{1-6}$)alkyl, hydroxy($C_{1-6}$)alkyl, carboxy($C_{3-7}$)cycloalkyloxy, $C_{1-6}$ alkylthio, amino($C_{1-6}$)alkyl, $C_{1-6}$ alkylamino, $(C_{2-6})$alkylcarbonylamino$(C_{1-6})$alkyl, N—[($C_{1-6}$)alkyl]-N—[($C_{1-6}$)alkylsulphonyl]-amino, formyl, $(C_{2-6})$alkylcarbonyloxy$(C_{1-6})$alkyl, morpholinyl$(C_{1-6})$alkoxycarbonyl, $C_{2-6}$ alkoxycarbonylmethylidenyl and $C_{1-6}$ alkoxyaminocarbonyl.

Particular examples of optional substituents on $R^{11}$ include one, two or three substituents independently selected from $C_{1-6}$ alkyl, hydroxy, $C_{1-6}$ alkoxy, $C_{1-6}$ alkylsulphonyl, oxo, amino, N—[($C_{1-6}$)alkyl]-N-[carboxy($C_{1-6}$)alkyl]amino, carboxy-($C_{3-7}$)cycloalkylamino, carboxy($C_{3-7}$)cycloalkyl($C_{1-6}$)alkylamino, $C_{1-6}$ alkylsulphonylamino, bis[($C_{1-6}$)alkylsulphonyl]amino, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, a carboxylic acid isostere or prodrug moiety Ω as defined herein, —($C_{1-6}$)alkyl-Ω, and aminosulphonyl. Additional examples include halogen, halo($C_{1-6}$)alkyl, cyano, nitro($C_{1-6}$)alkyl, trifluoromethyl, hydroxy($C_{1-6}$)-alkyl, carboxy($C_{3-7}$)cycloalkyloxy, $C_{1-6}$ alkylthio, amino($C_{1-6}$)alkyl, $C_{1-6}$ alkylamino, $(C_{2-6})$alkylcarbonylamino$(C_{1-6})$alkyl, N—[($C_{1-6}$)alkyl]-N—[($C_{1-6}$)alkylsulphonyl]amino, formyl, $(C_{2-6})$alkylcarbonyloxy$(C_{1-6})$alkyl, morpholinyl$(C_{1-6})$alkoxycarbonyl, $C_{2-6}$ alkoxycarbonylmethylidenyl and $C_{1-6}$ alkoxyaminocarbonyl.

Suitable examples of optional substituents on $R^{11}$ include one, two or three substituents independently selected from $C_{1-6}$ alkyl, hydroxy, $C_{1-6}$ alkoxy, oxo, amino, $C_{1-6}$ alkylsulphonylamino, carboxy and $C_{2-6}$ alkoxycarbonyl.

Typical examples of particular substituents on $R^{11}$ include one, two or three substituents independently selected from fluoro, chloro, cyano, cyanoethyl, methyl, trifluoromethyl, trifluoroethyl, ethenyl, hydroxy, methoxy, isopropoxy, trifluoroethoxy, methylsulphonyl, methylsulphonylethyl, oxo, amino, dimethylamino, methoxyethylamino, N-(hydroxyethyl)-N-(methyl)amino, methylsulphonylamino, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolyl, aminocarbonyl and methylsulphonylaminocarbonyl. Additional examples include bis(methylsulphonyl)amino, N-(carboxyethyl)-N-(ethyl)amino, carboxycyclopentylamino, carboxycyclopropylmethylamino, methoxycarbonylmethyl, tetrazolylmethyl, aminosulphonyl and acetylaminosulphonyl. Additional examples include fluoromethyl, fluoroisopropyl, nitromethyl, ethyl, isopropyl, hydroxymethyl, hydroxyisopropyl, carboxycyclobutyloxy, methylthio, aminomethyl, aminoisopropyl, methylamino, acetylaminomethyl, N-methyl-N-(methylsulphonyl)amino, formyl, acetoxyisopropyl, n-butoxycarbonyl, morpholinylethoxycarbonyl, ethoxycarbonylmethylidenyl, hydroxyoxadiazolyl and methoxyaminocarbonyl.

Representative examples of particular substituents on $R^{11}$ include one, two or three substituents independently selected from methyl, hydroxy, methoxy, methylsulphonyl, oxo, amino, methylsulphonylamino, bis(methylsulphonyl)amino, N-(carboxyethyl)-N-(ethyl)amino, carboxycyclopentylamino, carboxycyclopropylmethylamino, acetyl, carboxy, carboxyethyl, methoxycarbonyl, ethoxycarbonyl, tert-butoxycarbonyl, methoxycarbonylmethyl, ethoxycarbonylethyl, tetrazolyl, tetrazolylmethyl, aminosulphonyl and acetylaminosulphonyl. Additional examples include fluoro, chloro, fluoromethyl, fluoroisopropyl, cyano, nitromethyl, ethyl, isopropyl, trifluoromethyl, hydroxymethyl, hydroxyisopropyl, carboxycyclobutyloxy, methylthio, aminomethyl, aminoisopropyl, methylamino, acetylaminomethyl, N-methyl-N-(methylsulphonyl)amino, formyl, acetoxyisopropyl, carboxymethyl, n-butoxycarbonyl, morpholinylethoxycarbonyl, ethoxycarbonylmethylidenyl, hydroxyoxadiazolyl, methoxyaminocarbonyl and methylsulphonylaminocarbonyl.

Suitable examples of particular substituents on $R^{11}$ include one, two or three substituents independently selected from methyl, hydroxy, methoxy, oxo, amino, methylsulphonylamino, carboxy, methoxycarbonyl and tert-butoxycarbonyl.

In a particular embodiment, $R^{11}$ is substituted by hydroxy $(C_{1-6})$alkyl. In one aspect of that embodiment, $R^{11}$ is substituted by hydroxyisopropyl, especially 2-hydroxyprop-2-yl.

Selected values of $R^{11}$ include bromo, cyano, methoxycarbonylethyl, ethoxycarbonylethyl, chlorophenyl, hydroxyphenyl, acetylphenyl, aminocarbonylphenyl, oxopiperidinyl, methylsulphonylpiperazinyl, morpholinyl, tert-butoxycarbonyl-1,2,3,6-tetrahydropyridinyl, benzofuryl, thienyl, indolyl, pyrazolyl, methylpyrazolyl, dimethylpyrazolyl, methylindazolyl, dimethylisoxazolyl, methylimidazolyl, pyridinyl, fluoropyridinyl, cyanopyridinyl, methylpyridinyl, (cyano)(methyl)pyridinyl, dimethylpyridinyl, trifluoromethylpyridinyl, ethenylpyridinyl, methoxypyridinyl, (methoxy)(methyl)-pyridinyl, isopropoxypyridinyl, trifluoroethoxypyridinyl, (methyl)(trifluoroethoxy)-pyridinyl, oxopyridinyl, (methyl)(oxo)pyridinyl, (dimethyl)(oxo)pyridinyl, aminopyridinyl, dimethylaminopyridinyl, methoxyethylaminopyridinyl, N-(hydroxyethyl)-N-(methyl)aminopyridinyl, methylsulphonylaminopyridinyl, carboxypyridinyl, quinolinyl, hydroxypyridazinyl, pyrimidinyl, methoxypyrimidinyl, oxopyrimidinyl, aminopyrimidinyl, dimethylaminopyrimidinyl, methoxyethylaminopyrimidinyl, hydroxypyrazinyl, pyrrolidinylmethylphenyl, piperazinylmethylphenyl, pyridinylpiperazinyl, pyrrolidinylpyridinyl, hydroxypyrrolidinylpyridinyl, piperidinylpyridinyl, acetylpiperidinylpyridinyl, piperazinylpyridinyl, (methyl)(piperazinyl)pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)(methyl)pyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, hydroxypyrrolidinylpyrimidinyl, carboxypiperidinylpyrimidinyl, piperazinylpyrimidinyl, methylsulphonylpiperazinylpyrimidinyl, oxopiperazinylpyrimidinyl, tert-butoxycarbonylpiperazinylpyrimidinyl, morpholinylpyrimidinyl, thiomorpholinylpyrimidinyl, dioxothiomorpholinylpyrimidinyl, oxodiazepanylpyrimidinyl, dioxothiadiazepanylpyrimidinyl, morpholinylmethylthienyl, morpholinylethylpyrazolyl, 2-oxa-5-azabicyclo[2.2.1]heptanylpyrimidinyl, 2-oxa-6-azaspiro[3.3]heptanylpyrimidinyl, 2-oxa-6-azaspiro[3.4]octanylpyrimidinyl, 2-oxa-6-azaspiro[3.5]nonanylpyrimidinyl and 2-oxa-7-azaspiro[3.5]nonanylpyrimidinyl. Additional values include hydroxybutynyl, aminosulphonylphenyl, acetylaminosulphonylphenyl, methylsulphonyl-1,2,3,6-tetrahydropyridinyl, acetyl-1,2,3,6-tetrahydropyridinyl, methoxycarbonylmethyl-1,2,3,6-tetrahydropyridinyl, [bis(methylsulphonyl)amino]-pyridinyl, N-(carboxyethyl)-N-(methyl)aminopyrimidinyl, carboxycyclopentylaminopyrimidinyl, carboxycyclopropylmethylaminopyrimidinyl, ethoxycarbonylethylpyrimidinyl, carboxycyclohexylpyrimidinyl, carboxycyclohexenylpyrimidinyl, ethoxycarbonylcyclohexenylpyrimidinyl, carboxyazetidinylpyrimidinyl, carboxypyrrolidinylpyrimidinyl, (carboxy)(methyl)piperidinylpyrimidinyl, ethoxycarbonylpiperidinylpyrimidinyl, (methoxycarbonyl)(methyl)piperidinylpyrimidinyl, (ethoxycarbonyl)(methyl)piperidinylpyrimidinyl, tetrazolylpiperidinylpyrimidinyl, carboxyethylpiperazinylpyrimidinyl, tetrazolylmethylpiperazinylpyrimidinyl, carboxymorpholinylpyrimidinyl, carboxy-3-azabicyclo[3.1.0]hexanylpyrimidinyl, ethoxycarbonyl-3-azabicyclo[3.1.0]hexanylpyrimidinyl and carboxy-2-azaspiro-[3.3]heptanylpyrimidinyl. Additional values include methylsulphonylphenyl, aminomethylphenyl, aminoisopropylphenyl, acetylaminomethylphenyl, methoxycarbonylphenyl, (methoxycarbonyl)(methyl)pyrrolidinyl, ethoxycarbonylpiperidinyl, (methyl)[N-methyl-N-(methylsulfonyl)]pyrazolyl, hydroxyisopropylthiazolyl, dimethylimidazolyl, hydroxyisopropylpyridinyl, methylsulphonylpyridinyl, methylaminopyridinyl, fluoroisopropylpyrimidinyl, hydroxyisopropylpyrimidinyl, carboxycyclobutyloxypyrimidinyl, methylthiopyrimidinyl, methylsulphonylpyrimidinyl, acetoxyisopropylpyrimidinyl, hydroxyisopropylpyrazinyl, carboxycyclohexylpyrazolyl, carboxycyclohexylpyridinyl, fluoromethylcyclopropylpyrimidinyl, acetylaminomethylcyclopropylpyrimidinyl, hydroxycyclobutylpyrimidinyl, carboxycyclopentylpyrimidinyl, (carboxy)(methyl)cyclohexylpyrimidinyl, (carboxy)(hydroxy)cyclohexylpyrimidinyl, carboxymethylcyclohexylpyrimidinyl, ethoxycarbonylcyclohexylpyrimidinyl, (methoxycarbonyl)(methyl)cyclohexylpyrimidinyl, (ethoxycarbonyl)(methyl)cyclohexylpyrimidinyl, carboxycyclohexylpyrazinyl, carboxycyclohexylmethylpyrimidinyl, carboxycyclohexenylpyridinyl, carboxybicyclo[3.1.0]hexanylpyridinyl, carboxybicyclo-[3.1.0]hexanylpyrimidinyl, ethoxycarbonylbicyclo[3.1.0]hexanylpyrimidinyl, carboxybicyclo[4.1.0]heptanylpyrimidinyl, carboxybicyclo[2.2.2]octanylpyrimidinyl, hydroxytetrahydropyranylpyridinyl, (carboxy)(methyl)piperidinylpyridinyl, [(carboxy)-(methyl)piperidinyl](fluoro)pyridinyl, [(carboxy)(methyl)piperidinyl](chloro)pyridinyl, fluorooxetanylpyrimidinyl, hydroxyoxetanylpyrimidinyl, hydroxyazetidinylpyrimidinyl, (hydroxy)(methyl)azetidinylpyrimidinyl, (tert-butoxycarbonyl)(hydroxy)azetidinylpyrimidinyl, tetrazolylazetidinylpyrimidinyl, hydroxytetrahydrofuranylpyrimidinyl, (carboxy)(methyl)pyrrolidinylpyrimidinyl, carboxymethylpyrrolidinylpyrimidinyl, ethoxycarbonylpyrrolidinylpyrimidinyl, fluorotetrahydropyranylpyrimidinyl, hydroxytetrahydropyranylpyrimidinyl, difluoropiperidinylpyrimidinyl, (cyano)(methyl)-piperidinylpyrimidinyl, (hydroxy)(nitromethyl)piperidinylpyrimidinyl, (hydroxy)-(methyl)piperidinylpyrimidinyl, (hydroxy)(trifluoromethyl)piperidinylpyrimidinyl, (hydroxymethyl)(methyl)piperidinylpyrimidinyl, methylsulphonylpiperidinylpyrimidinyl, oxopiperidinylpyrimidinyl, (formyl)(methyl)piperidinylpyrimidinyl, (carboxy)(fluoro)-piperidinylpyrimidinyl, (carboxy)(ethyl)piperidinylpyrimidinyl, (carboxy)-(trifluoromethyl)piperidinylpyrimidinyl, (carboxy)(hydroxy)piperidinylpyrimidinyl, (carboxy)(hydroxymethyl)piperidinylpyrimidinyl, (carboxy)(methoxy)piperidinylpyrimidinyl, (amino)(carboxy)piperidinylpyrimidinyl, carboxymethylpiperidinylpyrimidinyl, methoxycarbonylpiperidinylpyrimidinyl, (ethoxycarbonyl)(fluoro)-piperidinylpyrimidinyl, (ethyl)(methoxycarbonyl)piperidinylpyrimidinyl, (isopropyl)-(methoxycarbonyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinylpyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, hydroxyoxadiazolylpiperidinylpyrimidinyl, methoxyaminocarbonylpiperidinylpyrimidinyl, methylsulphonylaminocarbonylpiperidinylpyrimidinyl, aminosulphonylpiperidinylpyrimidinyl, acetylaminosulphonylpiperidinylpyrimidinyl, carboxypiperazinylpyrimidinyl, trioxohexahydro-[1,2,5]thiadiazolo[2,3-a]pyrazinylpyrimidinyl, dimethylmorpholinylpyrimidinyl, hydroxymethylmorpholinylpyrimidinyl, (carboxy)(methyl)morpholinylpyrimidinyl, carboxymethylmorpholinylpyrimidinyl, carboxyazepanylpyrimidinyl, carboxyoxazepanylpyrimidinyl, (oxodiazepanyl)-(trifluoromethyl)pyrimidinyl, (oxodiazepanyl)(methoxy)pyrimidinyl, (methyl)(oxo)-diazepanylpyrimidinyl, hydroxyoxetanylpyrazinyl, (carboxy)(methyl)piperidinylpyrazinyl, (ethoxycarbonyl)(methyl)piperidinylpyrazinyl, carboxy-3-azabicyclo[3.1.0]-hexanylpyridinyl, carboxy-3-azabicyclo[4.1.0]heptanylpyridinyl, carboxy-3-azabicyclo-[3.1.0]hexanylpyridazinyl, (carboxy)(methyl)-3-azabicyclo[3.1.0]hexanylpyrimidinyl, methoxycarbonyl-3-azabicyclo[3.1.0]hexanylpyrimidinyl, carboxy-2-oxa-5-azabicyclo-[2.2.1]heptanylpyrimidinyl, carboxy-3-azabicyclo[3.1.1]heptanylpyrimidinyl, carboxy-3-azabicyclo[4.1.0]heptanylpyrimidinyl, methoxycarbonyl-3-azabicyclo[4.1.0]heptanylpyrimidinyl, ethoxycarbonyl-3-azabicyclo[4.1.0]

heptanylpyrimidinyl, (hydroxy)(methyl)-(oxo)-2-oxabicyclo[2.2.2]octanylpyrimidinyl, carboxy-3-azabicyclo[3.2.1]octanylpyrimidinyl, methoxycarbonyl-3-azabicyclo[3.2.1]octanylpyrimidinyl, oxo-8-azabicyclo-[3.2.1]octanylpyrimidinyl, ethoxycarbonylmethylidenyl-8-azabicyclo[3.2.1]octanylpyrimidinyl, 3-oxa-8-azabicyclo[3.2.1]octanylpyrimidinyl, oxo-3,6-diazabicyclo[3.2.2]-nonanylpyrimidinyl, carboxy-3-oxa-7-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro[2.4]heptanylpyrimidinyl and (dioxo)(methyl)-2,4,8-triazaspiro[4.5]-decanylpyrimidinyl.

Definitive values of $R^{11}$ include bromo, ethoxycarbonylethyl, hydroxybutynyl, methylsulfonylphenyl, aminomethylphenyl, aminoisopropylphenyl, acetylaminomethylphenyl, methoxycarbonylphenyl, aminosulphonylphenyl, acetylaminosulphonylphenyl, (methoxycarbonyl)(methyl)pyrrolidinyl, ethoxycarbonylpiperidinyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, methylpyrazolyl, (methyl)[N-methyl-N-(methylsulfonyl)]pyrazolyl, dimethylisoxazolyl, hydroxyisopropylthiazolyl, dimethylimidazolyl, hydroxyisopropylpyridinyl, methoxypyridinyl, (methoxy)(methyl)pyridinyl, methylsulphonylpyridinyl, oxopyridinyl, (methyl)(oxo)pyridinyl, aminopyridinyl, methylaminopyridinyl, methylsulphonylaminopyridinyl, [bis(methylsulphonyl)amino]-pyridinyl, carboxypyridinyl, fluoroisopropylpyrimidinyl, hydroxyisopropylpyrimidinyl, carboxycyclobutyloxypyrimidinyl, methylthiopyrimidinyl, methylsulphonylpyrimidinyl, N-(carboxyethyl)-N-(methyl)aminopyrimidinyl, carboxycyclopentylaminopyrimidinyl, carboxycyclopropylmethylaminopyrimidinyl, acetoxyisopropylpyrimidinyl, ethoxycarbonylethylpyrimidinyl, hydroxyisopropylpyrazinyl, carboxycyclohexylpyrazolyl, carboxycyclohexylpyridinyl, fluoromethylcyclopropylpyrimidinyl, acetyl-aminomethylcyclopropylpyrimidinyl, hydroxycyclobutylpyrimidinyl, carboxycyclopentylpyrimidinyl, carboxycyclohexylpyrimidinyl, (carboxy)(methyl)cyclohexylpyrimidinyl, (carboxy)(hydroxy)cyclohexylpyrimidinyl, carboxymethylcyclohexylpyrimidinyl, ethoxycarbonylcyclohexylpyrimidinyl, (methoxycarbonyl)(methyl)-cyclohexylpyrimidinyl, (ethoxycarbonyl)(methyl)cyclohexylpyrimidinyl, carboxycyclohexylpyrazinyl, carboxycyclohexylmethylpyrimidinyl, carboxycyclohexenylpyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexanylpyrimidinyl, ethoxycarbonylbicyclo[3.1.0]hexanylpyrimidinyl, carboxybicyclo[4.1.0]heptanylpyrimidinyl, carboxybicyclo[2.2.2]octanylpyrimidinyl, hydroxytetrahydropyranylpyridinyl, piperidinylpyridinyl, (carboxy)(methyl)piperidinylpyridinyl, [(carboxy)-(methyl)piperidinyl](fluoro)pyridinyl, [(carboxy)(methyl)piperidinyl](chloro)pyridinyl, piperazinylpyridinyl, morpholinylpyridinyl, fluorooxetanylpyrimidinyl, hydroxyoxetanylpyrimidinyl, hydroxyazetidinylpyrimidinyl, (hydroxy)(methyl)azetidinylpyrimidinyl, carboxyazetidinylpyrimidinyl, (tert-butoxycarbonyl)(hydroxy)azetidinylpyrimidinyl, tetrazolylazetidinylpyrimidinyl, hydroxytetrahydrofuranylpyrimidinyl, carboxypyrrolidinylpyrimidinyl, (carboxy)(methyl)pyrrolidinylpyrimidinyl, carboxymethylpyrrolidinylpyrimidinyl, ethoxycarbonylpyrrolidinylpyrimidinyl, fluorotetrahydropyranylpyrimidinyl, hydroxytetrahydropyranylpyrimidinyl, difluoropiperidinylpyrimidinyl, (cyano)(methyl)piperidinylpyrimidinyl, (hydroxy)(nitromethyl)piperidinylpyrimidinyl, (hydroxy)(methyl)piperidinylpyrimidinyl, (hydroxy)(trifluoromethyl)-piperidinylpyrimidinyl, (hydroxymethyl)(methyl)piperidinylpyrimidinyl, methylsulphonylpiperidinylpyrimidinyl, oxopiperidinylpyrimidinyl, (formyl)(methyl)-piperidinylpyrimidinyl, carboxypiperidinylpyrimidinyl, (carboxy)(fluoro)piperidinylpyrimidinyl, (carboxy)(methyl)piperidinylpyrimidinyl, (carboxy)(ethyl)piperidinylpyrimidinyl, (carboxy)(trifluoromethyl)piperidinylpyrimidinyl, (carboxy)(hydroxy)-piperidinylpyrimidinyl, (carboxy)(hydroxymethyl)piperidinylpyrimidinyl, (carboxy)-(methoxy)piperidinylpyrimidinyl, (amino)(carboxy)piperidinylpyrimidinyl, carboxymethylpiperidinylpyrimidinyl, methoxycarbonylpiperidinylpyrimidinyl, ethoxycarbonylpiperidinylpyrimidinyl, (ethoxycarbonyl)(fluoro)piperidinylpyrimidinyl, (methoxycarbonyl)(methyl)piperidinylpyrimidinyl, (ethyl)(methoxycarbonyl)piperidinylpyrimidinyl, (isopropyl)(methoxycarbonyl)piperidinylpyrimidinyl, (ethoxycarbonyl)-(methyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinylpyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, hydroxyoxadiazolylpiperidinylpyrimidinyl, tetrazolylpiperidinylpyrimidinyl, methoxyaminocarbonylpiperidinylpyrimidinyl, methylsulphonylaminocarbonylpiperidinylpyrimidinyl, aminosulphonylpiperidinylpyrimidinyl, acetylaminosulphonylpiperidinylpyrimidinyl, piperazinylpyrimidinyl, oxopiperazinylpyrimidinyl, methylsulfonylpiperazinylpyrimidinyl, carboxypiperazinylpyrimidinyl, carboxyethylpiperazinylpyrimidinyl, tert-butoxycarbonylpiperazinylpyrimidinyl, tetrazolylmethyl-piperazinylpyridinyl, trioxohexahydro-[1,2,5]thiadiazolo[2,3-a]pyrazinylpyrimidinyl, morpholinylpyrimidinyl, dimethylmorpholinylpyrimidinyl, hydroxymethylmorpholinylpyrimidinyl, carboxymorpholinylpyrimidinyl, (carboxy)(methyl)morpholinylpyrimidinyl, carboxymethylmorpholinylpyrimidinyl, dioxothiomorpholinylpyrimidinyl, carboxyazepanylpyrimidinyl, carboxyoxazepanylpyrimidinyl, oxodiazepanylpyrimidinyl, (carboxy)(trifluoromethyl)pyrimidinyl, (oxodiazepanyl)(methoxy)pyrimidinyl, (methyl)(oxo)diazepanylpyrimidinyl, dioxothiadiazepanylpyrimidinyl, hydroxyoxetanylpyrazinyl, (carboxy)(methyl)piperidinylpyrazinyl, (ethoxycarbonyl)(methyl)piperidinylpyrazinyl, carboxy-3-azabicyclo[3.1.0]hexanylpyridinyl, carboxy-3-azabicyclo[4.1.0]-heptanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanylpyrimidinyl, 2-oxa-5-azabicyclo[2.2.1]heptanylpyrimidinyl, carboxy-2-oxa-5-azabicyclo[2.2.1]heptanylpyrimidinyl, carboxy-3-azabicyclo[3.1.1]-heptanylpyrimidinyl, carboxy-3-azabicyclo[4.1.0]heptanylpyrimidinyl, methoxycarbonyl-3-azabicyclo[4.1.0]heptanylpyrimidinyl, ethoxycarbonyl-3-azabicyclo[4.1.0]heptanylpyrimidinyl, (hydroxy)(methyl)(oxo)-2-oxabicyclo[2.2.2]octanylpyrimidinyl, carboxy-3-azabicyclo[3.2.1]octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8- azabicyclo[3.2.1]octanylpyrimidinyl, 3-oxa-8-azabicyclo[3.2.1]octanylpyrimidinyl, oxo-3,6-diazabicyclo[3.2.2]nonanylpyrimidinyl, carboxy-3-oxa-7-azabicyclo[3.3.1]nonanylpyrimidinyl, carboxy-5-azaspiro[2.3]hexanylpyrimidinyl, (carboxy)(methyl)-5-azaspiro-[2.3]hexanylpyrimidinyl, carboxy-5-azaspiro[2.4]heptanylpyrimidinyl, carboxy-2-azaspiro[3.3]heptanylpyrimidinyl and (dioxo)(methyl)-2,4,8-triazaspiro[4.5]decanylpyrimidinyl.

Particular values of $R^{11}$ include ethoxycarbonylethyl, hydroxybutynyl, aminosulphonylphenyl, acetylaminosulphonylphenyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, methylpyrazolyl, methoxypyridinyl, (methoxy)(methyl)pyridinyl, oxopyridinyl, (methyl)(oxo)-pyridinyl, aminopyridinyl, methylsulphonylaminopyridinyl, [bis(methylsulphonyl)-amino]pyridinyl, N-(carboxyethyl)-N-(methyl)aminopyrimidinyl, carboxycyclopentylaminopyrimidinyl, carboxycyclopropylmethylaminopyrimidinyl, ethoxycarbonylethylpyrimidinyl, carboxycyclohexylpyrimidinyl, carboxycyclohexenylpyrimidinyl, ethoxycarbonylcyclohexenylpyrimidinyl, piperazinylpyridinyl, morpholinylpyridinyl, carboxyazetidinylpyrimidinyl, carboxypyrrolidinylpyrimidinyl, carboxypiperidinylpyrimidinyl, (carboxy)(methyl)piperidinylpyrimidinyl, ethoxycarbonylpiperidinylpyrimidinyl, (methoxycarbonyl)(methyl)piperidinylpyrimidinyl, (ethoxycarbonyl)-(methyl)piperidinylpyrimidinyl, tetrazolylpiperidinylpyrimidinyl, piperazinylpyrimidinyl, oxopiperazinylpyrimidinyl, carboxyethylpiperazinylpyrimidinyl, tetrazolylmethyl-piperazinylpyridinyl, morpholinylpyrimidinyl, carboxymorpholinylpyrimidinyl, dioxothiomorpholinylpyrimidinyl, oxodiazepanylpyrimidinyl, dioxothiadiazepanylpyrimidinyl, carboxy-3-azabicyclo[3.1.0]hexanylpyrimidinyl, ethoxycarbonyl-3-azabicyclo[3.1.0]hexanylpyrimidinyl, 2-oxa-5-azabicyclo[2.2.1]heptanylpyrimidinyl and carboxy-2-azaspiro[3.3]heptanylpyrimidinyl.

Illustrative values of $R^{11}$ include methoxycarbonylethyl, tert-butoxycarbonyl-1,2,3,6-tetrahydropyridinyl, methylpyrazolyl, methoxypyridinyl, (methoxy)(methyl)-pyridinyl, oxopyridinyl, (methyl)(oxo)pyridinyl, aminopyridinyl, methylsulphonylaminopyridinyl, piperazinylpyridinyl, morpholinylpyridinyl, carboxypiperidinylpyrimidinyl, piperazinylpyrimidinyl, oxopiperazinylpyrimidinyl, morpholinylpyrimidinyl, dioxothiomorpholinylpyrimidinyl, oxodiazepanylpyrimidinyl, dioxothiadiazepanylpyrimidinyl and 2-oxa-5-azabicyclo[2.2.1]heptanylpyrimidinyl.

Typical examples of optional substituents on $R^{12}$ include $C_{2-6}$ alkoxycarbonyl.

Typical examples of particular substituents on $R^{12}$ include ethoxycarbonyl.

In a first embodiment, $R^{12}$ represents hydrogen. In a second embodiment, $R^{12}$ represents halogen. In one aspect of that embodiment, $R^{12}$ represents fluoro. In another aspect of that embodiment, $R^{12}$ represents chloro. In a third embodiment, $R^{12}$ represents trifluoromethyl. In a fourth embodiment, $R^{12}$ represents optionally substituted $C_{1-6}$ alkyl. In one aspect of that embodiment, $R^{12}$ represents unsubstituted methyl. In another aspect of that embodiment, $R^{12}$ represents unsubstituted ethyl. In a further aspect of that embodiment, $R^{12}$ represents monosubstituted methyl or monosubstituted ethyl.

Typical values of $R^{12}$ include hydrogen, fluoro, trifluoromethyl, methyl and ethoxycarbonylethyl. Additionally, $R^{12}$ may represent chloro.

Suitable values of $R^{12}$ include hydrogen, fluoro, trifluoromethyl and methyl. Additionally, $R^{12}$ may represent chloro.

Typically, $R^{15}$ and $R^{16}$ may independently represent hydrogen, fluoro, chloro, bromo, cyano, nitro, methyl, isopropyl, trifluoromethyl, hydroxy, methoxy, difluoromethoxy, trifluoromethoxy, methylthio, methylsulfinyl, methylsulfonyl, amino, methylamino, tert-butylamino, dimethylamino, phenylamino, acetylamino, methylsulfonylamino, formyl, acetyl, cyclopropylcarbonyl, azetidinylcarbonyl, pyrrolidinylcarbonyl, piperidinyl-carbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl.

Typical values of $R^{15}$ include hydrogen, halogen, $C_{1-6}$ alkyl, trifluoromethyl, $C_{1-6}$ alkoxy, difluoromethoxy and trifluoromethoxy.

Illustrative values of $R^{15}$ include halogen, $C_{1-6}$ alkyl and difluoromethoxy.

In a first embodiment, $R^{15}$ represents hydrogen. In a second embodiment, $R^{15}$ represents halogen. In a first aspect of that embodiment, $R^{15}$ represents fluoro. In a second aspect of that embodiment, $R^{15}$ represents chloro. In a third embodiment, $R^{15}$ represents $C_{1-6}$ alkyl. In one aspect of that embodiment, $R^{15}$ represents methyl. In a fourth embodiment, $R^{15}$ represents trifluoromethyl. In a fifth embodiment, $R^{15}$ represents $C_{1-6}$ alkoxy. In one aspect of that embodiment, $R^{15}$ represents methoxy. In a sixth embodiment, $R^{15}$ represents difluoromethoxy. In a seventh embodiment, $R^{15}$ represents trifluoromethoxy.

Selected values of $R^{15}$ include hydrogen, fluoro, chloro, methyl, trifluoromethyl, methoxy, difluoromethoxy and trifluoromethoxy.

Suitable values of $R^{15}$ include chloro, methyl and difluoromethoxy.

Typical values of $R^{16}$ include hydrogen, halogen, $C_{1-6}$ alkyl, trifluoromethyl, difluoromethoxy and amino.

Illustrative values of $R^{16}$ include hydrogen, halogen and $C_{1-6}$ alkyl.

In a first embodiment, $R^{16}$ represents hydrogen. In a second embodiment, $R^{16}$ represents halogen. In a first aspect of that embodiment, $R^{16}$ represents fluoro. In a second aspect of that embodiment, $R^{16}$ represents chloro. In a third embodiment, $R^{16}$ represents $C_{1-6}$ alkyl. In one aspect of that embodiment, $R^{16}$ represents methyl. In a fourth embodiment, $R^{16}$ represents trifluoromethyl. In a fifth embodiment, $R^{16}$ represents difluoromethoxy. In a seventh embodiment, $R^{16}$ represents amino.

Selected values of $R^{16}$ include hydrogen, fluoro, chloro, methyl, trifluoromethyl, difluoromethoxy and amino.

Suitable values of $R^{16}$ include hydrogen, chloro and methyl.

In a particular embodiment, $R^{16}$ is attached at the para-position of the phenyl ring relative to the integer $R^{15}$.

A particular sub-group of the compounds of formula (IIA) above is represented by the compounds of formula (IIB) and N-oxides thereof, and pharmaceutically acceptable salts and solvates thereof, and glucuronide derivatives thereof, and co-crystals thereof:

(IIB)

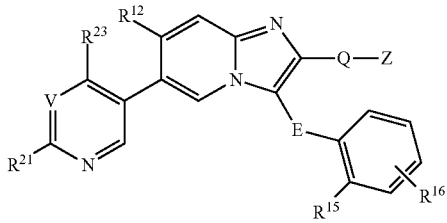

wherein

V represents C—R$^{22}$ or N;

R$^{21}$ represents hydrogen, halogen, halo(C$_{1-6}$)alkyl, cyano, C$_{1-6}$ alkyl, trifluoromethyl, C$_{2-6}$ alkenyl, C$_{2-6}$ alkynyl, hydroxy, hydroxy(C$_{1-6}$)alkyl, C$_{1-6}$ alkoxy, (C$_{1-6}$)alkoxy(C$_{1-6}$)alkyl, difluoromethoxy, trifluoromethoxy, trifluoroethoxy, carboxy(C$_{3-7}$)cycloalkyloxy, C$_{1-6}$ alkylthio, C$_{1-6}$ alkylsulphonyl, (C$_{1-6}$)alkylsulphonyl(C$_{1-6}$)alkyl, amino, amino-(C$_{1-6}$)alkyl, C$_{1-6}$ alkylamino, di(C$_{1-6}$)alkylamino, (C$_{1-6}$)alkoxy(C$_{1-6}$)alkylamino, N—[(C$_{1-6}$)-alkyl]-N-[hydroxy(C$_{1-6}$)alkyl]amino, C$_{2-6}$ alkylcarbonylamino, (C$_{2-6}$)alkylcarbonylamino-(C$_{1-6}$)alkyl, C$_{2-6}$ alkoxycarbonylamino, N—[(C$_{1-6}$)alkyl]-N-[carboxy(C$_{1-6}$)alkyl]amino, carboxy(C$_{3-7}$)cycloalkylamino, carboxy(C$_{3-7}$)cycloalkyl(C$_{1-6}$)alkylamino, C$_{1-6}$ alkylsulphonylamino, C$_{1-6}$ alkylsulphonylamino(C$_{1-6}$)alkyl, formyl, C$_{2-6}$ alkylcarbonyl, (C$_{2-6}$)alkylcarbonyloxy(C$_{1-6}$)alkyl, carboxy, carboxy(C$_{1-6}$)alkyl, C$_{2-6}$ alkoxycarbonyl, morpholinyl(C$_{1-6}$)alkoxycarbonyl, C$_{2-6}$ alkoxycarbonyl(C$_{1-6}$)alkyl, C$_{2-6}$ alkoxycarbonylmethylidenyl, aminocarbonyl, C$_{1-6}$ alkylaminocarbonyl, di(C$_{1-6}$)alkylaminocarbonyl, aminosulphonyl, C$_{1-6}$ alkylaminosulphonyl or di(C$_{1-6}$)alkylaminosulphonyl; or R$^{21}$ represents (C$_{3-7}$)cycloalkyl, (C$_{3-7}$)cycloalkyl(C$_{1-6}$)alkyl, (C$_{4-7}$)cycloalkenyl, (C$_{4-9}$)bicycloalkyl, (C$_{3-7}$)heterocycloalkyl, (C$_{3-7}$)heterocycloalkenyl, (C$_{4-9}$)heterobicycloalkyl or (C$_{4-9}$)spiroheterocycloalkyl, any of which groups may be optionally substituted by one or more substituents;

R$^{22}$ represents hydrogen, halogen or C$_{1-6}$ alkyl;

R$^{23}$ represents hydrogen, C$_{1-6}$ alkyl, trifluoromethyl or C$_{1-6}$ alkoxy; and E, Q, Z, R$^{12}$, R$^{15}$ and R$^{16}$ are as defined above.

The present invention also provides a compound of formula (IIB) as depicted above or an N-oxide thereof, or a pharmaceutically acceptable salt or solvate thereof, or a co-crystal thereof, wherein R$^{21}$ represents hydrogen, halogen, cyano, C$_{1-6}$ alkyl, trifluoromethyl, C$_{2-6}$ alkenyl, C$_{2-6}$ alkynyl, hydroxy, C$_{1-6}$ alkoxy, difluoromethoxy, trifluoromethoxy, trifluoroethoxy, C$_{1-6}$ alkylthio, C$_{1-6}$ alkylsulphonyl, amino, C$_{1-6}$ alkylamino, di(C$_{1-6}$)alkylamino, (C$_{1-6}$)alkoxy(C$_{1-6}$)alkylamino, N—[(C$_{1-6}$)alkyl]-N-[hydroxy(C$_{1-6}$)alkyl]amino, C$_{2-6}$ alkylcarbonylamino, C$_{2-6}$ alkoxycarbonylamino, N—[(C$_{1-6}$)alkyl]-N-[carboxy(C$_{1-6}$)alkyl]-amino, carboxy(C$_{3-7}$)cycloalkylamino, carboxy(C$_{3-7}$)cycloalkyl(C$_{1-6}$)alkylamino, C$_{1-6}$ alkylsulphonylamino, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, aminocarbonyl, C$_{1-6}$ alkylaminocarbonyl, di(C$_{1-6}$)alkylaminocarbonyl, aminosulphonyl, C$_{1-6}$ alkylaminosulphonyl or di(C$_{1-6}$)alkylaminosulphonyl; or R$^{21}$ represents (C$_{3-7}$)cycloalkyl, (C$_{4-7}$)cycloalkenyl, (C$_{3-7}$)heterocycloalkyl, (C$_{3-7}$)heterocycloalkenyl, (C$_{4-9}$)heterobicycloalkyl or (C$_{4-9}$)spiroheterocycloalkyl, any of which groups may be optionally substituted by one or more substituents;

R$^{23}$ represents hydrogen or C$_{1-6}$ alkyl; and

E, Q, Z, V, R$^{12}$, R$^{15}$ and R$^{16}$ are as defined above.

The present invention also provides a compound of formula (IIB) as depicted above or an N-oxide thereof, or a pharmaceutically acceptable salt or solvate thereof, or a co-crystal thereof, wherein R$^{21}$ represents hydrogen, halogen, cyano, C$_{1-6}$ alkyl, trifluoromethyl, C$_{2-6}$ alkenyl, C$_{2-6}$ alkynyl, hydroxy, C$_{1-6}$ alkoxy, difluoromethoxy, trifluoromethoxy, trifluoroethoxy, C$_{1-6}$ alkylthio, C$_{1-6}$ alkylsulphonyl, amino, C$_{1-6}$ alkylamino, di(C$_{1-6}$)alkylamino, (C$_{1-6}$)alkoxy(C$_{1-6}$)alkylamino, N—[(C$_{1-6}$)alkyl]-N-[hydroxy(C$_{1-6}$)alkyl]amino, C$_{2-6}$ alkylcarbonylamino, C$_{2-6}$ alkoxycarbonylamino, C$_{1-6}$ alkylsulphonylamino, formyl, C$_{2-6}$ alkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, aminosulphonyl, C$_{1-6}$ alkylaminosulphonyl or di(C$_{1-6}$)alkylaminosulphonyl; or R$^{21}$ represents (C$_{4-7}$)cycloalkenyl, (C$_{3-7}$)heterocycloalkyl, (C$_{3-7}$)heterocycloalkenyl, (C$_{4-9}$)heterobicycloalkyl or (C$_{4-9}$)spiroheterocycloalkyl, any of which groups may be optionally substituted by one or more substituents;

R$^{23}$ represents hydrogen; and

E, Q, Z, V, R$^{12}$, R$^{15}$ and R$^{16}$ are as defined above.

In one embodiment, V represents C—R$^{22}$. In another embodiment, V represents N.

Typically, R$^{21}$ represents hydrogen, halogen, cyano, C$_{1-6}$ alkyl, trifluoromethyl, C$_{2-6}$ alkenyl, hydroxy, C$_{1-6}$ alkoxy, trifluoroethoxy, amino, di(C$_{1-6}$)alkylamino, (C$_{1-6}$)-alkoxy(C$_{1-6}$)alkylamino, N—[(C$_{1-6}$)alkyl]-N-[hydroxy(C$_{1-6}$)alkyl] amino, C$_{1-6}$ alkylsulphonylamino or carboxy; or R$^{21}$ represents (C$_{3-7}$)heterocycloalkyl, (C$_{4-9}$)heterobicycloalkyl or (C$_{4-9}$)spiroheterocycloalkyl, any of which groups may be optionally substituted by one or more substituents. Additionally, R$^{21}$ may represent N—[(C$_{1-6}$)alkyl]-N-[carboxy(C$_{1-6}$)alkyl]-amino, carboxy(C$_{3-7}$)cycloalkylamino, carboxy(C$_{3-7}$)cycloalkyl(C$_{1-6}$)alkylamino or C$_{2-6}$ alkoxycarbonyl(C$_{1-6}$)alkyl; or R$^{21}$ may represent (C$_{3-7}$)cycloalkyl or (C$_{4-7}$)cycloalkenyl, either of which groups may be optionally substituted by one or more substituents. Additionally, R$^{21}$ may represent halo(C$_{1-6}$)alkyl, hydroxy(C$_{1-6}$)alkyl, carboxy(C$_{3-7}$)-cycloalkyloxy, C$_{1-6}$ alkylthio, C$_{1-6}$ alkylsulphonyl, C$_{1-6}$ alkylamino, (C$_{2-6}$)alkylcarbonyl-oxy(C$_{1-6}$)alkyl, morpholinyl(C$_{1-6}$)alkoxycarbonyl, C$_{2-6}$ alkoxycarbonylmethylidenyl; or R$^{21}$ may represent (C$_{3-7}$)cycloalkyl(C$_{1-6}$)alkyl or (C$_{4-9}$)bicycloalkyl, either of which groups may be optionally substituted by one or more substituents.

Appositely, R$^{21}$ represents hydroxy, C$_{1-6}$ alkoxy, N—[(C$_{1-6}$)alkyl]-N-[carboxy-(C$_{1-6}$)alkyl]amino, carboxy(C$_{3-7}$)cycloalkylamino, carboxy(C$_{3-7}$)cycloalkyl(C$_{1-6}$)alkylamino or C$_{2-6}$ alkoxycarbonyl(C$_{1-6}$)alkyl; or R$^{21}$ represents (C$_{3-7}$)cycloalkyl, (C$_{4-7}$)cycloalkenyl, (C$_{3-7}$)heterocycloalkyl, (C$_{4-9}$)heterobicycloalkyl or (C$_{4-9}$)spiroheterocycloalkyl, any of which groups may be optionally substituted by one or more substituents. Additionally, R$^{21}$ may represent halo(C$_{1-6}$)alkyl, hydroxy(C$_{1-6}$)alkyl, carboxy(C$_{3-7}$)cycloalkyloxy, C$_{1-6}$ alkylthio, C$_{1-6}$ alkylsulphonyl, C$_{1-6}$ alkylamino, C$_{1-6}$ alkylsulphonylamino, (C$_{2-6}$)alkylcarbonyloxy(C$_{1-6}$)alkyl, morpholinyl(C$_{1-6}$)alkoxycarbonyl, carboxy, C$_{2-6}$ alkoxycarbonylmethylidenyl; or R$^{21}$ may represent (C$_{3-7}$)-cycloalkyl (C$_{1-6}$)alkyl or (C$_{4-9}$)bicycloalkyl, either of which groups may be optionally substituted by one or more substituents.

Suitably, R$^{21}$ represents hydroxy or C$_{1-6}$ alkoxy; or R$^{21}$ represents (C$_{3-7}$)heterocycloalkyl or (C$_{4-9}$)heterobicycloalkyl, either of which groups may be optionally substituted by one or more substituents.

Where R$^{21}$ represents an optionally substituted (C$_{3-7}$)cycloalkyl group, typical values include cyclobutyl, cyclopentyl, cyclohexyl and cycloheptyl, any of which groups may be optionally substituted by one or more substituents. An additional value is cyclopropyl.

Where $R^{21}$ represents an optionally substituted $(C_{3-7})$cycloalkyl$(C_{1-6})$alkyl group, a typical value is cyclohexylmethyl, which group may be optionally substituted by one or more substituents.

Where $R^{21}$ represents an optionally substituted $(C_{4-7})$cycloalkenyl group, typical values include cyclobutenyl, cyclopentenyl, cyclohexenyl and cycloheptenyl, any of which groups may be optionally substituted by one or more substituents.

Where $R^{21}$ represents an optionally substituted $(C_{4-9})$bicycloalkyl group, typical values include bicyclo[3.1.0]hexanyl, bicyclo[4.1.0]heptanyl and bicyclo[2.2.2]octanyl, any of which groups may be optionally substituted by one or more substituents.

Where $R^{21}$ represents an optionally substituted $(C_{3-7})$heterocycloalkyl group, typical values include azetidinyl, pyrrolidinyl, piperidinyl, piperazinyl, morpholinyl, thiomorpholinyl, diazepanyl and thiadiazepanyl, any of which groups may be optionally substituted by one or more substituents. Additional values include oxetanyl, tetrahydrofuranyl, tetrahydropyranyl, hexahydro-[1,2,5]thiadiazolo[2,3-a]pyrazinyl, azepanyl and oxazepanyl, any of which groups may be optionally substituted by one or more substituents.

Where $R^{21}$ represents an optionally substituted $(C_{3-7})$heterocycloalkenyl group, a typical value is optionally substituted 1,2,3,6-tetrahydropyridinyl.

Where $R^{21}$ represents an optionally substituted $(C_{4-9})$heterobicycloalkyl group, typical values include 3-azabicyclo[3.1.0]hexanyl, 2-oxa-5-azabicyclo[2.2.1]heptanyl, quinuclidinyl, 2-oxa-5-azabicyclo[2.2.2]octanyl, 8-azabicyclo[3.2.1]octanyl, 3,8-diazabicyclo[3.2.1]octanyl and 3,9-diazabicyclo[4.2.1]nonanyl, any of which groups may be optionally substituted by one or more substituents. Additional values include 3-azabicyclo[3.1.1]heptanyl, 3-azabicyclo[4.1.0]heptanyl, 2-oxabicyclo[2.2.2]octanyl, 3-azabicyclo[3.2.1]octanyl, 3-oxa-8-azabicyclo[3.2.1]octanyl, 3,6-diazabicyclo[3.2.2]-nonanyl and 3-oxa-7-azabicyclo[3.3.1]nonanyl, any of which groups may be optionally substituted by one or more substituents.

Where $R^{21}$ represents an optionally substituted $(C_{4-9})$spiroheterocycloalkyl group, typical values include 2-azaspiro[3.3]heptanyl, 2-oxa-6-azaspiro[3.3]heptanyl, 2-oxa-6-azaspiro[3.4]octanyl, 2-oxa-6-azaspiro[3.5]nonanyl and 2-oxa-7-azaspiro[3.5]nonanyl, any of which groups may be optionally substituted by one or more substituents. Additional values include 5-azaspiro[2.3]hexanyl, 5-azaspiro[2.4]heptanyl and 2,4,8-triazaspiro[4.5]-decanyl, any of which groups may be optionally substituted by one or more substituents.

Illustratively, $R^{21}$ represents hydroxy, methoxy, N-[carboxyethyl]-N-methylamino, carboxycyclopentylamino, carboxycyclopropylmethylamino or ethoxycarbonylethyl; or $R^{21}$ represents cyclohexyl, cyclohexenyl, azetidinyl, pyrrolidinyl, piperidinyl, piperazinyl, morpholinyl, thiomorpholinyl, diazepanyl, thiadiazepanyl, 3-azabicyclo[3.1.0]hexanyl, 2-oxa-5-azabicyclo[2.2.1]heptanyl or 2-azaspiro[3.3]heptanyl, any of which groups may be optionally substituted by one or more substituents. Additionally, $R^{21}$ may represent hydroxy$(C_{1-6})$alkyl, carboxycyclobutyloxy, methylthio, methylsulphonyl or methylamino; or $R^{21}$ may represent cyclopropyl, cyclobutyl, cyclopentyl, cyclohexylmethyl, bicyclo[3.1.0]hexanyl, bicyclo[4.1.0]heptanyl, bicyclo[2.2.2]octanyl, oxetanyl, tetrahydrofuranyl, tetrahydropyranyl, hexahydro-[1,2,5]thiadiazolo[2,3-a]pyrazinyl, azepanyl, oxazepanyl, 3-azabicyclo[3.1.1]heptanyl, 3-azabicyclo[4.1.0]heptanyl, 2-oxabicyclo[2.2.2]octanyl, 3-azabicyclo[3.2.1]octanyl, 8-azabicyclo[3.2.1]octanyl, 3-oxa-8-azabicyclo[3.2.1]octanyl, 3,6-diazabicyclo[3.2.2]nonanyl, 3-oxa-7-azabicyclo[3.3.1]-nonanyl, 5-azaspiro[2.3]hexanyl or 5-azaspiro[2.4]heptanyl, any of which groups may be optionally substituted by one or more substituents.

Examples of optional substituents which may be present on $R^{21}$ include one, two or three substituents independently selected from halogen, cyano, cyano$(C_{1-6})$alkyl, $C_{1-6}$ alkyl, trifluoromethyl, trifluoroethyl, $C_{2-6}$ alkenyl, hydroxy, $C_{1-6}$ alkoxy, difluoromethoxy, trifluoromethoxy, trifluoroethoxy, $C_{1-6}$ alkylthio, $C_{1-6}$ alkylsulphonyl, $(C_{1-6})$alkylsulphonyl$(C_{1-6})$alkyl, oxo, amino, $C_{1-6}$ alkylamino, di$(C_{1-6})$alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, carboxy$(C_{1-6})$alkyl, $C_{2-6}$ alkoxycarbonyl, $C_{2-6}$ alkoxycarbonyl$(C_{1-6})$alkyl, a carboxylic acid isostere or prodrug moiety Ω as defined herein, aminocarbonyl, $C_{1-6}$ alkylaminocarbonyl, di$(C_{1-6})$alkylaminocarbonyl, aminosulphonyl and di$(C_{1-6})$alkylaminosulphonyl. An additional example is —$(C_{1-6})$alkyl-Ω, in which Ω is as defined herein. Additional examples include halo$(C_{1-6})$alkyl, nitro$(C_{1-6})$alkyl, hydroxy$(C_{1-6})$alkyl, $(C_{2-6})$alkylcarbonylamino$(C_{1-6})$alkyl, morpholinyl$(C_{1-6})$alkoxycarbonyl, $C_{2-6}$ alkoxycarbonylmethylidenyl and $C_{1-6}$ alkoxyaminocarbonyl.

Suitable examples of optional substituents on $R^{21}$ include one, two or three substituents independently selected from fluoro, chloro, bromo, cyano, cyanomethyl, methyl, ethyl, trifluoromethyl, trifluoroethyl, ethenyl, hydroxy, methoxy, ethoxy, difluoromethoxy, trifluoromethoxy, trifluoroethoxy, methylthio, methylsulphonyl, methylsulphonylmethyl, oxo, amino, methylamino, dimethylamino, acetylamino, methoxycarbonylamino, ethoxycarbonylamino, tert-butoxycarbonylamino, methylsulphonylamino, formyl, acetyl, carboxy, carboxymethyl, carboxyethyl, methoxycarbonyl, ethoxycarbonyl, tert-butoxycarbonyl, methoxycarbonylmethyl, ethoxycarbonylmethyl, tetrazolyl, aminocarbonyl, methylaminocarbonyl, dimethylaminocarbonyl, methylsulphonylaminocarbonyl, aminosulphonyl, methylaminosulphonyl and dimethylaminosulphonyl. An additional example is tetrazolylmethyl. Additional examples include fluoromethyl, nitromethyl, isopropyl, hydroxymethyl, acetylaminomethyl, n-butoxycarbonyl, morpholinylethoxycarbonyl, ethoxycarbonylmethylidenyl, hydroxyoxadiazolyl, methoxyaminocarbonyl and acetylaminosulphonyl.

Selected examples of optional substituents on $R^{21}$ include one, two or three substituents independently selected from cyano$(C_{1-6})$alkyl, trifluoroethyl, hydroxy, $C_{1-6}$ alkylsulphonyl, $(C_{1-6})$alkylsulphonyl$(C_{1-6})$alkyl, oxo, $C_{2-6}$ alkylcarbonyl, carboxy, carboxy$(C_{1-6})$alkyl, $C_{2-6}$ alkoxycarbonyl, $C_{2-6}$ alkoxycarbonyl$(C_{1-6})$alkyl, and a carboxylic acid isostere or prodrug moiety Ω as defined herein. Additional examples include $C_{1-6}$ alkyl and —$(C_{1-6})$alkyl-Ω, in which Ω is as defined herein. Additional examples include halogen, halo$(C_{1-6})$alkyl, cyano, nitro$(C_{1-6})$alkyl, trifluoromethyl, hydroxy$(C_{1-6})$alkyl, $C_{1-6}$ alkoxy, amino, $(C_{2-6})$alkylcarbonylamino$(C_{1-6})$alkyl, formyl, morpholinyl$(C_{1-6})$alkoxycarbonyl, $C_{2-6}$ alkoxycarbonylmethylidenyl, $C_{1-6}$ alkoxyaminocarbonyl and aminosulphonyl.

Examples of particular substituents on $R^{21}$ include one, two or three substituents independently selected from cyanoethyl, trifluoroethyl, hydroxy, methylsulphonyl, methylsulphonylethyl, oxo, acetyl, carboxy, carboxymethyl, carboxyethyl, tert-butoxycarbonyl, ethoxycarbonylmethyl, ethoxycarbonylethyl, tetrazolyl and methylsulphonylaminocarbonyl. Additional examples include methyl, methoxycarbonyl, ethoxycarbonyl, and tetrazolylmethyl. Additional examples include fluoro, fluoromethyl, cyano, nitromethyl, ethyl, isopropyl, trifluoromethyl, hydroxymethyl, methoxy, amino, acetylaminomethyl, formyl, n-butoxycarbonyl, morpholinylethoxycarbonyl, ethoxycarbonylmethylidenyl, hydroxyoxadiazolyl, methoxyaminocarbonyl, aminosulphonyl and acetylaminosulphonyl.

Particular examples of optional substituents on $R^{21}$ include one, two or three substituents independently selected from $C_{1-6}$ alkyl, oxo, carboxy, carboxy($C_{1-6}$)alkyl, $C_{2-6}$ alkoxycarbonyl, tetrazolyl and tetrazolyl($C_{1-6}$)alkyl. Additional examples include halogen, halo($C_{1-6}$)alkyl, cyano, nitro($C_{1-6}$)alkyl, trifluoromethyl, hydroxy, hydroxy($C_{1-6}$)alkyl, $C_{1-6}$ alkoxy, $C_{1-6}$ alkylsulphonyl, amino, ($C_{2-6}$)alkylcarbonylamino($C_{1-6}$)alkyl, formyl, morpholinyl($C_{1-6}$)alkoxycarbonyl, $C_{2-6}$ alkoxycarbonylmethylidenyl, hydroxyoxadiazolyl, $C_{1-6}$ alkoxyaminocarbonyl, $C_{1-6}$ alkylsulphonylaminocarbonyl, aminosulphonyl and $C_{2-6}$ alkylcarbonylaminosulphonyl.

Typical examples of particular substituents on $R^{21}$ include one, two or three substituents independently selected from methyl, oxo, carboxy, carboxyethyl, methoxycarbonyl, ethoxycarbonyl, tetrazolyl and tetrazolylmethyl. Additional examples include fluoro, fluoromethyl, cyano, nitromethyl, ethyl, isopropyl, trifluoromethyl, hydroxy, hydroxymethyl, methoxy, methylsulphonyl, amino, acetylaminomethyl, formyl, carboxymethyl, n-butoxycarbonyl, tert-butoxycarbonyl, morpholinylethoxycarbonyl, ethoxycarbonylmethylidenyl, hydroxyoxadiazolyl, methoxyaminocarbonyl, methylsulphonylaminocarbonyl, aminosulphonyl and acetylaminosulphonyl.

Selected examples of particular substituents on $R^{21}$ include one, two or three substituents independently selected from oxo and carboxy.

Typically, $R^{21}$ represents hydrogen, fluoro, cyano, methyl, trifluoromethyl, ethenyl, hydroxy, methoxy, isopropoxy, trifluoroethoxy, amino, dimethylamino, methoxyethylamino, N-(hydroxyethyl)-N-(methyl)amino, carboxy, pyrrolidinyl, hydroxypyrrolidinyl, piperidinyl, acetylpiperidinyl, carboxypiperidinyl, piperazinyl, cyanoethylpiperazinyl, trifluoroethylpiperazinyl, methylsulphonylpiperazinyl, methylsulphonylethylpiperazinyl, oxopiperazinyl, acetylpiperazinyl, tert-butoxycarbonylpiperazinyl, carboxymethyl-piperazinyl, carboxyethylpiperazinyl, ethoxycarbonylmethylpiperazinyl, ethoxycarbonyl-ethylpiperazinyl, morpholinyl, thiomorpholinyl, oxothiomorpholinyl, dioxothiomorpholinyl, oxodiazepanyl, dioxothiadiazepanyl, 2-oxa-5-azabicyclo[2.2.1]heptanyl, 2-oxa-6-azaspiro[3.3]heptanyl, 2-oxa-6-azaspiro[3.4]octanyl, 2-oxa-6-azaspiro[3.5]-nonanyl or 2-oxa-7-azaspiro[3.5]nonanyl. Additional values include N-[carboxyethyl]-N-methylamino, carboxycyclopentylamino, carboxycyclopropylmethylamino, ethoxycarbonylethyl, carboxycyclohexyl, carboxycyclohexenyl, ethoxycarbonylcyclohexenyl, carboxyazetidinyl, carboxypyrrolidinyl, (carboxy)(methyl)piperidinyl, ethoxycarbonylpiperidinyl, (methoxycarbonyl)(methyl)piperidinyl, (ethoxycarbonyl)(methyl)piperidinyl, tetrazolylpiperidinyl, tetrazolylmethylpiperazinyl, carboxymorpholinyl, carboxy-3-azabicyclo[3.1.0]hexanyl, ethoxycarbonyl-3-azabicyclo[3.1.0]hexanyl or carboxy-2-azaspiro[3.3]heptanyl. Additional values include fluoroisopropyl, hydroxyisopropyl, carboxycyclobutyloxy, methylthio, methylsulphonyl, methylamino, methylsulphonylamino, acetoxyisopropyl, fluoromethylcyclopropyl, acetylaminomethylcyclopropyl, hydroxycyclobutyl, carboxycyclopentyl, (carboxy)(methyl)cyclohexyl, (carboxy)-(hydroxy)cyclohexyl, carboxymethylcyclohexyl, ethoxycarbonylcyclohexyl, (methoxycarbonyl)(methyl)cyclohexyl, (ethoxycarbonyl)(methyl)cyclohexyl, carboxycyclohexylmethyl, carboxybicyclo[3.1.0]hexanyl, ethoxycarbonylbicyclo[3.1.0]hexanyl, carboxybicyclo[4.1.0]heptanyl, carboxybicyclo[2.2.2]octanyl, fluorooxetanyl, hydroxyoxetanyl, hydroxyazetidinyl, (hydroxy)(methyl)azetidinyl, (tert-butoxycarbonyl)-(hydroxy)azetidinyl, tetrazolylazetidinyl, hydroxytetrahydrofuranyl, (carboxy)(methyl)-pyrrolidinyl, carboxymethylpyrrolidinyl, ethoxycarbonylpyrrolidinyl, fluorotetrahydropyranyl, hydroxytetrahydropyranyl, difluoropiperidinyl, (cyano)(methyl)-piperidinyl, (hydroxy)(nitromethyl)piperidinyl, (hydroxy)(methyl)piperidinyl, (hydroxy)-(trifluoromethyl)piperidinyl, (hydroxymethyl)(methyl)piperidinyl, methylsulphonyl-piperidinyl, oxopiperidinyl, (formyl)(methyl)piperidinyl, (carboxy)(fluoro)piperidinyl, (carboxy)(ethyl)piperidinyl, (carboxy)(trifluoromethyl)piperidinyl, (carboxy)(hydroxy)-piperidinyl, (carboxy)(hydroxymethyl)piperidinyl, (carboxy)(methoxy)piperidinyl, (amino)(carboxy)piperidinyl, carboxymethylpiperidinyl, methoxycarbonylpiperidinyl, (ethoxycarbonyl)(fluoro)piperidinyl, (ethyl)(methoxycarbonyl)piperidinyl, (isopropyl)-(methoxycarbonyl)piperidinyl, (n-butoxycarbonyl)(methyl)piperidinyl, (ethoxycarbonyl)-(trifluoromethyl)piperidinyl, (ethoxycarbonyl)(hydroxymethyl)piperidinyl, (methoxy)-(methoxycarbonyl)piperidinyl, (carboxy)(methoxycarbonyl)piperidinyl, (methyl)-(morpholinylethoxycarbonyl)piperidinyl, ethoxycarbonylmethylpiperidinyl, hydroxyoxadiazolylpiperidinyl, methoxyaminocarbonylpiperidinyl, methylsulphonyl-aminocarbonylpiperidinyl, aminosulphonylpiperidinyl, acetylaminosulphonylpiperidinyl, carboxypiperazinyl, trioxohexahydro-[1,2,5]thiadiazolo[2,3-a]pyrazinyl, dimethylmorpholinyl, hydroxymethylmorpholinyl, (carboxy)(methyl)morpholinyl, carboxymethylmorpholinyl, carboxyazepanyl, carboxyoxazepanyl, (methyl)(oxo)diazepanyl, (carboxy)-(methyl)-3-azabicyclo[3.1.0]hexanyl, methoxycarbonyl-3-azabicyclo[3.1.0]hexanyl, carboxy-2-oxa-5-azabicyclo[2.2.1]heptanyl, carboxy-3-azabicyclo[3.1.1]heptanyl, carboxy-3-azabicyclo[4.1.0]heptanyl, methoxycarbonyl-3-azabicyclo[4.1.0]heptanyl, ethoxycarbonyl-3-azabicyclo[4.1.0]heptanyl, (hydroxy)(methyl)(oxo)-2-oxabicyclo[2.2.2]-octanyl, carboxy-3-azabicyclo[3.2.1]octanyl, methoxycarbonyl-3-azabicyclo[3.2.1]-octanyl, oxo-8-azabicyclo[3.2.1]octanyl, ethoxycarbonylmethylidenyl-8-azabicyclo[3.2.1]-octanyl, 3-oxa-8-azabicyclo[3.2.1]octanyl, oxo-3,6-diazabicyclo[3.2.2]nonanyl, carboxy-3-oxa-7-azabicyclo[3.3.1]nonanyl, carboxy-5-azaspiro[2.3]hexanyl, (carboxy)(methyl)-5-azaspiro[2.3]hexanyl, carboxy-5-azaspiro[2.4]heptanyl and (dioxo)(methyl)-2,4,8-triazaspiro[4.5]decanyl-.

Selected values of $R^{21}$ include fluoroisopropyl, hydroxy, hydroxyisopropyl, methoxy, carboxycyclobutyloxy, methylthio, methylsulphonyl, methylamino, methylsulphonylamino, N-[carboxyethyl]-N-methylamino, carboxycyclopentylamino, carboxycyclopropylmethylamino, acetoxyisopropyl, carboxy, ethoxycarbonylethyl, fluoromethylcyclopropyl, acetylaminomethylcyclopropyl, hydroxycyclobutyl, carboxycyclopentyl, carboxycyclohexyl, (carboxy)(methyl)cyclohexyl, (carboxy)(hydroxy)-cyclohexyl, carboxymethylcyclohexyl, ethoxycarbonylcyclohexyl, (methoxycarbonyl)-(methyl)cyclohexyl, (ethoxycarbonyl)(methyl)cyclohexyl, carboxycyclohexylmethyl, carboxycyclohexenyl, ethoxycarbonylcyclohexenyl, carboxybicyclo[3.1.0]hexanyl, ethoxycarbonylbicyclo[3.1.0]hexanyl, carboxybicyclo[4.1.0]heptanyl, carboxybicyclo-[2.2.2]octanyl, fluorooxetanyl, hydroxyoxetanyl, hydroxyazetidinyl, (hydroxy)(methyl)-azetidinyl, carboxyazetidinyl, (tert-butoxycarbonyl)(hydroxy)azetidinyl, tetrazolylazetidinyl, hydroxytetrahydrofuranyl, carboxypyrrolidinyl, (carboxy)(methyl)pyrrolidinyl, carboxymethylpyrrolidinyl, ethoxycarbonylpyrrolidinyl, fluorotetrahydropyranyl, hydroxytetrahydropyranyl, piperidinyl, difluoropiperidinyl, (cyano)(methyl) piperidinyl, (hydroxy)(nitromethyl)piperidinyl, (hydroxy) (methyl)piperidinyl, (hydroxy)-(trifluoromethyl)piperidinyl, (hydroxymethyl)(methyl)piperidinyl, methylsulphonyl-piperidinyl, oxopiperidinyl, (formyl)(methyl)piperidinyl, carboxypiperidinyl, (carboxy)-(fluoro)piperidinyl, (carboxy) (methyl)piperidinyl, (carboxy)(ethyl)piperidinyl, (carboxy)-(trifluoromethyl)piperidinyl, (carboxy)(hydroxy)piperidinyl, (carboxy)(hydroxymethyl)-piperidinyl, (carboxy)(methoxy) piperidinyl, (amino)(carboxy)piperidinyl, carboxymethylpiperidinyl, methoxycarbonylpiperidinyl, ethoxycarbonylpiperidinyl, (ethoxycarbonyl)-(fluoro)piperidinyl, (methoxycarbonyl)(methyl)piperidinyl, (ethyl)(methoxycarbonyl)-piperidinyl, (isopropyl)(methoxycarbonyl)piperidinyl, (ethoxycarbonyl)(methyl)-piperidinyl, (n-butoxycarbonyl)(methyl)piperidinyl, (ethoxycarbonyl)(trifluoromethyl)-piperidinyl, (ethoxycarbonyl)(hydroxymethyl)piperidinyl, (methoxy)(methoxycarbonyl)-piperidinyl, (carboxy)(methoxycarbonyl)piperidinyl, (methyl)(morpholinylethoxycarbonyl)piperidinyl, ethoxycarbonylmethylpiperidinyl, hydroxyoxadiazolylpiperidinyl, tetrazolylpiperidinyl, methoxyaminocarbonylpiperidinyl, methylsulphonyl-aminocarbonylpiperidinyl, aminosulphonylpiperidinyl, acetylaminosulphonylpiperidinyl, piperazinyl, oxopiperazinyl, methylsulphonylpiperazinyl, carboxypiperazinyl, carboxyethylpiperazinyl, tert-butoxycarbonylpiperazinyl, tetrazolylmethylpiperazinyl, trioxohexahydro-[1,2,5]thiadiazolo[2,3-a]pyrazinyl, morpholinyl, dimethylmorpholinyl, hydroxymethylmorpholinyl, carboxymorpholinyl, (carboxy) (methyl)morpholinyl, carboxymethylmorpholinyl, dioxothiomorpholinyl, carboxyazepanyl, carboxyoxazepanyl, oxodiazepanyl, (methyl)(oxo)diazepanyl, dioxothiadiazepanyl, carboxy-3-azabicyclo-[3.1.0]hexanyl, (carboxy) (methyl)-3-azabicyclo[3.1.0]hexanyl, methoxycarbonyl-3-azabicyclo[3.1.0]hexanyl, ethoxycarbonyl-3-azabicyclo [3.1.0]hexanyl, 2-oxa-5-azabicyclo[2.2.1]heptanyl, carboxy-2-oxa-5-azabicyclo[2.2.1]heptanyl, carboxy-3-azabicyclo [3.1.1]heptanyl, carboxy-3-azabicyclo[4.1.0]heptanyl, methoxycarbonyl-3-azabicyclo[4.1.0]heptanyl, ethoxycarbonyl-3-azabicyclo[4.1.0]heptanyl, (hydroxy)-(methyl) (oxo)-2-oxabicyclo[2.2.2]octanyl, carboxy-3-azabicyclo [3.2.1]octanyl, methoxycarbonyl-3-azabicyclo[3.2.1] octanyl, oxo-8-azabicyclo[3.2.1]octanyl, ethoxycarbonylmethylidenyl-8-azabicyclo[3.2.1]octanyl, 3-oxa-8-azabicyclo[3.2.1]-octanyl, oxo-3,6-diazabicyclo [3.2.2]nonanyl, carboxy-3-oxa-7-azabicyclo[3.3.1]nonanyl, (carboxy)(methyl)-5-azaspiro[2.3]hexanyl, carboxy-5-azaspiro[2.3]hexanyl, carboxy-5-azaspiro[2.4]heptanyl, carboxy-2-azaspiro[3.3]heptanyl and (dioxo)(methyl)-2,4,8-triazaspiro[4.5]decanyl.

Particular values of $R^{21}$ include hydroxy, methoxy, N-[carboxyethyl]-N-methylamino, carboxycyclopentylamino, carboxycyclopropylmethylamino, ethoxycarbonylethyl, carboxycyclohexyl, carboxycyclohexenyl, ethoxycarbonylcyclohexenyl, carboxyazetidinyl, carboxypyrrolidinyl, carboxypiperidinyl, (carboxy)(methyl)piperidinyl, ethoxycarbonylpiperidinyl, (methoxycarbonyl)(methyl) piperidinyl, (ethoxycarbonyl)-(methyl)piperidinyl, tetrazolylpiperidinyl, piperazinyl, oxopiperazinyl, carboxyethylpiperazinyl, tetrazolylmethylpiperazinyl, morpholinyl, carboxymorpholinyl, dioxothiomorpholinyl, oxodiazepanyl, dioxothiadiazepanyl, carboxy-3-azabicyclo[3.1.0]-hexanyl, ethoxycarbonyl-3-azabicyclo[3.1.0]hexanyl, 2-oxa-5-azabicyclo[2.2.1]heptanyl and carboxy-2-azaspiro[3.3]heptanyl.

Illustrative values of $R^{21}$ include hydroxy, methoxy, carboxypiperidinyl, piperazinyl, oxopiperazinyl, morpholinyl, dioxothiomorpholinyl, oxodiazepanyl, dioxothiadiazepanyl and 2-oxa-5-azabicyclo[2.2.1]heptanyl.

In a particular embodiment, $R^{21}$ represents hydroxy($C_{1-6}$) alkyl. In one aspect of that embodiment, $R^{21}$ represents hydroxyisopropyl, especially 2-hydroxyprop-2-yl.

Generally, $R^{22}$ represents hydrogen or $C_{1-6}$ alkyl.

Suitably, $R^{22}$ represents hydrogen, chloro or methyl.

Typically, $R^{22}$ represents hydrogen or methyl.

In one embodiment, $R^{22}$ represents hydrogen. In another embodiment, $R^{22}$ represents $C_{1-6}$ alkyl, especially methyl. In a further embodiment, $R^{22}$ represents halogen. In one aspect of that embodiment, $R^{22}$ represents fluoro. In another aspect of that embodiment, $R^{22}$ represents chloro.

Generally, $R^{23}$ represents hydrogen or $C_{1-6}$ alkyl.

Suitably, $R^{23}$ represents hydrogen, methyl, trifluoromethyl or methoxy.

Typically, $R^{23}$ represents hydrogen or methyl.

In one embodiment, $R^{23}$ represents hydrogen. In another embodiment, $R^{23}$ represents $C_{1-6}$ alkyl, especially methyl. In a further embodiment, $R^{23}$ represents trifluoromethyl. In an additional embodiment, $R^{23}$ represents $C_{1-6}$ alkoxy, especially methoxy.

Particular sub-groups of the compounds of formula (IIB) above are represented by the compounds of formula (IIC), (IID) and (IIE) and N-oxides thereof, and pharmaceutically acceptable salts and solvates thereof, and glucuronide derivatives thereof, and co-crystals thereof:

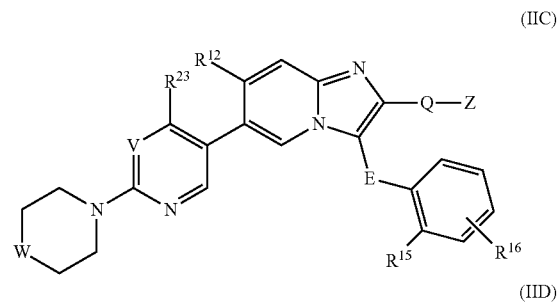

(IIC)

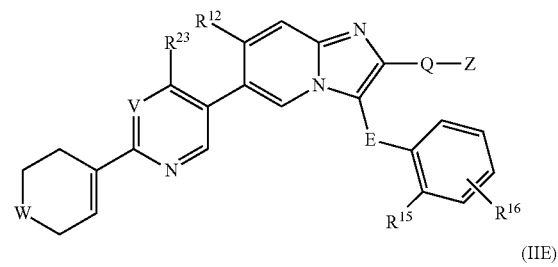

(IID)

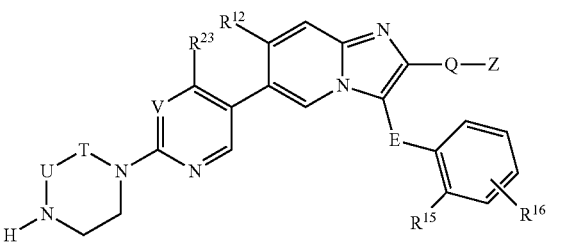

(IIE)

wherein
T represents —$CH_2$— or —$CH_2CH_2$—;
U represents C(O) or S(O)$_2$;
W represents O, S, S(O), S(O)$_2$, N($R^{31}$) or C($R^{32}$)($R^{33}$);

$R^{31}$ represents hydrogen, cyano($C_{1-6}$)alkyl, $C_{1-6}$ alkyl, trifluoromethyl, trifluoroethyl, $C_{1-6}$ alkylsulphonyl, ($C_{1-6}$)alkylsulphonyl($C_{1-6}$)alkyl, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, a carboxylic acid isostere or prodrug moiety Ω, —($C_{1-6}$)alkyl-Ω, aminocarbonyl, $C_{1-6}$ alkylaminocarbonyl, di($C_{1-6}$)alkylaminocarbonyl, aminosulphonyl or di($C_{1-6}$)alkylaminosulphonyl;

$R^{32}$ represents hydrogen, halogen, cyano, hydroxy, hydroxy($C_{1-6}$)alkyl, $C_{1-6}$ alkylsulphonyl, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, aminosulphonyl, a carboxylic acid isostere or prodrug moiety Ω, or —($C_{1-6}$)alkyl-Ω;

$R^{33}$ represents hydrogen, halogen, $C_{1-6}$ alkyl, trifluoromethyl, hydroxy, hydroxy-($C_{1-6}$)alkyl, $C_{1-6}$ alkoxy, amino or carboxy; and V, E, Q, Z, $R^{12}$, $R^{15}$, $R^{16}$, $R^{23}$ and Ω are as defined above.

In a first embodiment, T represents —$CH_2$—. In a second embodiment, T represents —$CH_2CH_2$—.

In a first embodiment, U represents C(O). In a second embodiment, U represents $S(O)_2$.

In one aspect, W represents O, S, S(O), $S(O)_2$, $N(R^{31})$, $CF_2$, $CH(CO_2H)$ or CH(tetrazolyl).

Generally, W represents O, $S(O)_2$, $N(R^{31})$ or $C(R^{32})(R^{33})$.

Suitably, W represents O, S, S(O), $S(O)_2$, $N(R^{31})$ or $CH(CO_2H)$.

Typically, W represents O, $S(O)_2$, $N(R^{31})$ or $CH(CO_2H)$.

In a first embodiment, W represents O. In a second embodiment, W represents S. In a third embodiment, W represents S(O). In a fourth embodiment, W represents $S(O)_2$. In a fifth embodiment, W represents $N(R^{31})$. In a sixth embodiment, W represents $C(R^{32})(R^{33})$.

In a first aspect of the sixth embodiment, W represents $CF_2$. In a second aspect of the sixth embodiment, W represents $CH(CO_2H)$. In a third aspect of the sixth embodiment, W represents CH(tetrazolyl).

In one aspect, $R^{31}$ represents hydrogen, cyano($C_{1-6}$)alkyl, $C_{1-6}$ alkyl, trifluoromethyl, trifluoroethyl, $C_{1-6}$ alkylsulphonyl, ($C_{1-6}$)alkylsulphonyl($C_{1-6}$)alkyl, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl-($C_{1-6}$)alkyl, aminocarbonyl, $C_{1-6}$ alkylaminocarbonyl, di($C_{1-6}$)alkylaminocarbonyl, aminosulphonyl, $C_{1-6}$ alkylaminosulphonyl or di($C_{1-6}$)alkylaminosulphonyl.

Suitably, $R^{31}$ represents hydrogen, cyano($C_{1-6}$)alkyl, trifluoroethyl, $C_{1-6}$ alkylsulphonyl, ($C_{1-6}$)alkylsulphonyl($C_{1-6}$)alkyl, $C_{2-6}$ alkylcarbonyl, carboxy($C_{1-6}$)alkyl, $C_{2-6}$ alkoxycarbonyl or $C_{2-6}$ alkoxycarbonyl($C_{1-6}$)alkyl. Additionally, $R^{31}$ may represent tetrazolyl($C_{1-6}$)alkyl. Additionally, $R^{31}$ may represent $C_{1-6}$ alkyl.

Appositely, $R^{31}$ represents hydrogen, $C_{1-6}$ alkyl, $C_{1-6}$ alkylsulphonyl, carboxy-($C_{1-6}$)alkyl, $C_{2-6}$ alkoxycarbonyl or tetrazolyl($C_{1-6}$)alkyl.

Typically, $R^{31}$ represents hydrogen, carboxy($C_{1-6}$)alkyl or tetrazolyl($C_{1-6}$)alkyl.

Typical values of $R^{31}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, aminocarbonyl, methylaminocarbonyl, dimethylaminocarbonyl, aminosulphonyl, methylaminosulphonyl and dimethylaminosulphonyl. An additional value is tetrazolylmethyl.

Selected values of $R^{31}$ include hydrogen, cyanoethyl, trifluoroethyl, methylsulphonyl, methylsulphonylethyl, acetyl, carboxymethyl, carboxyethyl, tert-butoxycarbonyl, ethoxycarbonylmethyl and ethoxycarbonylethyl. An additional value is tetrazolylmethyl. An additional value is methyl.

Apposite values of $R^{31}$ include hydrogen, methyl, methylsulphonyl, carboxymethyl, carboxyethyl, tert-butoxycarbonyl and tetrazolylmethyl.

Suitable values of $R^{31}$ include hydrogen, carboxyethyl and tetrazolylmethyl.

A particular value of $R^{31}$ is hydrogen.

Generally, $R^{32}$ represents halogen, carboxy, carboxy($C_{1-6}$)alkyl, $C_{2-6}$ alkoxycarbonyl, $C_{2-6}$ alkoxycarbonyl($C_{1-6}$)alkyl, a carboxylic acid isostere or prodrug moiety Ω, or —($C_{1-6}$)alkyl-Ω.

Suitably, $R^{32}$ represents hydrogen, halogen, cyano, hydroxy, hydroxy($C_{1-6}$)alkyl, $C_{1-6}$ alkylsulphonyl, formyl, carboxy, carboxy($C_{1-6}$)alkyl, $C_{2-6}$ alkoxycarbonyl, $C_{2-6}$ alkoxycarbonyl($C_{1-6}$)alkyl, aminosulphonyl, ($C_{1-6}$)alkoxyaminocarbonyl, ($C_{1-6}$)alkylsulphonylaminocarbonyl, ($C_{2-6}$)alkylcarbonylaminosulphonyl, hydroxyoxadiazolyl or tetrazolyl.

Typically, $R^{32}$ represents carboxy, $C_{2-6}$ alkoxycarbonyl or tetrazolyl.

Selected values of $R^{32}$ include hydrogen, fluoro, cyano, hydroxy, hydroxymethyl, methylsulphonyl, formyl, carboxy, carboxymethyl, methoxycarbonyl, ethoxycarbonyl, tert-butoxycarbonyl, ethoxycarbonylmethyl, aminosulphonyl, methoxyaminocarbonyl, methylsulphonylaminocarbonyl, acetylaminosulphonyl, hydroxyoxadiazolyl or tetrazolyl.

Typical values of $R^{32}$ include fluoro, carboxy, carboxymethyl, carboxyethyl, methoxycarbonyl, ethoxycarbonyl, methoxycarbonylmethyl, methoxycarbonylethyl, ethoxycarbonylmethyl, ethoxycarbonylethyl, tetrazolyl, tetrazolylmethyl and tetrazolylethyl.

Particular values of $R^{32}$ include carboxy, methoxycarbonyl, ethoxycarbonyl and tetrazolyl.

In a selected embodiment, $R^{32}$ represents carboxy.

Generally, $R^{33}$ represents hydrogen, halogen or $C_{1-6}$ alkyl.

Suitably, $R^{33}$ represents hydrogen or $C_{1-6}$ alkyl.

Selected values of $R^{33}$ include hydrogen, fluoro, methyl, ethyl, isopropyl, trifluoromethyl, hydroxy, hydroxymethyl, methoxy, amino and carboxy.

In a first embodiment, $R^{33}$ represents hydrogen. In a second embodiment, $R^{33}$ represents halogen. In one aspect of that embodiment, $R^{33}$ represents fluoro. In a third embodiment, $R^{33}$ represents $C_{1-6}$ alkyl. In a first aspect of that embodiment, $R^{33}$ represents methyl. In a second aspect of that embodiment, $R^{33}$ represents ethyl. In a third aspect of that embodiment, $R^{33}$ represents isopropyl. In a fourth embodiment, $R^{33}$ represents trifluoromethyl. In a fifth embodiment, $R^{33}$ represents hydroxy. In a sixth embodiment, $R^{33}$ represents hydroxy($C_{1-6}$)alkyl. In one aspect of that embodiment, $R^{33}$ represents hydroxymethyl. In a seventh embodiment, $R^{33}$ represents $C_{1-6}$ alkoxy. In one aspect of that embodiment, $R^{33}$ represents methoxy. In an eighth embodiment, $R^{33}$ represents amino. In a ninth embodiment, $R^{33}$ represents carboxy.

Another sub-group of the compounds of formula (IIB) above is represented by the compounds of formula (IIF) and N-oxides thereof, and pharmaceutically acceptable salts and solvates thereof, and glucuronide derivatives thereof, and co-crystals thereof:

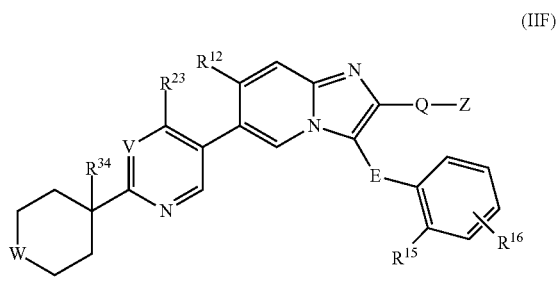

(IIF)

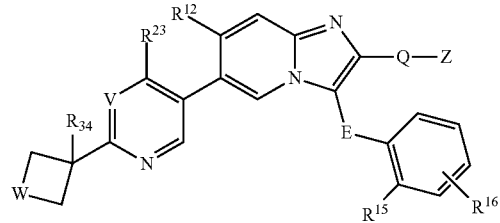

(IIG)

wherein

R$^{34}$ represents hydrogen, halogen, halo(C$_{1-6}$)alkyl, hydroxy, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino, di(C$_{1-6}$)alkylamino, (C$_{2-6}$)alkylcarbonylamino, (C$_{2-6}$)alkylcarbonylamino(C$_{1-6}$) alkyl, (C$_{1-6}$)alkylsulphonylamino or (C$_{1-6}$)alkylsulphonylamino(C$_{1-6}$)alkyl; and E, Q, Z, V, W, R$^{12}$, R$^{15}$, R$^{16}$ and R$^{23}$ are as defined above.

In a first embodiment, R$^{34}$ represents hydrogen. In a second embodiment, R$^{34}$ represents halogen. In one aspect of that embodiment, R$^{34}$ represents fluoro. In a third embodiment, R$^{34}$ represents halo(C$_{1-6}$)alkyl. In one aspect of that embodiment, R$^{34}$ represents fluoromethyl. In a fourth embodiment, R$^{34}$ represents hydroxy. In a fifth embodiment, R$^{34}$ represents C$_{1-6}$ alkoxy, especially methoxy. In a sixth embodiment, R$^{34}$ represents C$_{1-6}$ alkylthio, especially methylthio. In a seventh embodiment, R$^{34}$ represents C$_{1-6}$ alkylsulphinyl, especially methylsulphinyl. In an eighth embodiment, R$^{34}$ represents C$_{1-6}$ alkylsulphonyl, especially methylsulphonyl. In a ninth embodiment, R$^{34}$ represents amino. In a tenth embodiment, R$^{34}$ represents C$_{1-6}$ alkylamino, especially methylamino. In an eleventh embodiment, R$^{34}$ represents di(C$_{1-6}$)alkylamino, especially dimethylamino. In a twelfth embodiment, R$^{34}$ represents (C$_{2-6}$)alkylcarbonylamino, especially acetylamino. In a thirteenth embodiment, R$^{34}$ represents (C$_{2-6}$)alkylcarbonylamino(C$_{1-6}$)alkyl, especially acetylaminomethyl. In a fourteenth embodiment, R$^{34}$ represents (C$_{1-6}$)alkylsulphonylamino, especially methylsulphonylamino. In a fifteenth embodiment, R$^{34}$ represents (C$_{1-6}$)alkylsulphonylamino(C$_{1-6}$)alkyl, especially methylsulphonylaminomethyl.

Typically, R$^{34}$ represents hydrogen, halogen, halo(C$_{1-6}$)alkyl, hydroxy or (C$_{2-6}$)alkylcarbonylamino(C$_{1-6}$)alkyl.

Selected values of R$^{34}$ include hydrogen, fluoro, fluoromethyl, hydroxy, methoxy, methylthio, methylsulphinyl, methylsulphonyl, amino, methylamino, dimethylamino and acetylaminomethyl.

Particular values of R$^{34}$ include hydrogen, fluoro, fluoromethyl, hydroxy and acetylaminomethyl.

Suitably, R$^{34}$ represents hydrogen or hydroxy.

Further sub-groups of the compounds of formula (IIB) above are represented by the compounds of formula (IIG), (IIH), (IIJ), (IIK) and (IIL) and N-oxides thereof, and pharmaceutically acceptable salts and solvates thereof, and glucuronide derivatives thereof, and co-crystals thereof:

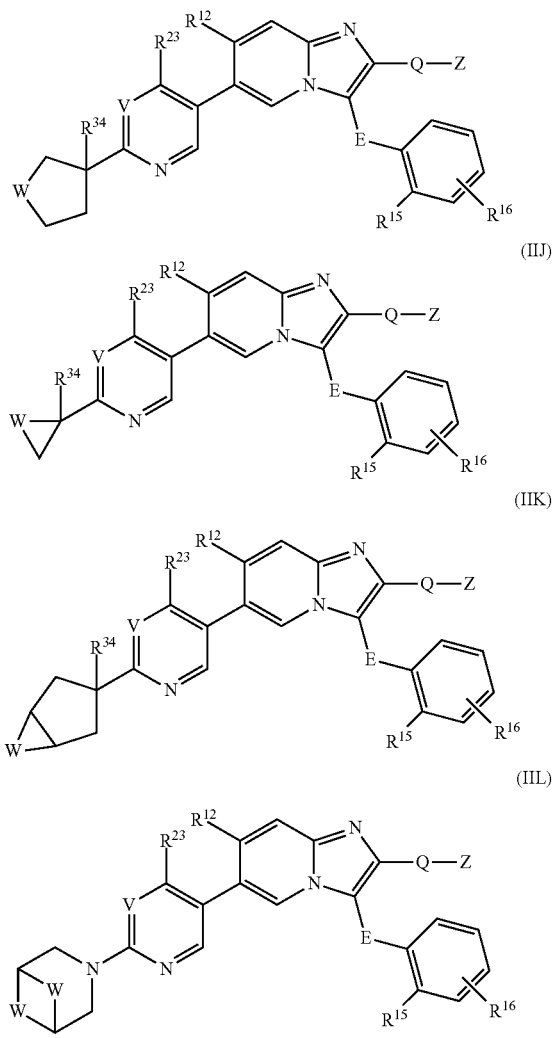

wherein

-M- represents —CH$_2$— or —CH$_2$CH$_2$—; and

E, Q, Z, V, W, R$^{12}$, R$^{15}$, R$^{16}$, R$^{23}$ and R$^{34}$ are as defined above.

In one embodiment, -M- represents —CH$_2$—. In another embodiment, -M- represents —CH$_2$CH$_2$—.

An alternative sub-class of compounds according to the invention is represented by the compounds of formula (IIM) and N-oxides thereof, and pharmaceutically acceptable salts and solvates thereof, and glucuronide derivatives thereof, and co-crystals thereof:

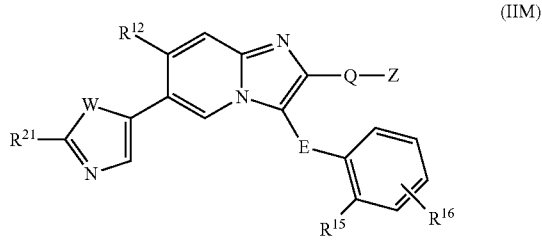

(IIM)

wherein

E, Q, Z, W, $R^{12}$, $R^{15}$, $R^{16}$ and $R^{21}$ are as defined above.

With specific reference to formula (IIM), the integer W is suitably O, S or N—$R^{31}$, especially S or N—$R^{31}$.

Specific novel compounds in accordance with the present invention include each of the compounds whose preparation is described in the accompanying Examples, and pharmaceutically acceptable salts and solvates thereof, and co-crystals thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, polymyositis, scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule such as methotrexate or prednisolone.

The compounds of formula (I) above may be prepared by a process which comprises reacting a compound of formula (III) with a compound of formula (IV):

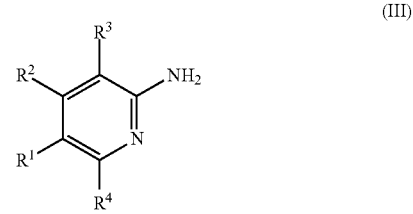

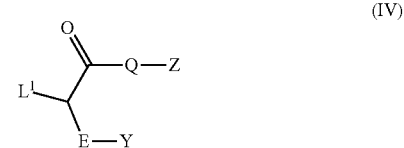

wherein E, Q, Y, Z, $R^1$, $R^2$, $R^3$ and $R^4$ are as defined above, and $L^1$ represents a suitable leaving group.

The leaving group $L^1$ is typically a halogen atom, e.g. bromo.

The reaction is conveniently effected at an elevated temperature in a suitable solvent, e.g. a $C_{1-4}$ alkanol such as ethanol, or a cyclic ether such as 1,4-dioxane.

The compounds of formula (I) above wherein E represents —C(O)— may be prepared by a process which comprises reacting a compound of formula (V) with a compound of formula (VI):

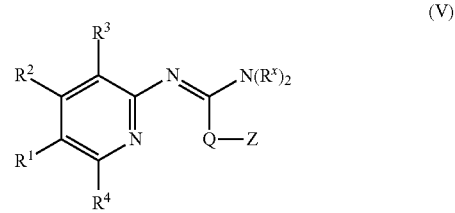

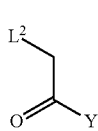
(VI)

wherein Q, Y, Z, $R^1$, $R^2$, $R^3$ and $R^4$ are as defined above, $R^x$ represents a $C_{1-4}$ alkyl group, e.g. methyl, and $L^2$ represents a suitable leaving group.

The leaving group $L^2$ is typically a halogen atom, e.g. bromo.

The reaction is conveniently effected at ambient or elevated temperature in a suitable solvent, e.g. a dipolar aprotic solvent such as N,N-dimethylformamide, a hydrocarbon solvent such as toluene, or a $C_{1-4}$ alkanol such as ethanol.

The intermediates of formula (V) above may be prepared by reacting a compound of formula (III) as defined above with a compound of formula (VII):

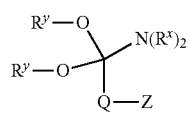
(VII)

wherein Q, Z and $R^x$ are as defined above, and $R^y$ represents a $C_{1-4}$ alkyl group, e.g. methyl.

The reaction is conveniently effected at an elevated temperature in a suitable solvent, e.g. a hydrocarbon solvent such as toluene, or a $C_{1-4}$ alkanol such as methanol.

The compounds of formula (I) above wherein E represents —CH(OH)— may be prepared by a process which comprises reacting a compound of formula Y—MgHal with a compound of formula (VIII):

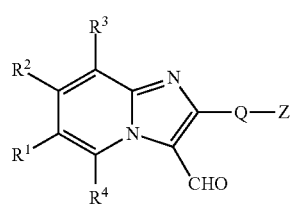
(VIII)

wherein Q, Y, Z, $R^1$, $R^2$, $R^3$ and $R^4$ are as defined above, and Hal represents a halogen atom.

The halogen atom Hal is typically bromo.

The reaction is conveniently effected at ambient temperature in a suitable solvent, e.g. a cyclic ether such as tetrahydrofuran.

The intermediates of formula (VIII) above may be prepared by treating a compound of formula (IX):

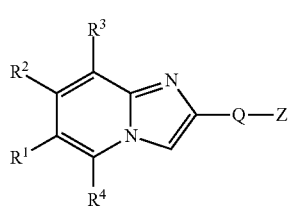
(IX)

wherein Q, Z, $R^1$, $R^2$, $R^3$ and $R^4$ are as defined above; with (chloromethylene)dimethyliminium chloride (Vilsmeier reagent).

The reaction is conveniently effected at an elevated temperature in a suitable solvent, e.g. a dipolar aprotic solvent such as N,N-dimethylformamide.

The compounds of formula (I) above wherein E represents —CH$_2$— and Y represents optionally substituted aryl or heteroaryl may be prepared by a process which comprises reacting a compound of formula $Y^1$—H with a compound of formula (X):

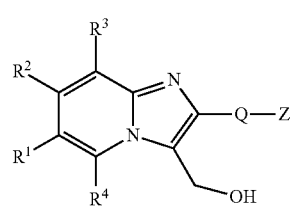
(X)

wherein Q, Z, $R^1$, $R^2$, $R^3$ and $R^4$ are as defined above, and $Y^1$ represents aryl or heteroaryl, either of which groups may be optionally substituted by one or more substituents; in the presence of a sulfonic acid derivative.

The sulfonic acid derivative of use in the foregoing reaction is suitably an organic sulfonic acid derivative such as methanesulfonic acid. The reaction is conveniently effected at an elevated temperature in a suitable solvent, e.g. water.

The intermediates of formula (X) above may be prepared by treating a compound of formula (IX) as defined above with formaldehyde. The reaction is conveniently effected at an elevated temperature in a suitable solvent, e.g. water.

The intermediates of formula (IX) above may be prepared by reacting a compound of formula (III) as defined above with a compound of formula (XI):

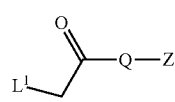
(XI)

wherein Q, Z and $L^1$ are as defined above; under conditions analogous to those described above for the reaction between compounds (III) and (IV).

The compounds of formula (I) above wherein -Q-Z represents —CH$_2$OH may be prepared by a process which comprises treating a compound of formula (XII):

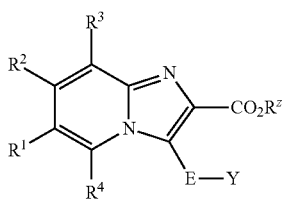
(XII)

wherein E, Y, $R^1$, $R^2$, $R^3$ and $R^4$ are as defined above, and $R^z$ represents a $C_{1-4}$ alkyl group, e.g. methyl; with a reducing agent.

The reducing agent of use in the foregoing reaction is suitably an alkali metal borohydride such as lithium borohydride. The reaction is conveniently effected at ambient temperature in a suitable solvent, e.g. a cyclic ether such as tetrahydrofuran, or a $C_{1-4}$ alkanol such as methanol, or a mixture thereof.

Alternatively, the reducing agent of use in the foregoing reaction may suitably be diisobutylaluminium hydride. The reaction is conveniently effected at a temperature in the region of 0° C. in a suitable solvent, e.g. a cyclic ether such as tetrahydrofuran.

The intermediates of formula (XII) above may be prepared by reacting a compound of formula (III) as defined above with a compound of formula (XIII):

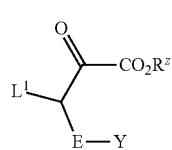

(XIII)

wherein E, Y, $R^z$ and $L^1$ are as defined above; under conditions analogous to those described above for the reaction between compounds (III) and (IV).

The compounds of formula (I) above wherein E represents —N(H)— may be prepared by a process which comprises reacting a compound of formula (III) as defined above with an isocyanide derivative of formula Y—NC and an aldehyde derivative of formula OHC-Q-Z; in the presence of a transition metal catalyst.

The transition metal catalyst of use in the foregoing reaction is suitably a zirconium derivative, e.g. a zirconium halide such as zirconium(IV) chloride. The reaction is conveniently effected at an elevated temperature in a suitable solvent, e.g. a $C_{1-4}$ alkanol such as n-butanol.

The compounds of formula (I) above wherein Q represents —$CH_2N(H)$— may be prepared by a process which comprises reacting a compound of formula Z—$NH_2$ with a compound of formula (XIV):

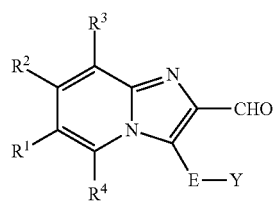

(XIV)

wherein E, Y, $R^1$, $R^2$, $R^3$ and $R^4$ are as defined above; in the presence of a reducing agent.

The reducing agent of use in the above reaction is suitably sodium borohyride.

The intermediates of formula (XIV) may be prepared from the corresponding compound of formula (I) wherein Q-Z represents —$CH_2OH$ by treatment with an oxidising agent such as Dess-Martin periodinane.

Where they are not commercially available, the starting materials of formula (III), (IV), (VI), (VII), (XI) and (XIII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) wherein E represents —C(O)— may be converted into the corresponding compound wherein E represents —CH(OH)— by treatment with a reducing agent such as sodium borohydride.

A compound of formula (I) wherein E represents —CH(OH)— may be converted into the corresponding compound wherein E represents —$CH_2$— by heating with elemental iodine and phosphinic acid in acetic acid; or by treating with triethylsilane and an acid, e.g. an organic acid such as trifluoroacetic acid, or a Lewis acid such as boron trifluoride diethyl etherate; or by a two-step procedure which comprises: (i) treatment with thionyl bromide; and (ii) treatment of the product thereby obtained with a transition metal catalyst, e.g. (2,2'-bipyridine)dichlororuthenium(II) hydrate, in the presence of diethyl 1,4-dihydro-2,6-dimethyl-3,5-pyridinedicarboxylate (Hantzsch ester) and a base, e.g. an organic base such as N,N-diisopropylethylamine.

A compound of formula (I) wherein E represents —$CH_2$— may be converted into the corresponding compound wherein E represents —$CH(CH_3)$— by treatment with a methyl halide, e.g. methyl iodide, in the presence of a base such as lithium hexamethyldisilazide.

A compound of formula (I) which contains a hydroxy group may be alkylated by treatment with the appropriate alkyl halide in the presence of a base, e.g. sodium hydride, or silver oxide. A compound of formula (I) wherein -Q-Z represents —$CH_2OH$ may be arylated in a two-step procedure which comprises: (i) treatment with thionyl chloride; and (ii) treatment of the chloro derivative thereby obtained with the appropriate aryl or heteroaryl hydroxide. A compound of formula (I) wherein -Q-Z represents —$CH_2OH$ may be converted into the corresponding compound of formula (I) wherein -Q-Z represents —$CH_2S$—Z via a two-step procedure which comprises: (i) treatment with thionyl chloride; and (ii) treatment of the chloro derivative thereby obtained with a compound of formula Z—SH, typically in the presence of a base, e.g. an inorganic base such as potassium carbonate. A compound of formula (I) wherein -Q-Z represents —$CH_2OH$ may be converted into the corresponding compound of formula (I) wherein -Q-Z represents —$CH_2CN$ via a two-step procedure which comprises: (i) treatment with thionyl chloride; and (ii) treatment of the chloro derivative thereby obtained with a cyanide salt such as sodium cyanide. A compound of formula (I) which contains hydroxy may be converted into the corresponding fluoro-substituted compound by treatment with diethylaminosulfur trifluoride (DAST) or bis(2-methoxyethyl)aminosulfur trifluoride (BAST). A compound of formula (I) which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound of formula (I) which contains an N—H moiety may be alkylated by treatment with the appropriate alkyl halide, typically at an elevated temperature in an organic solvent such as acetonitrile; or at ambient temperature in the presence of a base, e.g. an alkali metal carbonate such as potassium carbonate or cesium carbonate, in a suitable solvent, e.g. a dipolar aprotic solvent such as N,N-dimethylformamide. Alternatively, a compound of formula (I) which contains an N—H moiety may be alkylated by treatment with the appropriate alkyl tosylate in the presence of a base, e.g. an inorganic base such as sodium hydride, or an organic base such as 1,8-diazabicyclo[5.4.0]undec-7-ene (DBU).

A compound of formula (I) which contains an N—H moiety may be methylated by treatment with formaldehyde in the presence of a reducing agent, e.g. sodium triacetoxyborohydride.

A compound of formula (I) which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine.

A compound of formula (I) which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonic acid anhydride, e.g. methanesulphonic anhydride, typically at ambient temperature in the presence of a base, e.g. an organic base such as N,N-diisopropylethylamine.

A compound of formula (I) substituted by amino (—$NH_2$) may be converted into the corresponding compound substituted by $C_{1-6}$ alkylsulphonylamino, e.g. methylsulphonylamino, or bis[($C_{1-6}$)alkylsulphonyl]amino, e.g. bis(methylsulphonyl)amino, by treatment with the appropriate $C_{1-6}$ alkylsulphonyl halide, e.g. a $C_{1-6}$ alkylsulphonyl chloride such as methanesulphonyl chloride. Similarly, a compound of formula (I) substituted by hydroxy (—OH) may be converted into the corresponding compound substituted by $C_{1-6}$ alkylsulphonyloxy, e.g. methylsulphonyloxy, by treatment with the appropriate $C_{1-6}$ alkylsulphonyl halide, e.g. a $C_{1-6}$ alkylsulphonyl chloride such as methanesulphonyl chloride.

A compound of formula (I) containing the moiety —S— may be converted into the corresponding compound containing the moiety —S(O)— by treatment with 3-chloroperoxybenzoic acid. Likewise, a compound of formula (I) containing the moiety —S(O)— may be converted into the corresponding compound containing the moiety —$S(O)_2$— by treatment with 3-chloroperoxybenzoic acid. Alternatively, a compound of formula (I) containing the moiety —S— may be converted into the corresponding compound containing the moiety —$S(O)_2$— by treatment with Oxone® (potassium peroxymonosulfate).

A compound of formula (I) containing an aromatic nitrogen atom may be converted into the corresponding N-oxide derivative by treatment with 3-chloroperoxybenzoic acid.

A bromophenyl derivative of formula (I) may be converted into the corresponding optionally substituted 2-oxopyrrolidin-1-ylphenyl or 2-oxooxazolidin-3-ylphenyl derivative by treatment with pyrrolidin-2-one or oxazolidin-2-one, or an appropriately substituted analogue thereof. The reaction is conveniently effected at an elevated temperature in the presence of copper(I) iodide, trans-N,N'-dimethylcyclohexane-1,2-diamine and an inorganic base such as potassium carbonate.

A compound of formula (I) wherein $R^1$ represents halogen, e.g. bromo, may be converted into the corresponding compound wherein $R^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected in the presence of a transition metal catalyst, e.g. [1,1'-bis(diphenylphosphino)ferrocene]dichloropalladium(II), tetrakis (triphenylphosphine)palladium(0), or bis[3-(diphenylphosphanyl)cyclopenta-2,4-dien-1-yl]iron-dichloropalladium-dichloromethane complex, or tetrakis(triphenylphosphine) palladium(0), and a base, e.g. an inorganic base such as sodium carbonate or potassium carbonate, or potassium phosphate.

A compound of formula (I) wherein $R^1$ represents halogen, e.g. bromo, may be converted into the corresponding compound wherein $R^1$ represents an optionally substituted aryl, heteroaryl or heterocycloalkenyl moiety via a two-step procedure which comprises: (i) reaction with bis(pinacolato) diboron or bis(neopentyl glycolato)diboron; and (ii) reaction of the compound thereby obtained with an appropriately functionalised halo- or tosyloxy-substituted aryl, heteroaryl or heterocycloalkenyl derivative. Step (i) is conveniently effected in the presence of a transition metal catalyst such as [1,1'-bis-(diphenylphosphino)ferrocene]dichloropalladium (II), or bis[3-(diphenylphosphanyl)-cyclopenta-2,4-dien-1-yl]iron-dichloropalladium-dichloromethane complex. Step (ii) is conveniently effected in the presence of a transition metal catalyst such as tetrakis-(triphenylphosphine)palladium(0), or bis[3-(diphenylphosphanyl)cyclopenta-2,4-dien-1-yl]iron-dichloropalladium-dichloromethane complex, and a base, e.g. an inorganic base such as sodium carbonate or potassium carbonate.

A compound of formula (I) wherein $R^1$ represents halogen, e.g. bromo, may be converted into the corresponding compound wherein $R^1$ represents an optionally substituted $C_{2-6}$ alkynyl moiety by treatment with an appropriately substituted alkyne derivative, e.g. 2-hydroxybut-3-yne. The reaction is conveniently accomplished with the assistance of a transition metal catalyst, e.g. tetrakis(triphenylphosphine)palladium (0), typically in the presence of copper(I) iodide and a base, e.g. an organic base such as triethylamine.

A compound of formula (I) wherein $R^1$ represents halogen, e.g. bromo, may be converted into the corresponding compound wherein $R^1$ represents an optionally substituted imidazol-1-yl moiety by treatment with the appropriately substituted imidazole derivative, typically in the presence of copper (II) acetate and an organic base such as N,N,N',N'-tetramethylethylenediamine (TMEDA).

A compound of formula (I) wherein $R^1$ represents halogen, e.g. bromo, may be converted into the corresponding compound wherein $R^1$ represents 2-(methoxycarbonyl)-ethyl via a two-step procedure which comprises: (i) reaction with methyl acrylate; and (ii) catalytic hydrogenation of the alkenyl derivative thereby obtained, typically by treatment with a hydrogenation catalyst, e.g. palladium on charcoal, under an atmosphere of hydrogen gas. Step (i) is typically effected in the presence of a transition metal catalyst, e.g. palladium (II) acetate or bis(dibenzylideneacetone)palladium(0), and a reagent such as tri(ortho-tolyl)phosphine.

In general, a compound of formula (I) containing a —C≡C— functionality may be converted into the corresponding compound containing a —CH—CH— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide.

A compound of formula (I) wherein $R^1$ represents 6-methoxypyridin-3-yl may be converted into the corresponding compound wherein $R^1$ represents 2-oxo-1,2-dihydropyridin-5-yl by treatment with pyridine hydrochloride; or by heating with a mineral acid such as hydrochloric acid. By utilising similar methodology, a compound of formula (I) wherein $R^1$ represents 6-methoxy-4-methylpyridin-3-yl may be converted into the corresponding compound wherein $R^1$ represents 4-methyl-2-oxo-1,2-dihydropyridin-5-yl; and a compound of formula (I) wherein $R^1$ represents 6-methoxy-5- methylpyridin-3-yl may be converted into the corresponding compound wherein $R^1$ represents 3-methyl-2-oxo-1,2-dihydropyridin-5-yl.

A compound of formula (I) wherein $R^1$ represents 2-oxo-1,2-dihydropyridin-5-yl may be converted into the corresponding compound wherein $R^1$ represents 2-oxopiperidin-5-yl by catalytic hydrogenation, typically by treatment with gaseous hydrogen in the presence of a hydrogenation catalyst such as platinum(IV) oxide.

A compound of formula (I) containing an ester moiety, e.g. a $C_{2-6}$ alkoxycarbonyl group such as methoxycarbonyl or ethoxycarbonyl, may be converted into the corresponding compound containing a carboxy (—$CO_2H$) moiety by treatment with an acid, e.g. a mineral acid such as hydrochloric acid.

A compound of formula (I) containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

A compound of formula (I) containing an ester moiety, e.g. a $C_{2-6}$ alkoxycarbonyl group such as methoxycarbonyl or ethoxycarbonyl, may alternatively be converted into the corresponding compound containing a carboxy (—$CO_2H$) moiety by treatment with a base, e.g. an alkali metal hydroxide selected from lithium hydroxide, sodium hydroxide and potassium hydroxide; or an organic base such as sodium methoxide or sodium ethoxide.

A compound of formula (I) containing a carboxy (—$CO_2H$) moiety may be converted into the corresponding compound containing an amide moiety by treatment with the appropriate amine in the presence of a condensing agent such as 1-ethyl-3-(3-dimethyl-aminopropyl)carbodiimide.

A compound of formula (I) containing a carbonyl (C=O) moiety may be converted into the corresponding compound containing a —$C(CH_3)(OH)$— moiety by treatment with methylmagnesium bromide. Similarly, a compound of formula (I) containing a carbonyl (C=O) moiety may be converted into the corresponding compound containing a —$C(CF_3)(OH)$— moiety by treatment with (trifluoromethyl)trimethylsilane and cesium fluoride. A compound of formula (I) containing a carbonyl (C=O) moiety may be converted into the corresponding compound containing a —$C(CH_2NO_2)(OH)$— moiety by treatment with nitromethane.

A compound of formula (I) containing a hydroxymethyl moiety may be converted into the corresponding compound containing a formyl (—CHO) moiety by treatment with an oxidising agent such as Dess-Martin periodinane. A compound of formula (I) containing a hydroxymethyl moiety may be converted into the corresponding compound containing a carboxy moiety by treatment with an oxidising agent such as tetrapropylammonium perruthenate.

A compound of formula (I) wherein $R^1$ represents a substituent containing at least one nitrogen atom, which substituent is linked to the remainder of the molecule via a nitrogen atom, may be prepared by reacting a compound of formula (I) wherein $R^1$ represents halogen, e.g. bromo, with the appropriate compound of formula $R^1$—H [e.g. 1-(pyridin-3-yl)piperazine or morpholine]. The reaction is conveniently effected with the assistance of a transition metal catalyst, e.g. tris(dibenzylideneacetone)dipalladium(0), in the presence of an amination ligand such as 2-dicyclohexylphosphino-2',4',6'-triisopropyl-biphenyl (XPhos) or 2,2'-bis(diphenylphosphino)-1,1'-binaphthalene (BINAP) and a base, e.g. an inorganic base such as sodium tert-butoxide. Alternatively, the reaction may be effected using palladium diacetate, in the presence of a reagent such as [2',6'-bis(propan-2-yloxy)biphenyl-2-yl](dicyclohexyl)phosphane and a base, e.g. an inorganic base such as cesium carbonate.

A compound of formula (I) containing an oxo moiety can be concerted into the corresponding compound containing an ethoxycarbonylmethylidene moiety by treatment with triethyl phosphonoacetate in the presence of a base such as sodium hydride.

A compound of formula (IIB) wherein $R^{21}$ represents ethenyl may be prepared by reacting a compound of formula (IIB) wherein $R^{21}$ represents halogen, e.g. chloro, with potassium vinyl trifluoroborate. The reaction is typically effected in the presence of a transition metal catalyst, e.g. [1,1'-bis(diphenylphosphino)ferrocene]dichloropalladium(II), and a base, e.g. an organic base such as triethylamine.

A compound of formula (IIB) wherein $R^{21}$ represents halogen, e.g. chloro, may be converted into the corresponding compound wherein $R^{21}$ represents an optionally substituted $C_{4-7}$ cycloalkenyl moiety by treatment with the appropriately substituted cycloalkenyl boronic acid or a cyclic ester thereof formed with an organic diol, e.g. pinacol, 1,3-propanediol or neopentyl glycol. The reaction is typically effected in the presence of a transition metal catalyst, e.g. bis[3-(diphenylphosphanyl)cyclopenta-2,4-dien-1-yl]iron-dichloropalladium-dichloromethane complex, and a base, e.g. an inorganic base such as potassium carbonate.

A compound of formula (IIB) wherein $R^{21}$ represents a substituent containing at least one nitrogen atom, which substituent is linked to the remainder of the molecule via a nitrogen atom, may be prepared by reacting a compound of formula (IIB) wherein $R^{21}$ represents halogen, e.g. chloro, with the appropriate compound of formula $R^{21}$—H [e.g. 2-methoxyethylamine, N-methyl-L-alanine, 2-aminocyclopentanecarboxylic acid, 3-aminocyclopentanecarboxylic acid, 1-(aminomethyl)cyclopropanecarboxylic acid, methyl azetidine-3-carboxylate, pyrrolidin-3-ol, pyrrolidine-3-carboxylic acid, piperidine-2-carboxylic acid, piperidine-3-carboxylic acid, 4-(1H-tetrazol-5-yl)piperidine, piperazine, 1-(methylsulfonyl)piperazine, piperazin-2-one, 2-(piperazin-1-yl)propanoic acid, morpholine, morpholine-2-carboxylic acid, thiomorpholine, thiomorpholine 1,1-dioxide, 1,4-diazepan-5-one, 2-oxa-5-azabicyclo[2.2.1]heptane or an appropriately substituted azaspiroalkane], optionally in the presence of a base, e.g. an organic base such as triethylamine or N,N-diisopropylethylamine and/or 1-methyl-2-pyrrolidinone, or pyridine, or an inorganic base such as potassium carbonate.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g.

by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit TNFα-induced NF-κB activation in the following assay.

Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable transfectant expressing SEAP (secreted alkaline phosphatase) under the control of the IFNβ minimal promoter fused to five NF-κB binding sites. Secretion of SEAP by these cells is stimulated in a dose-dependent manner by TNFα (0.5 ng/mL). Compounds were diluted from 10 mM DMSO stocks (final assay concentration 0.3%) to generate a 10-point 3-fold serial dilution curve (30,000 nM to 2 nM final concentration). They were mixed with cells and stimulating ligand in a 384-well microtitre plate and incubated for 18 h. SEAP activity was determined in the supernatant using the colorimetric substrate QUANTI-Blue™ (InvivoGen). Percentage inhibitions for compound dilutions were calculated between a DMSO control and maximum inhibition (by excess control compound) and an $IC_{50}$ calculated using XLfit™ (4 parameter logistic model) in Activity-Base.

When tested in the above assay, the compounds of the accompanying Examples were all found to exhibit $IC_{50}$ values of 50 µM or better.

EXAMPLES

| Abbreviations | |
|---|---|
| DCM: dichloromethane | EtOAc: ethyl acetate |
| DMF: N,N-dimethylformamide | MeOH: methanol |
| DMSO: dimethylsulfoxide | EtOH: ethanol |
| THF: tetrahydrofuran | AcOH: acetic acid |
| DME: 1,2-dimethoxyethane | Et$_3$N: triethylamine |
| NBS: N-bromosuccinimide | NMP: 1-methyl-2-pyrrolidinone |
| LDA: lithium diisopropylamide | DIPEA: N,N-diisopropylethylamine |
| MeCN: acetonitrile | TFA: trifluoroacetic acid |
| TBME: tent-butyl methyl ether | TBAF: tetrabutylammonium fluoride |

| -continued | |
|---|---|
| Abbreviations | |
| DIBAL: diisobutylaluminium hydride | KHMDS: potassium hexamethyldisilazide |
| DAST: diethylaminosulfur trifluoride | DMP: Dess-Martin periodinane |
| SiO$_2$: silica | h: h |
| r.t.: room temperature | RT: retention time |
| br: broad | M: mass |
| SCX: strong cation exchange | SAX: strong anion exchange |
| FCC: flash column chromatography | |
| HPLC: High Performance Liquid Chromatography | |
| LCMS: Liquid Chromatography Mass Spectrometry | |
| ES+: Electrospray Positive Ionisation | |
| Pd(PPh$_3$)$_4$: tetrakis(triphenylphosphine)palladium(0) | |
| Pd(dba)$_2$: bis(dibenzylideneacetone)palladium(0) | |
| Pd$_2$(dba)$_3$: tris(dibenzylideneacetone)dipalladium(0) | |
| Pd(dppf)Cl$_2$: [1,1'-bis(diphenylphosphino)ferrocene]dichloropalladium(II) | |
| PdCl$_2$(PPh$_3$)$_2$: dichlorobis(triphenylphosphine)palladium(II) | |
| Xantphos: 4,5-bis(diphenylphosphino)-9,9-dimethylxanthene | |
| BINAP: 2,2'-bis(diphenylphosphino)-1,1'-binaphthalene | |
| BAST: bis(2-methoxyethyl)aminosulfur trifluoride | |

Nomenclature

Compounds were named with the aid of ACD/Name Batch (Network) version 11.01, and/or Accelrys Draw 4.0.

Analytical Conditions

NMR spectra were obtained using a Bruker DPX 250 MHz NMR spectrometer; a Bruker Fourier 300 MHz NMR spectrometer; a Bruker AVIII 400 MHz NMR spectrometer; a Bruker DRX 500 MHz NMR spectrometer; or an AV 600 MHz NMR spectrometer. Chemical shift values are reported in ppm (δ) with zero corresponding to the corrected residual deuterated solvent shift as an internal reference, or with zero corresponding to tetramethylsilane as an internal standard. The NMR spectra were recorded at a temperature ranging from 5 to 110° C. When more than one conformer was detected the chemical shifts for the most abundant conformer are reported.

Analytical HPLC

Method A

Column: Waters Atlantis dC18 (2.1×100 mm, 3 µm column)
Flow rate: 0.6 mL/minute
Solvent A: 0.1% formic acid/water
Solvent B: 0.1% formic acid/acetonitrile
Injection volume: 3 µL
Column temperature: 40° C.
UV detection wavelength: 215 nm
Eluent: 0.00-5.00 minutes, constant gradient from 95% solvent A+5% solvent B to 100% solvent B; 5.00-5.40 minutes, 100% solvent B; 5.40-5.42 minutes, constant gradient from 100% solvent B to 95% solvent A+5% solvent B; 5.42-7.00 minutes, 95% solvent A+5% solvent B.

Method B

Column: Waters Atlantis dC18 (2.1×50 mm, 3 µm column)
Flow rate: 1.0 mL/minute
Solvent A: 0.1% formic acid/water
Solvent B: 0.1% formic acid/acetonitrile
Injection volume: 3 µL
UV detection wavelength: 215 nm
Eluent: 0.00-2.50 minutes, constant gradient from 95% solvent A+5% solvent B to 100% solvent B; 2.50-2.70 minutes, 100% solvent B; 2.71-3.00 minutes, 95% solvent A+5% solvent B.

Method C

Column: Waters Atlantis dC18 (2.1×30 mm, 3 µm column)
Flow rate: 1.0 mL/minute
Solvent A: 0.1% formic acid/water
Solvent B: 0.1% formic acid/acetonitrile Injection volume: 3 μL
UV detection wavelength: 215 nm
Eluent: 0.00-1.50 minutes, constant gradient from 95% solvent A+5% solvent B to 100% solvent B; 1.50-1.60 minutes, 100% solvent B; 1.60-1.61 minutes, constant gradient from 100% solvent B to 95% solvent A+5% solvent B; 1.61-2.00 minutes, 95% solvent A+5% solvent B.
MS detection using Waters LCT or LCT Premier, or ZQ or ZMD.
UV detection using Waters 2996 photodiode array or Waters 2787 UV or Waters 2788 UV.
Method D (uPLC)
Column: Phenomenex, Kinetex-XB C18 (2.1 mm×100 mm, 1.7 μm column)
Flow rate: 0.6 mL/minute
Solvent A: 0.1% formic acid/water
Solvent B: 0.1% formic acid/acetonitrile
Injection volume: 3 μL
Column temperature: 40° C.
UV detection wavelength: 215 nm
Eluent: 0.00-5.30 minutes, constant gradient from 95% solvent A+5% solvent B to 100% solvent B; 5.30-5.80 minutes, 100% solvent B; 5.80-5.82 minutes, constant gradient from 100% solvent B to 95% solvent A+5% solvent B.
MS detection using Waters LCT or LCT Premier, or ZQ or ZMD.
UV detection using Waters 2996 photodiode array or Waters 2787 UV or Waters 2788 UV.
Method E (high pH)
Column: Phenomenex, Gemini C18 (2.0 mm×100 mm, 3 μm column)
Flow rate: 0.5 mL/minute
Solvent A: 2 nM ammonium hydrogencarbonate in water
Solvent B: acetonitrile
Injection volume: 3 μL
Column temperature: 50° C.
UV detection wavelength: 215 nm
Eluent: 0.00-5.50 minutes, constant gradient from 95% solvent A+5% solvent B to 100% solvent B; 5.50-5.90 minutes, 100% solvent B.
MS detection using Waters LCT or LCT Premier, or ZQ or ZMD.
UV detection using Waters 2996 photodiode array or Waters 2787 UV or Waters 2788 UV.
Method F
Waters Acquity SQD (QC LCMS)
The Waters Acquity SQD system comprises an Acquity PDA, Acquity Column Manager, Acquity Sample Manager and Acquity Sample Organiser, Acquity Binary Solvent 30 Manager and a Waters SQD mass spectrometer. The system is controlled via MassLynx PDA C11UPD846A.
Column Manager C11UPM180G
Sample Manager M10UPA441M
Sample Organiser F11UPO132M
Binary Solvent Manager E11UPB007A
SQD Mass Spectrometer LBA746
SQD Mass Spectrometer—ESI Source
Capillary Voltage 0.56 kV
Cone Voltage 55 V
Extractor Voltage 6 V
RF Lens 0.2 V
Source Temperature 150° C.
Desolvation Temperature 350° C.
Desolvation Gas 700 L/hour
Cone Gas 0 L/hour
Mass Range 150-650 amu
Scan Time 0.1 seconds Chromatography
Column: Waters Acquity UPLC BEH C18, 2.1×50 mm, 1.7 μm
Injection Volume: 1-5 μL
UV data: 210 to 400 nm
Sample Temperature: Ambient
Column Temperature: 40° C.
Flow Rate: 1 mL/min
Solvent A: 10 mM ammonium formate+0.1% ammonia
Solvent B: 95% MeCN+5% $H_2O$+0.1% ammonia
Gradient:

| Time | A% | B% |
| --- | --- | --- |
| 0.00 | 95.0 | 5.0 |
| 0.50 | 95.0 | 5.0 |
| 1.75 | 5.0 | 95.0 |
| 2.00 | 5.0 | 95.0 |
| 2.25 | 95.0 | 5.0 |

Preparative HPLC
Preparative Method A
Flow rate: 40 mL/minute
Mobile Phase A: water with 0.1% formic acid
Mobile Phase B: acetonitrile with 0.1% formic acid
Column: Waters Sunfire, C18, 30 mm×100 mm
Particle Size: 10 μm
Runtime: 25.5 minutes
Inlet method: LC7_40ml_7030_tubes.w60
Method Gradient:

| Time (min) | % A | % B |
| --- | --- | --- |
| 0.00 | 75 | 25 |
| 2.00 | 75 | 25 |
| 2.50 | 70 | 30 |
| 18.50 | 0 | 100 |
| 21.50 | 0 | 100 |
| 22.50 | 99 | 1 |
| 23.00 | 99 | 1 |

ACD Flow: 2 mL/minute (acetonitrile with 0.1% formic acid) throughout run.
Primary wavelength (collection): 215 nm
Equipment: Gilson 215 Liquid Handler with 819 valve, Gilson 307 pump (at Column Dilution), Waters 2487 Detector (prep cell), Waters FC II (waste collection), Knauer degasser, Waters 600 pump/controller (No. 3 pump heads).
Software: Masslynx v4.0 sp4
Preparative Method B
Flow rate: 40 mL/minute
Mobile Phase A: water with 0.1% formic acid
Mobile Phase B: acetonitrile with 0.1% formic acid
Column: Waters Sunfire, C18, 30 mm×100 mm
Particle Size: 10 μm
Runtime: 25.5 minutes
Inlet method: LC7_40ml_9010_tubes.w60
Method Gradient:

| Time (min) | % A | % B |
| --- | --- | --- |
| 0.00 | 95 | 5 |
| 2.00 | 95 | 5 |
| 2.50 | 90 | 10 |
| 18.50 | 0 | 100 |

-continued

| Time (min) | % A | % B |
|---|---|---|
| 21.50 | 0 | 100 |
| 22.50 | 95 | 5 |
| 23.00 | 95 | 5 |

ACD Flow: 2 mL/minute (acetonitrile with 0.1% formic acid) throughout run.
Primary wavelength (collection): 215 nm
Equipment: Gilson 215 Liquid Handler with 819 valve, Gilson 307 pump (at Column Dilution), Waters 2487 Detector (prep cell), Waters FC II (waste collection), Knauer degasser, Waters 600 pump/controller (No. 3 pump heads).
Software: Masslynx v4.0 sp4
Preparative Method C
Flow rate: 20 mL/minute
Mobile Phase A: water
Mobile Phase B: acetonitrile
Column: Waters Sunfire, C18, 30 mm×100 mm
Particle Size: 5 µm
Runtime: 19 minutes
Method Gradient:

| Time (min) | % A | % B |
|---|---|---|
| 0.00 | 95 | 5 |
| 2.00 | 95 | 5 |
| 2.50 | 90 | 10 |
| 14.50 | 0 | 100 |
| 16.50 | 0 | 100 |
| 17.00 | 95 | 5 |
| 19.00 | 95 | 5 |

Primary wavelength (collection): 215 nm
Secondary wavelength: 254 nm
Equipment: Gilson 215 Liquid Handler, Gilson 321 Pumps, Gilson 151 UV/Vis Detector.
Software: Gilson Unipoint V5.11
Preparative Method D (High pH)
Flow rate: 40 mL/minute
Mobile Phase A: acetonitrile+0.2% ammonium hydroxide
Mobile Phase B: acetonitrile+0.2% ammonium hydroxide
Column: Waters Sunfire, C18, 30 mm×100 mm
Particle Size: 5 µm
Runtime: 15.5 minutes
Method Gradient (isocratic):

| Time (min) | % A | % B |
|---|---|---|
| 0.00 | 95 | 5 |
| 2.00 | 85 | 15 |
| 12.00 | 70 | 30 |
| 12.50 | 5 | 95 |
| 15.00 | 5 | 95 |
| 15.50 | 95 | 5 |

Primary wavelength (collection): 215 nm
Secondary wavelength: 254 nm

Intermediate 1

5-(6-Methoxypyridin-3-yl)pyridin-2-amine

A degassed mixture of 2-amino-5-bromopyridine (3.5 g, 20.23 mmol), 6-methoxypyridin-3-ylboronic acid (3.71 g, 24.28 mmol) and bis[3-(diphenylphosphanyl)-cyclopenta-2,4-dien-1-yl]iron-dichloropalladium-dichloromethane complex (413 mg, 0.51 mmol) in 1,4-dioxane (36 mL) and a 2M aqueous potassium carbonate solution (36.4 mL) was heated at 90° C. under a nitrogen atmosphere for approximately 16 h. The reaction mixture was allowed to cool to room temperature and diluted with diethyl ether (100 mL). The organic phase was separated off, washed with brine, dried over sodium sulfate and concentrated under vacuum. The crude product was triturated with DCM (10 mL) and filtered, to afford the title compound (3.36 g, 83%) as a light brown solid. Method C LCMS: MH+ m/z 202, RT 0.60 minutes.

Intermediate 2

1-[2-(Difluoromethoxy)phenyl]ethan-1-one

Potassium hydroxide (105 g, 1872 mmol) was suspended in a mixture of acetonitrile (200 mL) and water (200 mL) and cooled to approximately −20° C. 1-(2-Hydroxyphenyl)ethanone (11.28 mL, 93.7 mmol) was added dropwise, followed by diethyl[bromo(difluoro)methyl]phosphonate (33.27 mL, 187.3 mmol) over 15 minutes. The mixture was then allowed to warm to room temperature over 1 h. The mixture was extracted with ethyl acetate (3×200 mL), then the combined organic layers were washed with brine (50 mL), dried over magnesium sulfate and concentrated under vacuum. The mixture was purified by flash chromatography to afford the title compound (16.0 g, 92%) as a colourless oil. Method B HPLC-MS: MH+ m/z 187, RT 1.77 minutes.

Intermediate 3

N'-(5-Bromopyridin-2-yl)-N,N-dimethylethenimidamide

2-Amino-5-bromopyridine (10 g, 57.8 mmol) was suspended in methanol (100 mL) and N,N-dimethylacetamide dimethyl acetal (25.5 mL, 174.4 mmol) was added. The mixture was heated to reflux at 80° C. for 16 h. The mixture was concentrated under vacuum and ethyl acetate (80 mL) was added. The resulting material was washed with saturated aqueous sodium bicarbonate solution (50 mL) followed by water (3×50 mL) and then brine (50 mL). The organic layer was dried over sodium sulfate and concentrated under vacuum to afford the title compound (13.72 g, 98%) as a dark red oil. $\delta_H$ (500 MHz, CDCl$_3$) 8.34 (d, J 2.4 Hz, 1H), 7.62 (d, J 7.8 Hz, 1H), 6.69 (br s, 1H), 3.08 (s, 6H), 2.01 (s, 3H).

Intermediate 4

2-Bromo-1-[2-(difluoromethoxy)phenyl]ethan-1-one

A solution of bromine (1.25 mL, 24.44 mmol) in glacial acetic acid (20 mL) was added dropwise over 60 minutes to a stirring solution of Intermediate 2 (4.6 g, 24.4 mmol) in glacial acetic acid (20 mL) in the dark. When the addition was complete the reaction was diluted with DCM (200 mL) and washed with water (200 mL). The aqueous layer was then extracted with DCM (50 mL). To the combined organic layers was added saturated aqueous sodium carbonate solution (100 mL), and further solid sodium carbonate was added portionwise with vigorous stirring until the mixture was neutralised. The organic phase was separated and the aqueous layer was extracted with DCM (2×50 mL). The combined organic layers were washed with brine (50 mL), dried over sodium sulphate, filtered and concentrated under vacuum to afford the title compound (6.48 g, 82%) as a light yellow oil. $\delta_H$ (500

MHz, CDCl₃) 7.83 (m, 1H), 7.58 (td, J 8.3, 1.7 Hz, 1H), 7.34 (m, 1H), 7.20 (d, J 8.3 Hz, 1H), 6.64 (t, J 72.9 Hz, 1H), 4.53 (s, 2H). Method C HPLC-MS: MH+ m/z 265/267, RT 1.32 minutes (80%).

Intermediate 5

6-Bromo-3-{[2-(difluoromethoxy)phenyl]carbonyl}-2-methylimidazo[1,2-a]pyridine

Intermediate 3 (9.94 g, 41.1 mmol) and Intermediate 4 (10.9 g, 41.1 mmol) were combined in toluene (120 mL) and heated at 140° C. for 10 minutes. The mixture was then allowed to cool gradually in the heating block for 1 h, before being cooled to room temperature. The volatiles were removed under vacuum and the residue was taken up in ethyl acetate (300 mL) and methanol (30 mL). The organic phase was washed with saturated aqueous sodium bicarbonate solution (150 mL) and the organic layer was dried over sodium sulphate, filtered and concentrated under vacuum to afford a red oil (~15 g). The residue was purified by flash chromatography, eluting with a gradient of 0-100% ethyl acetate in heptane, to afford the title compound (9.94 g, 63.5%) as a pink solid. $\delta_H$ (500 MHz, CDCl₃) 9.96 (s, 1H), 7.58 (m, 3H), 7.38 (m, 3H), 6.52 (t, J 73.5 Hz, 1H), 2.03 (s, 3H).

Intermediate 6

(6-Bromo-2-methylimidazo[1,2-a]pyridin-3-yl)[2-(difluoromethoxy)phenyl]methanol

Intermediate 5 (9.94 g, 26.1 mmol) was suspended in methanol (200 mL). The mixture was then cooled to 0° C. in an ice bath and sodium borohydride (1.03 g, 27.4 mmol) was added. After 10 minutes the mixture was warmed to room temperature and stirred for 1 h, after which time a light-coloured precipitate had formed. The mixture was reduced in volume in vacuo by approximately two-thirds and then diluted with ethyl acetate (400 mL). The organic phase was washed with saturated aqueous sodium bicarbonate solution (200 mL), dried over sodium sulphate and filtered, then concentrated in vacuo, to afford the title compound (9.8 g, 98%) as a cream-coloured solid. $\delta_H$ (500 MHz, CD₃OD) 8.54 (s, 1H), 7.94 (m, 1H), 7.39 (m, 4H), 7.12 (m, 1H), 6.54 (m, 2H), 2.29 (s, 3H).

Intermediate 7

6-Bromo-3-[2-(difluoromethoxy)benzyl]-2-methylimidazo[1,2-a]pyridine

Intermediate 6 (9.6 g, 25.1 mmol) was suspended in DCM (200 mL). Boron trifluoride diethyl etherate (7.5 mL, 60.8 mmol) and triethylsilane (8 mL, 50.1 mmol) were added and the mixture was stirred at room temperature for 6 h, before being left to stand at room temperature over the weekend. LCMS analysis indicated incomplete conversion, so further boron trifluoride diethyl etherate (3 mL, 24.3 mmol) and triethylsilane (2 mL, 12.5 mmol) were added and the mixture was stirred at room temperature for 6 h. The mixture was diluted with methanol (30 mL) to dissolve a small amount of precipitate, then the mixture was washed with saturated aqueous sodium bicarbonate solution (100 mL). The organic layer was dried over sodium sulfate and concentrated under vacuum to afford an orange gum. DCM (50 mL) was added, which caused a white precipitate to form. This was filtered off and washed further with DCM (100 mL) and methanol (20 mL) to afford the title compound (5.58 g, 54%) as a white solid. The filtrate was concentrated under vacuum and purified by flash chromatography, eluting with a gradient of 30-100% ethyl acetate in heptane, to afford a further quantity of the title compound (1.18 g, 12%) as a pale orange solid. Method C HPLC-MS: MH+ m/z 367/369, RT 1.01 minutes (90%).

Intermediate 8 tert-Butyl 4-(5-{3-[2-(difluoromethoxy)benzyl]-2-methylimidazo[1,2-a]pyridin-6-yl}-pyridin-2-yl)piperazine-1-carboxylate Intermediate 7 (200 mg, 0.54 mmol) and tert-butyl 4-[5-(4,4,5,5-tetramethyl-1,3,2-dioxaborolan-2-yl)pyridin-2-yl]piperazine-1-carboxylate (316 mg, 0.81 mmol) were dissolved in 1,4-dioxane (20 mL) and a 2M aqueous solution of potassium carbonate (1 mL) was added. The mixture was flushed with nitrogen and bis[3-(diphenylphosphanyl)-cyclopenta-2,4-dien-1-yl]iron-dichloropalladium-dichloromethane complex (12 mg, 0.01 mmol) was added. The mixture was heated at 90° C. under nitrogen for 16 h. LCMS indicated incomplete conversion so additional tert-butyl 4-[5-(4,4,5,5-tetramethyl-1,3,2-dioxaborolan-2-yl)pyridin-2-yl]piperazine-1-carboxylate (150 mg, 0.39 mmol) and bis[3-(diphenylphosphanyl)cyclopenta-2,4-dien-1-yl]iron-dichloropalladium-dichloromethane complex (12 mg, 0.01 mmol) were added and the mixture was heated at 90° C. under nitrogen for 4 h. The mixture was diluted with ethyl acetate (30 mL) and washed with water (2×10 mL), then brine (10 mL). The organic layer was dried over sodium sulphate, filtered and concentrated under vacuum to yield a dark grey solid. This was purified by flash chromatography, eluting with a gradient of 0-100% ethyl acetate in heptane, followed by 0-20% methanol in ethyl acetate. The resultant material was further purified by flash chromatography, eluting with a gradient of 0-5% methanol in DCM. The resultant material was then further purified by preparative HPLC (Preparative Method B) to afford the title compound (66 mg, 22%) as an off-white solid. $\delta_H$ (250 MHz, CD₃OD) 8.35-8.17 (m, 2H), 7.81-7.58 (m, 3H), 7.42-6.59 (m, 6H), 4.42 (s, 2H), 3.55 (br s, 8H), 2.48 (br s, 3H), 1.49 (s, 9H).

Intermediate 9

6-Bromo-2-methylimidazo[1,2-a]pyridine

2-Amino-5-bromopyridine (10 g, 57.8 mmol) was dissolved in ethanol (100 mL) and chloroacetone (9.3 mL, 115.59 mmol) was added. The mixture was heated to reflux at 90° C. for 16 h. The reaction mixture was concentrated under vacuum and the residue was purified by flash chromatography, eluting with a gradient of 0-20% methanol in DCM, to afford the title compound (9 g, 66.4%) as a yellow solid. $\delta_H$ (500 MHz, CD₃OD) 9.03 (s, 1H), 8.02 (m, 1H), 7.93 (s, 1H), 7.79 (d, J 9.4 Hz, 1H), 2.56 (s, 3H).

Intermediate 10

6-Bromo-2-methylimidazo[1,2-a]pyridine-3-carbaldehyde (Chloromethylene)dimethyliminium chloride (1.03 g, 8.05 mmol) was added to N,N-dimethylformamide (10 mL) at 0° C. and stirred for 5 minutes. Intermediate 9 (85% pure, 1 g, 4.03 mmol) was added. The mixture was warmed to room temperature and then heated at 80° C. for 1 h. The mixture was cooled to room temperature and quenched by adding saturated aqueous sodium bicarbonate solution. The mixture was extracted with ethyl acetate (3×100 mL) and the combined organic layers were washed with water (50 mL) followed by brine (50 mL), then dried over magnesium sulphate and concentrated under vacuum. The residue was purified by flash chromatography to afford the title compound (500 mg, 47%) as an orange solid. Method B HPLC-MS: MH+ m/z 239/241, RT 1.49 minutes (83%).

Intermediate 11

(6-Bromo-2-methylimidazo[1,2-a]pyridin-3-yl)(3-methylthien-2-yl)methanol

Intermediate 10 (100 mg, 0.42 mmol) was suspended in THF (1 mL) and added dropwise to a stirred 0.5M solution of 3-methylthien-2-ylmagnesium bromide in THF (1 mL, 0.50 mmol) at 0° C. The mixture was then warmed to room temperature and stirred for 2 h. The mixture was quenched by adding saturated aqueous ammonium chloride solution, then the mixture was extracted with ethyl acetate (3×20 mL). The combined organic layers were washed with water and brine (20 mL), then dried over magnesium sulfate and concentrated under vacuum. The residue was purified by flash chromatography to afford the title compound (100 mg, 71%) as a pale yellow solid. Method B HPLC-MS: MH+ m/z 337/339, RT 1.37 minutes (84%).

Intermediate 12

6-Bromo-2-methyl-3-[(3-methylthien-2-yl)methyl]imidazo[1,2-a]pyridine

Intermediate 11 (100 mg, 0.3 mmol) was suspended in DCM (5 mL) and cooled to 0° C. Boron trifluoride diethyl etherate (73.53 μL, 0.6 mmol) was added dropwise, followed by triethylsilane (94.54 μL, 0.59 mmol), then the mixture was warmed to room temperature and stirred for 3 h. The mixture was washed with saturated aqueous sodium bicarbonate solution (5 mL), dried over magnesium sulfate and concentrated under vacuum. The residue was purified by flash chromatography to afford the title compound (80 mg, 71.4%) of as a brown solid. Method B HPLC-MS: MH+ m/z 321/323, RT 1.47 minutes (81%).

Intermediate 13

(E)-N'-[5-Bromo-4-(trifluoromethyl)pyridin-2-yl]-N,N-dimethylethenimidamide

2-Amino-5-bromo-4-(trifluoromethyl)pyridine (5 g, 20.75 mmol) was suspended in methanol (50 mL) and N,N-dimethylacetamide dimethyl acetal (9.15 mL, 62.6 mmol) was added. The mixture was heated to reflux at 80° C. for 8 h. The mixture was concentrated under vacuum and diluted with ethyl acetate (150 mL), then washed with saturated aqueous sodium bicarbonate solution (50 mL), followed by water (3×50 mL) and brine (50 mL). The organic layers were dried over sodium sulfate and concentrated under vacuum to afford the title compound (6.45 g, 96%) as a dark red oil. $\delta_H$ (500 MHz, CDCl$_3$) 8.49 (s, 1H), 7.14-6.93 (m, 1H), 3.10 (s, 6H), 2.07 (s, 3H). Method C HPLC-MS: MH+ m/z 310/312, RT 1.23 minutes (96%).

Intermediate 14

6-Bromo-3-{[2-(difluoromethoxy)phenyl]carbonyl}-2-methyl-7-(trifluoromethyl)-imidazo[1,2-a]pyridine Intermediate 13 (6.4 g, 19.4 mmol) and Intermediate 4 (6.73 g, 21.34 mmol) were dissolved in DMF (100 mL) and heated at 80° C. under a nitrogen atmosphere for 8 h. The mixture was cooled to room temperature, then diluted with water (150 mL) and extracted with ethyl acetate (3×150 mL). The combined organic layers were washed with water (4×100 mL) and brine (50 mL), then dried over magnesium sulfate and concentrated under vacuum. The resulting dark brown solid was purified by biotage, eluting with a gradient of 25-50% ethyl acetate in heptane, to afford the title compound (5.4 g, 62%) as a beige solid. $\delta_H$ (500 MHz, CDCl$_3$) 10.06 (s, 1H), 8.04 (s, 1H), 7.58 (ddd, J 8.4, 7.3, 2.1 Hz, 1H), 7.44-7.37 (m, 2H), 7.34 (d, J 8.3 Hz, 1H), 6.50 (t, J 73.2 Hz, 1H), 2.08 (s, 3H). Method C HPLC-MS: MH+ m/z 449/451, RT 2.34 minutes (99%).

Intermediate 15

[6-Bromo-2-methyl-7-(trifluoromethyl)imidazo[1,2-a]pyridin-3-yl][2-(difluoromethoxy)-phenyl]methanol Intermediate 14 (3.6 g, 0.01 mol) was dissolved in methanol (40 mL). Sodium borohydride (0.3 g, 8.01 mmol) was then added portionwise at room temperature and the resulting mixture was stirred for 2 h. The mixture was concentrated under vacuum to afford the title compound (3.6 g, 100%) as a light pink solid. $\delta_H$ (500 MHz, CD$_3$OD) 10.32 (s, 1H), 9.53 (dd, J 6.9, 2.1 Hz, 1H), 9.45 (s, 1H), 9.00-8.87 (m, 2H), 8.69 (d, J 8.1 Hz, 1H), 8.30 (t, J 73.9 Hz, 1H), 8.06 (s, 1H), 4.91 (s, 1H), 3.90 (s, 3H). Method C HPLC-MS: MH+ m/z 451/453, RT 2.04 minutes (98%).

Intermediate 16

6-Bromo-3-[2-(difluoromethoxy)benzyl]-2-methyl-7-(trifluoromethyl)imidazo[1,2-a]pyridine Boron trifluoride diethyl etherate (3.9 mL, 31.9 mmol) was added dropwise to a stirred solution of Intermediate 15 (3.6 g, 7.98 mmol) in DCM (40 mL) at room temperature. Triethylsilane (5.1 mL, 31.92 mmol) was then added, and the mixture was heated at 45° C. for 5 h. The mixture was cooled to room temperature and washed with saturated aqueous NaHCO$_3$ solution (50 mL), water (50 mL) and brine (50 mL), then dried over magnesium sulfate and concentrated under vacuum. The resulting brownish oil was purified by biotage, eluting with a gradient of 25-50% ethyl acetate in heptane, to afford the title compound (1.78 g, 51%) as a light grey solid. $\delta_H$ (500 MHz, CDCl$_3$) 8.13 (s, 1H), 8.06 (s, 1H), 7.31 (t, J 7.8 Hz, 1H), 7.21-7.06 (m, 2H), 6.90 (d, J 7.7 Hz, 1H), 6.64 (t, J 73.4 Hz, 1H), 4.28 (s, 2H), 2.55 (s, 3H). Method C HPLC-MS: MH+ m/z 435/437, RT 2.16 minutes (98%).

Intermediate 17

(E)-N'-(5-Bromo-4-methylpyridin-2-yl)-N,N-dimethylethenimidamide

2-Amino-5-bromo-4-methylpyridine (5 g, 26.7 mmol) was dissolved in methanol (50 mL) and N,N-dimethylacetamide dimethyl acetal (12 mL, 82.1 mmol) was added. The mixture was heated at 80° C. for 16 h. Methanol was removed under vacuum and the residue was dissolved in ethyl acetate (100 mL), then washed with saturated aqueous sodium bicarbonate solution (50 mL). The organic layer was dried over sodium sulfate and concentrated under vacuum to afford the title compound (6.2 g, 90%) as a brown oil. $\delta_H$ (500 MHz, CDCl$_3$) 8.32 (s, 1H), 6.66 (s, 1H), 3.07 (s, 6H), 2.32 (s, 3H), 2.00 (s, 3H). Method B HPLC-MS: MH+ m/z 256/258, RT 0.92 minutes (97%).

Intermediate 18

6-Bromo-3-{[2-(difluoromethoxy)phenyl]carbonyl}-2,7-dimethylimidazo[1,2-a]pyridine Intermediate 17 (2 g, 7.8 mmol) and Intermediate 4 (2.5 g, 7.8 mmol) were dissolved in toluene (30 mL) and heated at 100° C. for 100 minutes. The reaction mixture was diluted with EtOAc (50 mL), then washed with saturated aqueous NaHCO$_3$ solution (30 mL), dried over Na$_2$SO$_4$ and concentrated under vacuum. The crude residue was purified by flash chromatography on silica, eluting with 0 to 90% EtOAc in heptane, to yield the title compound (2.4 g, 78%) as a beige solid. $\delta_H$ (250 MHz, CDCl$_3$) 9.98 (s, 1H), 7.53 (m, 2H), 7.36 (m, 3H), 6.52 (t, J 73.6 Hz, 1H), 2.55 (s, 3H), 2.01 (s, 3H). Method B HPLC-MS: MH+ m/z 395/397, RT 2.04 minutes (100%).

Intermediate 19

(6-Bromo-2,7-dimethylimidazo[1,2-a]pyridin-3-yl)[2-(difluoromethoxy)phenyl]methanol Intermediate 18 (2.4 g, 6.1 mmol) was dissolved in methanol (30 mL) and cooled to 0° C. in an ice bath. Sodium borohydride (0.24 g, 6.4 mmol) was added and the mixture was stirred at 0° C. for 75 minutes. A white precipitate was filtered off and washed with ethyl acetate (20 mL). The filtrate was concentrated under vacuum and was then diluted with ethyl acetate (50 mL). The organic phase was washed with brine (50 mL), and the organic layer was dried over sodium sulfate and concentrated under vacuum. The resultant solids were combined with the collected precipitate to afford the title compound (2.17 g, 90%). $\delta_H$ (500 MHz, DMSO-d$_6$) 8.55 (s, 1H), 7.90 (dd, J 6.7, 2.4 Hz, 1H), 7.45 (s, 1H), 7.37 (m, 2H), 7.11 (m, 2H), 6.34 (s, 1H), 6.23 (d, J 2.8 Hz, 1H), 2.35 (s, 3H), 2.13 (s, 3H). Method B HPLC-MS: MH+ m/z 397/399, RT 1.45 minutes (100%).

Intermediate 20

6-Bromo-3-[2-(difluoromethoxy)benzyl]-2,7-dimethylimidazo[1,2-a]pyridine

Intermediate 19 (2.2 g, 5.46 mmol) was suspended in DCM (35 mL) under nitrogen. Boron trifluoride diethyl etherate (2.3 mL, 18.6 mmol) was added, followed by triethylsilane (2.2 mL, 13.8 mmol), and the mixture was stirred at ambient temperature under nitrogen for 4 h. The reaction mixture was treated again with boron trifluoride diethyl etherate (1 mL) and the reaction mixture was stirred at ambient temperature for 16 h. The mixture was washed with saturated aqueous sodium bicarbonate solution (30 mL). The organic layer was dried over sodium sulfate and concentrated under vacuum. The resulting beige solid was triturated with DCM to yield the title compound (915 mg, 43.9%) as a white solid. The filtrate was purified by flash chromatography on silica, eluting with 25-100% EtOAc in heptanes, to yield a further quantity of the title compound (371 mg, 17.8%). $\delta_H$ (500 MHz, CD$_3$OD) 8.23 (s, 1H), 7.40 (s, 1H), 7.31 (t, J 7.8 Hz, 1H), 7.22 (d, J 8.0 Hz, 1H), 7.14 (t, J 7.5 Hz, 1H), 7.01 (d, J 7.7 Hz, 1H), 6.94 (t, J 74.0 Hz, 1H), 4.32 (s, 2H), 2.45 (s, 3H), 2.40 (s, 3H). Method B HPLC-MS: MH+ m/z 381/383, RT 1.52 minutes (92%).

Intermediate 21

2-Bromo-1-(2,5-dichlorophenyl)ethanone 2,5-Dichloroacetophenone (20.9 g, 0.11 mol) was dissolved in diethyl ether (300 mL) and the reaction mixture was cooled to 0° C. Bromine (5.66 mL, 0.11 mol) was added slowly dropwise and the reaction mixture was allowed to warm to room temperature over 20 minutes. The reaction mixture was treated with saturated aqueous NaHCO$_3$ solution (250 mL). The organic layer was separated, dried over MgSO$_4$ and concentrated in vacuo, yielding the title compound (20.0 g, 68%) as a yellow oil. $\delta_H$ (d$_6$-DMSO) 7.94 (dd, J 2.2, 0.3 Hz, 1H), 7.61 (m, 2H), 4.88 (s, 2H).

Intermediate 22

(E)-Ethyl 4-[2-(difluoromethoxy)phenyl]-2-oxobut-3-enoate

A suspension of 2-(difluoromethoxy)benzaldehyde (295 g, 1714 mmol) and ethyl (triphenylphosphoranylidene)pyruvate (279.1 g, 742 mmol) was heated at 100° C. The dark red aldehyde immediately decolorized, and a yellow suspension was obtained, which slowly changed to a dark brown solution. 2-(Difluoromethoxy)benzaldehyde (52.5 g, 305 mmol) was added to the reaction mixture. Residual aldehyde was separated from the reaction mixture by distillation. The resulting mixture was stirred in heptane (500 mL) and diethyl ether (500 mL). The brown solid precipitate was filtered off, and washed with a 1:1 mixture of heptane and diethyl ether (3×250 mL). The filtrate was concentrated, yielding a brown oil (218.5 g). Purification by flash column chromatography (1.5 kg silica, 2-20% EtOAc in heptane, 125 mL/minute) gave the title compound (91 g) as a yellow oil. $\delta_H$ (CDCl$_3$, 300 MHz) 1.42 (t, J 7.1 Hz, 3H), 4.40 (q, J 7.1 Hz, 2H), 6.59 (t, J 72.9 Hz, 1H), 7.20 (dd, J 7.3, 1.0 Hz, 1H), 7.28 (br t, J 7.6 Hz, 1H), 7.38 (d, J 16.3 Hz, 1H), 7.46 (dt, J 7.8, 1.7 Hz, 1H), 7.75 (dt, J 7.8, 1.6 Hz, 1H), 8.13 (d, J 16.3 Hz, 1H). MS [ES+] m/z 271 [M+H]$^+$.

Intermediate 23

Ethyl 4-[2-(difluoromethoxy)phenyl]-2-[(triethylsilyl)oxy]but-2-enoate

To a nitrogen-flushed solution of Intermediate 22 (50 g, 185 mmol) in dichloromethane (500 mL) were added rhodium(II) acetate dimer (0.818 g, 1.85 mmol) and triethylsilane (35.5 mL, 25.8 g, 222 mmol). The resulting mixture was stirred at reflux. Additional triethylsilane (10 mL, 7.28 g, 62.6 mmol) and rhodium(II) acetate dimer (0.2 g, 0.453 mmol) were added after 4 h. Heating at reflux was continued for 16 h. The reaction mixture was cooled to room temperature and filtered over a tight pad of kieselguhr. The resulting material was rinsed with DCM and concentrated in vacuo to yield the title compound (61 g) as a clear yellow oil that was employed in subsequent steps with no further purification.

Intermediate 24

Ethyl 3-bromo-4-[2-(difluoromethoxy)phenyl]-2-oxobutanoate

To a stirred solution of Intermediate 23 (69 g, 179 mmol) in anhydrous tetrahydrofuran (700 mL) at room temperature was added NBS (35.0 g, 196 mmol). The resulting mixture was stirred at reflux for 2 h before being cooled to room temperature. The reaction mixture was concentrated to approximately one-third of its original volume. DCM (500 mL) was added and the resulting mixture was washed with saturated aqueous NaHCO$_3$ solution (700 mL), then extracted with DCM (250 mL), dried over Na$_2$SO$_4$ and concentrated in vacuo, to yield a crude yellow oil (97 g). After storage overnight at room temperature under nitrogen, the product had partly solidified. The resulting material was triturated in diisopropyl ether (300 mL) for 1 h at room temperature. The precipitate was removed by filtration. The filtrate was concentrated in vacuo yielding a clear yellow-brown oil (88 g). Purification by flash column chromatography (1.5 kg silica, 2-20% EtOAc in heptane) afforded the title compound (58.3 g) as a light brown oil. $\delta_H$ (CDCl$_3$, 300 MHz) 1.38 (t, J 7.1 Hz, 3H), 3.32 (dd, J 14.5, 7.8 Hz, 1H), 3.55 (dd, J 14.5, 7.1 Hz, 1H), 4.36 (q, J 7.1 Hz, 2H), 5.37 (dd, J 7.8, 7.1 Hz, 1H), 6.58 (t, J 73.5 Hz, 1H), 7.09-7.19 (m, 2H), 7.26-7.33 (m, 2H). MS [ES+] m/z 271 [M-Br]$^+$.

Intermediate 25

Ethyl 3-[2-(difluoromethoxy)benzyl]-6-(6-methoxy-pyridin-3-yl)imidazo[1,2-a]pyridine-2-carboxylate Intermediate 1 (0.355 g, 1.76 mmol) and Intermediate 24 (0.62 g, 1.76 mmol) were dissolved in ethanol (5 mL) and heated at reflux for 18 h. The reaction mixture was concentrated in vacuo and the residue was partitioned between aqueous NaHCO$_3$ solution (20 mL) and EtOAc (50 mL). The organics were extracted and dried over MgSO$_4$, then concentrated in vacuo. The residue was purified by column chromatography (SiO$_2$, 0-100% EtOAc/hexane), yielding the title compound (0.26 g, 33%) as a cream solid. $\delta_H$ (d$_6$-DMSO) 8.53 (s, 1H), 8.49 (d, J 2.4 Hz, 1H), 8.03 (dd, J 8.7, 2.6 Hz, 1H), 7.77 (m, 1H), 7.72 (m, 1H), 7.29 (m, 2H), 7.21 (m, 1H), 7.09 (m, 1H), 6.94 (d, J 8.6 Hz, 1H), 6.84 (dd, J 7.6, 1.1 Hz, 1H), 4.80 (s, 2H), 4.29 (q, J 7.1 Hz, 2H), 3.90 (s, 3H), 1.27 (t, J 7.1 Hz, 3H). LCMS (ES$^+$) 454.0 (M+H)$^+$.

Intermediate 26

(6-Bromo-2-methylimidazo[1,2-a]pyridin-3-yl)(2,5-dichlorophenyl)methanone

A mixture of Intermediate 21 (5.2 g, 19 mmol) and Intermediate 3 (3.6 g, 15 mmol) in ethanol (25 mL) was heated at 75° C. for 4 h, then stood at room temperature overnight. The mixture was concentrated in vacuo, then the residue was partitioned between EtOAc and saturated aqueous NaHCO$_3$ solution. The organic layer was separated and extracted into EtOAc. The combined organic layers were washed with water and brine, then dried (MgSO$_4$), filtered and concentrated in vacuo. The resulting material was subjected to column chromatography (SiO$_2$, eluent hexane to 50% EtOAc). The resulting material was washed with diethyl ether to give the title compound (3.6 g, 63%) as a beige solid. $\delta_H$ (400 MHz, DMSO-d$_6$) 9.80 (d, 1H, J 1.4 Hz), 7.90 (dd, 1H, J 9.4, 2.0 Hz), 7.81 (d, 1H, J 9.4 Hz), 7.72 (s, 1H), 7.70 (m, 2H), 1.92 (s, 3H). MH+ 383.0.

Intermediate 27

(2,5-Dichlorophenyl)[2-methyl-6-(1-methylpyrazol-4-yl)imidazo[1,2-a]pyridin-3-yl]-methanone A mixture of Intermediate 26 (1.0 g, 2.6 mmol), 1-methyl-4-(4,4,5,5-tetramethyl-1,3,2-dioxaborolan-2-yl)pyrazole (0.59 g, 2.8 mmol) and Pd(dppf)Cl$_2$ (84 mg, 5 mol %) in 2M aqueous Na$_2$CO$_3$ solution (5 mL) and 1,4-dioxane (20 mL) was degassed with nitrogen. The mixture was heated at 100° C. for 15 minutes and then at 90° C. for 5 h. The mixture was partitioned between EtOAc (100 mL) and water (50 mL), then the aqueous phase was separated and re-extracted into EtOAc (50 mL). The combined organic fractions were washed with water (20 mL) and brine (20 mL), then dried (Na$_2$SO$_4$), filtered and concentrated in vacuo. The resulting dark oil was purified by column chromatography (SiO$_2$, eluent hexane to 100% EtOAc) to give the title compound (0.80 g, 81%) as a white foam. $\delta_H$ (400 MHz, DMSO-d$_6$) 9.84 (d, 1H, J 0.7 Hz), 8.33 (s, 1H), 7.99 (dd, 1H, J 9.2, 1.8 Hz), 7.96 (d, 1H, J 0.4 Hz), 7.85 (d, 1H, J 0.6 Hz), 7.84 (dd, 1H, J 9.1, 0.6 Hz), 7.76 (d, 1H, J 2.1 Hz), 7.70 (m, 1H), 3.92 (s, 3H), 1.92 (s, 3H). MH+ 385.0.

Intermediate 28 tert-Butyl 4-(5-{3-[2-(difluoromethoxy)benzyl]-2-methylimidazo[1,2-a]pyridin-6-yl}-pyrimidin-2-yl)piperazine-1-carboxylate Intermediate 7 (250 mg, 0.68 mmol) and tert-butyl 4-[5-(4,4,5,5-tetramethyl-1,3,2-dioxaborolan-2-yl)pyrimidin-2-yl]piperazine-1-carboxylate (319 mg, 0.82 mmol) were dissolved in 1,4-dioxane (3 mL). A 2M aqueous solution of potassium carbonate (1.2 mL) was added and the reaction mixture was degassed with nitrogen for 5 minutes. Bis[3-(diphenylphosphanyl)cyclopenta-2,4-dien-1-yl]iron-dichloropalladium-dichloromethane complex (28 mg, 0.03 mmol) was added and the reaction mixture was heated at 90° C. in a pressure tube for 18 h. The reaction mixture was diluted with EtOAc, washed with water and brine, then dried over sodium sulfate and concentrated under vacuum. The residue obtained was purified by flash column chromatography, eluting with 0-10% methanol in DCM, to yield the title compound (324 mg, 86%). $\delta_H$ (500 MHz, DMSO-d$_6$) 8.69 (s, 2H), 8.40 (s, 1H), 7.55 (d, J 9.3 Hz, 1H), 7.48 (d, J 10.7 Hz, 1H), 7.46-7.10 (m, 4H), 7.04 (d, J 6.8 Hz, 1H), 4.36 (s, 2H), 3.81-3.74 (m, 4H), 3.47-3.39 (m, 4H), 2.32 (s, 3H), 1.43 (s, J 3.5 Hz, 9H). Method B HPLC-MS: MH+ m/z 551, RT 1.72 minutes (80%).

Intermediate 29

2-Chloro-5-{3-[2-(difluoromethoxy)benzyl]-2-methylimidazo[1,2-a]pyridin-6-yl}-pyrimidine Intermediate 7 (1.0 g, 2.72 mmol) and 2-chloropyrimidin-5-ylboronic acid (517 mg, 3.3 mmol) were dissolved in 1,4-dioxane (10 mL) and a 2M aqueous solution of potassium carbonate (4.9 mL) was added. The reaction mixture was degassed with nitrogen for 5 minutes, then bis[3-(diphenylphosphanyl)cyclopenta-2,4-dien-1-yl]iron-dichloropalladium-dichloromethane complex (111.2 mg, 0.14 mmol) was added. The reaction mixture was heated at 90° C. under nitrogen for 18 h. The reaction mixture was re-treated with additional 2-chloropyrimidin-5-ylboronic acid (517.5 mg, 3.27 mmol) and heated at 90° C. under nitrogen for a further 24 h. The reaction mixture was diluted with EtOAc, washed with water (×2) and brine, filtered to remove a black solid, then dried over sodium sulfate and dried under vacuum. The residue obtained was purified by column chromatography, eluting with 0-90% EtOAc in heptanes, to yield the title compound (130 mg, 12%). $\delta_H$ (500 MHz, DMSO-$d_6$) 9.14 (s, 2H), 8.73 (s, 1H), 7.64 (s, 2H), 7.46-7.09 (m, 5H), 4.40 (s, 2H), 2.30 (s, 3H). Method B HPLC-MS: MH+ m/z 401/403, RT 1.47 minutes (88%).

Intermediate 30

2-Chloro-5-{3-[2-(difluoromethoxy)benzyl]-2-methylimidazo[1,2-a]pyridin-6-yl}-pyridine Intermediate 7 (250 mg, 0.68 mmol) and 6-chloropyridin-3-ylboronic acid (130 mg, 0.83 mmol) were dissolved in 1,4-dioxane (15 mL) and a 2M aqueous solution of potassium carbonate (1.25 mL) was added. The mixture was flushed with nitrogen and bis[3-(diphenylphosphanyl)cyclopenta-2,4-dien-1-yl]iron-dichloropalladium-dichloromethane complex (15 mg, 0.02 mmol) was added. The mixture was heated at 90° C. under nitrogen for 16 h. The mixture was diluted with ethyl acetate (30 mL), then washed with water (2×10 mL) and brine (10 mL). The organic layer was dried over sodium sulfate and concentrated under vacuum. The residue was purified by flash chromatography, eluting with a gradient of 0-10% methanol in DCM. The crude product was further purified by preparative HPLC (Method B) to afford the title compound (295 mg, 92%) as a brown solid. Method C HPLC-MS: MH+ m/z 400, RT 1.00 minutes (85%).

Intermediate 31

3-[2-(Difluoromethoxy)benzyl]-2-methylimidazo[1,2-a]pyridin-6-ylboronic acid

Intermediate 7 (2.5 g, 6.81 mmol), bis(neopentyl glycolato)diboron (1.85 g, 8.17 mmol) and potassium acetate (2.6 g, 27.2 mmol) were combined in anhydrous DMSO (50 mL) and the mixture was degassed under nitrogen. Bis[3-(diphenylphosphanyl)-cyclopenta-2,4-dien-1-yl]iron-dichloropalladium-dichloromethane complex (278 mg, 0.34 mmol) was added and the mixture was heated at 100° C. under nitrogen for 2 h. The mixture was diluted with ethyl acetate (100 mL) and filtered through celite, then the solids were washed with further ethyl acetate (50 mL). The filtrate was washed with water (3×50 mL) and brine (50 mL). The organic layer was then washed with 1M aqueous sodium hydroxide solution (3×50 mL). The aqueous layer was neutralised to approximately pH 6 by adding 6M hydrochloric acid. The aqueous layer was then extracted with ethyl acetate (3×100 mL). The combined organic layers were dried over sodium sulfate and concentrated under vacuum to afford the title compound (1.61 g, 50%) as a brown solid. Method C HPLC-MS: MH+ m/z 333, RT 0.89 minutes (93%).

Intermediate 32

2-Bromo-1-(2,4-dimethyl-1,3-thiazol-5-yl)ethanone

N,N,N-Trimethylanilinium bromide-bromine (1:1:1) (1.84 g, 4.9 mmol) was added to a solution of 1-(2,4-dimethyl-1,3-thiazol-5-yl)ethanone (800 mg, 5.15 mmol) in diethyl ether (9 mL) and acetonitrile (3 mL), and HBr in acetic acid (33% w/w, 4 mL). The mixture was stirred for 1 h. The reaction mixture was diluted with diethyl ether (25 mL) and washed with aqueous $Na_2S_2O_5$ solution (5% w/v, 20 mL). The organic phase was separated off, and the aqueous phase was extracted with diethyl ether (25 mL). The organic phases were combined, then washed with saturated aqueous $NaHCO_3$ solution (2×25 mL) and brine. The residue was dried over sodium sulfate, then filtered and concentrated under vacuum, to give the title compound (764 mg, 63%) as a light brown oil. $\delta_H$ (250 MHz, $CDCl_3$) 4.22 (s, 2H), 2.69-2.76 (br s, 6H).

Intermediate 33

(1E)-N'-(6'-Methoxy-3,3'-bipyridin-6-yl)-N,N-dimethylethanimidamide

A mixture of Intermediate 1 (626 mg, 3.11 mmol) and N,N-dimethylacetamide dimethyl acetal (2.27 mL, 15.55 mmol) in MeOH (3 mL) was heated at 80° C. in a sealed tube for 1 h. The reaction mixture was allowed to cool to ambient temperature, and concentrated under vacuum. The crude mixture was taken up in DCM (20 mL), then washed with saturated aqueous $NaHCO_3$ solution (2×25 mL) and brine The residue was dried over sodium sulfate, filtered and concentrated under vacuum, to afford the title compound (810 mg, 87%) as a brown viscous oil. Method C HPLC-MS: MH+ m/z 271, RT 0.81 minutes (90%).

Intermediate 34

(2,4-Dimethyl-1,3-thiazol-5-yl)[6-(6-methoxypyridin-3-yl)-2-methylimidazo[1,2-a]pyridin-3-yl]methanone A mixture of Intermediate 33 (2.56 mmol) and Intermediate 32 (600 mg, 2.56 mmol) in DMF (6 mL) was stirred at ambient temperature for 1 h. The reaction mixture was diluted with diethyl ether (6 mL) and filtered. The solid residue was washed with diethyl ether (2×6 mL) and air-dried, to give the title compound (1.41 g, 77%) as an off-white solid. $\delta_H$ (250 MHz, $CDCl_3$) 9.53-9.58 (m, 1H), 8.38-8.45 (m, 1H), 7.66-7.86 (m, 3H), 6.83-6.91 (m, 1H), 4.00 (s, 3H), 2.76 (s, 3H), 2.50 (s, 3H), 2.40 (s, 3H). Method C HPLC-MS: MH+ m/z 379, RT 1.16 minutes (97%).

Intermediate 35

(2,4-Dimethyl-1,3-thiazol-5-yl)[6-(6-methoxypyridin-3-yl)-2-methylimidazo[1,2-a]pyridin-3-yl]methanol Sodium borohydride (74.7 mg, 1.97 mmol) was added to Intermediate 34 (1.41 g, 1.97 mmol) in MeOH (14 mL) and the mixture was stirred at ambient temperature for 1 h. The reaction mixture was concentrated under vacuum. The crude mixture was taken up in saturated aqueous $NaHCO_3$ solution (20 mL) and chloroform (20 mL). The organic phase was separated off, and the aqueous phase was extracted with chloroform (20 mL). The organic phases were combined, washed with brine, dried over sodium sulfate, filtered, and concentrated under vacuum, to afford the title compound (865 mg, 97%) as a light brown solid. Method C HPLC-MS: MH+ m/z 381, RT 0.87 minutes (95%).

Intermediate 36

Methyl (2E)-3-{3-[2-(difluoromethoxy)benzyl]-2-methylimidazo[1,2-a]pyridin-6-yl}prop-2-enoate Methyl prop-2-enoate (63.3 mg, 0.74 mmol) was added to a stirred suspension of Intermediate 7 (200 mg, 0.49 mmol), Pd(dba)$_2$ (28 mg, 0.05 mmol), tris(2-methylphenyl)-phosphine (27 mg, 0.09 mmol) and triethylamine (74 mg, 0.74 mmol) in DMF (2 mL) at ambient temperature. The reaction mixture was thoroughly degassed under a stream of nitrogen and was then sealed and heated at 120° C. for 18 h. The reaction mixture was cooled, diluted with DCM (5 mL), washed with saturated aqueous NaHCO$_3$ solution (2×5 mL) and dried over sodium sulfate. The solvent was removed under vacuum and the resulting brown oil (220 mg) was purified by column chromatography, eluting with 25-100% EtOAc in heptanes, to afford the title compound (136 mg, 63%) as a pale brown oil. $\delta_H$ (500 MHz, CDCl$_3$) 7.79 (s, 1H), 7.57-7.46 (m, 2H), 7.35 (dd, J 9.4, 1.5 Hz, 1H), 7.25 (d, J 7.6 Hz, 1H), 7.17 (d, J 8.2 Hz, 1H), 7.09-7.03 (m, 1H), 6.85-6.46 (m, 2H), 6.34 (d, J 15.9 Hz, 1H), 4.27 (s, 2H), 3.78 (s, 3H), 2.48 (s, 3H).

Intermediate 37

1-(5-Boronopyrimidin-2-yl)piperidine-4-carboxylic acid

2-Chloropyrimidin-5-ylboronic acid (2.00 g, 12.6 mmol) and isonipecotic acid (1.63 g, 12.6 mmol) were suspended in ethanol (25 mL). Triethylamine (1.78 mL, 12.6 mmol) was added and the mixture was heated at 80° C. for 16 h. The reaction mixture was cooled and concentrated in vacuo to dryness. Water (30 mL) was added and the reaction mixture was swirled until the product completely dissolved. On standing, crystallisation occurred. The mixture was cooled in an ice bath for 30 minutes, then filtered. The resultant solid was washed sparingly with water and dried under suction, then freeze-dried, to give the title compound (1.90 g, 7.6 mmol, 60%) as a white solid. $\delta_H$ (d$_6$-DMSO) 8.60 (s, 2H), 8.06 (br s, 2H), 4.60-4.52 (m, 2H), 3.14-3.02 (m, 2H), 2.60-2.54 (m, 1H), 1.90-1.80 (m, 2H), 1.55-1.39 (m, 2H). LCMS (ES$^+$) 252 (M+H)$^+$.

Intermediate 38

2-(Morpholin-4-yl)pyrimidin-5-ylboronic acid

A mixture of 2-chloropyrimidin-5-ylboronic acid (3 g, 19.0 mmol), morpholine (1.66 mL, 19 mmol) and triethylamine (1.67 mL, 19.19 mmol) in EtOH (20 mL) was stirred at 80° C. for 5 h. LCMS indicated completion of the reaction. The reaction mixture was concentrated in vacuo and the residue was taken up in ethanol (approximately 5 mL). Diethyl ether was added, and the triethylamine hydrochloride salt that crystallised out was filtered off and discarded. The filtrate was concentrated in vacuo and water (approximately 10 mL) was added. The mixture was placed in a refrigerator for 1 h, after which time the resulting solid was filtered off, washed with the minimum amount of water and dried by suction, to give the title compound (2.7 g, 68%) as an off-white solid. $\delta_H$ (DMSO-d$_6$) 8.64 (s, 2H), 8.08 (s, 2H), 3.73 (m, 4H), 3.65 (m, 4H). LCMS (ES+) 210 (M+H)$^+$, RT 0.15 minutes.

Intermediate 39

6-Iodo-2-methylimidazo[1,2-a]pyridine

2-Amino-5-iodopyridine (5 g, 22.73 mmol) was dissolved in ethanol (20 mL). Chloroacetone (2.29 mL, 25 mmol) was added and the mixture was heated at reflux overnight. The reaction mixture was evaporated to dryness. The residue was dissolved in DCM (50 mL) and washed with saturated aqueous sodium bicarbonate solution (20 mL). The organic layer was dried over MgSO$_4$, filtered and evaporated. The resulting crude residue (4.8 g) was triturated with ethyl acetate to afford pure title compound (2.2 g). The filtrate was concentrated to dryness, yielding an additional quantity of less pure title compound (2.0 g). $\delta_H$ (CDCl$_3$) 7.33 (m, 4H), 2.48 (s, 3H). LCMS: MH+ 259.

Intermediate 40

(6-Iodo-2-methylimidazo[1,2-a]pyridin-3-yl)methanol

Intermediate 39 (1 g, 3.88 mmol) and formaldehyde (0.23 g, 7.75 mmol) were dissolved in water (120 mL) and placed in a vial. The vial was sealed and heated at 110° C. over 4 h. After cooling to room temperature, the resulting solid was filtered off. The precipitate was dissolved in MeOH (20 mL) and concentrated to dryness to give the title compound (1.1 g). $\delta_H$ (DMSO-d$_6$) 8.60 (m, 1H), 7.39 (m, 1H), 7.31 (m, 1H), 5.12 (t, J 5.5 Hz, 1H), 4.76 (d, J 5.4 Hz, 2H), 2.32 (m, 3H). LCMS: MH+ 289.

Intermediate 41

3-(2,5-Dimethylbenzyl)-6-iodo-2-methylimidazo[1,2-a]pyridine

Intermediate 40 (0.15 g, 0.5 mmol), p-xylene (10 mL), water (1 mL) and methanesulfonic acid (0.2 mL, 1.4 mmol) were introduced into a vial. The mixture was heated for 1 h at 100° C., until no more starting material was observed. The reaction mixture was concentrated under reduced pressure. The crude residue was dissolved in DCM (10 mL) and washed with saturated aqueous sodium bicarbonate solution (10 mL). The organic layer was dried over MgSO$_4$, filtered and evaporated, to afford the title compound (230 mg). $\delta_H$ (CDCl$_3$) 7.77 (m, 1H), 7.27 (m, 1H), 7.19 (m, 1H), 7.04 (m, 1H), 6.88 (m, 1H), 6.37 (s, 1H), 4.00 (s, 2H), 2.31 (s, 3H), 2.27 (s, 3H), 2.08 (s, 3H). LCMS: MH+ 377.

Intermediate 42 tert-Butyl N-[2-(vinylsulfonylamino)ethyl]carbamate tert-Butyl N-(2-aminoethyl)carbamate (5.00 g, 31.2 mmol) was dissolved in dry dichloromethane (50 mL). Triethylamine (7.02 g, 68.7 mmol) was added and the mixture was cooled in an ice bath, with stirring. 2-Chloroethanesulfonyl chloride (5.09 g, 31.2 mmol) was added dropwise, and the ice bath was removed. The mixture was stirred and allowed to warm to room temperature, stirring overnight. The mixture was partitioned between dichloromethane (150 mL) and 1.5M aqueous sodium carbonate solution (75 mL). The organic layer was dried (Na$_2$SO$_4$) and concentrated in vacuo to give the title compound (7.81 g, quantitative, contains 0.4 equivalents of triethylamine) as a colourless oil. $\delta_H$ (d$_6$-DMSO) 6.53 (dd, 1H, J 16.6, 9.9 Hz), 6.24 (d, 1H, J 16.6 Hz), 5.95 (d, 1H, J 9.9 Hz), 5.06 (br s, 2H), 3.31-3.27 (m, 2H), 3.16-3.12 (m, 2H), 1.45 (s, 9H). LCMS (ES$^+$) 251 (M+H)$^+$.

Intermediate 43

N-(2-Aminoethyl)ethenesulfonamide hydrochloride

Intermediate 42 (7.81 g, 31.2 mmol) was dissolved in 1,4-dioxane (30 mL) and 4.0M hydrochloric acid (100 mL) in 1,4-dioxane was added with stirring. After stirring at room temperature for 2 h, the mixture was concentrated in vacuo to give the title compound (6.50 g, quantitative, contains 0.4 equivalents of triethylamine hydrochloride) as a colourless gum. $\delta_H$ (d$_6$-DMSO) 8.25 (br s, 3H), 7.79 (br t, 1H, NH), 6.75 (dd, 1H, J 16.6, 10.0 Hz), 6.09-6.03 (m, 2H), 3.10-3.05 (m, 2H), 2.92-2.84 (m, 2H).

Intermediate 44

1,2,5-Thiadiazepane 1,1-dioxide

Intermediate 43 (5.82 g, 31.2 mmol) was dissolved in methanol (250 mL). Triethylamine (4.40 mL, 31.2 mmol) was added and the mixture was stirred at room temperature for 3.5 days. The mixture was pre-adsorbed onto silica (45 g) and subjected to flash chromatography (silica, 120 g, 4% conc. ammonia in acetonitrile, eluted with 2 L volume). Fractions were analysed by TLC, eluting with the foregoing solvent mix, and stained with potassium permanganate solution. Fractions in the middle of the chromatography showed two spots which co-eluted. These fractions were concentrated in vacuo. The resulting damp white solid was azeotroped with toluene (50 mL) to give the title compound (5.46 g, 70%, $^1$H NMR showed 1 equivalent of triethylamine) as a dry white solid. $\delta_H$ (d$_6$-DMSO) 7.50 (br s, 1H), 3.58-3.53 (m, 2H), 3.24-3.19 (m, 2H), 3.20-3.10 (m, 4H), 3.05 (q, Et$_3$N), 1.22 (t, Et$_3$N). LCMS (ES$^+$) 151 (M+H)$^+$.

Intermediate 45

2-(1,1-Dioxo-1,2,5-thiadiazepan-5-yl)pyrimidin-5-ylboronic acid

2-Chloropyrimidin-5-ylboronic acid (1.00 g, 6.32 mmol) and Intermediate 44 (1.75 g, 6.96 mmol) were dissolved in ethanol (25 mL) and heated at reflux overnight. Analysis by LCMS showed the major UV visible component to have the desired mass. The mixture was concentrated in vacuo, re-dissolved in water (20 mL) and acidified with acetic acid (1 mL). The mixture was concentrated in vacuo again and purified by chromatography (silica, 50 g, eluted with 82% DCM, 15% MeOH, 2% AcOH, 1% water) to give the title compound (1.40 g). The product was used in the next step without further purification.

Intermediate 46 tert-Butyl 4-(5-{3-[2-(difluoromethoxy)benzyl]-2,7-dimethylimidazo[1,2-a]pyridin-6-yl}pyridin-2-yl)piperazine-1-carboxylate Intermediate 20 (60 mg, 0.16 mmol) and tert-butyl 4-[5-(4,4,5,5-tetramethyl-1,3,2-dioxaborolan-2-yl)pyridin-2-yl]piperazine-1-carboxylate (61 mg, 0.16 mmol) were dissolved in 1,4-dioxane (1 mL). A 2M aqueous potassium carbonate solution (0.28 mL) was added and the reaction mixture was degassed with nitrogen for 5 minutes. Bis[3-(diphenylphosphanyl)cyclopenta-2,4-dien-1-yl]iron-dichloropalladium-dichloromethane complex (6 mg, 0.01 mmol) was added and the reaction mixture was heated at 90° C. in a pressure tube for 90 minutes. The reaction mixture was diluted with EtOAc and washed with water and brine, then dried (Na$_2$SO$_4$), filtered and concentrated to dryness. The residue obtained was purified by column chromatography (eluting with 40-100% EtOAc in heptane) to yield the title compound (50 mg, 56%). $\delta_H$ (250 MHz, CDCl$_3$) 8.03 (d, J 2.3 Hz, 1H), 7.49 (s, 1H), 7.45-7.35 (m, 2H), 7.21 (d, J 7.0 Hz, 1H), 7.15-6.98 (m, 2H), 6.90-6.23 (m, 3H), 4.23 (s, 2H), 3.59-3.54 (m, 7H), 2.46 (s, 3H), 2.33-2.16 (m, 4H), 1.49 (s, 9H). MH+ 564.

Intermediate 47

2-Chloro-5-{3-[2-(difluoromethoxy)benzyl]-2,7-dimethylimidazo[1,2-a]pyridin-6-yl}-pyrimidine Intermediate 20 (371 mg, 0.97 mmol) and 2-chloropyrimidin-5-ylboronic acid (462 mg, 2.92 mmol) were dissolved in 1,4-dioxane (3 mL) and a 2M aqueous sodium carbonate solution (1.5 mL) was added. The resulting mixture was degassed with nitrogen for 5 minutes. Bis(triphenylphosphine)palladium(II) dichloride (34 mg, 0.05 mmol) and tri-tert-butylphosphine (10 mg, 0.05 mmol) were added and the reaction mixture was heated at 110° C. under microwave irradiation for 30 minutes. Additional 2-chloropyrimidin-5-ylboronic acid (462 mg, 2.92 mmol) was added and the reaction mixture was heated at 120° C. under microwave irradiation for 30 minutes. The reaction mixture was diluted with EtOAc, and washed with water and brine, then dried (Na$_2$SO$_4$), filtered and concentrated to dryness. The residue obtained was purified by column chromatography to yield the title compound (280 mg, 52%). $\delta_H$ NMR (500 MHz, CDCl$_3$) 8.55 (s, 2H), 7.61 (s, 1H), 7.45 (s, 1H), 7.26 (m, 1H), 7.13 (d, J 8.0 Hz, 1H), 7.08 (t, J 7.6 Hz, 1H), 6.87 (d, J 7.7 Hz, 1H), 6.60 (t, J 73.7 Hz, 1H), 4.26 (s, 2H), 2.50 (d, J 4.3 Hz, 3H), 2.28 (s, 3H). MH+ 415.

Intermediate 48 tert-Butyl 4-(5-{3-[2-(difluoromethoxy)benzyl]-2-methyl-7-(trifluoromethyl)-imidazo[1,2-a]pyridin-6-yl}pyridin-2-yl)piperazine-1-carboxylate A mixture of Intermediate 16 (150 mg, 0.34 mmol), tert-butyl 4-[5-(4,4,5,5-tetramethyl-1,3,2-dioxaborolan-2-yl)pyridin-2-yl]piperazine-1-carboxylate (148 mg, 0.38 mmol) and 2M aqueous potassium carbonate solution (0.69 mL) in 1,4-dioxane (4 mL) was degassed with nitrogen for 5 minutes. Bis[3-(diphenylphosphanyl)cyclopenta-2,4-dien-1-yl]iron-dichloropalladium-dichloromethane complex (14 mg, 0.02 mmol) was added and the reaction mixture was heated at 120° C. for 8 h. The mixture was treated again with bis[3-(diphenylphosphanyl)cyclopenta-2,4-dien-1-yl]iron-dichloropalladium-dichloromethane complex (14 mg, 0.02 mmol) and heated for a further 3 h. The mixture was cooled to room temperature, filtered through Celite and purified by preparative HPLC (Method C) to afford the title compound (33 mg, 16%) as a clear oil. $\delta_H$ (500 MHz, CDCl$_3$) 8.09-7.90 (m, 2H), 7.65 (s, 1H), 7.46 (d, J 9.0 Hz, 1H), 7.26 (s, 1H), 7.14-7.03 (m, 2H), 6.82 (d, J 7.5 Hz, 1H), 6.74-6.32 (m, 2H), 4.27 (s, 2H), 3.58 (m, 8H), 2.53 (s, 3H), 1.49 (s, 9H). MH+ 618.

Intermediate 49

2-Chloro-5-{3-[2-(difluoromethoxy)benzyl]-2-methyl-7-(trifluoromethyl)imidazo[1,2-a]-pyridin-6-yl}pyrimidine A mixture of Intermediate 16 (1 g, 2.3 mmol), 2-chloropyrimidin-5-ylboronic acid (1.09 g, 6.89 mmol) and 2M aqueous sodium carbonate solution (4.6 mL) in 1,4-dioxane (50 mL) was degassed with nitrogen for 5 minutes. Tri-tert-butylphosphine (23 mg, 0.11 mmol) and bis(triphenylphosphine)palladium(II) dichloride (81 mg, 0.11 mmol) were added and the reaction mixture was heated at 120° C. for 8 h. The mixture was cooled to room temperature and concentrated under reduced pressure. The resulting dark brown gum was purified by column chromatography, eluting with 30-80% ethyl acetate in heptanes, to afford the title compound (604 mg, 56%). $\delta_H$ (500 MHz, CDCl$_3$) 8.58 (s, 2H), 8.18 (d, J 18.6 Hz, 1H), 7.85 (s, 1H), 7.31 (t, J 7.1 Hz, 1H), 7.20-7.05 (m, 2H), 6.97 (d, J 7.4 Hz, 1H), 6.57 (t, J 73.5 Hz, 1H), 4.31 (s, 2H), 2.61 (s, 3H). MH+ 469/471.

Intermediate 50 tert-Butyl 4-fluoropyridin-2-ylcarbamate

Palladium (II) acetate (1.69 g, 7.53 mmol) and Xantphos (8.71 g, 15.05 mmol) were dissolved/suspended in degassed 1,4-dioxane (1200 mL) in a nitrogen atmosphere. 2-Chloro-4-fluoropyridine (99 g, 753 mmol) and tert-butyl carbamate (97 g, 828 mmol) in 1,4-dioxane (550 mL) were added, followed by sodium hydroxide (45.2 g, 1.12 mol) and water (20 mL). The resulting mixture was heated at 100° C. for 2 h. The mixture was cooled to ambient temperature and filtered over celite. The residue was washed with 1,4-dioxane and the filtrate was concentrated to afford a yellow solid (206 g). The crude material was recrystallized from 2-propanol (400 mL) and dried to afford the title compound (120.8 g) as a white solid. LCMS 213 [M+H], RT 1.96 minutes, purity 94%.

Intermediate 51

4-Fluoropyridin-2-amine

Intermediate 50 (120 g, 565 mmol) was dissolved in DCM (1250 mL) and cooled with an ice bath. Trifluoroacetic acid (250 mL) was added dropwise. The resulting mixture was stirred overnight at ambient temperature. The mixture was concentrated and partitioned between saturated aqueous sodium bicarbonate solution and EtOAc. The aqueous layer was extracted twice with EtOAc. The combined organic layers were washed with brine, dried with sodium sulphate, filtered and concentrated, to afford the title compound (65.5 g) as a yellow solid. LCMS 113 [M+H], RT 0.17 minutes.

Intermediate 52

5-Bromo-4-fluoropyridin-2-amine

In an aluminium foil-covered flask, Intermediate 51 (62.3 g, 506 mmol) was dissolved in acetonitrile (1500 mL), and NBS (86 g, 481 mmol) was added. The mixture was stirred at ambient temperature for 2 h. The mixture was concentrated to afford a yellow solid. The crude material was dissolved in EtOAc (1000 mL), washed twice with saturated aqueous sodium bicarbonate solution, then with brine, dried with sodium sulphate, filtered and concentrated in vacuo, to afford a light brown solid (71.2 g). The crude material was crystallized from EtOAc (300 mL) and heptane (300 mL) to give the title compound (34.3 g) as brown crystals. LCMS 191 ($^{79}$Br)/ 193 ($^{81}$Br) [M+H], RT 0.79 minutes.

Intermediate 53

Ethyl 6-bromo-3-[2-(difluoromethoxy)benzyl]-7-fluoroimidazo[1,2-a]pyridine-2-carboxylate A solution of Intermediate 24 (5.07 g, 14.4 mmol) in 1,4-dioxane (30 mL) was treated with magnesium sulphate (5.1 g, 42 mmol), followed by Intermediate 52 (5.6 g, 29 mmol). The resulting suspension was heated at reflux under a nitrogen atmosphere for 24 h. The mixture was cooled and filtered, and the solid was washed with 1,4-dioxane (30 mL) and concentrated in vacuo. The resulting residue was partitioned between EtOAc (150 mL) and 10% aqueous Na$_2$CO$_3$ solution (150 mL). The aqueous layer was extracted with further EtOAc (150 mL), and the combined organic layers were washed with brine (100 mL), dried over MgSO$_4$, filtered and concentrated in vacuo. The crude residue was purified by column chromatography on silica gel, eluting with EtOAc in DCM (0% to 10%), to give the title compound (3.84 g, 62%) as a yellow solid. $\delta_H$ (DMSO-d$_6$) 8.81 (d, 1H), 7.76 (d, 1H), 7.29 (t, 1H), 7.26 (t, 1H), 7.19 (d, 1H), 7.08 (t, 1H), 6.81 (d, 1H), 4.67 (s, 2H), 4.25 (q, 2H), 1.23 (t, 3H). LCMS 445 (M+H)$^+$, RT 1.14 minutes.

Intermediate 54

{6-Bromo-3-[2-(difluoromethoxy)benzyl]-7-fluoroimidazo[1,2-a]pyridin-2-yl}methanol A solution of Intermediate 53 (3.7 g, 8.3 mmol) in THF (50 mL) was cooled to 0° C. under a nitrogen atmosphere and treated with diisobutylaluminium hydride (1.0 mol/L in DCM, 33 mL, 33 mmol), added slowly via a syringe. The reaction mixture was stirred at 0° C. for 20 minutes. The reaction mixture was quenched by the addition of MeOH (3 mL) and allowed to warm to ambient temperature, then 2M HCl solution (50 mL) was added. The mixture was extracted with DCM (2×100 mL). The combined organic layers were washed with saturated aqueous NaHCO$_3$ solution (200 mL) and brine (150 mL), then dried over MgSO$_4$. Filtration and concentration in vacuo gave the title compound (2.3 g, 69%) as a yellow powder, containing approximately 10% starting material. $\delta_H$ (DMSO-d$_6$) 8.71 (d, 1H), 7.75 (d, 1H), 7.42 (d, 1H), 7.40 (t, 1H), 7.33 (d, 1H), 7.24 (t, 1H), 7.07 (d, 1H), 4.69 (s, 2H), 4.54 (s, 2H). LCMS 403 (M+H)$^+$, RT 0.99 minutes.

Intermediate 55

6-Bromo-3-[2-(difluoromethoxy)benzyl]-7-fluoro-2-(methoxymethyl)imidazo[1,2-a]-pyridine A solution of Intermediate 54 (450 mg, 1.08 mmol) in DMF (7 mL) was cooled to 0° C. under a nitrogen atmosphere, then treated with iodomethane (120 µL, 1.92 mmol) followed by sodium hydride (60% suspension in mineral oil, 80 mg, 2.00 mmol) and stirred at 0° C. for 40 minutes. The mixture was quenched with water (50 mL) and extracted with EtOAc (2×50 mL). The combined organic extracts were washed with water (50 mL) and brine (50 mL), and dried over MgSO$_4$. Filtration and concentration in vacuo gave the title compound (450 mg, 87%) as a yellow solid. $\delta_H$ (DMSO-d$_6$) 8.62 (d, 1H), 7.64 (d, 1H), 7.30 (t, 1H), 7.25 (t, 1H), 7.20 (d, 1H), 7.12 (t, 1H), 6.93 (d, 1H), 4.44 (s, 2H), 4.38 (d, 2H), 3.02 (s, 3H). LCMS 415.0 (M+H)$^+$, RT 1.07 minutes.

Intermediate 56

Ethyl 4-(4,4,5,5-tetramethyl-1,3,2-dioxaborolan-2-yl)cyclohex-3-ene-1-carboxylate Lithium hexamethyldisilazide in THF/ethylbenzene (1M, 5.55 mL) was added dropwise to a stirred solution of ethyl 4-oxocyclohexanecarboxylate (900 mg, 5.29 mmol) in anhydrous THF (5 mL) under an inert atmosphere at −78° C., and the mixture was stirred for 1 h. 1,1,1-Trifluoro-N-phenyl-N-[(trifluoromethyl)sulfonyl]methanesulfonamide (1.98 g, 5.55 mmol) in THF (5 mL) was added over 5 minutes, and the mixture was stirred for 30 minutes. The reaction mixture was then warmed to room temperature and stirred for 12 h. The mixture was quenched with NaHSO$_4$ and diluted with ethyl acetate (250 mL), then washed with 0.5M aqueous NaOH solution (2×20 mL), saturated aqueous NH$_4$Cl solution (20 mL) and brine (20 mL). The organic fraction was then dried over MgSO$_4$ and concentrated under reduced pressure to afford the intermediate triflate (1.9 g, 83%). This material was dissolved in 1,4-dioxane (30 mL), bis(pinacolato)diboron (1.68 g, 6.6 mmol) and 1,1'-bis(diphenylphosphino)ferrocene (73 mg, 0.13 mmol) were added and the mixture was degassed with N$_2$ for 5 minutes. Bis[3-(diphenylphosphanyl)-cyclopenta-2,4-dien-1-yl]iron-dichloropalladium-dichloromethane complex (108 mg, 0.13 mmol) was added and the mixture was heated at 90° C. for 18 h. The mixture was diluted with water (100 mL) and extracted with ethyl acetate (2×100 mL). The combined organic layers were washed with brine (50 mL), dried over MgSO$_4$ and concentrated under reduced pressure. The residue was purified by silica gel chromatography, eluting with 10-20% ethyl acetate in heptane, to afford the title compound in two batches (440 mg, 26% yield, 73% purity; and 362 mg, 12% yield, 42% purity) as a colourless oil. Method B HPLC-MS: MH+ m/z 281, RT 2.37 minutes (73%).

Intermediate 57

[2-(4-Methoxycarbonyl-4-methylpiperidin-1-yl)pyrimidin-5-yl]boronic acid

Prepared from 4-methylpiperidine-4-carboxylic acid methyl ester and (2-chloropyrimidin-5-yl)boronic acid according to the method of Intermediate 45.

Intermediate 58

[2-(4-Ethoxycarbonyl-4-methylpiperidin-1-yl)pyrimidin-5-yl]boronic acid

To 2-chloropyrimidine-5-boronic acid (4.00 g, 25.3 mmol) were added ethyl 4-methylpiperidine-4-carboxylate hydrochloride (4.09 g, 23.9 mmol), ethanol (40 mL) and triethylamine (9.0 mL, 64.0 mmol). The mixture was heated at 80° C. for 3 h before being concentrated in vacuo. The reaction mixture was partitioned between water (100 mL) and ethyl acetate (100 mL), then the aqueous layer was separated and extracted with ethyl acetate (2×100 mL). The organic layers were combined and washed with brine (100 mL), then dried (Na$_2$SO$_4$). The solvent was then removed under reduced pressure and the crude reaction mixture was purified by flash column chromatography on silica (Biotage SNAP 100 g, Isolera). Gradient elution, with 100% dichloromethane to 30% methanol/dichloromethane, afforded the title compound (4.27 g, 43% yield, 74% purity) as a brown oil. LCMS (pH 10): MH+ m/z 294.1, RT 0.652 minutes.

Intermediate 59

4-(3-{[2-(Difluoromethoxy)phenyl]methyl}-2-methylimidazo[1,2-a]pyridin-6-yl)-1,2,3,6-tetrahydropyridine dihydrochloride Example 19 (650 mg, 1.4 mmol) was suspended in 4M HCl in 1,4-dioxane (3.46 mL) and stirred at room temperature for 2 h. The mixture was concentrated under reduced pressure and dried under vacuum to provide the title compound (630 mg, quantitative) as an off-white solid. The crude material was used directly in the next step. Method B HPLC-MS: MH+ m/z 370, RT 1.04 minutes (93%).

Intermediate 60

{2-[(1R,5S,6r)-6-(Ethoxycarbonyl)-3-azabicyclo[3.1.0]hexan-3-yl]pyrimidin-5-yl}boronic acid (2-Chloropyrimidin-5-yl)boronic acid (250 mg, 1.6 mmol), ethyl (1R,5S,6r)-3-azabicyclo[3.1.0]hexane-6-carboxylate hydrochloride (303 mg, 1.6 mmol) and triethylamine (0.22 mL, 1.6 mmol) were dissolved in ethanol (8 mL) and stirred at 80° C. overnight. The reaction mixture was cooled and concentrated under vacuum. Water (30 mL) was added and the resulting material was filtered and dried to afford the title compound (253 mg, 58%) as a pale brown solid. Method B HPLC-MS: MH+ m/z 278, RT 1.35 minutes (100%).

Intermediate 61

{2-[4-(Ethoxycarbonyl)piperidin-1-yl]pyrimidin-5-yl}boronic acid (2-Chloropyrimidin-5-yl)boronic acid (2 g, 13 mmol) and ethyl piperidine-4-carboxylate (1.94 mL, 13 mmol) were dissolved in 1,4-dioxane (20 mL) and heated to 60° C. under microwave irradiation for 1 h. The reaction mixture was concentrated to dryness and partitioned between EtOAc and water. The organic layer was separated, washed with brine, dried over Na$_2$SO$_4$ and concentrated to dryness, to afford the title compound (1.79 g, 51%) as a yellow gum. Method C HPLC-MS: MH+ m/z 280, RT 0.94 minutes (89%).

Intermediate 62

Ethyl 2-(5-bromopyrimidin-2-yl)propanoate

Ethyl 2-(5-bromopyrimidin-2-yl)acetate (500 mg, 2.04 mmol) was dissolved in THF (8 mL) and the mixture was cooled to −78° C. under nitrogen. LDA in THF/heptane/ethylbenzene (2M, 1.25 mL) was added dropwise, then the mixture was stirred for 15 minutes. Iodomethane (0.22 mL, 3.53 mmol) was added, then the reaction mixture was warmed to room temperature and stirred for a further 2 h. Water (10 mL) was added and the mixture was extracted with ethyl acetate (20 mL). The aqueous layer was acidified to pH ~5 with 1M HCl, then extracted with additional ethyl acetate (2×20 mL). The combined organic layers were dried over Na$_2$SO$_4$ and concentrated under vacuum. The residue was purified by silica gel chromatography, eluting with a gradient of 0-50% ethyl acetate in heptane, to afford the title compound (417 mg, 79%) as a yellow oil. $\delta_H$ (500 MHz, CDCl$_3$)

8.75 (s, 2H), 4.18 (m, 2H), 4.08 (q, J 7.2 Hz, 1H), 1.60 (d, J 7.3 Hz, 3H), 1.22 (t, J 7.1 Hz, 3H).

Intermediate 63

[2-(1-Ethoxy-1-oxopropan-2-yl)pyrimidin-5-yl]boronic acid

Intermediate 62 (417 mg, 1.6 mmol), bis(pinacolato)diboron (613 mg, 2.4 mmol) and potassium acetate (474 mg, 4.8 mmol) were combined in 1,4-dioxane (8 mL) and the mixture was degassed under nitrogen. Bis[3-(diphenylphosphanyl)cyclopenta-2,4-dien-1-yl]iron-dichloropalladium-dichloromethane complex (119 mg, 0.16 mmol) was added and the mixture was heated at 85° C. under nitrogen for 16 h. Water (20 mL) was added and the mixture was extracted with ethyl acetate (3×30 mL). The combined organic layers were dried over sodium sulfate and concentrated under vacuum to afford the title compound (0.86 g) as a dark brown oil, which was used without purification. Method B HPLC-MS: MH+ m/z 225, RT 1.15 minutes (76%).

Intermediate 64

(2S)-4-[5-(Dihydroxyboranyl)pyrimidin-2-yl]morpholine-2-carboxylic acid bis(triethylamine)dihydrochloride Prepared from 2(S)-morpholine-2-carboxylic acid and (2-chloropyrimidin-5-yl)boronic acid according to the method of Intermediate 45.

Intermediate 65

N-(5-Bromo-4-fluoropyridin-2-yl)-N,N-dimethylacetamidine

The title compound can be prepared from 5-bromo-4-fluoropyridin-2-amine according to the method of Intermediate 3.

Intermediate 66

(6-Bromo-7-fluoro-2-methylimidazo[1,2-a]pyridin-3-yl)[2-(difluoromethoxy)phenyl]-methanone The title compound can be prepared from Intermediate 4 and Intermediate 65 according to the method of Intermediate 5. $\delta_H$ (400 MHz, DMSO-$d_6$) 9.89 (d, 1H, J 7.0 Hz), 7.95 (d, 1H, J 9.1 Hz), 7.66 (m, 1H), 7.54 (dd, 1H, J 7.5, 1.7 Hz), 7.43 (m, 2H), 7.26 (t, 1H, J 74 Hz), 1.89 (s, 3H). LCMS RT 1.51 minutes, MH+ 399.

Intermediate 67

(6-Bromo-7-fluoro-2-methylimidazo[1,2-a]pyridin-3-yl)[2-(difluoromethoxy)phenyl]-methanol The title compound can be prepared from Intermediate 66 according to the method of Intermediate 6. $\delta_H$ (400 MHz, DMSO-$d_6$) 8.70 (d, 1H, J 6.8 Hz), 7.91 (dd, 1H, J 6.9, 2.2 Hz), 7.55 (d, 1H, J 9.6 Hz), 7.38 (m, 2H), 7.13 (m, 1H), 7.09 (t, 1H, J 7.4 Hz), 6.38 (m, 1H), 6.24 (d, 1H, J 4.4 Hz), 2.10 (s, 3H). LCMS RT 1.41 minutes, MH+ 401.

Intermediate 68

6-Bromo-3-{[2-(difluoromethoxy)phenyl]methyl}-7-fluoro-2-methylimidazo[1,2-a]-pyridine The title compound can be prepared from Intermediate 67 according to the method of Intermediate 7. $\delta_H$ (400 MHz, DMSO-$d_6$) 8.61 (d, 1H, J 6.7 Hz), 7.55 (d, 1H, J 9.7 Hz), 7.31 (m, 1H), 7.26 (t, 1H, J 74.1 Hz), 7.20 (d, 1H, J 7.9 Hz), 7.14 (td, 1H, J 7.5, 1.0 Hz), 7.00 (dd, 1H, J 7.6, 1.3 Hz), 4.31 (s, 2H), 2.26 (s, 3H). LCMS 1.53 minutes, MH+ 385.

Intermediate 69 tert-Butyl 4-[5-(3-{[2-(difluoromethoxy)phenyl]methyl}-2,7-dimethylimidazo[1,2-a]-pyridin-6-yl)pyrimidin-2-yl]piperazine-1-carboxylate Intermediate 20 (150 mg, 0.39 mmol) and (2-{4-[(tert-butoxy)carbonyl]piperazin-1-yl}pyrimidin-5-yl)boronic acid (133 mg, 0.43 mmol) were dissolved in 1,4-dioxane (1.5 mL) and 2M aqueous potassium carbonate solution (0.69 mL) was added. The reaction mixture was degassed with nitrogen for 5 minutes, then bis[3-(diphenylphosphanyl)-cyclopenta-2,4-dien-1-yl]iron-dichloropalladium-dichloromethane complex (16 mg, 0.02 mmol) was added. The mixture was heated at 90° C. for 3 h in a sealed tube under nitrogen. Further (2-{4-[(tert-butoxy)carbonyl]piperazin-1-yl}pyrimidin-5-yl)boronic acid (61 mg, 0.2 mmol), 2M aqueous potassium carbonate solution (0.3 mL) and bis[3-(diphenylphosphanyl)cyclopenta-2,4-dien-1-yl]iron-dichloropalladium-dichloromethane complex (8 mg, 0.01 mmol) were added. The mixture was degassed, then heated at 90° C. for 2 h in a sealed tube under nitrogen. The mixture was diluted with water (5 mL) and extracted into EtOAc (3×10 mL), then washed with brine (10 mL), dried over magnesium sulfate and concentrated under vacuum. The crude product was purified by flash column chromatography, eluting with 0-10% (7M ammonia in methanol) in DCM followed by 10-50% MeOH in DCM, to afford the title compound (160 mg, 69%). Method C HPLC-MS: MH+ m/z 565, RT 1.18 minutes (90%).

Intermediate 70

5-(3-{[2-(Difluoromethoxy)phenyl]methyl}-2,7-dimethylimidazo[1,2-a]pyridin-6-yl)-2-(piperazin-1-yl)pyrimidine Trifluoroacetic acid (0.21 mL, 2.72 mmol) was added to a solution of Intermediate 69 (96% pure, 160 mg, 0.27 mmol) in DCM (0.5 mL) and the mixture was stirred for 30 minutes. The mixture was loaded onto an SCX cartridge which was washed with MeOH, followed by 7M ammonia in MeOH. Product fractions were concentrated to afford the title compound (109 mg, 86%). Method C HPLC-MS: MH+ m/z 465, RT 0.85 minutes (83%).

Intermediate 71

[2-(3-Oxopiperazin-1-yl)pyrimidin-5-yl]boronic acid (2-Chloropyrimidin-5-yl)boronic acid (1.0 g, 6.32 mmol) and piperazin-2-one (1.6 g, 16.0 mmol) were suspended in 1,4-dioxane (10 mL) and the mixture was heated at 100° C. under microwave irradiation for 45 minutes. The supernatant liquid was decanted from the suspension and the residue was triturated with methanol and diethyl ether. The resultant solids were filtered off and dried under vacuum to afford the title compound (706 mg, 30%) as a pale pink solid. Method B HPLC-MS: MH+ m/z 223, RT 0.25 minutes.

Intermediate 72

[2-(5-Oxo-1,4-diazepan-1-yl)pyrimidin-5-yl]boronic acid (2-Chloropyrimidin-5-yl)boronic acid (200 mg, 1.26 mmol) and 1,4-diazepan-5-one (288.34 mg, 2.53 mmol) were suspended in 1,4-dioxane (3 mL) and the mixture was heated at 100° C. under microwave irradiation for 45 minutes. The resulting slurry was concentrated under vacuum and triturated with MeOH to afford the title compound (145 mg, 30%) as a cream precipitate, which was used without further purification. Method C HPLC-MS: MH+ m/z 237, RT 0.40 minutes.

Intermediate 73

4-(3-{[2-(Difluoromethoxy)phenyl]methyl}-2-methylimidazo[1,2-a]pyridin-6-yl)-2-fluoropyridine In a pressure tube Intermediate 7 (1.7 g, 4.63 mmol) and (2-fluoropyridin-4-yl)-boronic acid (935 mg, 6.64 mmol) were dissolved in 1,4-dioxane (10 mL) and a 2M solution of $K_2CO_3$ in water (7 mL) was added. The mixture was flushed with nitrogen and bis[3-(diphenylphosphanyl)cyclopenta-2,4-dien-1-yl]iron dichloropalladium dichloromethane complex (300 mg, 0.37 mmol) was added. The mixture was heated at 90° C. for 4 h. The mixture was diluted with ethyl acetate (20 mL), then washed with water (2×10 mL) and brine (10 mL). The organic layer was dried over sodium sulfate and concentrated under vacuum. The resulting dark brown solid was purified by FCC, eluting with a gradient of 70-100% ethyl acetate in heptane followed by 0-10% methanol in DCM, to afford the title compound (1.55 g, 87%) as a light pink solid. $\delta_H$ (250 MHz, CD$_3$OD) 8.52-8.49 (m, 1H), 8.24 (d, J 5.4 Hz, 1H), 7.63 (d, J 1.8 Hz, 1H), 7.60 (d, J 0.9 Hz, 1H), 7.56-7.52 (m, 1H), 7.33 (s, 1H), 7.31-7.25 (m, 1H), 7.24-6.64 (m, 4H), 4.43 (s, 2H), 2.44 (s, 3H). Method D HPLC-MS: MH+ m/z 384, RT 3.29 minutes.

Intermediate 74

Methyl 1-benzyl-2,5-dihydro-1H-pyrrole-3-carboxylate

To a stirred solution of benzyl(methoxymethyl)[(trimethylsilyl)methyl]amine (7.3 g, 0.03 mol) and methyl prop-2-ynoate (3.1 mL, 0.04 mol) in dichloromethane (150 mL) at 0° C. under nitrogen was added dropwise a solution of trifluoroacetic acid (0.12 mL, 0.002 mol) in dichloromethane (1 mL). The reaction mixture was allowed to stir at 0° C. for 20 minutes, then the ice bath was removed and the solution was allowed to warm to room temperature. The solution was stirred at room temperature for 2 h, then the solvent was evaporated. The residue was purified by FCC, eluting with 0-20% ethyl acetate in heptane, to afford the title compound (2.37 g, 29%) as a yellow oil. $\delta_H$ (250 MHz, CDCl$_3$) 7.35-7.15 (5H, m), 6.70 (1H, s), 3.79 (3H, s), 3.75-3.60 (6H, m).

Intermediate 75

Methyl 3-benzyl-3-azabicyclo[3.1.0]hexane-1-carboxylate

To a stirred suspension of sodium hydride (60%, 0.71 g, 0.02 mol) in anhydrous DMSO (20 mL) under nitrogen at 0° C. was added portionwise trimethylsulfoxonium iodide (4.16 g, 0.02 mol). The mixture was stirred until gas evolution had ceased, then warmed to 40° C. The mixture was cooled to 0° C., then a solution of Intermediate 74 (1.94 g, 0.01 mol) in DMSO (1 mL) was added dropwise. The mixture was warmed to room temperature, stirred for 10 minutes, then warmed to 50° C. and stirred for 2 h. The mixture was cooled to room temperature, then poured into water (20 mL) and ethyl acetate (20 mL). The phases were separated, and the aqueous phase was extracted twice with ethyl acetate (20 mL). The combined organic extracts were washed with water (2×10 mL) and concentrated under vacuum. The residue was purified by FCC, eluting with 0-25% ethyl acetate in heptane, to afford the title compound (411 mg, 20%) as a colourless oil. $\delta_H$ (500 MHz, CDCl$_3$) 7.26 (5H, m), 3.66 (3H, s), 3.57 (m, 2H), 3.27-2.98 (1H, m), 2.98-2.92 (1H, m), 2.72 (1H, m), 2.42 (1H, m), 1.93 (1H, m), 1.52-1.39 (1H, m), 1.28 (1H, m).

Intermediate 76

Methyl 3-azabicyclo[3.1.0]hexane-1-carboxylate hydrochloride

To palladium on carbon under nitrogen was added a solution of Intermediate 75 (0.4 g, 1.73 mmol) in methanol (10 mL). The flask was cycled thrice between vacuum and nitrogen, then filled with hydrogen and stirred vigorously for 5 h. The mixture was filtered through celite, washing with methanol. The filtrate was concentrated under vacuum, then treated with 4M hydrogen chloride in 1,4-dioxane (1 mL, 4 mmol). The solution was evaporated to dryness under a stream of nitrogen, then dried further in a vacuum oven at 40° C. for 5 h, to afford the title compound (291 mg, 95%) as a white solid. $\delta_H$ (500 MHz, DMSO-d$_6$) 9.67 (1H, s), 9.35 (1H, s), 3.62 (3H, s), 3.58-3.48 (1H, m), 3.39 (1H, d, J 11.5 Hz), 3.35 (1H, m), 3.26 (1H, d, J 11.5 Hz), 2.19 (1H, dt, J 9.1, 5.0 Hz), 1.56-1.41 (1H, m), 1.37 (1H, t, J 5.7 Hz).

Intermediate 77

Methyl 2-[1-(diphenylmethyl)azetidin-3-ylidene]acetate

Methyl (triphenylphosphoranylidene)acetate (2.77 g, 8.29 mmol) was added to a mixture of 1-(diphenylmethyl)azetidin-3-one (1.64 g, 6.91 mmol) in THF (24 mL) and the resultant mixture was left to stir overnight. The mixture was concentrated under vacuum, then the residue was dissolved in hot 1:4 EtOAc/heptane (40 mL) and allowed to cool to room temperature. The resultant solid was filtered off and the filtrate was concentrated under vacuum. The crude residue was purified by FCC, eluting with 20% EtOAc in heptane, to afford the title compound (917 mg, 44%) as a pale yellow solid. Method B HPLC-MS: MH+ m/z 294, RT 1.43 minutes.

Intermediate 78

Methyl 5-(diphenylmethyl)-5-azaspiro[2.3]hexane-1-carboxylate

A mixture of potassium tert-butoxide (1.33 g, 11.9 mmol) and trimethylsulfoxonium iodide (2.78 g, 12.5 mmol) in DMSO (10 mL) was heated at 50° C. until a solution resulted. Then a solution of Intermediate 77 (917 mg, 3.13 mmol) in DMSO (5 mL) was added dropwise. Upon complete addition, the mixture was heated for a further 2 h, then allowed to cool to room temperature. The mixture was diluted with water (90 mL) and extracted with diethyl ether (2×50 mL). The organic phases were combined, washed with water (50 mL) and brine, then dried over sodium sulfate and concentrated under vacuum. The crude product was purified by FCC, eluting with a gradient of 0-20% EtOAc in heptane, to afford the title compound (455 mg, 44%) as a yellow viscous oil. Method B HPLC-MS: MH+ m/z 308, RT 1.44 minutes (93%).

Intermediate 79

Methyl 5-azaspiro[2.3]hexane-1-carboxylate hydrochloride

A mixture of Intermediate 78 (570 mg, 1.85 mmol) and palladium(II) dihydroxide (12%, 109 mg, 0.09 mmol) in MeOH (20 mL) was stirred under an atmosphere of hydrogen overnight. A 1M solution of HCl in MeOH (10 mL) was added, and the mixture was filtered through celite. The filtrate was concentrated in vacuo, and the residue was washed with heptane (2×20 mL), to afford the title compound (351 mg, >100%) as a light brown viscous oil. $\delta_H$ (250 MHz, CDCl$_3$) 3.99-4.28 (m, 4H), 3.74-3.87 (m, 5H), 1.75-1.94 (m, 1H), 1.14-1.39 (m, 2H).

Intermediate 80

Methyl 5-[5-(3-{[2-(difluoromethoxy)phenyl]methyl}-2-methylimidazo[1,2-a]pyridin-6-yl)pyrimidin-2-yl]-5-azaspiro[2.3]hexane-1-carboxylate A mixture of (2-chloropyrimidin-5-yl)boronic acid (261 mg, 1.65 mmol), Intermediate 79 (351 mg, 1.98 mmol) and triethylamine (0.83 mL, 5.93 mmol) in EtOH (2 mL) were heated under microwave irradiation at 80° C. for 1 h. Intermediate 7 (403 mg, 1.1 mmol), 1,2-dimethoxyethane (18 mL) and 2M aqueous sodium carbonate solution (4 mL) were added and the reaction mixture was thoroughly degassed. Tetrakis(triphenylphosphine)palladium(0) (190 mg, 0.16 mmol) was added and the mixture was heated in a sealed tube at 80° C. under nitrogen overnight. The mixture was allowed to cool to room temperature, then water (10 mL) and EtOAc (15 mL) were added. The organic phase was separated and the aqueous phase was extracted with EtOAc (15 mL). The organic phases were combined, washed with brine, dried over sodium sulfate and concentrated under vacuum. The crude residue was purified by FCC, eluting with 0-10% MeOH in DCM, to afford the title compound (160 mg, 13%) as a light brown gummy solid. Method B HPLC-MS: MH+ m/z 506, RT 1.52 minutes (80%).

Intermediate 81

2-Bromo-5-(3-{[2-(difluoromethoxy)phenyl]methyl}-2-methylimidazo[1,2-a]pyridin-6-yl)pyrazine Intermediate 31 (200 mg, 0.602 mmol), 2-bromo-5-iodopyrazine (172 mg, 0.602 mmol), 2M aqueous sodium carbonate solution (0.903 mL, 1.807 mmol) and anhydrous DMSO (2 mL) were charged to a sealed tube. The mixture was degassed by bubbling with nitrogen for 5 minutes before the addition of tetrakis(triphenylphosphine)-palladium(0) (35 mg, 0.03 mmol). The mixture was sealed under nitrogen, then stirred at 100° C. for 1 h. The reaction mixture was partitioned between water (25 mL) and EtOAc (50 mL), then the organic phase was washed with saturated aqueous NaHCO$_3$ solution (10 mL) and brine (10 mL), dried over sodium sulfate and concentrated under vacuum. The residue was purified by FCC, eluting with a gradient of 17-100% EtOAc in heptane, to afford the title compound (160 mg, 42%) as an off white solid. $\delta_H$ (500 MHz, CDCl$_3$) 8.72-8.68 (m, 2H), 7.93 (s, 2H), 7.33-7.26 (m, 2H), 7.18 (d, J 8.0 Hz, 1H), 7.13 (t, J 7.5 Hz, 1H), 7.01 (t, J 8.3 Hz, 1H), 6.82-6.52 (t, 1H), 4.36 (s, 2H), 2.61 (s, 3H).

Intermediate 82

N-(5-Bromo-1-methyl-1H-pyrazol-3-yl)methanesulfonamide

5-Bromo-1-methyl-1H-pyrazol-3-amine (500 mg, 2.84 mmol) and DIPEA (2.47 mL, 14.2 mmol) were stirred in anhydrous 1,2-dichloroethane (8 mL) at room temperature, then mesyl chloride (550 µL, 7.1 mmol) in 1,2-dichloroethane (1.5 mL) was added dropwise. The mixture was stirred at room temperature for 3 h, then partitioned between DCM and water. The organic phases were separated and washed with brine, then dried over sodium sulfate and concentrated. To the resulting orange/brown solid was added 1M tetrabutylammonium fluoride in THF (10.5 mL) and the mixture was heated at reflux for 4 h. The reaction mixture was concentrated and diluted with DCM (40 mL), then washed with water (4×25 mL), followed by brine (25 mL). The organic layers were dried over sodium sulfate and concentrated under vacuum. The residue was purified by FCC, eluting with 35-50% EtOAc in heptane followed by 5-10% MeOH in DCM, to afford the title compound (388 mg, 54%) as a white solid. $\delta_H$ (250 MHz, CDCl$_3$) 6.33 (s, 1H), 3.85 (s, 3H), 3.02 (s, 3H).

Intermediate 83

N-(5-Bromo-1-methyl-1H-pyrazol-3-yl)-N-methylmethanesulfonamide

Potassium carbonate (422 mg, 3.05 mmol) was added to a solution of Intermediate 82 (388 mg, 1.53 mmol) in anhydrous MeCN (5.5 mL) in a round-bottom flask fitted with a condenser and a potassium hydroxide scrubber. Dimethyl sulfate (290 µL, 3.05 mmol) was added slowly. The reaction mixture was heated at 50° C. and stirred for 17 h. The mixture was concentrated under vacuum and the crude residue was purified by FCC, eluting with 25-50% EtOAc in heptane, to afford the title compound (350 mg, 86%) as a colourless oil. $\delta_H$ (250 MHz, DMSO-d$_6$) 6.35 (s, 1H), 3.80 (s, 3H), 3.29 (s, 3H), 2.90 (s, 3H).

Intermediate 84

3-Chloro-6-(3-{[2-(difluoromethoxy)phenyl]methyl}-2-methylimidazo[1,2-a]pyridin-6-yl)pyridazine Intermediate 31 (150 mg, 0.45 mmol), 3-chloro-6-iodopyridazine (109 mg, 0.45 mmol), 2M aqueous sodium carbonate solution (677 µL) and anhydrous DMSO (2 mL) were charged to a sealed tube. The mixture was degassed by bubbling with nitrogen for 5 minutes before the addition of tetrakis(triphenylphosphine)palladium(0) (26 mg, 0.023 mmol). The reaction mixture was sealed under nitrogen, then stirred at 90° C. for 2 h. The mixture was diluted with water (2 mL), extracted into EtOAc (3×10 mL) and washed with brine (10 mL), then dried over sodium sulfate and concentrated under vacuum. The crude residue was purified by FCC, eluting with 0-100% ethyl acetate in heptane followed by 0-10% methanolic ammonia in DCM, to afford the title compound (108 mg, 50%). Method C HPLC-MS: MH+ m/z 401, RT 1.06 minutes.

Intermediate 85

Ethyl (1R,5S,6r)-3-[6-(3-{[2-(difluoromethoxy)phenyl]methyl}-2-methylimidazo[1,2-a]-pyridin-6-yl)pyridazin-3-yl]-3-azabicyclo[3.1.0]hexane-6-carboxylate (cis isomer)

Intermediate 84 (84%, 108 mg, 0.23 mmol), ethyl (1R,5S,6r)-3-azabicyclo[3.1.0]-hexane-6-carboxylate hydrochloride (43 mg, 0.23 mmol) and triethylamine (32 µL, 0.23 mmol) were stirred in 1,4-dioxane (2 mL) at 90° C. for 2.5 h, then at 120° C. for 1.5 h, then at 130° C. for a total of 9 h. Further ethyl (1R,5S,6r)-3-azabicyclo[3.1.0]hexane-6-carboxylate hydrochloride (43 mg, 0.23 mmol) and triethylamine (63 µL, 0.45 mmol) were added and the reaction mixture was heated for 6 h at 150° C. The mixture was concentrated and diluted with EtOAc (25 mL), then washed with water (2×10 mL) and brine. The aqueous phase was basified with saturated aqueous sodium carbonate solution, then extracted with EtOAc (3×25 mL). The organic layers were washed with brine, dried over sodium sulfate and concentrated under vacuum, to afford the title compound (134 mg, 52%), which was used without purification. Method C HPLC-MS: MH+ m/z 520, RT 1.09 minutes.

Intermediate 86

5-(3-{[2-(Difluoromethoxy)phenyl]methyl}-2-methylimidazo[1,2-a]pyridin-6-yl)pyridin-2-amine Tetrakis(triphenylphosphine)palladium(0) (190 mg, 0.16 mmol) was added to a thoroughly degassed mixture of 5-(4,4,5,5-tetramethyl-1,3,2-dioxaborolan-2-yl)pyridin-2-amine (225 mg, 1.02 mmol) and Intermediate 7 (250 mg, 0.68 mmol) in 1,2-dimethoxyethane (8 mL) and 2M aqueous sodium carbonate solution (2 mL). The reaction mixture was heated in a sealed tube at 80° C. under nitrogen for 4 h. The mixture was allowed to cool to room temperature, then diluted with water (15 mL) and 9:1 chloroform/isopropanol (20 mL). The organic phase was separated and the aqueous phase was extracted with 9:1 chloroform/isopropanol (25 mL). The organic phases were combined, washed with brine, dried over sodium sulfate and concentrated under vacuum. The crude residue was purified by FCC, eluting with 0-10% MeOH in DCM, to afford the title compound (219 mg, 85%) as an orange solid. $\delta_H$ (250 MHz, CDCl$_3$) 8.15 (d, J 2.13 Hz, 1H), 7.77-7.85 (m, 1H), 7.48-7.65 (m, 2H), 7.27 (s, 4H), 6.31-6.97 (m, 3H), 4.56 (br s, 2H), 4.31 (s, 2H), 2.52 (s, 3H). Method B HPLC-MS: MH+ m/z 381, RT 1.17 minutes.

Intermediate 87

Methyl 1-[5-(3-{[2-(difluoromethoxy)phenyl]methyl}-2-methylimidazo[1,2-a]pyridin-6-yl)pyrimidin-2-yl]-3-methylpyrrolidine-3-carboxylate (2-Chloropyrimidin-5-yl)boronic acid (194 mg, 1.23 mmol), methyl 3-methylpyrrolidine-3-carboxylate (234 mg, 1.63 mmol) and K$_2$CO$_3$ (226 mg, 1.63 mmol) were stirred in N,N-dimethylformamide (4 mL) in a sealed tube at 80° C. for 1 h. Intermediate 7 (300 mg, 0.82 mmol) in 1,4-dioxane (6 mL) was added and the mixture was degassed with nitrogen for 5 minutes. Degassed 2M aqueous potassium carbonate solution (1.3 mL) and bis[3-(diphenylphosphanyl)cyclopenta-2,4-dien-1-yl]iron dichloropalladium dichloromethane complex (34 mg, 0.04 mmol) were added and the mixture was heated at 80° C. for 3 h in a sealed tube under nitrogen. The mixture was diluted with water (10 mL), extracted with EtOAc (3×20 mL), washed with brine (10 mL), dried over magnesium sulfate and concentrated under vacuum. The crude residue was purified by FCC, eluting with 0-2% ammonia/methanol in DCM, to afford the title compound (296 mg, 61%). $\delta_H$ (500 MHz, CDCl$_3$) 8.41 (s, 2H), 7.78 (s, 1H), 7.69 (d, J 9.2 Hz, 1H), 7.32-7.29 (m, 1H), 7.28-7.25 (m, 1H), 7.19 (d, J 8.1 Hz, 1H), 7.10 (t, J 7.5 Hz, 1H), 6.88 (d, J 6.9 Hz, 1H), 6.65 (t, J 73.7 Hz, 1H), 4.32 (s, 2H), 4.10 (d, J 11.4 Hz, 1H), 3.73 (d, J 9.7 Hz, 5H), 3.51 (d, J 11.4 Hz, 1H), 2.55 (s, 3H), 2.52 (dd, J 13.1, 6.5 Hz, 1H), 2.00-1.94 (m, 1H), 1.44 (s, 3H). Method C HPLC-MS: MH+ m/z 508, RT 1.12 minutes.

Intermediate 88

1-(tert-Butyl)3-ethyl 4-hydroxypiperidine-1,3-dicarboxylate 1-(tert-Butyl)3-ethyl 4-oxopiperidine-1,3-dicarboxylate (10 g, 36.86 mmol) was suspended in EtOH (200 mL) and cooled to 0° C. under a nitrogen atmosphere. Sodium borohydride (0.7 g, 18.43 mmol) was then added portionwise over 15 minutes and the reaction mixture was stirred for 0.5 h at 25° C. The mixture was evaporated to dryness, the residue was partitioned between EtOAc (200 mL) and saturated aqueous sodium bicarbonate solution (200 mL), then the aqueous layer was washed with EtOAc (2×100 mL). The combined organic layers were washed with brine (200 mL), dried over magnesium sulfate and concentrated. The residue was purified by FCC, eluting with 0-100% EtOAc in heptane, to afford the title compound (7.26 g, 85%) as a clear yellow oil. $\delta_H$ (500 MHz, CDCl$_3$) 4.32-4.25 (m, 1H), 4.19 (q, J 7.12 Hz, 2H), 4.13-3.85 (m, 1H), 3.71 (dt, J 13.35, 3.62 Hz, 1H), 3.51-3.34 (m, 1H), 3.21-2.82 (m, 1H), 2.67-2.56 (m, 1H), 1.89-1.76 (m, 1H), 1.73-1.60 (m, 1H), 1.46 (s, 9H), 1.28 (t, J 7.17 Hz, 3H).

Intermediate 89

1-(tert-Butyl)3-ethyl 1,2,5,6-tetrahydropyridine-1,3-dicarboxylate

Intermediate 88 (7.26 g, 0.03 mol) and triethylamine (22.21 mL, 159.37 mmol) were dissolved in DCM (150 mL) at 0° C. under a nitrogen atmosphere and methanesulfonyl chloride (6.17 mL, 79.69 mmol) was added. The reaction mixture was allowed to warm to room temperature and stirred for 3 days. The mixture was then partitioned between DCM (200 mL) and water (200 mL), and the aqueous layer was washed with DCM (2×100 mL). The combined organic layers were dried over magnesium sulfate and concentrated. The residue was purified by FCC, eluting with 0-50% EtOAc in heptane, to afford the title compound (3.62 g, 52%) as a yellow oil. $\delta_H$ (500 MHz, CDCl$_3$) 7.12-7.02 (m, 1H), 4.22 (q, J 7.07 Hz, 2H), 4.17-4.03 (m, 2H), 3.48 (t, J 5.65 Hz, 2H), 2.31 (m, 2H), 1.48 (s, 9H), 1.30 (t, J 7.10 Hz, 3H).

Intermediate 90

3-(tert-Butyl)1-ethyl 3-azabicyclo[4.1.0]heptane-1,3-dicarboxylate

Trimethylsulfoxonium iodide (5.39 g, 24.25 mmol) was slurried in DMSO (18 mL) under nitrogen. Potassium tert-butoxide (2.65 g, 23.65 mmol) was added in two portions and the mixture was stirred for 2 h at room temperature. A solution of Intermediate 89 (3.16 g, 12.13 mmol) in DMSO (9 mL) was heated at 80° C. and the pre-formed ylide was added slowly over 2 h. LCMS showed incomplete conversion so further ylide was formed as follows: trimethylsulfoxonium iodide (2.69 g, 12.13 mmol) was slurried in DMSO (9 mL) under nitrogen. Potassium tert-butoxide (1.3 g, 11.5 mmol) was added in two portions and the mixture was stirred for 2 h. This was added to the reaction mixture over 1 h at 80° C., then the mixture was stirred at 80° C. for 2 h. The reaction mixture was diluted with water (15 mL) and extracted with EtOAc (2×25 mL). The organic layers were combined, washed with brine (25 mL), dried over sodium sulfate and concentrated under vacuum. The residue was purified by FCC, eluting with 0-50% EtOAc in heptane, to afford the title compound (468 mg, 14%) as a yellow oil. $\delta_H$ (500 MHz, CDCl$_3$) 4.13 (q, J 7.1 Hz, 2H), 4.00-3.82 (m, 2H), 3.51-3.38 (m, 1H), 2.94 (ddd, J 13.3, 9.2, 5.6 Hz, 1H), 2.07-1.90 (m, 1H), 1.85-1.62 (m, 2H), 1.45 (s, 9H), 1.38 (dd, J 9.4, 4.4 Hz, 1H), 1.25 (t, J 7.1 Hz, 3H), 0.72 (dd, J 6.5, 4.4 Hz, 1H).

Intermediate 91

Ethyl 3-azabicyclo[4.1.0]heptane-1-carboxylate

Intermediate 90 (468 mg, 1.74 mmol) was stirred in DCM (2.5 mL), then TFA (2.5 mL) was added and the mixture was stirred at room temperature for 30 minutes. The mixture was concentrated. The residue was dissolved in EtOAc (30 mL), washed with aqueous sodium bicarbonate solution (2×10 mL) and brine (10 mL), then dried over sodium sulfate and concentrated, to afford the title compound (280 mg, 95%) as a yellow oil. $\delta_H$ (500 MHz, CDCl$_3$) 4.10 (q, J 7.1 Hz, 2H), 3.73-3.65 (m, 1H), 3.03 (d, J 13.2 Hz, 1H), 2.60-2.54 (m, 2H), 1.95-1.87 (m, 1H), 1.75-1.58 (m, 2H), 1.37 (dd, J 9.6, 3.9 Hz, 1H), 1.23 (t, J 7.1 Hz, 3H), 0.88 (dd, J 6.7, 4.0 Hz, 1H).

Intermediate 92

4-(3-{[2-(Difluoromethoxy)phenyl]methyl}-2-methylimidazo[1,2-a]pyridin-6-yl)-1H-pyrazole Intermediate 7 (250 mg, 0.681 mmol), 1H-pyrazol-4-ylboronic acid (84 mg, 0.749 mmol), 2M aqueous sodium carbonate solution (1.02 mL, 2.04 mmol) and anhydrous DMSO (2 mL) were charged to a sealed tube and degassed. Bis[3-(diphenylphosphanyl)-cyclopenta-2,4-dien-1-yl]iron dichloropalladium dichloromethane complex (28 mg, 0.034 mmol) was added. The reaction mixture was sealed under nitrogen and stirred at 100° C. for 18 h. Further 1H-pyrazol-4-ylboronic acid (42 mg, 0.37 mmol), 2M aqueous sodium carbonate solution (0.51 mL, 1.02 mmol) and anhydrous DMSO (1 mL) were added and the mixture was degassed. Bis[3-(diphenylphosphanyl)cyclopenta-2,4-dien-1-yl]iron dichloropalladium dichloromethane complex (28 mg, 0.034 mmol) was added, then the reaction mixture was sealed under nitrogen and stirred at 100° C. for 2 h. The reaction mixture was diluted with EtOAc (40 mL), washed with water (3×15 mL) followed by saturated aqueous sodium bicarbonate solution (15 mL) and brine (15 mL), then dried over sodium sulfate and concentrated. The residue was purified by FCC, eluting with 0-3% (7M NH$_3$ in MeOH) in DCM, to afford the title compound (220 mg, 91%) as a black solid. Method C HPLC-MS: MH+ m/z=355, RT 1.00 minutes.

Intermediate 93

Ethyl 4-[4-(3-{[2-(difluoromethoxy)phenyl]methyl}-2-methylimidazo[1,2-a]pyridin-6-yl)-1H-pyrazol-1-yl]cyclohexane-1-carboxylate Intermediate 92 (117 mg, 0.33 mmol), ethyl 4-(methanesulfonyloxy)cyclohexane-1-carboxylate (79 mg, 0.31 mmol), cesium carbonate (151 mg, 0.46 mmol) and anhydrous N,N-dimethylformamide (3 mL) were charged to a sealed tube under nitrogen. The mixture was stirred at 80° C. for 18 h, then at 100° C. for 3 h. Further ethyl 4-(methanesulfonyloxy)cyclohexane-1-carboxylate (79 mg, 0.31 mmol) and cesium carbonate (102 mg, 0.31 mmol) were added and the mixture was stirred at 100° C. for 6 h. Further ethyl 4-(methanesulfonyloxy)cyclohexane-1-carboxylate (79 mg, 0.31 mmol) and cesium carbonate (102 mg, 0.31 mmol) were added and the mixture was stirred at 100° C. for 4 h. The reaction mixture was diluted with EtOAc (50 mL), washed with water (3×10 mL) followed by saturated aqueous sodium carbonate solution (10 mL) and brine (10 mL), then dried over sodium sulfate and concentrated. The resulting material was purified by FCC, eluting with 0-2% MeOH in DCM. The residue was then further purified by FCC, eluting with 10-100% EtOAc in heptane, to afford the title compound (60 mg, 29%) as a brown gum. Method D HPLC-MS: MH+ m/z 508, RT 2.57 minutes.

Intermediate 94

2-Chloro-5-(3-{[2-(difluoromethoxy)phenyl]methyl}-2-methylimidazo[1,2-a]pyridin-6-yl)pyrazine Intermediate 31 (350 mg, 1.05 mmol), 2-chloro-5-iodopyrazine (252 mg, 1.05 mmol), 2M aqueous sodium carbonate solution (1.58 mL, 3.16 mmol) and anhydrous DMSO (5 mL) were charged to a sealed tube. The mixture was degassed by bubbling with nitrogen for 5 minutes before the addition of tetrakis(triphenylphosphine)-palladium(0) (61 mg, 0.05 mmol). The reaction mixture was sealed under nitrogen and stirred at 110° C. for 1 h. The mixture was diluted with water (40 mL) and extracted with EtOAc (3×20 mL). The organic phase was washed with saturated aqueous sodium bicarbonate solution (2×10 mL) followed by brine (10 mL), then dried over sodium sulfate and concentrated under vacuum. The residue was purified by FCC, eluting with 17-80% EtOAc in heptane, to afford the title compound (285 mg, 54% at 80% purity) as an off white solid. $\delta_H$ (500 MHz, CDCl$_3$) 8.73-8.64 (m, 2H), 8.63-8.59 (m, 1H), 7.92 (s, 2H), 7.33-7.27 (m, 1H), 7.17 (d, J 8.2 Hz, 1H), 7.15-7.07 (m, 1H), 7.00 (d, J 6.6 Hz, 1H), 6.67 (t, J 73.5 Hz, 1H), 4.36 (s, 2H), 2.60 (s, 3H). Method C HPLC-MS: MH+ m/z 401, RT 1.10 minutes.

Intermediate 95

Ethyl 2-[1-(diphenylmethyl)azetidin-3-ylidene]propanoate

Sodium hydride (60%, 202 mg, 5.06 mmol) was suspended in anhydrous THF (15 mL) and cooled in an ice bath. Ethyl 2-(diethoxyphosphoryl)propanoate (1.2 g, 5.06 mmol) was added dropwise under nitrogen and the mixture was stirred in an ice bath for 1 h. 1-(Diphenylmethyl)azetidin-3-one (1 g, 4.21 mmol) was added in portions as a solid and the mixture was stirred at room temperature for 1 h, then left to stir at room temperature overnight. Water (50 mL) was added and the mixture was extracted with DCM (3×50 mL). Brine was added, and the aqueous and organic layers were separated. The organic layer was dried over sodium sulfate and concentrated. The resulting crude yellow oil was purified by FCC, eluting with 0-50% EtOAc, to afford a clear oil which crystallised upon standing. The solids were sonicated with heptane and the remaining solid was collected by filtration. The filtrate was concentrated and sonicated with heptane to afford a second crop of solid. The filtrate was concentrated and the residue was sonicated with heptane to afford a further crop of solid material. The resultant solids were collected and combined to afford the title compound (892 mg, 66%) as a white solid. $\delta_H$ (250 MHz, CDCl$_3$) 7.56-7.39 (m, 4H), 7.38-7.15 (m, 6H), 4.63-4.45 (m, 1H), 4.24-4.01 (m, 4H), 3.96-3.76 (m, 2H), 1.72-1.58 (m, 3H), 1.27-1.14 (m, 3H).

Intermediate 96

Ethyl 5-(diphenylmethyl)-1-methyl-5-azaspiro[2.3]hexane-1-carboxylate

Trimethylsulfoxonium iodide (920 mg, 4.14 mmol) and potassium tert-butoxide (442 mg, 3.94 mmol) were heated in anhydrous DMSO (5 mL) at 50° C. for 20 minutes. Intermediate 95 (333 mg, 1.04 mmol) in DMSO (5 mL) was added dropwise at 50° C. and the mixture was stirred for 2 h. Water (50 mL) was added and the mixture was extracted with EtOAc (3×50 mL), then dried over sodium sulfate and concentrated to afford a clear oil. The procedure was then repeated using Intermediate 95 (559 mg, 1.75 mmol) with a heating time of 30 minutes, and worked up as described above, to afford a clear/yellow oil. The batches of crude material were combined and purified by FCC, eluting with 0-50% EtOAc in heptane, to afford the title compound (700 mg, 75%) as a clear oil which solidified to a white solid upon standing. $\delta_H$ (500 MHz, CDCl$_3$) 7.51-7.40 (m, 4H), 7.33-7.25 (m, 4H), 7.25-7.15 (m, 2H), 4.49 (s, 1H), 4.08 (q, J 7.1 Hz, 2H), 3.55-3.37 (m, 1H), 3.37-3.07 (m, 3H), 1.57-1.50 (m, 1H), 1.21 (t, J 7.1 Hz, 3H), 1.16 (s, 3H), 0.86-0.77 (m, 1H). Method B HPLC-MS: MH+ m/z 336, RT 1.48 minutes.

Intermediate 97

Ethyl 1-methyl-5-azaspiro[2.3]hexane-1-carboxylate hydrochloride

Intermediate 96 (700 mg, 2.09 mmol) was dissolved in EtOH (20 mL) and palladium dihydroxide (12%, 122 mg, 0.10 mmol) was added. The mixture was purged with nitrogen (×3) followed by hydrogen (×3), then stirred under a hydrogen atmosphere for 2.5 h. The mixture was filtered, then 1M HCl in EtOAc (4 mL) was added to the filtrate and the mixture was concentrated. Further 1M HCl in EtOAc (1 mL) was added and the mixture was concentrated. The resulting clear oil was sonicated in heptane, then concentrated, to afford a white solid with a moist appearance. The residue was then sonicated in diethyl ether, and the resultant solids were collected by filtration, to afford the title compound (393 mg, 92%) as a white solid. $\delta_H$ (500 MHz, DMSO-d$_6$) 9.45 (s, 1H), 9.08 (s, 1H), 4.15-3.97 (m, 5H), 3.97-3.87 (m, 1H), 1.35 (d, J 5.2 Hz, 1H), 1.18 (t, J 7.1 Hz, 3H), 1.15 (s, 3H), 1.09 (d, J 5.2 Hz, 1H). Method B HPLC-MS: MH+ m/z 336, RT 1.48 minutes.

Intermediate 98

Ethyl 5-[5-(3-{[2-(difluoromethoxy)phenyl]methyl}-2-methylimidazo[1,2-a]pyridin-6-yl)pyrimidin-2-yl]-1-methyl-5-azaspiro[2.3]hexane-1-carboxylate Intermediate 29 (85% pure, 229 mg, 0.49 mmol) and Intermediate 97 (110 mg, 0.53 mmol) were dissolved in 1-methyl-2-pyrrolidinone, then triethylamine (149 µL, 1.07 mmol) was added and the mixture was heated under microwave irradiation at 120° C. for 45 minutes. Water (10 mL) was added. The mixture was extracted with EtOAc (2×20 mL) and washed with brine, then dried over sodium sulfate and concentrated. The residue was purified by FCC, eluting with 0-3% MeOH in DCM, then further purified by preparative HPLC (Method C), to afford the title compound (22 mg). $\delta_H$ (500 MHz, DMSO-d$_6$) 8.67 (s, 2H), 8.39 (s, 1H), 7.59-7.52 (m, 1H), 7.50-7.41 (m, 1H), 7.33-7.26 (m, 2H) 7.23-7.17 (m, 1H), 7.17-7.10 (m, 1H), 7.08-7.01 (m, 1H), 4.37 (s, 2H), 4.22-4.17 (m, 1H), 4.17-3.99 (m, 5H), 2.32 (s, 3H), 1.48 (d, J 4.8 Hz, 1H), 1.22-1.16 (m, 6H), 1.07 (d, J 4.8 Hz, 1H).

Intermediate 99

5-Bromo-2-(3-{[2-(difluoromethoxy)phenyl]methyl}-2-methylimidazo[1,2-a]pyridin-6-yl)pyrimidine Intermediate 31 (320 mg, 0.964 mmol), 5-bromo-2-iodopyrimidine (275 mg, 0.964 mmol), 2M aqueous sodium carbonate solution (1.45 mL, 2.89 mmol) and anhydrous DMSO (5 mL) were charged to a sealed tube. The mixture was degassed by bubbling with nitrogen for 5 minutes before the addition of tetrakis(triphenylphosphine)-palladium(0) (56 mg, 0.048 mmol). The reaction mixture was sealed under nitrogen, then stirred at 100° C. for 2 h. The reaction mixture was treated with 5-bromo-2-iodopyrimidine (30 mg, 0.1 mmol), then degassed as above, sealed under nitrogen and stirred at 100° C. for 2 h. The mixture was partitioned between water (25 mL) and EtOAc (70 mL). The organic phase was washed with saturated aqueous sodium bicarbonate solution (12 mL) followed by brine (12 mL), then dried over sodium sulfate and concentrated under vacuum. The residue was purified by FCC, eluting with 17-80% EtOAc in heptane, to afford the title compound (195 mg) as a white solid. Method A HPLC-MS: MH+ m/z 445/447, RT 3.45 minutes.

Intermediate 100

Ethyl 1-[2-(3-{[2-(difluoromethoxy)phenyl]methyl}-2-methylimidazo[1,2-a]pyridin-6-yl)pyrimidin-5-yl]-4-methylpiperidine-4-carboxylate

[2',6'-Bis(propan-2-yloxy)biphenyl-2-yl](dicyclohexyl)phosphane (12 mg, 0.026 mmol) and palladium diacetate (5 mg, 0.021 mmol) were charged to a sealed tube with anhydrous 1,4-dioxane (2 mL) and heated at 80° C. for 5 minutes, then cooled to room temperature. A solution of Intermediate 99 (190 mg, 0.43 mmol) in 1,4-dioxane (3 mL) was added, together with ethyl 4-methylpiperidine-4-carboxylate hydrochloride (89 mg, 0.43 mmol) and cesium carbonate (278 mg, 0.85 mmol). The mixture was degassed, sealed under nitrogen and stirred at 110° C. for 2 h. Further [2',6'-bis(propan-2-yloxy)-biphenyl-2-yl](dicyclohexyl)phosphane (24 mg, 0.052 mmol) and palladium diacetate (10 mg, 0.042 mmol) were added. The mixture was thoroughly degassed, then heated at 110° C. for a total of 6 h. The mixture was diluted with water (20 mL) and extracted with EtOAc (3×20 mL). The combined organic extracts were washed with water (10 mL) followed by brine (10 mL), then dried over sodium sulfate and concentrated under vacuum. The residue was purified by FCC, eluting with 0-3% MeOH in DCM, to afford the title compound (125 mg) as a light brown solid. $\delta_H$ (500 MHz, CDCl$_3$) 8.78 (s, 1H), 8.35 (s, 2H), 8.09 (dd, J 9.4, 1.5 Hz, 1H), 7.57 (d, J 9.4 Hz, 1H), 7.23-7.18 (m, 1H), 7.14 (d, J 8.6 Hz, 1H), 7.06-6.99 (m, 1H), 6.90-6.86 (m, 1H), 6.85-6.53 (m, 1H), 4.33 (s, 2H), 4.18 (q, J 7.1 Hz, 2H), 3.50 (dt, J 12.9, 4.1 Hz, 2H), 3.04-2.92 (m, 2H), 2.46 (s, 3H), 2.25 (d, J 13.6 Hz, 2H), 1.60 (ddd, J 14.2, 10.9, 4.1 Hz, 2H), 1.25 (s, 6H). Method C HPLC-MS: MH+ m/z 536, RT 1.23 minutes.

Intermediate 101

5-(3-{[2-(Difluoromethoxy)phenyl]methyl}-2-methylimidazo[1,2-a]pyridin-6-yl)-2-fluoropyridine Intermediate 7 (500 mg, 1.36 mmol) and (6-fluoropyridin-3-yl)boronic acid (230 mg, 1.63 mmol) were dissolved in 1,4-dioxane (6 mL) and 2M aqueous potassium carbonate solution (2 mL) was added. The mixture was degassed for 10 minutes with nitrogen, then bis[3-(diphenylphosphanyl)cyclopenta-2,4-dien-1-yl]iron dichloropalladium dichloromethane complex (55 mg, 0.068 mmol) was added and the mixture was heated at 80° C. for 1 h. Further (6-fluoropyridin-3-yl)boronic acid (40 mg, 0.284 mmol) was added and the mixture was degassed for 10 minutes, then bis[3-(diphenylphosphanyl)cyclopenta-2,4-dien-1-yl]iron dichloropalladium dichloromethane complex (55 mg, 0.068 mmol) was added and the mixture was heated at 90° C. overnight. The mixture was diluted with EtOAc (20 mL), then washed with water (50 mL) and brine (20 mL), before being dried over sodium sulfate and concentrated under vacuum. The residue was purified by FCC, eluting with 90-100% EtOAc in heptane, to afford the title compound (293 mg, 51%) as an off-white solid. Method C HPLC-MS: MH+ m/z 384, RT 1.06 minutes.

Intermediate 102

Ethyl 1-[5-(3-{[2-(difluoromethoxy)phenyl]methyl}-2-methylimidazo[1,2-a]pyridin-6-yl)pyridin-2-yl]-4-methylpiperidine-4-carboxylate Intermediate 101 (300 mg, 0.493 mmol), ethyl 4-methylpiperidine-4-carboxylate (205 mg, 0.986 mmol) and pyridine (3 mL) were charged to a microwave tube and stirred under microwave irradiation at 180° C. for a total of 4 h. After this time, further ethyl 4-methylpiperidine-4-carboxylate (102 mg, 0.493 mmol) was added and the mixture was heated for a total of 3 h at 180° C. under microwave irradiation. Water (50 mL) was added, and the mixture was extracted with EtOAc (50 mL), then washed with more water (2×50 mL) and brine (50 mL). The organic layer was concentrated under vacuum. The resulting brown oil was combined with further crude product (80 mg at 81% purity) for purification. The residue was purified by FCC, eluting with 0-10% methanol in DCM, to afford the title compound (382 mg) as a brown oil. Method C HPLC-MS: MH+ m/z 535, RT 1.16 minutes.

Intermediate 103

5-Bromo-2-(3-{[2-(difluoromethoxy)phenyl]methyl}-2-methylimidazo[1,2-a]pyridin-6-yl)pyridine Intermediate 31 (600 mg, 1.807 mmol) and 5-bromo-2-iodopyridine (615 mg, 2.168 mmol) were dissolved in 1,4-dioxane (5 mL) and 2M aqueous potassium carbonate solution (3 mL) was added. The mixture was flushed with nitrogen and tetrakis-(triphenylphosphine)palladium(0) (104 mg, 0.09 mmol) was added. The mixture was heated at 90° C. overnight. 5-Bromo-2-iodopyridine (512 mg, 1.807 mmol) was added and the mixture was degassed for 10 minutes, then tetrakis(triphenylphosphine)palladium(0) (104 mg, 0.09 mmol) was added and the mixture was heated at 90° C. for 2 h. Aqueous potassium carbonate solution (2M, 3 mL) was added and the reaction mixture was heated at 90° C. for 1 h. The mixture was cooled to room temperature, diluted with EtOAc (100 mL) and washed with brine (100 mL), then dried over sodium sulfate and concentrated. The resulting brown solid (1.3 g) was purified by FCC, eluting with 70-100% EtOAc in heptane, to afford the title compound (363 mg, 43%) as an off-white solid. Method C HPLC-MS: MH+ m/z 444/446, RT 1.15 minutes.

Intermediate 104

Ethyl 1-[6-(3-{[2-(difluoromethoxy)phenyl]methyl}-2-methylimidazo[1,2-a]pyridin-6-yl)pyridin-3-yl]-4-methylpiperidine-4-carboxylate

[2',6'-Bis(propan-2-yloxy)biphenyl-2-yl](dicyclohexyl)phosphane (14 mg, 0.031 mmol) and palladium(II) acetate (5.7 mg, 0.026 mmol) were dissolved in degassed 1,4-dioxane (2 mL) and heated at 80° C. for 5 minutes. The mixture was then cooled to room temperature and a solution of Intermediate 103 (363 mg, 0.515 mmol) in 1,4-dioxane (6 mL) was added, followed by ethyl 4-methylpiperidine-4-carboxylate hydrochloride (117 mg, 0.566 mmol) and cesium carbonate (335 mg, 1.03 mmol). The reaction mixture was flushed with nitrogen for 10 minutes, then further [2',6'-bis(propan-2-yloxy)biphenyl-2-yl](dicyclohexyl)phosphane (14 mg, 0.031 mmol) and palladium(II) acetate (5.7 mg, 0.026 mmol) were added and the mixture was heated at 120° C. for 2 h. The reaction mixture was flushed with nitrogen for 10 minutes, then [2',6'-bis(propan-2-yloxy)-biphenyl-2-yl](dicyclohexyl)phosphane (30 mg, 0.062 mmol) and palladium(II) acetate (10 mg, 0.052 mmol) were added and the mixture was heated at 120° C. for 3 h. Further ethyl 4-methylpiperidine-4-carboxylate hydrochloride (117 mg, 0.566 mmol) and cesium carbonate (335 mg, 1.03 mmol) were added and the mixture was degassed for 10 minutes, before the addition of further [2',6'-bis(propan-2-yloxy)biphenyl-2-yl](dicyclohexyl)-phosphane (30 mg, 0.062 mmol) and palladium(II) acetate (10 mg, 0.052 mmol), and the mixture was heated at 120° C. for 2.5 h. The crude mixture was filtered through celite and washed with EtOAc (80 mL). The organic phase was washed with water (30 mL) and brine (30 mL), then dried over sodium sulfate and concentrated to dryness under vacuum. The crude material was purified by FCC, then further purified by preparative HPLC, to afford the title compound (139 mg, 51%) as a clear glass. Method C HPLC-MS: MH+ m/z 535, RT 1.25 minutes.

Intermediate 105

1-(6-Bromo-2,7-dimethylimidazo[1,2-a]pyridin-3-yl)-1-[2-(difluoromethoxy)phenyl]-ethanol Intermediate 18 (2 g, 5.06 mmol) was dissolved in THF (20 mL) and cooled to 0° C. under nitrogen. Methylmagnesium bromide in THF/toluene (1.4M, 6.51 mL) was added at 0° C. under nitrogen and the reaction mixture was stirred for 1 h at 0° C. under nitrogen. The reaction mixture was then allowed to warm to room temperature and stirred under nitrogen for 1 h. The reaction mixture was cooled to 0° C. under nitrogen and further methylmagnesium bromide in THF/toluene (1.4M, 1.81 mL) was added. The reaction mixture was stirred under nitrogen at 0° C. for 10 minutes, then at room temperature for 1 h. The reaction mixture was carefully quenched by the addition of saturated aqueous ammonium chloride solution (15 mL) at 0° C., and extracted into EtOAc (30 mL). The organic layer was separated, washed with brine (10 mL), dried over sodium sulfate and concentrated to dryness. The residue was triturated with 1:1 DCM/TBME (10 mL), and the solid was washed with TBME, to afford the title compound (1.51 g, 73%) as a pale yellow solid. Method C HPLC-MS: MH+ m/z 411/413, RT 1.00 minutes.

Intermediate 106

1-[6-(2-Chloropyrimidin-5-yl)-2,7-dimethylimidazo [1,2-a]pyridin-3-yl]-1-[2-(difluoromethoxy)phenyl] ethanol Intermediate 105 (477 mg, 1.16 mmol) and (2-chloropyrimidin-5-yl)boronic acid (552 mg, 3.48 mmol) were dissolved in 1,4-dioxane (7 mL) and 2M sodium carbonate in water (1.74 mL) was added. The resulting mixture was degassed with nitrogen for 5 minutes, then dichlorobis(triphenylphosphine)palladium(II) (41 mg, 0.058 mmol) and tri-tert-butylphosphine (12 mg, 0.058 mmol) were added. The reaction mixture was heated at 120° C. under microwave irradiation for a total of 70 minutes. The reaction was repeated on the same scale and the two reaction mixtures were combined, diluted with EtOAc (25 mL), washed with water (20 mL) and brine (20 mL), then dried over sodium sulfate and concentrated to dryness. The residue was purified by FCC, eluting with 50-100% EtOAc in heptane followed by 0-5% MeOH in EtOAc, to afford the title compound (585 mg, 57%) as a yellow gum. $\delta_H$ (500 MHz, CDCl$_3$) 8.40 (s, 2H), 8.11 (s, 1H), 7.66 (d, J 7.4 Hz, 1H), 7.40 (s, 1H), 7.38-7.34 (m, 1H), 7.26 (t, J 7.6 Hz, 1H), 7.08 (d, J 8.0 Hz, 1H), 6.19 (t, J 73.5 Hz, 1H), 2.45 (s, 3H), 2.26 (s, 3H), 2.17 (s, 3H). Method C HPLC-MS: MH+ m/z 445, RT 0.97 minutes.

Intermediate 107

2-Chloro-5-(3-{1-[2-(difluoromethoxy)phenyl]ethenyl}-2,7-dimethylimidazo[1,2-a]-pyridin-6-yl)pyrimidine Intermediate 106 (585 mg, 1.32 mmol) was dissolved in DCM (10 mL) under nitrogen and boron trifluoride diethyl etherate (600 µL, 4.86 mmol) was added. The reaction mixture was stirred for 30 minutes at room temperature. The reaction mixture was washed with saturated aqueous sodium bicarbonate solution (6 mL). The aqueous layer was re-extracted with DCM (6 mL), then the combined organic layers were dried over sodium sulfate and concentrated to dryness. The residue was triturated with 1:1 DCM/heptane (~4 mL) to afford the title compound (310 mg, 55%) as an off-white solid. $\delta_H$ (250 MHz, CD$_3$OD) 8.67 (s, 2H), 8.26 (s, 1H), 7.84 (s, 1H), 7.72-7.63 (m, 1H), 7.58-7.44 (m, 1H), 7.43-7.30 (m, 1H), 7.15 (d, J 8.1 Hz, 1H), 6.66 (t, J 73.9 Hz, 1H), 6.21 (s, 1H), 5.99 (s, 1H), 2.46 (s, 3H), 2.39 (s, 3H). Method C HPLC-MS: MH+ m/z 427, RT 1.06 minutes.

Intermediate 108

2-Chloro-5-(3-{1-[2-(difluoromethoxy)phenyl] ethyl}-2,7-dimethylimidazo[1,2-a]pyridin-6-yl)pyrimidine Intermediate 107 (310 mg, 0.73 mmol) was dissolved in EtOAc (10 mL) and platinum oxide (35 mg, 0.15 mmol) was added. The reaction mixture was placed under a hydrogen atmosphere and stirred for a total of 42 h. Further platinum oxide (35 mg, 0.15 mmol) was added and the mixture was stirred under a hydrogen atmosphere for a total of 24 h. The reaction mixture was filtered and concentrated to dryness, to afford the title compound (311 mg, 100%) as an off-white solid, which was used without further purification. $\delta_H$ (250 MHz, CD$_3$OD) 8.72 (s, 2H), 8.22 (s, 1H), 7.57-7.49 (m, 1H), 7.44 (s, 1H), 7.40-7.19 (m, 2H), 7.18-7.10 (m, 1H), 6.71 (t, J 74.2 Hz, 1H), 2.36-2.21 (m, 7H), 1.78 (d, J 7.3 Hz, 3H). Method C HPLC-MS: MH+ m/z 429, RT 1.07 minutes.

Intermediate 109

Ethyl (1R,5S,6r)-3-[5-(3-{1-[2-(difluoromethoxy) phenyl]ethyl}-2,7-dimethylimidazo-[1,2-a]pyridin-6-yl)pyrimidin-2-yl]-3-azabicyclo[3.1.0]hexane-6-carboxylate Intermediate 108 (312 mg, 0.73 mmol) and ethyl (1R,5S, 6r)-3-azabicyclo[3.1.0]-hexane-6-carboxylate hydrochloride (209 mg, 1.09 mmol) were dissolved in 1-methyl-2-pyrrolidinone (3 mL) and triethylamine (203 µL, 1.46 mmol) was added. The reaction mixture was heated at 150° C. under microwave irradiation for 1 h. The reaction mixture was diluted with water (3 mL) and extracted with EtOAc (3 mL). The resulting organic layer was washed with brine (1 mL), dried over sodium sulfate and concentrated to dryness. Purification was attempted by FCC, to afford the title compound (175 mg, 44%) as a yellow gum, which was used without further purification. Method C HPLC-MS: MH+ m/z 548, RT 1.16 minutes.

Intermediate 110

Ethyl 1-benzyl-4-methyl-2,5-dihydro-1H-pyrrole-3-carboxylate

Benzyl(methoxymethyl)[(trimethylsilyl)methyl]amine (10.78 mL, 42.12 mmol) and ethyl but-2-ynoate (5.89 mL, 50.54 mmol) were stirred in DCM (500 mL) at 0° C. under nitrogen, then trifluoroacetic acid (161 µL, 2.11 mmol) was added dropwise. The reaction mixture stirred at 0° C. for 20 minutes, then the ice bath was removed and the solution was allowed to warm to room temperature. The solution was stirred at room temperature overnight. The mixture was concentrated and purified by FCC, eluting with 0-70% EtOAc in heptane, to afford the title compound (2.76 g, 27%). $\delta_H$ (500 MHz, DMSO-d$_6$) 7.38-7.32 (m, 4H), 7.30-7.23 (m, 1H), 4.13 (q, J 7.1 Hz, 2H), 3.75 (s, 2H), 3.60-3.51 (m, 4H), 2.05 (s, 3H), 1.22 (t, J 7.1 Hz, 3H).

Intermediate 111

Ethyl 3-benzyl-5-methyl-3-azabicyclo[3.1.0]hexane-1-carboxylate

Trimethylsulfoxonium iodide (3.62 g, 16.31 mmol) and potassium tert-butoxide (1.74 g, 15.49 mmol) were heated in anhydrous DMSO (5 mL) at 50° C. for 30 minutes until all had dissolved. Intermediate 110 (1 g, 4.08 mmol) in DMSO (5 mL) was added dropwise and the mixture was stirred at 50° C. for 2.5 h. Water (20 mL) was added and the mixture was extracted with EtOAc (2×30 mL). The organic layers were washed with brine, dried over sodium sulfate and concentrated. The resulting yellow oil was purified by FCC, eluting with 0-50% EtOAc in heptane, to afford the title compound (483 mg, 46%). δ$_H$ (500 MHz, DMSO-d$_6$) 7.35-7.21 (m, 5H), 4.15-3.99 (m, 2H), 3.65-3.53 (m, 2H), 2.93 (d, J 8.9 Hz, 1H), 2.88 (d, J 8.9 Hz, 1H), 2.71 (d, J 8.9 Hz, 1H), 2.22 (d, J 8.9 Hz, 1H), 1.48 (d, J 3.5 Hz, 1H), 1.22 (s, 3H), 1.17 (t, J 7.1 Hz, 3H), 1.09 (d, J 3.5 Hz, 1H).

Intermediate 112

Ethyl 5-methyl-3-azabicyclo[3.1.0]hexane-1-carboxylate hydrochloride

Intermediate 111 (983 mg, 3.79 mmol) was dissolved in EtOH (20 mL) and palladium on carbon (10%, 225 mg, 0.21 mmol) was added. The mixture was flushed with nitrogen, then hydrogen, and stirred under a hydrogen atmosphere for 18 h. The mixture was filtered through celite and washed through with further EtOH. To this solution was added 1M HCl in EtOAc (10 mL), and the mixture was concentrated, to afford the title compound (784 mg, 100%) as a brown gum which solidified upon standing. δ$_H$ (500 MHz, DMSO-d$_6$) 9.85 (s, 1H), 9.39 (s, 1H), 4.22-4.07 (m, 2H), 3.69-3.59 (m, 1H), 3.47-3.33 (m, 2H), 3.26-3.17 (m, 1H), 1.55 (d, J 5.8 Hz, 1H), 1.34 (d, J 5.8 Hz, 1H), 1.31 (s, 3H), 1.21 (t, J 7.1 Hz, 3H).

Intermediate 113

Ethyl 3-[5-(3-{[2-(difluoromethoxy)phenyl]methyl}-2-methylimidazo[1,2-a]pyridin-6-yl)pyrimidin-2-yl]-5-methyl-3-azabicyclo[3.1.0]hexane-1-carboxylate Intermediate 29 (85% pure, 240 mg, 0.51 mmol) and Intermediate 112 (115 mg, 0.56 mmol) were dissolved in 1-methyl-2-pyrrolidinone (3 mL) and triethylamine (160 μL, 1.12 mmol) was added. The mixture was heated under microwave irradiation at 120° C. for 45 minutes. Water (30 mL) was added, and the mixture was extracted with EtOAc (3×30 mL) and washed with brine, then dried over sodium sulfate and concentrated. The resulting crude brown liquid was purified by FCC, eluting with 0-3% MeOH in DCM, then further purified by preparative HPLC (Method C), to afford the title compound (129 mg, 47%) as a brown solid. δ$_H$ (500 MHz, DMSO-d$_6$) 8.65 (s, 2H), 8.37 (s, 1H), 7.54 (d, J 9.3 Hz, 1H), 7.46 (dd, J 9.3, 1.6 Hz, 1H), 7.33-7.26 (m, 1H), 7.29 (t, J 74.1 Hz, 1H), 7.20 (d, J 8.1 Hz, 1H), 7.17-7.10 (m, 1H), 7.07-7.01 (m, 1H), 4.36 (s, 2H), 4.24-4.08 (m, 2H), 4.05-3.95 (m, 2H), 3.92 (d, J 11.2 Hz, 1H), 3.40 (d, J 11.1 Hz, 1H), 2.32 (s, 3H), 1.44 (d, J 4.4 Hz, 1H), 1.39 (s, 3H), 1.24 (t, J 7.1 Hz, 3H), 1.03 (d, J 4.6 Hz, 1H).

Intermediate 114

Methyl 3-azabicyclo[4.1.0]heptane-6-carboxylate hydrochloride (Racemic)

3-[(tert-Butoxy)carbonyl]-3-azabicyclo[4.1.0]heptane-6-carboxylic acid (5 g, 20.72 mmol) was dissolved in MeOH (200 mL) and 4M HCl in 1,4-dioxane (25.9 mL) was added. The reaction mixture was heated at 60° C. for 4 h. The reaction mixture was cooled to room temperature, then concentrated, to afford the title compound (4.0 g, 101%) as a pale yellow solid. δ$_H$ (250 MHz, CDCl$_3$) 3.69 (s, 3H), 3.42 (br s, 1H), 2.11 (br s, 5H), 1.84 (br s, 1H), 1.62 (d, J 4.2 Hz, 1H), 1.29 (br s, 1H).

Intermediate 115

3-Benzyl 6-methyl 3-azabicyclo[4.1.0]heptane-3,6-dicarboxylate (Racemic)

Intermediate 114 (4 g, 20.87 mmol) was stirred in DCM (100 mL) and 1-{[(benzyloxy)carbonyl]oxy}pyrrolidine-2,5-dione (5.20 g, 20.87 mmol) was added, followed by triethylamine (7.29 mL, 52.18 mmol). The reaction mixture was stirred at room temperature overnight. The mixture was washed with 1M HCl (2×30 mL), saturated sodium bicarbonate solution (50 mL) and brine (50 mL), then dried over sodium sulfate and concentrated. The resulting yellow oil was purified by FCC, eluting with 0-50% EtOAc in heptane, to afford the title compound (4.72 g, 78%) as a pale yellow oil. δ$_H$ (500 MHz, CDCl$_3$) 7.40-7.29 (m, 5H), 5.12 (s, 2H), 3.91 (d, J 13.6 Hz, 1H), 3.66 (s, 3H), 3.59 (dd, J 13.6, 4.4 Hz, 1H), 3.48 (br s, 1H), 3.09 (s, 1H), 2.56 (dt, J 14.5, 5.6 Hz, 1H), 1.91-1.66 (m, 2H), 1.44 (s, 1H), 0.75 (dd, J 6.4, 4.8 Hz, 1H).

Intermediate 116

Methyl 3-azabicyclo[4.1.0]heptane-6-carboxylate hydrochloride (Enantiomer A)

Intermediate 115 (4.72 g, 16.31 mmol) was separated using chiral preparative HPLC (Lux Amylose-2 column, 21.2×250 mm, 5 μm; 70% heptane/20% ethanol/10% isopropanol eluent; 21 mL/minute flow rate) and the first-eluting enantiomer was isolated (1.85 g, 6.38 mmol). This was dissolved in MeOH (20 mL) and 10% palladium on carbon (0.38 g) was added. The mixture was flushed with nitrogen (×3) and hydrogen (×3), then stirred under a hydrogen atmosphere for 18 h. The mixture was filtered through celite and washed through with MeOH. The filtrate was concentrated to near dryness and diethyl ether (10 mL) was added, followed by 4M HCl in 1,4-dioxane (3 mL). The mixture was allowed to stand for ~30 minutes and the resultant precipitate was collected by filtration, washed with diethyl ether and dried under vacuum, to afford the title compound (1.1 g, 90%) as a white solid. δ$_H$ (250 MHz, DMSO-d$_6$) 8.91 (s, 1H), 8.79 (s, 1H), 3.60 (s, 3H), 3.52-3.43 (m, 1H), 3.16-2.98 (m, 1H), 2.98-2.68 (m, 2H), 2.67-2.53 (m, 1H), 1.96-1.81 (m, 1H), 1.79-1.64 (m, 1H), 1.33 (dd, J 9.4, 4.8 Hz, 1H), 1.22 (dd, J 6.7, 4.8 Hz, 1H).

Intermediate 117

Methyl 3-azabicyclo[4.1.0]heptane-6-carboxylate hydrochloride (Enantiomer B)

Intermediate 115 (4.72 g, 16.31 mmol) was separated using chiral preparative HPLC (Lux Amylose-2 column, 21.2×250 mm, 5 μm; 70% heptane/20% ethanol/10% isopropanol eluent; 21 mL/minute flow rate) and the second-eluting enantiomer was isolated (1.63 g, 5.64 mmol). This was dissolved in MeOH (20 mL) and 10% palladium on carbon (0.34 g) was added. The mixture was flushed with nitrogen (×3) and hydrogen (×3), then stirred under a hydrogen atmosphere for 18 h. The mixture was filtered through celite and washed through with MeOH. The filtrate was concentrated to near dryness and diethyl ether (10 mL) was added, followed by 4M HCl in 1,4-dioxane (3 mL). The mixture was allowed to stand for ~30 minutes and the resultant precipitate was collected by filtration, washed with diethyl ether and dried under vacuum, to afford the title compound (980 mg, 91%) as a white solid. δ$_H$ (250 MHz, DMSO-d$_6$) 8.97 (s, 1H), 8.83 (s, 1H), 3.60 (s, 3H), 3.50-3.33 (m, 1H), 3.16-2.99 (m, 1H), 2.98-2.69 (m, 2H), 2.67-2.52 (m, 1H), 1.96-1.80 (m, 1H), 1.77-1.63 (m, 1H), 1.32 (dd, J 9.4, 4.7 Hz, 1H), 1.24 (dd, J 6.8, 4.8 Hz, 1H).

Intermediate 118

3-Benzyl 1-ethyl 3-azabicyclo[4.1.0]heptane-1,3-dicarboxylate (Racemic)

The hydrochloride salt of Intermediate 91 (1.6 g, 7.78 mmol) was suspended in DCM (60 mL) at 25° C. under a nitrogen atmosphere and triethylamine (2.72 mL, 19.45 mmol) was added. 1-{[(Benzyloxy)carbonyl]oxy}pyrrolidine-2,5-dione (1.94 g, 7.78 mmol) was added, and the reaction mixture was stirred for 2 h. The mixture was diluted with DCM (60 mL), washed with 1M HCl (60 mL), saturated aqueous sodium bicarbonate solution (50 mL) and brine (50 mL), then dried over sodium sulfate and concentrated. The residue was purified by FCC, eluting with 0-50% EtOAc in heptane, to afford the title compound (2.36 g, 82%) as a yellow oil. $\delta_H$ (500 MHz, CDCl$_3$) 7.45-7.33 (m, 5H), 5.13 (s, 2H), 4.18-4.09 (m, 2H), 4.08-3.88 (m, 2H), 3.50 (dt, J 12.2, 5.7 Hz, 1H), 3.11-3.01 (m, 1H), 2.02 (dd, J 13.3, 6.3 Hz, 1H), 1.87-1.66 (m, 2H), 1.39 (dd, J 9.4, 4.5 Hz, 1H), 1.23 (t, J 6.7 Hz, 3H), 0.79-0.68 (m, 1H). Method D HPLC-MS: MH+ m/z 508, RT 2.27 minutes.

Intermediate 119

Ethyl 3-azabicyclo[4.1.0]heptane-1-carboxylate hydrochloride (Enantiomer A)

Intermediate 118 (90% pure, 1.72 g, 5.10 mmol) was separated using chiral preparative HPLC (Lux Cellulose 4 column, 21.2×250 mm, 5 µm; 80% heptane/20% isopropanol eluent; 20 mL/minute flow rate) and the first-eluting enantiomer was isolated (561 mg, 1.85 mmol). This was dissolved in ethanol (15 mL) and the mixture was degassed and purged with nitrogen. Palladium on carbon (10%, 98 mg, 0.09 mmol) was added, and the reaction mixture was stirred under a hydrogen balloon at room temperature for 18 h. The reaction mixture was filtered through celite and the solids were washed with excess methanol. The filtrate was concentrated to ~10 mL volume, then 2M hydrochloric acid in ether (8 mL) was added and the mixture was stirred at room temperature for 10 minutes. The reaction mixture was evaporated and the resulting residue was sonicated in diethyl ether for 1 h. The resultant precipitate was filtered, washed with diethyl ether and dried, to afford the title compound (255 mg, 67%) as an off-white solid. $\delta_H$ (500 MHz, DMSO-d$_6$) 9.11 (s, 1H), 8.79 (s, 1H), 4.08 (q, J 7.1 Hz, 2H), 3.97 (d, J 13.6 Hz, 1H), 3.10 (d, J 13.6 Hz, 1H), 2.97 (dt, J 11.2, 5.2 Hz, 1H), 2.76-2.66 (m, 1H), 2.17 (ddt, J 12.2, 10.3, 6.1 Hz, 1H), 1.94-1.83 (m, 1H), 1.83-1.67 (m, 1H), 1.41 (dd, J 9.6, 4.7 Hz, 1H), 1.29 (dd, J 7.2, 4.8 Hz, 1H), 1.19 (t, J 7.1 Hz, 3H).

Intermediate 120

Ethyl 3-azabicyclo[4.1.0]heptane-1-carboxylate hydrochloride (Enantiomer B)

Intermediate 118 (90% pure, 1.72 g, 5.10 mmol) was separated using chiral preparative HPLC (Lux Cellulose 4 column, 21.2×250 mm, 5 µm; 80% heptane/20% isopropanol eluent; 20 mL/minute flow rate) and the second-eluting enantiomer was isolated (608 mg, 2.00 mmol). This was dissolved in ethanol (15 mL) and the mixture was degassed and purged with nitrogen. Palladium on carbon (10%, 106 mg, 0.10 mmol) was added, and the reaction mixture was stirred under a hydrogen balloon at room temperature for 18 h. The reaction mixture was filtered through celite and the solids were washed with excess methanol. The filtrate was concentrated to ~10 mL volume, then 2M HCl in ether (8 mL) was added and the mixture was stirred at room temperature for 10 minutes. The reaction mixture was evaporated and the resulting residue was sonicated in diethyl ether for 1 h. The resultant precipitate was filtered, washed with diethyl ether and dried, to afford the title compound (316 mg, 76%) as an off-white solid. $\delta_H$ (500 MHz, DMSO-d$_6$) 8.90 (d, J 134.2 Hz, 2H), 4.08 (q, J 7.1 Hz, 2H), 3.98 (d, J 13.6 Hz, 1H), 3.10 (d, J 13.6 Hz, 1H), 2.97 (dt, J 11.1, 5.2 Hz, 1H), 2.70 (td, J 12.9, 11.7, 4.5 Hz, 1H), 2.16 (ddd, J 16.2, 11.2, 6.2 Hz, 1H), 1.93-1.83 (m, 1H), 1.78 (q, J 7.4 Hz, 1H), 1.42 (dd, J 9.6, 4.7 Hz, 1H), 1.28 (dd, J 7.1, 4.9 Hz, 1H), 1.19 (t, J 7.1 Hz, 3H).

Intermediate 121

Methyl 2-{4-[5-(3-{[2-(difluoromethoxy)phenyl]methyl}-2-methylimidazo[1,2-a]pyridin-6-yl)pyrimidin-2-yl]morpholin-3-yl}acetate Intermediate 29 (150 mg, 0.37 mmol), methyl 2-(morpholin-3-yl)acetate hydrochloride (125 mg, 0.64 mmol) and triethylamine (0.26 mL, 1.87 mmol) were suspended in 1-methyl-2-pyrrolidinone (3 mL) and the reaction mixture was heated for a total of 3 h at 160° C. under microwave irradiation. The reaction mixture was allowed to cool to room temperature, then diluted with DCM (20 mL) and saturated aqueous sodium bicarbonate solution (10 mL). The organic phase was separated, washed with brine, dried over sodium sulfate and concentrated under vacuum. The residue was purified by preparative HPLC (Method C) to afford the title compound (50 mg, 15%) as a brown oil. $\delta_H$ (500 MHz, CD$_3$OD) 8.50 (s, 2H), 8.13 (s, 1H), 7.52 (d, J 9.3 Hz, 1H), 7.43 (d, J 9.3 Hz, 1H), 7.27 (t, J 7.7 Hz, 1H), 7.19 (d, J 8.2 Hz, 1H), 7.12 (t, J 7.5 Hz, 1H), 7.07-6.75 (m, 2H), 5.04 (d, J 5.9 Hz, 1H), 4.41 (d, J 13.7 Hz, 1H), 4.37 (s, 2H), 3.96 (dd, J 11.4, 3.5 Hz, 1H), 3.91 (d, J 11.8 Hz, 1H), 3.66 (dd, J 11.8, 2.9 Hz, 1H), 3.56 (s, 3H), 3.53 (dd, J 11.6, 3.0 Hz, 1H), 3.25 (td, J 13.1, 3.7 Hz, 1H), 2.88 (dd, J 15.0, 8.5 Hz, 1H), 2.64 (dd, J 15.0, 6.1 Hz, 1H), 2.43 (s, 3H).

Intermediate 122

Methyl 1-[5-(3-{[2-(difluoromethoxy)phenyl]methyl}-2-methylimidazo[1,2-a]pyridin-6-yl)pyrimidin-2-yl]azepane-4-carboxylate Intermediate 29 (85% pure, 150 mg, 0.32 mmol), methyl azepane-4-carboxylate (75 mg, 0.48 mmol) and 1M aqueous potassium carbonate solution (1 mL) were suspended in 1-methyl-2-pyrrolidinone (3 mL) and the reaction mixture was heated for 1 h at 120° C. under microwave irradiation. The mixture was allowed to cool to room temperature, then diluted with ethyl acetate (20 mL) and saturated aqueous sodium bicarbonate solution (10 mL). The organic phase was separated, washed with brine, dried over sodium sulfate and concentrated under vacuum. The product was purified by preparative HPLC (Method C) to afford the title compound (130 mg, 39%) as a light brown solid. $\delta_H$ (500 MHz, DMSO-d$_6$) 8.63 (s, 2H), 8.38 (s, 1H), 7.53 (d, J 9.2 Hz, 1H), 7.48-7.10 (m, 5H), 7.03-6.99 (m, 1H), 4.35 (s, 2H), 3.92 (ddd, J 14.1, 6.1, 4.6 Hz, 1H), 3.82 (dt, J 13.8, 5.1 Hz, 1H), 3.72-3.63 (m, 2H), 3.56 (s, 3H), 3.16 (d, J 5.1 Hz, 1H), 2.30 (s, 3H), 2.07 (dq, J 14.2, 4.3 Hz, 1H), 1.90 (td, J 12.3, 10.2, 5.4 Hz, 2H), 1.79 (ddq, J 14.3, 10.1, 4.4 Hz, 1H), 1.68 (dq, J 11.1, 5.5 Hz, 1H), 1.56-1.46 (m, 1H).

Intermediate 123

5-(3-{[2-(Difluoromethoxy)phenyl]methyl}-2-methylimidazo[1,2-a]pyridin-6-yl)-2,3-difluoropyridine Intermediate 7 (250 mg, 0.68 mmol) and (5,6-difluoropyridin-3-yl)boronic acid (165 mg, 1.02 mmol) were suspended in acetonitrile (2.5 mL). Aqueous sodium carbonate solution (2M, 520 µL) was added and mixture was de-gassed for 5 minutes. Pd(dppf)Cl$_2$ complex with DCM (30 mg, 0.03 mmol) was added. The reaction mixture was heated under microwave irradiation for 30 minutes at 150° C. The reaction mixture was diluted with water (20 mL) and extracted with ethyl acetate (2×50 mL). The organic extracts were combined, washed with brine, dried over sodium sulfate and concentrated. The resulting black solid was purified by column chromatography, using 0-3% MeOH in DCM on 50 g silica isolute, to afford the title compound (170 mg) as a pink solid. $\delta_H$ (500 MHz, DMSO-d$_6$) 8.63 (s, 1H), 8.45 (ddd, J 11.1, 9.2, 2.1 Hz, 1H), 8.42-8.39 (m, 1H), 7.62-7.56 (m, 2H), 7.33-7.26 (m, 1H), 7.48-7.12 (m, 1H), 7.23-7.17 (m, 1H), 7.16-7.08 (m, 1H), 7.04-6.97 (m, 1H), 4.41 (s, 2H), 2.30 (s, 3H). Method B HPLC-MS: MH+ m/z 402, RT 1.69 minutes.

Intermediate 124

Ethyl 1-[5-(3-{[2-(difluoromethoxy)phenyl]methyl}-2-methylimidazo[1,2-a]pyridin-6-yl)-3-fluoropyridin-2-yl]-4-methylpiperidine-4-carboxylate Intermediate 123 (86% purity, 110 mg, 0.24 mmol) and ethyl 4-methylpiperidine-4-carboxylate hydrochloride (98 mg, 0.47 mmol) in pyridine (4 mL) were heated under microwave irradiation at 180° C. for 4 h. To the reaction mixture were added 1M HCl (30 mL), ethyl acetate (50 mL) and brine (100 mL). The phases were separated and the aqueous phase was extracted with ethyl acetate (3×50 mL). The organic extracts were combined and washed with brine. The brine wash was extracted with ethyl acetate (20 mL). The organic extracts were combined, dried over sodium sulphate and concentrated. The crude residue was successively purified by column chromatography, using 0-4% MeOH in DCM, and by preparative HPLC (Method C), to afford the title compound (41 mg) as a yellow solid. $\delta_H$ (500 MHz, DMSO-d$_6$) 8.47-8.40 (m, 1H), 8.35-8.29 (m, 1H), 7.88 (dd, J 14.8, 2.0 Hz, 1H), 7.56-7.50 (m, 2H), 7.47-7.10 (m, 1H), 7.33-7.25 (m, 1H), 7.22-7.18 (m, 1H), 7.16-7.09 (m, 1H), 7.03-6.96 (m, 1H), 4.38 (s, 2H), 4.13 (q, J 7.1 Hz, 2H), 3.75 (dt, J 13.3, 4.2 Hz, 2H), 3.17-3.06 (m, 2H), 2.30 (s, 3H), 2.12-2.03 (m, 2H), 1.58-1.48 (m, 2H), 1.23-1.17 (m, 6H).

Intermediate 125 tert-Butyl 4-[5-(3-{[2-(difluoromethoxy)phenyl]methyl}-2-methylimidazo[1,2-a]pyridin-6-yl)pyrimidin-2-yl]-1,2,3,6-tetrahydropyridine-1-carboxylate Intermediate 29 (0.70 g, 1.46 mmol), {1-[(tert-butoxy)carbonyl]-1,2,3,6-tetrahydropyridin-4-yl}boronic acid (0.59 g, 2.62 mmol) and a 2M sodium carbonate solution in water (5.59 mL) were combined in DME (27.5 mL) in a sealed tube and degassed thoroughly under nitrogen for 15 minutes. Pd(PPh$_3$)$_4$ (202 mg, 0.17 mmol) was added and the mixture was heated at 90° C. for 120 minutes. The reaction mixture was cooled to r.t., then diluted using DCM (40 mL). The mixture was washed using an aqueous saturated solution of sodium bicarbonate (2×40 mL) and brine (40 mL). The organic phase was dried over sodium sulfate and concentrated under vacuum. The crude residue was successively purified using Biotage (50 g cartridge; eluent: 0-10% MeOH/DCM) and Biotage (50 g cartridge; eluent: 0-7% MeOH/DCM with the gradient held steady at 4% MeOH/DCM), to afford the title compound (1.13 g, 94%) as a pink oil. Method C HPLC-MS: MH+ m/z 548, RT 1.82, 1.88 minutes.

Intermediate 126

5-(3-{[2-(Difluoromethoxy)phenyl]methyl}-2-methylimidazo[1,2-a]pyridin-6-yl)-2-(1,2,3,6-tetrahydropyridin-4-yl)pyrimidine hydrochloride Intermediate 125 (80%, 1.13 g, 1.65 mmol) was dissolved in 1,4-dioxane (10 mL) and 4M HCl in 1,4-dioxane (2.06 mL) was added. The reaction mixture was stirred at r.t. for 2 h. Additional 4M HCl in 1,4 dioxane (5 equivalents) was added and the reaction mixture was stirred at r.t. over the weekend. The solvent was removed under vacuum and the crude residue was triturated using ethyl acetate, to afford the title compound (1.01 g, 94%) as a pale orange solid. Method C HPLC-MS: MH+ m/z 448, RT 0.77 minutes.

Intermediate 127

Ethyl 2-{4-[5-(3-{[2-(difluoromethoxy)phenyl]methyl}-2-methylimidazo[1,2-a]pyridin-6-yl)pyrimidin-2-yl]-1,2,3,6-tetrahydropyridin-1-yl}acetate Intermediate 126 (75%, 1.01 g, 1.57 mmol) was stirred in DMF (30 mL) and potassium carbonate (0.65 g, 4.71 mmol) was added. The reaction mixture was stirred for 5 minutes at r.t. before the addition of ethyl 2-bromoacetate (0.17 mL, 1.57 mmol). The reaction mixture was stirred at r.t. for 90 minutes. Water (30 mL) and EtOAc (30 mL) were added, the layers were shaken and separated, then the organic layer was further washed using water (2×20 mL) and brine (20 mL). The organic layer was dried over sodium sulfate and concentrated. The crude residue was purified using Biotage (50 g cartridge), with an eluent of 0-8% MeOH/DCM over 18 column volumes, to afford the title compound (254 mg, 33%) as a pale pink solid. $\delta_H$ (250 MHz, CDCl$_3$) 8.75 (s, 2H), 7.92 (s, 1H), 7.70 (d, J 9.5 Hz, 1H), 7.35 (d, J 9.2 Hz, 1H), 7.24 (s, 1H), 7.17 (d, J 8.0 Hz, 1H), 7.09 (t, J 7.4 Hz, 1H), 6.89 (m, 1H), 6.98-6.30 (t, J 73.5 Hz, 1H), 4.32 (s, 2H), 4.22 (q, J 7.1 Hz, 2H), 3.47 (d, J 3.4 Hz, 2H), 3.41 (s, 2H), 2.89 (d, J 4.8 Hz, 2H), 2.81 (s, 2H), 2.54 (s, 3H), 1.30 (t, J 7.1 Hz, 3H). Method B HPLC-MS: MH+ m/z 534, RT 1.39 minutes.

Intermediate 128

Ethyl 2-{4-[5-(3-{[2-(difluoromethoxy)phenyl]methyl}-2-methylimidazo[1,2-a]pyridin-6-yl)pyrimidin-2-yl]piperidin-1-yl}acetate Intermediate 127 (100 mg, 0.18 mmol) was dissolved in ethanol (10 mL), then palladium on carbon was added. The suspension was de-gassed using vacuum/nitrogen/hydrogen, and the reaction mixture was stirred under hydrogen at ambient temperature and atmospheric pressure for 2 h. The reaction mixture was flushed with nitrogen, then the catalyst was filtered and washed with ethanol (70 mL). The filtrate was concentrated under vacuum. The resulting crude yellow oil was purified using Biotage (25 g cartridge), with an eluent of 0-10% MeOH/DCM with the gradient held steady at 4% MeOH/DCM for 3 column volumes, to afford the title compound (40 mg, 40%) as a pink oil. $\delta_H$ (250 MHz, CDCl$_3$) 8.74 (s, 2H), 7.90 (d, J 0.8 Hz, 1H), 7.67 (dd, J 9.3, 0.8 Hz, 1H), 7.31 (dd, J 9.3, 1.8 Hz, 1H), 7.23 (d, J 1.7 Hz, 1H), 7.16 (d, J 7.2 Hz, 1H), 7.08 (td, J 7.4, 1.4 Hz, 1H), 6.87 (dd, J 7.6, 1.4 Hz, 1H), 6.64 (t, J 73.5 Hz, 1H), 4.32 (s, 2H), 4.20 (q, J 7.1 Hz, 2H), 3.28 (s, 2H), 3.09 (d, J 11.4 Hz, 2H), 2.99-2.84 (m, 1H), 2.53 (s, 3H), 2.47-2.32 (m, 2H), 2.07 (q, J 5.5 Hz, 4H), 1.28 (t, J 7.1 Hz, 3H).

Intermediate 129 tert-Butyl(cyclopent-3-en-1-yloxy)dimethylsilane

Cyclopent-3-en-1-ol (10 g, 118.9 mmol) was dissolved in DMF (100 mL) at 0° C., then 1H-imidazole (17.29 mL, 261.5 mmol) was added, followed by tert-butyl(chloro)-dimethylsilane (21.5 g, 142.7 mmol). The mixture was warmed to room temperature and stirred for 14 h. The mixture was diluted with ethyl acetate (300 mL), washed with 5% aqueous LiCl solution (2×100 mL) and brine (50 mL), then dried over sodium sulfate, filtered, and concentrated. The crude residue was purified by chromatography, eluting with 0-10% EtOAc in hexane, to afford the title compound (17.2 g, 73%) as a colourless clear liquid. $\delta_H$ (250 MHz, CDCl$_3$) 5.66 (s, 2H), 4.53 (tt, J 7.0, 3.6 Hz, 1H), 2.57 (dd, J 15.2, 6.8 Hz, 2H), 2.27 (dd, J 15.3, 3.6 Hz, 2H), 0.89 (s, 9H), 0.06 (s, 6H).

Intermediate 130

Ethyl 3-[(tert-butyldimethylsilyl)oxy]bicyclo[3.1.0]hexane-6-carboxylate 1-(2-Ethoxy-2-oxoethylidene)diazenium (6.07 mL, 48.4 mmol) in DCM (4 mL) was added slowly via syringe pump over 6 h to a stirred solution of Intermediate 129 (8 g, 40.3 mmol) and rhodium(II) acetate (178.24 mg, 0.4 mmol) in DCM (150 mL) under nitrogen at room temperature. The mixture was stirred for 14 h, then filtered through celite and concentrated under reduced pressure. The resulting crude light brown oil was purified by column chromatography, eluting with 5-30% ethyl acetate in heptane, to afford the title compound (7.15 g, 59%) as a mixture of isomers (exo:endo 2.5:1) as a colourless clear oil. $\delta_H$ (500 MHz, CDCl$_3$) 4.12-4.03 (m, 2H), 2.13 (dd, J 13.0, 7.2 Hz, 1H), 2.05 (ddd, J 13.2, 5.8, 3.4 Hz, 1H), 1.88-1.69 (m, 4H), 1.51 (d, J 14.7 Hz, 1H), 1.28-1.19 (m, 4H), 0.88-0.82 (m, 9H), 0.04-0.03 (m, 6H).

Intermediate 131

Ethyl 3-hydroxybicyclo[3.1.0]hexane-6-carboxylate

TBAF (1M, 68.13 mL) was added dropwise to a stirred solution of Intermediate 130 (95% pure, 10.2 g, 34.06 mmol) in THF (100 mL) at room temperature, then the mixture was heated at 50° C. for 1 h. The mixture was cooled to room temperature and concentrated under reduced pressure. The resulting light brownish oil was diluted with ethyl acetate (300 mL), washed with water (2×100 mL) and brine (50 mL), then dried over magnesium sulfate and concentrated under reduced pressure, to provide the title compound (9.4 g crude) as a light reddish oil. $\delta_H$ (500 MHz, CDCl$_3$) 4.15-4.05 (m, 2H), 2.26 (dd, J 13.1, 7.1 Hz, 1H), 2.20-2.11 (m, 1H), 1.99-1.93 (m, 1H), 1.92-1.84 (m, 4H), 1.84-1.75 (m, 1H), 1.64-1.53 (m, 1H), 1.30-1.20 (m, 3H).

Intermediate 132

Ethyl 3-oxobicyclo[3.1.0]hexane-6-carboxylate

Intermediate 131 (60% pure, 9.4 g, 33.14 mmol) was dissolved in DCM (100 mL), then DMP (28.11 g, 0.07 mol) was added as a solid and the mixture was stirred at room temperature for 15 h. The mixture was diluted with DCM (200 mL), washed with saturated aqueous sodium bicarbonate solution (2×100 mL), water (100 mL) and brine (50 mL), then dried over sodium sulfate and concentrated under reduced pressure. The resulting crude sticky off-white solid was purified by flash chromatography, eluting with 30-100% ethyl acetate in heptane, to afford the title compound (3.15 g, 56%) as a light brown oil. $\delta_H$ (500 MHz, CDCl$_3$) 4.15 (q, J 7.1 Hz, 2H), 2.66 (ddt, J 18.5, 3.9, 1.6 Hz, 2H), 2.31 (d, J 1.8 Hz, 1H), 2.27 (d, J 1.7 Hz, 2H), 2.18 (td, J 3.4, 1.6 Hz, 2H), 1.31-1.23 (m, 4H).

Intermediate 133

Ethyl 3-(trifluoromethanesulfonyloxy)bicyclo[3.1.0]hex-2-ene-6-carboxylate

Intermediate 132 (3 g, 17.84 mmol) was dissolved in dry toluene (60 mL), then DIPEA (12.5 mL, 71.35 mmol) was added and the reaction mixture was heated at 45° C. Trifluoromethanesulfonic anhydride (12 mL, 71.35 mmol) was added, the temperature rose to 70° C. and the reaction mixture was cooled using an ice bath. The mixture was stirred for 1.5 h at 45° C. The reaction mixture was diluted with ethyl acetate (200 mL) and washed with saturated aqueous sodium bicarbonate solution (2×100 mL). The aqueous washes were extracted with ethyl acetate (200 mL) and washed with saturated aqueous sodium bicarbonate solution (2×100 mL). The aqueous washes were extracted (100 mL), then the organic extracts were combined, washed with brine (50 mL), dried over sodium sulfate and concentrated. The crude product was purified by chromatography, eluting with 0-20% ethyl acetate (200 mL), then washed with saturated aqueous sodium bicarbonate solution (2×100 mL). The aqueous washes were extracted in heptane to afford the title compound (2.73 g, 51%). $\delta_H$ (250 MHz, CDCl$_3$) 5.87 (d, J 1.9 Hz, 1H), 4.14 (q, J 7.1 Hz, 2H), 3.00 (dd, J 17.2, 6.2 Hz, 1H), 2.75-2.60 (m, 1H), 2.46-2.31 (m, 1H), 2.23-2.11 (m, 1H), 1.39-1.32 (m, 1H), 1.32-1.16 (m, 3H).

Intermediate 134

Ethyl 3-(4,4,5,5-tetramethyl-1,3,2-dioxaborolan-2-yl)bicyclo[3.1.0]hex-2-ene-6-carboxylate Intermediate 133 (2.73 g, 9.09 mmol) was dissolved in 1,4-dioxane (60 mL) and degassed using nitrogen for 5 minutes. Bis(pinacolato)diborane (3.46 g, 13.64 mmol), potassium acetate (2.68 g, 27.28 mmol), 1,1'-bis(diphenylphosphanyl)ferrocene (0.15 g, 0.27 mmol) and Pd(dppf)Cl$_2$ complex with dichloromethane (0.22 g, 0.27 mmol) were added, and the reaction mixture was heated under nitrogen at 90° C. for 18 h. The reaction mixture was diluted with ethyl acetate (200 mL) and washed with a saturated aqueous solution of sodium bicarbonate (2×100 mL). The aqueous washes were re-extracted with ethyl acetate (50 mL). The organic extracts were combined, washed with brine, dried over sodium sulfate and concentrated. The crude residue was purified by chromatography, eluting with 0-40% ethyl acetate in heptane, to afford the title compound (2.0 g, 59%) containing bis(pinacolato)diborane impurity. $\delta_H$ (250 MHz, CDCl$_3$) 6.66 (d, J 1.9 Hz, 1H), 4.11 (q, J 7.1 Hz, 2H), 2.88-2.73 (m, 1H), 2.66-2.44 (m, 2H), 2.33-2.22 (m, 1H), 1.34-1.18 (m, 16H).

Intermediate 135

Ethyl 3-[5-(3-{[2-(difluoromethoxy)phenyl]methyl}-2-methylimidazo[1,2-a]-pyridin-6-yl)pyrimidin-2-yl]bicyclo[3.1.0]hex-2-ene-6-carboxylate Intermediate 134 (70%, 230 mg, 0.58 mmol) and Intermediate 29 (230 mg, 0.58 mmol) were dissolved in 1,4-dioxane (3 mL). Aqueous potassium carbonate solution (2M, 0.87 mL) was added. The reaction mixture was degassed with nitrogen for 5 minutes. Tetrakis(triphenylphosphine)palladium(0) (67 mg, 0.06 mmol) was added and the reaction mixture was heated under microwave irradiation for 2 h at 120° C. The reaction mixture was allowed to cool, diluted with ethyl acetate (50 mL), washed with aqueous sodium bicarbonate solution (20 mL) and brine (20 mL), dried over sodium sulfate and concentrated. The resulting black oil was successively purified by column chromatography, using 0-10% methanol in dichloromethane, and preparative HPLC, to afford the title compound (85 mg, 28%) as a white sticky solid. Method B HPLC-MS: MH+ m/z 517, RT 1.70 minutes.

Intermediate 136

4-(tert-Butyl)2-methyl morpholine-2,4-dicarboxylate 4-(tert-Butoxycarbonyl)morpholine-2-carboxylic acid (500 mg, 2.16 mmol) and potassium carbonate (900 mg, 6.51 mmol) were placed in a round-bottom flask. The flask was flushed with nitrogen and DMF (5 mL) was added. The mixture was cooled to 0° C. while stirring and iodomethane (0.54 mL, 8.67 mmol) was added dropwise. The reaction mixture was allowed to warm to r.t. and stirred for 15 h. The reaction mixture was quenched with saturated aqueous ammonium chloride solution (15 mL), diluted with water (30 mL) and extracted with ethyl acetate (3×15 mL). The combined organic layers were washed with brine (25 mL), dried over sodium sulfate and concentrated under vacuum. The residue was purified by flash chromatography (0-25% ethyl acetate in heptane) to afford the title compound (478 mg, 90%). $\delta_H$ (500 MHz, DMSO-d$_6$) 4.18 (dd, J 8.4, 3.4 Hz, 1H), 3.84 (dt, J 11.6, 4.1 Hz, 2H), 3.67 (s, 3H), 3.54-3.44 (m, 2H), 3.31 (s, 1H), 3.09 (ddd, J 13.2, 9.1, 3.4 Hz, 1H), 1.40 (s, 9H).

Intermediate 137

4-tert-Butyl 2-methyl 2-methylmorpholine-2,4-dicarboxylate

Diisopropylamine (0.35 mL, 2.48 mmol) was added dropwise to 2.5M butyllithium solution (1 mL) in THF (2 mL) at −74° C. The mixture was allowed to warm to r.t. whilst stirring for 1 h. The mixture was re-cooled and Intermediate 136 (478 mg, 1.95 mmol) in THF (5 mL) was added dropwise at −78° C. The reaction mixture was allowed to stir for 1 h, then iodomethane (0.15 mL, 2.41 mmol) was added dropwise. The reaction mixture was allowed to warm to room temperature and was stirred for 16 h. The reaction mixture was cooled to −78° C. and 2M lithium dipropan-2-ylazanide (10 mL) was added dropwise. The reaction mixture was allowed to stir for 1 h. Iodomethane (0.05 mL, 0.8 mmol) was added dropwise at −78° C. The reaction mixture was allowed to stir at r.t. overnight. The reaction mixture was cooled to 0° C. and quenched with saturated aqueous ammonium chloride solution (10 mL), diluted with water (20 mL) and extracted with ethyl acetate (3×20 mL). The combined organic layers were washed with brine (25 mL), dried over sodium sulfate and concentrated under vacuum. The crude residue was purified onto a 25 g silica cartridge, eluting with a gradient of 0-25% ethyl acetate in heptane, to afford the title compound (110 mg, 22%) as a pale yellow oil. $\delta_H$ (500 MHz, CD$_3$OD) 4.39 (d, J 13.2 Hz, 1H), 3.79-3.70 (m, 6H), 2.99 (s, 1H), 2.85 (d, J 12.3 Hz, 1H), 1.46 (s, 9H), 1.33 (s, 3H).

Intermediate 138

Methyl 2-methylmorpholine-2-carboxylate hydrochloride

Intermediate 137 (110 mg, 0.42 mmol) was dissolved in a 4M solution of hydrogen chloride in 1,4-dioxane (3 mL) and allowed to stir for 18 h at r.t. The reaction mixture was concentrated under vacuum to afford the title compound (83 mg, 100%) as a yellow oil. $\delta_H$ (500 MHz, CD$_3$OD) 4.01-3.96 (m, 1H), 3.86 (s, 3H), 3.83-3.79 (m, 1H), 3.66 (s, 2H), 3.21 (d, J 2.8 Hz, 1H), 3.08 (d, J 13.1 Hz, 1H), 1.44 (s, 3H).

Intermediate 139

Methyl 4-[5-(3-{[2-(difluoromethoxy)phenyl]methyl}-2-methylimidazo[1,2-a]pyridin-6-yl)pyrimidin-2-yl]-2-methylmorpholine-2-carboxylate Intermediate 29 (85%, 130 mg, 0.28 mmol), Intermediate 138 (80 mg, 0.41 mmol) and a 1M solution of potassium carbonate in water (0.85 mL) were suspended in NMP (3 mL). The reaction mixture was heated at 120° C. under microwave irradiation (2×1 h). The reaction mixture was allowed to cool to r.t., diluted with DCM (20 mL) and acidified using 1M HCl (5 mL). The organic phase was separated, washed with brine and dried over sodium sulphate, then filtered and concentrated under vacuum. The residue was purified by preparative HPLC (Method C) to afford the title compound (48 mg, 17%) as a light brown solid. $\delta_H$ (500 MHz, CD$_3$OD) 8.51 (d, J 2.1 Hz, 2H), 8.31 (s, 1H), 7.64 (s, 2H), 7.32-7.27 (m, 1H), 7.22-7.12 (m, 3H), 6.93 (t, J 74.0 Hz, 1H), 5.05 (d, J 13.3 Hz, 1H), 4.40 (d, 3H), 3.88-3.82 (m, 2H), 3.67 (s, 3H), 3.17 (dt, J 13.8, 7.5 Hz, 1H), 3.03 (d, J 13.3 Hz, 1H), 2.46 (s, 3H), 1.40 (s, 3H).

Intermediate 140

Ethyl 3-azabicyclo[4.1.0]heptane-6-carboxylate hydrochloride (Racemic)

A 4M solution of hydrogen chloride in 1,4-dioxane (2.07 mL, 8 mmol) was added to a solution of 3-(tert-butyl)6-ethyl 3-azabicyclo[4.1.0]heptane-3,6-dicarboxylate (1 g, 4 mmol) in ethanol (10 mL) at room temperature. The mixture was stirred at room temperature for 2.5 h. Additional ethanol (10 mL) and 4M solution of hydrogen chloride in 1,4-dioxane (4.14 mL) were added and the mixture was heated at 50° C. for 1.5 h. The reaction mixture was cooled and evaporated under vacuum. A second reaction batch was prepared whereby a 4M solution of hydrogen chloride in 1,4-dioxane (10.4 mL, 40 mmol) was added to a solution of 3-(tert-butyl) 6-ethyl 3-azabicyclo[4.1.0]heptane-3,6-dicarboxylate (1 g, 4 mmol) in ethanol (40 mL) and the reaction mixture was warmed to 75° C. and stirred at this temperature overnight. The reaction mixture was cooled to r.t. The batches were combined, then concentrated under vacuum, to afford the title compound (3.1 g) as a pale yellow solid. $\delta_H$ (250 MHz, DMSO-$d_6$) 9.07 (d, J 37.9 Hz, 2H), 4.05 (q, J 7.1 Hz, 2H), 3.08 (d, J 13.1 Hz, 1H), 2.83 (s, 2H), 2.61 (dt, J 13.7, 6.5 Hz, 1H), 2.00-1.81 (m, 1H), 1.71 (q, J 7.0 Hz, 1H), 1.36-1.22 (m, 2H), 1.18 (q, J 7.1, 6.4 Hz, 3H).

Intermediate 141

Methyl 4-[5-(3-{[2-(difluoromethoxy)phenyl]methyl}-2-methylimidazo[1,2-a]pyridin-6-yl)pyridin-2-yl]cyclohex-3-ene-1-carboxylate Intermediate 30 (470 mg, 1.17 mmol), Intermediate 56 (375 mg, 1.41 mmol) and 2M aqueous dipotassium carbonate solution (1.76 mL) were added to 1,4-dioxane (4 mL) in a microwave tube. The mixture was degassed for 10 minutes, then Bedford's catalyst (126 mg, 0.12 mmol) was added. The reaction mixture was heated under microwave irradiation for 30 minutes at 150° C., then filtered through celite. The celite was washed with ethyl acetate. The filtrate was washed with water (50 mL) and brine (25 mL), dried with sodium sulphate and concentrated under vacuum. The crude brown oil was purified on Biotage using 100 g SNAP cartridge (loaded with DCM, eluent: 95% EtOAc/heptane to 100% EtOAc) to afford the title compound (262 mg, 40%) as an off-white solid. Method C HPLC-MS: MH+ m/z 504, RT 1.09 minutes.

Intermediate 142

Methyl 1-[(1R)-1-phenylethyl]-2,5-dihydro-1H-pyrrole-3-carboxylate

To a stirred solution of (1R)-N-(methoxymethyl)-1-phenyl-N-[(trimethylsilyl)-methyl]ethanamine (55.83 mL, 205.62 mmol) and methyl prop-2-ynoate (22.5 mL, 252.9 mmol) in dichloromethane (500 mL) at 0° C. under nitrogen was added trifluoroacetic acid (800 µL, 10.45 mmol). The reaction mixture was allowed to stir at 0° C. for 20 minutes, then the ice bath was removed and the solution was allowed to warm to room temperature. The solution was stirred at room temperature for 1 h. The reaction mixture was concentrated to dryness and the residue was purified by FCC, eluting with 0-70% EtOAc in heptane, to afford the title compound (26.5 g, 56%) as a yellow oil. $\delta_H$ (500 MHz, CDCl$_3$) 7.41-7.29 (m, 4H), 7.28-7.21 (m, 1H), 6.77-6.70 (m, 1H), 3.72 (s, 3H), 3.71-3.65 (m, 1H), 3.65-3.42 (m, 4H), 1.40 (d, J 6.6 Hz, 3H). Method F HPLC-MS: MH+ m/z 232, RT 1.62 minutes.

Intermediate 143

Methyl 3-[(1R)-1-phenylethyl]-3-azabicyclo[3.1.0]hexane-1-carboxylate

To a stirred suspension of potassium tert-butoxide (12.86 g, 114.57 mmol) in anhydrous DMSO (80 mL) under nitrogen in a cold water bath (~5° C.) was added trimethylsulfoxonium iodide (26.72 g, 120.3 mmol) portionwise. The mixture was stirred for 15 minutes, then warmed to 40° C. The mixture was cooled to approximately 5° C. with a cold water bath, then a solution of Intermediate 142 (13.25 g, 57.30 mmol) in DMSO (40 mL) was added portionwise. The mixture was stirred for 1 minute, then warmed to 50° C. and stirred for 1 h. The mixture was cooled to room temperature, then poured into water (120 mL) and ethyl acetate (120 mL). The phases were separated and the organic layer was washed with brine (80 mL), dried over sodium sulfate and concentrated to dryness. The residue was purified by FCC, eluting with 0-30% EtOAc in heptane. The procedure was repeated on the same scale as above, and the purified products were combined, to afford the title compound (11.9 g, 42%) as a colourless oil. Method F HPLC-MS: MH+ m/z 246, RT 1.77 minutes.

Intermediate 144

Methyl 3-azabicyclo[3.1.0]hexane-1-carboxylate hydrochloride (Enantiomer A)

Intermediate 143 (5 g, 20 mmol) was separated using chiral preparative HPLC (Chiracel OJ column, 20×250 mm, 5 µm; 100% acetonitrile eluent; 20 mL/minute flow rate) and the second-eluting diastereomer was isolated (1.87 g, 7.62 mmol). This was dissolved in methanol (55 mL) and the mixture was degassed with nitrogen, then palladium on carbon (10%, 195 mg, 0.18 mmol) was added. The reaction mixture was stirred under a hydrogen balloon at room temperature for 5 h. The reaction mixture was filtered through celite and the solids were washed with excess methanol. The filtrate was concentrated by evaporation. To the residue was added 4M hydrochloric acid in diethyl ether (10 mL) and the mixture was stirred at room temperature for 10 minutes. The resulting precipitate was filtered, washed with diethyl ether and dried, to afford the title compound (1.21 g, 93%) as an off-white solid. $\delta_H$ (500 MHz, CD$_3$OD) 3.83 (dd, J 11.8, 1.3 Hz, 1H), 3.75 (s, 3H), 3.59-3.52 (m, 2H), 3.44 (d, J 11.7 Hz, 1H), 2.40-2.30 (m, 1H), 1.76-1.69 (m, 1H), 1.17 (t, J 5.9 Hz, 1H).

Intermediate 145

3-Chloro-5-(3-{[2-(difluoromethoxy)phenyl]methyl}-2-methylimidazo[1,2-a]pyridin-6-yl)-2-fluoropyridine A mixture of Intermediate 7 (100 mg, 0.27 mmol), 3-chloro-2-fluoro-5-(4,4,5,5-tetramethyl-1,3,2-dioxaborolan-2-yl)pyridine (105 mg, 0.41 mmol) and aqueous 2M sodium carbonate solution (0.2 mL) in acetonitrile (1 mL) was purged with nitrogen for 5 minutes. Bis[3-(diphenylphosphanyl)cyclopenta-2,4-dien-1-yl]iron dichloropalladium dichloromethane complex (11 mg, 0.01 mmol) was then added and the reaction mixture was heated at 150° C. under microwave irradiation for 30 minutes. The reaction mixture was combined and partitioned between ethyl acetate (50 mL) and water (30 mL). The aqueous layer was separated and extracted with ethyl acetate (50 mL). The combined organic extracts were washed with brine (15 mL), dried over sodium sulfate and concentrated by evaporation. The residue was purified by FCC, using a KP-NH cartridge (Biotage®) and eluting with 0-50% ethyl acetate in heptane. The material was then triturated with dichloromethane/heptane to afford the title compound (0.14 g, 39%) as a white solid. $\delta_H$ (500 MHz, CDCl$_3$) 8.18 (dd, J 2.2, 1.3 Hz, 1H), 7.97 (s, 1H), 7.91 (dd, J 8.4, 2.3 Hz, 1H), 7.76 (d, J 9.4 Hz, 1H), 7.39-7.30 (m, 2H), 7.20 (d, J 7.8 Hz, 1H), 7.13 (t, J 7.5 Hz, 1H), 6.96 (d, J 7.7 Hz, 1H), 6.67 (t, J 73.6 Hz, 1H), 4.35 (s, 2H), 2.59 (s, 3H). Method C HPLC-MS: MH+ m/z 418, RT 1.11 minutes.

Intermediate 146

Ethyl 1-[3-chloro-5-(3-{[2-(difluoromethoxy)phenyl]methyl}-2-methylimidazo[1,2-a]-pyridin-6-yl)pyridin-2-yl]-4-methylpiperidine-4-carboxylate A mixture of Intermediate 145 (97% pure, 50 mg, 0.12 mmol) and ethyl 4-methylpiperidine-4-carboxylate hydrochloride (48 mg, 0.23 mmol) in pyridine (2 mL) was heated at 180° C. under microwave irradiation for a total of 4 h. The reaction mixture was concentrated under vacuum. The residue was purified by FCC, using a KP-NH cartridge (Biotage®) and eluting with 0-30% ethyl acetate in heptane followed by 100% EtOAc. The material was then triturated with MeCN/water, and purified by preparative HPLC (Method C), to afford the title compound (56 mg, 32%) as an orange oil. $\delta_H$ (500 MHz, DMSO-d$_6$) 8.55-8.44 (m, 2H), 8.12 (d, J 2.2 Hz, 1H), 7.54 (d, J 1.1 Hz, 2H), 7.46-7.05 (m, 4H), 7.05-6.93 (m, 1H), 4.39 (s, 2H), 4.13 (q, J 7.1 Hz, 2H), 3.59-3.46 (m, 2H), 3.09-2.90 (m, 2H), 2.30 (s, 3H), 2.11 (d, J 14.0 Hz, 2H), 1.58 (ddd, J 13.4, 10.2, 3.5 Hz, 2H), 1.27-1.11 (m, 6H). Method A HPLC-MS: MH+ m/z 569, RT 4.15 minutes.

Intermediate 147

Ethyl 3-methyl-4-oxocyclohexane-1-carboxylate

Lithium hexamethyldisilazanide in THF/ethylbenzene (1M, 117.5 mL) was added dropwise to a stirred solution of ethyl 4-oxocyclohexane-1-carboxylate (20 g, 0.12 mol) in THF (100 mL) at −78° C. The mixture was stirred for 30 minutes. Iodomethane (7.32 mL, 0.12 mol) was added dropwise, then the mixture was gradually warmed to room temperature over 1 h and stirred for 4 h. The mixture was quenched with water (200 mL) and extracted with ethyl acetate (2×200 mL). The combined organic layers were washed with brine (100 mL), dried over magnesium sulfate and concentrated under reduced pressure. The residue was purified twice by FCC, eluting with 20-70% ethyl acetate in cyclohexane, to afford the title compound (3.3 g, 15%) as a colourless oil. $\delta_H$ (500 MHz, CDCl$_3$) 4.15 (q, J 7.1 Hz, 2H), 2.82 (tt, J 12.2, 3.5 Hz, 1H), 2.50-2.40 (m, 2H), 2.40-2.27 (m, 3H), 1.91-1.78 (m, 1H), 1.59 (q, J 13.0 Hz, 1H), 1.27 (t, J 7.1 Hz, 3H), 1.05 (d, J 6.5 Hz, 3H).

Intermediate 148

Ethyl 5-methyl-4-(trifluoromethanesulfonyloxy)cyclohex-3-ene-1-carboxylate

Lithium hexamethyldisilazanide in THF/ethylbenzene (1M, 18.64 mL) was added dropwise to a stirred solution of Intermediate 147 (3.27 g, 17.75 mmol) in THF (15 mL) at −78° C. The mixture was stirred for 1 h. 1,1,1-Trifluoro-N-phenyl-N-[(trifluoromethyl)-sulfonyl]methanesulfonamide (6.66 g, 18.64 mmol) in THF (25 mL) was added over 10 minutes and the mixture was stirred for another 30 minutes. The mixture was warmed to room temperature and stirred for 12 h. The mixture was quenched with aqueous sodium hydrogensulfate solution (100 mL), extracted into ethyl acetate (300 mL), and washed with 0.5M aqueous NaOH solution (2×50 mL), saturated ammonium chloride (50 mL) and brine (50 mL), then dried over magnesium sulfate and concentrated under reduced pressure. The residue was purified by FCC, eluting with 5-10% ethyl acetate in heptane, to afford the title compound (5.3 g, 90%) as a colourless oil. $\delta_H$ (500 MHz, CDCl$_3$) 5.79-5.66 (m, 1H), 4.16 (q, J 7.1 Hz, 2H), 2.75-2.54 (m, 2H), 2.52-2.34 (m, 2H), 2.33-2.22 (m, 1H), 1.58-1.44 (m, 1H), 1.27 (t, J 7.1 Hz, 3H), 1.17 (d, J 6.9 Hz, 3H).

Intermediate 149

Ethyl 5-methyl-4-(4,4,5,5-tetramethyl-1,3,2-dioxaborolan-2-yl)cyclohex-3-ene-1-carboxylate Intermediate 148 (95% pure, 5.3 g, 15.92 mmol), 4,4,5,5-tetramethyl-2-(4,4,5,5-tetramethyl-1,3,2-dioxaborolan-2-yl)-1,3,2-dioxaborolane (6.06 g, 23.88 mmol) and potassium acetate (4.69 g, 47.76 mmol) were suspended in 1,4-dioxane (80 mL) and degassed for 15 minutes. 1,1'-Bis(diphenylphosphanyl)ferrocene (0.26 g, 0.48 mmol) was added, followed by bis[3-(diphenylphosphanyl)cyclopenta-2,4-dien-1-yl]iron dichloropalladium dichloromethane complex (0.39 g, 0.48 mmol), and the mixture was heated at 90° C. for 2 h. The mixture was cooled to room temperature, diluted with water (100 mL) and extracted with ethyl acetate (2×150 mL). The combined organic layers were washed with brine (50 mL), dried over magnesium sulfate and concentrated. The residue was purified by FCC, eluting with 10-50% ethyl acetate in heptane, to afford the title compound (3.4 g, 69%) as a colourless thick oil. $\delta_H$ (500 MHz, CDCl$_3$) 6.52-6.45 (m, 1H), 4.17-4.08 (m, 2H), 2.54-2.45 (m, 1H), 2.45-2.36 (m, 1H), 2.35-2.18 (m, 2H), 2.13-2.05 (m, 1H), 1.26 (d, J 5.5 Hz, 16H), 1.10 (d, J 7.0 Hz, 3H).

Intermediate 150

Ethyl 4-[5-(3-{[2-(difluoromethoxy)phenyl]methyl}-2-methylimidazo[1,2-a]pyridin-6-yl)pyrimidin-2-yl]-5-methylcyclohex-3-ene-1-carboxylate Intermediate 29 (430 mg, 0.86 mmol), Intermediate 149 (73% pure, 395 mg, 1.03 mmol) and 2M aqueous potassium carbonate solution (1.72 mL) were suspended in 1,4-dioxane (15 mL) and the mixture was degassed with nitrogen for 10 minutes. Tetrakis-(triphenylphosphine)palladium(0) (64 mg, 0.06 mmol) was added and the mixture was heated at 120° C. for 8 h. The mixture was cooled to room temperature, diluted with water (100 mL) and extracted with ethyl acetate (3×100 mL). The combined organic layers were washed with water (50 mL), dried over magnesium sulfate and concentrated. The residue was purified by FCC, eluting with 2-10% methanol in DCM, to afford the title compound (120 mg, 20%) as an brownish oil. $\delta_H$ (500 MHz, CDCl$_3$) 8.76 (s, 2H), 7.92 (s, 1H), 7.68 (d, J 9.2 Hz, 1H), 7.33 (dd, J 9.3, 1.7 Hz, 1H), 7.29-7.23 (m, 1H), 7.17 (d, J 7.9 Hz, 1H), 7.13-7.04 (m, 1H), 6.95-6.86 (m, 2H), 6.64 (t, J 73.7 Hz, 1H), 4.32 (s, 2H), 4.17 (q, J 7.1 Hz, 2H), 3.20-3.06 (m, 1H), 2.67-2.57 (m, 1H), 2.54 (s, 4H), 2.52-2.43 (m, 1H), 2.40-2.28 (m, 1H), 1.58 (ddd, J 13.1, 12.1, 10.3 Hz, 1H), 1.29 (t, J 7.1 Hz, 3H), 1.11 (d, J 6.8 Hz, 3H). Method B HPLC-MS: MH+ m/z 533.5, RT 1.77 minutes.

Intermediate 151

Ethyl 4-[5-(3-{[2-(difluoromethoxy)phenyl]methyl}-2-methylimidazo[1,2-a]pyridin-6-yl)pyrimidin-2-yl]-3-methylcyclohexane-1-carboxylate (unknown isomer)

To a stirring solution of Intermediate 150 (50 mg, 0.09 mmol) in ethanol (5 mL), degassed and purged with nitrogen, was added palladium on carbon (10%, 10 mg, 0.01 mmol). The reaction mixture was degassed and purged with nitrogen, then stirred under a hydrogen balloon at room temperature for 4 h. The reaction mixture was filtered through celite and the solids were washed with excess methanol. The filtrate was concentrated by evaporation. The resulting pale oil was purified by preparative HPLC (Method D), and the second-eluting peak was isolated, to afford the title compound (13 mg, 26%) as a pale oil. $\delta_H$ (500 MHz, CDCl$_3$) 8.74 (s, 2H), 7.92 (s, 1H), 7.71 (d, J 9.2 Hz, 1H), 7.35 (dd, J 9.2, 1.6 Hz, 1H), 7.30-7.27 (m, 1H), 7.18 (d, J 7.9 Hz, 1H), 7.09 (t, J 7.5 Hz, 1H), 6.88 (d, J 6.6 Hz, 1H), 6.65 (t, J 73.7 Hz, 1H), 4.33 (s, 2H), 4.15 (q, J 7.1 Hz, 2H), 3.30 (q, J 4.8 Hz, 1H), 2.54 (s, 3H), 2.46 (tt, J 11.1, 3.8 Hz, 1H), 2.35-2.23 (m, 1H), 2.18-2.00 (m, 3H), 1.86 (ddd, J 13.4, 9.8, 5.3 Hz, 1H), 1.74 (ddd, J 16.9, 8.7, 4.4 Hz, 2H), 1.27 (t, J 7.1 Hz, 3H), 0.86 (d, J 7.0 Hz, 3H). Method E HPLC-MS: MH+ m/z 535, RT 5.32 minutes.

Intermediate 152

2-Chloro-5-(3-{[2-(difluoromethoxy)phenyl]methyl}-7-fluoro-2-methylimidazo[1,2-a]-pyridin-6-yl)pyrimidine Intermediate 68 (5.5 g, 14.28 mmol) and 2-chloro-5-(4,4,5,5-tetramethyl-1,3,2-dioxaborolan-2-yl)pyrimidine (6.85 g, 28.48 mmol) were dissolved in 1,4-dioxane (180 mL) and DMSO (50 mL). Sodium carbonate in water (2M, 21 mL) was added and the resulting mixture was degassed with nitrogen for 45 minutes. Dichlorobis(triphenylphosphine)palladium (II) (505 mg, 0.72 mmol) and tri-tert-butylphosphonium tetrafluoro-borate (410 mg, 1.41 mmol) were added and the reaction mixture was heated at 120° C. under nitrogen for 6.5 h. The reaction mixture was diluted with water (200 mL) and extracted with EtOAc (3×200 mL). The combined organic layers were dried over sodium sulphate, filtered and concentrated to dryness. The residue was purified by FCC, using a KP-NH cartridge (Biotage®) and eluting with 0-50% EtOAc in heptane, to afford the title compound (3.52 g, 59%) as a white solid. $\delta_H$ (500 MHz, CDCl$_3$) 8.67 (d, J 1.4 Hz, 2H), 7.81 (d, J 7.2 Hz, 1H), 7.35 (d, J 10.7 Hz, 1H), 7.30-7.26 (m, 1H), 7.16 (d, J 7.9 Hz, 1H), 7.11 (t, J 7.5 Hz, 1H), 6.97-6.91 (m, 1H), 6.62 (t, J 73.6 Hz, 1H), 4.29 (s, 2H), 2.52 (s, 3H). Method C HPLC-MS: MH+ m/z 419, RT 1.03 minutes.

Intermediate 153

Ethyl 4-{[5-(3-{[2-(difluoromethoxy)phenyl]methyl}-2-methylimidazo[1,2-a]pyridin-6-yl)pyrimidin-2-yl]methyl}cyclohexane-1-carboxylate Ethyl 4-methylidenecyclohexanecarboxylate (50 mg, 0.3 mmol) was stirred with 0.5M 9-borabicyclo[3.3.1]nonane in THF (0.89 mL), which was added slowly under nitrogen. The reaction mixture was stirred at room temperature overnight. The crude mixture was cooled to 0° C. and Intermediate 29 (203 mg, 0.51 mmol) in DMF (3 mL) was added, followed by bis[3-(diphenylphosphanyl)cyclopenta-2,4-dien-1-yl]iron dichloropalladium dichloromethane complex (24 mg, 0.03 mmol) and 2M aqueous potassium carbonate solution (0.22 mL). The reaction mixture was stirred at room temperature over the weekend, then heated at 60° C. for 1.5 h. Further bis[3-(diphenylphosphanyl)-cyclopenta-2,4-dien-1-yl]iron dichloropalladium dichloromethane complex (50 mg, 0.061 mmol) was added and the mixture was heated at 80° C. overnight under nitrogen. The reaction mixture was added to cold water and 0.5M aqueous NaOH solution (0.5 mL) was added. The mixture was extracted with DCM (100 mL), dried over sodium sulphate, filtered and concentrated under vacuum. The resulting brown oil was purified twice by FCC, eluting with 0-30% MeOH in DCM. The material was further purified by preparative HPLC (Method C), to afford the title compound (11.4 mg, 7%) as a brown oil. Method B HPLC-MS: MH+ m/z 535, RT 1.72 minutes.

Intermediate 154

1,4-Dioxaspiro[4.5]dec-7-en-8-yl trifluoromethanesulfonate

Lithium hexamethyldisilazanide in THF/ethylbenzene (1M, 6.75 mL) was added dropwise to a stirred solution of 1,4-dioxaspiro[4.5]decan-8-one (1 g, 6.41 mmol) in THF (5 mL) at −78° C. The mixture was stirred for 1 h. 1,1,1-Trifluoro-N-phenyl-N-[(trifluoromethyl)sulfonyl]methanesulfonamide (2.4 g, 6.75 mmol) in THF (5 mL) was added over 5 minutes and the mixture was stirred for another 30 minutes. The reaction mixture was warmed to room temperature and stirred for 12 h. The reaction mixture was quenched with aqueous sodium hydrogensulphate solution, extracted with ethyl acetate (100 mL) and washed with 0.5M aqueous NaOH solution (50 mL), saturated aqueous ammonium chloride solution (50 mL) and brine (50 mL), then dried over magnesium sulfate and concentrated under reduced pressure, to afford the title compound (2.3 g, 87% yield at 70% purity) as a yellow oil, which was used without further purification. $\delta_H$ (500 MHz, CDCl$_3$) 5.53 (t, J 4.1 Hz, 1H), 3.91-3.80 (m, 4H), 2.46-2.37 (m, 2H), 2.32-2.24 (m, 2H), 1.78 (t, J 6.6 Hz, 2H).

Intermediate 155

Methyl 1,4-dioxaspiro[4.5]dec-7-ene-8-carboxylate

Palladium diacetate (125 mg, 0.555 mmol, 10 mol %) was added to a mixture of Intermediate 154 (1.6 g, 5.55 mmol), triphenylphosphine (291 mg, 1.11 mmol, 20 mol %), triethylamine (1.53 mL, 11.04 mmol) and MeOH (20 mL, 624 mmol) in DMF (20 mL). The mixture was placed under a carbon monoxide atmosphere at 5 bar pressure and stirred at room temperature for 16 h. The reaction mixture was quenched with water (100 mL), extracted with diethyl ether (2×100 mL), dried over MgSO$_4$ and concentrated. The resulting brown oil (1.85 g) was redissolved in EtOAc, washed with water (6 times), dried over MgSO$_4$ and concentrated, to afford the title compound (900 mg, 82%) as a brown oil. $\delta_H$ (500 MHz, CDCl$_3$) 6.79 (tt, J 3.8, 1.6 Hz, 1H), 3.91 (s, 4H), 3.65 (s, 3H), 2.45 (tq, J 6.5, 2.3 Hz, 2H), 2.38-2.34 (m, 2H), 1.72 (t, J 6.6 Hz, 2H).

Intermediate 156

1,4-Dioxaspiro[4.5]dec-7-en-8-ylmethanol

To a 1.2M solution of DIBAL in toluene (10.64 mL) in DCM (10 mL) at −78° C. was added Intermediate 155 (1.1 g, 5.55 mmol) in DCM (10 mL) over 2 minutes. After 1.5 h, the reaction mixture was quenched with methanol (10 mL) and diluted with 10% w/v aqueous NaOH solution (30 mL). The resulting slurry was allowed to warm to room temperature, and after 30 minutes the layers were separated. The aqueous layer was washed with DCM (2×50 mL), and the combined organic phases were dried over sodium sulphate, then filtered and concentrated under vacuum, to afford the title compound (840 mg, 85%) as a yellow-orange oil, which was used without further purification. 5.44 (tt, J 3.5, 1.5 Hz, 1H), 4.65 (t, J 5.5 Hz, 1H), 3.87 (s, 4H), 3.78 (d, J 3.9 Hz, 2H), 2.15 (s, 2H), 2.06 (t, J 5.8 Hz, 2H), 1.65 (t, J 6.6 Hz, 2H).

Intermediate 157

Spiro[bicyclo[4.1.0]heptane-3,2'-[1,3]dioxolane]-6-ylmethanol

Diethylzinc in toluene (1.1M, 17.76 mL) was added to DCM (20 mL) under a stream of nitrogen at 0° C. Diiodomethane (1.57 mL, 19.54 mmol) in DCM (10 mL) was added and stirring was continued at 0° C. for 30 minutes. Intermediate 156 (95% pure, 1.75 g, 9.77 mmol) in DCM (20 mL) was added dropwise over 20 minutes, then the reaction mixture was warmed to room temperature and stirred for 2 h. DCM (50 mL) was added, together with 1N HCl (50 mL), and the layers were separated. The organic layers were washed with water (50 mL), saturated NaHCO$_3$ solution (50 mL) and brine (50 mL), then dried over sodium sulfate and concentrated, to afford the title compound (1.57 g, 79% yield at 90% purity) as a yellow oil, which was used without further purification. $\delta_H$ (500 MHz, DMSO-d$_6$) 4.40 (t, J 5.8 Hz, 1H), 3.84-3.73 (m, 4H), 3.24-3.18 (m, 1H), 3.11 (dd, J 10.9, 5.8 Hz, 1H), 1.92 (tdd, J 9.8, 4.9, 2.7 Hz, 2H), 1.74 (dt, J 13.5, 5.6 Hz, 1H), 1.59 (d, J 14.3 Hz, 1H), 1.41 (dtd, J 11.7, 5.8, 1.8 Hz, 1H), 1.30 (ddd, J 13.3, 10.0, 5.2 Hz, 1H), 0.82-0.76 (m, 1H), 0.48 (dd, J 9.0, 4.0 Hz, 1H), 0.29 (t, J 4.7 Hz, 1H).

Intermediate 158

Methyl 4-oxobicyclo[4.1.0]heptane-1-carboxylate

Intermediate 157 (90% pure, 1.57 g, 7.67 mmol) was suspended in water (100 mL), then KMnO$_4$ (4.61 g, 29.14 mmol) and 2M aqueous KOH solution (14.6 mL) were added. The mixture was heated under reflux for 2 h. The hot solution was filtered through celite and the solids were washed with water. The filtrate was acidified to pH 2 with 1N HCl, extracted into EtOAc (3×150 mL), dried over sodium sulfate and concentrated. The resulting orange oil (0.84 g) was dissolved in DCM (28 mL) and MeOH (12 mL) under a nitrogen atmosphere. (Diazomethyl)(trimethyl)silane in diethyl ether (2M, 4.22 mL) was added, and the reaction mixture was stirred at room temperature for 16 h. Acetic acid was added to the reaction mixture until the yellow colour disappeared, then the mixture was evaporated to dryness. The residue was dissolved in MeOH (50 mL) and concentrated HCl (4 mL) was added dropwise. The reaction mixture was stirred at 70° C. for 1.5 h before the solvent was removed under vacuum. The residue was partitioned between ethyl acetate (100 mL) and 2M aqueous KOH solution (100 mL). The organic layer was separated and washed with brine (2×50 mL), then dried over sodium sulfate and concentrated. The residue was purified by FCC, eluting with 0-100% EtOAc in heptane, to afford the title compound (423 mg, 31%) as a yellow oil. 3.61 (s, 3H), 2.71 (dd, J 18.1, 5.5 Hz, 1H), 2.50 (p, J 1.7 Hz, 1H), 2.42 (dd, J 18.1, 3.1 Hz, 1H), 2.24-2.10 (m, 2H), 2.01 (dt, J 14.0, 5.8 Hz, 1H), 1.68 (dtd, J 9.0, 5.8, 3.2 Hz, 1H), 1.31 (dd, J 9.2, 5.0 Hz, 1H), 1.15-1.10 (m, 1H).

Intermediate 159

Methyl 4-(trifluoromethanesulfonyloxy)bicyclo [4.1.0]heptene-1-carboxylate

Lithium hexamethyldisilazanide in THF/ethylbenzene (1M, 2.52 mL) was added dropwise to a stirred solution of Intermediate 158 (423 mg, 2.52 mmol) in THF (15 mL) at −78° C. Stirring was continued at this temperature for 1 h, then 1,1,1-trifluoro-N-phenyl-N-[(trifluoromethyl)sulfonyl] methanesulfonamide (943 mg, 2.64 mmol) in THF (5 mL) was added over 5 minutes and stirring was continued for another 30 minutes. The reaction mixture was allowed to warm to room temperature and was stirred for 16 h. The reaction mixture was quenched with saturated ammonium chloride solution (20 mL), the layers were separated and the aqueous layer was extracted with ethyl acetate (2×50 mL). The organic phase was sequentially washed with 0.5M aqueous NaOH solution (2×25 mL), saturated aqueous ammonium chloride solution (50 mL) and brine (50 mL), then dried over sodium sulphate, filtered and concentrated in vacuo, to afford the title compound (1.27 g, 100% yield at 60% purity) as an orange oil, which was used without further purification. $\delta_H$ (500 MHz, DMSO-d$_6$) 6.25 (dd, J 6.2, 2.0 Hz, 1H), 3.62 (s, 3H), 2.33-2.20 (m, 3H), 2.14 (ddd, J 13.5, 11.3, 7.1 Hz, 1H), 1.91 (dt, J 9.0, 5.9 Hz, 1H), 1.52 (dd, J 9.0, 4.5 Hz, 1H), 1.28-1.25 (m, 1H).

Intermediate 160

Methyl 4-(4,4,5,5-tetramethyl-1,3,2-dioxaborolan-2-yl)bicyclo[4.1.0]heptene-1-carboxylate (unknown regioisomer)

To a flask were added bis(pinacolato)diboron (0.71 g, 2.79 mmol), potassium acetate (0.75 g, 7.61 mmol), bis[3-(diphenylphosphanyl)cyclopenta-2,4-dien-1-yl]iron dichloropalladium (42 mg, 0.076 mmol) and 1,1'-bis(diphenylphosphanyl) ferrocene (56 mg, 0.076 mmol), and the contents were flushed with nitrogen. A solution of Intermediate 159 (60% pure, 1.27 g, 2.54 mmol) in 1,4-dioxane (20 mL) was added and the mixture was stirred at 80° C. for 16 h. The reaction mixture was cooled to room temperature and filtered through a pad of celite. The solids were washed with EtOAc and the filtrate was evaporated to dryness. The residue was purified by FCC, eluting with 0-50% EtOAc in heptane, to afford the title compound (270 mg, 38%) as a colourless oil. $\delta_H$ (500 MHz, DMSO-d$_6$) 6.74 (dd, J 5.5, 2.9 Hz, 1H), 3.60 (s, 3H), 2.19-2.11 (m, 1H), 2.09-2.01 (m, 1H), 1.85-1.62 (m, 3H), 1.40 (dd, J 9.2, 4.1 Hz, 1H), 1.37-1.32 (m, 1H), 1.18 (d, J 2.0 Hz, 12H).

Intermediate 161

Methyl 4-[5-(3-{[2-(difluoromethoxy)phenyl]methyl}-7-fluoro-2-methylimidazo[1,2-a]-pyridin-6-yl) pyrimidin-2-yl]bicyclo[4.1.0]heptane-1-carboxylate (unknown regioisomer)

A mixture of Intermediate 152 (97% pure, 315 mg, 0.73 mmol), Intermediate 160 (99% pure, 205 mg, 0.73 mmol) and 2M aqueous sodium carbonate solution (1.1 mL) in 1,4-dioxane (4.0 mL) was degassed with nitrogen for 5 minutes. Tetrakis(triphenylphosphine)palladium(0) (84 mg, 0.073 mmol) was added, then the reaction mixture was heated at 120° C. under microwave irradiation for 2 h. The reaction mixture was filtered through a pad of celite, then the solids were washed with EtOAc and the filtrate was evaporated to dryness. The residue was purified by FCC, eluting with 0-100% EtOAc in heptane. The resulting yellow oil was further purified by FCC, eluting with 80-100% EtOAc in heptane, to afford the title compound (155 mg, 38%) as a yellow-orange oil. $\delta_H$ (500 MHz, DMSO-d$_6$) 8.91 (dd, J 7.4, 1.4 Hz, 2H), 8.54 (d, J 7.4 Hz, 1H), 7.61 (dd, J 6.0, 2.7 Hz, 1H), 7.53 (d, J 11.4 Hz, 1H), 7.44-7.09 (m, 4H), 7.04 (d, J 6.6 Hz, 1H), 4.35 (s, 2H), 3.65 (d, J 2.6 Hz, 3H), 3.14-3.07 (m, 1H), 2.28 (s, 4H), 2.13-2.02 (m, 2H), 1.93 (td, J 13.2, 5.8 Hz, 1H), 1.57 (dd, J 9.2, 4.1 Hz, 1H), 1.49 (t, J 4.7 Hz, 1H). Method D HPLC-MS: MH+ m/z 535, RT 2.67 minutes.

Intermediate 162

Methyl 4-[5-(3-{[2-(difluoromethoxy)phenyl]methyl}-7-fluoro-2-methylimidazo[1,2-a]-pyridin-6-yl) pyrimidin-2-yl]bicyclo[4.1.0]heptane-1-carboxylate Intermediate 161 (95% pure, 26 mg, 0.05 mmol) was dissolved in ethanol (3 mL) and the reaction vessel was purged and evacuated thrice with nitrogen. Palladium on carbon (10%, 50% wet, 15 mg, 0.01 mmol) was added and the reaction vessel was purged and evacuated thrice with nitrogen gas, then purged and evacuated thrice with hydrogen gas. The reaction was stirred at room temperature under a hydrogen atmosphere for 3 days. The vessel was evacuated and purged with nitrogen gas. The mixture was filtered through a pad of Celite, then the solids were washed with MeOH (50 mL) and the filtrate was evaporated to dryness. The residue was purified by FCC, eluting with 0-100% MeOH in DCM, to afford the title compound (13 mg, 47%) as a yellow oil. Method D HPLC-MS: MH+ m/z 537, RT 2.54-2.55 minutes.

Intermediate 163

Methyl 6-[5-(3-{[2-(difluoromethoxy)phenyl]methyl}-2-methylimidazo[1,2-a]pyridin-6-yl)pyrimidin-2-yl]bicyclo[4.1.0]heptane-3-carboxylate A solution of trimethylsulfoxonium iodide (176 mg, 0.79 mmol) and potassium tert-butoxide (85 mg, 0.75 mmol) in DMSO (2 mL) was stirred at 50° C. for 45 minutes. A solution of methyl 4-[5-(3-{[2-(difluoromethoxy)phenyl]methyl}-2-methylimidazo[1,2-a]pyridin-6-yl)pyrimidin-2-yl]cyclohex-3-ene-1-carboxylate (prepared in an analogous manner to that described for Example 39, 100 mg, 0.2 mmol) in DMSO (2 mL) was added and the mixture was stirred at 50° C. for 4 h, then at room temperature for 3 days. The reaction mixture was diluted with DCM (10 mL) and washed with water (3×3 mL). The aqueous washes were combined and further extracted with DCM (2×3 mL). The organic extracts were combined, dried over sodium sulfate and evaporated. The resulting crude brown residue was diluted with DCM (3 mL) and washed with 1N aqueous NaOH solution (3×1 mL). The organic phase was dried over sodium sulfate and evaporated. The resulting pale brown residue was purified by preparative TLC, eluting with 1% MeOH in DCM, to afford the title compound (38.3 mg, 37%) as an off-white solid. Method B HPLC-MS: MH+ m/z 519, RT 1.80 minutes.

Intermediate 164

2-Bromo-5-(3-{[2-(difluoromethoxy)phenyl]methyl}-2-methylimidazo[1,2-a]pyridin-6-yl)pyrazine A mixture of Intermediate 31 (70% pure, 50 mg, 0.10 mmol), 2-bromo-5-iodopyrazine (60 mg, 0.21 mmol) and 2M aqueous sodium carbonate solution (0.32 mL) in DMSO (1 mL) was purged with nitrogen for 5 minutes. Tetrakis(triphenylphosphine)-palladium(0) (12 mg, 0.01 mmol) was added, then the reaction mixture was heated at 110° C. for 1 h. The reaction mixture was combined and partitioned between ethyl acetate (20 mL) and water (10 mL). The aqueous layer was separated and extracted with ethyl acetate (3×20 mL). The combined organic extracts were washed with brine (20 mL), dried over sodium sulphate, filtered and evaporated. The crude residue was purified by FCC, eluting with 25-100% ethyl acetate in heptane, then further purified by trituration with dichloromethane/heptane, to afford the title compound (214 mg, 44%) as an off-white solid. $\delta_H$ (500 MHz, CDCl$_3$) 8.68 (s, 1H), 8.65 (s, 1H), 8.57 (s, 1H), 7.75 (q, J 9.8 Hz, 2H), 7.28 (m, 1H), 7.17 (d, J 8.1 Hz, 1H), 7.09 (t, J 7.5 Hz, 1H), 6.96 (d, J 7.6 Hz, 1H), 6.67 (t, J 73.6 Hz, 1H), 4.35 (s, 2H), 2.55 (s, 3H). Method B HPLC-MS: MH+ m/z 535, RT 445/447 minutes.

Intermediate 165

Methyl 4-[5-(3-{[2-(difluoromethoxy)phenyl]methyl}-2-methylimidazo[1,2-a]pyridin-6-yl)pyrazin-2-yl]cyclohex-3-ene-1-carboxylate A mixture of Intermediate 164 (50 mg, 0.10 mmol), methyl 4-(4,4,5,5-tetramethyl-1,3,2-dioxaborolan-2-yl)cyclohex-3-ene-1-carboxylate (prepared in an analogous manner to Intermediate 56, 40 mg, 0.15 mmol) and 2M aqueous sodium carbonate solution (0.15 mL) in 1,4-dioxane (1 mL) was purged with nitrogen for 5 minutes. Tetrakis(triphenylphosphine)palladium(0) (6 mg, 0.005 mmol) was added and the reaction mixture was heated at 120° C. under microwave irradiation for 30 minutes. The reaction mixture was partitioned between ethyl acetate (20 mL) and water (10 mL). The aqueous layer was separated and extracted with ethyl acetate (3×20 mL). The combined organic extracts were washed with brine (20 mL), dried over sodium sulfate and evaporated. The resulting crude residue was purified by FCC, eluting with 25-100% ethyl acetate in heptane followed by 1-10% methanol in ethyl acetate, to afford the title compound (120 mg) as a pale yellow solid. $\delta_H$ (500 MHz, DMSO-d$_6$) 9.15 (d, J 1.2 Hz, 1H), 8.88 (s, 1H), 8.86 (d, J 1.2 Hz, 1H), 7.92 (dd, J 9.4, 1.6 Hz, 1H), 7.60 (d, J 9.4 Hz, 1H), 7.47-7.10 (m, 4H), 7.04 (d, J 7.6 Hz, 1H), 6.89 (s, 1H), 4.40 (s, 2H), 3.65 (s, 3H), 2.69 (dd, J 16.5, 3.2 Hz, 2H), 2.55 (s, 1H), 2.44 (dd, J 18.0, 9.3 Hz, 2H), 2.33 (s, 3H), 2.14-2.06 (m, 1H), 1.83-1.67 (m, 1H).

Intermediates 166 & 167

Methyl (1R*,4R*)-4-[5-(3-{[2-(difluoromethoxy)phenyl]methyl}-2-methylimidazo[1,2-a]pyridin-6-yl)pyrazin-2-yl]cyclohexane-1-carboxylate (trans isomer) and Methyl (1S*,4S*)-4-[5-(3-{[2-(difluoromethoxy)phenyl]methyl}-2-methylimidazo[1,2-a]pyridin-6-yl)pyrazin-2-yl]cyclohexane-1-carboxylate (cis isomer)

To a stirring solution of Intermediate 165 (200 mg, 0.40 mmol) in ethyl acetate (10 mL) and triethylamine (55 µL, 0.4 mmol), degassed and purged with nitrogen, was added palladium on carbon (10%, 42 mg, 0.04 mmol). The reaction mixture was degassed and purged with nitrogen, then stirred under a hydrogen balloon at room temperature until the reduction was complete. The reaction mixture was filtered through celite and the solids were washed with excess 1:1 ethyl acetate/methanol. The filtrate was evaporated. The resulting dark orange residue was purified by FCC, eluting with 50-100% ethyl acetate in heptane followed by 1-20% methanol in ethyl acetate. The material was then further purified to isomeric purity, using SFC (Cellulose-3 column; 10% MeOH/90% CO$_2$ eluent), to afford the title compounds as the trans isomer (25 mg, 12%) and the cis isomer (74 mg, 36%).

Intermediate 166 (trans isomer): $\delta_H$ (500 MHz, CDCl$_3$) 8.82 (s, 1H), 8.61 (s, 1H), 8.49 (s, 1H), 7.98 (m, 2H), 7.29 (m, 1H), 7.18 (d, J 8.1 Hz, 1H), 7.12 (t, J 7.4 Hz, 1H), 6.98 (d, J 7.5 Hz, 1H), 6.68 (t, J 73.4 Hz, 1H), 4.35 (s, 2H), 3.71 (s, 3H), 2.82 (d, J 8.2 Hz, 1H), 2.42 (t, J 9.8 Hz, 1H), 2.18 (d, J 10.5 Hz, 2H), 2.06 (d, J 10.4 Hz, 2H), 1.65 (q, J 12.2 Hz, 4H). Method B HPLC-MS: MH+ m/z 507, RT 1.73 minutes.

Intermediate 167 (cis isomer): $\delta_H$ (500 MHz, CDCl$_3$) 8.79 (d, J 1.4 Hz, 1H), 8.53 (s, 1H), 8.48 (d, J 1.3 Hz, 1H), 7.91-7.79 (m, 2H), 7.28 (d, J 1.4 Hz, 1H), 7.18 (d, J 7.9 Hz, 1H), 7.09 (t, J 7.5 Hz, 1H), 6.94 (d, J 7.6 Hz, 1H), 6.68 (t, J 73.5 Hz, 1H), 4.35 (s, 2H), 3.72 (s, 3H), 2.93-2.85 (m, 1H), 2.74 (d, J 4.3 Hz, 1H), 2.54 (s, 3H), 2.28-2.22 (m, 2H), 1.87

(td, J 9.9, 8.8, 4.2 Hz, 4H), 1.71 (td, J 15.2, 14.4, 5.1 Hz, 2H). Method B HPLC-MS: MH+ m/z 507, RT 1.74 minutes.

Intermediate 168

Methyl 3-(trifluoromethanesulfonyloxy)cyclopentene-1-carboxylate

Methyl 3-oxocyclopentane-1-carboxylate (1.5 g, 10.55 mmol) was dissolved in anhydrous toluene (30 mL) under nitrogen, DIPEA (2.76 mL, 15.83 mmol) was added and the mixture was warmed to 45° C. Trifluoromethanesulfonic anhydride (2.66 mL, 15.83 mmol) was added dropwise and the reaction mixture was stirred at 45° C. for a further 20 minutes. The reaction mixture was treated with additional DIPEA (3 mL) and trifluoromethanesulfonic anhydride (2.5 mL), then stirred at 45° C. for a further 20 minutes. The reaction mixture was diluted with ethyl acetate (150 mL), and washed with saturated aqueous sodium bicarbonate solution (60 mL), saturated aqueous ammonium chloride solution (60 mL) and brine (40 mL), then dried over sodium sulfate and concentrated under vacuum. The resulting dark brown oil was purified by chromatography (Biotage 100 g SNAP cartridge), eluting with constant gradient EtOAc:heptane 0:1 to 1:9, to afford the title compound (2.89 g, 38%) as a mixture of double bond isomers (~1:1 ratio) as a light brown oil. $\delta_H$ (500 MHz, CDCl$_3$) 5.71 (q, J 2.1 Hz, 0.5H), 5.59 (p, J 2.3 Hz, 0.5H), 3.73 (d, J 5.7 Hz, 3H), 3.62 (ddq, J 8.7, 5.6, 2.6 Hz, 0.5H), 3.33-3.24 (m, 0.5H), 3.02-2.94 (m, 0.5H), 2.87-2.67 (m, 2H), 2.62 (dddd, J 14.1, 9.0, 4.1, 2.1 Hz, 0.5H), 2.38-2.26 (m, 1H).

Intermediate 169

Methyl 3-(4,4,5,5-tetramethyl-1,3,2-dioxaborolan-2-yl)cyclopentene-1-carboxylate A mixture of 4,4,5,5-tetramethyl-2-(4,4,5,5-tetramethyl-1,3,2-dioxaborolan-2-yl)-1,3,2-dioxaborolane (833 mg, 3.28 mmol), Intermediate 168 (1.20 g, 4.38 mmol), potassium acetate (0.43 g, 4.38 mmol), 1,1'-bis(diphenylphosphanyl)ferrocene (24 mg, 0.04 mmol) and 1,4-dioxane (12 mL) was degassed for 30 minutes. Pd(dppf)Cl$_2$ complex with dichloromethane (36 mg, 0.04 mmol) was added and the reaction mixture was sealed under nitrogen, then stirred at 90° C. for 18 h. The reaction mixture was allowed to cool to room temperature and diluted with ethyl acetate (100 mL). The organic layers were washed with water (20 mL), saturated aqueous sodium bicarbonate solution (20 mL) and brine (20 mL), then dried over sodium sulphate, filtered and concentrated under vacuum. The residue was purified by chromatography (Biotage SNAP 100 g cartridge), eluting with heptane:ethyl acetate 1:0 to 1:1, to afford the title compound (223 mg, 40%) as a mixture of double bond isomers (~1:1 ratio) as a light brown oil. $\delta_H$ (500 MHz, CDCl$_3$) 6.44 (tt, J 5.3, 2.7 Hz, 1H), 3.78-3.59 (m, 3.5H), 3.23-3.07 (m, 0.5H), 2.87-2.68 (m, 2H), 2.68-2.42 (m, 1H), 2.22-2.11 (m, 1H), 1.29 (d, J 3.5 Hz, 12H).

Intermediate 170

Methyl 3-[5-(3-{[2-(difluoromethoxy)phenyl]methyl}-2-methylimidazo[1,2-a]pyridin-6-yl)pyrimidin-2-yl]cyclopentene-1-carboxylate Intermediate 29 (90%, 262 mg, 0.59 mmol) and Intermediate 169 (178 mg, 0.71 mmol) were charged to a sealed tube with 2M aqueous potassium carbonate solution (1.18 mL) and 1,4-dioxane (5 mL). The mixture was degassed for 30 minutes. Tetrakis-(triphenylphosphine)palladium(0) (34 mg, 0.03 mmol) was added and the reaction mixture was sealed under nitrogen. The reaction mixture was stirred at 90° C. for 18 h. Additional Intermediate 168 (50 mg) was added, then the reaction mixture was degassed for 20 minutes and stirred at 90° C. for 4 h. The reaction mixture was diluted with ethyl acetate (80 mL), and washed with water (15 mL), saturated sodium bicarbonate solution (15 mL) and brine (15 mL), then dried over sodium sulfate, filtered and concentrated under vacuum. The residue was purified by flash chromatography (eluting with heptane:ethyl acetate 3:7 to 0:1) to afford the title compound (160 mg, 53%) as a mixture of double bond isomers (~1:1 ratio) as a brown solid. $\delta_H$ (500 MHz, CDCl$_3$) 8.75 (d, J 9.4 Hz, 2H), 7.91 (s, 1H), 7.66 (d, J 9.3 Hz, 1H), 7.31 (dd, J 9.3, 1.6 Hz, 1H), 7.29-7.22 (m, 1H), 7.16 (d, J 8.0 Hz, 1H), 7.08 (t, J 7.5 Hz, 1H), 6.94 (dq, J 18.6, 2.3 Hz, 1H), 6.91-6.46 (m, 2H), 4.31 (s, 2H), 3.84 (ddd, J 11.5, 5.8, 2.5 Hz, 0.54H), 3.72 (d, J 1.6 Hz, 3H), 3.40-3.30 (m, 0.44H), 3.20 (dd, J 5.4, 2.7 Hz, 1H), 3.10-2.83 (m, 2H), 2.53 (s, 3H), 2.46-2.32 (m, 1H).

Intermediate 171

Methyl 3-[5-(3-{[2-(difluoromethoxy)phenyl]methyl}-2-methylimidazo[1,2-a]pyridin-6-yl)pyrimidin-2-yl]cyclopentane-1-carboxylate Intermediate 170 (96%, 160 mg, 0.31 mmol) was dissolved in ethanol (3 mL) and the solution was degassed with nitrogen. The mixture was added to palladium on carbon (10%, 35 mg, 0.03 mmol), then degassed with nitrogen and allowed to stir under a hydrogen balloon at room temperature for 3 h. The reaction mixture was filtered through celite which was washed with ethanol (150 mL). The filtrate was concentrated under vacuum. The residue was purified by flash chromatography (0-6% methanol in DCM) to afford the title compound (43 mg, 27%) as a red oil. $\delta_H$ (500 MHz, CDCl$_3$) 8.66 (s, 2H), 7.84 (s, 1H), 7.64 (d, J 9.2 Hz, 1H), 7.27 (dd, J 9.2, 1.7 Hz, 1H), 7.22-7.17 (m, 1H), 7.10 (d, J 8.0 Hz, 1H), 7.02 (t, J 7.5 Hz, 1H), 6.82 (d, J 7.6 Hz, 1H), 6.57 (t, J 73.6 Hz, 1H), 4.26 (s, 2H), 3.62 (s, 3H), 3.41 (td, J 8.1, 2.5 Hz, 1H), 2.94-2.86 (m, 1H), 2.48 (s, 3H), 2.42-2.35 (m, 1H), 2.25-2.17 (m, 1H), 2.13-1.94 (m, 4H). Method B HPLC-MS: MH+ m/z 493, RT 1.72 minutes.

Intermediate 172

2-Methyl-4-oxocyclohexane-1-carboxylate

Ethyl 2-methyl-4-oxocyclohex-2-ene-1-carboxylate (5 g, 27.44 mmol) was dissolved in ethanol (50 mL) and palladium on carbon (10%, 1.46 g, 1.37 mmol) was added. The suspension was degassed using vacuum/N$_2$/H$_2$ and the reaction mixture was stirred under H$_2$ at room temperature and atmospheric pressure for 18 h. The mixture was filtered through celite, concentrated and purified by column chromatography (eluting with 10-50% ethyl acetate in heptane), to afford the title compound (4.19 g, 80%) as a 93:7 cis:trans isomer mixture as a colourless liquid. $\delta_H$ (500 MHz, CDCl$_3$) 4.18 (qd, J 7.1, 4.4 Hz, 2H), 2.84 (dt, J 8.4, 4.2 Hz, 1H), 2.60-2.48 (m, 2H), 2.49-2.42 (m, 2H), 2.31 (ddd, J 14.6, 8.5, 6.2 Hz, 1H), 2.22-2.10 (m, 2H), 2.10-2.00 (m, 1H), 1.28 (t, J 7.1 Hz, 3H), 0.98 (d, J 6.8 Hz, 3H).

Intermediate 173

Ethyl 6-methyl-4-(trifluoromethanesulfonyloxy)cyclohexene-1-carboxylate

Intermediate 172 (3.2 g, 17.37 mmol) and DIPEA (12.1 ml, 69.48 mmol) were dissolved in toluene (5 mL) and heated at 45° C. for 10 minutes. Trifluoromethanesulfonic anhydride in dichloromethane (1M, 70 mL) was added dropwise over 10 minutes and the mixture was heated for 2 h. The mixture was allowed to cool to room temperature, concentrated, diluted with water (150 mL) and extracted with ethyl acetate (2×100 mL). The organic layer was washed with saturated sodium bicarbonate solution (50 mL) and brine (50 mL), then dried over magnesium sulphate, filtered and concentrated. The resulting dark brown solid was purified by column chromatography, eluting with 20-50% ethyl acetate in heptane, to afford the title compound (4.8 g, 74%) as a mixture of double bond isomers (1.2:1) as a light reddish oil. $\delta_H$ (250 MHz, CDCl$_3$) 5.75 (d, J 5.4 Hz, 1H), 4.17 (qd, J 7.2, 2.2 Hz, 2H), 2.89-2.55 (m, 2H), 2.55-2.25 (m, 2H), 2.23-1.81 (m, 1H), 1.27 (m, 4H), 0.98 (dd, 3H). Method B HPLC-MS: MH+ m/z 317, RT 2.44 minutes.

Intermediate 174

Ethyl 6-methyl-4-(4,4,5,5-tetramethyl-1,3,2-dioxaborolan-2-yl)cyclohexene-1-carboxylate Intermediate 173 (85%, 2 g, 5.37 mmol), 4,4,5,5-tetramethyl-2-(4,4,5,5-tetramethyl-1,3,2-dioxaborolan-2-yl)-1,3,2-dioxaborolane (2.05 g, 8.06 mmol) and potassium acetate (1.58 g, 16.12 mmol) were suspended in 1,4-dioxane (20 mL). The reaction mixture was degassed for 10 minutes, then 1,1'-bis(diphenylphosphanyl)-ferrocene (89 mg, 0.16 mmol) was added, followed by Pd(dppf)Cl$_2$ complex with dichloromethane (132 mg, 0.16 mmol). The mixture was heated at 90° C. for 5 h. The mixture was cooled to room temperature, diluted with water (200 mL) and extracted with ethyl acetate (2×200 mL). The combined organic layers were washed with brine (100 mL), dried over magnesium sulphate, filtered and concentrated. The resulting brown oil was purified by chromatography on Biotage, eluting with 10-50% ethyl acetate in heptane, to afford the title compound (9:1 cis:trans ratio, 1.2:1 mixture of double bond isomers) (725 mg, 46%) as a pale yellow oil. $\delta_H$ (250 MHz, CDCl$_3$) 6.59-6.35 (m, 1H), 4.25-3.95 (m, 2H), 2.73-2.54 (m, 1H), 2.46-2.19 (m, 3H), 2.12-1.99 (m, 1H), 1.90-1.56 (m, 1H), 1.26 (d, J 2.9 Hz, 15H), 0.90 (dd, J 23.8, 7.0 Hz, 3H). Method B HPLC-MS: MH+ m/z 295, RT 2.48 minutes.

Intermediate 175

Ethyl 4-[5-(3-{[2-(difluoromethoxy)phenyl]methyl}-7-fluoro-2-methylimidazo[1,2-a]-pyridin-6-yl)pyrimidin-2-yl]-2-methylcyclohexene-1-carboxylate A mixture of Intermediate 152 (95%, 600 mg, 1.36 mmol), Intermediate 174 (506 mg, 1.63 mmol) and 2M aqueous sodium carbonate solution (2.04 mL) in 1,4-dioxane (6 mL) was degassed with nitrogen for 5 minutes, then tetrakis(triphenylphosphine)-palladium(0) (79 mg, 0.07 mmol) was added and the mixture was heated at 120° C. for 1 h under microwaveirradiation. The reaction mixture were diluted with ethyl acetate (150 mL), then washed with water (25 mL) and brine (25 mL). The organic layer was dried over magnesium sulfate, filtered and concentrated. The resulting crude material was purified twice by column chromatography, eluting with 70-100% ethyl acetate in heptane, to afford the title compound (541 mg, 72%) as a mixture of double bond isomers (1:1) as a light pink sticky oil. $\delta_H$ (500 MHz, CDCl$_3$) 8.78-8.57 (m, 2H), 7.80 (d, J 6.7 Hz, 1H), 7.55-7.39 (m, 1H), 7.38-7.27 (m, 2H), 7.17 (d, J 8.1 Hz, 1H), 7.12 (t, J 7.5 Hz, 1H), 6.92 (d, J 7.4 Hz, 1H), 6.62 (t, J 73.6 Hz, 1H), 4.29 (s, 2H), 4.24-4.15 (m, 2H), 4.12 (q, J 7.1 Hz, 1H), 3.01-2.84 (m, 1H), 2.81-2.71 (m, 1H), 2.70-2.61 (m, 1H), 2.54 (s, 3H), 2.12-2.05 (m, 1H), 1.95-1.81 (m, 1H), 1.31-1.27 (m, 3H), 1.03 (dd, J 36.2, 7.0 Hz, 3H). Method A HPLC-MS: MH+ m/z 551, RT 5.39 minutes.

Intermediate 176

Methyl 4-[5-(3-{[2-(difluoromethoxy)phenyl]methyl}-2,7-dimethylimidazo[1,2-a]-pyridin-6-yl)pyrimidin-2-yl]cyclohex-3-ene-1-carboxylate Intermediate 47 (50 mg, 0.12 mmol), methyl 4-(4,4,5,5-tetramethyl-1,3,2-dioxaborolan-2-yl)cyclohex-3-ene-1-carboxylate (38 mg, 0.15 mmol) and 2M aqueous potassium carbonate solution (0.19 mL) were added to 1,4-dioxane (1 mL) in a microwave tube, and the mixture was degassed for 10 minutes. Bedford's catalyst (13 mg, 0.01 mmol) was added and reaction mixture was heated under microwave irradiation for 30 minutes at 120° C. The reaction mixture was further heated at 150° C. for 30 minutes under microwave irradiation. Water (5 mL) was added, and the reaction mixture was extracted with ethyl acetate (50 mL). The organic phase was washed with brine (30 mL), dried with sodium sulphate, filtered and concentrated under vacuum. The resulting black oil was purified by chromatography on a Biotage, using 10 g SNAP cartridge (eluent 80% ethyl acetate in heptane to 100% EtOAc), to afford the title compound (110 mg, 41%) as a black oil. Method B HPLC-MS: MH+ m/z 519, RT 1.68 minutes.

Intermediate 177

Methyl 4-[5-(3-{[2-(difluoromethoxy)phenyl]methyl}-2,7-dimethylimidazo[1,2-a]-pyridin-6-yl)pyrimidin-2-yl]cyclohexane-1-carboxylate Intermediate 176 (76%, 110 mg, 0.16 mmol) and triethylamine (0.03 mL, 0.22 mmol) were dissolved in ethyl acetate (3 mL) and degassed with nitrogen. Palladium (10% on carbon, 18 mg, 0.02 mmol) was added and the reaction mixture was purged with nitrogen (3 times) before replacing nitrogen by hydrogen gas. The reaction mixture was stirred under hydrogen for 3 h at room temperature. The reaction mixture was filtered through celite, washed with ethyl acetate (15 mL) and concentrated to ~3 mL under vacuum. Additional triethylamine (30 µL) and fresh palladium on carbon (10%, 17.67 mg, 0.02 mmol) were added, and the reaction mixture was stirred at room temperature overnight under hydrogen. The reaction mixture was filtered through celite and washed with ethyl acetate (2 mL). The organic filtrate was washed with water (20 mL) and brine (20 mL), then dried with sodium sulphate, filtered and concentrated under vacuum. The resulting orange oil was purified, using the Biotage system on a 10 g SNAP cartridge (eluent: 25 to 100% EtOAc in heptane), to afford the title compound (45 mg, 53%) as a clear oil (69:31 mixture of cis and trans isomers). Method B HPLC-MS: MH+ m/z 521, RT 1.75 minutes.

Intermediate 178

Methyl 2-[4-(trifluoromethanesulfonyloxy)cyclohex-3-en-1-yl]acetate

Methyl (4-oxocyclohexyl)acetate (900 mg, 5.29 mmol) was dissolved in anhydrous toluene (2 mL) under nitrogen, DIPEA (2.7 mL 15.5 mmol) was added and the mixture was warmed to 45° C. Trifluoromethanesulfonic anhydride (2.7 mL, 16.05 mmol) was added dropwise and the reaction mixture was stirred at 45° C. for 1 h. The reaction mixture was diluted with EtOAc (15 mL), and washed with saturated aqueous sodium bicarbonate solution (10 mL), saturated aqueous ammonium chloride solution (10 mL) and brine (10 mL), then dried over sodium sulfate and concentrated under vacuum. The residue was purified by column chromatography on silica (0-25% ethyl acetate in heptane) to afford the title compound (682 mg, 48%) as a viscous clear yellow liquid. $\delta_H$ (500 MHz, CDCl$_3$) 5.76-5.66 (m, 1H), 3.68 (s, 3H), 2.48-2.25 (m, 5H), 2.22-2.04 (m, 1H), 1.92 (dtd, J 14.4, 6.1, 3.3 Hz, 2H), 1.59-1.43 (m, 1H).

Intermediate 179

Methyl 2-[4-(4,4,5,5-tetramethyl-1,3,2-dioxaborolan-2-yl)cyclohex-3-en-1-yl]acetate Intermediate 178 (680 mg, 2.25 mmol), 4,4,4',4',5,5,5',5'-octamethyl-2,2'-bi-1,3,2-dioxaborolane (855 mg, 3.37 mmol), potassium acetate (660 mg, 6.72 mmol) and 1,1'-bis(diphenylphosphanyl)ferrocene (65 mg, 0.12 mmol) were charged in a tube with anhydrous 1,4-dioxane (5 mL). The mixture was degassed by bubbling nitrogen for 30 minutes. Pd(dppf)Cl$_2$ complex with dichloromethane (90 mg, 0.11 mmol) was added and the mixture was sealed under nitrogen. The reaction mixture was stirred at 90° C. for 18 h. The reaction mixture was allowed to cool to room temperature, then diluted with ethyl acetate (50 mL) and water (10 mL). The aqueous phase was separated and the organic phase was washed with saturated aqueous sodium bicarbonate solution (10 mL) and brine (10 mL), then dried over sodium sulphate, filtered and concentrated under vacuum. The crude residue was purified by column chromatography on silica (0 to 100% DCM in heptane, followed by 0 to 2% methanol in DCM), to afford the title compound (259 mg, 29%) as a viscous light brown liquid. 6.46 (s, 1H), 3.65-3.58 (m, 3H), 2.26-2.12 (m, 4H), 2.11-1.96 (m, 2H), 1.81-1.65 (m, 2H), 1.38-1.24 (m, 1H), 1.25-1.14 (m, 12H).

Intermediate 180

Methyl 2-{4-[5-(3-{[2-(difluoromethoxy)phenyl]methyl}-7-fluoro-2-methylimidazo[1,2-a]pyridin-6-yl)pyrimidin-2-yl]cyclohexyl}acetate Intermediate 152 (250 mg, 0.6 mmol) and Intermediate 179 (66%, 253 mg, 0.6 mmol) were dissolved in 1,4-dioxane (40 mL) and 2M aqueous sodium carbonate solution (0.90 mL) was added. The resulting mixture was degassed with nitrogen for 5 minutes, then tetrakis(triphenylphosphine)palladium(0) (70 mg, 0.06 mmol) was added and the reaction mixture was heated at 120° C. for 2 h under microwave irradiation. Additional tetrakis(triphenylphosphine)palladium(0) (35 mg, 0.03 mmol) was added and the reaction mixture was heated at 120° C. for a further 1 h under microwave irradiation. The mixture was diluted with ethyl acetate (15 mL), then washed with saturated sodium bicarbonate solution (10 mL), water (2×10 mL) and brine (10 mL). The organic layer was dried over sodium sulphate, filtered and concentrated under vacuum. The resulting bright yellow solid was purified by column chromatography on silica (0 to 10% methanol in DCM) to afford a yellow solid (300 mg), which was dissolved in ethyl acetate (3 mL). Triethylamine (60 μL, 0.43 mmol) was added and the mixture was degassed with nitrogen. Palladium on carbon (10%, 40 mg, 0.04 mmol) was added. The mixture was degassed with nitrogen and allowed to stir under a hydrogen balloon at room temperature for 17 h. The reaction mixture was filtered over a celite pad which was washed with ethyl acetate (200 mL). The filtrate was concentrated under vacuum, and the crude residue was purified by preparative HPLC (Method C), to afford the title compound (81 mg, 45%) as a yellow oil. $\delta_H$ (500 MHz, CD$_3$OD) 8.80 (d, J 9.2 Hz, 2H), 8.30 (t, J 6.7 Hz, 1H), 7.32 (d, J 10.8 Hz, 1H), 7.27 (t, J 7.7 Hz, 1H), 7.17 (d, J 8.2 Hz, 1H), 7.14-7.07 (m, 2H), 6.89 (td, J 74.0, 1.2 Hz, 1H), 4.37 (s, 2H), 3.65 (d, J 7.9 Hz, 3H), 3.06-2.79 (m, 1H), 2.39 (s, 3H), 2.36 (d, J 7.5 Hz, 1H), 2.26 (d, J 6.7 Hz, 1H), 2.19-1.61 (m, 7H), 1.58-1.48 (m, 1H), 1.17 (q, J 12.7 Hz, 1H).

Intermediate 181

Methyl 3-[5-(3-{[2-(difluoromethoxy)phenyl]methyl}-7-fluoro-2-methylimidazo[1,2-a]-pyridin-6-yl)pyrimidin-2-yl]cyclopentane-1-carboxylate Intermediate 152 (200 mg, 0.48 mmol) and Intermediate 169 (150 mg, 0.59 mmol) were dissolved in 1,4-dioxane (2 mL) and 2M aqueous sodium carbonate solution (0.75 mL) was added. The resulting mixture was degassed with nitrogen for 5 minutes, then tetrakis(triphenylphosphine)palladium(0) (55 mg, 0.05 mmol) was added and the reaction mixture was heated at 120° C. for 2 h under microwave irradiation. The reaction mixture was diluted with dichloromethane (15 mL), then washed with saturated sodium bicarbonate solution (10 mL), water (2×10 mL) and brine (10 mL). The organic layer was dried over sodium sulphate, filtered and concentrated under vacuum. The resulting dark oil was purified by column chromatography (0-10% methanol in dichloromethane). The resulting material (150 mg) and triethylamine (0.05 mL, 0.36 mmol) were dissolved in ethanol (3 mL) and the reaction mixture was degassed with nitrogen. The mixture was added to palladium on carbon (10%, 35 mg, 0.03 mmol) and the mixture was degassed with nitrogen, then allowed to stir under a hydrogen balloon at room temperature for 18 h. The reaction mixture was filtered through celite which was washed with ethanol (200 mL). The filtrate was concentrated under vacuum, and the resulting crude residue was purified by preparative HPLC (Method C), to afford the title compound (84 mg, 57%) as a red oil. $\delta_H$ (500 MHz, CD$_3$OD) 8.79 (s, 2H), 8.29 (d, J 7.1 Hz, 1H), 7.32 (d, J 10.8 Hz, 1H), 7.25 (d, J 7.5 Hz, 1H), 7.16 (d, J 8.1 Hz, 1H), 7.13-7.07 (m, 2H), 6.89 (t, J 74.0 Hz, 1H), 4.37 (s, 2H), 3.66 (s, 3H), 3.46 (dd, J 10.9, 5.7 Hz, 1H), 3.03-2.94 (m, 1H), 2.38 (s, 4H), 2.28-2.17 (m, 1H), 2.17-2.00 (m, 4H).

Intermediate 182

Methyl 5-oxobicyclo[2.2.2]octane-2-carboxylate

To a cooled solution of diisopropylamine (7.72 mL, 54.62 mmol) in ether (40 mL) at −78° C. was added 2.5M n-butyllithium (21.8 mL) dropwise. The reaction mixture was allowed to warm to −11° C. A solution of cyclohex-2-en-1-one (5.04 mL, 52.01 mmol) in diethyl ether (60 mL) was added over 45 minutes. During the addition, the temperature was maintained between −11° C. and −3° C. The mixture was stirred for an additional 25 minutes before a solution of methyl prop-2-enoate (4.68 mL, 52.01 mmol) in THF (40 mL) was added dropwise over 60 minutes. The reaction mixture was stirred at this temperature for 1 h and stored in a freezer overnight. The reaction mixture was poured into saturated ammonium chloride solution (200 mL) and stirred for 15 minutes. A brown sticky polymer was formed and removed using tweezers. The organic layer was separated and the aqueous layer was extracted with tert-butyl methyl ether (2×300 mL). The combined organic layers were dried over sodium sulfate and concentrated. The crude residue was purified by column chromatography (Biotage; 0-60% ethyl acetate in heptane) in 2 batches, to afford the title compound (2.98 g, 31%) as the trans isomer as a clear colourless liquid. $\delta_H$ (500 MHz, CDCl$_3$) 3.70 (s, 3H), 2.76 (ddt, J 10.6, 6.4, 1.8 Hz, 1H), 2.53-2.48 (m, 1H), 2.47-2.38 (m, 1H), 2.37-2.31 (m, 1H), 2.22 (ddt, J 14.2, 6.3, 2.5 Hz, 1H), 2.13 (ddd, J 19.1, 2.9, 1.8 Hz, 1H), 2.02 (ddd, J 14.3, 11.0, 3.5 Hz, 1H), 1.89-1.74 (m, 3H), 1.70-1.60 (m, 1H).

Intermediate 183

Methyl 5-(trifluoromethanesulfonyloxy)bicyclo
[2.2.2]oct-5-ene-2-carboxylate

Intermediate 182 (1 g, 5.49 mmol) was dissolved in toluene (10 mL), DIPEA (3.82 mL, 21.95 mmol) was added and the mixture was heated at 45° C. Trifluoromethanesulfonic anhydride (3.69 mL, 21.95 mmol) was added dropwise and the reaction mixture was stirred for 2 h at 45° C. The reaction mixture was allowed to cool and diluted with ethyl acetate (50 mL), then aqueous sodium bicarbonate solution (70 mL) was added. The phases were separated and the aqueous phase was extracted with ethyl acetate (2×30 mL). The organic extracts were washed with saturated aqueous ammonium chloride solution (20 mL), dried over sodium sulphate, filtered and concentrated. The crude residue was purified by chromatography (Biotage; 0-30% ethyl acetate in heptane) to afford the title compound (2.33 g, quantitative) as the trans isomer as a yellow liquid. $\delta_H$ (500 MHz, CDCl$_3$) 5.98 (dd, J 7.4, 2.5 Hz, 1H), 3.65 (s, 3H), 3.23-3.17 (m, 1H), 2.79 (q, J 2.7 Hz, 1H), 2.66 (ddd, J 10.0, 5.2, 2.3 Hz, 1H), 2.03-1.95 (m, 1H), 1.88 (ddd, J 12.9, 10.0, 2.7 Hz, 1H), 1.66-1.52 (m, 3H), 1.46-1.34 (m, 1H).

Intermediate 184

Methyl 5-[5-(3-{[2-(difluoromethoxy)phenyl]methyl}-7-fluoro-2-methylimidazo[1,2-a]-pyridin-6-yl) pyrimidin-2-yl]bicyclo[2.2.2]octane-2-carboxylate Intermediate 183 (1 g, 3.18 mmol) was dissolved in dry 1,4-dioxane (10 mL) and the mixture was degassed for 5 minutes with nitrogen. Bis(pinacolato)diboron (1.21 g, 4.77 mmol), potassium acetate (1 g, 10.19 mmol), 1,1'-bis(diphenylphosphanyl)ferrocene (90 mg, 0.16 mmol) and Pd(dppf)Cl$_2$ complex with dichloromethane (130 mg, 0.16 mmol) were added. The mixture was heated at 90° C. and stirred for 2 h. The reaction mixture was diluted with ethyl acetate (50 mL) and saturated aqueous sodium bicarbonate solution (50 mL) was added. The phases were separated. The aqueous phase was washed with ethyl acetate (50 mL), then the organic extracts were washed with brine (50 mL), dried over sodium sulphate, filtered and concentrated. The crude product was purified twice by column chromatography (Biotage, 0-30% ethyl acetate in heptane; then Biotage, 0-100% dichloromethane in heptane). The material thus obtained was added to Intermediate 152 (240 mg, 0.57 mmol) in a microwave vial. Dry 1,4-dioxane (3 mL) and 2M aqueous sodium carbonate solution (900 µL) were added. The mixture was degassed with nitrogen for 2 minutes. Tetrakis(triphenylphosphine) palladium(0) (66 mg, 0.06 mmol) was added and the reaction mixture was heated for 45 minutes under microwave irradiation at 120° C. The reaction mixture was quenched with water (20 mL) and extracted with ethyl acetate (2×25 mL), then dried over sodium sulphate, filtered and concentrated. The crude residue was purified by chromatography (0-3% methanol in dichloromethane). The residue (204 mg) was filtered through charcoal, eluting with ethyl acetate. The resulting solution was concentrated and re-dissolved in ethyl acetate (5 mL). Triethylamine (51.32 µL, 0.37 mmol) and palladium on carbon (10%, 50 mg, 0.05 mmol) were added. The mixture was flushed with nitrogen (3 times) and hydrogen (3 times). The mixture was stirred under hydrogen for 20 h. The reaction mixture was filtered through celite and concentrated. The crude residue was purified by column chromatography (0-2% methanol in dichloromethane), to afford the title compound (139 mg, 75%) as a pink oil. Method B HPLC-MS: MH+ m/z 551, RT 1.80 minutes.

Intermediates 185 to 189 [Removed]

Intermediate 190

Ethyl (1S,5S,6R)-3-[5-(3-{[2-(difluoromethoxy)
phenyl]methyl}-7-fluoro-2-methylimidazo[1,2-a]
pyridin-6-yl)pyrimidin-2-yl]bicyclo[3.1.0]hex-2-ene-
6-carboxylate Intermediate 152 (190 mg, 0.45 mmol) and Intermediate 134 (75%, 185 mg, 0.5 mmol) were dissolved in 1,4-dioxane (3 mL). Aqueous potassium carbonate solution (2M, 0.7 mL) was added and the reaction mixture was degassed for 5 minutes using nitrogen. Tetrakis(triphenylphosphine)palladium (0) (52 mg, 0.05 mmol) was added and the mixture was heated under microwave irradiation for 2.5 h at 120° C. The phases were separated and the aqueous phase was extracted with ethyl acetate (2×3 mL). The organic extracts were combined, dried over sodium sulphate, filtered and concentrated. The resulting crude residue was purified by preparative HPLC (Method C), to afford the title compound (120 mg, 45%) as a pink oily solid. Method D HPLC-MS: MH+ m/z 536, RT 2.65 minutes.

Intermediate 191

Ethyl 4-[5-(3-{[2-(difluoromethoxy)phenyl]methyl}-
7-fluoro-2-methylimidazo[1,2-a]-pyridin-6-yl)pyri-
midin-2-yl]-1-methylcyclohex-3-ene-1-carboxylate Intermediate 68 (1.0 g, 2.60 mmol) and Intermediate 221 (1.16 g, 3.12 mmol) were dissolved in 1,4-dioxane (20 mL). Aqueous sodium carbonate solution (2M, 4 mL) was added and the mixture was degassed with nitrogen for 15 minutes, then bis[3-(diphenylphosphanyl)cyclopenta-2,4-dien-1-yl] iron dichloropalladium dichloromethane complex (110 mg, 0.13 mmol) was added and the reaction mixture was heated at 100° C. under nitrogen for 4.5 h. The reaction mixture was diluted with water (30 mL) and extracted with ethyl acetate (30 mL). The organic layer was washed with brine (20 mL), dried over sodium sulphate, filtered and concentrated to dryness. The resulting residue was purified by flash chromatography (50 g KP-silica cartridge, eluting with 60 to 100% ethyl acetate in heptane) to afford the title compound (820 mg, 57%) as a beige solid. $\delta_H$ (500 MHz, CDCl$_3$) 8.70 (d, J 1.4 Hz, 2H), 7.76 (d, J 7.0 Hz, 1H), 7.40-7.32 (m, 2H), 7.30-7.27 (m, 1H), 7.16 (d, J 7.9 Hz, 1H), 7.13-7.06 (m, 1H), 6.96-6.84 (m, 1H), 6.61 (t, J 73.5 Hz, 1H), 4.29 (s, 2H), 4.21-4.06 (m, 2H), 2.93-2.83 (m, 1H), 2.73-2.61 (m, 2H), 2.51 (s, 3H), 2.28-2.18 (m, 1H), 2.18-2.10 (m, 1H), 1.83-1.74 (m, 1H), 1.28 (s, 3H), 1.25 (t, J 7.2 Hz, 3H). Method C HPLC-MS: MH+ m/z 551, RT 1.23 minutes.

Intermediate 192

4-[5-(3-{[2-(Difluoromethoxy)phenyl]methyl}-7-fluoro-2-methylimidazo[1,2-a]pyridin-6-yl)pyrimidin-2-yl]-1-methylcyclohex-3-ene-1-carboxylic acid Intermediate 191 (275 mg, 0.5 mmol) was dissolved in 1,4-dioxane (3 mL) and water (1.5 mL), then a 2M solution of potassium hydroxide in water (1.5 mL) was added and the reaction mixture was heated at 85° C. for 2 h. The reaction mixture was adjusted to pH 6 with 1M aqueous hydrogen chloride solution, and the solid that formed was collected by filtration, to afford the title compound (200 mg, 77%) as an off-white solid. The filtrate was acidified to pH 5 with 1M aqueous hydrogen chloride solution and the solid that formed was collected by filtration. A further crop was obtained from re-filtering the filtrate. The two crops were combined to afford an additional quantity of the title compound (40 mg, 15%) as a pale yellow solid. $\delta_H$ (500 MHz, DMSO-d$_6$) 8.92 (d, J 1.5 Hz, 2H), 8.54 (d, J 7.5 Hz, 1H), 7.53 (d, J 11.3 Hz, 1H), 7.42-7.10 (m, 5H), 7.04 (d, J 6.3 Hz, 1H), 4.36 (s, 2H), 2.81-2.68 (m, 1H), 2.61-2.55 (m, 2H), 2.28 (s, 3H), 2.16 (dd, J 18.6, 3.1 Hz, 1H), 2.05-1.96 (m, 1H), 1.74-1.62 (m, 1H), 1.20 (s, 3H). Method C HPLC-MS: MH+ m/z 523, RT 1.08 minutes.

Intermediate 193

Cyclohex-3-en-1-ol

A solution of 9-borabicyclo[3.3.1]nonane in tetrahydrofuran (0.5M, 80 mL, 40 mmol) was added dropwise to cyclohexa-1,4-diene (3.2 g, 40 mmol). The solution was stirred overnight at room temperature. An aqueous solution of sodium hydroxide (3M, 12 mL) was added, followed by dropwise addition of hydrogen peroxide (30%, 12 mL). The resulting solution was heated at reflux for 1 h, then allowed to cool. The reaction mixture was poured into brine (200 mL) and extracted with diethyl ether (3×200 mL). The combined ethereal layers were dried over magnesium sulfate, filtered and concentrated. The residue was purified by chromatography, eluting with 0 to 100% ethyl acetate in heptane, then 0 to 50% methanol in ethyl acetate, to afford the title compound (1.25 g, 32%) as a clear oil. $\delta_H$ (250 MHz, CDCl$_3$) 5.82-5.45 (m, 1H), 4.03-3.74 (m, 1H), 2.60-0.71 (m, 8H).

Intermediate 194 tert-Butyl(cyclohex-3-en-1-yloxy)dimethylsilane

To a solution of Intermediate 193 (1.25 g, 12.74 mmol) and imidazole (1.75 g, 25.71 mmol) in dichloromethane (25 mL) was added tert-butyldimethylsilyl chloride (1M, 12.75 mL, 12.75 mmol) and the solution was stirred over 2 days at room temperature. The mixture was poured into water (50 mL) and extracted with diethyl ether (3×50 mL). The combined ethereal layers were dried over magnesium sulfate, filtered and concentrated. The resulting crude residue was purified by chromatography, eluting with 0 to 30% ethyl acetate in heptane, to afford the title compound (1.87 g, 69%) as a clear oil. $\delta_H$ (500 MHz, CDCl$_3$) 5.58-5.45 (m, 1H), 3.86-3.71 (m, 1H), 2.26-1.85 (m, 2H), 1.82-1.14 (m, 5H), 0.89-0.74 (m, 9H), 0.06-0.11 (m, 6H).

Intermediate 195

Ethyl-3-[(tert-butyldimethylsilyl)oxy]bicyclo[4.1.0]heptane-7-carboxylate 1-(2-Ethoxy-2-oxoethylidene)diazenium (1.1 mL, 8.77 mmol) in dichloromethane (2 mL) was added slowly via syringe pump over 6 h to a stirred solution of Intermediate 194 (1.55 g, 7.30 mmol) and rhodium(II) acetate (1:2) (33 mg, 0.075 mmol) in dichloromethane (50 mL) under nitrogen at room temperature. The reaction mixture was stirred at room temperature overnight. The reaction mixture was filtered through celite and concentrated. The crude orange oil was purified by chromatography, eluting with 5-30% ethyl acetate in heptane, to afford the title compound (1.23 g, 56%) as a clear oil. $\delta_H$ (500 MHz, CDCl$_3$) 4.15-4.00 (m, 2H), 3.67-3.46 (m, 1H), 2.27-2.06 (m, 1H), 2.06-1.80 (m, 2H), 1.76 (dq, J 20.7, 7.7, 7.1 Hz, 1H), 1.68-1.38 (m, 4H), 1.35-1.17 (m, 3H), 1.11 (dtd, J 13.3, 10.2, 5.1 Hz, 1H), 0.92-0.76 (m, 9H), 0.01 (dq, J 4.5, 2.5 Hz, 6H).

Intermediate 196

Ethyl-3-hydroxybicyclo[4.1.0]heptane-7-carboxylate

TBAF (1M in tetrahydrofuran, 8.1 mL, 8.1 mmol) was added dropwise to a stirred solution of Intermediate 195 (1.2 g, 4.02 mmol) in tetrahydrofuran (25 mL) at room temperature and the reaction mixture was heated at 50° C. for 1 h. The mixture was cooled to room temperature and concentrated under reduced pressure. The resulting light brownish oil was diluted with ethyl acetate (50 mL) and washed with water (2×20 mL) and brine (20 mL), then dried over magnesium sulphate, filtered and concentrated under reduced pressure. The crude residue was purified by chromatography, eluting with 20 to 100% ethyl acetate in heptane, to afford the title compound (0.49 g, 66%) as a clear oil. $\delta_H$ (500 MHz, CDCl$_3$) 4.01 (qd, J 7.1, 0.9 Hz, 2H), 3.53 (dtd, J 11.1, 6.4, 3.3 Hz, 1H), 2.31-2.06 (m, 1H), 1.95 (ddt, J 12.1, 9.5, 4.5 Hz, 1H), 1.90-1.68 (m, 1H), 1.66-1.25 (m, 6H), 1.24-1.11 (m, 4H).

Intermediate 197

Ethyl-3-oxobicyclo[4.1.0]heptane-7-carboxylate

Intermediate 196 (490 mg, 2.66 mmol) was dissolved in dichloromethane (10 mL) and Dess-Martin Periodinane (2.26 g, 5.33 mmol) was added. The mixture was stirred at room temperature overnight. The reaction mixture was diluted with dichloromethane (100 mL) and washed with saturated aqueous sodium bicarbonate solution (2×50 mL), water (50 mL) and brine (50 mL), then dried over sodium sulphate, filtered and concentrated under reduced pressure. The residue was purified by flash chromatography, eluting with 20 to 100% ethyl acetate in heptane, to afford the title compound (400 mg, 82%) as a yellow oil. $\delta_H$ (500 MHz, CDCl$_3$) 4.15 (q, J 7.1 Hz, 2H), 2.77-2.59 (m, 2H), 2.41-2.27 (m, 2H), 2.22-2.06 (m, 2H), 1.87 (s, 2H), 1.67 (t, J 4.1 Hz, 1H), 1.29 (t, J 7.2 Hz, 3H).

Intermediate 198

Ethyl 3-(trifluoromethanesulfonyloxy)bicyclo[4.1.0]heptene-7-carboxylate

Intermediate 197 (400 mg, 2.195 mmol) was dissolved in toluene (10 mL), then DIPEA (1.55 mL, 8.90 mmol) was added and the mixture was heated at 45° C. for 10 minutes. 1M trifluoromethanesulfonic anhydride (8.8 mL, 8.8 mmol) was added dropwise and the mixture was heated for 1 h. The reaction mixture was allowed to cool to room temperature, diluted with water (50 mL) and extracted with dichloromethane (2×100 mL). The organic layer was washed with saturated aqueous sodium bicarbonate solution (50 mL) and brine (50 mL), then dried over magnesium sulfate and concentrated. The residue was purified by column chromatography, eluting with 10 to 100% ethyl acetate in heptane, to afford the title compound (0.40 g, 56%) as a mixture of double bond isomers as an orange oil. $\delta_H$ (500 MHz, CDCl$_3$) 5.86 (ddd, J 236.4, 5.6, 2.5 Hz, 1H), 4.16 (qd, J 7.1, 3.1 Hz, 2H), 2.95-1.47 (m, 7H), 1.37-1.21 (m, 3H). Method C HPLC-MS: MH+ m/z 315, RT 1.53 minutes.

Intermediate 199

Ethyl 3-(4,4,5,5-tetramethyl-1,3,2-dioxaborolan-2-yl)bicyclo[4.1.0]heptene-7-carboxylate Intermediate 198 (400 mg, 1.27 mmol), 4,4,5,5-tetramethyl-2-(4,4,5,5-tetramethyl-1,3,2-dioxaborolan-2-yl)-1,3,2-dioxaborolane (485 mg, 1.91 mmol), and potassium acetate (375 mg, 3.82 mmol) were suspended in dry 1,4-dioxane (10 mL) and the mixture was degassed for 10 minutes, then 1,1'-bis(diphenylphosphanyl)ferrocene (21 mg, 38 µmol) was added, followed by PdCl$_2$(dppf) complex with dichloromethane (31 mg, 38 µmol). The reaction mixture was heated at 90° C. for 3 h in a microwave reactor. Additional 4,4,5,5-tetramethyl-2-(4,4,5,5-tetramethyl-1,3,2-dioxaborolan-2-yl)-1,3,2-dioxaborolane, 1,1'-bis(diphenylphosphanyl)ferrocene and PdCl$_2$(dppf) complex with dichloromethane were added and the mixture was heated at 90° C. in a microwave reactor for a total of 7 h, then at 100° C. for 2 h. The mixture was cooled to room temperature, diluted with water (50 mL) and extracted with ethyl acetate (2×100 mL). The combined organic layers were washed with brine (80 mL), dried over sodium sulphate, filtered and concentrated. The residue was purified by chromatography, eluting with 5 to 50% ethyl acetate in heptanes, to afford the title compound (418 mg, 47% yield at 41% purity) as a yellow solid. $\delta_H$ (500 MHz, CDCl$_3$) 6.87-6.23 (m, 1H), 4.22-3.95 (m, 2H), 2.62-1.40 (m, 7H), 1.18 (d, J 9.2 Hz, 15H). Method C HPLC-MS: MH+ m/z 293, RT 1.59 minutes.

Intermediate 200

Ethyl 3-[5-(3-{[2-(difluoromethoxy)phenyl]methyl}-7-fluoro-2-methylimidazo[1,2-a]-pyridin-6-yl)pyrimidin-2-yl]bicyclo[4.1.0]hept-2-ene-7-carboxylate A mixture of Intermediate 152 (95%, 200 mg, 0.454 mmol), Intermediate 199 (355 mg, 0.499 mmol), and 2M aqueous sodium carbonate solution (0.69 mL) in 1,4-dioxane (3 mL) was purged with nitrogen for 10 minutes, then tetrakis(triphenylphosphine)palladium(0) (26 mg, 5 mol %) was added and the reaction mixture was heated at 120° C. for 1 h under microwave irradiation. The reaction mixture was diluted with ethyl acetate (25 mL), then washed with water (5 mL) and brine (5 mL). The organic layer was dried over sodium sulfate, filtered and concentrated. The crude residue was purified by flash chromatography, eluting with 5 to 100% ethyl acetate in heptane, to afford the title compound (169 mg, 68%) as a brown oil. $\delta_H$ (500 MHz, CDCl$_3$) 8.70 (dd, J 5.2, 1.5 Hz, 2H), 7.77 (dd, J 7.0, 1.6 Hz, 1H), 7.73-7.63 (m, 1H), 7.35 (d, J 10.6 Hz, 1H), 7.28-7.14 (m, 2H), 7.11 (t, J 7.5 Hz, 1H), 6.91 (d, J 7.7 Hz, 1H), 6.63 (td, J 73.6, 0.7 Hz, 1H), 4.30 (s, 2H), 4.19-4.08 (m, 2H), 3.30-3.02 (m, 1H), 2.85-2.70 (m, 1H), 2.52 (s, 3H), 2.36-2.09 (m, 2H), 2.05 (s, 1H), 1.82 (ddq, J 19.4, 10.0, 3.4, 3.0 Hz, 1H), 1.69-1.58 (m, 1H), 1.26 (td, J 7.1, 2.4 Hz, 3H). Method A HPLC-MS: MH+ m/z 549, RT 3.67 minutes.

Intermediate 201

Ethyl 3-[5-(3-{[2-(difluoromethoxy)phenyl]methyl}-7-fluoro-2-methylimidazo[1,2-a]-pyridin-6-yl)pyrimidin-2-yl]bicyclo[4.1.0]heptane-7-carboxylate Intermediate 200 (145 mg, 0.243 mmol) was dissolved in ethyl acetate (5 mL) and palladium on carbon (10%, 26 mg, 10 mol %) and triethylamine (34 µL, 0.243 mmol) were added. The suspension was degassed using vacuum/nitrogen/hydrogen and the reaction mixture was stirred under hydrogen at room temperature for 2 h. The mixture was filtered through celite, then concentrated under reduced pressure. The residue was treated several times as described above until starting material was consumed. The reaction mixture was filtered through celite and concentrated to afford a crude yellow oil. The crude residues obtained from batches 1 and 2 were combined and purified by preparative HPLC (basic method), to afford the title compound (12.4 mg, 8%) as a pink oil. $\delta_H$ (250 MHz, CDCl$_3$) 8.69 (dd, J 4.8, 1.6 Hz, 2H), 7.76 (d, J 7.0 Hz, 1H), 7.36 (d, J 10.6 Hz, 1H), 7.32-7.23 (m, 1H), 7.21-7.05 (m, 2H), 6.95-6.30 (m, 2H), 4.29 (s, 2H), 4.12 (q, J 7.1 Hz, 2H), 2.96-2.68 (m, 1H), 2.51 (s, 4H), 2.27-2.09 (m, 1H), 2.09-1.98 (m, 1H), 1.97-1.81 (m, 2H), 1.79-1.64 (m, 2H), 1.55 (t, J 4.4 Hz, 1H), 1.41 (td, J 12.9, 4.7 Hz, 1H), 1.27 (t, J 7.1 Hz, 3H).

Intermediate 202

2-Chloro-5-(3-{[2-(difluoromethoxy)phenyl]methyl}-7-fluoro-2-methylimidazo[1,2-a]-pyridin-6-yl)pyridine Intermediate 68 (1 g, 2.6 mmol) and (6-chloropyridin-3-yl)boronic acid (368 mg, 2.34 mmol) were dissolved in 1,4-dioxane (6 mL) and 2M aqueous potassium carbonate solution (3.9 mL). The mixture was added to a sealed tube and degassed for 10 minutes with nitrogen. Pd(dppf)Cl$_2$ complex with dichloromethane (106 mg, 0.13 mmol) was added and the mixture was heated at 80° C. for 1.5 h. Additional (6-chloropyridin-3-yl)-boronic acid (123 mg, 0.78 mmol) was added, and the reaction mixture was degassed for 10 minutes. Pd(dppf)Cl$_2$ complex with dichloromethane (106 mg, 0.13 mmol) was added and the mixture was heated at 80° C. overnight. The mixture was extracted with ethyl acetate (2×25 mL). The organic phase was washed with brine (2×25 mL), dried with sodium sulphate, filtered and concentrated under vacuum. The resulting black oily residue was purified by chromatography using Biotage (100 g SNAP cartridge), eluting with 100% ethyl acetate, then further purified by trituration in ethyl acetate (4 mL), to afford the title compound (173 mg, 15%) as a white solid. Further solid in the filtrate was triturated with ethyl acetate (4 mL) and filtered, to afford an additional quantity of the title compound (145 mg, 13%) as a white solid. Method B HPLC-MS: MH+ m/z 417, RT 1.60 minutes.

Intermediate 203

Ethyl (1s,5s,6r)-3-[5-(3-{[2-(difluoromethoxy)phenyl]methyl}-7-fluoro-2-methylimidazo[1,2-a]pyridin-6-yl)pyridin-2-yl]bicyclo[3.1.0]hex-2-ene-6-carboxylate Intermediate 202 (350 mg, 0.84 mmol) and Intermediate 134 (75%, 372 mg, 1.00 mmol) were dissolved in 1,4-dioxane (4 mL), then 2M aqueous potassium carbonate solution (1.3 mL) was added and the reaction mixture was degassed for 10 minutes before addition of tetrakis(triphenylphosphine)palladium(0) (484 mg, 0.42 mmol). The reaction mixture was stirred at 120° C. under microwave irradiation for 1.5 h. The reaction mixture was extracted with ethyl acetate (30 mL), and the organic phase was washed with water (2×20 mL) and brine (25 mL). The solid present in the organic phase was filtered and discarded. The organic phase was dried over sodium sulphate, filtered and concentrated under vacuum. The resulting orange residue was purified on the Biotage system (100 g SNAP cartridge used, eluting with 25 to 100% ethyl acetate in heptane), to afford the title compound (92 mg, 20%) as a yellow gum. Method B HPLC-MS: MH+ m/z 534, RT 1.76, 1.87 minutes.

Intermediate 204

Ethyl (1R,5s,6r)-3-[5-(3-{[2-(difluoromethoxy)phenyl]methyl}-7-fluoro-2-methylimidazo[1,2-a]pyridin-6-yl)pyridin-2-yl]bicyclo[3.1.0]hexane-6-carboxylate Intermediate 203 (192 mg, 0.17 mmol) was dissolved in ethyl acetate (2 mL), then triethylamine (30 μL, 0.21 mmol) and palladium on carbon (10%, 183 mg, 0.17 mmol) were added. The reaction mixture was purged with nitrogen, then evacuated (3 times), filled with hydrogen and evacuated (3 times). The reaction mixture was stirred at room temperature for 2.5 h under hydrogen. The reaction mixture was filtered through celite and washed with ethyl acetate (25 mL), then the filtrate was concentrated under vacuum. The residue was purified by preparative HPLC (Method C) to afford the title compound (47 mg, 51%) as an orange gum. Method B HPLC-MS: MH+ m/z 536, RT 1.78 minutes.

Intermediate 205

7-Benzyl-3-oxa-7-azabicyclo[3.3.1]nonan-9-one

To a solution of tetrahydro-4H-pyran-4-one (6 g, 60 mmol) and powdered paraformaldehyde (4.50 g, 150 mmol) in isopropanol (150 mL) at 65° C. was added a solution of benzylamine (7.2 mL, 66 mmol) and acetic acid (3.77 mL, 66 mmol) in isopropanol (150 mL) dropwise over 1.5 h. The reaction mixture was stirred at 65° C. for 1.5 h. Upon cooling, the solvent was removed in vacuo. The residue was diluted with water (250 mL) and 1M hydrogen chloride solution (22.5 mL), and extracted with tert-butyl methyl ether (2×100 mL). The aqueous phase was basified to pH 13 with 1M aqueous sodium hydroxide solution and extracted with ethyl acetate (3×100 mL). The combined organic extracts were dried over sodium sulfate, filtered and concentrated. The residue was purified by flash column chromatography (Biotage Isolera 4, SNAP 100 g), eluting with 0 to 100% ethyl acetate in heptanes, to afford the title compound 6 g, 37%) as a yellow oil. $\delta_H$ (500 MHz, DMSO-d$_6$) 7.40-7.18 (m, 5H), 4.09 (d, J 10.9 Hz, 2H), 3.73 (dd, J 11.2, 2.8 Hz, 2H), 3.52 (s, 2H), 2.97 (dd, J 11.1, 2.9 Hz, 2H), 2.89 (dd, J 11.1, 6.8 Hz, 2H), 2.49-2.44 (m, 2H). Method E HPLC-MS: MH+ m/z 232, RT 4.10 minutes.

Intermediate 206

7-Benzyl-3-oxa-7-azabicyclo[3.3.1]nonane-9-carbonitrile

To a solution of Intermediate 205 (85%, 6 g, 22.05 mmol) and 1-[(isocyano-methyl)sulfonyl]-4-methylbenzene (10.33 g, 52.92 mmol) in 1,2-dimethoxyethane (73 mL) and ethanol (2 mL) at 0° C. was added potassium tert-butoxide (5.94 g, 52.92 mmol) portionwise over 20 minutes. The reaction mixture was stirred at 0° C. for 1.5 h, then at 40° C. for 1 h. Upon cooling, the mixture was filtered and the filtrate was concentrated in vacuo. The residue was dissolved in ethyl acetate (200 mL), and washed with water (100 mL) and brine (100 mL), then dried over sodium sulfate, filtered and concentrated in vacuo. The residue was purified by flash column chromatography (Biotage Isolera 4, SNAP 100 g), eluting with 0 to 10% methanol in dichloromethane, to afford the title compound (4.1 g 58%) as an orange-brown gum. $\delta_H$ (500 MHz, DMSO-d$_6$) 7.45-7.18 (m, 5H), 3.85 (d, J 12.1 Hz, 1H), 3.77 (t, J 13.0 Hz, 2H), 3.65 (d, J 11.8 Hz, 1H), 3.45 (d, J 18.1 Hz, 2H), 2.86 (dd, J 26.6, 10.9 Hz, 2H), 2.54 (d, J 11.8 Hz, 1H), 2.44-2.26 (m, 2H), 2.00 (s, 2H). Method E HPLC-MS: MH+ m/z 243, RT 4.25 minutes.

Intermediate 207

Methyl 7-benzyl-3-oxa-7-azabicyclo[3.3.1]nonane-9-carboxylate

Intermediate 206 (75%, 4.1 g, 12.69 mmol) in a 12N hydrogen chloride solution in water (50 mL) was heated at reflux for 12 h. The solvent was removed in vacuo, then the residue was dissolved in methanol (100 mL) and concentrated sulphuric acid (2 mL) was added. The mixture was heated at reflux for 20 h. Upon cooling, the reaction mixture was concentrated in vacuo and partitioned between saturated aqueous sodium bicarbonate solution (200 mL) and ethyl acetate (300 mL). The aqueous layer was extracted with ethyl acetate (2×200 mL). The combined organic layers were washed with brine (200 mL), dried over sodium sulfate, filtered and concentrated in vacuo. The residue was purified by flash column chromatography (Biotage Isolera 4, SNAP 100 g), eluting with 0 to 100% methanol in dichloromethane, to afford the title compound (1.67 g, 47%) as a red-brown oil. $\delta_H$ (250 MHz, CDCl$_3$) 7.46-7.10 (m, 5H), 4.15-3.77 (m, 2H), 3.73 (d, J 1.9 Hz, 3H), 3.69-3.49 (m, 3H), 3.48-3.34 (m, 1H), 2.95-2.74 (m, 2H), 2.56-2.09 (m, 5H). Method B HPLC-MS: MH+ m/z 276, RT 1.03 minutes.

Intermediate 208

Methyl 3-oxa-7-azabicyclo[3.3.1]nonane-9-carboxylate hydrochloride

Intermediate 207 (98%, 1.3 g, 4.63 mmol) was dissolved in ethyl acetate (15 mL) and the solution was degassed with nitrogen. Palladium on carbon (10%, 500 mg, 0.47 mmol)

was added and the mixture was degassed with nitrogen. The reaction mixture was allowed to stir under hydrogen at room temperature for 18 h. Additional palladium on carbon (10%, 250 mg, 0.23 mmol) was added and the mixture was degassed with nitrogen. The reaction mixture was allowed to stir under hydrogen at room temperature for 18 h. Additional palladium on carbon (10%, 250 mg, 0.23 mmol) and 1M hydrogen chloride in ethyl acetate (5 mL) were added and the mixture was degassed with nitrogen. The reaction mixture was allowed to stir under hydrogen at room temperature for 18 h. The reaction mixture was filtered through celite which was washed excessively with ethyl acetate (200 mL) followed by dichloromethane (200 mL). The filtrate was concentrated under vacuum to afford the title compound (1.03 g, 98%) as an orange solid. $\delta_H$ (500 MHz, CD$_3$OD) 4.19 (d, J 11.6 Hz, 1H), 4.01 (d, J 12.0 Hz, 1H), 3.79 (dd, J 25.6, 2.6 Hz, 5H), 3.65 (d, J 12.7 Hz, 1H), 3.49 (d, J 13.3 Hz, 1H), 3.42 (d, J 12.7 Hz, 1H), 3.35-3.31 (m, 1H), 3.09 (s, 1H), 2.36 (d, J 13.3 Hz, 2H).

Intermediate 209

Methyl 7-[5-(3-{[2-(difluoromethoxy)phenyl]methyl}-7-fluoro-2-methylimidazo[1,2-a]-pyridin-6-yl)pyrimidin-2-yl]-3-oxa-7-azabicyclo[3.3.1]nonane-9-carboxylate Intermediate 152 (95%, 200 mg, 0.45 mmol), Intermediate 208 (150 mg, 0.68 mmol) and a 1M solution of potassium carbonate in water (1.4 mL) were suspended in 1-methylpyrrolidin-2-one (3 mL) and the reaction mixture was heated at 120° C. under microwave irradiation for 1 h. The reaction mixture was concentrated under vacuum. The residue was diluted with dichloromethane (25 mL) and saturated aqueous sodium bicarbonate solution (25 mL). The organic phase was separated, washed with brine, dried over sodium sulfate, filtered and concentrated under vacuum. The residue was purified by flash column chromatography, eluting with 0 to 10% methanol in dichloromethane, and further purified by preparative HPLC (Method C), to afford the title compound (210 mg, 82%) as an orange gum. $\delta_H$ (500 MHz, CD$_3$OD) 8.34 (d, J 5.3 Hz, 2H), 8.05 (d, J 5.1 Hz, 1H), 7.31-7.22 (m, 2H), 7.17 (d, J 8.1 Hz, 1H), 7.12 (s, 1H), 7.08-6.73 (m, 2H), 5.00 (d, J 13.3 Hz, 1H), 4.62 (d, J 13.8 Hz, 1H), 4.34 (s, 2H), 3.99 (d, J 11.3 Hz, 1H), 3.81 (d, J 11.6 Hz, 1H), 3.78-3.69 (m, 5H), 3.47 (d, J 13.6 Hz, 1H), 3.24 (d, J 13.2 Hz, 1H), 2.92 (s, 1H), 2.39 (s, 3H), 2.29 (s, 2H).

Intermediate 210

1-tert-Butyl 2-methyl 5-oxopiperidine-1,2-dicarboxylate 1-(tert-Butoxycarbonyl)-5-oxopiperidine-2-carboxylic acid (2.0 g, 8.22 mmol) was dissolved in DMF (20 mL) under nitrogen and potassium carbonate (1.7 g, 12.33 mmol) was added, followed by iodomethane (620 µL, 9.95 mmol). The reaction mixture was stirred at room temperature under nitrogen for 23 h. Additional methyl iodide (256 µL, 4.11 mmol) was added and the reaction mixture was stirred at room temperature for 24 h. The reaction mixture was diluted with ethyl acetate (100 mL) and washed with saturated aqueous sodium bicarbonate solution (2×25 mL) and brine (2×25 mL), then dried over sodium sulfate and concentrated to dryness. The crude residue was purified by flash column chromatography (Biotage), eluting with 0 to 100% ethyl acetate in heptanes, to afford the title compound (2.42 g, 53%) as a pale yellow oil. $\delta_H$ (250 MHz, CDCl$_3$) 4.70 (dt, J 59.4, 6.3 Hz, 1H), 4.35 (dd, J 27.3, 19.0 Hz, 1H), 3.90 (dd, J 19.0, 12.4 Hz, 1H), 3.77 (s, 3H), 2.56-1.95 (m, 4H), 1.45 (s, 9H).

Intermediate 211

1-tert-Butyl 2-methyl 5-(trifluoromethanesulfonyloxy)-1,2,3,6-tetrahydropyridine-1,2-dicarboxylate and 1-tert-Butyl 2-methyl 5-(trifluoromethanesulfonyloxy)-1,2,3,4-tetrahydropyridine-1,2-dicarboxylate To a stirred solution of Intermediate 210 (1.05 g, 4.08 mmol) in tetrahydrofuran (70 mL) cooled to −78° C. was added dropwise 1M lithium 1,1,1,3,3,3-hexamethyl-disilazan-2-ide in tetrahydrofuran (4.29 mL). The reaction mixture was stirred at −78° C. for 1 h prior to the addition of 1,1,1-trifluoro-N-phenyl-N-[(trifluoromethyl)sulfonyl]-methanesulfonamide (1.53 g, 4.29 mmol) in tetrahydrofuran (30 mL). The reaction mixture was stirred at −78° C. for 30 minutes, then allowed to warm to room temperature, and stirred at room temperature over 2 days. The reaction mixture was quenched with aqueous sodium hydrogensulphate solution (50 mL) and extracted with ethyl acetate (70 mL). The organic layer was washed with 0.5M aqueous sodium hydroxide solution (70 mL), saturated aqueous ammonium chloride solution (70 mL) and brine (70 mL), then dried over sodium sulphate, filtered and concentrated under vacuum. The resulting crude yellow oil was purified twice by column chromatography (Biotage Isolera 4, 50 g cartridge), eluting with 0% to 100% tert-butyl methyl ether in heptane for the first column and 0 to 50% tert-butyl methyl ether in heptane for the second column, to afford the title compounds (597 mg, 32%) as a colourless oil. Method B HPLC-MS: [M-BOC]+ m/z 290, RT 2.25 minutes.

Intermediate 212

1-tert-Butyl 2-methyl 5-(4,4,5,5-tetramethyl-1,3,2-dioxaborolan-2-yl)-1,2,3,6-tetrahydropyridine-1,2-dicarboxylate and 1-tert-Butyl 2-methyl 5-(4,4,5,5-tetramethyl-1,3,2-dioxaborolan-2-yl)-1,2,3,4-tetrahydropyridine-1,2-dicarboxylate Intermediate 211 (595 mg, 1.33 mmol), bis(pinacolato)diborane (508 mg, 2.00 mmol) and potassium acetate (393 mg, 4.00 mmol) were suspended in 1,4-dioxane (12 mL) and the mixture was degassed with nitrogen for 5 minutes. 1,1'-Bis(diphenyl-phosphanyl)ferrocene (22 mg, 0.04 mmol) and Pd(dppf)Cl$_2$ complex with dichloromethane (33 mg, 0.04 mmol) were added and the mixture was heated in a sealed tube at 90° C. for 3 h. The cooled reaction mixture was diluted with ethyl acetate (30 mL) and washed with saturated aqueous sodium bicarbonate solution (15 mL). The aqueous layer was further extracted with ethyl acetate (2×30 mL). The combined organic layers were washed with brine, dried over sodium sulphate, filtered and concentrated. The resulting dark residue was purified by column chromatography (Biotage Isolera 4, 50 g cartridge), eluting with 0% to 50% ethyl acetate in heptane, to afford the title compounds (296 mg, 60%) as a pale yellow oil. Method B HPLC-MS: [M-BOC]+ m/z 268, RT 2.24, 2.29 minutes.

Intermediate 213

1-tert-Butyl 2-methyl 5-[5-(3-{[2-(difluoromethoxy)phenyl]methyl}-7-fluoro-2-methylimidazo[1,2-a]pyridin-6-yl)pyrimidin-2-yl]-1,2,3,6-tetrahydropyridine-1,2-dicarboxylate and 1-tert-Butyl 2-methyl 5-[5-(3-{[2-(difluoromethoxy)phenyl]methyl}-7-fluoro-2-methylimidazo[1,2-a]pyridin-6-yl)pyrimidin-2-yl]-1,2,3,4-tetrahydropyridine-1,2-dicarboxylate A mixture of Intermediate 152 (280 mg, 0.70 mmol), Intermediate 212 (294 mg, 0.80 mmol) and 2M aqueous sodium carbonate solution (1.0 mL) in 1,4-dioxane (5.0 mL) was purged with nitrogen for 5 minutes. Tetrakis(triphenylphosphine)palladium(0) (38 mg, 0.03 mmol) was then added and the reaction mixture was heated at 120° C. under microwave irradiation for 1 h. The cooled reaction mixture was partitioned between ethyl acetate (20 mL) and water (10 mL). The aqueous layer was separated and extracted into ethyl acetate (3×20 mL). The combined organic extracts were washed with brine (20 mL), dried over sodium sulphate, filtered and evaporated. The resulting crude residue was successively purified by column chromatography (Biotage Isolera, 25 g cartridge), eluting with 40% to 100% ethyl acetate in heptane, and by preparative chromatography (Method C), to afford the title compounds (205 mg, 49%) as a pale brown solid. Method B HPLC-MS: MH+ m/z 624, RT 1.92 minutes.

Intermediate 214

1-tert-Butyl 2-methyl 5-[5-(3-{[2-(difluoromethoxy)phenyl]methyl}-7-fluoro-2-methylimidazo[1,2-a]pyridin-6-yl)pyrimidin-2-yl]piperidine-1,2-dicarboxylate To a stirring solution of Intermediate 213 (200 mg, 0.32 mmol) in ethyl acetate (5 mL), dichloromethane (5 mL) and triethylamine (45 µl, 0.32 mmol), degassed and purged with nitrogen, was added palladium on carbon (10%, 34 mg, 0.03 mmol). The reaction mixture was stirred under hydrogen at room temperature until the reaction was complete. The reaction mixture was filtered through celite and the solids were washed with excess ethyl acetate. The filtrate was evaporated to give a pale residue which was successively purified by column chromatography (Biotage Isolera 4, 25 g cartridge), eluting with 20% to 100% ethyl acetate in heptanes, and by preparative HPLC (Method C), to afford the title compound (52 mg, 26%) as a pale crystallising oil (55:45 mixture of diastereoisomers). $\delta_H$ (500 MHz, CDCl$_3$) 8.71 (d, J 1.5 Hz, 2H), 7.76 (dd, J 7.0, 3.0 Hz, 1H), 7.36 (d, J 10.6 Hz, 1H), 7.28 (m, 1H), 7.16 (d, J 8.2 Hz, 1H), 7.10 (t, J 7.5 Hz, 1H), 6.89 (t, J 8.5 Hz, 1H), 6.62 (t, J 73.6 Hz, 1H), 5.09-4.32 (m, 2H), 4.28 (s, 2H), 3.76 (d, J 4.9 Hz, 3H), 3.58-2.96 (m, 2H), 2.50 (s, 3H), 2.41 (t, J 11.2 Hz, 1H), 2.14-2.06 (m, 2H), 1.88 (ddd, J 13.9, 10.7, 5.4 Hz, 1H), 1.43 (d, J 50.8 Hz, 9H). Method B HPLC-MS: MH+ m/z 626, RT 1.74, 1.78 minutes.

Intermediate 215

Methyl 5-[5-(3-{[2-(difluoromethoxy)phenyl]methyl}-7-fluoro-2-methylimidazo[1,2-a]-pyridin-6-yl)pyrimidin-2-yl]piperidine-2-carboxylate To a stirred solution of Intermediate 214 (50 mg, 0.08 mmol) in dichloromethane (2 mL) was added trifluoroacetic acid (0.6 mL). The reaction mixture was stirred at room temperature for 4.5 h. The reaction mixture was loaded onto a 1 g SCX cartridge and eluted with methanol, followed by 7N ammonia in methanol, to afford the title compound (25 mg, 59%) as a pale crystallising oil (mixture of diastereoisomers). $\delta_H$ (500 MHz, CDCl$_3$) 8.71 (dd, J 7.2, 1.3 Hz, 2H), 7.75 (dd, J 6.8, 5.2 Hz, 1H), 7.37-7.30 (m, 1H), 7.29-7.26 (m, 1H), 7.16 (d, J 8.1 Hz, 1H), 7.09 (t, J 7.5 Hz, 1H), 6.88 (d, J 7.5 Hz, 1H), 6.62 (td, J 73.6, 4.6 Hz, 1H), 4.28 (s, 2H), 3.75 (d, J 7.2 Hz, 3H), 3.56-3.38 (m, 2H), 3.27-2.90 (m, 2H), 2.50 (s, 3H), 2.35-2.13 (m, 2H), 1.96-1.61 (m, 2H). Method B HPLC-MS: MH+ m/z 526, RT 1.22 minutes.

Intermediate 216 [Removed]

General Method C

Formation of Functionalised Pyrimidine Boronic Acids

To a suspension of (2-chloropyrimidin-5-yl)boronic acid (1.0 eq) in ethanol is added the appropriate amine (0.95 eq). Triethylamine (2.5 eq) is added and the mixture stirred at either ambient temperature or 80° C. until the reaction is complete by TLC or LCMS. If the product precipitates the desired compound is isolated by filtration. For soluble products the reaction mixture is concentrated in vacuo and the crude product mixture is partitioned between aqueous medium and ethyl acetate. The aqueous layer is separated and re-extracted with ethyl acetate. The organic layers are combined and washed with brine, then dried (Na$_2$SO$_4$), filtered and concentrated in vacuo. The product can be further purified if required by column chromatography on silica gel or preparative mass-directed HPLC.

Intermediate 217

4-(5-Boronopyrimidin-2-yl)-1,4-oxazepane-7-carboxylic acid

The title compound was prepared from 1,4-oxazepane-7-carboxylic acid and (2-chloropyrimidin-5-yl)boronic acid in accordance with General Method C.

Intermediate 218

(2R)-4-(5-Boronopyrimidin-2-yl)morpholine-2-carboxylic acid

The title compound was prepared from (2R)-morpholine-2-carboxylic acid and (2-chloropyrimidin-5-yl)boronic acid in accordance with General Method C.

Intermediate 219

[2-(7-oxo-3,6-diazabicyclo[3.2.2]nonan-3-yl)pyrimidin-5-yl]boronic acid

The title compound was prepared from 3,6-diazabicyclo[3.2.2]nonan-7-one and (2-chloropyrimidin-5-yl)boronic acid in accordance with General Method C.

Intermediate 220

Ethyl 4-[5-(4,4,5,5-tetramethyl-1,3,2-dioxaborolan-2-yl)pyrimidin-2-yl]cyclohex-3-ene-1-carboxylate The title compound was synthesised from Intermediate 56 in accordance with the method outlined for Intermediate 221.

Intermediate 221

Ethyl 1-methyl-4-[5-(4,4,5,5-tetramethyl-1,3,2-dioxaborolan-2-yl)pyrimidin-2-yl]cyclohex-3-ene-1-carboxylate A stirred mixture of ethyl 1-methyl-4-(4,4,5,5-tetramethyl-1,3,2-dioxaborolan-2-yl)cyclohex-3-enecarboxylate (prepared in an analogous manner to Intermediate 273; 70 g, 190 mmol, 80%), 5-bromo-2-iodopyrimidine (54.2 g, 190 mmol) and sodium carbonate (60.5 g, 571 mmol) in 1,2-dimethoxyethane (750 mL) and water (250 mL) was flushed with argon. 1,1'-Bis(diphenylphosphino)ferrocenepalladium (II) dichloride (4.66 g, 5.71 mmol) was added and the resulting mixture was stirred at 100° C. until the reaction was complete by LCMS or TLC. The reaction mixture was quenched into aqueous NaCl solution (~10 wt %, 1000 mL) and EtOAc (200 mL) with stirring. The layers were separated and the aqueous layer was extracted with EtOAc (3×200 mL). The combined extracts were dried with $Na_2SO_4$ and concentrated in vacuo. The resulting brown-black tar (95 g) was triturated in diisopropyl ether/heptane (1:1, 400 mL) under slight heating for 1 h. The whole was filtered over kieselguhr and rinsed with diisopropyl ether/heptane (1:1). Upon concentration in vacuo the residue was triturated in warm heptane (1 L) together with Norit® activated charcoal. The whole was again filtered over kieselguhr and concentrated in vacuo. The resulting clear yellow-orange oil (69 g), which solidified upon standing, was purified by gravity column chromatography. The resulting white solid (27 g, 83 mmol) was stirred with bis(pinacolato)diboron (21.08 g, 83 mmol) and potassium acetate (24.4 g, 249 mmol) in 1,4-dioxane (anhydrous, 300 mL) and flushed with argon (3 vacuum-argon cycles) for 5 minutes. 1,1'-Bis(diphenylphosphino)-ferrocenepalladium (II) dichloride (2.034 g, 2.491 mmol) was added, and the resulting mixture was stirred at 90° C. for 3 h. The reaction mixture was cooled to ~40° C. and filtered over a pad of kieselguhr, which was rinsed with EtOAc (300 mL). The filtrate was concentrated in vacuo. The resulting dark brown solid (51 g) was triturated in heptane/diisopropyl ether (1:1, 400 mL) at ~50° C., and some scoops of Norit® activated charcoal were added. After 30 minutes the insoluble materials were removed by filtration over kieselguhr. The residue was rinsed with heptane/diisopropyl ether (1:1, 500 mL) at ~50° C. More insoluble material (sticky dark gum) precipitated from the filtrate. Norit® activated charcoal was added and the resulting suspension was stirred for 30 minutes at room temperature. The residue was filtered over a new pad of kieselguhr and rinsed with warm heptane/diisopropyl ether (1:1, 500 mL). Concentration of the filtrate in vacuo yielded the title compound (38 g) as a beige solid.

General Method B

Pyrimidine Displacements

The appropriate 2-chloropyrimidine (e.g. Intermediate 29 or Intermediate 152; 1 eq), the appropriate amine (1 eq) and triethylamine (1 eq) are dissolved in ethanol and heated at 80° C. until the reaction is complete by TLC or LCMS analysis. The ethanol is removed under vacuum and water added. Depending on solubility, the product is isolated by filtration or extracted into ethyl acetate. Ethyl acetate solutions are subsequently dried over sodium sulphate, filtered and concentrated in vacuo. The crude residue thus obtained is purified by an appropriate technique, typically column chromatography on silica gel or preparative mass-directed HPLC.

Intermediate 222

1-[5-Bromo-4-(trifluoromethyl)pyrimidin-2-yl]-1,4-diazepan-5-one

Synthesised from 5-bromo-2-chloro-4-(trifluoromethyl)pyrimidine (1.14 g, 4.35 mmol) and 1,4-diazepan-5-one (490 mg, 4.30 mmol) in accordance with General Method B, giving the title compound (1.20 g, 81%) as a white solid. $\delta_H$ (300 MHz, DMSO-$d_6$) 8.79 (s, 1H), 7.71 (t, J 4.8 Hz, 1H), 3.90 (m, 4H), 3.21 (m, 2H), 2.54 (m, 2H). LC-MS (pH 3) MH+ m/z 339.0, RT 1.93 minutes. LC-MS (pH 10) MH+ m/z 339.0, RT 1.91 minutes.

Intermediate 223

{2-[4-Ethoxycarbonyl-4-(hydroxymethyl)piperidin-1-yl]pyrimidin-5-yl}boronic acid A solution of 1-tert-butyl 4-ethyl piperidine-1,4-dicarboxylate (1 g, 3.89 mmol) in THF (5 mL) was stirred at −78° C. and lithium bis(trimethylsilyl)amide (1M in toluene, 5.8 mL, 29 mmol) was added dropwise, then stirred for 1 h. Paraformaldehyde (0.7370 g, 7.773 mmol) was added and the mixture was stirred for 16 h, allowing the temperature to rise slowly to ambient. The reaction mixture was quenched using saturated aqueous ammonium chloride solution, then partitioned between EtOAc and brine. The aqueous layer was further extracted using EtOAc. The combined organic extracts were dried ($MgSO_4$) and the solvent was removed under vacuum. The resulting material was dissolved and stirred for 1 h in TFA (10 mL), then rotary evaporated to dryness. The crude residue (theoretical 0.7 g, 3.891 mmol) was dissolved in ethanol (12 mL), then sodium carbonate (1.03 g, 9.72 mmol) and (2-chloropyrimidin-5-yl)boronic acid (0.68 g, 4.3 mmol) were added and the reaction mixture was stirred at 60° C. for 2 h. LC/MS showed completion of reaction. The mixture was cooled to ambient temperature and filtered through celite. The solvent was removed to give the crude title compound (1 g, 83%) as a cream solid, which was used without further purification. LCMS (pH 10) MH+ 310, RT 0.95 minutes.

Intermediate 224

[2-(1-Ethoxycarbonyl-3-azabicyclo[4.1.0]heptan-3-yl)pyrimidin-5-yl]boronic acid

The title compound was synthesized from Intermediate 91 in accordance with General Method C.

Intermediate 225

{2-[4-Ethoxycarbonyl-4-(trifluoromethyl)piperidin-1-yl]pyrimidin-5-yl}boronic acid TFA (5 mL) was added to 1-tert-butyl 4-ethyl 4-(trifluoromethyl)piperidine-1,4-dicarboxylate (0.42 g, 1.29 mmol). The mixture was stirred for 30 minutes, then rotary evaporated to dryness and left on a high vacuum line for 1 h. The residual syrup was dissolved in ethanol (4 mL), anhydrous sodium carbonate (0.35 g, 3.3 mmol) was added, and the mixture was stirred for 10 minutes. (2-Chloropyrimidin-5-yl)boronic acid (0.23 g, 1.4 mmol) was added and the reaction mixture was stirred at 60° C. for 6 h. The mixture was filtered through celite and concentrated to give the title compound (0.4 g, 89%) as an off-white foam, which was used without further purification. LCMS (pH 10) MH+ 348, RT 1.31 minutes.

Intermediate 226

[2-(4-Ethoxycarbonyl-4-fluoropiperidin-1-yl)pyrimidin-5-yl]boronic acid

A mixture of ethyl 4-fluoropiperidine-4-carboxylate hydrochloride (2 g, 9.4491 mmol), (2-chloropyrimidin-5-yl)boronic acid (1.5426 g, 9.4493 mmol) and sodium carbonate decahydrate (2.53 g, 23.6 mmol) in ethanol (15 mL) was stirred at 60° C. for 12 h. The reaction mixture was filtered through celite, the solvent was evaporated and the residue was dried under vacuum to give the title compound (2.7 g, 97%) as a pale yellow gum, which was used without further purification. LCMS (pH 10) MH+ 298, RT 1.19 minutes.

Intermediate 227

{2-[4-Methoxy-4-(methoxycarbonyl)piperidin-1-yl]pyrimidin-5-yl}boronic acid

A 2% solution of HCl in MeOH was prepared by adding acetyl chloride (1.1 mL) to MeOH (25 mL). To this solution was added 1-[(tert-butoxy)carbonyl]-4-methoxypiperidine-4-carboxylic acid (1 g, 3.6637 mmol) and the solution was heated under reflux for 6 h. The reaction mixture was evaporated to dryness and left on a vacuum line for 30 minutes. The material thus obtained was dissolved in ethanol (8 mL) and stirred with sodium carbonate (0.96 g, 9.1 mmol) for 10 minutes, then (2-chloropyrimidin-5-yl)-boronic acid (0.57 g, 3.61 mmol) was added and the mixture was stirred at 60° C. for 6 h. The reaction mixture was filtered through celite and the solvents removed in vacuo to give the title compound (0.8 g, 71%) as a white foam, which was used without further purification. LCMS (pH 10) MH+ 296, RT 0.86 minutes.

Intermediate 228

{2-[4-Ethyl-4-(methoxycarbonyl)piperidin-1-yl]pyrimidin-5-yl}boronic acid

TFA (8 mL) was added to a stirred solution of 1-tert-butyl 4-methyl 4-ethylpiperidine-1,4-dicarboxylate (0.61 g, 2.25 mmol) in 1,4-dioxane (2 mL). The reaction mixture was stirred for 2 h, then the volatiles were removed by rotary evaporation and the residue was left on a high vacuum line for 1 h. The syrupy material thus obtained was dissolved in ethanol (8 mL), anhydrous sodium carbonate (0.72 g, 6.79 mmol) was added and the mixture was stirred for 10 minutes. (2-Chloropyrimidin-5-yl)boronic acid (0.37 g, 2.3 mmol) was added and the mixture was stirred at 80° C. for 7 h. The reaction mixture was filtered through celite, then the solvent was removed under vacuum, and water was added. The mixture was decanted and washed again with water, then the residual gum was freeze-dried, to give the title compound (0.4 g, 60%) as a pale yellow lyophilised solid, which was used without further purification. LCMS (pH 10) MH+ 294, RT 1.15 minutes.

Intermediate 229

{2-[(1R,5S)-8-(Methoxycarbonyl)-3-azabicyclo[3.2.1]octan-3-yl]pyrimidin-5-yl}boronic acid Prepared from methyl 3-azabicyclo[3.2.1]octane-8-carboxylate hydrochloride (0.57 g, 2.8 mmol) and (2-chloropyrimidin-5-yl)boronic acid (0.45 g, 2.8 mmol) in accordance with General Method C to afford the title compound (1 g) as an off-white gum. LCMS (pH 3) MH+ 292, RT 0.79 minutes.

Intermediate 230

{2-[(1R,5S,8s)-8-(Methoxycarbonyl)-3-azabicyclo[3.2.1]octan-3-yl]pyrimidin-5-yl}-boronic acid (1R,5S)-3-tert-Butoxycarbonyl-3-azabicyclo[3.2.1]octane-8-carboxylic acid (9.0 g, 35.3 mmol) was suspended in HCl solution (2.25M in MeOH) and the reaction mixture was heated at reflux for 4 h. The reaction mixture was allowed to cool to r.t., then concentrated in vacuo. To the resulting white solid was added (2-chloropyrimidin-5-yl)boronic acid (5.58 g, 35.2 mmol) and the mixture was suspended in EtOH (130 mL). Triethylamine (9.90 mL, 70.5 mmol) was added and the reaction mixture was heated at 80° C. for 5 h. The reaction mixture was allowed to cool to r.t., then water (30 mL) was added. The reaction mixture was concentrated to around one-third volume, then more water (100 mL) was added. The resulting off-white solid precipitate was filtered and washed with water (2×30 mL), to afford the title compound (8.9 g, 86%) as an off-white powder. $\delta_H$ (300 MHz, DMSO-$d_6$) 8.59 (2H, s), 8.02 (2H, s), 4.45 (2H, dd, J 13.1, 3.4 Hz), 3.62 (3H, s), 2.98 (2H, br d, J 12.4 Hz), 2.77 (1H, s), 2.59 (2H, br s), 1.66-1.63 (2H, m), 1.38-1.33 (2H, m). HPLC-MS (pH 10): MH+ m/z 292, RT 0.97 minutes.

Intermediate 231

{2-[(1S,6R or 1R,6S)-6-(Methoxycarbonyl)-3-azabicyclo[4.1.0]heptan-3-yl]pyrimidin-5-yl}boronic acid Prepared from Intermediate 116 (301 mg, 1.57 mmol) and (2-chloropyrimidin-5-yl)boronic acid (249 mg, 1.57 mmol) in accordance with General Method C to give the title compound (306 mg, 70%) as an off-white foam. $\delta_H$ (DMSO-$d_6$) 8.60 (s, 1H), 8.03 (s, 1H), 4.19-4.30 (m, 1H), 3.81-3.92 (m, 1H), 3.70-3.80 (m, 1H), 3.60 (s, 3H), 3.33-3.43 (m, 2H), 1.70-1.83 (m, 2H), 1.29 (dd, 1H, J 9.1, 4.4 Hz), 0.75-0.82 (m, 1H). LCMS (ES+) 278 (M+H)+, RT 0.79 minutes.

Intermediate 232

{2-[(1R,5R or 1S,5S)-5-(Methoxycarbonyl)-3-azabicyclo[3.1.0]hexan-3-yl]pyrimidin-5-yl}boronic acid Prepared from Intermediate 144 (300 mg, 1.69 mmol) and (2-chloropyrimidin-5-yl)boronic acid (267 mg, 1.57 mmol) in accordance with General Method C to give the title compound (269 mg, 60%). $\delta_H$ (DMSO-$d_6$) 8.60 (s, 2H), 8.05 (s, 2H), 3.78-3.96 (m, 2H), 3.66 (s, 3H), 3.55 (dd, 1H, J 11.3, 4.4 Hz), 3.04-3.14 (m, 1H), 2.18-2.28 (m, 1H), 1.50-1.57 (m, 1H), 0.92 (t, 1H, J 5.0 Hz). LCMS (ES+) 264 (M+H)+, RT 0.49 minutes.

Intermediate 233

Methyl 3-azabicyclo[3.1.0]hexane-1-carboxylate hydrochloride (Enantiomer B)

Intermediate 143 (5 g, 20 mmol) was separated using chiral preparative HPLC (Chiracel OJ column, 20×250 mm, 5 μm; 100% acetonitrile eluent; 20 mL/minute flow rate) and the first-eluting diastereomer was isolated (1.87 g, 7.62 mmol). This was dissolved in methanol (55 mL) and the mixture was degassed with nitrogen, then palladium on carbon (10%, 195 mg, 0.18 mmol) was added. The reaction mixture was stirred under a hydrogen balloon at room temperature for 5 h. The reaction mixture was filtered through celite and the solids were washed with excess methanol. The filtrate was concentrated by evaporation. To the residue was added 4M hydrochloric acid in diethyl ether (10 mL), and the mixture was stirred at room temperature for 10 minutes. The resulting precipitate was filtered, washed with diethyl ether and dried, to afford the title compound as an off-white solid. $\delta_H$ (500 MHz, CD$_3$OD) 3.83 (dd, J 11.8, 1.3 Hz, 1H), 3.75 (s, 3H), 3.59-3.52 (m, 2H), 3.44 (d, J 11.7 Hz, 1H), 2.40-2.30 (m, 1H), 1.76-1.69 (m, 1H), 1.17 (t, J 5.9 Hz, 1H).

Intermediate 234

{2-[(1R,6S or 1S,6R)-6-(Methoxycarbonyl)-3-azabicyclo[4.1.0]heptan-3-yl]pyrimidin-5-yl}boronic acid (Enantiomer B)

Prepared from Intermediate 117 (299 mg, 1.56 mmol) and (2-chloropyrimidin-5-yl)boronic acid (250 mg, 1.58 mmol) in accordance with General Method C to give the title compound (232 mg, 54%) as a white solid. $\delta_H$ (DMSO-d$_6$) 8.53 (s, 2H), 7.96 (s, 2H), 4.16 (dd, 1H, J 13.9, 2.3 Hz), 3.79 (dd, 1H, J 13.8, 4.7 Hz), 3.62-3.72 (m, 1H), 3.53 (s, 3H), 3.25-3.36 (m, 1H), 2.35-2.43 (m, 1H), 1.64-1.82 (m, 2H), 1.23 (dd, 1H, J 9.2, 4.4 Hz), 0.71 (dd, 1H, J 6.2, 4.5 Hz). LCMS (ES+) 278 (M+H)$^+$, RT 0.79 minutes.

Intermediate 235

{2-[(1R,6S or 1S,6R)-6-(Ethoxycarbonyl)-4-azabicyclo[4.1.0]heptan-4-yl]pyrimidin-5-yl}boronic acid (Enantiomer B)

Prepared from Intermediate 120 (237 mg, 1.15 mmol) and 2-chloropyrimidin-5-yl)boronic acid (152 mg, 0.96 mmol) in accordance with General Method C to give the title compound (241 mg, 86%) as a pale yellow solid. $\delta_H$ (DMSO-d$_6$) 8.67 (s, 2H), 4.24-4.34 (m, 1H), 4.07 (q, 2H, J 7.1 Hz), 3.98-4.06 (m, 1H), 3.64-3.77 (m, 1H), 3.32-3.45 (m, 1H), 1.94-2.16 (m, 1H), 1.60-1.85 (m, 2H), 1.21-1.33 (m, 1H), 1.18 (t, 3H, J 7.1 Hz), 0.78-0.81 (m, 1H). LCMS (ES+) 292 (M+H)$^+$, RT 1.14 minutes.

Intermediate 236

Ethyl 3-(trifluoromethylsulfonyloxy)cyclohex-2-ene-1-carboxylate

To a stirred solution of ethyl 3-oxocyclohexanecarboxylate (0.47 mL, 2.9 mmol) in THF (2.5 mL, 100 mass %) at –78° C. was added lithium bis(trimethylsilyl)amide (3.10 mL, 1M in THF) dropwise. The reaction mixture stirred at –78° C. for 1 h, after which time N-phenyltrifluoromethanesulfonimide (1.10 g, 3.08 mmol) in THF (2.5 mL, 100 mass %) was added to the mixture. The reaction mixture was stirred at –78° C. for a further 1.5 h, after which time the reaction mixture allowed to warm to room temperature and stirred overnight. The reaction mixture was quenched with aqueous sodium hydrogensulphate solution (~10 mL) and diluted with ethyl acetate (50 mL). The layers were separated and organic layers were washed with 5% aqueous NaOH solution (2×30 mL), saturated aqueous ammonium chloride solution (20 mL) and brine (20 mL), then dried (MgSO$_4$), filtered and concentrated in vacuo, to give the title compound (932 mg, quantitative) as a yellow oil. $\delta_H$ (DMSO-d$_6$) 5.89-5.95 (m, 1H), 4.00-4.15 (m, 2H), 2.77-2.91 (m, 1H), 2.16-2.35 (m, 2H), 1.51-1.97 (m, 4H), 1.12-1.24 (m, 3H).

Intermediate 237

Ethyl 3-(4,4,5,5-tetramethyl-1,3,2-dioxaborolan-2-yl)cyclohex-2-ene-1-carboxylate To a stirred solution of Intermediate 236 (888 mg, 2.9 mmol) in 1,4-dioxane (20 mL) were added bis(pinacolato)diboron (1.18 g, 4.63 mmol), potassium acetate (913 mg, 9.30 mmol), 1,1'-bis(diphenylphosphino)ferrocene (62 mg, 0.11 mmol) and [1,1'-bis-(diphenylphosphino)ferrocene]dichloropalladium(II)-DCM adduct (91 mg, 0.11 mmol), and the mixture was stirred at 90° C. for 18 h. The reaction mixture was cooled to room temperature, filtered through celite, washed with EtOAc and concentrated in vacuo. The crude material was purified by column chromatography (SiO$_2$, 5-100% EtOAc in hexane and 0-10% MeOH in EtOAc) to give the title compound (412 mg, 50%) as a yellow oil. $\delta_H$ (DMSO-d$_6$) 6.37-6.45 (m, 1H), 3.98-4.14 (m, 2H), 2.20-2.32 (m, 1H), 2.04-2.17 (m, 2H), 1.41-2.03 (m, 4H), 1.11-1.24 (m, 15H).

Intermediate 238

Ethyl 3-[5-(3-{[2-(difluoromethoxy)phenyl]methyl}-2-methylimidazo[1,2-a]pyridin-6-yl)pyrimidin-2-yl]cyclohex-2-ene-1-carboxylate To a stirred solution of Intermediate 29 (480 mg, 1.20 mmol) and Intermediate 237 (400 mg, 1.43 mmol) in 1,4-dioxane (15 mL) was added 2M aqueous potassium carbonate solution (2.40 mL). The reaction mixture was degassed, then [1,1'-bis-(diphenylphosphino)ferrocene]dichloropalladium (II) DCM adduct (51 mg, 0.062 mmol) was added and the reaction mixture was heated under nitrogen at 100° C. for 18 h. The reaction mixture was cooled to room temperature, diluted with water (50 mL) and extracted with ethyl acetate (3×50 mL). The combined organic layers were washed with brine (30 mL), then dried (MgSO$_4$), filtered and concentrated in vacuo. The crude material was purified by column chromatography (SiO$_2$, 25-100% EtOAc in hexane) to give the title compound (353 mg, 57%) as a brown oil. $\delta_H$ (DMSO-d$_6$) 9.09 (s, 1H), 8.65 (s, 1H), 7.54-7.66 (s, 3H), 7.29-7.33 (m, 1H), 7.29 (t, 1H, J 73.9 Hz), 7.25-7.29 (m, 1H), 7.05-7.22 (m, 3H), 4.37-4.44 (m, 2H), 4.07-4.17 (m, 2H), 2.86-2.89 (m, 1H), 2.66-2.75 (m, 1H), 2.54 (s, 1H), 2.33-2.42 (m, 2H), 2.32 (s, 3H), 2.00-2.08 (m, 1H), 1.57-1.73 (m, 1H), 1.22 (t, 3H, J 7.1 Hz). LCMS (ES+) 519 (M+H)$^+$, RT 2.51 minutes.

Intermediate 239

Ethyl 3-[5-(3-{[2-(difluoromethoxy)phenyl]methyl}-2-methylimidazo[1,2-a]pyridin-6-yl)pyrimidin-2-yl]cyclohexanecarboxylate To a stirred solution of Intermediate 238 (350 mg, 0.68 mmol) in EtOH (25 mL) was added 10% palladium on carbon (16 mg, 0.15 mmol) and the reaction mixture was stirred under an atmosphere of hydrogen for 72 h. The reaction mixture was filtered through celite, washed with EtOH and MeOH, and concentrated in vacuo, to give the title compound (300 mg, 85%) as a yellow oil. LCMS (ES+) 521 (M+H)$^+$, RT 2.41, 2.46 minutes.

Intermediate 240

{2-[4-(tert-Butoxycarbonylamino)-4-(methoxycarbonyl)piperidin-1-yl]pyrimidin-5-yl}-boronic acid The title compound was synthesised from methyl 4-(tert-butoxycarbonylamino)-piperidine-4-carboxylate and (2-chloropyrimidin-5-yl)boronic acid in accordance with General Method C.

Intermediate 241

Methyl 4-(tert-butoxycarbonylamino)-1-[5-(3-{[2-(difluoromethoxy)phenyl]methyl}-7-fluoro-2-methylimidazo[1,2-a]pyridin-6-yl)pyrimidin-2-yl]piperidine-4-carboxylate Intermediate 68 (0.50 g, 1.30 mmol) and Intermediate 240 (0.642 g, 1.69 mmol) were dissolved in 1,4-dioxane (30 mL). Tetrakis(triphenylphosphine)palladium(0) (45 mg, 0.039 mmol) and 2M aqueous sodium carbonate solution (6 mL, 12 mmol) were added, and the mixture was heated at reflux for 4 h. The mixture was diluted with ethyl acetate (100 mL) and washed with water (100 mL). The organic phase was dried (Na$_2$SO$_4$), filtered and concentrated in vacuo. The residue was purified by chromatography (silica, EtOAc, 50 g, R$_f$ 0.35) to give the title compound (720 mg, 86.6%) as a foamy white solid. $\delta_H$ (DMSO-d$_6$) 8.50 (d, 2H, J 1.5 Hz), 8.35 (d, 1H, J 7.5 Hz), 7.52-6.90 (m, 6H), 4.33 (s, 2H), 4.32-4.28 (m, 2H), 3.61 (s, 3H), 3.40-3.30 (m, 2H), 2.28 (s, 3H), 2.05-1.95 (m, 2H), 1.90-1.82 (m, 2H), 1.39 (s, 9H). LCMS (pH10): MH$^+$ (641.8), RT 2.73 minutes.

Intermediate 242

Methyl 4-amino-1-[5-(3-{[2-(difluoromethoxy)phenyl]methyl}-7-fluoro-2-methylimidazo[1,2-a]pyridin-6-yl)pyrimidin-2-yl]piperidine-4-carboxylate Intermediate 241 (250 mg, 0.390 mmol) was dissolved in 4.0M hydrochloric acid (10 mL, 40 mmol) in 1,4-dioxane. The mixture was stirred under nitrogen for 4 h, then concentrated in vacuo. The residue was redissolved in methanol/ethyl acetate and concentrated to dryness, then dried under high vacuum for 30 minutes, to give the title compound (210 mg, 88%) as a white solid. $\delta_H$ (DMSO-d$_6$) 8.87 (br s, 3H, NH$_3^+$), 8.62 (d, 2H, J 2.2 Hz), 8.10 (d, 1H, J 9.4 Hz), 7.40-7.15 (m, 6H), 4.48 (s, 3H), 4.28-4.20 (m, 2H), 3.97-3.80 (m, 2H), 3.80 (s, 3H), 2.41 (s, 3H), 2.20-2.10 (m, 2H), 1.99-1.91 (m, 2H). LCMS (pH10): MH$^+$ (541.8), RT 2.21 minutes.

Intermediate 243

[2-(3-oxo-8-azabicyclo[3.2.1]octan-8-yl)pyrimidin-5-yl]boronic acid

Prepared from nortropan-3-one (2.00 g, 16.0 mmol) and (2-chloropyrimidin-5-yl)-boronic acid (2.53 g, 16.0 mmol) in accordance with General Method C to give the title compound (1.90 g, 48%) as a pale orange oil. $\delta_H$ (DMSO-d$_6$) 8.93 (s, 2H), 8.70 (s, 2H), 4.95-4.90 (m, 2H), 3.68-3.60 (m, 2H), 2.65-2.59 (m, 2H), 2.35-2.26 (m, 2H), 2.12-2.07 (m, 2H), 1.75-1.68 (m, 2H). LCMS (pH 3): MH$^+$ (248.8), RT 0.87 minutes.

Intermediate 244

2-(Bromomethyl)-3-{[2-(difluoromethoxy)phenyl]methyl}-7-fluoro-6-[4-(methylsulfonyl)phenyl]imidazo[1,2-a]pyridine Example 226 (180 mg, 0.3778 mmol) was dissolved in tetrahydrafuran (3 mL) at 0° C. and phosphorous tribromide (10% solution in THF, 38 µL, 0.3966 mmol) was added dropwise. After 30 minutes, the reaction mixture was quenched with water, extracted with DCM and washed with water, then dried over NaSO$_4$, filtered, evaporated onto silica and purified by column chromatography, to give a white foam-like solid, which was used without further purification. LCMS (pH 3): (M+H)+ 539.6, RT 2.46 minutes. LCMS (pH 10): (M+H)+ 541.6, RT 2.35 minutes.

Intermediate 245

6-Bromo-2-(chloromethyl)-3-{[2-(difluoromethoxy)phenyl]methyl}-7-fluoroimidazo[1,2-a]pyridine Intermediate 54 (1.0 g, 2.5 mmol) was cooled (iced bath) and thionyl chloride (10 mL, 137 mmol) was added with stirring. The reaction mixture was stirred for 1 h. The volatiles were removed in vacuo and the residue was separated between DCM and sodium bicarbonate solution. The organic layer was passed through a phase separator, then evaporated in vacuo, to give the title compound (1.0 g, 96%) as an off white solid. LCMS (ES+) 421 (M+H)$^+$, RT 2.5 minutes.

Intermediate 246

3-{3-[(6-Bromo-3-{[2-(difluoromethoxy)phenyl]methyl}-7-fluoroimidazo[1,2-a]pyridin-2-yl)methoxy]phenyl}oxazolidin-2-one Intermediate 245 (300 mg, 0.72 mmol), potassium carbonate (148 mg, 1.07 mmol) and 3-(3-hydroxyphenyl)oxazolidin-2-one (141 mg, 0.79 mmol) were stirred together in DMF (5 mL) for 2 h. Further potassium carbonate (148 mg, 1.07 mmol) was added, and the reaction mixture was stirred for a further 4 h. The reaction mixture was partitioned between ethyl acetate and water. The organic layer was dried over sodium sulphate, filtered, and evaporated in vacuo. The residue was purified by column chromatography (SiO$_2$, 10 to 100% ethyl acetate in hexanes) to give the title compound (100 mg, 24%) as a white powder. $\delta_H$ (300 MHz, DMSO-d$_6$) 8.67 (d, 1H, J 6.7 Hz), 7.70 (d, 1H, J 9.6 Hz), 7.22 (m, 6H), 7.07 (td, 1H, J 7.5, 1.2 Hz), 6.93 (dd, 1H, J 7.7, 1.5 Hz), 6.75 (m, 1H), 5.14 (s, 2H), 4.42 (m, 4H), 4.01 (m, 2H). LCMS (ES+) 564 (M+H)+, RT 2.50 minutes.

Intermediate 247

1-tert-Butyl 4-methyl 4-isopropylpiperidine-1,4-dicarboxylate

A solution of 1-tert-butyl 4-methyl piperidine-1,4-dicarboxylate (0.55 g, 2.26 mmol) and 2-iodopropane (0.32 mL, 3.2 mmol) in THF (2.5 mL) was stirred at −78° C. Lithium hexamethyldisilazane (3.2 mL, 3.2 mmol) was added, then the reaction mixture was allowed to warm to ambient temperature and stirred for 18 h. The reaction mixture was partitioned between diethyl ether and brine. The ether extract was dried (MgSO$_4$), filtered and concentrated in vacuo, to give the title compound (0.54 g, 84%) as a pale yellow syrup, which was used without further purification. $\delta_H$ (400 MHz, DMSO-d$_6$) 3.86 (m, 2H), 3.68 (m, 3H), 2.69 (m, 2H), 1.99 (m, 2H), 1.68 (m, 1H), 1.53 (m, 1H), 1.36 (s, 9H), 1.28 (m, 1H), 0.80 (d, J 6.9 Hz, 6H).

Intermediate 248

{2-[4-Isopropyl-4-(methoxycarbonyl)piperidin-1-yl]pyrimidin-5-yl}boronic acid

TFA (10 mL) was added to a stirred solution of Intermediate 247 (0.54 g, 1.90 mmol) in 1,4-dioxane (2 mL). The mixture was stirred for 2 h, then the solvent was removed by rotary evaporation and the residue was dried under vacuum for 1 h. The residual syrup was dissolved in ethanol (10 mL), then sodium carbonate (0.5 g, 4.72 mmol) and (2-chloropyrimidin-5-yl)boronic acid (0.37 g, 2.3 mmol) were added and the reaction mixture was stirred at 80° C. for 5 h. The cooled reaction mixture was filtered through celite and concentrated to dryness, to give the title compound as a foam, which was used without further purification. LCMS (pH 10): MH+ 308, RT 1.23 minutes.

Intermediate 249

Methyl 4-hydroxypiperidine-4-carboxylate

4-Hydroxy-4-piperidinecarboxylic acid hydrochloride salt (1 g, 5.1 mmol) was added to a 2% hydrochloric acid solution in methanol (25 mL) and the mixture was stirred at room temperature overnight. The solvent was removed under reduced pressure to give the title compound as the hydrochloride salt (1 g, 92%) as a white solid. $\delta_H$ (400 MHz, DMSO-d$_6$) 9.06 (broad, 2H), 5.89 (broad, 1H), 3.68 (m, 3H), 3.14 (m, 2H), 3.02 (m, 2H), 2.07 (m, 2H), 1.79 (m, 2H).

Intermediate 250

{2-[4-Hydroxy-4-(methoxycarbonyl)piperidin-1-yl]pyrimidin-5-yl}boronic acid

Prepared from Intermediate 249 in accordance with General Method C to give the title compound (1.5 g) as an off white solid, which was used without further purification. LCMS (pH 10): MH+ 282, RT 0.23 minutes.

Intermediate 251

5-Bromo-4-chloropyridin-2-amine

To a stirred solution of 2-amino-4-chloropyridine (1 g) in acetonitrile (8 mL) was added dropwise a solution of N-bromosuccinimide (1.5 g) in acetonitrile (2 mL). The reaction mixture was stirred at 25-28° C. for 1 h. The solvent was evaporated, then the residue was suspended in water and extracted with dichloromethane (2×20 mL). The organic layer was dried over anhydrous sodium sulphate, filtered and concentrated under vacuum. The resulting crude material was purified by column chromatography, using 100-200 mesh size silica and 10-25% EtOAc in hexane as eluent, to give the title compound (1 g) as a yellow solid. $\delta_H$ (400 MHz, CDCl$_3$) 8.16 (s, 1H), 6.62 (s, 1H), 4.55 (br s, 2H). LCMS: m/z 208.9, RT 2.19 minutes.

Intermediate 252

N'-(5-Bromo-4-chloropyridin-2-yl)-N,N-dimethylacetimidamide

To a stirred solution of Intermediate 251 (0.1 g) in ethanol (5 mL) was added N,N-dimethylacetamide dimethyl acetal (0.064 g) and the reaction mixture was heated at 90° C. for 1 h. The solvent was evaporated, then the residue was suspended in water and extracted with dichloromethane (3×10 mL). The organic layer was dried over anhydrous sodium sulphate, filtered and concentrated in vacuo. The resulting crude material was purified by column chromatography, using 100-200 mesh size silica and 10-25% EtOAc in hexane as eluent, to give the title compound (0.08 g) as a yellow oil. $\delta_H$ (400 MHz, CDCl$_3$) 8.39 (s, 1H), 6.86 (s, 1H), 3.06 (s, 1H), 3.06 (s, 6H), 2.02 (s, 3H). LCMS m/z 277.95, RT 2.4 minutes.

Intermediate 253

(6-Bromo-7-chloro-2-methylimidazo[1,2-a]pyridin-3-yl)[2-(difluoromethoxy)phenyl]-methanone A solution of Intermediate 252 (16 g) and Intermediate 4 (15.3 g, 0.0577 mol) in ethanol (30 mL) was heated at 100° C. for 2 h. The solvent was evaporated, then the residue was suspended in water and extracted with dichloromethane (3×25 mL). The organic layer was dried over anhydrous sodium sulphate, then filtered and concentrated in vacuo. The crude material was purified by column chromatography, using 100-200 mesh size silica and 10-25% EtOAc in hexane as eluent, to give the title compound (10.6 g) as an off-white solid. $\delta_H$ (400 MHz, DMSO-d$_6$) 9.88 (s, 1H), 8.23 (s, 1H), 7.68-7.63 (m, 1H), 7.53 (dd, J 6.0, 1.6 Hz, 1H), 7.44-7.41 (m, 2H), 7.26 (t, J 73.2 Hz, 1H), 1.89 (s, 3H). LCMS: m/z 417.1, RT 3.00 minutes.

Intermediate 254

(6-Bromo-7-chloro-2-methylimidazo[1,2-a]pyridin-3-yl)[2-(difluoromethoxy)phenyl]-methanol Sodium borohydride (1.15 g, 0.0305 mol) was added in one portion to a stirred solution of Intermediate 253 (10.6 g, 0.0254 mol) in ethanol (30 mL) at 25-28° C. The reaction mixture was quenched with aqueous ammonium chloride solution (20 mL) and further concentrated under vacuum. The residue was suspended in water and extracted with dichloromethane (3×20 mL). The combined organic layer was dried over anhydrous sodium sulphate and filtered, then concentrated under vacuum and washed with diethyl ether (2×20 mL), to obtain the title compound (10.6 g) as a yellow solid. $\delta_H$ (400 MHz, DMSO-d$_6$) 8.76 (s, 1H), 7.90 (dd, J 4.8, 2.0 Hz, 1H), 7.85 (s, 1H), 7.40-6.91 (m, 4H), 6.40 (s, 1H), 2.10 (s, 3H). LCMS m/z 219.1, RT 2.59 minutes.

Intermediate 255

6-Bromo-7-chloro-3-[2-(difluoromethoxy)benzyl]-2-methylimidazo[1,2-a]pyridine

A mixture of Intermediate 254 (10.6 g) and sodium iodide (37.9 g) in acetonitrile (40 mL) was heated at 80° C. under nitrogen for 2 h. Chlorotrimethylsilane (8.27 g) was added dropwise over 1 h, and the mixture was stirred for an additional 1 h at 80° C. The reaction mixture was concentrated under vacuum. The residue was suspended in water, extracted with dichloromethane (3×20 mL) and washed with a saturated aqueous solution of sodium bicarbonate (~20 mL). The combined organic layer was dried over anhydrous sodium sulphate, filtered and concentrated under vacuum. The crude material was purified by column chromatography, using 100-200 mesh size silica gel and 10-25% EtOAc in hexane as eluent, to give the title compound (5.2 g) as a brown solid. $\delta_H$ (400 MHz, DMSO-$d_6$) 8.67 (s, 1H), 7.87 (s, 1H), 7.43-6.99 (m, 5H), 4.32 (s, 2H), 2.27 (s, 3H).

Intermediate 256

{2-[4-(Methylsulfonyl)piperazin-1-yl]pyrimidin-5-yl}boronic acid

The title compound was synthesised from 1-(methylsulfonyl)piperazine in accordance with General Method C. MS: m/z 403.05, RT 3.20 minutes.

Intermediate 257

Ethyl 3-(2,5-dimethylbenzyl)imidazo[1,2-a]pyridine-2-carboxylate

A mixture of ethyl imidazo[1,2-a]pyridine-2-carboxylate (0.48 g, 2.5 mmoL), 2-(chloromethyl)-1,4-dimethylbenzene (0.6 mL, 3.75 mmol), palladium pivalate (15 mg, 0.05 mmol), 2-(diphenylphosphino)-2'-(N,N-dimethylamino)biphenyl (38 mg, 0.1 mmol), pivalic acid (51 mg, 0.5 mmol) and cesium carbonate (1.22 g, 3.75 mmol) in toluene (5 mL) was degassed and flushed with $N_2$ three times. The reaction mixture was heated with stirring at 110° C. until TLC or LCMS analysis indicated that the reaction was complete. The reaction mixture was allowed to cool to room temperature and evaporated in vacuo. The crude residue was suspended in EtOAc (30 mL) and washed with water. The aqueous phases were extracted with further EtOAc (4×30 mL), then the combined organic layers were dried (MgSO$_4$), filtered and concentrated in vacuo. The crude material was purified by chromatography (SiO$_2$; 2-60% EtOAc in DCM) to afford the title compound (420 mg, 55%) as a pale orange solid. $\delta_H$ (400 MHz, CDCl$_3$) 7.74 (d, J 9.2 Hz, 1H), 7.66 (d, J 7.0 Hz, 1H), 7.20-7.26 (m, 1H), 7.11 (d, J 7.7 Hz, 1H), 6.94 (d, J 7.6 Hz, 1H), 6.75 (t, J 6.9 Hz, 1H), 6.39 (s, 1H), 4.70 (s, 2H), 4.50 (q, J 7.1 Hz, 2H), 2.41 (s, 3H), 2.12 (s, 3H), 1.44 (t, J 7.1 Hz, 3H). LCMS (ES+) (M+H)+ 308, RT 2.31 minutes.

Intermediate 258

{3-[(2,5-Dimethylphenyl)methyl]imidazo[1,2-a]pyridin-2-yl}methanol

To a solution of Intermediate 257 (0.8 g, 0.025 mmol) in THF (10 mL) was added a 2M solution of borane dimethyl sulphide in THF (1.2 mL) at 0° C. The mixture was stirred at r.t. for 30 minutes and heated under reflux for 2 h, then cooled to ambient temperature and hydrolyzed with methanol (3 mL). To the mixture was added 2M aqueous sodium hydroxide solution until pH >8 was reached. The aqueous phases were extracted with EtOAc (4×30 mL), then the combined organic layers were dried (MgSO$_4$), filtered and concentrated in vacuo. The crude product was used without further purification.

Intermediate 259

{2-[4-(Hydroxymethyl)-4-methylpiperidin-1-yl]pyrimidin-5-yl}boronic acid (4-Methylpiperidin-4-yl)methanol hydrochloride (2.09 g, 12.63 mmol), (2-chloropyrimidin-5-yl)boronic acid (2 g, 12.63 mmol) and triethylamine (1.8 mL, 12.630 mmol) in ethanol (15 mL) was stirred at 80° C. overnight. The reaction mixture was cooled to r.t. and concentrated in vacuo to give the title compound as an orange semi-solid. This material was used without any further purification. HPLC-MS: MH+ m/z 252.2, RT 0.34 minutes.

Intermediate 260

{2-[4-(Sulfamoyl)piperidin-1-yl]pyrimidin-5-yl}boronic acid

Prepared from piperidine-4-sulfonamide hydrochloride (1.27 g, 6.315 mmol) and (2-chloropyrimidin-5-yl)boronic acid (1 g, 6.32 mmol) in accordance with General Method C to give the title compound as an off-white semi-solid. HPLC-MS: m/z (M−H)+ 285.1, RT 0.14 minutes.

Intermediate 261

{2-[4-(Methylsulfonyl)piperidin-1-yl]pyrimidin-5-yl}boronic acid

Prepared from 4-(methylsulfonyl)piperidine (0.515 g, 3.16 mmol) and (2-chloropyrimidin-5-yl)boronic acid (0.5 g, 3.16 mmol) in accordance with General Method C to give the title compound as an off-white semi-solid. HPLC-MS: m/z MH+ 286.2, RT 0.17 minutes.

Intermediate 262

{2-[4-(5-Hydroxy-1,3,4-oxadiazol-2-yl)piperidin-1-yl]pyrimidin-5-yl}boronic acid Prepared from 5-(piperidin-4-yl)-1,3,4-oxadiazol-2-ol hydrochloride (1.30 g, 6.32 mmol) and (2-chloropyrimidin-5-yl)boronic acid (1 g, 6.32 mmol) in accordance with General Method C to give the title compound as an off-white semi-solid. HPLC-MS: m/z (M−H)+ 290.2, RT 0.17 minutes.

Intermediate 263

6-Bromo-3-{1-[2-(difluoromethoxy)phenyl]ethyl}-7-fluoro-2-methylimidazo[1,2-a]-pyridine A solution of Intermediate 68 (15.5 g, 40.2 mmol) and methyl iodide (5.71 g, 40.2 mmol, 2.52 mL) in anhydrous tetrahydrofuran (200 mL) was cooled to between −110° C. and −100° C. under $N_2$ and potassium bis(trimethylsilyl)amide solution (1M in THF, 47 mL, 47 mmol) was added dropwise. The reaction mixture was stirred at approximately −110° C. for 1.5 h. The reaction mixture was treated with water (200 mL) and stirred overnight at 5° C. EtOAc (300 mL) was added and the layers were separated. The aqueous layer was extracted twice with EtOAc and the combined organic layers were washed with brine, then dried over Na$_2$SO$_4$, filtered and concentrated in vacuo. The resulting crude brown oil (17.8 g) was triturated with a 1:1 mixture of heptane and Et$_2$O. The resulting powder was further triturated with diisopropyl ether to give the title compound (8.9 g, 55%) as a pale brown solid. HPLC-MS (pH 3): m/z 399.0 [M+H]$^+$, RT 1.77 minutes.

Intermediate 264

6-Bromo-3-{[2-(difluoromethoxy)phenyl]methyl}-7-fluoroimidazo[1,2-a]pyridine-2-carbaldehyde The title compound can be synthesised from Intermediate 54 by treatment with a suitable oxidant such as Dess Martin Periodinane in dichloromethane and subsequent purification by column chromatography on silica gel.

Intermediates 265 to 269

The following compounds were prepared by reaction of (2-chloropyrimidin-5-yl)boronic acid with the appropriate amine according to General Method C.

| Intermediate | Name | m/z |
|---|---|---|
| 265 | [2-(4-Cyano-4-methylpiperidin-1-yl)pyrimidin-5-yl]boronic acid | 247.2 |
| 266 | [2-(1,1,3-Trioxo-3a,4,6,7-tetrahydro-[1,2,5]thiadiazolo[2,3-a]-pyrazin-5-yl)pyrimidin-5-yl]boronic acid | 314.2 |
| 267 | [2-(2-Methyl-5-oxo-1,4-diazepan-1-yl)pyrimidin-5-yl]boronic acid | 251.2 |
| 268 | [2-(7-Methyl-5-oxo-1,4-diazepan-1-yl)pyrimidin-5-yl]boronic acid | 251.2 |
| 269 | [2-(4-(2H-Tetrazol-5-yl)piperidin-1-yl)pyrimidin-5-yl]boronic acid | 276.8 |

Intermediate 270

2-{1-[7-Fluoro-2-methyl-6-(1-methyl-1H-pyrazol-4-yl)imidazo[1,2-a]pyridin-3-yl]-ethyl}phenol A suspension of Example 259 (3.7 g, 7.12 mmol) in DCM (100 mL) was cooled to 0° C. and treated with 1M boron tribromide in DCM (21.35 mL, 21.35 mmol). The resulting solution was allowed to warm to room temperature and was stirred for 16 h. The reaction mixture was cooled in an ice bath and quenched by careful addition of MeOH (8 mL). Saturated aqueous NaHCO$_3$ solution (50 mL) was added and the layers were separated. The aqueous layer was extracted with DCM. The combined organic layers were washed with 1M aqueous NaOH solution (80 mL) and brine (80 mL), then dried over Na$_2$SO$_4$ and concentrated in vacuo. The resulting crude brown foam was coated onto C18-silica gel (8 g) and purified in 3 batches by C18-reversed phase column chromatography (120 g, eluent: water to 100% acetonitrile+0.1% formic acid). The fractions containing the product were combined and neutralised (pH 7-8) by addition of saturated aqueous NaHCO$_3$ solution. The aqueous layer was extracted with DCM (3×75 ml), and the combined DCM layers were concentrated in vacuo, to afford the title compound (1.0 g, 35%) as a brown foam. LCMS (pH 10): m/z 351 [M+H]$^+$, RT 2.09 minutes.

Intermediate 271

1-(tert-Butoxycarbonyl)-4-[5-(3-{[2-(difluoromethoxy)phenyl]methyl}-2-methylimidazo-[1,2-a]pyridin-6-yl)pyrimidin-2-yl]piperazine-2-carboxylic acid Prepared from 1-(tert-butoxycarbonyl)piperazine-2-carboxylic acid and Intermediate 29 in accordance with General Method B to give the title compound (80 mg, 58%) as a solid. HPLC-MS (pH 10): m/z 595.8 [M+H]$^+$, RT 2.09 minutes.

Intermediate 272

Methyl 1-methyl-4-(trifluoromethylsulfonyloxy)cyclohex-3-ene-1-carboxylate

To a stirred solution of 1-methyl-4-oxocyclohexanecarboxylic acid methyl ester (1.05 g, 6.15 mmol) in THF (5 mL) at −78° C. was added lithium bis(trimethylsilyl)amide (6.25 mL, 1M in THF). The reaction mixture was stirred at −78° C. for 30 minutes, after which time N-phenyltrifluoromethanesulfonimide (2.20 g, 6.17 mmol) in THF (5 mL) was added and the reaction mixture was allowed to warm slowly to room temperature, then stirred for 18 h. The reaction mixture was quenched with aqueous sodium hydrogensulphate solution (15 mL) and diluted with ethyl acetate (50 mL). The layers were separated. The organic layers were washed with 5% aqueous NaOH solution (2×30 mL), saturated aqueous ammonium chloride solution (20 mL) and brine (20 mL), then dried over MgSO$_4$, filtered and concentrated in vacuo, to give the title compound (2.79 g, quantitative) as a yellow oil. $\delta_H$ (300 MHz, DMSO-d$_6$) 5.83-5.89 (m, 1H), 3.61 (s, 3H), 2.54-2.66 (m, 1H), 2.29-2.38 (m, 2H), 2.11 (dq, 1H, J 17.8, 3.1 Hz), 1.96-2.06 (m, 1H), 1.67-1.78 (m, 1H), 1.17 (s, 3H).

Intermediate 273

Methyl 1-methyl-4-(4,4,5,5-tetramethyl-1,3,2-dioxaborolan-2-yl)cyclohex-3-ene-1-carboxylate To a stirred solution of Intermediate 272 (1.77 g, 5.86 mmol) in 1,4-dioxane (50 mL) were added bis(pinacolato)diboron (4.46 g, 17.6 mmol), potassium acetate (3.46 g, 35.3 mmol) and [1,1'-bis(diphenylphosphino)ferrocene]dichloropalladium(II)-DCM adduct (338 mg, 0.41 mmol). The mixture was stirred at 90° C. for 18 h. The reaction mixture was cooled to room temperature, filtered through celite, washed with EtOAc and concentrated in vacuo. The residue was purified by column chromatography on silica gel (eluting with hexane:EtOAc, a gradient from 1:0 to 9:1), to afford the title compound (0.9 g, 55%) as a pale gum.

Intermediate 274

Methyl 4-[5-(3-{[2-(difluoromethoxy)phenyl]methyl}-7-fluoro-2-methylimidazo[1,2-a]-pyridin-6-yl)pyrimidin-2-yl]-1-methylcyclohex-3-ene-1-carboxylate A solution of Intermediate 273 (340 mg, 1.2 mmol) and Intermediate 152 (335 mg, 0.8 mmol) in 1,4-dioxane (10 mL) was treated with 2N aqueous K$_2$CO$_3$ solution (2.5 mL) and

[1,1'-bis(diphenylphosphino)ferrocene]dichloropalladium (II) (30 mg, 0.04 mmol) and heated at 100° C. under $N_2$ for 1.5 h. The reaction mixture was diluted with water (40 mL) and extracted with EtOAc (3×40 mL). The combined organic extracts were washed with water (40 mL) and brine (50 mL), dried over $MgSO_4$, filtered and concentrated in vacuo. The resulting crude brown gum was purified by FCC on silica gel (eluting with DCM/EtOAc, a gradient from 1:0 to 0:1) to give the title compound (300 mg, 70%) as a white powder. HPLC-MS (pH 10): m/z 537.2 $[M+H]^+$, RT 1.20 minutes.

General Method A

Palladium-Catalysed Suzuki Coupling

Aryl bromide (e.g. Intermediate 7 or Intermediate 68) (1 eq), boronic acid or ester (1.2 eq) and 2M aqueous sodium carbonate solution (3 eq) are dissolved in 1,4-dioxane. The mixture is degassed with three cycles of vacuum and nitrogen prior to the addition of [1,1'-bis(diphenylphosphino)ferrocene]dichloropalladium(II) (5 mol %). The reaction mixture is heated for sufficient time (typically 3-5 h) at 100° C. until TLC or LCMS indicates that the reaction is complete. After being allowed to cool to room temperature the solution is filtered through celite, diluted with water and extracted with ethyl acetate. The combined organic phases are dried over sodium sulphate and filtered, and the volatiles are removed in vacuo. The crude residue thus obtained is purified by an appropriate technique, typically column chromatography on silica gel or preparative mass-directed HPLC.

Intermediate 275

Methyl (1R,5S)-3-[5-(3-{[2-(difluoromethoxy)phenyl]methyl}-7-fluoro-2-(hydroxymethyl)imidazo[1,2-a]pyridin-6-yl)pyrimidin-2-yl]-3-azabicyclo[3.2.1]octane-8-carboxylate Prepared from Intermediate 54 and Intermediate 230 in accordance with General Method A to give the title compound (200 mg, 40%) as a pale solid. LCMS (pH 10) m/z 568.3 [M+H]+, RT 2.08 minutes.

Intermediate 276

(3R)-1-(5-Boronopyrimidin-2-yl)piperidine-3-carboxylic acid

The title compound was synthesised from (2-chloropyrimidin-5-yl)boronic acid and (3R)-piperidine-3-carboxylic acid in accordance with General Method C.

Intermediate 277

(3S)-1-(5-Boronopyrimidin-2-yl)piperidine-3-carboxylic acid

The title compound was synthesised from (2-chloropyrimidin-5-yl)boronic acid and (3S)-piperidine-3-carboxylic acid in accordance with General Method C.

Intermediate 278

(2S)-4-(5-Boronopyrimidin-2-yl)morpholine-2-carboxylic acid; triethylammonium; dichloride Prepared from (2-chloropyrimidin-5-yl)boronic acid and (2S)-morpholine-2-carboxylic acid in accordance with General Method C to give the title compound as a yellow gum. LCMS (pH 10) $MH^+$ (253.5), RT 0.2 minutes.

Intermediate 279

(2R)-4-(5-Boronopyrimidin-2-yl)morpholine-2-carboxylic acid; triethylammonium; dichloride The title compound was synthesised from (2-chloropyrimidin-5-yl)boronic acid and (2R)-morpholine-2-carboxylic acid in accordance with General Method C.

Intermediate 280

N-{(6-Bromo-2-methylimidazo[1,2-a]pyridin-3-yl)[2-(difluoromethoxy)phenyl]methyl}-acetamide To a suspension of Intermediate 6 (0.1 g, 0.26 mmol) in acetonitrile (1 mL) at room temperature was added concentrated sulphuric acid (4 drops) and the mixture was heated to 60° C. for 1 h. The reaction mixture was diluted with EtOAc (5 mL) and basified with saturated aqueous $NaHCO_3$ solution. The organic layers were separated, dried ($Na_2SO_4$), filtered and concentrated in vacuo, to give the title compound (89 mg, 80%) as a white solid. $\delta_H$ (400 MHz, DMSO-$d_6$) 9.00 (d, 1H, J 8.2 Hz), 8.28 (s, 1H), 7.58 (m, 1H), 7.48 (m, 1H), 7.44 (m, 1H), 7.34 (m, 2H), 7.20 (d, 1H, J 8.1 Hz), 7.13 (t, 1H, J 78 Hz), 6.73 (d, 1H, J 8.2 Hz), 2.01 (s, 3H), 1.96 (s, 3H). LCMS (pH 3): 426.6 MH+, RT 1.32 minutes.

Intermediate 281

(6-Bromo-2-methylimidazo[1,2-a]pyridin-3-yl)[2-(difluoromethoxy)phenyl]methanamine A mixture of Intermediate 280 (3.24 g, 7.64 mmol), 6N aqueous HCl solution (30 mL) and MeOH (30 mL) was heated at 100° C. for 7 h. The mixture was allowed to cool to room temperature, then concentrated under reduced pressure. The aqueous residue was treated until alkaline with 1N aqueous NaOH solution, and extracted with EtOAc (3 times). The combined organic extracts were washed with brine, dried over $Na_2SO_4$, filtered and concentrated under reduced pressure. The resulting off-white solid was triturated with diisopropyl ether and filtered, to afford the title compound (2.30 g, 79%) as an off-white solid. $\delta_H$ (300 MHz, DMSO-$d_6$) 8.71 (dd, 1H, J 1.8, 0.6 Hz), 7.93 (m, 1H), 7.40 (dd, 1H, J 9.4, 0.6 Hz), 7.34 (m, 2H), 7.24 (dd, 1H, J 9.5, 1.9 Hz), 7.11 (m, 2H), 5.80 (s, 1H), 2.42 (s, 2H), 2.14 (s, 3H). LCMS (pH 3): 382.6 MH+, RT 0.88 minutes.

Intermediate 282 tert-Butyl 2-{(6-bromo-2-methylimidazo[1,2-a]pyridin-3-yl)[2-(difluoromethoxy)-phenyl]methoxy}acetate To a solution of Intermediate 6 (0.65 g, 1.7 mmol) in THF (15 mL) at room temperature was added sodium hydride (0.075 g, 1.9 mmol). The mixture was stirred for 15 minutes prior to the addition of tert-butyl bromoacetate (0.36 g, 1.8 mmol, 0.27 mL). After stirring for 30 minutes, the mixture was diluted with EtOAc (50 mL) and water (25 mL). The organic layers were separated, washed with brine (20 mL) and concentrated in vacuo. The resulting crude product was subjected to column chromatography (eluent: hexane to 35% EtOAc in hexane). The resulting clear oil solidified on standing to give the title compound (0.64 g, 76%) as a white solid. $\delta_H$ (400 MHz, CDCl$_3$) 8.57 (s, 1H), 7.80 (d, 1H, J 7.5 Hz), 7.35 (m, 3H), 7.21 (d, 1H, J 9.4 Hz), 7.10 (d, 1H, J 7.8 Hz), 6.35 (s, 1H), 3.98 (s, 2H), 2.34 (s, 3H), 1.45 (s, 9H). LCMS (pH 10): MH+, 499.0 (Br isotope), RT 1.62 minutes.

Intermediate 283 tert-Butyl 2-([2-(difluoromethoxy)phenyl]{2-methyl-6-[2-(morpholin-4-yl)pyrimidin-5-yl]imidazo[1,2-a]pyridin-3-yl}methoxy)acetate Prepared from Intermediate 282 (0.6 g, 1.21 mmol) and Intermediate 38 (0.33 g, 1.56 mmol) in accordance with General Method A to provide the title compound (0.542 g, 77.2%) as an off-white foam. $\delta_H$ (400 MHz, DMSO-d$_6$) 8.71 (s, 1H), 8.67 (s, 2H), 7.92 (m, 1H), 7.56 (s, 2H), 7.43 (m, 2H), 7.20 (d, 1H, J 7.8 Hz), 7.15 (s, 1H), 6.40 (s, 1H), 4.08 (m, 2H), 3.73 (m, 8H), 2.12 (s, 3H), 1.34 (s, 9H). LCMS (pH 10): MH+ 582.2, RT 1.59 minutes.

Intermediate 284

6-Bromo-3-{1-[2-(difluoromethoxy)phenyl]ethyl}-2-methylimidazo[1,2-a]pyridine

To a degassed, cold (−78° C.) solution of Intermediate 7 (1.00 g, 2.72 mmol) in THF (10 mL) was added methyl iodide (0.427 g, 2.99 mmol, 0.187 mL). To the mixture was added dropwise a solution of potassium hexamethyldisilylazide (0.5M in toluene, 5.7 mL, 2.9 mmol). The mixture was stirred at this temperature for 1 h. Additional methyl iodide (0.05 mL) and potassium hexamethyldisilylazide (0.5M in toluene, 1 mL) were added at −78° C., and stirring was continued for a further 1 h. The mixture was quenched at −78° C. by the addition of saturated aqueous ammonium chloride solution (5 mL), warmed to room temperature, diluted with EtOAc (20 mL), washed with water (10 mL) and brine (10 mL), then dried (Na$_2$SO$_4$), filtered and concentrated in vacuo. The resulting crude brown oil was purified by column chromatography (eluent: hexane to 70% EtOAc in hexane) to give the title compound (0.94 g, 91%) as a pale solid.

Intermediate 285

6-Bromo-3-{[2-(difluoromethoxy)phenyl](methoxy)methyl}-2-methylimidazo[1,2-a]-pyridine To a solution of Intermediate 6 (0.5 g, 1.30 mmol) in methanol (10 mL) at room temperature was added concentrated sulphuric acid (0.1 g, 0.9 mmol, 0.05 mL). The mixture was heated at 60° C. overnight. The reaction mixture was concentrated in vacuo, diluted with EtOAc (30 mL) and basified by the addition of saturated aqueous Na$_2$CO$_3$ solution (~5 mL). The organic layers were separated and washed with brine (5 mL), then dried (Na$_2$SO$_4$), filtered and concentrated in vacuo. The resulting crude material was purified by column chromatography (eluent: hexane to 50% EtOAc in hexane) to give the title compound (0.418 g, 81%) as a clear colourless oil. $\delta_H$ (400 MHz, DMSO-d$_6$) 8.63 (s, 1H), 7.75 (m, 1H), 7.55 (m, 1H), 7.44 (m, 2H), 7.36 (m, 1H), 7.18 (d, 1H, J 8.0 Hz), 7.13 (t, 1H, J 78 Hz), 6.14 (s, 1H), 3.34 (s, 3H), 2.23 (s, 3H). LCMS (pH 10): MH+ 397.0 (bromine pattern), RT 1.32 minutes.

Intermediate 286

Benzyl 2-(6-bromo-2-methylimidazo[1,2-a]pyridin-3-yl)-2-[2-(difluoromethoxy)phenyl]-acetate To a cold (−78° C.) solution of Intermediate 7 (0.6 g, 1.64 mmol) in THF (10 mL) was added benzyl chloroformate (0.58 g, 3.43 mmol, 0.48 mL), followed by KHMDS (0.5M solution in toluene, 6.7 mL, 3.4 mmol). The reaction mixture was quenched by addition of saturated aqueous ammonium chloride solution (10 mL), and allowed to warm to room temperature. The mixture was diluted with EtOAc (15 mL) and stood at room temperature overnight. The organic layer was separated, and washed with water (5 mL) and brine (5 mL), then dried (Na$_2$SO$_4$), filtered and concentrated in vacuo. The resulting brown solid was subjected to column chromatography (eluent: hexane to EtOAc) to give the title compound. LCMS (pH 10): MH+ 503.0, RT 1.613 minutes.

Intermediate 287 tert-Butyl 4-(5-{3-[2-(difluoromethoxy)benzoyl]-2-methylimidazo[1,2-a]pyridin-6-yl}-pyridin-2-yl)piperazine-1-carboxylate Prepared from Intermediate 5 (0.500 g, 1.31 mmol) and tert-butyl 4-[5-(4,4,5,5-tetramethyl-1,3,2-dioxaborolan-2-yl)pyridin-2-yl]piperazine-1-carboxylate (0.562 g, 1.44 mmol) in accordance with General Method A to give the title compound (0.559 g, 76%) as an off-white solid. $\delta_H$ (400 MHz, DMSO-d$_6$) 9.83 (s, 1H), 8.52 (d, 1H, J 2.4 Hz), 8.01 (dd, 1H, J 9.2, 1.6 Hz), 7.95 (m, 1H), 7.85 (d, 1H, J 9.2 Hz), 7.66 (m, 1H), 7.56 (dd, 1H, J 7.4, 1.2 Hz), 7.43 (m, 2H), 7.13 (t, 1H, J 78 Hz), 7.02 (d, 1H, J 8.9 Hz), 3.60 (m, 4H), 3.46 (m, 4H), 1.92 (s, 3H), 1.44 (s, 9H). LCMS (pH 10): MH+ 564.2, RT 1.578 minutes.

Intermediate 288 tert-Butyl 4-[5-(3-{1-[2-(difluoromethoxy)phenyl]-1-hydroxyethyl}-2-methylimidazo-[1,2-a]pyridin-6-yl)pyridin-2-yl]piperazine-1-carboxylate To a cooled (−78° C.) solution of Intermediate 287 (0.203 g, 0.36 mmol) in THF (3 mL) was added methyllithium (0.25 mL, 0.50 mmol, 2M solution in THF). The mixture was allowed to warm to room temperature. The mixture was cooled to −78° C. and quenched by the addition of saturated aqueous ammonium chloride solution (1 mL) and water (1 mL). The mixture was allowed to warm and EtOAc (5 mL) was added. The mixture was partitioned, and the organic phases were separated and washed with brine (1 mL), then dried (Na$_2$SO$_4$), filtered and concentrated in vacuo. The residue was washed with diethyl ether, filtered, washed on a sinter with diethyl ether and sucked dry, to give the title compound (0.172 g, 82%) as an off-white powder. $\delta_H$ (400 MHz, DMSO-d$_6$) 8.23 (s, 1H), 8.15 (m, 1H), 8.08 (d, 1H, J 2.4 Hz), 7.50 (dd, 1H, J 8.8, 2.6 Hz), 7.46 (d, J 0.6 Hz), 7.45 (dd, 1H, J 9.3, 0.6 Hz), 7.38 (m, 3H), 7.13 (t, 1H, J 78 Hz), 7.03 (m, 1H), 6.93 (m, 1H), 6.27 (s, 1H), 3.53 (m, 4H), 3.44 (dd, 3H, J 3.3, 2.7 Hz), 3.32 (s, 16H), 2.57 (s, 3H), 2.06 (s, 3H), 1.44 (s, 9H). LCMS (pH 10): MH+ 580.8, RT 2.63 minutes.

Intermediate 289 tert-Butyl 4-[5-(3-{[2-(difluoromethoxy)phenyl](hydroxy)methyl}-2-methylimidazo[1,2-a]pyridin-6-yl)pyridin-2-yl]piperazine-1-carboxylate To a suspension of Intermediate 287 (0.2 g, 0.35 mmol) in methanol (5 mL) was added sodium borohydride (0.025 g, 0.66 mmol). The mixture was stirred at room temperature. After 30 minutes extra sodium borohydride (0.050 g) was added, and stirring was continued for 10 minutes. The reaction mixture was quenched by addition of saturated aqueous NH$_4$Cl solution (5 mL), and stirred overnight. The resultant mixture was filtered and washed on a sinter with diethyl ether, and dried under vacuum, to give the title compound (0.141 g, 70%) as a grey solid. $\delta_H$ (400 MHz, DMSO-d$_6$) 8.50 (s, 1H), 8.36 (d, 1H, J 1.8 Hz), 8.00 (m, 1H), 7.79 (m, 1H), 7.49 (m, 2H), 7.38 (m, 2H), 7.18 (t, 1H, J 78 Hz), 7.13 (m, 2H), 6.98 (d, 1H, J 8.9 Hz), 6.43 (d, 1H, J 4.4 Hz), 6.19 (d, 1H, J 4.1 Hz), 3.56 (m, 4H), 3.46 (m, 5H), 2.19 (s, 3H), 1.44 (s, 9H). LCMS (pH 10): MH+566.2, RT 2.29 minutes.

Intermediate 290

3-{[2-(Difluoromethoxy)phenyl]methyl}-7-fluoro-2-methyl-6-(4,4,5,5-tetramethyl-1,3,2-dioxaborolan-2-yl)imidazo[1,2-a]pyridine Intermediate 68 (1.0 g, 2.60 mmol) and 4,4,4',4',5,5,5',5'-octamethyl-2,2'-bi-1,3,2-dioxaborolane (1.85 g, 7.27 mmol) were dissolved in dry 1,4-dioxane (50 mL) under nitrogen. Potassium acetate (764.4 mg, 7.79 mmol) was added, and the mixture was degassed for 5 minutes under a stream of nitrogen. Pd(dppf)Cl$_2$ complex with DCM (106 mg, 0.13 mmol) was added, and the reaction mixture was heated at 110° C. for 5 h. The mixture was cooled to room temperature, diluted with EtOAc (200 mL) and filtered through celite. The filtrate was reduced in vacuo, then azeotroped twice with heptane (10 mL) and diethyl ether (5 mL), to afford the crude title compound (2.24 g, quantitative) as a dark brown solid/oil, which was used without further purification. Method B HPLC-MS: (M-pinacol)-H+ m/z 351, RT 0.85 minutes.

Intermediate 291

2-(5-Bromopyridin-2-yl)propan-2-ol 2,5-Dibromopyridine (5 g, 0.021 mol) was dissolved in toluene (100 mL). The mixture was cooled to −78° C. n-Butyllithium (2.5M solution in hexane, 8.44 mL, 0.021 mol) was added dropwise. The mixture was stirred for 30 minutes, followed by the addition of acetone (10 mL). The mixture was stirred for 45 minutes, then allowed to warm to room temperature for 1 h. The mixture was washed with 5% aqueous ammonium chloride solution (100 mL), water (100 mL) and brine (100 mL). The organic layer was dried over sodium sulfate, filtered and concentrated under vacuum. The residue was purified by flash chromatography (0 to 10% ethyl acetate in heptanes) to afford the title compound (2.21 g, 48%) as a yellow oil. $\delta_H$ (500 MHz, CDCl$_3$) 8.57 (d, J 2.1 Hz, 1H), 7.81 (dd, J 8.4, 2.3 Hz, 1H), 7.31 (d, J 8.4 Hz, 1H), 4.41 (s, 1H), 1.53 (s, 6H).

Intermediate 292

5-Bromo-2-{2-[(trimethylsilyl)oxy]propan-2-yl}pyridine

Intermediate 291 (1 g, 4.63 mmol) and imidazole (630 mg, 9.26 mmol) were dissolved in DCM (20 mL) and the solution was cooled in an ice bath prior to addition of chlorotrimethylsilane (553 mg, 5.09 mmol). The ice bath was removed and the reaction mixture was stirred at room temperature for 0.75 h. Additional chlorotrimethylsilane (1.65 eq) was added, and the reaction mixture was stirred for 45 minutes. The reaction mixture was washed with water (2×20 mL), then dried over magnesium sulphate and filtered. The solvent was removed under reduced pressure to afford the title compound (1.142 g, 82%) as a colourless oil. $\delta_H$ (500 MHz, CDCl$_3$) 8.54 (d, J 2.3 Hz, 1H), 7.76 (dd, J 8.5, 2.4 Hz, 1H), 7.56 (d, J 8.5 Hz, 1H), 1.58 (s, 6H), 0.15 (s, 9H).

Intermediate 293 tert-Butyl 3-(5-bromopyrimidin-2-yl)-3-hydroxyazetidine-1-carboxylate

A solution of 5-bromo-2-iodopyrimidine (2 g, 7.02 mmol) in anhydrous toluene (25 mL) was cooled to −78° C. with stirring under nitrogen, forming a thick paste. n-Butyllithium (2.5M solution in hexanes, 2.83 mL) was then added dropwise over 10 minutes. The reaction mixture was stirred at −78° C. for 30 minutes, then solid tert-butyl 3-oxoazetidine-1-carboxylate (1.33 g, 7.74 mmol) was added portionwise. The reaction mixture was allowed to warm to ambient temperature and stirred for 1 h. The reaction mixture was quenched with saturated aqueous ammonium chloride solution (20 mL) and further diluted with water (20 mL). The crude material was extracted into ethyl acetate (2×30 mL). The combined organic phases were dried over sodium sulphate, filtered and concentrated under vacuum. The resulting brown oil (2.66 g) was loaded onto a 50 g KP-silica cartridge, and eluted from a 0-90% ethyl acetate in heptane gradient using a Biotage isolera 4, to afford the title compound (1.083 g, 46%) as a yellow solid. $\delta_H$ (500 MHz, CDCl$_3$) 8.84 (s, 2H), 4.91 (s, 1H), 4.35 (d, J 9.0 Hz, 2H), 4.22 (d, J 9.1 Hz, 2H), 1.48 (s, 9H).

Intermediate 294 tert-Butyl 3-(5-bromopyrimidin-2-yl)-3-[(trimethylsilyl)oxy]azetidine-1-carboxylate A solution of Intermediate 293 (1.07 g, 3.24 mmol) and imidazole (265 mg, 3.89 mmol) in dichloromethane (20 mL) was treated with chlorotrimethylsilane (0.44 mL, 3.41 mmol) at room temperature and stirred for 1 h under nitrogen. Further imidazole (100 mg) and chlorotrimethylsilane (0.15 mL) were added, and stirring was continued at room temperature for another h. The reaction mixture was washed with water (2×20 mL). The aqueous washes were extracted with dichloromethane (20 mL), and the combined organic extracts were dried over sodium sulphate, then filtered and concentrated under vacuum. The resulting crude brown oil (1.19 g) was loaded onto a 25 g KP-silica cartridge, and eluted from a 0-30% ethyl acetate in heptane gradient using a Biotage isolera 4, to afford the title compound (814 mg, 62.4%) as a pale yellow solid. $\delta_H$ (500 MHz, CDCl$_3$) 8.82 (s, 2H), 4.48 (d, J 9.5 Hz, 2H), 4.17 (d, J 9.5 Hz, 2H), 1.45 (s, 9H), 0.05 (s, 9H).

Intermediate 295 tert-Butyl 3-[5-(4,4,5,5-tetramethyl-1,3,2-dioxaborolan-2-yl)pyrimidin-2-yl]-3-[(trimethylsilyl)oxy]azetidine-1-carboxylate To a stirring solution of Intermediate 294 (810 mg, 2.01 mmol) in 1,4-dioxane (20 mL) were added bis(pinacolato)diboron (610 mg, 2.40 mmol) and potassium acetate (600 mg, 6.11 mmol). The stirring mixture was degassed with nitrogen for 5 minutes, then Pd(dppf)Cl$_2$ complex with DCM (80 mg, 0.098 mmol) was added and the mixture was stirred at 100° C.

for 3 h. The reaction mixture was allowed to cool, then filtered through celite, washing through with ethyl acetate (30 mL). The filtrate was concentrated under vacuum. The resulting dark oil was loaded onto a 25 g KP-silica cartridge, and eluted from a 0-80% ethyl acetate in heptane gradient using a Biotage isolera 4 system, to afford the title compound (578 mg, 63.9%) as a brown solid. $\delta_H$ (500 MHz, CDCl$_3$) 9.04 (s, 2H), 4.52 (d, J 9.2 Hz, 2H), 4.17 (d, J 9.2 Hz, 2H), 1.45 (s, 9H), 1.36 (s, 12H), 0.02 (s, 9H).

Intermediate 296

3-(5-Bromopyrimidin-2-yl)oxetan-3-ol

5-Bromo-2-iodopyrimidine (2 g, 7.02 mmol) was dissolved in dry toluene (30 mL) and cooled to −78° C. under N$_2$. n-Butyllithium (2.5M solution in hexanes, 2.95 mL) was added dropwise, and the reaction mixture was aged for 30 minutes prior to dropwise addition of oxetan-3-one (0.452 mL, 7.72 mmol). The reaction mixture was stirred at −78° C. for 30 minutes, then allowed to warm to room temperature for 1 h. The reaction mixture was diluted with water (100 mL) and extracted with ethyl acetate (3×100 mL). The combined organic extracts were successively washed with water and brine, then dried over magnesium sulphate and filtered. The solvent was removed under reduced pressure. The resulting crude brown oily solid was absorbed onto a 25 g KP-Sil Biotage column with minimal DCM, and eluted using a Biotage Isolera 4 with 10-100% ethyl acetate in heptanes, to afford the title compound (687 mg, 42%) as a crystalline yellow solid. $\delta_H$ (500 MHz, DMSO-d$_6$) 9.07 (s, 2H), 6.43 (s, 1H), 4.94 (d, J 6.5 Hz, 2H), 4.67 (d, J 6.5 Hz, 2H).

Intermediate 297

5-Bromo-2-{3-[(trimethylsilyl)oxy]oxetan-3-yl}pyrimidine

Intermediate 296 (4.0 g, 17.3 mmol) and imidazole (1.76 g, 26 mmol) were stirred in DCM (80 mL). Chlorotrimethylsilane (2.85 mL, 22.5 mmol) was added dropwise and the reaction mixture was stirred at room temperature for 1 h. The reaction mixture was washed with water (2×50 mL). The aqueous phase was re-extracted using DCM (2×10 mL) and the combined organic extracts were dried over magnesium sulfate, filtered and concentrated in vacuo, to afford the title compound (4.88 g, 88%) as a colourless oil. $\delta_H$ (250 MHz, DMSO-d$_6$) 9.11 (s, 2H), 4.97 (d, J 7.0 Hz, 2H), 4.75 (d, J 7.0 Hz, 2H), −0.05 (s, 9H).

Intermediate 298

5-(4,4,5,5-Tetramethyl-1,3,2-dioxaborolan-2-yl)-2-{3-[(trimethylsilyl)oxy]oxetan-3-yl}pyrimidine In a pressure tube, a stirring solution of Intermediate 297 (4.88 g, 16.1 mmol) in 1,4-dioxane (50 mL) was treated with bis(pinacolato)diboron (4.90 g, 19.31 mmol) and potassium acetate (4.74 g, 48.28 mmol). The stirring mixture was degassed with nitrogen for 10 minutes, then Pd(dppf)Cl$_2$ complex with DCM (657 mg, 0.80 mmol) was added. The pressure tube was sealed and the contents were stirred at 80° C. for 1 h. The reaction mixture was allowed to cool, concentrated in vacuo and redissolved in ethyl acetate (100 mL). The brown solution was washed using water (50 mL) and brine (50 mL), then the organic phase was dried over magnesium sulphate and filtered and concentrated in vacuo. The resulting brown solid was triturated in 2:1 diethyl ether:heptane (40 mL) and the suspension was filtered, then the filtrate was concentrated in vacuo, to afford the title compound (7.65 g, 68% at 40% purity) as an orange solid. $\delta_H$ (500 MHz, DMSO-d$_6$) 9.00 (d, J 10.6 Hz, 2H), 5.00 (d, J 6.8 Hz, 2H), 4.75 (d, J 6.8 Hz, 2H), 1.33 (s, 12H), −0.06 (s, 9H).

Intermediate 299

5-(3-{[2-(Difluoromethoxy)phenyl]methyl}-7-fluoro-2-methylimidazo[1,2-a]pyridin-6-yl)-2-{3-[(trimethylsilyl)oxy]oxetan-3-yl}pyrimidine Intermediate 298 (400 mg, 0.8 mmol), Intermediate 68 (277.1 mg, 0.72 mmol) and a 2M solution of potassium carbonate in water (1.2 mL) were combined in 1,4-dioxane (10 mL), and the mixture was degassed thoroughly under nitrogen. Pd(dppf)Cl$_2$ complex with DCM (65 mg, 0.08 mmol) was added and the mixture was heated at 90° C. in a sealed tube for 2 h. The reaction mixture was cooled to room temperature, then diluted using ethyl acetate (10 mL) and filtered through a plug of Celite. The mixture was washed using water (10 mL), the aqueous phase was re-extracted using ethyl acetate (2×10 mL) and the combined organics were washed using brine (15 mL). The organic phase was dried over sodium sulphate, filtered and concentrated in vacuo. The resulting crude dark brown oil was purified by chromatography on silica (Biotage, 25 g cartridge), eluting with 0 to 5% methanol in dichloromethane, to afford the title compound (379 mg, 30%) as a yellow oil. LC-MS: MH+ m/z 529.5, RT 1.20 minutes.

Intermediate 300

4-(5-Bromopyrimidin-2-yl)oxan-4-ol

5-Bromo-2-iodopyrimidine (2 g, 7.02 mmol) was dissolved in dry toluene (30 mL) and cooled to −78° C. under N$_2$. n-Butyllithium (2.5M solution in hexanes, 2.95 mL) was added dropwise, and the reaction mixture was aged for 15 minutes prior to dropwise addition of tetrahydro-4H-pyran-4-one (0.77 g, 7.72 mmol). The reaction was stirred at −78° C. for 30 minutes, then allowed to warm to room temperature. The reaction mixture was diluted with water (50 mL) and extracted with ethyl acetate (2×50 mL). The combined organic extracts were dried over magnesium sulphate and filtered, then the solvent was removed under reduced pressure. The resulting crude orange oil (1.91 g) was absorbed onto a 50 g KP-Sil column, and eluted with 10-100% ethyl acetate in heptanes on a Biotage Isolera 4, to afford the title compound (762 mg, 42%) as a yellow oil. $\delta_H$ (500 MHz, CDCl$_3$) 8.79 (s, 2H), 4.24 (s, 1H), 3.99-3.89 (m, 4H), 2.37 (td, J 12.3, 11.6, 6.3 Hz, 2H), 1.54 (dd, J 13.6, 2.0 Hz, 2H).

Intermediate 301

2-(5-Chloropyrazin-2-yl)propan-2-ol

2-Bromo-5-chloropyrazine (900 mg, 4.65 mmol) was dissolved in toluene (20 mL). The reaction vessel was flushed with nitrogen and cooled to −78° C. n-Butyllithium (2.5M solution in hexanes, 2.23 mL) was added slowly under stirring and allowed to stir for a further 10 minutes upon complete addition. Acetone (3.42 mL, 46.53 mmol) was added and the reaction mixture was stirred at −78° C. for 30 minutes. The reaction mixture was allowed to warm to room temperature and the solvent was removed in vacuo. The residue was taken up in EtOAc (50 mL) and washed using saturated aqueous sodium bicarbonate solution. The organic phase was dried over sodium sulphate, filtered and concentrated in vacuo. The crude brown oil was purified by chromatography on silica (Biotage, 25 g cartridge), eluting with 0 to 100% ethyl acetate in heptanes, to afford the title compound (450 mg, 56%) as a yellow oil. Method B HPLC-MS: MH+ m/z 173, RT 1.31 minutes.

Intermediate 302

5-Bromo-2-{4-[(trimethylsilyl)oxy]oxan-4-yl}pyrimidine

Chlorotrimethylsilane (277 mg, 2.55 mmol) was added to a stirred solution of Intermediate 300 (85%, 740 mg, 2.43 mmol) and imidazole (198 mg, 2.91 mmol) in DCM (15 mL), and the reaction mixture was stirred for 1 h. Additional chlorotrimethylsilane (0.25 eq) and imidazole were added, and stirring was continued for 1 h. The reaction mixture was washed with water (2×15 mL) and the aqueous phase was re-extracted with DCM (20 mL). The combined organic extracts were dried over magnesium sulfate and concentrated under reduced pressure. The resulting yellow oil was purified on a Biotage Isolera Snap 25 g KP-Sil column, eluting with 0-15% ethyl acetate in heptanes, to afford the title compound (623 mg, 77%) as a yellow oil, which crystallised upon standing. $\delta_H$ (500 MHz, CDCl$_3$) 8.80 (s, 2H), 3.90 (td, J 11.0, 2.5 Hz, 2H), 3.74 (dt, J 11.4, 4.1 Hz, 2H), 2.26 (ddd, J 14.1, 10.4, 4.4 Hz, 2H), 1.99 (dt, J 11.6, 2.1 Hz, 2H), −0.05 (s, 9H).

Intermediate 303

5-(4,4,5,5-Tetramethyl-1,3,2-dioxaborolan-2-yl)-2-{4-[(trimethylsilyl)oxy]oxan-4-yl}-pyrimidine A round-bottom flask containing a solution of Intermediate 302 (623 mg, 1.88 mmol) in anhydrous 1,4-dioxane (25 mL) was treated with bis(pinacolato)diboron (573 mg, 2.26 mmol) and potassium acetate (0.35 mL, 5.64 mmol). The mixture was degassed with nitrogen for 10 minutes prior to addition of Pd(dppf)Cl$_2$ complex with DCM (77 mg, 0.09 mmol). The reaction mixture was stirred at 80° C. for 1 h. The reaction mixture was concentrated and redissolved in ethyl acetate (30 mL), then washed with 10% w/v citric acid solution (30 mL). The organic phase was dried (magnesium sulfate) and the solvent was removed under reduced pressure. The resulting crude brown oil was purified on Biotage Isolera (Snap 25 g KP-sil), eluting with 10-40% ethyl acetate in heptanes, to afford the title compound (228 mg) as a yellow oil that crystallised upon standing. $\delta_H$ (500 MHz, CDCl$_3$) 9.01 (s, 2H), 3.91 (t, J 9.9 Hz, 2H), 3.79-3.69 (m, 2H), 2.38-2.23 (m, 2H), 1.98 (d, J 13.2 Hz, 2H), 1.36 (s, 12H), −0.06 (s, 9H).

Intermediate 304

4-(5-Bromopyrimidin-2-yl)-1-methylpiperidin-4-ol

5-Bromo-2-iodopyrimidine (2 g, 7.02 mmol) was dissolved in dry toluene (30 mL) and cooled to −78° C. under nitrogen. n-Butyllithium (2.5M solution in hexanes, 2.95 mL) was added dropwise, and the reaction mixture was stirred for 30 minutes before dropwise addition of 1-methylpiperidin-4-one (0.9 mL, 0.01 mol). The reaction mixture was stirred at −78° C. for 1 h. The reaction mixture was allowed to warm to room temperature, then diluted with 5% aqueous ammonium chloride solution (50 mL) and extracted with ethyl acetate (3×50 mL). The combined organic extracts were washed with brine (50 mL) and dried over magnesium sulphate, then the solvent removed under reduced pressure. The resulting crude material (1.55 g) was sonicated in ethyl acetate (10 mL) and DCM (1 mL), then heptane was added. The solid that formed was filtered to afford the title compound (580 mg, 29.4%) as a brown solid. LCMS Method F: MH+: m/z 272/274, RT 1.20 minutes.

Intermediate 305

Ethyl 4-(5-bromopyrimidin-2-yl)-4-hydroxycyclohexane-1-carboxylate

5-Bromo-2-iodopyrimidine (5 g, 17.55 mmol) was dissolved in dry toluene (90 mL) and cooled to −50 to −60° C. in a dry ice/acetone bath. n-Butyllithium (2.5M solution in hexanes, 7.3 mL) was added dropwise, and the reaction mixture was aged for 20 minutes. A solution of ethyl 4-oxocyclohexanecarboxylate (2.99 g, 17.55 mmol) in toluene (10 mL) was added in one portion, and the reaction mixture was allowed to warm to r.t. and stirred for 30 minutes. The reaction mixture was quenched with water (50 mL) and extracted with EtOAc (2×100 mL). The combined organic layers were washed with brine, dried over Na$_2$SO$_4$, filtered and concentrated under vacuum. The resulting crude brown oil (6 g) was purified by chromatography on silica (Biotage, 100 g cartridge), eluting with a gradient of 0-50% ethyl acetate in heptanes, to afford a mixture of diastereoisomers of the title compound (2.99 g, 51%) as a yellow oil. Method C HPLC-MS: MH+ m/z 330, RT 1.32, 1.36 minutes.

Intermediate 306

Ethyl 4-[5-(3-{[2-(difluoromethoxy)phenyl]methyl}-7-fluoro-2-methylimidazo[1,2-a]-pyridin-6-yl)pyrimidin-2-yl]-4-hydroxycyclohexane-1-carboxylate Intermediate 305 (0.15 g, 0.46 mmol) and Intermediate 290 (50%, 0.4 g, 0.57 mmol) were dissolved in 1,4-dioxane (3 mL) and 2M aqueous K$_2$CO$_3$ solution (0.68 mL). The solution was degassed under a stream of nitrogen gas for 15 minutes. Pd(dppf)Cl$_2$ complex with DCM (17 mg, 0.02 mmol) was added and the solution was degassed for 5 minutes. The reaction mixture was heated at 100° C. under microwave irradiation for 1 h with stirring. The reaction mixture was cooled and diluted with EtOAc (5 mL), and washed with water (5 mL). The organic phase was dried over MgSO$_4$ and the solvent was removed under reduced pressure, to afford the crude title compound (101 mg, 31%) as a brown glassy oil. Method C HPLC-MS: MH+ m/z 555, RT 1.14 minutes.

Intermediate 307

1-(5-Bromopyrimidin-2-yl)cyclobutan-1-ol

5-Bromo-2-iodopyrimidine (12.5 g, 43.88 mmol) was suspended in dry toluene (250 mL), then cooled to −78° C. under N$_2$. n-Butyllithium (2.5M solution in hexanes, 20 mL) was added dropwise, and the reaction mixture was aged for 20 minutes prior to dropwise addition of a solution of cyclobutanone (3.75 g, 53.5 mmol) in dry toluene (10 mL). The reaction mixture was stirred at −78° C. for 45 minutes, then allowed to warm to room temperature. The reaction mixture was diluted with water (100 mL) and extracted with EtOAc (3×300 mL). The combined organic extracts were dried over MgSO$_4$ and the solvent removed under reduced pressure. The resulting brown oil was purified by chromatography on silica (Biotage, 340 g cartridge), eluting with a gradient of 0-100% ethyl acetate in heptanes, to afford the title compound (4.76 g) as a bright yellow solid. $\delta_H$ (500 MHz, CD$_3$OD) 8.80 (s, 2H), 2.57 (dddd, J 11.2, 5.2, 4.4, 2.5 Hz, 2H), 2.32-2.23 (m, 2H), 1.93-1.76 (m, 2H). Method C HPLC-MS: MH+ m/z 230, RT 1.06 minutes.

Intermediate 308

5-Bromo-2-{1-[(trimethylsilyl)oxy]cyclobutyl}pyrimidine

Intermediate 307 (12.18 g, 53.17 mmol) and imidazole (4.5 g, 66.1 mmol) were dissolved in DCM (50 mL) and cooled with an ice-brine bath. Chlorotrimethylsilane (7.5 mL, 59.09 mmol) was added dropwise, then the ice bath was removed and reaction was stirred at r.t. for 35 minutes. The reaction mixture was washed with saturated aqueous NaHCO$_3$ solution (2×150 mL), then the organic layer was dried over MgSO$_4$, filtered and concentrated under vacuum, to afford the title compound (14.2 g, 84.2%) as a dark yellow oil. $\delta_H$ (500 MHz, CD$_3$OD) 8.91 (s, 2H), 2.76 (tt, J 8.6, 3.1 Hz, 2H), 2.43 (qd, J 9.6, 2.7 Hz, 2H), 1.85 (tdd, J 13.1, 6.7, 3.3 Hz, 1H), 1.69-1.55 (m, 1H), −0.02 (s, 9H).

Intermediate 309

5-(4,4,5,5-Tetramethyl-1,3,2-dioxaborolan-2-yl)-2-{1-[(trimethylsilyl)oxy]cyclobutyl}-pyrimidine Intermediate 308 (12.7 g, 42.2 mmol), 4,4,4',4',5,5,5',5'-octamethyl-2,2'-bi-1,3,2-dioxaborolane (12.7 g, 50.0 mmol) and potassium acetate (12.5 g, 127.4 mmol) were added to a sealed tube with anhydrous 1,4-dioxane (100 mL). The mixture was degassed by bubbling with nitrogen for 30 minutes. Pd(dppf)Cl$_2$ complex with DCM (1.75 g, 2.14 mmol) was added and the mixture was sealed under nitrogen. The reaction mixture was stirred at 80° C. for 4 h. The reaction mixture was allowed to cool to r.t., then diluted with EtOAc (150 mL) and water (100 mL). The aqueous phase was separated and the organic phases were washed with saturated aqueous NaHCO$_3$ solution (100 mL) and brine (100 mL), then dried over sodium sulfate and concentrated under vacuum. The resulting dark brown oil was dissolved in a mixture of diethyl ether and heptanes and the solid was filtered off. The filtrate was concentrated under vacuum. The resulting orange oil was dissolved in heptanes and the solid was filtered off. The filtrate was concentrated under vacuum to afford the title compound (16.7 g, 93.8%) as an orange-brown viscous oil. $\delta_H$ (500 MHz, CDCl$_3$) 9.03 (s, 2H), 2.79 (tt, J 8.6, 3.2 Hz, 2H), 2.53-2.41 (m, 2H), 1.86 (dddd, J 13.2, 9.9, 6.7, 3.4 Hz, 1H), 1.70-1.60 (m, 1H), 1.36 (s, 16H), 1.27 (s, 11H), 1.26 (s, 7H), −0.03 (s, 9H).

Intermediate 310

4-(5-Bromopyridin-2-yl)oxan-4-ol

A solution of 2,5-dibromopyridine (1 g, 4.22 mmol) in anhydrous toluene (15 mL) was cooled to −78° C. with stirring under nitrogen. n-Butyllithium (2.5M solution in hexanes, 1.7 mL) was added dropwise over 10 minutes. The reaction mixture was stirred at −78° C. for 1 h, then tetrahydro-4H-pyran-4-one (0.43 mL, 4.66 mmol) was added slowly. The reaction mixture was allowed to warm to ambient temperature, then stirred for 2 h. The reaction mixture was quenched with saturated aqueous ammonium chloride solution (20 mL) and extracted into ethyl acetate (2×20 mL). The combined organic phases were dried over sodium sulfate and concentrated under vacuum. The resulting pale brown oil (983 mg) was purified by chromatography on silica (Biotage, 25 g cartridge), eluting with 0-60% ethyl acetate in heptanes. The resulting yellow solid (578 mg) was re-purified by chromatography on silica (Biotage, 10 g cartridge), eluting with 0-50% ethyl acetate in heptanes, to afford the title compound (363 mg, 32.3%) as a yellow solid. $\delta_H$ (500 MHz, DMSO-d$_6$) 8.60 (d, J 2.2 Hz, 1H), 7.86 (dd, J 8.4, 2.3 Hz, 1H), 7.31 (d, J 8.4 Hz, 1H), 4.67 (s, 1H), 3.98 (td, J 11.7, 1.8 Hz, 2H), 3.94-3.89 (m, 2H), 2.11 (td, J 12.7, 5.5 Hz, 2H), 1.56 (d, J 12.2 Hz, 2H). Method B HPLC-MS: MH+ m/z 258/260, RT 1.44 minutes.

Intermediate 311

[2-(Difluoromethoxy)phenyl]{7-fluoro-6-[2-(1-hydroxy-1-methylethyl)pyrimidin-5-yl]-2-methylimidazo[1,2-a]pyridin-3-yl}methanone Prepared from Intermediate 66 (500 mg, 1.25 mmol) and 2-[5-(4,4,5,5-tetramethyl-1,3,2-dioxaborolan-2-yl)pyrimidin-2-yl]propan-2-ol (1.75 mmol) in accordance with General Method A to afford the title compound as an off white solid. $\delta_H$ (400 MHz, DMSO-d$_6$) 9.85 (d, 1H, J 7.5 Hz), 9.10 (d, 2H, J 1.2 Hz), 7.96 (d, 1H, J 10.4 Hz), 7.67 (m, 1H), 7.55 (dd, H, J 7.5, 1.6 Hz), 7.45 (m, 2H), 7.30 (t, 1H, J 78 Hz), 5.19 (s, 1H), 1.94 (s, 3H), 1.57 (s, 6H). LCMS (pH 10): m/z 457 (M+H)$^+$, RT 1.99 minutes.

Intermediate 312

N-{[1-(5-Bromopyrimidin-2-yl)cyclopropyl]methyl}acetamide

Intermediate 307 (380 mg, 1.66 mmol) was dissolved in acetonitrile (10 mL) and treated with H$_2$SO$_4$ (0.5 mL, 9.38 mmol). The mixture was stirred at 65° C. for 18 h. The reaction mixture was cooled to room temperature and poured onto ice/water (50 mL). The pH was adjusted to ~10 using a 5M aqueous solution of NaOH and the crude material was extracted with EtOAc (3×50 mL). The combined organic layers were washed with brine (50 mL), dried over MgSO$_4$ and concentrated under vacuum, to afford the title compound (166 mg, 28%) as a yellow oil, which was used without further purification. $\delta_H$ (500 MHz, CD$_3$OD) 8.62 (s, 2H), 6.65 (s, 1H), 3.64 (d, J 6.2 Hz, 2H), 2.01 (s, 3H), 1.34 (q, J 4.0 Hz, 2H), 1.22-1.16 (m, 2H).

Intermediate 313

1-[2-(Difluoromethoxyoxy)-5-fluorophenyl]ethan-1-one

Potassium hydroxide (40 g, 714 mmol) was dissolved in water (100 mL) and acetonitrile (100 mL). The reaction mixture was cooled to −78° C. 1-(5-Fluoro-2-hydroxyphenyl)ethan-1-one (5 g, 32.44 mmol) was added to the reaction mixture and stirred for 5 minutes at −78° C. Diethyl[bromo(difluoro)methyl]phosphonate (11.5 mL, 64.88 mmol) was added dropwise to the mixture. The reaction mixture was stirred at −78° C. for 30 minutes, then warmed to room temperature over 1.5 h. The reaction mixture was diluted using EtOAc (2×100 mL). The mixture was washed with brine (50 mL). The organic phase was dried over sodium sulfate and concentrated in vacuo. The crude orange oil was purified by chromatography on silica (Biotage, 100 g cartridge), eluting with 0 to 40% ethyl acetate in heptanes, to afford the title compound (4.86 g, 74%) as a clear oil. $\delta_H$ (500 MHz, CDCl$_3$) 7.47 (ddd, J 0.5, 3.0, 8.5 Hz, 1H), 7.24-7.14 (m, 2H), 6.55 (t, J 73.3 Hz, 1H), 2.62 (s, 3H). Method B HPLC-MS: RT 1.84 minutes, no mass ion observed.

Intermediate 314

2-Bromo-1-[2-(difluoromethoxy)-5-fluorophenyl]ethan-1-one

To a stirred solution of Intermediate 313 (4.45 g, 21.8 mmol) in acetic acid (210 mL) was added pyridinium tribromide (6.95 g, 21.8 mmol), followed by hydrogen bromide (3.0 mL, 12.31 mmol). The reaction mixture was stirred at room temperature for 18 h. The solvent was removed under reduced pressure and the residue was quenched with saturated aqueous NaHCO$_3$ solution (50 mL). The aqueous layer was extracted with ethyl acetate (3×25 mL). The organic extracts were combined, washed with water (3×25 mL) and brine (25 mL), then dried over Na$_2$SO$_4$. The solvent was removed under reduced pressure to afford the title compound (5.75 g, 75%) as a red solid. $\delta_H$ (250 MHz, CDCl$_3$) 7.52 (ddd, J 0.5, 2.5, 8.5 Hz, 1H), 7.25-7.15 (m, 2H), 6.59 (t, J 72.5 Hz, 1H), 4.49 (s, 2H). Method B HPLC-MS: RT 1.90 minutes, no mass ion observed.

Intermediate 315

6-Bromo-3-[2-(difluoromethoxy)-5-fluorobenzoyl]-7-fluoro-2-methylimidazo[1,2-a]-pyridine Intermediate 65 (260 mg, 1 mmol) was dissolved in toluene (5 mL), Intermediate 314 (371.3 mg, 1.05 mmol) was added, and mixture were heated at 100° C. for 3 h. The mixture was cooled to room temperature and evaporated under reduced pressure. The residue was dissolved in ethyl acetate (10 mL) and washed with 10% aqueous citric acid solution (10 mL), brine (10 mL) and water (10 mL). The solvent was removed under reduced pressure and the crude product was purified by chromatography on silica (Biotage, 10 g cartridge), eluting with 0 to 80% ethyl acetate in heptanes, to afford the title compound (417 mg, 32%) as a yellow solid. $\delta_H$ (250 MHz, DMSO-d$_6$) 9.85 (d, J 6.9 Hz, 1H), 7.97 (d, J 9.1 Hz, 1H), 7.49 (m, 3H), 7.20 (t, J 72.5 Hz, 1H), 1.93 (s, 3H). Method A HPLC-MS: MH+ m/z 418, RT 1.36 minutes.

Intermediate 316

{6-Bromo-7-fluoro-2-methylimidazo[1,2-a]pyridin-3-yl}[2-(difluoromethoxy)-5-fluorophenyl]methanol Intermediate 315 (0.41 g, 0.99 mmol) was dissolved in MeOH (10 mL). NaBH$_4$ (79 mg, 2.08 mmol) was added, and the mixture was stirred for 1 h at room temperature. The reaction mixture was concentrated under vacuum before being diluted with EtOAc (50 mL) and washed with aqueous NaHCO$_3$ solution (20 mL). The organic phase was dried over Na$_2$SO$_4$, and concentrated under vacuum, to afford the title compound (335 mg, 81%) as a brown solid, which was used without further purification. $\delta_H$ (500 MHz, CDCl$_3$) 8.43 (d, J 6.5 Hz, 1H), 7.40 (dd, J 8.8, 2.9 Hz, 1H), 7.24 (d, J 8.4 Hz, 1H), 7.13-7.02 (m, 2H), 6.42 (s, 1H), 6.37 (t, J 73.3 Hz, 1H), 2.30 (s, 3H). Method B HPLC-MS: MH+ m/z 420, RT 1.60 minutes.

Intermediate 317

6-Bromo-3-{[2-(difluoromethoxy)-5-fluorophenyl]methyl}-7-fluoro-2-methylimidazo-[1,2-a]pyridine Intermediate 316 (374 mg, 0.89 mmol) was dissolved in DCM (4 mL) and triethylsilane (296 μL, 1.78 mmol) was added. Methanesulfonic acid (286 μL, 4.46 mmol) was added dropwise at 0° C. The biphasic mixture was stirred at room temperature for 30 minutes. Triethylsilane (296 μL, 1.78 mmol) and methanesulfonic acid (286 μL, 4.46 mmol) were added to the mixture at room temperature and stirred for 18 h. The mixture was diluted with DCM (15 mL), then washed with saturated aqueous NaHCO$_3$ solution and brine. The organic phase was dried over MgSO$_4$ and filtered, then the filtrate was evaporated under reduced pressure. The crude product was purified by chromatography on silica (Biotage, 10 g cartridge), eluting with 0 to 15% MeOH in DCM, to afford the title compound (268 mg, 74%) as a yellow solid. $\delta_H$ (500 MHz, DMSO-d$_6$) 8.66 (d, J 6.7 Hz, 1H), 7.56 (d, J 9.7 Hz, 1H), 7.25 (dd, J 9.0, 4.7 Hz, 1H), 7.21 (t, J 75 Hz 1H), 7.17 (td, J 8.5, 3.1 Hz, 1H), 6.87 (dd, J 9.2, 3.1 Hz, 1H), 4.31 (s, 2H), 2.25 (s, 3H). Method B HPLC-MS: MH+ m/z 404, RT 1.55 minutes.

Intermediate 318

3-(5-Bromopyrazin-2-yl)oxetan-3-ol 2,5-Dibromopyrazine (1 g, 4.2 mmol) was dissolved in toluene (20 mL) under nitrogen and cooled to −78° C. n-Butyllithium (2.5M solution in hexanes, 1.77 mL) was added slowly with stirring and allowed to stir for a further 10 minutes upon complete addition. Oxetan-3-one (270 μL, 4.62 mmol) was added, and the reaction mixture was stirred at −78° C. for 30 minutes. The reaction mixture was allowed to warm to room temperature and the solvent was removed in vacuo. The residue was taken up in DCM (50 mL) and washed with saturated aqueous sodium bicarbonate solution (40 mL). The aqueous layer was re-extracted with DCM (50 mL). The organic extracts were combined, dried over sodium sulfate and concentrated in vacuo. The crude brown oil was purified by chromatography on silica (Biotage, 25 g cartridge), eluting with 0 to 100% ethyl acetate in heptanes, to afford the title compound (470 mg, 45%) as a yellow solid. Method B HPLC-MS: MH+ m/z 231, RT 1.13 minutes.

Intermediate 319

3-(5-Bromopyrimidin-2-yl)oxolan-3-ol

5-Bromo-2-iodopyrimidine (10 g, 35.1 mmol) was dissolved in dry toluene (100 mL) and cooled to −78° C. under N$_2$. n-Butyllithium (2.5M solution in hexanes, 14.7 mL) was added dropwise and the reaction mixture was aged for 30 minutes prior to dropwise addition of oxolan-3-one (2.97 mL, 38.6 mmol). The reaction mixture was stirred at −78° C. for 30 minutes, then allowed to warm to room temperature for 1 h. The reaction mixture was diluted with water (200 mL) and extracted with ethyl acetate (3×200 mL). The combined organic extracts were washed successively with water and brine, then dried over magnesium sulphate. The solvent was removed under reduced pressure to afford a dark yellow oil. The crude material was purified by chromatography on silica (Biotage, 100 g cartridge), eluting with 0-100% ethyl acetate in heptanes, to afford the title compound (2.15 g, 25% at 86% purity) as a yellow oil. $\delta_H$ (500 MHz, DMSO-d$_6$) 9.01 (s, 2H), 5.66 (s, 1H), 3.99-3.93 (m, 2H), 3.88-3.77 (m, 2H), 2.46 (dt, J 12.6, 8.9 Hz, 1H), 2.16 (ddd, J 12.6, 6.4, 3.5 Hz, 1H).

Intermediate 320

Ethyl (3S)-1-[5-(3-{[2-(difluoromethoxy)phenyl]methyl}-2-methylimidazo[1,2-a]pyridin-6-yl)pyrimidin-2-yl]-3-methylpiperidine-3-carboxylate Intermediate 29 (150 mg, 0.37 mmol), ethyl (3S)-3-methylpiperidine-3-carboxylate (85 mg, 0.5 mmol) and triethylamine (0.26 mL, 1.87 mmol) were suspended in 1-methyl-2-pyrrolidone (3 mL) and the reaction mixture was heated three times for 1 h at 160° C. under microwave irradiation. After cooling to room temperature, the reaction mixture was diluted with dichloromethane (20 mL) and a saturated solution of sodium bicarbonate in water (10 mL). The organic phase was separated and washed with brine, then dried over sodium sulfate, filtered and concentrated under vacuum. The resulting residue was purified by preparative HPLC (Method C) to afford the title compound (75 mg, 22%) as a light brown solid. $\delta_H$ (500 MHz, CD$_3$OD) 8.42-8.37 (m, 2H), 8.06 (s, 1H), 7.49 (d, J 9.2 Hz, 1H), 7.40-7.33 (m, 1H), 7.26 (t, J 7.6 Hz, 1H), 7.19 (d, J 8.1 Hz, 1H), 7.10 (t, J 7.4 Hz, 1H), 7.00-6.75 (m, 2H), 4.54 (d, J 13.2 Hz, 1H), 4.34 (s, 2H), 4.10-4.08 (m, 1H), 4.03 (qq, J 8.2, 3.7 Hz, 2H), 3.44-3.35 (m, 1H), 3.29 (d, J 12.3 Hz, 1H), 2.42 (s, 3H), 2.20-2.12 (m, 1H), 1.70-1.57 (m, 2H), 1.53 (ddd, J 13.4, 9.3, 4.5 Hz, 1H), 1.17 (s, 3H), 1.11 (t, J 7.1 Hz, 3H).

Intermediate 321 cis-1-(tert-Butyl)4-methyl-3-methylpiperidine-1,4-dicarboxylate (Racemic)

cis-1-(tert-Butoxycarbonyl)-3-methylpiperidine-4-carboxylic acid (935 mg, 3.84 mmol) was dissolved in DMF (10 mL) under nitrogen and potassium carbonate (800 mg, 5.79 mmol) was added, followed by iodomethane (290 μL, 4.66 mmol). The reaction mixture was stirred under nitrogen overnight. The reaction mixture was diluted with ethyl acetate (30 mL), and washed with water (25 mL) and brine (25 mL), then dried over sodium sulfate and concentrated, to afford the title compound (containing 16% of the trans isomer) (940 mg, 95%) as a pale oil. $\delta_H$ (500 MHz, CDCl$_3$) 4.00 (s, 1H), 3.77 (ddd, J 13.3, 4.3, 1.2 Hz, 1H), 3.68 (s, 3H), 3.07 (dd, J 13.3, 3.4 Hz, 1H), 2.89 (s, 1H), 2.59 (dt, J 10.5, 4.3 Hz, 1H), 2.24-2.13 (m, 1H), 1.90-1.74 (m, 1H), 1.74-1.59 (m, 1H), 1.45 (s, 9H), 0.89 (d, J 7.0 Hz, 3H). Method D HPLC-MS: MH+ m/z 258, RT 3.24 minutes.

Intermediate 322 cis-Methyl 3-methylpiperidine-4-carboxylate hydrochloride (Racemic)

Intermediate 321 (940 mg, 3.65 mmol) was dissolved in a 4M solution of hydrogen chloride in 1,4-dioxane (10 mL) and stirred under nitrogen for 2 h. The reaction mixture was concentrated to afford the title compound (containing 17% of the trans isomer) (1.02 g, 100% as a white solid. $\delta_H$ (500 MHz, CD$_3$OD) 3.71 (s, 3H), 3.39-3.32 (m, 1H), 3.24 (dd, J 12.7, 8.5 Hz, 1H), 3.20-3.12 (m, 2H), 2.92-2.84 (m, 1H), 2.42-2.26 (m, 1H), 2.13-1.95 (m, 2H), 1.03 (d, J 7.2 Hz, 3H).

Intermediate 323 cis-methyl 1-[5-(3-{[2-(difluoromethoxy)phenyl]methyl}-2-methylimidazo[1,2-a]pyridin-6-yl)pyrimidin-2-yl]-3-methylpiperidine-4-carboxylate Intermediate 29 (400 mg, 1 mmol) was dissolved in 1-methyl-2-pyrrolidone (4 mL) and Intermediate 322 (75%, 390 mg, 1.51 mmol) was added, followed by triethylamine (310 μL, 2.22 mmol). The reaction mixture was heated at 120° C. under microwave irradiation for 45 minutes. The reaction mixture was partitioned between ethyl acetate (6 mL) and water (4 mL), then the organic layer was separated, washed with brine (4 mL), dried over sodium sulfate and concentrated to dryness. The residue was purified by column chromatography (Biotage, KP-NH cartridge), eluting with 0 to 80% ethyl acetate in heptane, affording a yellow gum (250 mg), which was further purified by preparative HPLC (Method A) to afford the title compound (126 mg, 24%) as a pale yellow solid. $\delta_H$ (500 MHz, CD$_3$OD) 8.47 (s, 2H), 8.18 (s, 1H), 7.57 (d, J 9.3 Hz, 1H), 7.51 (dd, J 9.3, 1.5 Hz, 1H), 7.30 (t, J 6.9 Hz, 1H), 7.21 (d, J 8.1 Hz, 1H), 7.15 (t, J 7.5 Hz, 1H), 7.10 (d, J 7.6 Hz, 1H), 6.92 (t, J 74.0 Hz, 1H), 4.54 (d, J 13.3 Hz, 1H), 4.40 (s, 3H), 3.70 (s, 3H), 3.43 (dd, J 13.2, 3.3 Hz, 1H), 3.29-3.24 (m, 1H), 2.87-2.78 (m, 1H), 2.44 (s, 3H), 2.31 (d, J 6.9 Hz, 1H), 1.89 (qd, J 10.1, 5.2 Hz, 1H), 1.82-1.72 (m, 1H), 0.88 (d, J 7.0 Hz, 3H). Method D HPLC-MS: MH+ m/z 521, RT 2.50 minutes.

Intermediate 324 trans-Methyl 1-[5-(3-{[2-(difluoromethoxy)phenyl]methyl}-2-methylimidazo[1,2-a]-pyridin-6-yl)pyrimidin-2-yl]-3-methylpiperidine-4-carboxylate Sodium (50 mg, 2.17 mmol) was added to anhydrous methanol (2.5 mL) under nitrogen and stirred until dissolution was complete. A solution of Intermediate 323 (80%, containing 16% trans isomer, 215 mg, 0.41 mmol) in anhydrous methanol (2.5 mL) was added under nitrogen and the reaction mixture was heated at 68° C. under nitrogen for 2 h. The reaction mixture was added to saturated aqueous ammonium chloride solution (10 mL), which was then basified to pH 9 by addition of saturated aqueous sodium bicarbonate solution. The resulting suspension was extracted into ethyl acetate (20 mL), washed with brine (10 mL), dried over sodium sulfate and concentrated to dryness. The resulting yellow gum was purified by preparative HPLC (Method A) to afford the title compound (66 mg, 31%) as a pale yellow solid. $\delta_H$ (500 MHz, DMSO-d$_6$) 8.49 (s, 2H), 8.16 (s, 1H), 7.54 (d, J 9.3 Hz, 1H), 7.47 (dd, J 9.3, 1.7 Hz, 1H), 7.29 (t, J 7.8 Hz, 1H), 7.21 (d, J 8.1 Hz, 1H), 7.14 (t, J 7.5 Hz, 1H), 7.10-6.75 (m, 2H), 4.80 (s, 1H), 4.73 (dd, J 14.0, 3.5 Hz, 1H), 4.40 (s, 2H), 3.69 (s, 3H), 2.94 (td, J 13.1, 2.8 Hz, 1H), 2.62 (dd, J 13.3, 11.3 Hz, 1H), 2.44 (s, 3H), 2.33 (td, J 11.7, 3.8 Hz, 1H), 1.98-1.87 (m, 1H), 1.87-1.75 (m, 1H), 1.72-1.56 (m, 1H), 0.95 (d, J 6.6 Hz, 3H). Method D HPLC-MS: MH+ m/z 521, RT 2.56 minutes.

Intermediate 325

Methyl (2S)-2-{[(tert-butoxy)carbonyl]amino}-5-(3-{[2-(difluoromethoxy)phenyl]-methyl}-2-methylimidazo[1,2-a]pyridin-6-yl)pent-4-ynoate Intermediate 7 (1.2 g, 3.27 mmol 1), methyl (2S)-2-{[(tert-butoxy)carbonyl]amino}-pent-4-ynoate (891.23 mg, 3.92 mmol) and diethylamine (675 µL, 6.55 mmol) were combined in DMF (20 mL) and the mixture was degassed under nitrogen. CuI (62 mg, 0.33 mmol) and PdCl$_2$(PPh$_3$)$_2$ (115 mg, 0.16 mmol) were added and the mixture was heated at 80° C. under nitrogen for 16 h. The mixture was diluted with ethyl acetate (100 mL) and filtered through celite. The solids were washed with further ethyl acetate (30 mL) and the filtrate was washed with water (3×50 mL), followed by brine (50 mL). The organic layer was dried over sodium sulfate and concentrated under vacuum. The resulting dark brown oil (~3 g) was dissolved in a minimum of DCM and loaded onto a 100 g silica cartridge, eluting with a gradient of 0-10% methanol in DCM. Product fractions were concentrated under vacuum to afford the title compound (1.8 g, 64%) as a brown gum. Method B HPLC-MS: MH+ m/z 514, RT 1.73 minutes.

Intermediate 326

Methyl (2S)-2-amino-5-(3-{[2-(difluoromethoxy)phenyl]methyl}-2-methylimidazo[1,2-a]pyridin-6-yl)pent-4-ynoate Intermediate 325 (60%, 1.8 g, 2.1 mmol) was suspended in 4M HCl in 1,4-dioxane (10 mL, 40 mmol) and the mixture was stirred at room temperature for 5 h. The mixture was concentrated under vacuum, then the residue was dissolved in methanol (~20 mL) and divided across two pre-conditioned 10 g SCX cartridges. These were each washed with methanol (50 mL) followed by 7M ammonia in methanol (50 mL). The ammonia fractions were combined and concentrated under vacuum. The resulting brown oil (1.5 g) was dissolved in a minimum of DCM and loaded onto a 50 g silica cartridge, eluting with a gradient of 0-10% methanol in DCM, to afford the title compound (651 mg, 75%) as a pale orange oil that solidified upon standing. $\delta_H$ (500 MHz, CDCl$_3$) 7.85 (s, 1H), 7.60 (d, J 8.8 Hz, 1H), 7.28 (d, J 7.3 Hz, 1H), 7.21-7.15 (m, 2H), 7.09 (t, J 7.5 Hz, 1H), 6.84-6.51 (m, 2H), 4.24 (s, 2H), 3.75 (s, 3H), 3.72-3.69 (m, 1H), 2.83 (dd, J 8.3, 5.8 Hz, 2H), 2.50 (s, 3H).

Intermediate 327

Methyl (2S)-5-(3-{[2-(difluoromethoxy)phenyl]methyl}-2-methylimidazo[1,2-a]pyridin-6-yl)-3,4-dihydro-2H-pyrrole-2-carboxylate Intermediate 326 (651 mg, 1.57 mmol) was dissolved in acetonitrile (10 mL) and silver(I) trifluoromethanesulfonate (41 mg, 0.16 mmol) was added. The mixture was stirred for 5 h at room temperature in the dark, then left to stand at ambient temperature over the weekend. The mixture was concentrated under vacuum. The residue was dissolved in ethyl acetate (30 mL) and washed with water (30 mL). The aqueous phase was extracted with ethyl acetate (20 mL), then the combined organic layers were dried over sodium sulfate and concentrated under vacuum, to afford the title compound (720 mg, 99.5%) as an orange gum. $\delta_H$ (500 MHz, CDCl$_3$) 8.32 (s, 1H), 8.01 (d, J 9.4 Hz, 1H), 7.82 (s, 1H), 7.30 (t, J 7.8 Hz, 1H), 7.18 (d, J 8.1 Hz, 1H), 7.14 (t, J 7.6 Hz, 1H), 6.99 (d, J 7.2 Hz, 1H), 6.68 (t, J 73.4 Hz, 1H), 4.92 (t, J 7.5 Hz, 1H), 4.31 (s, 2H), 3.79 (s, 3H), 3.10-2.98 (m, 1H), 2.88 (m, 1H), 2.59 (s, 3H), 2.37 (m, 1H), 2.29 (m, 1H).

Intermediate 328

Methyl (2S)-5-(3-{[2-(difluoromethoxy)phenyl]methyl}-2-methylimidazo[1,2-a]pyridin-6-yl)pyrrolidine-2-carboxylate Intermediate 327 (90%, 720 mg, 1.57 mmol) was dissolved in methanol (10 mL) and cooled to 0° C. under nitrogen. NaBH$_3$CN (148 mg, 2.36 mmol) was added, and the mixture was warmed to room temperature and stirred for 16 h. Further NaBH$_3$CN (200 mg, 3.18 mmol) was added and the mixture was stirred at r.t. for 3 h. Acetic acid (0.11 ml, 1.92 mmol) and further NaBH$_3$CN (200 mg, 3.18 mmol) were added and the mixture was stirred at r.t. for 2 h. The solvent was removed under vacuum, and saturated aqueous ammonium chloride (10 mL) was added to the residue. The mixture was extracted with DCM (3×30 mL), then the combined organic layers were dried over sodium sulfate and concentrated under vacuum. The residue was dissolved in a minimum of DCM and loaded onto a 25 g silica cartridge, eluting with a gradient of 0-10% methanol in DCM, to afford the title compound (482 mg, 74%) as a pale yellow gum. Method D HPLC-MS: MH+ m/z 416, RT 1.21 minutes.

Example 1

N-(2,5-Dichlorophenyl)-6-(6-methoxypyridin-3-yl)-2-methylimidazo[1,2-a]pyridin-3-amine To a mixture of Intermediate 1 (0.20 g, 1 mmol), acetaldehyde (89 mg, 1 mmol) and n-butanol (1 mL) in a microwave vial were added 1,4-dichloro-2-isocyanobenzene (0.17 g, 0.11 mL, 1 mmol) and ZrCl$_4$ (0.023 g, 10 mol %). The vessel was sealed and the mixture was heated under microwave irradiation at 140° C. for 7 minutes. After cooling to room temperature, the reaction mixture was diluted with DCM (5 mL), washed with 1M hydrochloric acid (2×5 mL), dried over sodium sulfate and concentrated under vacuum. The resulting crude brown oil was purified by preparative HPLC (Preparative Method A) to afford the title compound (19 mg, 4.3%) as a white solid. $\delta_H$ (500 MHz, CDCl$_3$) 8.25 (d, J 2.5 Hz, 1H), 7.92 (s, 1H), 7.85 (d, J 9.3 Hz, 1H), 7.68 (dd, J 8.6, 2.6 Hz, 1H), 7.54 (dd, J 9.3, 1.6 Hz, 1H), 7.25 (d, J 8.5 Hz, 1H), 7.20 (s, 1H), 6.82-6.70 (m, 2H), 6.20-6.10 (m, 1H), 3.90 (s, 3H), 2.37 (s, 3H). Method A HPLC-MS: MH+ m/z 399, RT 3.49 minutes.

Example 2

3-[2-(Difluoromethoxy)benzyl]-6-(6-methoxy-5-methylpyridin-3-yl)-2-methylimidazo[1,2-a]pyridine Intermediate 7 (77 mg, 0.21 mmol) and 6-methoxy-5-methylpyridin-3-ylboronic acid (52 mg, 0.31 mmol) were dissolved in 1,4-dioxane (3 mL) and 2M aqueous potassium carbonate solution (0.38 mL) was added. The mixture was degassed with nitrogen, and bis[3-(diphenylphosphanyl)cyclopenta-2,4-dien-1-yl]iron-dichloropalladium-dichloromethane complex (4.5 mg, 0.01 mmol) was added. The mixture was heated at 90° C. under nitrogen for 16 h. LCMS showed incomplete conversion, so further 6-methoxy-5-methylpyridin-3-ylboronic acid (52 mg, 0.31 mmol) and bis[3-(diphenyl-phosphanyl)cyclopenta-2,4-dien-1-yl]iron-dichloropalladium-dichloromethane complex (4.5 mg, 0.01 mmol) were added and the mixture was heated at 90° C. under nitrogen for an additional 4 h. The mixture was diluted with ethyl acetate (30 mL) and washed with water (2×10 mL), then brine (10 mL). The organic layer was dried over sodium sulfate and concentrated under vacuum. The resulting dark orange oil was purified by flash chromatography, eluting with a gradient of 0-100% ethyl acetate in heptane followed by 0-20% methanol in ethyl acetate, to afford crude product (68 mg). A portion (35 mg) of this material was reserved, and the remaining material was further purified by flash chromatography, eluting with a slow gradient of 0-5% methanol in DCM, to afford the title compound (28 mg, 33%) as a cream-coloured solid. $\delta_H$ (500 MHz, CD$_3$OD) 8.15 (s, 1H), 8.09 (s, 1H), 7.67 (s, 1H), 7.53 (m, 2H), 7.29 (t, J 7.7 Hz, 1H), 7.21 (d, J 8.2 Hz, 1H), 7.13 (t, J 7.5 Hz, 1H), 6.93 (m, 2H), 4.39 (s, 2H), 3.97 (s, 3H), 2.45 (s, 3H), 2.23 (s, 3H). Method A HPLC-MS: MH+ m/z 410, RT 3.35 minutes (97%).

Example 3

5-{3-[2-(Difluoromethoxy)benzyl]-2-methylimidazo[1,2-a]pyridin-6-yl}-3-methylpyridin-2(1H)-one Example 2 (35 mg, 0.09 mmol) was dissolved in 1,4-dioxane (1 mL). Hydrochloric acid (6M, 150 µL) was added and the reaction mixture was heated to reflux at 70° C. for approximately 16 h. The reaction mixture was diluted with ethyl acetate (5 mL) and neutralised with 1M aqueous NaOH solution. Water (5 mL) was added, the organic layer was separated and the aqueous phase was extracted with further ethyl acetate (3×5 mL). The organic layers were combined, dried over sodium sulfate and concentrated under vacuum. The resulting white solid was purified by preparative HPLC (Preparative Method A). The product fractions were concentrated under vacuum to afford the title compound (24.5 mg, 72.5%) as a white solid. $\delta_H$ (500 MHz, CD$_3$OD) 8.36 (s, 1H), 7.76-7.65 (m, 3H), 7.57 (d, J 2.3 Hz, 1H), 7.32 (m, 1H), 7.26-7.12 (m, 3H), 7.14-6.62 (m, 1H), 4.43 (s, 2H), 2.48 (s, 3H), 2.18 (s, 3H). Method A HPLC-MS: MH+ m/z 396, RT 2.89 minutes (100%).

Example 4

3-[2-(Difluoromethoxy)benzyl]-2-methyl-6-[6-(piperazin-1-yl)pyridin-3-yl]imidazo[1,2-a]pyridine To Intermediate 8 (318 mg, 0.58 mmol) were added 4M HCl in 1,4-dioxane (1 mL) and 1,4-dioxane (3 mL) and the mixture was stirred at room temperature for 5 h. The reaction mixture was diluted with ethyl acetate (30 mL) and washed with water (2×10 mL), then brine (10 mL). The organic layer was dried over sodium sulfate and concentrated under vacuum, then dried further in a vacuum oven, to afford the title compound (58 mg, 93%) as an off-white solid. $\delta_H$ (500 MHz, CD$_3$OD) 8.89 (s, 1H), 8.45 (s, 1H), 8.39 (d, J 8.0 Hz, 1H), 8.23 (d, J 9.1 Hz, 1H), 8.00 (d, J 9.1 Hz, 1H), 7.57 (d, J 8.2 Hz, 1H), 7.43 (d, J 7.1 Hz, 1H), 7.36 (t, J 7.7 Hz, 1H), 7.22 (m, 2H), 6.95 (t, J 73.9 Hz, 1H), 4.58 (s, 2H), 4.10 (s, 4H), 3.74-3.59 (m, 1H), 3.50 (s, 4H), 2.52 (s, 3H). Method A HPLC-MS: MH+ m/z 450, RT 2.45 minutes (94%).

Example 5

2-Methoxy-5-{2-methyl-3-[(3-methylthien-2-yl)methyl]imidazo[1,2-a]pyridin-6-yl}-pyridine Intermediate 12 (80 mg, 0.25 mmol) and 6-methoxypyridin-3-ylboronic acid (57 mg, 0.37 mmol) were mixed with 2M aqueous potassium carbonate solution (0.5 mL) and 1,4-dioxane (3 mL) and flushed with nitrogen for 2 minutes. Bis[3-(diphenyl-phosphanyl)cyclopenta-2,4-dien-1-yl]iron-dichloropalladium-dichloromethane complex (7 mg, 0.01 mmol) was added and the mixture was heated at 90° C. for 2 h. Further bis[3-(diphenylphosphanyl)cyclopenta-2,4-dien-1-yl]iron-dichloropalladium-dichloromethane complex (7 mg, 0.01 mmol) was added and the heating was continued for 1 h. The mixture was cooled to room temperature, filtered through Celite and concentrated. The crude mixture was purified by preparative HPLC (Preparative Method C) to afford the title compound (12 mg, 14%) as a light brown solid. $\delta_H$ NMR (500 MHz, CDCl$_3$) 8.25 (d, J 2.5 Hz, 1H), 7.88 (s, 1H), 7.69-7.60 (m, 2H), 7.32 (dd, J 9.2, 1.6 Hz, 1H), 7.03 (d, J 5.1 Hz, 1H), 6.86-6.78 (m, 2H), 4.33 (s, 2H), 3.97 (s, 3H), 2.53 (s, 3H), 2.26 (s, 3H). Method A HPLC-MS: MH+ m/z 350, RT 3.32 minutes (100%).

Example 6

3-[2-(Difluoromethoxy)benzyl]-6-(6-methoxypyridin-3-yl)-2-methylimidazo[1,2-a]-pyridine Intermediate 7 (200 mg, 0.54 mmol) and 6-methoxypyridin-3-ylboronic acid (125 mg, 0.82 mmol) were dissolved in 1,4-dioxane (20 mL) and 2M aqueous potassium carbonate solution (1 mL) was added. The mixture was degassed with nitrogen and bis[3-(diphenylphosphanyl)cyclopenta-2,4-dien-1-yl]iron-dichloropalladium-dichloromethane complex (12 mg, 0.02 mmol) was added. The mixture was heated at 90° C. under nitrogen for 16 h. LCMS indicated incomplete conversion, so further 6-methoxypyridin-3-ylboronic acid (125 mg, 0.82 mmol) and bis[3-(diphenylphosphanyl)cyclopenta-2,4-dien-1-yl]iron-dichloropalladium-dichloromethane complex (8.5 mg, 0.02 mmol) were added and the mixture was heated at 90° C. under nitrogen for 4 h. The mixture was diluted with ethyl acetate (20 mL) and washed with water (2×10 mL), then brine (10 mL). The organic layer was dried over sodium sulfate and concentrated under vacuum. The resulting dark grey oil was purified by preparative HPLC (Preparative Method B). The crude product was then further purified by flash chromatography, eluting with a gradient of 0-5% methanol in DCM, to afford the title compound (41 mg, 19%) as a cream solid. $\delta_H$ (500 MHz, CD$_3$OD) 8.27 (d, J 2.0 Hz, 1H), 8.17 (s, 1H), 7.85 (dd, J 8.6, 2.3 Hz, 1H), 7.54 (m, 2H), 7.29 (t, J 7.7 Hz, 1H), 7.21 (d, J 8.1 Hz, 1H), 7.14 (t, J 7.5 Hz, 1H), 6.95 (m, 3H), 4.40 (s, 2H), 3.94 (s, 3H), 2.45 (s, 3H). Method A HPLC-MS: MH+ m/z 396, RT 3.18 minutes (100%).

Example 7

{3-[2-(Difluoromethoxy)benzyl]-6-(6-methoxypyridin-3-yl)imidazo[1,2-a]pyridin-2-yl}-methanol Intermediate 25 (0.150 g, 0.33 mmol) was dissolved in THF (5.0 mL) and methanol (3 mL). Lithium borohydride (0.008 g, 0.33 mmol) was added and the reaction mixture was stirred at room temperature under nitrogen for 2 h. Aqueous sodium hydroxide solution (2M, 5 mL) was added and the reaction mixture was extracted with DCM (10 mL). The organic layers were dried over MgSO$_4$ and concentrated in vacuo. The residue was purified by column chromatography (SiO$_2$, 0-20% MeOH:EtOAc), yielding the title compound (108 mg, 79%) as a white solid. $\delta_H$ (d$_6$-DMSO) 8.43 (d, J 2.4 Hz, 1H), 8.34 (s, 1H), 7.98 (dd, J 8.6, 2.6 Hz, 1H), 7.62 (m, 1H), 7.52 (m, 1H), 7.29 (m, 2H), 7.21 (m, 1H), 7.11 (m, 1H), 6.99 (dd, J 7.4, 0.7 Hz, 1H), 6.93 (d, J 8.6 Hz, 1H), 5.10 (t, J 5.6 Hz, 1H), 4.64 (d, J 5.6 Hz, 2H), 4.49 (s, 2H), 3.90 (s, 3H). LCMS (ES+) 412.0 (M+H)+.

Example 8

(2,5-Dichlorophenyl)[2-methyl-6-(1-methylpyrazol-4-yl)imidazo[1,2-a]pyridin-3-yl]-methanol To a solution of Intermediate 27 (0.20 g, 0.52 mmol) in ethanol (8 mL) was added sodium borohydride (22 mg) in one portion. After 1.5 h, a second portion of sodium borohydride (10 mg) was added and the mixture was stirred for an additional 1 h. The reaction mixture was partitioned between saturated aqueous ammonium chloride solution (20 mL) and EtOAc (30 mL). The resulting solid was filtered to give a first crop of the title compound (0.14 g, 70%) as a white solid. The ethyl acetate solution was washed with water (10 mL) and brine (10 mL), then dried ($Na_2SO_4$), filtered and concentrated in vacuo. The resulting off-white powder was washed with diethyl ether to yield a second crop of the title compound (0.06 g). The two crops were combined to give a total yield in excess of 95%. $\delta_H$ (400 MHz, DMSO-$d_6$) 8.62 (s, 1H), 8.18 (s, 1H), 8.04 (m, 1H), 7.87 (d, 1H, J 0.7 Hz), 7.48 (m, 3H), 7.02 (m, 1H), 6.37 (m, 2H), 3.89 (s, 3H), 1.93 (s, 3H). MH+ 387.

Example 9

3-(2,5-Dichlorobenzyl)-2-methyl-6-(1-methylpyrazol-4-yl)imidazo[1,2-a]pyridine

To a suspension of Example 8 (0.10 g) in a mixture of acetic acid (2 mL) and phosphinic acid (0.1 mL) was added iodine (0.05 g). The mixture was heated at 100° C. for 1.5 h before the addition of extra iodine (8 mg) and phosphinic acid (0.02 mL). Heating was continued for 4 h and then the mixture was cooled to room temperature overnight. The mixture was concentrated in vacuo and the residue was partitioned between DCM (20 mL) and saturated aqueous $NaHCO_3$ solution (20 mL). The organic phase was separated, dried ($Na_2SO_4$), filtered and concentrated in vacuo. The resulting crude product was purified by preparative HPLC to give the title compound (0.025 g) as a white solid. $\delta_H$ (400 MHz, DMSO-$d_6$) 7.21 (t, 1H, J 1.2 Hz), 6.95 (s, 1H), 6.78 (d, 1H, J 0.6 Hz), 6.55 (m, 2H), 6.46 (d, 1H, J 8.5 Hz), 6.27 (dd, 1H, J 8.5, 2.5 Hz), 5.93 (d, 1H, J 2.5 Hz), 3.45 (s, 2H), 2.91 (s, 3H), 1.36 (s, 3H). MH+ 372.

Example 10

3-[2-(Difluoromethoxy)benzyl]-2-methyl-6-[2-(piperazin-1-yl)pyrimidin-5-yl]-imidazo[1,2-a]pyridine Intermediate 28 (324 mg, 0.59 mmol) was dissolved in 4M HCl in 1,4-dioxane (5 mL) and stirred for 75 minutes. The reaction mixture was concentrated under vacuum. The crude material was purified by preparative HPLC, using MeCN/$H_2O$ (with 0.2% aqueous $NH_4OH$ solution) as eluent, to yield the title compound (97 mg, 36%). $\delta_H$ (500 MHz, DMSO-$d_6$) 8.64 (s, 2H), 8.38 (s, 1H), 7.54 (d, J 9.3 Hz, 1H), 7.46 (dd, J 9.2, 1.7 Hz, 1H), 7.45-7.09 (m, 4H), 7.03 (d, J 6.8 Hz, 1H), 4.36 (s, 2H), 3.74-3.64 (m, 4H), 2.78-2.67 (m, 4H), 2.31 (s, 3H). Method A HPLC-MS: MH+ m/z 451, RT 2.52 minutes (97%).

Example 11

4-(5-{3-[2-(Difluoromethoxy)benzyl]-2-methylimidazo[1,2-a]pyridin-6-yl}pyrimidin-2-yl)piperazin-2-one Intermediate 29 (30 mg, 0.07 mmol) and piperazin-2-one (25 mg, 0.25 mmol) were dissolved in NMP (1 mL) and heated at 200° C. under microwave irradiation for 40 minutes. The reaction mixture was diluted with MeOH (approximately 6 mL) and loaded onto a 1 g SCX cartridge. The cartridge was flushed with MeOH (approximately 15 mL), then with 7M ammonia in MeOH (approximately 12 mL) in two equal-sized fractions. A solid precipitated out of the first ammonia/MeOH fraction and was collected by filtration to yield the title compound (17 mg, 50%). $\delta_H$ (500 MHz, DMSO-$d_6$) 8.72 (s, 2H), 8.42 (s, 1H), 8.14 (s, 1H), 7.54 (d, J 9.3 Hz, 1H), 7.48 (dd, J 9.3, 1.7 Hz, 1H), 7.45-7.10 (m, 4H), 7.03 (d, J 6.6 Hz, 1H), 4.36 (s, 2H), 4.21 (s, 2H), 3.98-3.90 (m, 2H), 3.30 (t, J 6.6 Hz, 2H), 2.31 (s, 3H). Method A HPLC-MS: MH+ m/z 465, RT 2.88 minutes (99%).

Example 12

3-[2-(Difluoromethoxy)benzyl]-6-[2-(1,1-dioxidothiomorpholin-4-yl)pyrimidin-5-yl]-2-methylimidazo[1,2-a]pyridine Intermediate 29 (50 mg, 0.12 mmol) and thiomorpholine 1,1-dioxide (55 mg, 0.41 mmol) were dissolved in NMP and the mixture was heated at 200° C. under microwave irradiation for 45 minutes. The reaction mixture was diluted with MeOH (approximately 6 mL) and loaded onto a 1 g SCX cartridge. The cartridge was flushed with MeOH (approximately 15 mL), then with 7M ammonia in MeOH (approximately 12 mL) in two equal-sized fractions. A solid precipitated out of the first ammonia/MeOH fraction and was collected by filtration to yield the title compound (18 mg, 29%) as an off-white solid. $\delta_H$ (500 MHz, DMSO-$d_6$) 8.76 (s, 2H), 8.43 (s, 1H), 7.56 (d, J 9.3 Hz, 1H), 7.50 (d, J 10.7 Hz, 1H), 7.45-7.14 (m, 3H), 7.12 (t, J 7.5 Hz, 1H), 7.01 (d, J 7.3 Hz, 1H), 4.37 (s, 2H), 4.31-4.17 (m, 4H), 3.24-3.10 (m, 4H), 2.31 (s, 3H). Method A HPLC-MS: MH+ m/z 500, RT 3.04 minutes (99%).

Example 13

5-{3-[2-(Difluoromethoxy)benzyl]-2-methylimidazo[1,2-a]pyridin-6-yl}pyridin-2(1H)-one Example 6 (25 mg, 0.06 mmol) was dissolved in 1,4-dioxane (1 mL). Hydrochloric acid (6M, 0.1 mL) was added and the reaction mixture was heated under reflux at 70° C. for 6 h. The reaction mixture was then diluted with ethyl acetate (5 mL) and neutralised with 1M aqueous sodium hydroxide solution. Water (5 mL) was added, the organic layer was separated and the aqueous phase was extracted with further ethyl acetate (3×5 mL). The organic layers were combined, dried over sodium sulfate and concentrated under vacuum. The residue was purified by flash chromatography, eluting with a gradient of 0-10% methanol in DCM, to afford the title compound (25 mg) as an off-white solid. $\delta_H$ (500 MHz, $CD_3OD$) 8.17 (s, 1H), 7.83 (dd, J 9.5, 2.7 Hz, 1H), 7.64 (d, J 2.5 Hz, 1H), 7.53 (d, J 9.3 Hz, 1H), 7.44 (dd, J 9.3, 1.6 Hz, 1H), 7.29 (m, 1H), 7.20 (d, J 8.0 Hz, 1H), 7.13 (t, J 7.5 Hz, 1H), 6.98 (m, 2H), 6.63 (d, J 9.5 Hz, 1H), 4.62 (s, 1H), 4.39 (s, 2H), 2.43 (s, 3H). Method A HPLC-MS: MH+ m/z 382, RT 2.66 minutes (93%).

Example 14

4-(5-{3-[2-(Difluoromethoxy)benzyl]-2-methylimidazo[1,2-a]pyridin-6-yl}pyridin-2-yl)-morpholine Intermediate 30 (295 mg, 0.74 mmol) was added to morpholine (192 mg, 2.21 mmol) and NMP (5 mL) in a microwave tube. The reaction mixture was heated at 200° C. under microwave irradiation for 90 minutes. The mixture was loaded onto a 10 g SCX cartridge, which was washed with methanol, followed by 7N ammonia in methanol. The ammonia fraction was concentrated under vacuum, and the residue was purified by Preparative Method D, to afford the title compound (70 mg, 21%) as a light brown solid. Method A HPLC-MS: MH+ m/z 451, RT 3.06 minutes (100%).

Example 15

N-(6-{3-[2-(Difluoromethoxy)benzyl]-2-methylimidazo[1,2-a]pyridin-6-yl}pyridin-3-yl)-methanesulfonamide Example 20 (100 mg, 0.26 mmol) was dissolved in dichloromethane (6 mL) at 0° C. Triethylamine (45 µL, 0.32 mmol) was added, followed by methanesulfonyl chloride (25 µL, 0.32 mmol). The mixture was stirred for 30 minutes at 0° C., then for a further 18 h at ambient temperature. The reaction mixture was diluted with ethyl acetate (5 mL) and neutralised with 1M aqueous sodium hydroxide solution. Water (5 mL) was added, the organic layer was separated and the aqueous phase was extracted with ethyl acetate (3×5 mL). The organic layers were combined, dried over sodium sulfate and concentrated under vacuum. The residue was purified by flash chromatography, eluting with 0-10% methanol in DCM. The product was then further purified by preparative HPLC (Method B) to afford the title compound (9.5 mg, 8%) as an off-white solid. $\delta_H$ (500 MHz, CD$_3$OD) 8.67 (s, 1H), 8.48 (s, 1H), 7.90 (d, J 9.4 Hz, 1H), 7.80 (s, 2H), 7.57 (d, J 9.4 Hz, 1H), 7.28 (t, J 7.2 Hz, 1H), 7.21 (d, J 8.1 Hz, 1H), 7.02 (m, 3H), 4.42 (s, 2H), 3.04 (s, 3H), 2.45 (s, 3H). Method A HPLC-MS: MH+ m/z 459, RT 3.00 minutes (97%).

Example 16

5-{3-[2-(Difluoromethoxy)benzyl]-2-methylimidazo[1,2-a]pyridin-6-yl}-2-methoxy-4-methylpyridine Intermediate 31 (50% purity, 165 mg, 0.25 mmol), 5-bromo-2-methoxy-4-methylpyridine (75 mg, 0.37 mmol) and 2M aqueous potassium carbonate solution (0.43 mL) were combined in 1,4-dioxane (5 mL). Bis[3-(diphenylphosphanyl)cyclopenta-2,4-dien-1-yl]iron-dichloropalladium-dichloromethane complex (10 mg, 0.01 mmol) was added, and the mixture was heated at 90° C. for 18 h. The mixture was partitioned between ethyl acetate (20 mL) and water (15 mL). The organic layer was dried over sodium sulfate and concentrated under vacuum. The residue was purified by flash chromatography, eluting with 0-100% ethyl acetate in heptanes followed by 0-20% methanol in DCM. The crude product was then further purified by preparative HPLC (Method C) to afford the title compound (23 mg, 23%) as a white solid. $\delta_H$ NMR (500 MHz, CDCl$_3$) 7.89 (s, 1H), 7.62 (d, J 9.2 Hz, 1H), 7.59 (s, 1H), 7.24 (d, J 7.3 Hz, 1H), 7.13 (d, J 8.1 Hz, 1H), 7.10 (dd, J 9.2, 1.3 Hz, 1H), 7.06 (t, J 7.5 Hz, 1H), 6.83 (d, J 7.4 Hz, 1H), 6.55 (m, 2H), 4.28 (s, 2H), 3.93 (s, 3H), 2.52 (s, 3H), 2.11 (s, 3H). Method A HPLC-MS: MH+ m/z 410, RT 3.20 minutes (99%).

Example 17

5-{3-[2-(Difluoromethoxy)benzyl]-2-methylimidazo[1,2-a]pyridin-6-yl}-4-methylpyridin-2(1H)-one Example 16 (150 mg, 0.37 mmol) was dissolved in 1,4-dioxane (3 mL). Hydrochloric acid (6M, 600 µL) was added and the reaction mixture was heated under reflux at 70° C. for approximately 16 h. LCMS indicated incomplete conversion, so further 6M hydrochloric acid (0.3 mL) was added and the mixture was heated at reflux for a further 6 h. The reaction mixture was diluted with ethyl acetate (5 mL) and neutralised with 1M aqueous sodium hydroxide solution. Water (5 mL) was added, the organic layer was separated and the aqueous phase was extracted with ethyl acetate (3×5 mL). The organic layers were combined, dried over sodium sulfate and concentrated under vacuum. The residue was purified by flash chromatography, eluting with a gradient of 0-10% methanol in DCM, to afford the title compound (71 mg, 49%) as an off-white solid. $\delta_H$ (500 MHz, CD$_3$OD) 7.96 (s, 1H), 7.51 (d, J 9.2 Hz, 1H), 7.27 (d, J 8.5 Hz, 2H), 7.22 (dd, J 9.2, 1.4 Hz, 1H), 7.17 (d, J 8.1 Hz, 1H), 7.11 (t, J 7.5 Hz, 1H), 6.93 (m, 2H), 6.45 (s, 1H), 4.35 (s, 2H), 2.43 (s, 3H), 2.05 (s, 3H). Method A HPLC-MS: MH+ m/z 396, RT 2.77 minutes (100%).

Example 18

[6-(6-Methoxypyridin-3-yl)-2-methylimidazo[1,2-a]pyridin-3-yl](3-methylthien-2-yl)-methanol Intermediate 11 (525 mg, 1.56 mmol) and 6-methoxypyridin-3-ylboronic acid (357 mg, 2.34 mmol) were dissolved in 2M aqueous potassium carbonate solution (3.1 mL) and 1,4-dioxane (12 mL). The solution was purged with nitrogen for 5 minutes, then bis[3-(diphenylphosphanyl)cyclopenta-2,4-dien-1-yl]iron-dichloropalladium-dichloromethane complex (63 mg, 0.08 mmol) was added and the reaction mixture was heated at 100° C. for 3 h. The mixture was filtered though Celite and concentrated under vacuum. The resulting red oil was purified by column chromatography, eluting with a gradient of 5-10% DCM in methanol, to afford the title compound (412 mg, 72%) as a pale yellow solid. $\delta_H$ (500 MHz, DMSO-d$_6$) 8.58 (s, 1H), 8.37 (d, J 2.5 Hz, 1H), 7.92 (dd, J 8.6, 2.6 Hz, 1H), 7.60-7.49 (m, 2H), 7.36 (d, J 5.0 Hz, 1H), 6.96 (d, J 8.6 Hz, 1H), 6.84 (d, J 5.0 Hz, 1H), 6.54-6.47 (m, 2H), 3.90 (s, 3H), 2.29 (s, 3H), 1.87 (s, 3H). Method A HPLC-MS: MH+ m/z 366, RT 1.80 minutes (99%).

Example 19 tert-Butyl 4-{3-[2-(difluoromethoxy)benzyl]-2-methylimidazo[1,2-a]pyridin-6-yl}-1,2,3,6-tetrahydropyridine-1-carboxylate tert-Butyl 4-[(trifluoromethane)sulfonyloxy]-1,2,3,6-tetrahydropyridine-1-carboxylate (450 mg, 1.36 mmol), Intermediate 31 (75% pure, 0.84 g, 1.9 mmol) and lithium chloride (172 mg, 4.07 mmol) were suspended in 2M aqueous Na$_2$CO$_3$ solution (2.7 mL) and DME (10 mL) and the mixture was purged with nitrogen for 5 minutes. Tetrakis(triphenylphosphine)palladium(0) (78.5 mg, 0.07 mmol) was added and the reaction mixture was heated at 90° C. for 3 h. The mixture was filtered though Celite and concentrated under vacuum. The resulting red oil was purified by column chromatography, eluting with a gradient of 5-10% DCM in methanol, to afford the title compound (315 mg, 49%) as an off white solid. $\delta_H$ (500 MHz, CDCl$_3$) 7.71 (s, 1H), 7.61 (s, 1H), 7.35 (d, J 8.1 Hz, 1H), 7.28 (d, J 7.7 Hz, 1H), 7.17 (d, J 8.1 Hz, 1H), 7.09 (t, J 7.6 Hz, 1H), 6.90 (d, J 7.7 Hz, 1H), 6.65 (t, J 73.6 Hz, 1H), 6.02 (s, 1H), 4.26 (s, 2H), 4.06 (s, 2H), 3.61 (t, J 5.3 Hz, 2H), 2.53 (s, 3H), 2.37 (s, 2H), 1.48 (s, 9H). Method A HPLC-MS: MH+ m/z 470, RT 3.40 minutes (99%).

Example 20

6-{3-[2-(Difluoromethoxy)benzyl]-2-methylimidazo[1,2-a]pyridin-6-yl}pyridin-3-amine Intermediate 31 (200 mg, 0.6 mmol) and 3-amino-6-bromopyridine (160 mg, 0.92 mmol) were dissolved in 1,4-dioxane (20 mL) and 2M aqueous potassium carbonate solution (1 mL) was added. The mixture was flushed with nitrogen and bis[3-(diphenyl-phosphanyl)cyclopenta-2,4-dien-1-yl]iron-dichloropalladium-dichloromethane complex (12 mg, 0.01 mmol) was added. The mixture was heated at 90° C. for 16 h. The reaction mixture was diluted with ethyl acetate (30 mL) and washed with water (2×10 mL) and then brine (10 mL). The organic layer was dried over sodium sulfate and concentrated under vacuum. The residue was purified by flash chromatography, eluting with ethyl acetate followed by 1-10% methanol in DCM. The crude product was further purified by flash chromatography, eluting with a gradient of 0-8% methanol in DCM, to afford the title compound (137 mg, 40%) as a light brown solid. Method A HPLC-MS: MH+ m/z 381, RT 2.87 minutes (97%).

Example 21

5-{3-[(2,4-Dimethyl-1,3-thiazol-5-yl)methyl]-2-methylimidazo[1,2-a]pyridin-6-yl}-2-methoxypyridine Trifluoroacetic acid (5.1 mL) was added to a mixture of Intermediate 35 (100 mg, 0.26 mmol) and triethylsilane (1.7 mL, 10.5 mmol) in chloroform (1.7 mL). The mixture was heated in sealed tube at 40° C. for 72 h. The mixture was allowed to cool to ambient temperature and concentrated under vacuum. The mixture was taken up in DCM (20 mL), washed with 2M aqueous potassium carbonate solution (20 mL) and brine, dried over sodium sulphate, filtered and concentrated under vacuum. The crude mixture was purified by flash column chromatography, eluting with 0-5% MeOH in DCM, to afford the title compound (21 mg, 21%) as a yellow solid. $\delta_H$ (500 MHz, CDCl$_3$) 8.28 (d, J 2.5 Hz, 1H), 7.83 (s, 1H), 7.73 (d, J 9.2 Hz, 1H), 7.67 (dd, J 8.6, 2.6 Hz, 1H), 7.41 (d, J 9.3 Hz, 1H), 6.85 (d, J 8.6 Hz, 1H), 4.29 (s, 2H), 3.98 (s, 3H), 2.55 (s, 3H), 2.54 (s, 3H), 2.46 (s, 3H). Method D HPLC-MS: MH+ m/z 365, RT 1.50 minutes (95%).

Example 22

Methyl 3-{3-[2-(difluoromethoxy)benzyl]-2-methylimidazo[1,2-a]pyridin-6-yl}-propanoate Intermediate 36 (86 mg, 0.11 mmol) was dissolved in EtOH (2 mL) and Pd/C (10 mg) was added. The suspension was degassed using 3 cycles of vacuum/N$_2$ and regassed using 3 cycles of vacuum/H$_2$. The reaction mixture was stirred at ambient temperature and pressure for 18 h. The reaction mixture was then degassed using vacuum/N$_2$ and filtered through a plug of celite, washing with MeOH (5 mL). The solvent was removed under vacuum and the crude product was purified by Preparative Method A to afford the title compound (12 mg, 17%) as a white solid. $\delta_H$ (500 MHz, CD$_3$OD) 7.82 (s, 1H), 7.40 (d, J 9.2 Hz, 1H), 7.30-7.24 (m, 1H), 7.22-7.14 (m, 2H), 7.12-6.80 (m, 3H), 4.30 (s, 2H), 3.54 (s, 3H), 2.86 (t, J 7.3 Hz, 2H), 2.61 (t, J 7.3 Hz, 2H), 2.40 (s, 3H). Method E HPLC-MS: MH+ m/z 375, RT 4.50 minutes (100%).

Example 23

1-(5-{3-[2-(Difluoromethoxy)benzyl]-2-methylimidazo[1,2-a]pyridin-6-yl}pyrimidin-2-yl)piperidine-4-carboxylic acid A mixture of Intermediate 7 (0.5 g, 1.36 mmol), Intermediate 37 (0.5 g, 1.99 mmol 1) and [1,1'-bis(diphenylphosphino)ferrocene]dichloropalladium(II) dichloromethane adduct (20 mg, 0.025 mmol) in 2M aqueous Na$_2$CO$_3$ solution (2 mL) and 1,4-dioxane (30 mL) was degassed with nitrogen and stirred at 110° C. overnight. LCMS showed completion of reaction. The reaction mixture was cooled to room temperature and partitioned between EtOAc and water to form an emulsion which was filtered through celite. LCMS of the organic extract showed that it contained very little of the product and was discarded. The aqueous layer was neutralised by the dropwise addition of acetic acid. The resulting solid was filtered, washed with water and dried by suction to give the title compound (0.57 g, 85%) as a cream solid. $\delta_H$ (DMSO-d$_6$) 12.26 (br, 1H), 8.65 (s, 2H), 8.39 (s, 1H), 7.54 (m, 1H), 7.47 (m, 1H), 7.30 (m, 1.5H), 7.20 (m, 1H), 7.13 (m, 1.5H), 7.04 (dd, J$_1$ 7.5 Hz, J$_2$ 0.8 Hz, 1H), 4.56 (m, 2H), 4.36 (s, 2H), 3.12 (m, 2H), 2.57 (m, 1H), 2.32 (s, 3H), 1.90 (m, 2H), 1.51 (m, 2H). LCMS (ES+) 494 (M+H)$^+$, RT 1.12 minutes.

Example 24

4-(5-{3-[2-(Difluoromethoxy)benzyl]-2-methylimidazo[1,2-a]pyridin-6-yl}pyrimidin-2-yl)morpholine A mixture of Intermediate 7 (0.5 g, 1.36 mmol), Intermediate 38 (0.4 g, 1.91 mmol) and [1,1'-bis(diphenylphosphino)ferrocene]dichloropalladium(II) dichloromethane adduct (20 mg, 0.025 mmol) in 2M aqueous Na$_2$CO$_3$ solution (2 mL) and 1,4-dioxane was degassed with nitrogen and stirred at 110° C. for 4 h. LCMS analysis showed completion of the reaction. The reaction mixture was cooled to room temperature and partitioned between EtOAc and brine. The organic layer was dried (MgSO$_4$) and the solvents were removed in vacuo. The resulting material was subjected to column chromatography, eluting first with 4:1 EtOAc-hexane, then 100% EtOAc. The product was triturated in ether, filtered, washed with ether and hexane, then dried, to give the title compound (0.45 g, 70%) as an off-white solid. $\delta_H$ (DMSO-d$_6$) 8.70 (s, 2H), 8.41 (s, 1H), 7.55 (m, 1H), 7.48 (m, 1H), 7.30 (m, 1.5H), 7.20 (m, 1H), 7.13 (m, 1.5H), 7.04 (dd, J$_1$ 7.6 Hz, J$_2$ 1.3 Hz, 1H), 4.37 (s, 2H), 3.75 (m, 4H), 3.68 (m, 4H), 2.32 (s, 3H). LCMS (ES+) 452 (M+H)$^+$, RT 1.46 minutes.

Example 25

3-(2,5-Dimethylbenzyl)-2-methyl-6-(1-methyl-1H-pyrazol-4-yl)imidazo[1,2-a]pyridine Intermediate 41 (0.23 g, 0.61 mmol) and 1-methyl-4-(4,4,5,5-tetramethyl-1,3,2-dioxaborolan)-1H-pyrazole (0.165 g, 0.8 mmol) were dissolved in a mixture of 1,4-dioxane and water (10:1, 15 mL) and placed in a vial. Potassium carbonate (0.253 g, 1.84 mmol) and tetrakis(triphenylphosphine)palladium(0) (0.7 mg, 0.01 mmol, 10 mol %) were added. The mixture was degassed with argon. The vial was sealed, then heated at 100° C. for 1 h. The reaction mixture was stirred for 1 h at room temperature, then evaporated to dryness. The resulting crude material was dissolved in DCM (20 mL) and washed with water (20 mL). The organic layer was dried over MgSO$_4$, then evaporated. The resulting crude material (220 mg) was purified by chromatography (SiO$_2$, DCM:MeOH: NH$_4$OH 97.0:3.0:0.3) to afford the title compound (180 mg, 89%). δ$_H$ (CDCl$_3$) 7.71 (m, 1H), 7.62 (d, J 9.2 Hz, 1H), 7.58 (s, 1H), 7.49 (s, 1H), 7.25 (m, 1H), 7.12 (m, 1H), 7.00 (m, 1H), 6.60 (s, 1H), 4.17 (m, 2H), 3.94 (s, 3H), 2.46 (s, 3H), 2.38 (s, 3H), 2.17 (m, 3H). LCMS: MH+ 331.

Example 26

1-(5-{3-[2-(Difluoromethoxy)benzyl]-2-methylimidazo[1,2-a]pyridin-6-yl}pyrimidin-2-yl)-1,4-diazepan-5-one To Intermediate 29 (116 mg, 0.29 mmol) were added 2,3,6,7-tetrahydro-(1H)-1,4-diazepin-5(4H)-one (330.4 mg, 0.29 mmol), triethylamine (0.04 mL, 0.29 mmol) and ethanol (2.5 mL). The reaction mixture was stirred at 85° C. for 18 h, then concentrated to dryness. The crude residue was purified by flash chromatography (10-20% MeOH/EtOAc). The resulting white solid (100 mg) was purified by preparative HPLC to give the title compound (25 mg, 18%) as a white solid. δ$_H$ (400 MHz, d$_6$-DMSO) 8.69 (2H, s), 8.40 (1H, s), 7.68 (1H, t, J 5.4 Hz), 7.55 (1H, dd, J 9.3, 0.7 Hz), 7.50-7.47 (1H, m), 7.32-7.28 (2H, m, incl. 1H, t, J 74.1 Hz), 7.22-7.20 (1H, m), 7.16-7.11 (1H, m), 7.02 (1H, dd, J 7.6, 1.4 Hz), 4.37 (2H, s), 3.98-3.95 (4H, m), 3.46-3.40 (2H, m), 2.52-2.50 (2H, m), 2.32 (3H, s). LCMS (pH 3) MH+ 479.8, RT 1.52 minutes, 100% UV; LCMS (pH 10) MH+479.8, RT 1.57 minutes, 100% UV.

Example 27

5-(5-{3-[2-(Difluoromethoxy)benzyl]-2-methylimidazo[1,2-a]pyridin-6-yl}pyrimidin-2-yl)-1,2,5-thiadiazepane 1,1-dioxide Intermediate 7 (250 mg, 0.68 mmol), Intermediate 45 (1.40 g, 5 mmol) and tetrakis-(triphenylphosphine)palladium(0) (0.0236 g, 0.020 mmol) were dissolved in 1,4-dioxane (30 mL) and 1.0M aqueous sodium carbonate solution (3 mL) was added. The mixture was heated to 100° C. under nitrogen for 2 h. The reaction mixture was cooled and diluted with water (100 mL), then extracted twice with dichloromethane. The combined organic layers were dried (Na$_2$SO$_4$), filtered and concentrated in vacuo. The residue was purified by chromatography (silica, 25 g, gradient 3 to 8% methanol in dichloromethane). The resulting off-white solid (145 mg) was further purified by preparative HPLC to give the title compound (45 mg, 13%) as a white solid. δ$_H$ (d$_6$-DMSO) 8.73 (s, 2H), 8.44 (s, 1H), 7.58-7.51 (m, 2H), 7.43-7.24 (m, 3H), 7.29-7.26 (m, 1H), 7.12 (dt, 1H, J 7.5, 1.3 Hz), 6.99 (dd, 1H, J 7.5, 1.5 Hz), 4.37 (s, 2H), 4.04-3.95 (m, 4H), 3.46-3.41 (m, 2H), 3.25-3.16 (m, 2H), 2.81 (s, 3H). LCMS (ES$^+$) 515 (M+H)$^+$.

Example 28

4-(5-{3-[2-(Difluoromethoxy)benzyl]-2-methyl-7-(trifluoromethyl)imidazo[1,2-a]-pyridin-6-yl}pyrimidin-2-yl)piperazin-2-one Intermediate 49 (120 mg, 0.26 mmol) and piperazin-2-one (77 mg, 0.77 mmol) were dissolved in 1,4-dioxane (2 mL) and heated at 100° C. under microwave irradiation for 1 h. The mixture was concentrated under reduced pressure and purified using preparative HPLC (Method C) to afford the title compound (51 mg, 39%). δ$_H$ (500 MHz, CDCl$_3$) 8.25 (s, 2H), 8.00 (s, 1H), 7.65 (s, 1H), 7.26 (s, 1H), 7.14-7.03 (m, 2H), 6.85 (d, J 7.6 Hz, 1H), 6.74-6.39 (m, 2H), 4.47 (s, 2H), 4.28 (s, 2H), 4.15-4.06 (m, 2H), 3.50 (dq, J 5.6, 2.8 Hz, 2H), 2.53 (s, 3H). MH+ 533.

Example 29

4-(5-{3-[2-(Difluoromethoxy)benzyl]-2-methyl-7-(trifluoromethyl)imidazo[1,2-a]-pyridin-6-yl}pyrimidin-2-yl)morpholine Intermediate 49 (120 mg, 0.26 mmol) and morpholine (68 μL, 0.77 mmol) were dissolved in 1,4-dioxane (2 mL) and heated at 100° C. under microwave irradiation for 1 h. The mixture was concentrated under reduced pressure and purified using preparative HPLC (Method C) to afford the title compound (60 mg, 47%) as a pale yellow sticky solid. δ$_H$ (500 MHz, CDCl$_3$) 8.22 (s, 2H), 7.98 (s, 1H), 7.63 (s, 1H), 7.26 (s, 1H), 7.15-7.01 (m, 2H), 6.83 (d, J 7.6 Hz, 1H), 6.57 (t, J 73.6 Hz, 1H), 4.27 (s, 2H), 3.84 (q, J 3.6, 2.8 Hz, 4H), 3.78 (q, J 4.3, 3.5 Hz, 4H), 2.52 (s, 3H). MH+ 520.

Example 30

5-{3-[2-(Difluoromethoxy)benzyl]-2-methyl-7-(trifluoromethyl)imidazo[1,2-a]pyridin-6-yl}-2-(piperazin-1-yl)pyrimidine Intermediate 49 (120 mg, 0.26 mmol) and piperazine (66 mg, 0.77 mmol) were dissolved in 1,4-dioxane (2 mL) and heated at 100° C. under microwave irradiation for 1 h. The mixture was concentrated under reduced pressure and purified using preparative HPLC (Method C) to afford the title compound (68 mg, 54%) as an off-white solid. δ$_H$ (500 MHz, CDCl$_3$) 8.21 (s, 2H), 7.95 (s, 1H), 7.61 (s, 1H), 7.26 (s, 2H), 7.16-7.00 (m, 2H), 6.82 (d, J 7.6 Hz, 1H), 6.57 (t, J 73.6 Hz, 1H), 4.27 (s, 2H), 3.94-3.80 (m, 4H), 3.04-2.93 (m, 4H), 2.51 (s, 3H). MH+ 519.

Example 31

1-(5-{3-[2-(Difluoromethoxy)benzyl]-2-methyl-7-(trifluoromethyl)imidazo[1,2-a]-pyridin-6-yl}pyridin-2-yl)piperazine Intermediate 48 (33 mg, 0.05 mmol) was suspended in 4M HCl in 1,4-dioxane (0.13 mL) and stirred at room temperature for 2 h. The mixture was concentrated under reduced pressure and dissolved in methanol, then purified by column chromatography using an SCX cartridge, to afford the title compound (28 mg, 99%) as a brown solid. δ$_H$ (500 MHz, CD$_3$OD) 8.04 (d, J 2.8 Hz, 1H), 8.00-7.96 (m, 1H), 7.89 (d, J 6.7 Hz, 1H), 7.53 (d, J 6.2 Hz, 1H), 7.29 (q, J 9.0, 8.1 Hz, 1H), 7.18-7.06 (m, 3H), 7.02-6.65 (m, 2H), 4.38 (d, J 7.5 Hz, 2H), 4.10 (s, 1H), 3.67 (s, 2H), 3.63-3.58 (m, 2H), 3.08 (s, 2H), 2.85-2.75 (m, 2H), 2.46 (d, J 4.9 Hz, 3H). MH+ 518.

Example 32

4-(5-{3-[2-(Difluoromethoxy)benzyl]-2,7-dimethylimidazo[1,2-a]pyridin-6-yl}pyrimidin-2-yl)piperazin-2-one Intermediate 47 (135 mg, 0.33 mmol) and piperazin-2-one (104 mg, 1.04 mmol) were combined in 1,4-dioxane (2 mL) and heated at 100° C. under microwave irradiation for 90 minutes. The reaction mixture was partitioned between EtOAc and water. The organic layer was separated, washed with brine, dried (Na$_2$SO$_4$), filtered and concentrated to dryness. The residue was purified by column chromatography to yield the title compound (23 mg, 15%) as a white solid. δ$_H$ (500 MHz, CD$_3$OD) 8.34 (s, 2H), 7.87 (s, 1H), 7.38 (s, 1H), 7.28 (t, J 7.0 Hz, 1H), 7.17 (d, J 8.0 Hz, 1H), 7.11 (t, J 7.6 Hz, 1H), 7.05-6.71 (m, 2H), 4.40 (s, 2H), 4.33 (s, 2H), 4.09-4.06 (m, 2H), 3.48-3.40 (m, 2H), 2.41 (s, 3H), 2.29 (s, 3H). MH+ 479.

Example 33

4-(5-{3-[2-(Difluoromethoxy)benzyl]-2,7-dimethylimidazo[1,2-a]pyridin-6-yl}pyrimidin-2-yl)morpholine Intermediate 47 (140 mg, 0.34 mmol) and morpholine (100 μL, 1.14 mmol) were dissolved in 1,4-dioxane (2 mL) and heated at 100° C. under microwave irradiation for 1 h. The reaction mixture was partitioned between ethyl acetate (5 mL) and water (3 mL). The organic layer was separated, washed with brine, dried (Na$_2$SO$_4$), filtered and concentrated to dryness. The residue was purified by preparative HPLC (Method C) to yield the title compound (60 mg, 38%) as an off-white solid. δ$_H$ (500 MHz, CD$_3$OD) 8.27 (s, 2H), 7.84 (s, 1H), 7.36 (s, 1H), 7.27 (m, 1H), 7.17 (d, J 8.0 Hz, 1H), 7.11 (t, J 7.6 Hz, 1H), 6.87 (m, 2H), 4.32 (s, 2H), 3.83 (m, 4H), 3.75 (m, 4H), 2.40 (s, 3H), 2.28 (s, 3H). MH+ 466.

Example 34

1-(5-{3-[2-(Difluoromethoxy)benzyl]-2,7-dimethylimidazo[1,2-a]pyridin-6-yl}pyridin-2-yl)piperazine Intermediate 46 (50 mg, 0.09 mmol) was suspended in 4M HCl in 1,4-dioxane (1 mL) and stirred for 45 minutes. The reaction mixture was concentrated to dryness, redissolved in MeOH (2 mL) and loaded onto an SCX column. The column was flushed with MeOH (12 mL), then the product was washed off with 7M NH$_3$ in MeOH (12 mL). The volatiles were removed under reduced pressure to yield the title compound (27 mg, 67%) as a yellow gum. δ$_H$ (500 MHz, CD$_3$OD) 7.95 (d, J 2.4 Hz, 1H), 7.76 (s, 1H), 7.51 (dd, J 8.8, 2.5 Hz, 1H), 7.34 (s, 1H), 7.29-7.23 (m, 1H), 7.16 (d, J 8.0 Hz, 1H), 7.10 (t, J 7.5 Hz, 1H), 7.02-6.70 (m, 3H), 4.30 (s, 2H), 3.60-3.51 (m, 4H), 3.00-2.92 (m, 4H), 2.40 (s, 3H), 2.26 (s, 3H). MH+ 464.

Example 35

1-(5-{3-[2-(Difluoromethoxy)benzyl]-7-fluoro-2-(methoxymethyl)imidazo[1,2-a]pyridin-6-yl}pyrimidin-2-yl)piperidine-4-carboxylic acid A mixture of Intermediate 55 (148 mg, 0.36 mmol) and Intermediate 37 (110 mg, 0.44 mmol) in 1,4-dioxane (8 mL) and 2M aqueous K$_3$PO$_4$ solution (3 mL) was treated with [1,1'-bis(diphenylphosphino)ferrocene]dichloropalladium (II) (19 mg, 0.023 mmol). The reaction mixture was heated at reflux for 3.5 h under nitrogen. After this time, the reaction mixture was allowed to cool to room temperature, then diluted with EtOAc (20 mL). The mixture was acidified to pH 4 with acetic acid and washed with water (20 mL), then the aqueous phase was extracted with further EtOAc (3×20 mL). The combined organic phases were dried (MgSO$_4$), filtered and concentrated in vacuo. The residue was purified by chromatography (SiO$_2$, 0-10% MeOH/DCM) and the resultant material was freeze-dried from acetonitrile/water/methanol to give the title compound (30 mg, 16%) as a beige solid. δ$_H$ (DMSO-d$_6$, 300 MHz) 8.49 (d, 2H, J 1.6 Hz), 8.37 (d, 1H, J 7.5 Hz), 7.55 (d, 1H, J 11.2 Hz), 7.25-7.33 (m, 1H), 7.26 (t, 1H, J 74.1 Hz), 7.16-7.22 (m, 1H), 7.11 (td, 1H, J 7.5, 1.1 Hz), 6.93-6.98 (m, 1H), 4.50-4.59 (m, 2H), 4.47 (s, 2H), 4.41 (s, 2H), 3.21 (s, 3H), 3.05-3.17 (m, 2H), 2.52-2.59 (m, 1H), 1.84-1.94 (m, 2H), 1.40-1.56 (m, 2H). LCMS (ES+) 542 (M+H)$^+$, RT 1.72 minutes (pH 10) and (ES+) 542 (M+H)$^+$, RT 1.89 minutes (pH 3).

Example 36

5-(5-{3-[2-(Difluoromethoxy)benzyl]-2-methylimidazo[1,2-a]pyridin-6-yl}pyrimidin-2-yl)-2-oxa-5-azabicyclo[2.2.1]heptane Prepared from Intermediate 29 and the hydrochloride salt of 2-oxa-5-azabicyclo[2.2.1]heptane in accordance with the experimental procedure described for Example 26. δ$_H$ (d$_6$-DMSO, 300 MHz) 8.64 (2H, s), 8.38 (1H, s), 7.56-7.53 (1H, m), 7.48-7.44 (1H, m), 7.38-7.26 (2H, m, incl. 7.29 ppm, 1H, t, J 74.1 Hz), 7.20-7.11 (2H, m), 7.05-7.01 (1H, m), 4.96 (1H, s), 4.68 (1H, s), 4.36 (2H, s), 3.81 (1H, dd, J 7.3, 1.3 Hz), 3.66 (1H, d, J 7.3 Hz), 3.53-3.40 (2H, m), 2.31 (3H, s), 1.99-1.85 (2H, m). LCMS (pH 10) MH+ 464.8, RT 1.83 minutes; LCMS (pH 3) MH+ 464.8, RT 1.65 minutes.

Example 37

Ethyl 1-[5-(3-{[2-(difluoromethoxy)phenyl]methyl}-2-methylimidazo[1,2-a]pyridin-6-yl)pyrimidin-2-yl]-3-methylpiperidine-3-carboxylate (2-Chloropyrimidin-5-yl)boronic acid (100 mg, 0.63 mmol), ethyl 3-methylpiperidine-3-carboxylate hydrochloride (131 mg, 0.63 mmol) and triethylamine (0.18 mL, 1.26 mmol) were dissolved in ethanol (3 mL) and the mixture was heated at 90° C. in a sealed tube for 2 h. The mixture was cooled to room temperature and diluted with 1,4-dioxane (3 mL), then Intermediate 7 (232 mg, 0.63 mmol) and 2M aqueous potassium carbonate solution (0.93 mL) were added. The mixture was degassed with nitrogen, then bis[3-(diphenylphosphanyl)cyclopenta-2,4-dien-1-yl]iron-dichloropalladium-dichloromethane complex (26 mg, 0.03 mmol) was added and the mixture was heated at 90° C. for 4 h. The mixture was cooled to room temperature, diluted with water and extracted with ethyl acetate (2×50 mL). The combined organic layers were washed with brine, dried over MgSO$_4$ and concentrated under reduced pressure. The residue was purified by preparative HPLC (Method C) to afford the title compound (130 mg, 38%) as a sticky brown oil. δ$_H$ (500 MHz, CDCl$_3$) 8.36 (s, 2H), 7.73 (s, 1H), 7.61 (d, J 9.2 Hz, 1H), 7.26-7.20 (m, 2H), 7.15 (d, J 8.1 Hz, 1H), 7.06 (t, J 7.5 Hz, 1H), 6.83 (d, J 7.6 Hz, 1H), 6.63 (t, J 73.7 Hz, 1H), 4.54 (d, J 13.2 Hz, 1H), 4.28 (s, 2H), 4.16-3.99 (m, 3H), 3.45 (ddd, J 12.9, 8.9, 3.7 Hz, 1H), 3.35 (d, J 13.2 Hz, 1H), 2.50 (s, 3H), 2.18 (dt, J 11.5, 4.8 Hz, 1H), 1.67 (ddtt, J 26.8, 13.3, 8.6, 4.2 Hz, 2H), 1.51 (ddd, J 13.5, 9.4, 4.3 Hz, 1H), 1.21 (s, 3H), 1.15 (t, J 7.1 Hz, 3H). Method D HPLC-MS: MH+ m/z 536, RT 2.78 minutes (100%).

Example 38

1-[5-(3-{[2-(Difluoromethoxy)phenyl]methyl}-2-methylimidazo[1,2-a]pyridin-6-yl)-pyrimidin-2-yl]-3-methylpiperidine-3-carboxylic acid hydrochloride Example 37 (125 mg, 0.23 mmol) was suspended in THF (5 mL), 6M aqueous NaOH solution (0.39 mL) was added and the mixture was heated at 80° C. for 18 h. The mixture was concentrated under reduced pressure, acidified with 1M HCl (pH 2-3) and extracted with 1:1 isopropanol/chloroform (2×25 mL). The organic layer was washed with water (10 mL), then dried over $Na_2SO_4$ and concentrated under reduced pressure, to afford the title compound (124 mg, 87%) as a brown solid. $\delta_H$ (500 MHz, $CDCl_3$) 8.69 (s, 1H), 8.63 (s, 2H), 8.07 (dd, J 9.3, 1.6 Hz, 1H), 7.85 (d, J 9.3 Hz, 1H), 7.34-7.25 (m, 2H), 7.17-7.10 (m, 2H), 6.84 (t, J 73.9 Hz, 1H), 4.45 (s, 2H), 4.40 (d, J 13.4 Hz, 1H), 4.33-4.23 (m, 1H), 3.45-3.37 (m, 1H), 3.37-3.32 (m, 1H), 2.42 (s, 3H), 2.20-2.08 (m, 1H), 1.70 (q, J 5.8 Hz, 1H), 1.64-1.48 (m, 2H), 1.16 (s, 3H). Method D HPLC-MS: MH+ m/z 508, RT 2.27 minutes (90%).

Example 39

Ethyl 4-[5-(3-{[2-(difluoromethoxy)phenyl]methyl}-2-methylimidazo[1,2-a]pyridin-6-yl)pyrimidin-2-yl]cyclohex-3-ene-1-carboxylate Intermediate 29 (430 mg, 0.86 mmol), Intermediate 56 (395 mg, 1.03 mmol) and 2M aqueous $K_2CO_3$ solution (1.72 mL) were suspended in 1,4-dioxane (15 mL). The mixture was degassed with nitrogen for 2 minutes. Bis[3-(diphenylphosphanyl)-cyclopenta-2,4-dien-1-yl]iron-dichloropalladium-dichloromethane complex (35 mg, 0.04 mmol) was added and the mixture was heated at 100° C. for 12 h. The mixture was cooled to room temperature, diluted with water (50 mL) and extracted with ethyl acetate (3×50 mL). The combined organic layers were washed with water (20 mL), dried over $MgSO_4$ and purified by silica gel chromatography, eluting with 80-100% ethyl acetate in heptane, to afford the title compound (217 mg, 47%) as a brown oil. $\delta_H$ (500 MHz, $CDCl_3$) 8.77 (s, 2H), 8.39 (d, J 9.4 Hz, 1H), 8.21 (s, 1H), 7.86 (d, J 9.2 Hz, 1H), 7.45-7.31 (m, 2H), 7.21 (t, J 7.1 Hz, 2H), 7.08-7.02 (m, 1H), 6.65 (t, J 73.3 Hz, 1H), 4.43 (s, 2H), 4.19 (q, J 7.1 Hz, 2H), 2.87 (d, J 17.8 Hz, 1H), 2.75 (s, 3H), 2.67-2.57 (m, 3H), 2.28-2.22 (m, 1H), 1.89-1.82 (m, 1H), 1.41 (d, J 12.5 Hz, 1H), 1.29 (t, J 7.1 Hz, 3H). Method D HPLC-MS: MH+ m/z 519, RT 2.67 minutes (97%).

Example 40

4-[5-(3-{[2-(Difluoromethoxy)phenyl]methyl}-2-methylimidazo[1,2-a]pyridin-6-yl)-pyrimidin-2-yl]cyclohex-3-ene-1-carboxylic acid Example 39 (200 mg, 0.39 mmol) was suspended in THF (5 mL), then 6M aqueous NaOH solution (0.64 mL) was added and the mixture was heated at 80° C. for 2 h. The mixture was concentrated under reduced pressure, acidified with 1M HCl (pH 2-3) and extracted with 1:1 isopropanol/chloroform (2×25 mL). The organic layer was washed with water (10 mL), then dried over $Na_2SO_4$ and concentrated under reduced pressure, to afford the title compound (175 mg, 86%) as a beige solid. $\delta_H$ (500 MHz, $CD_3OD$) 8.97 (s, 2H), 8.77 (s, 1H), 8.08 (d, J 8.8 Hz, 1H), 7.89 (d, J 9.3 Hz, 1H), 7.36 (dd, J 14.2, 6.6 Hz, 3H), 7.26-7.18 (m, 2H), 6.94 (t, J 73.9 Hz, 1H), 4.53 (s, 2H), 2.86 (d, J 17.4 Hz, 1H), 2.71-2.55 (m, 4H), 2.52 (s, 3H), 2.23 (d, J 9.7 Hz, 1H), 1.92-1.78 (m, 1H). Method D HPLC-MS: MH+ m/z 491, RT 2.06 minutes (97%).

Example 41 trans-4-[5-(3-{[2-(Difluoromethoxy)phenyl]methyl}-2-methylimidazo[1,2-a]pyridin-6-yl)pyrimidin-2-yl]cyclohexane-1-carboxylic acid Example 40 (160 mg, 0.33 mmol) was dissolved in a mixture of 4M aqueous NaOH solution (0.5 mL), water (5 mL) and ethanol (10 mL), then palladium on carbon was added. The suspension was degassed using vacuum/nitrogen/hydrogen and the mixture was stirred under hydrogen at ambient temperature and pressure for 39 h. The reaction was then degassed using vacuum/nitrogen and filtered through celite, then the filter cake was washed with MeOH (30 mL). The solvent was removed under reduced pressure and the crude residue was purified by preparative HPLC (Method A) to afford the title compound (47 mg, 30%) as a white solid. $\delta_H$ (500 MHz, $CD_3OD$) 8.91 (s, 2H), 8.39 (s, 1H), 7.65-7.55 (m, 2H), 7.30 (t, J 7.7 Hz, 1H), 7.20 (d, J 8.2 Hz, 1H), 7.13 (dt, J 15.4, 7.1 Hz, 2H), 6.92 (t, J 74.0 Hz, 1H), 4.43 (s, 2H), 2.92 (tt, J 11.7, 3.2 Hz, 1H), 2.44 (s, 3H), 2.36 (tt, J 12.2, 3.0 Hz, 1H), 2.20-2.05 (m, 4H), 1.80-1.68 (m, 2H), 1.67-1.53 (m, 2H). Method D HPLC-MS: MH+ m/z 493, RT 1.98 minutes (94%).

Example 42 cis-4-[5-(3-{[2-(Difluoromethoxy)phenyl]methyl}-2-methylimidazo[1,2-a]pyridin-6-yl)-pyrimidin-2-yl]cyclohexane-1-carboxylic acid Purification of the mixture obtained as described in Example 41 by preparative HPLC (Method A) also afforded the title compound (34 mg, 22%) as a white solid. $\delta_H$ (500 MHz, $CD_3OD$) 8.90 (s, 2H), 8.39 (s, 1H), 7.65-7.54 (m, 2H), 7.33-7.25 (m, 1H), 7.20 (d, J 8.1 Hz, 1H), 7.16-7.08 (m, 2H), 6.92 (t, J 74.0 Hz, 1H), 4.43 (s, 2H), 3.02 (tt, J 9.5, 3.8 Hz, 1H), 2.65 (m, J 4.2 Hz, 1H), 2.44 (s, 3H), 2.21-2.13 (m, 2H), 2.04 (q, J 12.3, 11.2 Hz, 2H), 1.92-1.84 (m, 2H), 1.77-1.68 (m, 2H). Method D HPLC-MS: MH+ m/z 493, RT 2.11 minutes (93%).

Example 43

Methyl 1-[5-(3-{[2-(difluoromethoxy)phenyl]methyl}-2-methylimidazo[1,2-a]pyridin-6-yl)pyrimidin-2-yl]-4-methylpiperidine-4-carboxylate A mixture of Intermediate 7 (0.5 g, 1.0 mmol), Intermediate 57 (0.5 g, 1.8 mmol), [1,1'-bis(diphenylphosphino)ferrocene]palladium(II) dichloride dichloromethane adduct (30 mg, 0.04 mmol) and 2M aqueous $Na_2CO_3$ solution (2 mL) in 1,4-dioxane (8 mL) was degassed with nitrogen and heated at 110° C. for 2.5 h. The solution was allowed to cool to room temperature, then partitioned between EtOAc and brine. The organic layer was dried ($MgSO_4$) and the solvent was removed under reduced pressure. The crude residue was purified using silica gel column chromatography (EtOAc-hexane, 4:1), then triturated in diethyl ether, to give the title compound (0.35 g, 60%) as white solid. $\delta_H$ (400 Mz, DMSO-$d_6$) 8.65 (s, 2H), 8.38 (s, 1H), 7.55 (m, 1H), 7.47 (m, 1H), 7.30 (m, 2H), 7.21 (m, 1H), 7.13 (m, 1H), 7.04 (dd, J 7.6, 1.4 Hz, 1H), 4.37 (s, 2H), 4.24 (m, 2H), 3.68 (s, 3H), 3.33 (m, 2H), 2.32 (s, 3H), 2.02 (m, 2H), 1.43 (m, 2H), 1.20 (s, 3H). LCMS (pH 10) MH+ 522, RT 1.62 minutes.

Example 44

1-[5-(3-{[2-(Difluoromethoxy)phenyl]methyl}-2-methylimidazo[1,2-a]pyridin-6-yl)-pyrimidin-2-yl]-4-methylpiperidine-4-carboxylic acid Example 43 (0.35 g, 0.67 mmol) was dissolved in THF (6 mL), then water (2 mL) and lithium hydroxide hydrate (35 mg, 0.83 mmol) were added and the mixture was stirred for 48 h. The reaction mixture was diluted with water (3 mL) and washed with EtOAc (10 mL), then the aqueous layer was neutralised using acetic acid. The precipitate was filtered off, washed thoroughly with water and dried to give the title compound (0.34 g, quantitative) as a white solid. $\delta_H$ (400 Mz, DMSO-$d_6$) 12.43 (br, 1H), 8.64 (s, 2H), 8.38 (s, 1H), 7.55 (m, 1H), 7.47 (m, 1H), 7.30 (m, 2H), 7.21 (m, 1H), 7.13 (m, 1H), 7.04 (dd, J 7.6, 1.3 Hz, 1H), 4.37 (s, 2H), 4.26 (m, 2H), 3.33 (m, 2H), 2.32 (s, 3H), 2.00 (m, 2H), 1.38 (m, 2H), 1.19 (s, 3H). LCMS (pH 10) MH+ 508, RT 1.21 minutes.

Example 45

Ethyl 1-[5-(3-{[2-(difluoromethoxy)phenyl]methyl}-7-fluoro-2-methylimidazo[1,2-a]-pyridin-6-yl)pyrimidin-2-yl]-4-methylpiperidine-4-carboxylate To Intermediate 68 (252 mg, 0.66 mmol) was added [1,1'-bis(diphenyl-phosphino)ferrocene]palladium(II) dichloride (52.6 mg, 0.072 mmol) and the reaction mixture was degassed under three cycles of vacuum and nitrogen. To the mixture were added 2M aqueous $K_2CO_3$ solution (0.63 mL, 1.26 mmol) and Intermediate 58 (269 mg, 0.679 mmol) dissolved in tetrahydrofuran (5 mL). The reaction mixture was degassed under three cycles of vacuum and nitrogen and was heated under microwave irradiation at 100° C. for 3 h. The reaction mixture was cooled to room temperature and left to stand for 12 h. The reaction mixture was then partitioned between water (5 mL) and dichloromethane (5 mL) and filtered through a phase separation cartridge. The solution was concentrated in vacuo to yield an oil which was purified by flash column chromatography on silica (Biotage SNAP 25 g, Isolera). Gradient elution, with 50% ethyl acetate/isohexane to 100% ethyl acetate, afforded the title compound (261 mg, 69%) as a brown oil. $\delta_H$ (300 MHz, DMSO-$d_6$) 8.32 (d, J 1.6 Hz, 2H), 7.62 (d, J 7.1 Hz, 1H), 7.31-7.23 (m, 2H), 7.19-7.14 (m, 1H), 7.09 (td, J 7.5, 1.1 Hz, 1H), 6.85 (dd, J 7.7, 1.5 Hz, 1H), 6.64 (t, J 73.6 Hz, 1H), 4.38 (dt, J 13.8, 4.1 Hz, 2H), 4.27 (s, 2H), 4.21 (q, J 7.1 Hz, 2H), 3.31 (ddd, J 13.8, 10.8, 3.0 Hz, 2H), 2.49 (s, 3H), 2.25-2.15 (m, 2H), 1.52-1.41 (m, 2H), 1.30 (t, J 7.1 Hz, 3H), 1.25 (s, 3H). LCMS (pH 3): MH+ m/z 554.8, RT 2.4 minutes. LCMS (pH 10): MH+ m/z 554.8, RT 2.9 minutes.

Example 46

1-[5-(3-{[2-(Difluoromethoxy)phenyl]methyl}-7-fluoro-2-methylimidazo[1,2-a]pyridin-6-yl)pyrimidin-2-yl]-4-methylpiperidine-4-carboxylic acid To Example 45 (216 mg, 0.39 mmol) were added tetrahydrofuran (4 mL), water (1 mL) and lithium hydroxide monohydrate (76.4 mg, 1.8 mmol). The mixture was stirred at room temperature for 60 h. Methanol (2 mL) was added and the mixture was heated at 70° C. for 12 h. 2M HCl was added to acidify the sample to pH 3, then the reaction mixture was partitioned between ethyl acetate (20 mL) and water (20 mL). The aqueous layer was discarded and the organic phase washed with additional water (20 mL). The organic layer was separated, dried ($Na_2SO_4$) and filtered under reduced pressure, then the solvent was removed in vacuo. The resulting brown oil was purified by preparative HPLC and freeze-dried from acetonitrile/water to give the title compound (87 mg, 41%). $\delta_H$ (300 MHz, DMSO-$d_6$) 8.41 (d, J 1.6 Hz, 2H), 8.32 (s, 0.17H, formate), 8.27 (d, J 7.5 Hz, 1H), 7.38 (d, J 11.4 Hz, 1H), 7.26-7.18 (m, 1H), 7.19 (t, J 74.1 Hz, 1H), 7.14-7.09 (m, 1H), 7.06 (td, J 7.5, 1.1 Hz, 1H), 6.96-6.91 (m, 1H), 4.26 (s, 2H), 4.26-4.14 (m, 2H), 3.32-3.17 (m, 2H), 2.21 (s, 3H), 1.99-1.88 (m, 2H), 1.35-1.23 (m, 2H), 1.10 (s, 3H). LCMS (pH 3): MH+ m/z 526.8, RT 1.926 minutes, 91.0%. LCMS (pH 10): MH+ m/z 526.8, RT 1.979 minutes, 100.0%.

Example 47

Methyl 2-[4-(3-{[2-(difluoromethoxy)phenyl]methyl}-2-methylimidazo[1,2-a]pyridin-6-yl)-1,2,3,6-tetrahydropyridin-1-yl]acetate Intermediate 59 (300 mg, 0.74 mmol) and caesium carbonate (723 mg, 2.2 mmol) were suspended in N,N-dimethylformamide (10 mL), then methyl bromoacetate (78 µL, 0.81 mmol) was added dropwise at room temperature. The reaction mixture was stirred for 18 h. The mixture was diluted with water (20 mL) and extracted with ethyl acetate (3×25 mL). The combined organic layers were washed with water (3×10 mL) and brine (10 mL), then dried over $MgSO_4$ and concentrated under reduced pressure. The residue was purified by silica gel chromatography, eluting with a gradient of 25-100% ethyl acetate in heptane, to afford the title compound (148 mg, 45%) as a light brown solid. $\delta_H$ (500 MHz, CDCl$_3$) 7.64 (s, 1H), 7.48 (d, J 9.4 Hz, 1H), 7.26 (s, 2H), 7.15 (d, J 8.1 Hz, 1H), 7.05 (t, J 7.5 Hz, 1H), 6.85 (d, J 7.4 Hz, 1H), 6.63 (t, J 73.7 Hz, 1H), 6.00 (s, 1H), 4.24 (s, 2H), 3.74 (s, 3H), 3.36 (s, 2H), 3.29 (d, J 2.9 Hz, 2H), 2.81 (t, J 5.7 Hz, 2H), 2.49 (s, 3H), 2.47-2.41 (m, 2H). Method D HPLC-MS: MH+ m/z 442, RT 1.18 minutes (97%).

Example 48

4-(3-{[2-(Difluoromethoxy)phenyl]methyl}-2-methylimidazo[1,2-a]pyridin-6-yl)-1-methanesulfonyl-1,2,3,6-tetrahydropyridine Intermediate 59 (100 mg, 0.25 mmol) was suspended in DCM (3 mL), then DIPEA (87 µL, 0.49 mmol) was added, followed by methanesulfonyl methanesulfonate (43 mg, 0.25 mmol) at room temperature. The mixture was stirred for 2 h, then concentrated under reduced pressure and purified by preparative HPLC (Method C), to afford the title compound (44.4 mg, 40%) as an off-white solid. $\delta_H$ (500 MHz, CDCl$_3$) 7.69 (s, 1H), 7.51 (d, J 9.4 Hz, 1H), 7.24 (dd, J 9.3, 1.4 Hz, 2H), 7.15 (d, J 8.1 Hz, 1H), 7.07 (t, J 7.5 Hz, 1H), 6.94-6.85 (m, 1H), 6.65 (t, J 73.7 Hz, 1H), 6.03 (t, J 3.3 Hz, 1H), 4.25 (s, 2H), 3.93 (d, J 3.0 Hz, 2H), 3.48 (t, J 5.7 Hz, 2H), 2.84 (s, 3H), 2.51 (d, J 6.3 Hz, 5H). Method D HPLC-MS: MH+ m/z 448, RT 1.88 minutes (98%).

Example 49

1-[4-(3-{[2-(Difluoromethoxy)phenyl]methyl}-2-methylimidazo[1,2-a]pyridin-6-yl)-1,2,3,6-tetrahydropyridin-1-yl]ethan-1-one Intermediate 59 (100 mg, 0.25 mmol) was dissolved in DCM (5 mL), then triethylamine (0.07 mL, 0.49 mmol) and acetic anhydride (23 µL, 0.25 mmol) were added. The mixture was stirred at room temperature for 2 h, then concentrated under reduced pressure and purified by HPLC (Method C), to afford the title compound (65 mg, 64%) as a beige solid. $\delta_H$ (500 MHz, CDCl$_3$) 7.68 (s, 1H), 7.52 (d, J 9.4 Hz, 1H), 7.26 (s, 2H), 7.16 (d, J 7.9 Hz, 1H), 7.08 (t, J 7.5 Hz, 1H), 6.89 (d, J 7.7 Hz, 1H), 6.65 (td, J 73.7, 7.2 Hz, 1H), 6.01 (d, J 23.2 Hz, 1H), 4.26 (s, 2H), 4.22 (d, J 2.8 Hz, 1H), 4.11 (d, J 2.9 Hz, 1H), 3.78 (t, J 5.7 Hz, 1H), 3.64 (t, J 5.7 Hz, 1H), 2.50 (s, 3H), 2.47-2.35 (m, 2H), 2.14 (d, J 16.9 Hz, 3H). Method D HPLC-MS: MH+ m/z 412, RT 1.73 minutes (97%).

Example 50

4-(3-{[2-(Difluoromethoxy)phenyl]methyl}-2-methylimidazo[1,2-a]pyridin-6-yl)but-3-yn-2-ol Intermediate 7 (200 mg, 0.54 mmol), but-3-yn-2-ol (60 µL, 0.81 mmol) and triethylamine (152 µL, 1.1 mmol) were combined in anhydrous N,N-dimethylformamide (5 mL) and the mixture was degassed under nitrogen. CuI (10 mg, 0.05 mmol) and Pd(PPh$_3$)$_4$ (32 mg, 0.03 mmol) were added and the mixture was heated at 70° C. for 16 h. After cooling to r.t., the mixture was degassed under nitrogen and further but-3-yn-2-ol (60 µL, 0.81 mmol), CuI (10 mg, 0.05 mmol) and Pd(PPh$_3$)$_4$ (32 mg, 0.03 mmol) were added. The mixture was heated at 90° C. for 4 h. The mixture was then diluted with ethyl acetate (50 mL) and was washed with water (2×20 mL) followed by brine (20 mL). The organic layer was dried over Na$_2$SO$_4$ and concentrated under reduced pressure. The residue was then purified by preparative HPLC (Method B). The resulting crude material was further purified by silica gel chromatography, eluting with a gradient of 50-100% ethyl acetate in heptane, to afford the title compound (29 mg, 15%) as a white solid. δ$_H$ (500 MHz, CD$_3$OD) 8.08 (s, 1H), 7.43 (d, J 9.3 Hz, 1H), 7.32-7.27 (m, 1H), 7.24-7.18 (m, 3H), 7.11 (t, J 7.5 Hz, 1H), 7.08-6.76 (m, 2H), 4.65 (q, J 6.6 Hz, 1H), 4.32 (s, 2H), 2.40 (s, 3H), 1.46 (d, J 6.6 Hz, 3H). Method A HPLC-MS: MH+ m/z 357, RT 2.24 minutes (95%).

Example 51

N-[6-(3-{[2-(Difluoromethoxy)phenyl]methyl}-2-methylimidazo[1,2-a]pyridin-6-yl)-pyridin-3-yl]-N-(methanesulfonyl)methanesulfonamide Example 20 (100 mg, 0.26 mmol) was dissolved in DCM (6 mL) and triethylamine (45 µL, 0.32 mmol) was added, followed by methanesulfonyl chloride (25 µL, 0.32 mmol), at 0° C. The mixture stirred for 30 minutes at 0° C., then for a further 100 h at ambient temperature. The reaction mixture was diluted with ethyl acetate (5 mL) and neutralised with 1M aqueous sodium hydroxide solution. Water (5 mL) was added, then the organic layer was separated and the aqueous layer was extracted with ethyl acetate (3×5 mL). The organic layers were combined, dried over sodium sulfate and concentrated under vacuum. The residue was purified by flash chromatography, eluting with 0-10% methanol in DCM. The resulting crude material was washed with DMSO and the remaining solids were further purified by chromatography, eluting with a gradient of 0-100% ethyl acetate in heptane, to afford the title compound (16 mg, 11%). δ$_H$ (500 MHz, acetone-d$_6$) 8.86 (s, 1H), 8.71 (t, J 1.7 Hz, 1H), 8.01 (d, J 1.7 Hz, 2H), 7.93 (dd, J 9.4, 1.8 Hz, 1H), 7.56 (d, J 9.4 Hz, 1H), 7.45-6.81 (m, 5H), 4.46 (s, 2H), 3.56 (s, 6H), 2.42 (s, 3H). Method A HPLC-MS: MH+ m/z 537, RT 3.14 minutes (100%).

Example 52

Ethyl 3-[5-(3-{[2-(difluoromethoxy)phenyl]methyl}-2,7-dimethylimidazo[1,2-a]pyridin-6-yl)pyrimidin-2-yl]-3-azabicyclo[3.1.0]hexane-6-carboxylate A solution of Intermediate 20 (120 mg, 0.31 mmol) and Intermediate 60 (113 mg, 0.41 mmol) in 2M aqueous K$_2$CO$_3$ solution (0.5 mL) and 1,4-dioxane (5 mL) was degassed with nitrogen for 5 minutes. Bis[3-(diphenylphosphanyl)cyclopenta-2,4-dien-1-yl]iron-dichloropalladium-dichloromethane complex (13 mg, 0.02 mmol) was added and the reaction was heated at 100° C. for 3 h. The mixture was cooled to room temperature and filtered through celite, then the filtrate was concentrated under vacuum. The crude residue was purified by preparative HPLC (Method C) to afford the title compound (110 mg, 65%) as an orange solid. δ$_H$ (500 MHz, CDCl$_3$) 8.21 (s, 2H), 7.48 (d, J 20.7 Hz, 2H), 7.25 (t, J 7.8 Hz, 1H), 7.14 (d, J 8.1 Hz, 1H), 7.07 (t, J 7.5 Hz, 1H), 6.82 (d, J 7.5 Hz, 1H), 6.60 (t, J 73.7 Hz, 1H), 4.25 (s, 2H), 4.16 (q, J 7.1 Hz, 2H), 4.02 (d, J 11.5 Hz, 2H), 3.67 (d, J 11.4 Hz, 2H), 2.49 (s, 3H), 2.29 (s, 5H), 1.59 (t, J 3.0 Hz, 1H), 1.29 (t, J 7.1 Hz, 3H). Method D HPLC-MS: MH+ m/z 534, RT 2.43 minutes (95%).

Example 53

3-[5-(3-{[2-(Difluoromethoxy)phenyl]methyl}-2,7-dimethylimidazo[1,2-a]pyridin-6-yl)-pyrimidin-2-yl]-3-azabicyclo[3.1.0]hexane-6-carboxylic acid Example 52 (70 mg, 0.13 mmol) was dissolved in THF (3 mL), then aqueous 2M NaOH solution (0.56 mL) was added and the mixture was heated at 80° C. for 18 h. The mixture was concentrated under vacuum, then acidified to pH 4-5 with 1M HCl and extracted with isopropanol/chloroform (1:1, 2×25 mL). The combined organic extracts were washed with water (10 mL), dried over Na$_2$SO$_4$ and concentrated under vacuum to afford the title compound (64 mg, 96%) as a brown solid. δ$_H$ (500 MHz, CD$_3$OD) 8.32 (d, J 11.9 Hz, 3H), 7.72 (s, 1H), 7.38-7.27 (m, 2H), 7.19 (t, J 7.5 Hz, 2H), 6.90 (t, J 73.9 Hz, 1H), 4.44 (s, 2H), 4.01 (d, J 11.6 Hz, 2H), 3.67 (d, J 11.6 Hz, 2H), 2.48 (s, 3H), 2.44 (s, 3H), 2.28 (s, 2H), 1.46 (t, J 3.0 Hz, 1H). Method D HPLC-MS: MH+ m/z 506, RT 1.90 minutes (97%).

Example 54

Ethyl 1-[5-(3-{[2-(difluoromethoxy)phenyl]methyl}-2,7-dimethylimidazo[1,2-a]pyridin-6-yl)pyrimidin-2-yl]piperidine-4-carboxylate A suspension of Intermediate 20 (150 mg, 0.39 mmol), Intermediate 61 (165 mg, 0.59 mmol) and 2M aqueous K$_2$CO$_3$ solution (0.79 mL) was purged with nitrogen for 5 minutes, then bis[3-(diphenylphosphanyl)cyclopenta-2,4-dien-1-yl]iron-dichloropalladium-dichloromethane complex (16 mg, 0.02 mmol) was added and the mixture was heated at 100° C. for 4 h. The mixture was cooled to room temperature and filtered through celite, then the filtrate was concentrated under reduced pressure. The residue was purified by preparative HPLC (Method C) to afford the title compound (140 mg, 66%) as a light grey sticky gum. δ$_H$ (500 MHz, CDCl$_3$) 8.18 (s, 2H), 7.48 (s, 1H), 7.42 (s, 1H), 7.25-7.20 (m, 1H), 7.12 (d, J 8.1 Hz, 1H), 7.04 (t, J 7.5 Hz, 1H), 6.80 (d, J 7.6 Hz, 1H), 6.58 (t, J 73.7 Hz, 1H), 4.66 (dt, J 13.4, 3.5 Hz, 2H), 4.23 (s, 2H), 4.15 (q, J 7.1 Hz, 2H), 3.16-3.00 (m, 2H), 2.59 (tt, J 11.0, 3.9 Hz, 1H), 2.47 (s, 3H), 2.28 (s, 3H), 2.00 (dd, J 13.5, 3.2 Hz, 2H), 1.73 (qd, J 11.4, 4.1 Hz, 2H), 1.26 (t, J 7.1 Hz, 3H). Method D HPLC-MS: MH+ m/z 536, RT 2.59 minutes (99%).

Example 55

1-[5-(3-{[2-(Difluoromethoxy)phenyl]methyl}-2,7-dimethylimidazo[1,2-a]pyridin-6-yl)-pyrimidin-2-yl]piperidine-4-carboxylic acid Example 54 (100 mg, 0.19 mmol) was suspended in THF (5 mL), then 2M aqueous NaOH solution (0.93 mL) was added and the mixture was heated at 80° C. for 7 h. The mixture was concentrated under vacuum, then acidified to pH 4-5 with 1M HCl and extracted with isopropanol/chloroform (1:1, 2×25 mL). The combined organic extracts were washed with water (10 mL), dried over $Na_2SO_4$ and concentrated under vacuum to afford the title compound (73 mg, 77%) as a beige solid. $\delta_H$ (500 MHz, $CD_3OD$) 8.30 (s, 2H), 8.24 (s, 1H), 7.65 (s, 1H), 7.37-7.29 (m, 1H), 7.26 (d, J 6.6 Hz, 1H), 7.22-7.12 (m, 2H), 6.90 (t, J 73.9 Hz, 1H), 4.75-4.63 (m, 2H), 4.42 (s, 2H), 3.22-3.08 (m, 2H), 2.65 (tt, J 11.0, 3.9 Hz, 1H), 2.47 (s, 3H), 2.43 (s, 3H), 2.00 (dd, J 13.4, 3.3 Hz, 2H), 1.75-1.54 (m, 2H). Method D HPLC-MS: MH+ m/z 508, RT 2.05 minutes (96%).

Example 56

2-[5-(3-{[2-(Difluoromethoxy)phenyl]methyl}-2,7-dimethylimidazo[1,2-a]pyridin-6-yl)-pyrimidin-2-yl]-2-azaspiro[3.3]heptane-6-carboxylic acid Intermediate 47 (125 mg, 0.3 mmol) and 2-azaspiro[3.3] heptane-6-carboxylic acid hydrochloride (107 mg, 0.6 mmol) were suspended in DMSO (2 mL), then triethylamine (0.08 mL, 0.61 mmol) was added. The mixture was heated at 100° C. for 30 minutes under microwave irradiation. The mixture was diluted with water (10 mL) and extracted with DCM (2×20 mL). The combined organic layers were dried over $Na_2SO_4$ and concentrated under reduced pressure. The residue was purified by silica gel chromatography, eluting with a gradient of 0-15% methanol in DCM. The resulting material was further purified, eluting with a gradient of 0-15% methanol in DCM, to afford the title compound (31 mg, 20%) as a white solid. $\delta_H$ (500 MHz, $CD_3OD$) 8.24 (s, 2H), 7.95 (s, 1H), 7.43 (s, 1H), 7.28 (t, J 7.8 Hz, 1H), 7.16 (d, J 8.2 Hz, 1H), 7.12 (t, J 7.5 Hz, 1H), 7.07 (d, J 7.6 Hz, 1H), 6.87 (t, J 74.0 Hz, 1H), 4.34 (s, 2H), 4.17 (s, 2H), 4.10 (s, 2H), 3.03 (br s, 1H), 2.51 (m, 4H), 2.41 (s, 3H), 2.30 (s, 3H). Method D HPLC-MS: MH+ m/z 520, RT 1.93 minutes (95%).

Example 57

5-(3-{[2-(Difluoromethoxy)phenyl]methyl}-2,7-dimethylimidazo[1,2-a]pyridin-6-yl)-2-[4-(1H-tetrazol-5-ylmethyl)piperazin-1-yl]pyrimidine formate Intermediate 70 (109 mg, 0.23 mmol) and $K_2CO_3$ (32 mg, 0.23 mmol) were stirred in N,N-dimethylformamide (2 mL) for 10 minutes, followed by the addition of 5-(chloromethyl)-1H-tetrazole (28 mg, 0.23 mmol) in two portions, 30 minutes apart. The mixture was stirred for 6 h, then allowed to stand over a weekend. The mixture was diluted with EtOAc (25 mL), then washed with water (25 mL) and brine (25 mL). The aqueous layer was concentrated and extracted with additional EtOAc (25 mL). The combined organic layers were dried over $MgSO_4$ and concentrated under reduced pressure. The residue was purified by silica gel chromatography, eluting with 10-50% MeOH in DCM. The resulting material was further purified by preparative HPLC (Method B), to afford the title compound (52 mg, 40%). $\delta_H$ (250 MHz, $CDCl_3$) 8.15 (s, 2H), 7.70 (d, J 10.4 Hz, 2H), 7.29 (d, J 7.3 Hz, 1H), 7.10 (t, J 7.4 Hz, 2H), 6.97-6.29 (m, 2H), 4.26 (s, 2H), 4.13 (s, 2H), 3.87 (s, 4H), 2.71 (s, 4H), 2.56 (s, 3H), 2.29 (s, 3H). Method D HPLC-MS: MH+m/z 547, RT 1.50 minutes (98%).

Example 58

5-(3-{[2-(Difluoromethoxy)phenyl]methyl}-2,7-dimethylimidazo[1,2-a]pyridin-6-yl)-2-[4-(1H-tetrazol-5-yl)piperidin-1-yl]pyrimidine Intermediate 47 (130 mg, 0.31 mmol) and 4-(1H-tetrazol-5-yl)piperidine hydrochloride (119 mg, 0.63 mmol) were suspended in DMSO (2 mL), then triethylamine (0.09 mL, 0.65 mmol) was added. The mixture was heated at 100° C. under microwave irradiation for a total of 75 minutes. NMP (1 mL) was added, then the mixture was heated at 150° C. under microwave irradiation for 30 minutes. The mixture was diluted with water (10 mL) and extracted with DCM (2×20 mL). The combined organic layers were dried over $Na_2SO_4$ and concentrated under vacuum. The residue was purified by preparative HPLC (Method B), to afford the title compound (22 mg, 13%) as a yellow glassy solid. $\delta_H$ (500 MHz, $CD_3OD$) 8.30 (s, 2H), 8.24 (s, 1H), 8.17 (s, 1H), 7.60 (s, 1H), 7.36-7.29 (m, 1H), 7.22-7.21 (m, 1H), 7.19-7.15 (m, 2H), 6.89 (t, J 73.9 Hz, 1H), 4.85 (m, 1H), 4.40 (s, 2H), 3.39-3.33 (m, 2H), 3.24-3.16 (m, 2H), 2.46 (s, 3H), 2.41 (s, 3H), 2.19-2.07 (m, 2H), 1.83 (qd, J 12.4, 4.0 Hz, 2H). Method D HPLC-MS: MH+ m/z 532, RT 1.96 minutes (100%).

Example 59

(3R)-1-[5-(3-{[2-(Difluoromethoxy)phenyl]methyl}-2,7-dimethylimidazo[1,2-a]pyridin-6-yl)pyrimidin-2-yl]pyrrolidine-3-carboxylic acid Intermediate 47 (70 mg, 0.17 mmol), (3R)-pyrrolidine-3-carboxylic acid (25 mg, 0.22 mmol) and triethylamine (0.5 mL) were suspended in NMP (2.5 mL) and the reaction mixture was heated for 1 h at 150° C. under microwave irradiation. The reaction mixture was diluted with DCM (20 mL) and saturated aqueous sodium bicarbonate solution (10 mL). The organic phase was separated, washed with brine (20 mL), dried over $Na_2SO_4$ and concentrated under vacuum. The residue was purified by preparative HPLC (Method D), to afford the title compound (41 mg, 50%) as an off-white solid. $\delta_H$ (500 MHz, DMSO-$d_6$) 8.35 (s, 2H), 7.98 (s, 1H), 7.37 (s, 1H), 7.27 (d, J 6.0 Hz, 1H), 7.24 (t, J 29 Hz, 1H), 7.17 (d, J 7.6 Hz, 1H), 7.14-7.07 (m, 1H), 6.94 (d, J 7.0 Hz, 1H), 4.28 (s, 2H), 3.70 (d, J 6.9 Hz, 2H), 3.59-3.51 (m, 2H), 3.21-3.13 (m, 1H), 2.29 (s, 3H), 2.24 (s, 3H), 2.21-2.11 (m, 2H). Method D HPLC-MS: MH+ m/z 494, RT 1.90 minutes (100%).

Example 60

2-{4-[5-(3-{[2-(Difluoromethoxy)phenyl]methyl}-2,7-dimethylimidazo[1,2-a]pyridin-6-yl)pyrimidin-2-yl]piperazin-1-yl}propanoic acid Intermediate 47 (100 mg, 0.24 mmol), 2-(piperazin-1-yl) propanoic acid (40 mg, 0.25 mmol) and triethylamine (0.5 mL) were suspended in NMP (2.5 mL) and the reaction mixture was heated for 1 h at 150° C. under microwave irradiation. The reaction mixture was diluted with DCM (20 mL) and saturated aqueous $NaHCO_3$ solution (10 mL). The organic phase was separated, washed with brine (20 mL), dried over $Na_2SO_4$ and concentrated under vacuum. The residue was purified by preparative HPLC (Method D), to afford the title compound (57 mg, 44%) as a brown gum. $\delta_H$ (250 MHz, $CD_3OD$) 8.32 (s, 2H), 7.85 (s, 1H), 7.38 (s, 1H), 7.31-7.23 (m, 1H), 7.18 (s, 1H), 7.15-6.57 (m, 3H), 4.32 (s, 2H), 4.12 (m, 4H), 3.54 (q, J 7.1 Hz, 1H), 3.30-3.23 (m, 4H), 2.41 (s, 3H), 2.28 (s, 3H), 1.51 (d, J 7.1 Hz, 3H). Method D HPLC-MS: MH+ m/z 537, RT 1.52 minutes (100%).

Example 61

(3S)-1-[5-(3-{[2-(Difluoromethoxy)phenyl]methyl}-2,7-dimethylimidazo[1,2-a]pyridin-6-yl)pyrimidin-2-yl]pyrrolidine-3-carboxylic acid Intermediate 47 (100 mg, 0.24 mmol), (3S)-pyrrolidine-3-carboxylic acid (30 mg, 0.26 mmol) and triethylamine (0.5 mL) were suspended in NMP (2.5 mL) and the reaction mixture was heated for 1 h at 150° C. under microwave irradiation. The reaction mixture was diluted with DCM (20 mL) and saturated aqueous NaHCO$_3$ solution (10 mL). The organic phase was separated, washed with brine (20 mL), dried over Na$_2$SO$_4$ and concentrated under vacuum. The residue was purified by preparative HPLC (Method D), to afford the title compound (31 mg, 26%) as a white solid. $\delta_H$ (250 MHz, DMSO-d$_6$) 8.33 (s, 2H), 7.97 (s, 1H), 7.36 (s, 1H), 7.30-7.24 (m, 1H), 7.23 (t, J 30 Hz, 1H), 7.15 (d, J 8.1 Hz, 1H), 7.10 (td, J 7.5, 1.3 Hz, 1H), 6.95-6.91 (m, 1H), 4.27 (s, 2H), 3.69 (d, J 6.8 Hz, 2H), 3.54 (td, J 10.6, 3.9 Hz, 2H), 3.13 (p, J 6.9 Hz, 1H), 2.28 (s, 3H), 2.23 (s, 3H), 2.20-2.08 (m, 2H). Method D HPLC-MS: MH+ m/z 494, RT 1.90 minutes (100%).

Example 62

(1R,2S)-2-{[5-(3-{[2-(Difluoromethoxy)phenyl]methyl}-2,7-dimethylimidazo[1,2-a]-pyridin-6-yl)pyrimidin-2-yl]amino}cyclopentane-1-carboxylic acid Intermediate 47 (100 mg, 0.24 mmol), (1R,2S)-2-aminocyclopentanecarboxylic acid (62 mg, 0.48 mmol) and triethylamine (0.05 g, 0.48 mmol) were suspended in 1,4-dioxane (2.5 mL). The reaction vessel was sealed and the mixture was heated at 90° C. for 1 h. NMP (2.5 mL) was added and the mixture was heated at 120° C. for a further 17 h. The mixture was partitioned between DCM (10 mL) and water (10 mL), then the organic layer was dried over Na$_2$SO$_4$ and concentrated under vacuum. The residue was purified by preparative HPLC (Method D). The resulting material was then further purified by preparative HPLC (Method B), to afford the title compound (13 mg, 11%) as a brown oil. $\delta_H$ (250 MHz, CDCl$_3$) 9.28 (br s, 1H), 8.37 (s, 2H), 7.85 (s, 1H), 7.68-7.58 (m, 2H), 7.33-7.22 (m, 1H), 7.15-7.05 (m, 2H), 6.92 (s, 1H), 6.59 (t, J 73.5 Hz, 1H), 4.77-4.61 (m, 1H), 4.22 (s, 2H), 3.18 (td, J 8.0, 5.1 Hz, 1H), 2.53 (s, 3H), 2.32 (s, 3H), 2.25-1.61 (m, 6H).
Method D HPLC-MS: MH+ m/z 508, RT 2.10 minutes (99%).

Example 63

Ethyl 1-[5-(3-{[2-(difluoromethoxy)phenyl]methyl}-2,7-dimethylimidazo[1,2-a]pyridin-6-yl)pyrimidin-2-yl]-4-methylpiperidine-4-carboxylate Intermediate 20 (150 mg, 0.39 mmol) and Intermediate 58 (115 mg, 0.39 mmol) were dissolved in 1,4-dioxane (2 mL) and 2M aqueous K$_2$CO$_3$ solution (0.7 mL) was added. The reaction mixture was degassed with nitrogen for 5 minutes, then bis[3-(diphenylphosphanyl)cyclopenta-2,4-dien-1-yl]iron-dichloropalladium-dichloromethane complex (16 mg, 0.02 mmol) was added. The mixture was heated at 80° C. for 16 h in a sealed tube under nitrogen. Further Intermediate 58 (50 mg, 0.17 mmol), 2M aqueous K$_2$CO$_3$ solution (0.24 mL) and bis[3-(diphenylphosphanyl)cyclopenta-2,4-dien-1-yl]iron-dichloropalladium-dichloromethane complex (5 mg, 0.005 mmol) were added and the mixture was heated for a further 2 h. Further Intermediate 58 (50 mg, 0.17 mmol), 2M aqueous K$_2$CO$_3$ solution (0.24 mL) and bis[3-(diphenylphosphanyl)cyclopenta-2,4-dien-1-yl]iron-dichloropalladium-dichloromethane complex (5 mg, 0.005 mmol) were added and the mixture was heated for a further 4 h. The mixture was diluted with water (5 mL) and extracted with EtOAc (3×10 mL). The organic layer was washed with brine (10 mL), dried over MgSO$_4$ and concentrated under vacuum. The residue was purified by silica gel chromatography, eluting with 0-100% ethyl acetate in heptane, followed by 0-30% MeOH in DCM. The resulting material was further purified by preparative HPLC (Method B), to afford the title compound (25 mg, 12%). Method A HPLC-MS: MH+ m/z 551, RT 2.75 minutes (95%).

Example 64

4-[5-(3-{[2-(Difluoromethoxy)phenyl]methyl}-2,7-dimethylimidazo[1,2-a]pyridin-6-yl)-pyrimidin-2-yl]morpholine-2-carboxylic acid Intermediate 47 (100 mg, 0.241 mmol), morpholine-2-carboxylic acid (35 mg, 0.27 mmol) and triethylamine (0.5 mL) were suspended in NMP (2.5 mL) and the reaction mixture was heated for 1 h at 150° C. under microwave irradiation. The mixture was allowed to cool to r.t. and was then diluted with DCM (20 mL) and saturated aqueous sodium bicarbonate solution (10 mL). The organic phase was separated, washed with brine (20 mL), dried over Na$_2$SO$_4$ and concentrated under vacuum. The residue was then purified by preparative HPLC (Method D), to afford the title compound (20 mg, 17%). $\delta_H$ (500 MHz, CD$_3$OD) 8.29 (s, 2H), 7.96 (s, 1H), 7.45 (s, 1H), 7.29 (t, J 7.0 Hz, 1H), 7.17 (d, J 8.1 Hz, 1H), 7.13 (t, J 7.5 Hz, 1H), 7.08 (d, J 7.4 Hz, 1H), 6.88 (t, J 74.0 Hz, 1H), 4.95 (d, 1H), 4.49 (d, J 13.4 Hz, 1H), 4.35 (s, 2H), 4.11 (d, J 10.5 Hz, 1H), 4.01 (d, J 8.7 Hz, 1H), 3.67 (t, J 10.5 Hz, 1H), 3.21-3.13 (m, 1H), 3.09 (dd, J 13.3, 10.7 Hz, 1H), 2.42 (s, 3H), 2.32 (s, 3H). Method A HPLC-MS: MH+ m/z 510, RT 3.00 minutes (100%).

Example 65

(3S)-1-[5-(3-{[2-(Difluoromethoxy)phenyl]methyl}-2,7-dimethylimidazo[1,2-a]pyridin-6-yl)pyrimidin-2-yl]piperidine-3-carboxylic acid Intermediate 47 (109 mg, 0.26 mmol), (3S)-piperidine-3-carboxylic acid (54 mg, 0.42 mmol), DIPEA (138 mL, 0.79 mmol) and NMP (2 mL) were added to a sealed tube under nitrogen and the mixture was stirred at 100° C. for 3 h. The reaction mixture was partitioned between DCM (15 mL) and water (15 mL). The organic phase was washed with water (10 mL) followed by brine (10 mL), then dried over Na$_2$SO$_4$ and concentrated under vacuum. The residue was diluted with MeOH (0.5 mL) and water (0.5 mL). The resulting white precipitate was isolated by filtration and purified by preparative HPLC (Method D), to afford the title compound (25 mg, 18%) as a white solid. $\delta_H$ (500 MHz, CD$_3$OD) 8.25 (s, 2H), 7.93 (s, 1H), 7.42 (s, 1H), 7.29 (t, J 7.3 Hz, 1H), 7.17 (d, J 8.1 Hz, 1H), 7.13 (t, J 7.5 Hz, 1H), 7.07 (d, J 7.5 Hz, 1H), 6.88 (t, J 74.0 Hz, 1H), 4.83 (d, J 13.3 Hz, 1H), 4.59 (d, J 13.4 Hz, 1H), 4.34 (s, 2H), 3.19 (dd, J 13.1, 10.6 Hz, 1H), 3.11-3.02 (m, 1H), 2.50-2.39 (m, 4H), 2.32 (s, 3H), 2.14 (dd, J 12.4, 7.6 Hz, 1H), 1.85-1.70 (m, 2H), 1.54 (q, J 12.0 Hz, 1H). Method D HPLC-MS: MH+ m/z 508, RT 2.17 minutes (100%).

Example 66

1-[5-(3-{[2-(Difluoromethoxy)phenyl]methyl}-2,7-dimethylimidazo[1,2-a]pyridin-6-yl)-pyrimidin-2-yl]-4-methylpiperidine-4-carboxylic acid Example 63 (25 mg, 0.05 mmol) was stirred in THF (1 mL) and MeOH (0.1 mL). Aqueous NaOH solution (2M, 0.23 mL)

and lithium hydroxide hydrate (4 mg, 0.09 mmol) were added. The mixture was heated at 110° C. for 4 h, then at 85° C. for 18 h, and then at 110° C. for a further 8 h. Additional lithium hydroxide hydrate (4 mg, 0.09 mmol) was added and the mixture was heated at 110° C. for 8 h. The organic solvent was removed under vacuum and the solids were partitioned between EtOAc (30 mL) and water (30 mL). The organic layer was separated and the aqueous layer was washed a second time with DCM (30 mL). The combined organic layers were dried over $Na_2SO_4$ and the solvent was removed under vacuum. The residue was purified by preparative HPLC (Method D) to afford the title compound (17.7 mg, 75%) as a white solid. $\delta_H$ (250 MHz, $CDCl_3$) 8.17 (s, 2H), 7.63 (s, 1H), 7.53 (s, 1H), 7.26 (s, 1H), 7.16-7.02 (m, 2H), 6.90-6.27 (m, 2H), 4.39 (d, J 13.8 Hz, 2H), 4.23 (s, 2H), 3.40 (t, J 10.8 Hz, 2H), 2.50 (s, 3H), 2.26 (m, 5H), 1.47 (dd, J 20.0, 10.0 Hz, 2H), 1.34 (s, 3H). Method A HPLC-MS: MH+ m/z 523, RT 2.23 minutes (100%).

Example 67

(1R,3S)-3-{[5-(3-{[2-(Difluoromethoxy)phenyl] methyl}-2,7-dimethylimidazo[1,2-a]-pyridin-6-yl) pyrimidin-2-yl]amino}cyclopentane-1-carboxylic acid Intermediate 47 (100 mg, 0.24 mmol) and (1R,3S)-3-aminocyclopentanecarboxylic acid (47 mg, 0.36 mmol) were dissolved in NMP (2 mL) and heated under microwave irradiation at 120° C. for 1 h, then at 150° C. for an additional 2 h. Further (1R,3S)-3-aminocyclopentanecarboxylic acid (25 mg, 0.19 mmol) was added and the mixture was heated at 150° C. under microwave irradiation for 1 h. The reaction mixture was partitioned between DCM (4 mL) and water (3 mL), then the organic layer was separated, dried over $Na_2SO_4$ and concentrated under reduced pressure. The residue was purified by preparative HPLC (Method D), to afford the title compound (18 mg, 15%) as an off-white solid. $\delta_H$ (500 MHz, DMSO-$d_6$) 8.26 (s, 2H), 7.99 (s, 1H), 7.43-7.08 (m, 6H), 6.93 (d, J 7.1 Hz, 1H), 4.28 (s, 2H), 4.21 (q, J 7.4 Hz, 1H), 2.74 (p, J 8.7 Hz, 1H), 2.28 (s, 3H), 2.24 (s, 3H), 2.21 (dd, J 13.6, 6.5 Hz, 1H), 1.93 (dd, J 12.5, 5.6 Hz, 1H), 1.85 (td, J 14.7, 13.7, 6.5 Hz, 2H), 1.70 (dt, J 12.6, 9.0 Hz, 1H), 1.62-1.52 (m, 1H). Method A HPLC-MS: MH+ m/z 508, RT 3.26 minutes (100%).

Example 68

Ammonium (3R)-1-[5-(3-{[2-(difluoromethoxy) phenyl]methyl}-2,7-dimethylimidazo -[1,2-a]pyridin-6-yl)pyrimidin-2-yl]piperidine-3-carboxylate Intermediate 47 (115 mg, 0.28 mmol) and (3R)-piperidine-3-carboxylic acid (107 mg, 0.83 mmol) were dissolved in 1,4-dioxane (2 mL). Triethylamine (0.11 mL, 0.83 mmol) was added, and the mixture was heated at 100° C. under microwave irradiation for 1 h. The mixture was partitioned between DCM (10 mL) and water (10 mL), then the organic layer was dried over $Na_2SO_4$ and concentrated under reduced pressure. The residue was purified by preparative HPLC (Method D), to afford the title compound (30 mg, 22%) as a yellow solid. $\delta_H$ (500 MHz, DMSO-$d_6$) 8.36 (s, 2H), 8.01 (s, 1H), 7.39 (s, 1H), 7.37-7.12 (t, J 74 Hz, 1H), 7.27 (t, J 7.7 Hz, 1H), 7.17 (d, J 8.0 Hz, 1H), 7.10 (d, J 8.7 Hz, 1H), 6.91 (t, J 9.1 Hz, 1H), 4.76-4.66 (m, 1H), 4.49 (d, J 13.0 Hz, 1H), 4.28 (s, 2H), 3.14-3.06 (m, 2H), 3.01 (t, J 10.9 Hz, 1H), 2.39-2.31 (m, 1H), 2.27 (d, J 8.4 Hz, 3H), 2.25 (s, 3H), 1.98 (t, J 16.8 Hz, 1H), 1.72 (dd, J 9.6, 3.6 Hz, 1H), 1.68-1.56 (m, 1H), 1.50-1.34 (m, 1H). Method D HPLC-MS: MH+ m/z 508, RT 2.16 minutes (99%).

Example 69

Ammonium 1-({[5-(3-{[2-(difluoromethoxy)phenyl] methyl}-2,7-dimethylimidazo[1,2-a]pyridin-6-yl) pyrimidin-2-yl]amino}methyl)cyclopropane-1-carboxylate Intermediate 47 (109 mg, 0.26 mmol), 1-(aminomethyl) cyclopropane-1-carboxylic acid hydrochloride (60 mg, 0.39 mmol), DIPEA (0.138 mL, 0.79 mmol) and NMP (2 mL) were added to a sealed tube under nitrogen. The mixture was stirred at 120° C. for 8 h. Additional 1-(aminomethyl)cyclopropane-1-carboxylic acid hydrochloride (60 mg, 0.39 mmol) and DIPEA (0.138 mL, 0.79 mmol) were added and the mixture was stirred at 150° C. for 3 h. The reaction mixture was partitioned between DCM (15 mL) and water (15 mL), and the organic phase was separated. The organic phase was washed with water (10 mL) and brine (10 mL), then dried over $Na_2SO_4$ and concentrated under reduced pressure. The residue was purified by preparative HPLC (Method D), to afford the title compound (35 mg, 27%) as an off-white solid. $\delta_H$ (250 MHz, $CD_3OD$) 8.20 (s, 2H), 7.92 (s, 1H), 7.40 (s, 1H), 7.33-7.22 (m, 1H), 7.21-6.56 (m, 4H), 4.33 (s, 2H), 3.67 (s, 2H), 2.41 (s, 3H), 2.31 (s, 3H), 1.19 (q, J 3.9 Hz, 2H), 0.96 (q, J 3.9 Hz, 2H). Method D HPLC-MS: MH+ m/z 494, RT 1.96 minutes (99%).

Example 70

Ethyl 2-[5-(3-{[2-(difluoromethoxy)phenyl]methyl}-2,7-dimethylimidazo[1,2-a]pyridin -6-yl)pyrimidin-2-yl]propanoate Intermediate 20 (150 mg, 0.39 mmol) and Intermediate 63 (330 mg, 0.59 mmol) were dissolved in 1,4-dioxane (3 mL) and 2M aqueous $K_2CO_3$ solution (0.6 mL) was added. The mixture was degassed under nitrogen and bis[3-(diphenylphosphanyl)-cyclopenta-2,4-dien-1-yl]iron-dichloropalladium-dichloromethane complex (15 mg, 0.02 mmol) was added. The mixture was heated to 80° C. in a sealed tube for 4.5 h. The mixture was diluted with water (10 mL), then extracted with ethyl acetate (3×10 mL). The combined organic layers were dried over $Na_2SO_4$ and concentrated under vacuum. The residue was purified by silica gel chromatography, eluting with a gradient of 0-100% EtOAc in heptane, to afford the title compound (102 mg, 54%) as a brown gum. $\delta_H$ (500 MHz, $CDCl_3$) 8.64 (s, 2H), 8.21 (s, 1H), 7.90 (s, 1H), 7.35 (t, J 8.0 Hz, 1H), 7.22-7.10 (m, 2H), 6.99 (d, J 7.8 Hz, 1H), 6.59 (t, J 73.3 Hz, 1H), 4.28 (s, 2H), 4.26-4.17 (m, 3H), 2.67 (s, 3H), 2.41 (s, 3H), 1.68 (d, J 7.2 Hz, 3H), 1.26 (t, J 7.1 Hz, 3H). Method A HPLC-MS: MH+ m/z 481, RT 3.26 minutes (93%).

Example 71

Ammonium (2S)-1-[5-(3-{[2-(difluoromethoxy)phenyl]methyl}-2,7-dimethylimidazo -[1,2-a]pyridin-6-yl)pyrimidin-2-yl]piperidine-2-carboxylate Intermediate 47 (107 mg, 0.26 mmol) and (2S)-piperidine-2-carboxylic acid (100 mg, 0.77 mmol) were dissolved in NMP (2 mL). Triethylamine (0.11 mL, 0.83 mmol) was added, and the mixture was heated at 150° C. under microwave irradiation for 1 h. The mixture was partitioned between DCM (10 mL) and water (10 mL). The organic layer was separated, dried over $Na_2SO_4$ and concentrated under vacuum. The resulting dark oil was purified by preparative HPLC (Method D), to afford the title compound (40 mg, 31%) as an orange solid. $\delta_H$ (500 MHz, DMSO-$d_6$) 8.37 (s, 2H), 8.01 (s, 1H), 7.39-7.12 (t, J 74 Hz, 1H), 7.38 (s, 1H), 7.27 (dd, J 11.4, 4.2 Hz, 1H), 7.18 (d, J 8.1 Hz, 1H), 7.12-7.08 (m, 1H), 6.92 (d, J 7.1 Hz, 1H), 4.71 (dd, J 13.0, 3.6 Hz, 1H), 4.48 (d, J 13.1 Hz, 1H), 4.28 (s, 2H), 3.19-3.09 (m, 1H), 3.09-2.99 (m, 1H), 2.45-2.34 (m, 1H), 2.29 (s, 3H), 2.25 (s, 3H), 2.01 (dd, J 12.8, 3.5 Hz, 1H), 1.77-1.59 (m, 2H), 1.51-1.37 (m, 1H). Method D HPLC-MS: MH+ m/z 508, RT 2.31 minutes (99%).

Example 72

(2S)-2-{N-[5-(3-{[2-(Difluoromethoxy)phenyl]methyl}-2,7-dimethylimidazo[1,2-a]-pyridin-6-yl)pyrimidin-2-yl]-Methyl)amino}propanoic acid Intermediate 47 (0.1 g, 0.2 mmol), N-methyl-L-alanine (0.02 g, 0.2 mmol), $K_2CO_3$ (0.08 g, 0.6 mmol) and DMF (2 mL) were charged to a sealed tube under nitrogen. The reaction mixture was stirred at 80° C. for 5 h. After cooling to room temperature, the mixture was diluted with EtOAc (10 mL), then extracted with water (5 mL) followed by 2M aqueous $K_2CO_3$ solution (5 mL). The combined aqueous layers were acidified to pH 4 by the addition of 6M HCl, then extracted with DCM (5×10 mL). The organic phase was dried over $MgSO_4$ and concentrated under reduced pressure. The residue was purified by preparative HPLC (Method D), to afford the title compound (12 mg, 12%) as a colourless oil. $\delta_H$ (500 MHz, DMSO-$d_6$) 8.36 (s, 2H), 8.02 (s, 1H), 7.37 (s, 1H), 7.27 (t, J 7.1 Hz, 1H), 7.40-7.10 (m, 1H), 7.17 (d, J 7.9 Hz, 1H), 7.14-7.10 (m, 1H), 6.93 (d, J 7.0 Hz, 1H), 5.25 (q, J 7.3 Hz, 1H), 4.28 (s, 2H), 3.05 (s, 3H), 2.28 (s, 3H), 2.25 (s, 3H), 1.40 (d, J 7.3 Hz, 3H). Method D HPLC-MS: MH+ m/z 482, RT 2.05 minutes (100%).

Example 73

1-[5-(3-{[2-(Difluoromethoxy)phenyl]methyl}-2,7-dimethylimidazo[1,2-a]pyridin-6-yl)-pyrimidin-2-yl]azetidine-3-carboxylic acid Intermediate 47 (90 mg, 0.17 mmol), azetidine-3-carboxylic acid methyl ester hydrochloride (0.03 g, 0.17 mmol), $K_2CO_3$ (120 mg, 0.87 mmol) and DMF (1.5 mL) were charged to a sealed tube under nitrogen. The reaction mixture was stirred at 80° C. for 40 h. After cooling to room temperature, the mixture was diluted with EtOAc (20 mL), then extracted with water (10 mL) followed by 2M aqueous $K_2CO_3$ solution (10 mL). The combined aqueous layers were acidified to pH 4 by the addition of 6M hydrochloric acid. The aqueous layer was then extracted into DCM (5×25 mL), followed by 1:1 isopropanol/chloroform (3×25 mL). The combined organic layers were dried over $MgSO_4$ and concentrated to dryness under reduced pressure. The residue was dissolved in THF (10 mL), 2M aqueous NaOH solution (2 mL) was added and the mixture was stirred at 80° C. for 4 h. The mixture was cooled to room temperature and evaporated to dryness. The residue was acidified with 6M HCl (pH 1), extracted with 1:1 isopropanol/chloroform (3×25 mL), dried over $MgSO_4$ and concentrated under reduced pressure. The residue was purified by preparative HPLC (Method D), to afford the title compound (14 mg, 16%) as a white solid. $\delta_H$ (500 MHz, $CD_3OD$) 8.27 (s, 2H), 8.00 (s, 1H), 7.47 (s, 1H), 7.33-7.26 (m, 1H), 7.20-7.08 (m, 3H), 6.88 (t, J 74.0 Hz, 1H), 4.36 (s, 2H), 4.33 (d, J 8.9 Hz, 2H), 4.28 (dd, J 8.9, 6.1 Hz, 2H), 3.51 (ddd, J 15.0, 8.9, 6.1 Hz, 1H), 2.43 (s, 3H), 2.33 (s, 3H). Method D HPLC-MS: MH+ m/z 480, RT 1.78 minutes (94%).

Example 74

(1S,3R)-3-{[5-(3-{[2-(Difluoromethoxy)phenyl]methyl}-2,7-dimethylimidazo[1,2-a]-pyridin-6-yl)pyrimidin-2-yl]amino}cyclopentane-1-carboxylic acid Intermediate 47 (150 mg, 0.36 mmol) and (1S,3R)-3-aminocyclopentanecarboxylic acid (120 mg, 0.93 mmol) were dissolved in NMP (2 mL) and triethylamine (130 µL, 0.93 mmol) was added. The reaction mixture was heated at 150° C. under microwave irradiation for 1 h. The reaction mixture was diluted with water (2 mL) and extracted with EtOAc (2 mL). The aqueous layer was acidified with 1M HCl to pH 6 and extracted into EtOAc (2 mL). The resulting organic layer was washed with brine (1 mL) and dried over $Na_2SO_4$, then heptane (2 mL) was added. The resulting solid precipitate was collected by filtration and washed with 1:1 EtOAc/heptane (2 mL). The filtrate was concentrated to approximately half the volume and the resultant solid was collected by filtration, triturated with 1:1 DCM/heptane (2 mL) and collected by filtration again. The resulting materials were combined to afford the title compound (27 mg, 15%) as a light brown solid. $\delta_H$ (500 MHz, $CD_3OD$) 8.21 (s, 2H), 7.92 (s, 1H), 7.41 (s, 1H), 7.29 (t, J 7.1 Hz, 1H), 7.17 (d, J 8.0 Hz, 1H), 7.13 (t, J 7.5 Hz, 1H), 7.06 (d, J 7.6 Hz, 1H), 6.88 (t, J 74.0 Hz, 1H), 4.40-4.27 (m, 3H), 2.93-2.83 (m, 1H), 2.41 (s, 3H), 2.40-2.28 (m, 4H), 2.08-1.95 (m, 3H), 1.88-1.78 (m, 1H), 1.77-1.67 (m, 1H). Method D HPLC-MS: MH+ m/z 508, RT 2.00 minutes (93%).

Example 75

4-(3-{[2-(Difluoromethoxy)phenyl]methyl}-2,7-dimethylimidazo[1,2-a]pyridin-6-yl)-morpholine Intermediate 20 (50 mg, 0.13 mmol), morpholine (0.05 mL, 0.57 mmol), sodium tert-butoxide (40 mg, 0.42 mmol) and BINAP (15 mg, 0.02 mmol) were added to a microwave tube containing 1,4-dioxane (2 mL). The tube was flushed with nitrogen, then $Pd_2(dba)_3$ (12 mg, 0.01 mmol) was added and the reaction mixture was heated at 120° C. for 1 h under microwave irradiation. The solvent was removed under reduced pressure and the residue was purified by silica gel chromatography, eluting with a gradient of 0-100% EtOAc in heptane. The residue was further purified by preparative HPLC (Method A), to afford the title compound (11.6 mg, 23%). $\delta_H$ (500 MHz, $CDCl_3$) 7.58 (s, 1H), 7.28-7.23 (m, 2H), 7.17 (d, J 8.1 Hz, 1H), 7.10 (t, J 7.5 Hz, 1H), 7.07-6.75 (m, 2H), 4.27 (s, 2H), 3.78-3.73 (m, 4H), 2.81-2.75 (m, 4H), 2.38 (s, 3H), 2.35 (s, 3H). Method A HPLC-MS: MH+ m/z 388, RT 1.97 minutes (96%).

Example 76

Ammonium (2R)-1-[5-(3-{[2-(difluoromethoxy)phenyl]methyl}-2,7-dimethylimidazo-[1,2-a]pyridin-6-yl)pyrimidin-2-yl]piperidine-2-carboxylate (2R)-Piperidine-2-carboxylic acid (37 mg, 0.29 mmol) and Intermediate 47 (100 mg, 0.24 mmol) were stirred in NMP (2 mL) for 3.5 h at 80° C. Triethylamine (0.03 g, 0.29 mmol) was added and the reaction mixture was heated at 80° C. for 2 h, then at 100° C. for 18 h, and then at 120° C. for 4 h. Further (2R)-piperidine-2-carboxylic acid (37 mg, 0.29 mmol) and triethylamine (0.03 g, 0.29 mmol) were added and the mixture was heated at 150° C. for 4 h. The solvent was removed and the residue was purified by preparative HPLC (Method D), to afford the title compound (15.5 mg, 13%) as a yellow solid. $\delta_H$ (250 MHz, CDCl$_3$) 8.18 (s, 2H), 7.59 (s, 1H), 7.48 (s, 1H), 7.20 (d, J 7.6 Hz, 1H), 7.11-6.99 (m, 2H), 6.89-6.27 (m, 2H), 5.56 (s, 1H), 4.69 (d, J 11.9 Hz, 1H), 4.20 (s, 2H), 3.27 (t, J 11.2 Hz, 1H), 2.44 (s, 4H), 2.24 (s, 3H), 1.77 (s, 3H), 1.55 (s, 2H). Method A HPLC-MS: MH+ m/z 508, RT 2.32 minutes (96%).

Example 77

(2S)-4-[5-(3-{[2-(Difluoromethoxy)phenyl]methyl}-2-methylimidazo[1,2-a]pyridin-6-yl)pyrimidin-2-yl]morpholine-2-carboxylic acid Intermediate 7 (150 mg, 0.41 mmol) and Intermediate 64 (0.22 g, 0.41 mmol) were dissolved in 1,4-dioxane (3 mL), and 2M aqueous K$_2$CO$_3$ solution (0.72 mL) was added. The reaction mixture was degassed with nitrogen for 5 minutes, then bis[3-(diphenylphosphanyl)cyclopenta-2,4-dien-1-yl]iron-dichloropalladium-dichloromethane complex (17 mg, 0.02 mmol) was added. The reaction mixture was heated at 80° C. for 16 h in a sealed tube under nitrogen. Further Intermediate 64 (108 mg, 0.20 mmol), 2M aqueous K$_2$CO$_3$ solution (0.2 mL) and bis[3-(diphenylphosphanyl)cyclopenta-2,4-dien-1-yl]iron-dichloropalladium-dichloromethane complex (17 mg, 0.02 mmol) were added, and the mixture was degassed and heated for 2.5 h. The mixture was acidified to pH 5 with 2M HCl and extracted with EtOAc (3×10 mL). The combined organic layers were washed with brine (10 mL), dried over MgSO$_4$ and concentrated under vacuum. The crude residue was purified by preparative HPLC (Method D), to afford the title compound (17.7 mg, 9%) as a tan-coloured solid. $\delta_H$ (250 MHz, DMSO-d$_6$) 8.67 (s, 2H), 8.39 (s, 1H), 7.63-7.40 (m, 2H), 7.37-6.94 (m, 5H), 4.60 (d, J 12.3 Hz, 1H), 4.35 (s, 2H), 4.26 (d, J 13.0 Hz, 1H), 3.98 (m, 1H), 3.81 (d, J 7.0 Hz, 1H), 3.56-3.41 (m, 1H), 3.22-3.00 (m, 2H), 2.31 (s, 3H). Method A HPLC-MS: MH+ m/z 496, RT 1.89 minutes (95%).

Example 78

4-(3-{[2-(Difluoromethoxy)phenyl]methyl}-2,7-dimethylimidazo[1,2-a]pyridin-6-yl)-benzene-1-sulfonamide Intermediate 20 (150 mg, 0.39 mmol) and (4-sulfamoylphenyl)boronic acid (109 mg, 0.43 mmol) were dissolved in 1,4-dioxane (2 mL) and 2M aqueous K$_2$CO$_3$ solution (0.69 mL) was added. The reaction mixture was degassed with nitrogen for 5 minutes, then bis[3-(diphenylphosphanyl)cyclopenta-2,4-dien-1-yl]iron-dichloropalladium-dichloromethane complex (16 mg, 0.02 mmol) was added. The reaction mixture was heated at 80° C. for 16 h in a sealed tube under nitrogen. The mixture was diluted with water (5 mL), then extracted with EtOAc (3×10 mL), washed with brine (10 mL), dried over MgSO$_4$ and concentrated under vacuum. The crude residue was purified by silica gel chromatography, eluting with a gradient of 0-5% 7M ammonia/methanol in DCM, to afford the title compound (154 mg, 80%) as a yellow solid. Method C HPLC-MS: MH+m/z 458, RT 1.00 minute (94%).

Example 79

N-[4-(3-{[2-(Difluoromethoxy)phenyl]methyl}-2,7-dimethylimidazo[1,2-a]pyridin-6-yl) -benzenesulfonyl]acetamide Acetyl chloride (24 µL, 0.34 mmol) and triethylamine (47 µL, 0.34 mmol) were added to a solution of Example 78 (154 mg, 0.34 mmol) in DCM (3 mL). The reaction mixture was stirred at room temperature for 2.5 h. Further acetyl chloride (12 µL, 0.17 mmol) and triethylamine (23 µL, 0.17 mmol) were added, and the mixture was stirred at room temperature for 24 h. Further acetyl chloride (49 µL, 0.68 mmol) and triethylamine (94 µL, 0.34 mmol) were added, and the mixture was stirred for 3 days. The solvent was removed and the mixture was purified by silica gel chromatography, eluting with a 0-5% gradient of 7M ammonia/methanol in DCM, to afford the title compound (24.8 mg, 14%) as a white solid. $\delta_H$ (250 MHz, CDCl$_3$) 8.09 (d, J 8.4 Hz, 2H), 7.64 (d, J 19.1 Hz, 2H), 7.42 (s, 1H), 7.35 (d, J 8.3 Hz, 2H), 7.26 (m, 1H), 7.07 (td, J 8.4, 2.1 Hz, 2H), 6.94-6.24 (m, 2H), 4.24 (s, 2H), 2.49 (s, 3H), 2.25 (s, 3H), 2.09 (s, 3H). Method A HPLC-MS: MH+ m/z 500, RT 1.96 minutes (100%).

Example 80

3-{[5-(3-{[2-(Difluoromethoxy)phenyl]methyl}-2-methylimidazo[1,2-a]pyridin-6-yl) -pyrimidin-2-yl]oxy}cyclobutane-1-carboxylic acid Methyl 3-hydroxycyclobutanecarboxylate (30 mg, 0.23 mmol) and sodium hydride (60%, 9 mg, 0.23 mmol) were dissolved in DMF (2 mL) under a nitrogen atmosphere at 0° C. and allowed to stir for 15 minutes. Intermediate 29 (86% pure, 80 mg, 0.17 mmol) was added to the reaction mixture, then the solution was allowed to warm to room temperature and stirred for 2 h. The mixture was diluted with DCM (15 mL) and saturated aqueous sodium bicarbonate solution (10 mL). The organic phase was separated, washed with brine, dried over sodium sulfate and concentrated under vacuum. The product was purified by preparative HPLC (Method D) to afford the title compound (25 mg, 31%). $\delta_H$ (250 MHz, DMSO-d$_6$) 8.90 (s, 2H), 8.56 (s, 1H), 7.59-7.52 (m, 2H), 7.46-7.15 (m, 3H), 7.13-7.10 (m, 1H), 7.01 (d, J 7.6 Hz, 1H), 5.10 (p, J 7.5 Hz, 1H), 4.37 (s, 2H), 2.77 (q, J 9.1, 8.7 Hz, 1H), 2.71-2.62 (m, 2H), 2.30 (s, 3H), 2.24 (qd, J 9.4, 2.5 Hz, 2H). Method D HPLC-MS: MH+ m/z 481, RT 1.29 minutes.

Example 81

4-(3-{[2-(Difluoromethoxy)phenyl]methyl}-2-methylimidazo[1,2-a]pyridin-6-yl)-N -methylpyridin-2-amine Intermediate 73 (500 mg, 1.3 mmol) was dissolved in 1-methyl-2-pyrrolidinone (1.5 mL) and methylamine (40% in water, 2.5 mL, 0.03 mol) was added. The mixture was heated for 1 h at 140° C. under microwave irradiation. The mixture was diluted with DCM (20 mL), then washed with water (2×10 mL) and brine (10 mL). The organic layer was dried over sodium sulfate and concentrated under vacuum. The resulting light brown oil was diluted with methanol (10 mL), then loaded onto a 5 g SCX cartridge. This was flushed with methanol, followed by 7N ammonia in methanol (3CVs). The ammonia fractions were concentrated under vacuum to afford crude product (540 mg). A portion of this material (80 mg) was further purified by preparative HPLC (Method C) to afford the title compound (72.2 mg, 14%) as a white solid. $\delta_H$ (250 MHz, CD$_3$OD) 8.25 (t, J 1.1 Hz, 1H), 7.96 (d, J 5.6 Hz, 1H), 7.53 (d, J 1.3 Hz, 2H), 7.31-7.26 (m, 1H), 7.20 (d, J 7.9 Hz, 1H), 7.13 (td, J 7.6, 1.1 Hz, 1H), 7.08-6.77 (m, 2H), 6.70 (dd, J 5.5, 1.6 Hz, 1H), 6.63-6.60 (m, 1H), 4.38 (s, 2H), 2.89 (s, 3H), 2.44 (s, 3H). Method D HPLC-MS: MH+ m/z 395, RT 1.52 minutes.

Example 82

Ammonium 3-[5-(3-{[2-(difluoromethoxy)phenyl]methyl}-2,7-dimethylimidazo[1,2-a]pyridin-6-yl)pyrimidin-2-yl]-3-azabicyclo[3.1.0]hexane-1-carboxylate Intermediate 47 (90 mg, 0.217 mmol) and Intermediate 76 (116 mg, 0.65 mmol) were dissolved in 1-methyl-2-pyrrolidinone (2 mL), triethylamine (0.12 mL, 0.87 mmol) was added and the mixture was heated at 150° C. under microwave irradiation for 1 h. The mixture was partitioned between DCM (10 mL) and water (10 mL), then the organic layer was dried over sodium sulfate and concentrated under vacuum. The residue was dissolved in THF (2 mL), 1M aqueous NaOH solution (0.25 mL) was added and the reaction mixture was stirred at 80° C. overnight. Further 1M aqueous NaOH solution (0.25 mL) was added and the reaction was heated at 80° C. for 15 h. The reaction mixture was concentrated and the pH was adjusted to pH 5 using 1M HCl. The mixture was extracted with 1:1 isopropanol/chloroform (2×10 mL), then the organic layer was dried over sodium sulfate and concentrated. The crude product was purified by preparative HPLC (Method D), then further purified by SCX cartridge, to afford the title compound (11.4 mg, 13%) as a colourless solid. $\delta_H$ (250 MHz, DMSO-d$_6$) 8.34 (d, J 6.0 Hz, 2H), 7.97 (s, 1H), 7.54-6.94 (t, J 74 Hz, 1H), 7.36 (s, 1H), 7.28 (dd, J 10.1, 3.2 Hz, 1H), 7.16 (d, J 7.4 Hz, 1H), 7.10 (td, J 7.5, 1.2 Hz, 1H), 6.90 (dt, J 7.8, 3.9 Hz, 1H), 4.27 (s, 2H), 3.82 (s, 2H), 3.78 (s, 1H), 3.55 (dd, J 11.1, 4.2 Hz, 1H), 2.28 (s, 3H), 2.23 (s, 3H), 1.98 (dt, J 8.5, 4.6 Hz, 1H), 1.41 (dt, J 10.3, 5.3 Hz, 1H), 0.65 (t, J 4.4 Hz, 1H). Method D HPLC-MS: MH+ m/z 506, RT 2.09 minutes.

Example 83

Ammonium 4-[5-(3-{[2-(difluoromethoxy)phenyl]methyl}-2-methylimidazo[1,2-a]-pyridin-6-yl)pyrimidin-2-yl]-1,4-oxazepane-7-carboxylate Intermediate 7 (135 mg, 0.37 mmol) and Intermediate 217 (147 mg, 0.44 mmol) were dissolved in 1,4-dioxane (2 mL) and 2M aqueous potassium carbonate solution (0.645 mL) was added. The reaction mixture was degassed with nitrogen for 5 minutes, then bis[3-(diphenylphosphanyl)cyclopenta-2,4-dien-1-yl]iron dichloropalladium dichloromethane complex (15 mg, 0.02 mmol) was added. The reaction mixture was heated at 80° C. for 3 h in a sealed tube under nitrogen. Further Intermediate 217 was added, then the mixture was degassed and bis[3-(diphenylphosphanyl)cyclopenta-2,4-dien-1-yl]iron dichloropalladium dichloromethane complex (15 mg, 0.02 mmol) was added. The mixture was heated at 80° C. for 1 h. The mixture was then retreated as above and heated for a further 3 h at 80° C. The mixture was diluted with water (5 mL), extracted into EtOAc (3×10 mL) and washed with brine (10 mL), then dried over magnesium sulfate and concentrated under vacuum. The crude product was purified by preparative HPLC (Method D) to afford the title compound (25 mg, 12%) as a white solid. $\delta_H$ (250 MHz, CDCl$_3$) 8.33 (s, 2H), 7.77 (s, 1H), 7.57 (d, J 9.3 Hz, 1H), 7.29 (d, J 1.5 Hz, 1H), 7.19 (d, J 7.2 Hz, 1H), 7.10 (d, J 8.0 Hz, 1H), 7.03 (t, J 7.4 Hz, 1H), 6.84-6.30 (m, 2H), 4.72 (dd, J 14.6, 4.6 Hz, 1H), 4.44-4.26 (m, 2H), 4.23 (s, 2H), 4.13-3.99 (m, 1H), 3.60 (dd, J 8.2, 4.1 Hz, 1H), 3.43-3.26 (m, 2H), 2.43 (s, 3H), 2.08-1.80 (m, 2H).

Method D HPLC-MS: MH+ m/z 510, RT 1.95 minutes.

Example 84

2-[(2R)-1-[5-(3-{[2-(Difluoromethoxy)phenyl]methyl}-2-methylimidazo[1,2-a]pyridin-6-yl)pyrimidin-2-yl]pyrrolidin-2-yl]acetic acid Intermediate 29 (150 mg, 0.37 mmol) was dissolved in 1-methyl-2-pyrrolidinone (2 mL), then (2R)-pyrrolidin-2-ylacetic acid hydrochloride (93 mg, 0.56 mmol) and triethylamine (104 µL, 0.75 mmol) were added and the mixture was heated at 120° C. under microwave irradiation for 45 minutes. The reaction mixture was diluted with water (4 mL) and extracted into EtOAc (5 mL). The organic layer was washed with brine, dried over sodium sulfate and concentrated to dryness. The residue was triturated with 1:1 DCM/heptane (~3 mL) twice to afford the title compound (12 mg, 7%) as a pale yellow solid. $\delta_H$ (250 MHz, CD$_3$OD) 8.54 (s, 2H), 8.31 (s, 1H), 7.71-7.58 (m, 2H), 7.37-7.29 (m, 1H), 7.23 (d, J 8.2 Hz, 1H), 7.18 (d, J 4.3 Hz, 2H), 6.94 (t, J 73.9 Hz, 1H), 4.59-4.52 (m, 1H), 4.45 (s, 2H), 3.72-3.64 (m, 1H), 3.64-3.54 (m, 1H), 3.05 (dd, J 15.4, 3.5 Hz, 1H), 2.48 (s, 3H), 2.39 (dd, J 15.6, 10.1 Hz, 1H), 2.24-2.16 (m, 1H), 2.16-2.08 (m, 1H), 2.07-1.97 (m, 2H). Method E HPLC-MS: MH+ m/z 494, RT 3.03 minutes.

Example 85

5-(3-{[2-(Difluoromethoxy)phenyl]methyl}-2-methylimidazo[1,2-a]pyridin-6-yl)-2-[3-(2H-1,2,3,4-tetrazol-5-yl)azetidin-1-yl]pyrimidine (2-Chloropyrimidin-5-yl)boronic acid (0.78 g, 4.93 mmol) and 5-(azetidin-3-yl)-2H-1,2,3,4-tetrazole (0.8 g, 4.93 mmol) were dissolved in DMF (12 mL) and K$_2$CO$_3$ (4.08 g, 29.55 mmol) was added. The mixture was heated at 80° C. in a sealed tube for 2 h, after which time the reaction mixture was cooled to room temperature. To the mixture were added Intermediate 7 (0.3 g, 0.82 mmol), 2M aqueous K$_2$CO$_3$ solution (2.5 mL) and 1,4-dioxane (9 mL). The mixture was degassed with nitrogen for 15 minutes, then tetrakis-(triphenylphosphine) palladium(0) (0.14 g, 0.12 mmol) was added. The mixture was heated at 80° C. in a sealed tube for 16 h. Upon cooling to room temperature, the mixture was evaporated to dryness and the residue was purified by FCC, eluting with 0-100% MeOH in DCM. The material was further purified by preparative HPLC (Method D) to afford the title compound (7.7 mg, 2%) as a white solid. $\delta_H$ (500 MHz, CD$_3$OD) 10.12 (s, 2H), 9.97 (s, 1H), 9.33 (dd, J 9.3, 1.5 Hz, 1H), 9.27 (d, J 9.3 Hz, 1H), 8.93-8.85 (m, 1H), 8.81-8.70 (m, 3H), 8.49 (t, J 74.0 Hz, 1H), 6.19 (t, J 8.7 Hz, 2H), 6.02 (s, 2H), 5.96 (dd, J 8.4, 6.3

Hz, 2H), 5.93-5.85 (m, 1H), 4.04 (s, 3H). Method E HPLC-MS: MH+ m/z 490, RT 1.75 minutes.

Example 86

Ammonium 3-[5-(3-{[2-(difluoromethoxy)phenyl]methyl}-2-methylimidazo[1,2-a]-pyridin-6-yl)pyrimidin-2-yl]-3-azabicyclo[3.1.0]hexane-1-carboxylate (2-Chloropyrimidin-5-yl)boronic acid (147 mg, 0.93 mmol), Intermediate 76 (165 mg, 0.93 mmol) and $K_2CO_3$ (193 mg, 1.397 mmol) were combined in DMF (2 mL) and the mixture was heated at 80° C. for a total of 5 h in a sealed tube. Further $K_2CO_3$ was added and the mixture was heated for 10 minutes at 80° C. To the mixture were added Intermediate 7 (228 mg, 0.621 mmol), 2M aqueous $K_2CO_3$ solution (0.3 mL, 0.6 mmol) and 1,4-dioxane (3 mL). The mixture was degassed with nitrogen, the bis[3-(diphenyl-phosphanyl)cyclopenta-2,4-dien-1-yl]iron dichloropalladium dichloromethane complex (25 mg, 0.31 mmol) was added and the mixture was heated at 80° C. overnight. EtOAc (20 mL) was added, then the mixture was washed with water (2×20 mL) and brine. The mixture was extracted with further EtOAc (2×20 mL) and washed with brine (10 mL). The organic layers were combined and dried over sodium sulfate. The crude product was purified using an SCX cartridge. The resulting material was dissolved in THF (2 mL), 1M aqueous NaOH solution (0.73 mL) was added and the mixture was stirred at 80° C. for 1.5 h. The mixture was concentrated to dryness and water was added. The mixture was acidified to pH 5 using 1M HCl, then extracted with 1:1 isopropanol/chloroform (3×20 mL), dried over sodium sulfate and concentrated under vacuum. The residue was purified by preparative HPLC (Method D) to afford the title compound (50.5 mg, 11%) as an off-white solid. $\delta_H$ (500 MHz, DMSO-$d_6$) 8.64 (s, 2H), 8.37 (s, 1H), 7.53 (d, J 9.3 Hz, 1H), 7.47-7.09 (m, 5H), 7.06-7.01 (m, 1H), 4.35 (s, 2H), 3.91-3.85 (m, 1H), 3.85-3.80 (m, 1H), 3.59 (dd, J 11.1, 4.3 Hz, 1H), 2.54 (s, 1H), 2.31 (s, 3H), 2.13 (dt, J 8.9, 4.8 Hz, 1H), 1.50 (dd, J 8.2, 4.1 Hz, 1H), 0.82 (t, J 4.7 Hz, 1H). Method D HPLC-MS: MH+ m/z 492, RT 2.02 minutes.

Example 87

5-[5-(3-{[2-(Difluoromethoxy)phenyl]methyl}-2-methylimidazo[1,2-a]pyridin-6-yl)-pyrimidin-2-yl]-5-azaspiro[2.4]heptane-1-carboxylic acid (2-Chloropyrimidin-5-yl)boronic acid (135 mg, 0.85 mmol), 5-azaspiro[2.4]-heptane-1-carboxylic acid (100 mg, 0.71 mmol) and triethylamine (0.2 mL, 1.43 mmol) were dissolved in ethanol (5 mL), and the mixture was stirred for 2 h at 80° C. in a sealed tube. To the mixture were added Intermediate 7 (200 mg, 0.54 mmol), 2M aqueous $K_2CO_3$ solution (0.8 mL) and 1,4-dioxane (3 mL). The mixture was degassed with nitrogen, then bis[3-(diphenylphosphanyl)cyclopenta-2,4-dien-1-yl]iron dichloropalladium dichloromethane complex (40 mg, 0.05 mmol) was added. The mixture was heated at 80° C. in a sealed tube and allowed to stir for 18 h. Further Intermediate 7 (50 mg, 0.135 mmol) was added and the mixture was stirred for a further 16 h at 80° C. The mixture was diluted with DCM (20 mL) and extracted with water (10 mL), followed by 2M aqueous potassium carbonate solution (10 mL). The combined aqueous layers were extracted with 1:1 isopropanol/chloroform (20 mL). The crude material was twice purified by preparative HPLC (Method D) to afford the title compound (12.8 mg, 5%). $\delta_H$ (500 MHz, CD$_3$OD) 8.45 (s, 2H), 8.13 (s, 1H), 7.54 (d, J 9.2 Hz, 1H), 7.46 (d, J 9.1 Hz, 1H), 7.29 (t, J 7.4 Hz, 1H), 7.20 (d, J 8.1 Hz, 1H), 7.14 (t, J 7.4 Hz, 1H), 7.09-6.76 (m, 2H), 4.39 (s, 2H), 3.81-3.67 (m, 4H), 2.44 (s, 3H), 2.08 (dt, J 13.5, 7.1 Hz, 1H), 1.95 (dd, J 12.8, 6.0 Hz, 1H), 1.76 (d, J 6.3 Hz, 1H), 1.31-1.26 (m, 1H), 1.05 (s, 1H). Method D HPLC-MS: MH+ m/z 506, RT 2.08 minutes.

Example 88

5-[5-(3-{[2-(Difluoromethoxy)phenyl]methyl}-2-methylimidazo[1,2-a]pyridin-6-yl)-pyrimidin-2-yl]-5-azaspiro[2.3]hexane-1-carboxylic acid Aqueous lithium hydroxide solution (2M, 0.76 mL, 1.52 mmol) was added to a solution of Intermediate 80 (154 mg, 0.31 mmol) in THF (2.3 mL) and MeOH (0.75 mL). The mixture was left to stir overnight, then quenched with 1M HCl (~1.5 mL) to pH ~7. The mixture was diluted with water (10 mL) and extracted with 9:1 chloroform/isopropanol (2×10 mL). The organic phases were combined, washed with brine, dried over sodium sulfate and concentrated under vacuum. The crude product was purified by preparative HPLC to afford the title compound (24 mg, 15%) as an off-white solid. $\delta_H$ (500 MHz, DMSO-$d_6$) 8.66 (s, 2H), 8.39 (s, 1H), 7.58-7.52 (m, 1H), 7.50-7.10 (m, 5H), 7.08-7.02 (m, 1H), 4.36 (s, 2H), 4.23-4.08 (m, 4H), 2.31 (s, 3H), 1.85 (dd, J 8.6, 5.5 Hz, 1H), 1.29 (dd, J 8.6, 4.8 Hz, 1H), 1.18 (t, J 5.2 Hz, 1H). Method D HPLC-MS: MH+ m/z 492, RT 1.92 minutes.

Example 89

Ammonium (2R)-4-[5-(3-{[2-(difluoromethoxy)phenyl]methyl}-2-methylimidazo[1,2-a]-pyridin-6-yl)pyrimidin-2-yl]morpholine-2-carboxylate Intermediate 7 (150 mg, 0.41 mmol) and Intermediate 218 (324 mg, 0.61 mmol) were dissolved in 1,4-dioxane (3 mL) and 2M aqueous potassium carbonate solution (0.715 mL) was added. The reaction mixture was degassed with nitrogen for 5 minutes, then bis[3-(diphenylphosphanyl)cyclopenta-2,4-dien-1-yl]iron dichloropalladium dichloromethane complex (17 mg, 0.02 mmol) was added. The reaction mixture was heated at 80° C. for 2 h in a sealed tube under nitrogen. Further Intermediate 218 (100 mg) was added, together with water (0.5 mL) and DMSO (0.5 mL), and the mixture was heated at 80° C. overnight. The mixture was diluted with water (5 mL), extracted into EtOAc (3×10 mL), washed with brine (10 mL), dried over magnesium sulfate and concentrated under vacuum. Insoluble solids at the interphase boundary were collected and combined with the organic residue. The crude material was purified by preparative HPLC (Method D) to afford the title compound (34 mg, 17%) as an off-white solid. $\delta_H$ (500 MHz, DMSO-$d_6$) 8.71 (s, 2H), 8.42 (s, 1H), 7.55 (d, J 9.2 Hz, 1H), 7.48 (dd, J 9.3, 1.7 Hz, 1H), 7.45-7.10 (m, 4H), 7.07-7.02 (m, 1H), 4.46 (dd, J 13.2, 3.1 Hz, 1H), 4.36 (s, 2H), 4.16 (dd, J 8.9, 3.3 Hz, 2H), 3.99 (dt, J 11.4, 3.4 Hz, 1H), 3.60 (td, J 11.9, 10.8, 2.9 Hz, 1H), 3.40 (dd, J 13.2, 8.9 Hz, 2H), 2.31 (s, 3H). Method D HPLC-MS: MH+ m/z 496, RT 1.89 minutes.

Example 90

3-[5-(3-{[2-(Difluoromethoxy)phenyl]methyl}-2-methylimidazo[1,2-a]pyridin-6-yl)-pyrimidin-2-yl]-3,6-diazabicyclo[3.2.2]nonan-7-one Intermediate 7 (135 mg, 0.37 mmol) and Intermediate 219 (145 mg, 0.44 mmol) were dissolved in 1,4-dioxane (2 mL)

and 2M aqueous potassium carbonate solution (0.65 mL) was added. The reaction mixture was degassed with nitrogen for 5 minutes, then bis[3-(diphenylphosphanyl)cyclopenta-2,4-dien-1-yl]iron dichloropalladium dichloromethane complex (15 mg, 0.02 mmol) was added. The mixture was heated at 80° C. for 3 h in a sealed tube under nitrogen. Further bis[3-(diphenylphosphanyl)-cyclopenta-2,4-dien-1-yl]iron dichloropalladium dichloromethane complex (15 mg, 0.02 mmol) and Intermediate 219 (70 mg, 0.2 mmol) were added and the mixture was heated for a further 1 h. The mixture was diluted with water (5 mL), extracted into EtOAc (3×10 mL), washed with brine (10 mL), dried over magnesium sulfate and concentrated under vacuum. DMSO (3 mL) was added and the resultant precipitate was filtered off. The solids were further purified by preparative HPLC (Method D), then by crystallisation from acetonitrile/water, to afford the title compound (15.9 mg, 8%) as a white solid. $\delta_H$ (500 MHz, CDCl$_3$) 8.38 (s, 2H), 7.78 (s, 1H), 7.63 (d, J 9.2 Hz, 1H), 7.25 (m, 2H), 7.17 (d, J 7.8 Hz, 1H), 7.07 (td, J 7.6, 1.0 Hz, 1H), 6.86 (dd, J 7.7, 1.2 Hz, 1H), 6.85-6.49 (m, 2H), 5.06-4.96 (m, 2H), 4.30 (s, 2H), 3.74 (q, J 5.2 Hz, 1H), 3.34 (d, J 14.2 Hz, 1H), 3.24 (d, J 14.2 Hz, 1H), 2.83 (d, J 5.1 Hz, 1H), 2.52 (s, 3H), 1.98-1.74 (m, 4H). Method D HPLC-MS: MH+ m/z 505, RT 1.90 minutes.

Example 91

Ammonium (1R,5S,6r)-3-[5-(3-{[2-(difluoromethoxy)phenyl]methyl}-2-methylimidazo-[1,2-a]pyridin-6-yl)pyridin-2-yl]-3-azabicyclo[3.1.0]hexane-6-carboxylate Intermediate 30 (66% pure, 282 mg, 0.46 mmol), ethyl 3-azabicyclo[3.1.0]-hexane-6-carboxylate (216 mg, 1.397 mmol) and triethylamine (0.2 mL, 1.43 mmol) were combined in 1-methyl-2-pyrrolidinone (2 mL) in a microwave tube and the mixture was heated at 200° C. under microwave irradiation with stirring for 1 h. Further triethylamine (2 eq) was added and the mixture was heated for a further 1.5 h. Further triethylamine (3 eq) was added and the mixture was heated for a further 2 h. The mixture was loaded onto an SCX column, flushing with MeOH (70 mL), followed by 7N ammonia in MeOH (100 mL). The methanol fraction was concentrated under vacuum and further purified by SCX. The ammonia fractions were combined and concentrated under vacuum. The crude product fractions were combined. The resulting material was dissolved in THF (3 mL), then 2M aqueous NaOH solution (1.2 mL) was added and the reaction mixture was stirred at 80° C. for 1.5 h. The mixture was concentrated and acidified to pH 4 using 1M HCl, then extracted with isopropanol/chloroform (3×25 mL), dried over sodium sulfate and concentrated under vacuum. The crude material was purified by preparative HPLC (Method D) to afford the title compound (14 mg, 6%) as a yellow solid. $\delta_H$ (500 MHz, DMSO-d$_6$) 8.33 (d, J 2.5 Hz, 1H), 8.25 (s, 1H), 7.76 (dd, J 8.8, 2.5 Hz, 1H), 7.55-6.98 (m, 7H), 6.53 (d, J 8.8 Hz, 1H), 4.36 (s, 2H), 3.76 (d, J 10.7 Hz, 2H), 3.17 (s, 1H), 2.32 (s, 3H), 2.14 (s, 2H), 1.37 (t, J 3.0 Hz, 1H). Method D HPLC-MS: MH+ m/z 491, RT 1.58 minutes.

Example 92

Ethyl 1-[5-(3-{[2-(difluoromethoxy)phenyl]methyl}-2-methylimidazo[1,2-a]pyridin-6-yl)pyrazin-2-yl]-4-methylpiperidine-4-carboxylate Intermediate 81 (70% pure, 150 mg, 0.236 mmol), ethyl 4-methylpiperidine-4-carboxylate hydrochloride (147 mg, 0.707 mmol), K$_2$CO$_3$ (130 mg, 0.943 mmol) and 1-methyl-2-pyrrolidinone (2 mL) were charged to a microwave tube and stirred in a microwave reactor at 180° C. for 2 h. The reaction mixture was diluted with EtOAc (40 mL), and washed with water (3×15 mL) and brine (15 mL), then dried over sodium sulfate and concentrated under vacuum. The crude product was purified by FCC, eluting with 0-2% MeOH in DCM, to afford the title compound (20 mg, 14%) as a brown glass. $\delta_H$ (500 MHz, CDCl$_3$) 8.34 (d, J 1.4 Hz, 1H), 8.29 (s, 1H), 8.13 (d, J 1.4 Hz, 1H), 7.68-7.58 (m, 2H), 7.25-7.19 (m, 1H), 7.15 (d, J 7.7 Hz, 1H), 7.05 (td, J 7.6, 1.1 Hz, 1H), 6.88 (dd, J 7.7, 1.2 Hz, 1H), 6.67 (t, J 73.7 Hz, 1H), 4.31 (s, 2H), 4.19 (q, J 7.1 Hz, 2H), 4.02 (dt, J 13.7, 4.2 Hz, 2H), 3.21 (ddd, J 13.6, 10.9, 3.0 Hz, 2H), 2.49 (s, 3H), 2.22 (d, J 13.6 Hz, 3H), 1.51 (ddd, J 14.3, 10.9, 4.1 Hz, 2H), 1.32-1.22 (m, 5H). Method D HPLC-MS: MH+ m/z 536, RT 2.90 minutes.

Example 93

N-[5-(3-{[2-(Difluoromethoxy)phenyl]methyl}-2-methylimidazo[1,2-a]pyridin-6-yl)-1-methyl-1H-pyrazol-3-yl]-N-methylmethanesulfonamide Intermediate 31 (143 mg, 0.43 mmol) and Intermediate 83 (139 mg, 0.52 mmol) were dissolved in DMSO (2 mL) and 2M aqueous sodium carbonate solution (0.650 mL) was added. The mixture was degassed with nitrogen for 5 minutes, then tetrakis-(triphenylphosphine)palladium(0) (25 mg, 0.02 mmol) was added. The mixture was heated to 80° C. for 2.5 h in a sealed tube under nitrogen. The mixture was diluted with water (5 mL), extracted with EtOAc (3×10 mL), washed with brine (10 mL), dried over magnesium sulfate and concentrated under vacuum. The crude residue was purified by FCC, eluting with 50-100% ethyl acetate in heptane followed by 0-10% ammonia/MeOH in DCM. Impure fractions were further purified by FCC, eluting with 0-2% ammonia/MeOH in DCM. Clean fractions from both purifications were combined to afford the title compound (81.2 mg, 38%) as a light brown solid. $\delta_H$ (500 MHz, CDCl$_3$) 7.79 (s, 1H), 7.65 (d, J 9.0 Hz, 1H), 7.29-7.24 (m, 1H), 7.17 (t, J 9.2 Hz, 2H), 7.09 (t, J 7.5 Hz, 1H), 6.88 (d, J 7.6 Hz, 1H), 6.63 (t, J 73.6 Hz, 1H), 6.30 (s, 1H), 4.29 (s, 2H), 3.66 (s, 3H), 3.34 (s, 3H), 2.95 (s, 3H), 2.54 (s, 3H). Method D HPLC-MS: MH+ m/z 476, RT 1.92 minutes.

Example 94

Ammonium (1R,5S,6r)-3-[6-(3-{[2-(difluoromethoxy)phenyl]methyl}-2-methylimidazo-[1,2-a]pyridin-6-yl)pyridazin-3-yl]-3-azabicyclo[3.1.0]hexane-6-carboxylate Aqueous NaOH solution (2M, 0.59 mL) was added to a solution of Intermediate 85 (46%, 134 mg, 0.12 mmol) in THF (3 mL) and the tube was sealed. The mixture was stirred at 80° C. for 5 h, then at 100° C. for 2 h. The mixture was concentrated, DMSO (1.5 mL) was added and the mixture was sonicated. The inorganic solids were filtered off, and the filtrate was purified by preparative HPLC (Method D), to afford the title compound (13.6 mg, 23%) as a yellow solid. $\delta_H$ (500 MHz, CD$_3$OD) 8.52 (s, 1H), 7.87 (dd, J 9.4, 1.5 Hz, 1H), 7.74-7.67 (m, 1H), 7.57 (d, J 9.4 Hz, 1H), 7.28-7.23 (m, 1H), 7.17 (d, J 8.1 Hz, 1H), 7.09 (t, J 7.5 Hz, 1H), 7.02-6.70 (m, 3H), 4.38 (s, 2H), 3.90 (d, J 10.7 Hz, 2H), 3.64 (d, J 10.5

Hz, 2H), 2.44 (s, 3H), 2.31 (s, 2H), 1.52 (t, J 3.1 Hz, 1H). Method D HPLC-MS: MH+ m/z 492, RT 1.66 minutes.

Example 95

3-[5-(3-{[2-(Difluoromethoxy)phenyl]methyl}-2-methylimidazo[1,2-a]pyridin-6-yl)-pyrimidin-2-yl]-3-azabicyclo[4.1.0]heptane-6-carboxylic acid (2-Chloropyrimidin-5-yl)boronic acid (0.22 g, 1.39 mmol) and 3-azabicyclo-[4.1.0]heptane-6-carboxylic acid hydrochloride (0.25 g, 1.39 mmol) were dissolved in DMF (5 mL) and $K_2CO_3$ (1.15 g, 8.34 mmol) was added. The mixture was heated at 80° C. in a sealed tube for 2 h, then cooled to room temperature. To the mixture were added Intermediate 7 (0.5 g, 1.36 mmol), 2M aqueous $K_2CO_3$ solution (2.04 mL) and 1,4-dioxane (6 mL). The mixture was degassed with nitrogen for 15 minutes, then tetrakis-(triphenylphosphine)palladium (0) (236 mg, 0.2 mmol) was added. The mixture was heated at 80° C. in a sealed tube for 16 h. Upon cooling to room temperature, the mixture was diluted with EtOAc (40 mL) and extracted with water (20 mL), followed by 2M aqueous potassium carbonate solution (20 mL). The combined aqueous layers were acidified to pH 4 by the addition of 6M hydrochloric acid. The aqueous layer was extracted into 1:1 isopropanol/chloroform (6×25 mL), then the combined organic layers were dried over magnesium sulfate and concentrated. The residue was purified by FCC, eluting with 0-100% MeOH in DCM, to afford the title compound (81.7 mg, 11%) as an off-white solid. $δ_H$ (500 MHz, DMSO-$d_6$) 8.63 (s, 2H), 8.38 (s, 1H), 7.53 (d, J 9.3 Hz, 1H), 7.46 (dd, J 9.3, 1.6 Hz, 1H), 7.44-7.09 (m, 4H), 7.03 (d, J 6.6 Hz, 1H), 4.35 (s, 2H), 4.22 (d, J 12.5 Hz, 1H), 4.15-3.99 (m, 1H), 3.88 (dd, J 13.7, 4.7 Hz, 1H), 3.75 (dt, J 12.6, 5.9 Hz, 1H), 3.17 (d, J 3.9 Hz, 2H), 2.31 (s, 3H), 1.87-1.74 (m, 1H), 1.75-1.67 (m, 1H), 1.34-1.16 (m, 1H). Method A HPLC-MS: MH+ m/z 506, RT 3.13 minutes.

Example 96

2-[(2S)-1-[5-(3-{[2-(Difluoromethoxy)phenyl]methyl}-2-methylimidazo[1,2-a]pyridin-6-yl)pyrimidin-2-yl]pyrrolidin-2-yl]acetic acid Intermediate 29 (59%, 200 mg, 0.29 mmol) was dissolved in 1-methyl-2-pyrrolidinone (1.5 mL) and 2-[(2S)-pyrrolidin-2-yl]acetic acid hydrochloride (75 mg, 0.45 mmol) was added, followed by triethylamine (90 µL, 0.65 mmol). The reaction mixture was heated at 120° C. under microwave irradiation for 45 minutes. The reaction mixture was diluted with water (2 mL), acidified to pH 6 with 1M HCl and extracted into EtOAc (4 mL). The organic layer was washed with brine (3 mL) and dried over sodium sulphate, then heptane (4 mL) was added. The resultant solid was collected by filtration and combined with a second crop that precipitated in the filtrate. The combined solids were triturated with DCM/heptane, followed by EtOAc/heptane. The resulting material was combined with a precipitate collected from the aqueous layer, to afford the title compound (61.1 mg, 42%) as a white solid. $δ_H$ (250 MHz, DMSO-$d_6$) 8.65 (s, 2H), 8.37 (s, 1H), 7.59-6.96 (m, 7H), 4.47-4.28 (m, 3H), 3.65-3.48 (m, 2H), 2.89 (dd, J 15.4, 3.0 Hz, 1H), 2.34-2.26 (m, 4H), 2.11-1.79 (m, 4H). Method D HPLC-MS: MH+ m/z 494, RT 2.06 minutes.

Example 97

N-[5-(3-{[2-(Difluoromethoxy)phenyl]methyl}-2-methylimidazo[1,2-a]pyridin-6-yl)-pyridin-2-yl] methanesulfonamide Methanesulfonyl chloride (96 µL, 1.24 mmol) was added to a solution of Intermediate 86 (214 mg, 0.56 mmol) and triethylamine (0.24 mL, 1.69 mmol) in DCM (4 mL) under a nitrogen atmosphere using an ice/water bath for cooling. The mixture was allowed to warm to room temperature and was stirred overnight. The reaction mixture was concentrated under vacuum, then taken up in THF (4.2 mL) and MeOH (1.4 mL). Aqueous LiOH solution (2M, 1.4 mL, 2.81 mmol) was added and the mixture was stirred for 72 h. The reaction mixture was diluted with water (10 mL) and adjusted to pH ~7 using 1M aqueous HCl. The mixture was extracted with 9:1 chloroform/isopropanol (2×20 mL). The organic phases were combined, washed with brine, dried over sodium sulfate and concentrated under vacuum. The crude material was purified by preparative HPLC to afford the title compound (65 mg, 24%) as a pale yellow solid. $δ_H$ (250 MHz, DMSO-$d_6$) 10.87 (br s, 1H), 8.56 (d, J 2.3 Hz, 1H), 8.45 (s, 1H), 8.03 (dd, J 8.6, 2.5 Hz, 1H), 7.61-7.46 (m, 2H), 7.34-6.97 (m, 6H), 4.38 (s, 2H), 3.31 (s, 3H), 2.31 (s, 3H). Method D HPLC-MS: MH+ m/z 459, RT 1.80 minutes.

Example 98

Ethyl 1-(3-{[2-(difluoromethoxy)phenyl]methyl}-2-methylimidazo[1,2-a]pyridin-6-yl)-piperidine-4-carboxylate

[2',6'-Bis(propan-2-yloxy)biphenyl-2-yl](dicyclohexyl)phosphane (15 mg, 0.03 mmol) and palladium diacetate (6 mg, 0.03 mmol) were dissolved in 1,4-dioxane (5 mL) and heated at 80° C. for 5 minutes. The mixture was cooled to room temperature, then Intermediate 7 (200 mg, 0.54 mmol), ethyl piperidine-4-carboxylate (94 mg, 0.6 mmol) and cesium carbonate (355 mg, 1.09 mmol) were added. The mixture was flushed with nitrogen and heated at 120° C. for 2 h. Further palladium diacetate (6 mg, 0.03 mmol) and [2',6'-bis(propan-2-yloxy)biphenyl-2-yl](dicyclohexyl)phosphane (15 mg, 0.03 mmol) were added, and the mixture was heated at 120° C. for 4 h. The mixture was cooled to room temperature, diluted with water and extracted with ethyl acetate (3×25 mL). The combined organic layers were washed with brine, dried over magnesium sulfate and concentrated under reduced pressure. The residue was purified by FCC, eluting with ethyl acetate, then further purified by preparative HPLC (Method C), to afford the title compound (98 mg, 40%) as a light brown solid. $δ_H$ (500 MHz, DMSO-$d_6$) 7.66 (d, J 9.0 Hz, 1H), 7.32-7.28 (m, 1H), 7.24 (s, 1H), 7.19 (t, J 9.0 Hz, 2H), 7.13 (t, J 7.7 Hz, 1H), 6.99-6.93 (m, 1H), 6.66 (t, J 73.6 Hz, 1H), 4.24 (s, 2H), 4.18 (q, J 7.1 Hz, 2H), 3.39 (dt, J 12.2, 3.5 Hz, 2H), 2.68 (td, J 11.9, 2.6 Hz, 2H), 2.56 (s, 3H), 2.43 (tt, J 9.3, 4.0 Hz, 1H), 2.04 (dd, J 13.1, 2.9 Hz, 2H), 1.87 (qd, J 11.1, 3.9 Hz, 2H), 1.29 (t, J 7.1 Hz, 3H). Method D HPLC-MS: MH+ m/z 444, RT 2.39 minutes.

Example 99

Ammonium 1-[5-(3-{[2-(difluoromethoxy)phenyl] methyl}-2-methylimidazo[1,2-a]-pyridin-6-yl)pyrimidin-2-yl]-3-methylpyrrolidine-3-carboxylate Intermediate 87 (92% pure, 272 mg, 0.49 mmol) was stirred in THF (2 mL) and water (2 mL), then lithium hydroxide monohydrate (41 mg, 0.99 mmol) was added and the mixture was stirred at 100° C. for 1 h. The reaction mixture was concentrated and the residue was triturated with MeOH. The filtrate and solid were recombined and the mixture was purified by preparative HPLC (Method D). A solid precipitate was collected from the fractions to afford the title compound (100 mg, 40%) as a white solid. $\delta_H$ (250 MHz, CDCl$_3$) 8.34 (s, 2H), 7.78 (s, 1H), 7.63 (d, J 9.2 Hz, 1H), 7.26 (s, 2H), 7.15-7.01 (m, 2H), 6.92-6.32 (m, 2H), 4.25 (s, 2H), 4.05 (d, J 11.4 Hz, 1H), 3.66 (t, J 7.1 Hz, 2H), 3.45-3.36 (m, 1H), 2.42-2.52 (m, 4H), 1.96-1.84 (m, 1H), 1.39 (s, 3H). Method A HPLC-MS: MH+ m/z 494, RT 3.42 minutes.

Example 100

2-[(2R)-1-[5-(3-{[2-(Difluoromethoxy)phenyl]methyl}-2-methylimidazo[1,2-a]pyridin-6-yl)pyrimidin-2-yl]piperidin-2-yl]acetic acid Intermediate 29 (85% pure, 150 mg, 0.37 mmol), 2-[(2R)-piperidin-2-yl]acetic acid hydrochloride (100 mg, 0.56 mmol) and triethylamine (0.23 mL, 1.68 mmol) were suspended in 1-methyl-2-pyrrolidinone (3 mL) and the reaction mixture was heated for 4 h at 150° C. under microwave irradiation. The mixture was cooled to room temperature, then diluted with DCM (20 mL) and saturated aqueous sodium bicarbonate solution (10 mL). The organic phase was separated, washed with brine, dried over sodium sulfate and concentrated under vacuum. The residue was purified by preparative HPLC (Method C) to afford the title compound (28.3 mg, 18%) as a light brown solid. $\delta_H$ (500 MHz, CD$_3$OD) 8.47 (s, 2H), 8.16 (s, 1H), 7.55 (d, J 9.3 Hz, 1H), 7.48 (dd, J 9.3, 1.6 Hz, 1H), 7.31-7.26 (m, 1H), 7.20 (d, J 8.1 Hz, 1H), 7.16-7.11 (m, 1H), 7.09-6.76 (m, 2H), 4.68 (d, J 9.8 Hz, 1H), 4.39 (s, 2H), 3.01 (td, J 13.4, 2.7 Hz, 1H), 2.70 (dd, J 14.5, 8.8 Hz, 1H), 2.59 (dd, J 14.5, 6.5 Hz, 1H), 2.44 (s, 3H), 1.85-1.65 (m, 5H), 1.54-1.40 (m, 1H), 1.28 (s, 1H). Method D HPLC-MS: MH+ m/z 508, RT 2.31 minutes.

Example 101

5-[5-(3-{[2-(Difluoromethoxy)phenyl]methyl}-2-methylimidazo[1,2-a]pyridin-6-yl) -pyrimidin-2-yl]-2-oxa-5-azabicyclo[2.2.1]heptane-1-carboxylic acid Intermediate 29 (59%, 150 mg, 0.22 mmol) was dissolved in 1-methyl-2-pyrrolidinone (1 mL) and 2-oxa-5-azabicyclo[2.2.1]heptane-1-carboxylic acid hydrochloride (60 mg, 0.33 mmol) was added, followed by triethylamine (70 µL, 0.5 mmol). The reaction mixture was heated at 120° C. under microwave irradiation for 45 minutes. Further 2-oxa-5-azabicyclo[2.2.1]heptane-1-carboxylic acid hydrochloride (60 mg, 0.33 mmol) and triethylamine (70 µL, 0.5 mmol) were added and the mixture was heated at 120° C. under microwave irradiation for a total of 1.5 h. The reaction mixture was diluted with EtOAc (3 mL) and washed with a 1:1 mixture of water and saturated aqueous sodium bicarbonate solution (2 mL). The organic layer was discarded, then the aqueous layer was acidified to pH 6 with 1M HCl and extracted with EtOAc (2×2 mL). During the extraction a solid formed and was collected by filtration. The organic layers were washed with brine (2 mL), dried over sodium sulfate and concentrated to dryness. The residue was triturated with EtOAc/heptane to afford a solid. The aqueous phase was further extracted with 1:1 isopropanol/chloroform (2×3 mL), dried over sodium sulfate and concentrated to dryness. The residue was triturated with EtOAc/heptane to afford a solid. The three crops of solid were combined, and triturated with a minimum of water, to afford the title compound (22 mg, 20%) as a beige solid. $\delta_H$ (500 MHz, DMSO-d$_6$) 8.68 (s, 2H), 8.40 (s, 1H), 7.55 (d, J 9.2 Hz, 1H), 7.48 (dd, J 9.3, 1.7 Hz, 1H), 7.44-7.09 (m, 4H), 7.04 (d, J 7.6 Hz, 1H), 5.04 (s, 1H), 4.36 (s, 2H), 4.01 (d, J 6.1 Hz, 1H), 3.86-3.76 (m, 2H), 3.61 (d, J 10.4 Hz, 1H), 2.31 (s, 3H), 2.25 (d, J 8.2 Hz, 1H), 2.13 (d, J 10.1 Hz, 1H). Method A HPLC-MS: MH+ m/z 508, RT 2.98 minutes.

Example 102

Ammonium 3-[5-(3-{[2-(difluoromethoxy)phenyl]methyl}-2-methylimidazo[1,2-a]-pyridin-6-yl)pyrimidin-2-yl]-3-azabicyclo[4.1.0]heptane-1-carboxylate Intermediate 91 (280 mg, 1.57 mmol) and Intermediate 29 (80%, 700 mg, 1.4 mmol) were stirred in DMF (5 mL) and K$_2$CO$_3$ (386 mg, 2.79 mmol) was added. The reaction mixture was heated at 80° C. for 1 h, then at 100° C. for 2 h. The mixture was diluted with EtOAc (150 mL), and washed with water (2×75 mL) and brine (50 mL), then dried over sodium sulfate and concentrated. The crude residue was purified by FCC, eluting with 0-4% ammonia/methanol in DCM. The resulting material was dissolved in 1:1 THF/water (3 mL), then lithium hydroxide monohydrate (7 mg, 0.17 mmol) was added and mixture was heated at 80° C. for 1 h. Further lithium hydroxide monohydrate (14 mg, 0.34 mmol) was added and the mixture was heated at 80° C. for 4 h. The mixture was concentrated, then purified by preparative HPLC (Method D), to afford the title compound (128 mg) as a pale yellow solid. $\delta_H$ (250 MHz, DMSO-d$_6$) 8.61 (s, 2H), 8.37 (s, 1H), 7.59-7.41 (m, 2H), 7.31-6.98 (m, 5H), 4.38-4.12 (m, 4H), 3.63 (dd, J 12.8, 6.3 Hz, 1H), 3.43-3.29 (m, 1H), 2.30 (s, 3H), 2.08-1.96 (m, 1H), 1.76 (s, 1H), 1.52 (s, 1H), 1.15-1.04 (m, 1H), 0.52 (s, 1H). Method D HPLC-MS: MH+ m/z 506, RT 2.15 minutes.

Example 103

3-[5-(3-{[2-(Difluoromethoxy)phenyl]methyl}-2-methylimidazo[1,2-a]pyridin-6-yl) -pyrimidin-2-yl]-3-azabicyclo[3.1.1]heptane-6-carboxylic acid (2-Chloropyrimidin-5-yl)boronic acid (100 mg, 0.63 mmol), methyl 3-azabicyclo-[3.1.1]heptane-6-carboxylate hydrochloride (100 mg, 0.52 mmol) and triethylamine (0.25 mL, 1.79 mmol) were dissolved in ethanol (5 mL) and stirred for 2 h at 80° C. in a sealed tube. To the mixture were added Intermediate 7 (170 mg, 0.46 mmol), 2M aqueous potassium carbonate solution (0.7 mL) and 1,4-dioxane (3 mL). The mixture was degassed with nitrogen, then bis[3-(diphenylphosphanyl)cyclopenta-2,4-dien-1-yl]iron dichloropalladium dichloromethane complex (40 mg, 0.05 mmol) was added. The mixture was heated at 80° C. in a sealed tube for 4 h. The mixture was diluted with ethyl acetate (20 mL), then washed with water (2×10 mL), followed by brine (10 mL). The organic layer was dried over sodium sulfate and concentrated under vacuum. The residue was purified by FCC, eluting with 0-10% methanol in DCM. The resulting material (250 mg) was dissolved in 1:1 THF/water (4 mL), then 2M aqueous NaOH solution (0.5 mL) was added and the mixture was stirred at room temperature for 3 h. The mixture was diluted with DCM (20 mL), then extracted with water (10 mL), followed by 2M aqueous potassium carbonate solution (10 mL). The combined aqueous layers were extracted with 1:1 isopropanol/chloroform (20 mL), then the organic layer was separated and concentrated under vacuum. The residue was purified by chiral preparative SFC (Method A), eluting with methanol (+0.2% diethylamine) in carbon dioxide to afford the two stereoisomers of the title compound.

Isomer A (12.8 mg, 5%) was obtained as a light brown solid. $\delta_H$ (500 MHz, DMSO-$d_6$) 8.76 (s, 2H), 8.63 (s, 1H), 7.82 (d, J 9.3 Hz, 1H), 7.75 (d, J 9.3 Hz, 1H), 7.44-7.14 (m, 5H), 4.45 (s, 2H), 3.83 (q, J 11.7 Hz, 4H), 2.77 (d, J 6.2 Hz, 2H), 2.55 (d, J 5.7 Hz, 1H), 2.45 (d, J 8.9 Hz, 1H), 2.37 (s, 3H), 1.39 (dd, J 9.4, 5.9 Hz, 1H). SFC-MS: MH+ m/z 506, RT 16.42 minutes.

Isomer B (44.8 mg, 18%) was obtained as a light brown solid. $\delta_H$ (500 MHz, DMSO-$d_6$) 8.68 (s, 2H), 8.44 (s, 1H), 7.71 (d, J 3.6 Hz, 1H), 7.68 (s, 1H), 7.45-7.12 (m, 4H), 7.08 (d, J 7.5 Hz, 1H), 4.38 (s, 2H), 4.22-4.18 (m, 1H), 4.10 (d, J 11.8 Hz, 2H), 3.55 (d, J 11.9 Hz, 2H), 3.12 (t, J 6.0 Hz, 1H), 2.74 (t, J 5.8 Hz, 2H), 2.33 (s, 3H), 2.12-2.04 (m, 1H). SFC-MS: MH+ m/z 506, RT 17.88 minutes.

Example 104

Ammonium 4-[4-(3-{[2-(difluoromethoxy)phenyl] methyl}-2-methylimidazo[1,2-a]-pyridin-6-yl)-1H-pyrazol-1-yl]cyclohexane-1-carboxylate Intermediate 93 (80% pure, 60 mg, 0.09 mmol) and lithium hydroxide monohydrate (12 mg, 0.28 mmol) were stirred at room temperature overnight. The mixture was then treated with further lithium hydroxide monohydrate (12 mg, 0.28 mmol) and stirred at 50° C. for 4 h. The reaction mixture was concentrated under vacuum and partitioned between DCM and an acidic aqueous phase. LCMS showed product present in both phases, so the two phases were combined, concentrated and purified by preparative HPLC (Method D), to afford the title compound (9 mg, 19%) as a white solid, as a mixture of cis and trans isomers. $\delta_H$ (500 MHz, DMSO-$d_6$) 8.36 (d, J 8.7 Hz, 1H), 8.19 (d, J 3.5 Hz, 1H), 7.83 (s, 1H), 7.49-7.10 (m, 6H), 7.02 (t, J 6.7 Hz, 1H), 4.33 (s, 2H), 4.16 (ddq, J 23.6, 11.7, 4.4, 3.7 Hz, 1H), 2.31-2.22 (m, 4H), 2.14-1.87 (m, 5H), 1.77 (qd, J 12.7, 3.2 Hz, 1H), 1.69-1.60 (m, 1H), 1.52 (qd, J 13.3, 3.0 Hz, 1H). Method A HPLC-MS: MH+ m/z 481, RT 3.16-3.20 minutes.

Example 105

2-[(2S)-1-[5-(3-{[2-(Difluoromethoxy)phenyl]methyl}-2-methylimidazo[1,2-a]pyridin-6-yl)pyrimidin-2-yl]piperidin-2-yl]acetic acid Intermediate 29 (150 mg, 0.37 mmol), 2-[(2S)-piperidin-2-yl]acetic acid hydrochloride (100 mg, 0.56 mmol) and triethylamine (0.23 mL, 1.68 mmol) were suspended in 1-methyl-2-pyrrolidinone (3 mL) and the reaction mixture was heated for 4 h at 150° C. under microwave irradiation. The mixture was allowed to cool to room temperature, then diluted with DCM (20 mL) and saturated aqueous sodium bicarbonate solution (10 mL). The organic phase was separated, washed with brine, dried over sodium sulfate and concentrated under vacuum. The residue was purified by preparative HPLC (Method D) to afford the title compound (10 mg, 5%) as an off-white solid. $\delta_H$ (500 MHz, CD$_3$OD) 8.48 (d, J 5.6 Hz, 2H), 8.15 (s, 1H), 7.55 (dd, J 9.3, 1.7 Hz, 1H), 7.51-7.46 (m, 1H), 7.29 (t, J 7.8 Hz, 1H), 7.21 (d, J 8.2 Hz, 1H), 7.14 (d, J 7.5 Hz, 1H), 7.09-6.76 (m, 2H), 5.43 (s, 1H), 4.68 (d, J 11.6 Hz, 1H), 4.39 (s, 2H), 3.02 (t, J 13.3 Hz, 1H), 2.70 (dd, J 14.4, 8.9 Hz, 1H), 2.57 (dd, J 14.4, 6.4 Hz, 1H), 2.44 (s, 3H), 1.86-1.64 (m, 5H), 1.48 (d, J 12.9 Hz, 1H). Method D HPLC-MS: MH+ m/z 508, RT 2.32 minutes.

Example 106

Ammonium 1-[5-(3-{[2-(difluoromethoxy)phenyl] methyl}-2-methylimidazo[1,2-a]-pyridin-6-yl) pyrazin-2-yl]-4-methylpiperidine-4-carboxylate Intermediate 94 (80% pure, 0.29 g, 0.498 mmol), ethyl 4-methylpiperidine-4-carboxylate hydrochloride (319 mg, 1.53 mmol), potassium carbonate (283 mg, 2.05 mmol) and 1-methyl-2-pyrrolidinone (3 mL) were charged to a microwave tube and stirred under microwave irradiation at 180° C. for 2 h. The reaction mixture was diluted with EtOAc (5 mL) and separated, then the inorganic residue was washed with EtOAc (2×5 mL). The combined organic layers were extracted with water (2×5 mL). LCMS of the aqueous and organic layers showed product evenly distributed between both. The aqueous and organic layers were combined and concentrated under vacuum. The residue was purified by preparative HPLC (Method D) to afford the title compound (54 mg, 20%) as a light brown solid. $\delta_H$ (250 MHz, DMSO-$d_6$) 8.66-8.54 (m, 2H), 8.36 (d, J 1.2 Hz, 1H), 7.77 (dd, J 9.4, 1.6 Hz, 1H), 7.63-7.01 (m, 5H), 6.98 (dd, J 7.6, 1.4 Hz, 1H), 4.35 (s, 2H), 4.01 (d, J 13.7 Hz, 2H), 3.26-3.16 (m, 2H), 2.33 (s, 3H), 2.09-1.95 (m, 2H), 1.41 (t, J 9.9 Hz, 2H), 1.17 (s, 3H). Method D HPLC-MS: MH+ m/z 508, RT 2.29 minutes.

Example 107

Potassium 5-[5-(3-{[2-(difluoromethoxy)phenyl] methyl}-2-methylimidazo[1,2-a]pyridin-6-yl)pyrimidin-2-yl]-1-methyl-5-azaspiro[2.3]hexane-1-carboxylate Intermediate 98 (115 mg, 0.22 mmol) was dissolved in EtOH (2 mL), then 2M aqueous potassium hydroxide solution (0.11 mL) was added. The mixture was heated at 70° C. for 2.5 h, then left to stand at room temperature over the weekend. The mixture was then heated for 5 h before additional 2M aqueous potassium hydroxide solution (0.005 mL) was added. Heating was continued for 1 h. The mixture was filtered, but only a small amount of solid was collected on the filter paper. The filtrate and solids were recombined using EtOH and diethyl ether, then the mixture was concentrated to an approximate volume of 1.5 mL. The resultant precipitate was filtered, but little solid was recovered. The mixture was recombined and concentrated to dryness. EtOAc (~5 mL) was added and the mixture was sonicated. The resultant precipitate was collected by filtration to afford the title compound (81 mg, 69%) as a yellow solid. $\delta_H$ (500 MHz, DMSO-$d_6$) 8.62 (s, 2H), 8.38 (s, 1H), 7.56-7.49 (m, 1H), 7.45 (dd, J 9.3, 1.6 Hz, 1H), 7.33-7.25 (m, 2H), 7.22-7.17 (m, 1H), 7.17-7.10 (m, 1H), 7.08-7.01 (m, 1H), 4.35 (s, 2H), 4.10-3.89 (m, 4H), 2.31 (s, 3H), 1.20 (d, J 3.3 Hz, 1H), 1.03 (s, 3H), 0.38 (d, J 3.4 Hz, 1H). Method D HPLC-MS: MH+ m/z 506, RT 2.07 minutes.

Example 108

Ammonium 1-[2-(3-{[2-(difluoromethoxy)phenyl]methyl}-2-methylimidazo[1,2-a]-pyridin-6-yl)pyrimidin-5-yl]-4-methylpiperidine-4-carboxylate Intermediate 100 (88% pure, 48 mg, 0.08 mmol), KOH (5 mg, 0.08 mmol) and EtOH (2.5 mL) were combined and stirred at 70° C. overnight. Further KOH (20 mg, 0.24 mmol)

was added and the mixture was stirred at 80° C. for 18 h. Further KOH (40 mg, 0.48 mmol) was added and the mixture was stirred at 90° C. for 6 h. Further KOH (30 mg, 0.36 mmol) was added and the mixture was stirred at 80° C. for 8 h, then heated to 100° C. for 4 h. The mixture was concentrated under vacuum, then purified by preparative HPLC (Method D), to afford the title compound (12 mg, 25% at approximately 83% purity) as a light brown solid. $\delta_H$ (500 MHz, DMSO-$d_6$) 8.79 (s, 1H), 8.53 (s, 2H), 8.03-7.99 (m, 1H), 7.53 (d, J 9.4 Hz, 1H), 7.49-7.16 (m, 4H), 7.11 (t, J 7.5 Hz, 1H), 6.91 (d, J 7.5 Hz, 1H), 4.34 (s, 2H), 3.62-3.57 (m, 2H), 3.03-2.97 (m, 2H), 2.34 (s, 3H), 2.04 (d, J 13.6 Hz, 2H), 1.52-1.45 (m, 2H), 1.17 (s, 3H). Method D HPLC-MS: MH+ m/z 508, RT 2.30 minutes.

Example 109

Potassium 1-[5-(3-{[2-(difluoromethoxy)phenyl]methyl}-2-methylimidazo[1,2-a]pyridin-6-yl)pyridin-2-yl]-4-methylpiperidine-4-carboxylate Intermediate 102 (78% pure, 82 mg, 0.12 mmol) was dissolved in ethanol (2 mL) and 2M aqueous potassium hydroxide solution (0.12 mL) was added. The reaction mixture was heated at 80° C. overnight. The mixture was concentrated under vacuum, then the residue was triturated with EtOAc/heptane and concentrated under vacuum. The resulting off-white solid was triturated twice with 1:1 MeCN/EtOAc. The resulting off-white solid was purified by preparative HPLC (Method A). The resulting white solid (25 mg) was dissolved in ethanol (2 mL) and 2M aqueous potassium hydroxide solution (0.025 mL) was added in a sealed tube. The reaction mixture was stirred at room temperature for 1.5 h and concentrated under vacuum, then triturated with EtOAc (5 mL), MeCN (2 mL) and heptane (1 mL). The residue was concentrated under vacuum to afford the title compound (13.2 mg, 20%) as an off-white solid. $\delta_H$ (500 MHz, CD$_3$OD) 8.18 (d, J 2.4 Hz, 1H), 8.08 (s, 1H), 7.68 (dd, J 8.9, 2.5 Hz, 1H), 7.55-7.43 (m, 2H), 7.33-6.73 (m, 6H), 4.38 (s, 2H), 4.03-3.82 (m, 2H), 3.30-3.21 (m, 2H), 2.44 (s, 3H), 2.18 (d, J 13.3 Hz, 2H), 1.46-1.32 (m, 2H), 1.17 (s, 3H). Method D HPLC-MS: MH+ m/z 507, RT 1.92 minutes.

Example 110

Potassium 1-[6-(3-{[2-(difluoromethoxy)phenyl]methyl}-2-methylimidazo[1,2-a]pyridin-6-yl)pyridin-3-yl]-4-methylpiperidine-4-carboxylate Intermediate 104 (139 mg, 0.26 mmol) was dissolved in ethanol (2 mL), and 2M aqueous potassium hydroxide solution (0.13 mL) was added. The reaction mixture was heated at 70° C. overnight in a sealed tube. The mixture was evaporated to dryness under vacuum, then triturated with EtOAc (2×10 mL) and MeCN (2×10 mL). The resulting crude off-white solid was purified by preparative HPLC (Method D). To the resulting material were added isopropanol/water (20 mL) and 2M aqueous potassium hydroxide solution (0.05 mL). The mixture was heated with a heat gun until dissolution was observed, then stirred at room temperature for 1 h under nitrogen. The mixture was concentrated, and dried under vacuum, to afford the title compound (59.8 mg, 42%) as a white solid. $\delta_H$ (500 MHz, CD$_3$OD) 8.48 (s, 1H), 8.26 (d, J 2.9 Hz, 1H), 7.79 (dd, J 9.4, 1.7 Hz, 1H), 7.58 (d, J 8.8 Hz, 1H), 7.52 (d, J 9.4 Hz, 1H), 7.39 (dd, J 8.9, 3.0 Hz, 1H), 7.32-6.76 (m, 5H), 4.39 (s, 2H), 3.53 (dt, J 12.4, 4.0 Hz, 2H), 3.13-3.03 (m, 2H), 2.43 (s, 3H), 2.22 (d, J 13.3 Hz, 2H), 1.58-1.40 (m, 2H), 1.18 (s, 3H). Method D HPLC-MS:
MH+ m/z 507, RT 2.29 minutes.

Example 111

(1R,5S,6r)-3-[5-(3-{1-[2-(Difluoromethoxy)phenyl]ethyl}-2,7-dimethylimidazo[1,2-a]-pyridin-6-yl)pyrimidin-2-yl]-3-azabicyclo[3.1.0]hexane-6-carboxylic acid Intermediate 109 (175 mg, 0.32 mmol) was dissolved in THF (5 mL) and 4M aqueous sodium hydroxide solution (800 µL) was added. The reaction mixture was heated at 80° C. overnight. The reaction mixture was diluted with water (5 mL) and extracted with EtOAc (5 mL). The organic layer was discarded and the aqueous layer was acidified to pH 6 with 1M HCl. The resulting aqueous layer was extracted with EtOAc (2×4 mL). The combined organic phases were washed with brine (3 mL), dried over sodium sulfate and concentrated to dryness. A second portion of Intermediate 109 (319 mg, 0.58 mmol) was dissolved in THF (8 mL) and 4M aqueous sodium hydroxide solution (1.5 mL) was added. The reaction mixture was heated at 80° C. overnight. The reaction mixture was diluted with water (8 mL) and extracted with EtOAc (8 mL). The organic layer was discarded and the aqueous layer was acidified to pH 6 with 1M HCl. The resulting aqueous layer was extracted with EtOAc (2×5 mL). The combined organic phases were washed with brine (4 mL), dried over sodium sulfate and concentrated to dryness. The two batches were combined, and purified by preparative HPLC, to afford the title compound (56 mg, 12%) as a beige solid. $\delta_H$ (500 MHz, DMSO-$d_6$) 8.32 (s, 2H), 7.96 (s, 1H), 7.45 (d, J 7.3 Hz, 1H), 7.35-7.28 (m, 2H), 7.25-6.93 (m, 3H), 4.84 (q, J 7.2 Hz, 1H), 3.88 (d, J 11.4 Hz, 2H), 3.58 (d, J 10.8 Hz, 2H), 2.84-2.75 (m, 1H), 2.23 (s, 3H), 2.21 (s, 3H), 2.13 (s, 2H), 1.67 (d, J 7.2 Hz, 3H). Method D HPLC-MS: MH+ m/z 519, RT 2.06 minutes.

Example 112

Ethyl 2-{1-[5-(3-{[2-(difluoromethoxy)phenyl]methyl}-2-methylimidazo[1,2-a]pyridin-6-yl)pyrimidin-2-yl]piperidin-4-yl}acetate Intermediate 29 (50 mg, 0.12 mmol) was dissolved in 1-methyl-2-pyrrolidinone (1 mL) and ethyl piperidin-4-ylacetate (33 mg, 0.19 mmol) was added, followed by triethylamine (39 µL, 0.28 mmol). The reaction mixture was heated at 120° C. under microwave irradiation for 45 minutes. A second portion of Intermediate 29 (150 mg, 0.37 mmol) was dissolved in 1-methyl-2-pyrrolidinone (2 mL) and ethyl piperidin-4-ylacetate (99 mg, 0.58 mmol) was added, followed by triethylamine (117 µL, 0.84 mmol). The reaction mixture was heated at 120° C. under microwave irradiation for 45 minutes. The two mixtures were combined, diluted with EtOAc (3 mL), and washed with water (2 mL) and brine (2 mL), then dried over sodium sulfate and concentrated to dryness. The residue was purified by FCC, eluting with 0-8% MeOH in DCM, then further purified by FCC, eluting with 30-100% EtOAc in heptane, to afford the title compound (170 mg, 64%) as a white solid. $\delta_H$ (500 MHz, CD$_3$OD) 8.48 (s, 2H), 8.15 (s, 1H), 7.55 (d, J 9.2 Hz, 1H), 7.47 (dd, J 9.3, 1.4 Hz, 1H), 7.34-7.27 (m, 1H), 7.22 (d, J 8.0 Hz, 1H), 7.15 (t, J 7.5 Hz, 1H), 7.11-6.75 (m, 2H), 4.78 (d, J 13.4 Hz, 2H), 4.41 (s, 2H), 4.15 (q, J 7.1 Hz, 2H), 3.02-2.93 (m, 2H), 2.45 (s, 3H), 2.30 (d, J 7.1 Hz, 2H), 2.10 (dd, J 7.4, 3.7 Hz, 1H), 1.82 (d, J 11.0 Hz, 2H), 1.30-1.18 (m, 5H). Method A HPLC-MS: MH+ m/z 536, RT 5.29 minutes.

Example 113

Potassium 3-[5-(3-{[2-(difluoromethoxy)phenyl]methyl}-2-methylimidazo[1,2-a]pyridin-6-yl)pyrimidin-2-yl]-5-methyl-3-azabicyclo[3.1.0]hexane-1-carboxylate Intermediate 113 (66 mg, 0.12 mmol) was dissolved in EtOH (3 mL), then 2M aqueous potassium hydroxide solution (62 µL) was added and the mixture was heated at 70° C. for a total of 21 h. The mixture was allowed to cool, then concentrated. EtOAc (~3 mL) was added to the resulting orange oil/gum, and the mixture was sonicated. Heptane (1 mL) was added and the mixture was sonicated further. Using a flow of nitrogen, solvent was removed to a remaining volume of ~2 mL, and the resultant precipitate was collected by filtration, to afford the title compound (46 mg, 66%) as a yellow solid. $\delta_H$ (500 MHz, CD$_3$OD) 8.59 (s, 2H), 8.36 (s, 1H), 7.52 (d, J 9.2 Hz, 1H), 7.49-7.39 (m, 1H), 7.33-7.25 (m, 1H), 7.29 (t, J 74.2 Hz, 1H), 7.23-7.18 (m, 1H), 7.17-7.10 (m, 1H), 7.04 (dd, J 7.6, 1.2 Hz, 1H), 4.36 (s, 2H), 3.96 (d, J 11.3 Hz, 1H), 3.85 (d, J 11.0 Hz, 1H), 3.69 (d, J 11.3 Hz, 1H), 3.25 (d, J 10.9 Hz, 1H), 2.31 (s, 3H), 1.31 (s, 3H), 1.19-1.14 (m, 1H), 0.31 (d, J 3.1 Hz, 1H). Method A HPLC-MS: MH+ m/z 506.5, RT 2.15 minutes.

Example 114

Potassium 2-{1-[5-(3-{[2-(difluoromethoxy)phenyl]methyl}-2-methylimidazo[1,2-a]-pyridin-6-yl)pyrimidin-2-yl]piperidin-4-yl}acetate Example 112 (154.5 mg, 0.29 mmol) was suspended in ethanol (2 mL) and 2M aqueous potassium hydroxide solution (146 µL) was added. The reaction mixture was stirred at room temperature for 2 h, then heated at 50° C. for 16 h. The mixture was concentrated to dryness to afford the title compound (131 mg, 83%). $\delta_H$ (500 MHz, DMSO-d$_6$) 8.60 (s, 2H), 8.36 (s, 1H), 7.53 (d, J 9.3 Hz, 1H), 7.46-7.10 (m, 5H), 7.06 (s, 1H), 4.63 (d, J 13.0 Hz, 2H), 4.35 (s, 2H), 2.89 (s, 2H), 2.32 (s, 3H), 1.97-1.81 (m, 1H), 1.76 (d, J 6.8 Hz, 4H), 1.00 (dd, J 12.1, 3.2 Hz, 2H). Method D HPLC-MS: MH+ m/z 508, RT 2.10 minutes.

Example 115

Potassium 3-[5-(3-{[2-(difluoromethoxy)phenyl]methyl}-2,7-dimethylimidazo[1,2-a]-pyridin-6-yl)pyrimidin-2-yl]-3-azabicyclo[4.1.0]heptane-6-carboxylate (Enantiomer A)

Intermediate 47 (35 mg, 0.08 mmol) was dissolved in 1-methyl-2-pyrrolidinone (1 mL) and Intermediate 116 (25 mg, 0.13 mmol) was added, followed by triethylamine (27 µL, 0.19 mmol). The reaction mixture was heated at 120° C. under microwave irradiation for 45 minutes. A second portion of Intermediate 47 (100 mg, 0.24 mmol) was dissolved in 1-methyl-2-pyrrolidinone (2 mL) and Intermediate 116 (70 mg, 0.36 mmol) was added, followed by triethylamine (76 µL, 0.54 mmol). The reaction mixture was heated at 120° C. under microwave irradiation for 45 minutes. The two mixtures were combined, then partitioned between ethyl acetate (5 mL) and water (3 mL). The aqueous layer was separated and extracted into ethyl acetate (5 mL). The combined organic extracts were washed with water (2×10 mL) and brine (10 mL), then dried over sodium sulfate and evaporated. The residue was purified by FCC, eluting with 50-100% ethyl acetate in heptane. The resulting yellow oil was dissolved in ethanol (4 mL) and 2M aqueous potassium hydroxide solution (0.12 mL) was added. The reaction mixture was heated at 80° C. in a sealed tube for a total of 7 h. Further 2M aqueous potassium hydroxide solution (0.24 mL) was added and the reaction mixture was heated at 80° C. in a sealed tube for 2 h. The cooled reaction mixture was acidified with 2M HCl to pH 2, then partitioned between 10% isopropanol/chloroform (10 mL) and water (5 mL). The aqueous layer was separated and further extracted into 10% isopropanol/chloroform (2×10 mL). The combined organic extracts were washed with brine (10 mL), dried over sodium sulfate and evaporated. To the resulting yellow foam were added isopropanol (3 mL), water (1 mL) and 2M aqueous potassium hydroxide solution (0.10 mL). The mixture was brought into solution with a heat gun, then stirred at room temperature for 1 h. The reaction mixture was evaporated to afford the title compound (109 mg, 61%) as a yellow solid. $\delta_H$ (500 MHz, DMSO-d$_6$) 8.31 (s, 2H), 8.00 (s, 1H), 7.43-7.07 (m, 5H), 6.93 (d, J 7.5 Hz, 1H), 4.28 (s, 2H), 4.01 (dd, J 13.5, 2.6 Hz, 1H), 3.87 (dd, J 13.5, 5.1 Hz, 1H), 3.61 (dt, J 12.2, 5.8 Hz, 1H), 2.62 (dt, J 13.7, 5.7 Hz, 1H), 2.28 (s, 3H), 2.24 (s, 3H), 1.61 (ddd, J 13.9, 8.6, 5.2 Hz, 1H), 1.44-1.35 (m, 1H), 1.00 (dd, J 8.5, 2.8 Hz, 1H), 0.29-0.19 (m, 1H). Method D HPLC-MS: MH+ m/z 520.5, RT 2.13 minutes.

Example 116

Potassium 3-[5-(3-{[2-(difluoromethoxy)phenyl]methyl}-2,7-dimethylimidazo[1,2-a]-pyridin-6-yl)pyrimidin-2-yl]-3-azabicyclo[4.1.0]heptane-6-carboxylate (Enantiomer B)

Intermediate 47 (133 mg, 0.32 mmol) was dissolved in 1-methyl-2-pyrrolidinone (2.5 mL) and Intermediate 117 (92 mg, 0.48 mmol) was added, followed by triethylamine (0.10 mL, 0.72 mmol). The reaction mixture was heated at 120° C. under microwave irradiation for 45 minutes. The reaction mixture was partitioned between ethyl acetate (5 mL) and water (3 mL). The aqueous layer was separated and extracted into ethyl acetate (5 mL). The combined organic extracts were washed with water (2×10 mL) and brine (10 mL), then dried over sodium sulfate and evaporated. The residue was purified by FCC, eluting with 50-100% ethyl acetate in heptane. The resulting yellow oil was dissolved in ethanol (4 mL) and 2M aqueous potassium hydroxide solution (0.38 mL) was added. The reaction mixture was heated at 80° C. in a sealed tube for 2 h. The cooled reaction mixture was acidified with 2M HCl to pH 2, then partitioned between 10% isopropanol/chloroform (10 mL) and water (5 mL). The aqueous layer was separated and further extracted into 10% isopropanol/chloroform (2×10 mL). The combined organic extracts were washed with brine (10 mL), dried over sodium sulfate and evaporated. To the resulting yellow foam were added isopropanol (3 mL), water (1 mL) and 2M aqueous potassium hydroxide solution (0.10 mL). The mixture was brought into solution with a heat gun, then stirred at room temperature for 1 h. The reaction mixture was evaporated to afford the title compound (114 mg, 64%) as a yellow solid. $\delta_H$ (500 MHz, DMSO-d$_6$) 8.32 (s, 2H), 8.01 (s, 1H), 7.43-7.07 (m, 5H), 6.93 (d, J 7.1 Hz, 1H), 4.28 (s, 2H), 4.04 (dd, J 13.5, 2.4 Hz, 1H), 3.88 (dd, J 13.5, 5.1 Hz, 1H), 3.64 (dd, J 12.7, 6.0 Hz, 1H), 2.66-2.58 (m, 1H), 2.28 (s, 3H), 2.24 (s, 3H), 1.64 (ddd, J 13.9, 8.5, 5.3 Hz, 1H), 1.46 (s, 1H), 1.05 (dd, J 8.6, 2.8 Hz, 1H), 0.33 (s, 1H). Method D HPLC-MS: MH+ m/z 520, RT 2.14 minutes.

Example 117

Potassium 3-[5-(3-{[2-(difluoromethoxy)phenyl]methyl}-2,7-dimethylimidazo[1,2-a]-pyridin-6-yl)pyrimidin-2-yl]-3-azabicyclo[4.1.0]heptane-1-carboxylate (Enantiomer A)

Intermediate 47 (133 mg, 0.32 mmol) was dissolved in 1-methyl-2-pyrrolidinone (2.5 mL) and Intermediate 119 (100 mg, 0.48 mmol) was added, followed by triethylamine (0.10 mL, 0.72 mmol). The reaction mixture was heated at 120° C. under microwave irradiation for 45 minutes. The reaction mixture was partitioned between ethyl acetate (5 mL) and water (3 mL). The aqueous layer was separated and extracted into ethyl acetate (5 mL). The combined organic extracts were washed with water (2×10 mL) and brine (10 mL), then dried over sodium sulfate and evaporated. The residue was purified by FCC, eluting with 50-100% ethyl acetate in heptane. The resulting yellow oil was dissolved in ethanol (3 mL) and 2M aqueous potassium hydroxide solution (0.26 mL) was added. The reaction mixture was heated at 80° C. in a sealed tube for 2 h. The cooled reaction mixture was acidified with 2M HCl to pH 2, then partitioned between 10% isopropanol/chloroform (10 mL) and water (5 mL). The aqueous layer was separated and further extracted into 10% isopropanol/chloroform (2×10 mL). The combined organic extracts were washed with brine (10 mL), dried over sodium sulfate and evaporated. To the resulting yellow foam were added isopropanol (3 mL), water (1 mL) and 2M aqueous potassium hydroxide solution (84 μL). The mixture was brought into solution with a heat gun, then stirred at room temperature for 1 h. The reaction mixture was evaporated to afford the title compound (87 mg, 49%) as a yellow solid. $\delta_H$ (500 MHz, DMSO-$d_6$) 8.34 (s, 2H), 8.01 (s, 1H), 7.44-7.07 (m, 5H), 6.93 (d, J 7.6 Hz, 1H), 4.34 (d, J 13.8 Hz, 1H), 4.28 (s, 2H), 4.13 (d, J 13.8 Hz, 1H), 3.64-3.60 (m, 1H), 2.28 (s, 3H), 2.25 (s, 3H), 2.06 (dq, J 13.1, 6.5 Hz, 1H), 1.81-1.71 (m, 1H), 1.57 (s, 1H), 1.19-1.08 (m, 1H), 0.61 (s, 1H). Method D HPLC-MS: MH+ m/z 520, RT 2.21 minutes.

Example 118

Potassium 3-[5-(3-{[2-(difluoromethoxy)phenyl]methyl}-2,7-dimethylimidazo[1,2-a]-pyridin-6-yl)pyrimidin-2-yl]-3-azabicyclo[4.1.0]heptane-1-carboxylate (Enantiomer B)

Intermediate 47 (133 mg, 0.32 mmol) was dissolved in 1-methyl-2-pyrrolidinone (2.5 mL) and Intermediate 120 (100 mg, 0.48 mmol) was added, followed by triethylamine (0.10 mL, 0.72 mmol). The reaction mixture was heated at 120° C. under microwave irradiation for 45 minutes. The reaction mixture was partitioned between ethyl acetate (5 mL) and water (3 mL). The aqueous layer was separated and extracted into ethyl acetate (5 mL). The combined organic extracts were washed with water (2×10 mL) and brine (10 mL), then dried over sodium sulfate and evaporated. The residue was purified by FCC, eluting with 50-100% ethyl acetate in heptane. The resulting yellow oil was dissolved in ethanol (4 mL) and 2M aqueous potassium hydroxide solution (0.33 mL) was added. The reaction mixture was heated at 80° C. in a sealed tube for 2 h. The cooled reaction mixture was acidified with 2M HCl to pH 2, then partitioned between 10% isopropanol/chloroform (10 mL) and water (5 mL). The aqueous layer was separated and further extracted into 10% isopropanol/chloroform (2×10 mL). The combined organic extracts were washed with brine (10 mL), dried over sodium sulfate and evaporated. To the resulting yellow foam were added isopropanol (3 mL), water (1 mL) and 2M aqueous potassium hydroxide solution (90 μL). The mixture was brought into solution with a heat gun, then stirred at room temperature for 1 h. The reaction mixture was evaporated to afford the title compound (90 mg, 50%) as a yellow solid. $\delta_H$ (500 MHz, DMSO-$d_6$) 8.34 (s, 2H), 8.00 (s, 1H), 7.42-7.06 (m, 5H), 6.92 (d, J 7.6 Hz, 1H), 4.37 (d, J 13.8 Hz, 1H), 4.27 (s, 2H), 4.12 (d, J 13.8 Hz, 1H), 3.62 (dd, J 13.4, 6.3 Hz, 1H), 3.45-3.42 (m, 1H), 2.27 (s, 3H), 2.24 (s, 3H), 2.08 (dq, J 12.9, 6.3 Hz, 1H), 1.81-1.72 (m, 1H), 1.71-1.60 (m, 1H), 1.22 (dd, J 9.1, 4.0 Hz, 1H), 0.79-0.70 (m, 1H). Method D HPLC-MS: MH+ m/z 520, RT 2.22 minutes.

Example 119

Potassium 2-{4-[5-(3-{[2-(difluoromethoxy)phenyl]methyl}-2-methylimidazo[1,2-a]-pyridin-6-yl)pyrimidin-2-yl]morpholin-3-yl}acetate Intermediate 121 (50 mg, 0.1 mmol) was suspended in ethanol (3 mL), then 2M aqueous potassium hydroxide solution (0.05 mL) was added and the mixture was heated at 80° C. for 18 h. The mixture was concentrated under reduced pressure, and purified using preparative HPLC (Method C), to afford the title compound (8.4 mg, 16%) as a pale yellow solid. $\delta_H$ (500 MHz, CD$_3$OD) 8.56 (s, 2H), 8.21 (s, 1H), 7.58 (d, J 9.3 Hz, 1H), 7.53 (dd, J 9.3, 1.5 Hz, 1H), 7.34-7.29 (m, 1H), 7.22 (d, J 8.1 Hz, 1H), 7.16 (t, J 7.5 Hz, 1H), 7.12-7.09 (m, 1H), 6.93 (t, J 74.0 Hz, 1H), 5.10-5.03 (m, 1H), 4.48-4.40 (m, 3H), 4.01 (t, J 9.8 Hz, 2H), 3.73-3.67 (m, 1H), 3.57 (td, J 11.9, 3.0 Hz, 1H), 3.31-3.23 (m, 1H), 2.95 (dd, J 15.4, 9.6 Hz, 1H), 2.52 (dd, J 15.3, 4.4 Hz, 1H), 2.46 (s, 3H). Method D HPLC-MS: MH+ m/z 510, RT 1.98 minutes.

Example 120

Potassium 3-[5-(3-{[2-(difluoromethoxy)phenyl]methyl}-2-methylimidazo[1,2-a]pyridin-6-yl)pyridin-2-yl]-3-azabicyclo[4.1.0]heptane-6-carboxylate (Enantiomer A)

A mixture of Intermediate 101 (150 mg, 0.39 mmol) and Intermediate 116 (150 mg, 0.78 mmol) in pyridine (2 mL) was heated at 180° C. under microwave irradiation for a total of 3.5 h. The reaction mixture was diluted with water (10 mL) and extracted into EtOAc (3×10 mL). The organic layer was washed with brine (10 mL), then dried over magnesium sulfate and concentrated under vacuum. The residue was purified by FCC, eluting with 20-100% EtOAc in heptane followed by 20% MeOH in EtOAc, to afford 18.5 mg of the ester, 11 mg of the desired acid and a further 54 mg of impure acid. The impure acid was triturated in MeCN/water to give a combined total of 34 mg of the acid. This was suspended in isopropanol (1.5 mL) and water (0.5 mL), then 2M aqueous potassium hydroxide solution (34 μL) was added. The mixture was warmed to 40° C. for 20 minutes, until all the starting material had gone into solution. The solvent was removed under nitrogen, and the residue dried under vacuum, to afford the title compound (30 mg, 14%) as a cream/brown solid. $\delta_H$ (500 MHz, DMSO-$d_6$) 8.32 (d, J 2.5 Hz, 1H), 8.26 (s, 1H), 7.73 (dd, J 8.9, 2.6 Hz, 1H), 7.52-7.10 (m, 6H), 7.04 (d, J 7.6 Hz, 1H), 6.67 (d, J 9.0 Hz, 1H), 4.36 (s, 2H), 3.78 (d, J 4.2 Hz, 2H), 3.22 (ddd, J 12.9, 8.2, 5.2 Hz, 1H), 2.63-2.57 (m, 1H), 2.32 (s, 3H), 1.69-1.61 (m, 1H), 1.37 (dd, J 8.3, 3.9 Hz, 1H), 0.94 (dd, J 8.4, 2.8 Hz, 1H), 0.21 (dd, J 5.1, 3.0 Hz, 1H). Method D HPLC-MS: MH+ m/z 505, RT 1.74 minutes.

Example 121

Potassium 3-[5-(3-{[2-(difluoromethoxy)phenyl]methyl}-2-methylimidazo[1,2-a]pyridin-6-yl)pyridin-2-yl]-3-azabicyclo[4.1.0]heptane-6-carboxylate (Enantiomer B)

A mixture of Intermediate 101 (150 mg, 0.39 mmol) and Intermediate 117 (150 mg, 0.78 mmol) in pyridine (2 mL) was heated at 180° C. under microwave irradiation for 4 h. The reaction mixture was concentrated under vacuum and the residue was purified by FCC, eluting with 20-100% EtOAc in heptane followed by 20% MeOH in EtOAc. The resulting brown solid (85 mg) was dissolved in methanol (3 mL), then 2M aqueous potassium hydroxide solution (246 µL) was added and the reaction mixture was heated at 80° C. for 16 h. The reaction mixture was cooled to room temperature and the solvent was removed under vacuum. The residue was diluted with water and washed with EtOAc (3×2 mL). The aqueous phase was acidified with 2M HCl and washed with EtOAc (3×2 mL), followed by 1:1 isopropanol/chloroform (3×2 mL). The aqueous layer was concentrated under vacuum and the residue was triturated with 1:1 isopropanol/chloroform. The mixture was filtered and the filtrate was concentrated under vacuum. The material was suspended in water with potassium hydroxide (1.1 eq), and isopropanol was added. The suspension was heated with a heat gun until all the solid had dissolved, then the mixture was stirred at room temperature for 20 minutes. The mixture was concentrated under vacuum, and the residue was triturated with EtOAc, to afford the title compound (19.7 mg, 9%) as a cream solid. $\delta_H$ (500 MHz, DMSO-$d_6$) 8.32 (d, J 2.5 Hz, 1H), 8.27 (s, 1H), 7.73 (dd, J 8.9, 2.6 Hz, 1H), 7.53-7.11 (m, 6H), 7.04 (d, J 7.7 Hz, 1H), 6.68 (d, J 8.9 Hz, 1H), 4.36 (s, 2H), 3.81-3.76 (m, 2H), 3.22 (td, J 8.1, 4.1 Hz, 1H), 2.59 (d, J 14.1 Hz, 1H), 2.33 (s, 3H), 1.65 (s, 1H), 1.38 (s, 1H), 0.96 (d, J 8.1 Hz, 1H), 0.25 (s, 1H). Method A HPLC-MS: MH+ m/z 505, RT 3.04 minutes.

Example 122

Potassium 3-[5-(3-{[2-(difluoromethoxy)phenyl]methyl}-2-methylimidazo[1,2-a]pyridin-6-yl)pyridin-2-yl]-3-azabicyclo[4.1.0]heptane-1-carboxylate (Enantiomer A)

A mixture of Intermediate 101 (150 mg, 0.39 mmol) and Intermediate 119 (161 mg, 0.78 mmol) in pyridine (2 mL) was heated at 180° C. under microwave irradiation for 4 h. The reaction mixture was concentrated under vacuum and the residue was purified by FCC, eluting with 20-100% EtOAc in heptane followed by 20% MeOH in EtOAc. The resulting material (83.5 mg) was dissolved in methanol (3 mL), then 2M aqueous potassium hydroxide solution (290 µL) was added and the reaction mixture was heated at 80° C. for 16 h. The reaction mixture was cooled to room temperature and the solvent was removed under vacuum. The residue was diluted with water and washed with EtOAc (3×2 mL). The aqueous phase was acidified with 2M HCl and washed with EtOAc (3×2 mL). The aqueous phase was concentrated under vacuum and the residue was triturated with 1:1 isopropanol/chloroform. The mixture was filtered, and the filtrate was concentrated under vacuum. The material was suspended in water with potassium hydroxide (1.1 eq), and isopropanol was added. The suspension was heated with a heat gun until all the solid had dissolved, then the mixture was stirred at room temperature for 20 minutes. The mixture was concentrated under vacuum, and triturated with EtOAc, to afford the title compound (42.9 mg, 20%) as a cream solid. $\delta_H$ (500 MHz, DMSO-$d_6$) 8.31 (d, J 2.4 Hz, 1H), 8.26 (s, 1H), 7.73 (dd, J 8.9, 2.6 Hz, 1H), 7.53-7.10 (m, 6H), 7.04 (d, J 7.6 Hz, 1H), 6.74 (d, J 8.9 Hz, 1H), 4.36 (s, 2H), 4.20 (d, J 13.6 Hz, 1H), 3.78 (d, J 13.6 Hz, 1H), 2.32 (s, 3H), 1.97 (d, J 6.0 Hz, 1H), 1.77-1.67 (m, 1H), 1.36 (s, 1H), 0.95 (d, J 6.4 Hz, 1H), 0.35 (s, 1H). Method A HPLC-MS: MH+ m/z 505, RT 3.03 minutes.

Example 123

Potassium 3-[5-(3-{[2-(difluoromethoxy)phenyl]methyl}-2-methylimidazo[1,2-a]pyridin-6-yl)pyridin-2-yl]-3-azabicyclo[4.1.0]heptane-1-carboxylate (Enantiomer B)

A mixture of Intermediate 101 (150 mg, 0.39 mmol) and Intermediate 120 (161 mg, 0.78 mmol) in pyridine (2 mL) was heated at 180° C. under microwave irradiation for 4 h. The reaction mixture was concentrated under vacuum and the residue was purified by FCC, eluting with 20-100% EtOAc in heptane followed by 20% MeOH in EtOAc. The resulting material (64 mg) was dissolved in methanol (3 mL), then 2M aqueous potassium hydroxide solution (349 µL) was added and the reaction mixture was heated at 80° C. for 16 h. The reaction mixture was cooled to room temperature and the methanol was removed under vacuum. The residue was diluted with water and washed with EtOAc (3×2 mL). The aqueous phase was acidified with 2M HCl and washed with EtOAc (3×2 mL). The aqueous phase was concentrated under vacuum and the residue was triturated with 1:1 isopropanol/chloroform. The mixture was filtered, and the filtrate was concentrated under vacuum. The residue was triturated with several solvents (DCM, water, MeCN, EtOAc) but this failed to increase the purity. The material was suspended in water with potassium hydroxide (1.1 eq), and isopropanol was added. The suspension was heated with a heat gun until all the solid had dissolved, then the mixture was stirred at room temperature for 20 minutes. The mixture was concentrated under vacuum, and triturated with EtOAc, to afford the title compound (35.6 mg, 17%) as a cream solid. $\delta_H$ (500 MHz, DMSO-$d_6$) 8.31 (d, J 2.4 Hz, 1H), 8.26 (s, 1H), 7.73 (dd, J 8.9, 2.5 Hz, 1H), 7.52-7.11 (m, 6H), 7.04 (d, J 7.6 Hz, 1H), 6.75 (d, J 9.0 Hz, 1H), 4.36 (s, 2H), 4.20 (d, J 13.5 Hz, 1H), 3.79 (d, J 13.8 Hz, 1H), 2.32 (s, 3H), 1.98 (d, J 6.6 Hz, 1H), 1.74 (s, 1H), 1.38 (s, 1H), 0.96 (s, 1H), 0.39 (s, 1H). Method A HPLC-MS: MH+ m/z 505, RT 3.05 minutes.

Example 124

Potassium 1-[5-(3-{[2-(difluoromethoxy)phenyl]methyl}-2-methylimidazo[1,2-a]pyridin-6-yl)pyrimidin-2-yl]azepane-4-carboxylate Intermediate 122 (128.5 mg, 0.25 mmol) was suspended in ethanol (3 mL), then 2M aqueous potassium hydroxide solution (0.12 mL) was added and the mixture was heated at 80° C. for 18 h. The mixture was concentrated under reduced pressure and acidified with 1N HCl to pH 2-3. The mixture was extracted with 1:1 isopropanol/chloroform (2×25 mL). The organic layer was washed with water (10 mL), then dried over sodium sulfate and concentrated under reduced pressure, to provide the title compound (120 mg, 89%) as a brown solid. $\delta_H$ (500 MHz, DMSO-$d_6$) 8.60 (s, 2H), 8.38 (s, 1H), 7.52 (d, J 9.3 Hz, 1H), 7.46 (dd, J 9.3, 1.7 Hz, 1H), 7.33-7.26 (m, 1H), 7.49-7.05 (m, 1H), 7.23-7.18 (m, 1H), 7.18-7.10 (m, 1H), 7.08-7.01 (m, 1H), 4.35 (s, 2H), 3.91-3.83 (m, 1H), 3.83-3.76 (m, 1H), 3.68-3.60 (m, 1H), 3.60-3.52 (m, 1H), 2.31 (s, 3H), 2.02-1.93 (m, 1H), 1.92-1.79 (m, 3H), 1.72-1.61 (m, 1H), 1.61-1.48 (m, 1H), 1.40-1.28 (m, 1H).
Method D HPLC-MS: MH+ m/z 508, RT 3.12 minutes.

Example 125

5-(3-{[2-(Difluoromethoxy)phenyl]methyl}-2-methylimidazo[1,2-a]pyridin-6-yl)-2-(piperidin-1-yl)pyridine A mixture of Intermediate 30 (350 mg, 0.52 mmol), and piperidine (2 mL) in a sealed microwave vial was heated under microwave irradiation at 180° C. for 4 h. After cooling to r.t., the reaction mixture was diluted with DCM (20 mL) and saturated aqueous sodium bicarbonate solution (10 mL). The organic phase was separated, washed with brine, dried over sodium sulphate, filtered and concentrated under vacuum, to afford the title compound (233 mg, 74%) as an off-white solid. $\delta_H$ (500 MHz, CD$_3$OD) 8.20 (d, J 2.5 Hz, 1H), 8.08 (s, 1H), 7.69 (dd, J 8.9, 2.6 Hz, 1H), 7.54-7.46 (m, 2H), 7.31-7.26 (m, 1H), 7.21 (d, J 8.1 Hz, 1H), 7.14 (td, J 7.6, 1.0 Hz, 1H), 7.08-6.77 (m, 3H), 4.39 (s, 2H), 3.59-3.54 (m, 4H), 2.45 (s, 3H), 1.73-1.67 (m, 2H), 1.65 (q, J 10.8, 8.3 Hz, 4H). Method D HPLC-MS: MH+ m/z 449, RT 1.97 minutes.

Example 126

1-[5-(3-{[2-(Difluoromethoxy)phenyl]methyl}-2-methylimidazo[1,2-a]pyridin-6-yl)-3-fluoropyridin-2-yl]-4-methylpiperidine-4-carboxylic acid Intermediate 124 (82 mg, 0.15 mmol) was dissolved in EtOH (2 mL) and 2M aqueous potassium hydroxide solution (74 μL) was added. The mixture was heated at 70° C. for 16 h. Additional 2M aqueous potassium hydroxide solution (74 μL) was added and the mixture was stirred at 70° C. until the reaction was complete. The reaction mixture was concentrated, then a 1:1 mixture of isopropanol:chloroform (2 mL), saturated aqueous ammonium chloride solution (2 mL) and a drop of 6M hydrogen chloride were added. The mixture was extracted with a 1:1 mixture of isopropanol:chloroform (3×2 mL). The organic extracts were combined, dried over sodium sulphate and concentrated. The resulting yellow oil was sonicated with diethyl ether. The resulting solid was collected by filtration to afford the title compound (71 mg, 85%) as a yellow solid. $\delta_H$ (500 MHz, DMSO-d$_6$) 8.44 (s, 1H), 8.37-8.28 (m, 1H), 7.85 (dd, J 14.9, 1.9 Hz, 1H), 7.55-7.50 (m, 2H), 7.34-7.26 (m, 1H), 7.48-7.05 (m, 1H), 7.26-7.18 (m, 1H), 7.18-7.09 (m, 1H), 7.05-6.96 (m, 1H), 4.38 (s, 2H), 3.81-3.69 (m, 2H), 3.19-3.08 (m, 3H), 2.30 (s, 3H), 2.09-2.01 (m, 2H), 1.47-1.34 (m, 2H), 1.12 (s, 3H). Method D HPLC-MS: MH+ m/z 525, RT 2.40 minutes.

Example 127

2-{4-[5-(3-{[2-(Difluoromethoxy)phenyl]methyl}-2-methylimidazo[1,2-a]pyridin-6-yl)-pyrimidin-2-yl]piperidin-1-yl}acetic acid Intermediate 128 (40 mg, 0.07 mmol) was suspended in ethanol (5 mL) and 2M aqueous potassium hydroxide solution (0.03 mL) was added. The mixture was stirred overnight at r.t. The reaction mixture was concentrated under vacuum to afford the title compound (35.9 mg, 95%) as a yellow solid. $\delta_H$ (250 MHz, CD$_3$OD) 8.91 (s, 2H), 8.39 (s, 1H), 7.59 (d, J 1.7 Hz, 2H), 7.36-6.60 (m, 5H), 4.42 (s, 2H), 3.15 (d, J 11.1 Hz, 2H), 3.04 (s, 2H), 2.91 (dt, J 10.7, 5.6 Hz, 1H), 2.44 (s, 3H), 2.37-2.19 (m, 2H), 2.17-1.91 (m, 4H). Method D HPLC-MS: MH+ m/z 507, RT 1.36 minutes.

Example 128

Ethyl (1R,5S,6r)-3-[5-(3-{[2-(difluoromethoxy)phenyl]methyl}-2-methylimidazo[1,2-a]-pyridin-6-yl)pyrimidin-2-yl]bicyclo[3.1.0]hexane-6-carboxylate Intermediate 135 (85 mg, 0.16 mmol) was dissolved in ethyl acetate (6 mL) and triethylamine (25 μL, 0.18 mmol) was added, followed by palladium on carbon (10%, 30 mg, 0.03 mmol). The flask was flushed with nitrogen (3 times), then hydrogen (3 times). The reaction mixture was stirred under hydrogen overnight before being filtered through Kieselguhr. The residue was washed through with ethyl acetate (30 mL), and concentrated, to afford the title compound (35 mg, 39%) as a light yellow oil/gum. $\delta_H$ (500 MHz, CDCl$_3$) 8.74 (s, 2H), 7.94 (s, 1H), 7.75 (d, J 9.0 Hz, 1H), 7.37 (d, J 9.3 Hz, 1H), 7.32-7.27 (m, 1H), 7.19-7.15 (m, 1H), 7.13-7.07 (m, 1H), 6.93-6.88 (m, 1H), 6.65 (t, J 73.6 Hz, 1H), 4.33 (s, 2H), 4.07 (q, J 7.1 Hz, 2H), 3.84-3.71 (m, 1H), 2.59-2.45 (m, 7H), 2.02-1.95 (m, 2H), 1.58-1.53 (m, 1H), 1.21 (t, J 7.1 Hz, 3H).

Example 129

Ammonium (1R,5S,6r)-3-[5-(3-{[2-(difluoromethoxy)phenyl]methyl}-2-methylimidazo-[1,2-a]pyridin-6-yl)pyrimidin-2-yl]bicyclo[3.1.0]hexane-6-carboxylate Example 128 (33 mg, 0.06 mmol) was dissolved in ethanol (4 mL), then 1M aqueous potassium hydroxide solution (65 μL) was added and the mixture was stirred at 70° C. overnight. Further 1M aqueous potassium hydroxide solution (13 μL) was added and the reaction mixture was heated for 3 h, stirred at r.t. over 2 days, then heated at 70° C. overnight. The reaction mixture was allowed to cool to r.t. and ethanol was removed using nitrogen. The residue was sonicated with diethyl ether (3 mL) and acetonitrile (1 mL). The resulting brown solid was collected by filtration, before being recombined with the filtrate and purified using preparative HPLC (Method D), to afford the title compound (12 mg, 38%). $\delta_H$ (500 MHz, DMSO-d$_6$) 9.01 (s, 2H), 8.60 (s, 1H), 7.62-7.56 (m, 2H), 7.43-7.10 (m, 4H), 7.05 (d, J 6.6 Hz, 1H), 4.41-4.36 (m, 2H), 3.18-3.07 (m, 1H), 2.33-2.29 (m, 3H), 2.27-2.21 (m, 2H), 2.20-2.11 (m, 2H), 1.87-1.81 (m, 2H), 1.64-1.58 (m, 1H). Method D HPLC-MS: MH+ m/z 492, RT 1.90 minutes.

Example 130

Potassium 4-[5-(3-{[2-(difluoromethoxy)phenyl]methyl}-2-methylimidazo[1,2-a]pyridin-6-yl)pyrimidin-2-yl]-2-methylmorpholine-2-carboxylate Intermediate 139 (47.8 mg, 0.09 mmol) was suspended in ethanol (2 mL), then 1M aqueous potassium hydroxide solution (0.1 mL) was added and the mixture was heated at 70° C. for 18 h. The reaction mixture was allowed to cool to r.t., diluted with DCM (15 mL), washed with water (2×10 mL) and dried over sodium sulphate, then filtered and concentrated under vacuum. The solid was triturated with ethyl acetate, and dried in air, to afford the title compound (44.4 mg, 89%) as a light brown solid. $\delta_H$ (500 MHz, DMSO-$d_6$) 8.60 (s, 2H), 8.36 (s, 1H), 7.53 (d, J 9.3 Hz, 1H), 7.47-7.12 (m, 5H), 7.08 (d, J 6.4 Hz, 1H), 4.76 (d, J 12.2 Hz, 1H), 4.36 (s, 2H), 4.08 (d, J 12.9 Hz, 1H), 4.04-3.99 (m, 1H), 3.55 (dt, J 11.5, 3.3 Hz, 1H), 3.13-3.06 (m, 1H), 2.81 (d, J 12.2 Hz, 1H), 2.32 (s, 3H), 1.12 (s, 3H). Method D HPLC-MS: MH+ m/z 510, RT 1.98 minutes.

Example 131

Methyl 4-(3-{[2-(difluoromethoxy)phenyl]methyl}-2-methylimidazo[1,2-a]pyridin-6-yl)-benzoate A mixture of Intermediate 7 (200 mg, 0.54 mmol), [4-(methoxycarbonyl)phenyl]-boronic acid (108 mg, 0.60 mmol), 2M aqueous potassium carbonate solution (0.82 mL, 1.63 mmol) and 1,4-dioxane (4 mL) in a pressure tube was degassed with nitrogen for 15 minutes at room temperature. Pd(dppf)Cl$_2$ complex with DCM (22 mg, 0.03 mmol) was added and the reaction mixture was stirred at 80° C. for 18 h. The reaction mixture was cooled to room temperature and concentrated under vacuum. The resulting brown residue was purified by flash chromatography (DCM:MeOH 1:0 to 98:2), to afford the title compound (85 mg, 35%) as a pale brown solid. $\delta_H$ (500 MHz, CDCl$_3$) 8.10 (d, J 8.4 Hz, 2H), 8.03 (s, 1H), 7.70 (d, J 20.5 Hz, 1H), 7.51 (dd, J 19.0, 8.6 Hz, 3H), 7.26 (m, 1H), 7.17 (d, J 8.0 Hz, 1H), 7.10 (t, J 7.5 Hz, 1H), 6.94 (d, J 6.7 Hz, 1H), 6.64 (t, J 73.6 Hz, 1H), 4.33 (s, 2H), 3.94 (s, 3H), 2.56 (s, 3H). Method D HPLC-MS: MH+ m/z 423, RT 2.33 minutes.

Example 132

(1R,4R)-4-[5-(3-{[2-(Difluoromethoxy)phenyl]methyl}-2-methylimidazo[1,2-a]pyridin-6-yl)pyridin-2-yl]cyclohexane-1-carboxylic acid To a solution of Intermediate 141 (262 mg, 0.52 mmol) in ethanol (20 mL) was added palladium on carbon (10%, 55 mg, 0.05 mmol). The reaction mixture was purged with nitrogen (3 times), then filled with hydrogen and stirred at room temperature overnight. The reaction mixture was filtered through celite, washed with ethanol (70 mL) and concentrated under vacuum. The resulting pink residue and a 2M solution of sodium ethoxide in ethanol (1.23 mL) in ethanol (10 mL) was heated at 80° C. overnight under nitrogen. The reaction mixture was cooled to r.t. and acidified to pH 2 using 2M HCl. Water (10 mL) and a 1:1 isopropanol/chloroform mixture (30 mL) were added. The mixture was further extracted with 1:1 isopropanol/chloroform (30 mL). Purification by preparative HPLC (Method A) afforded the title compound (15 mg, 69%) as a white solid. $\delta_H$ (500 MHz, DMSO-$d_6$) 8.75 (d, J 2.3 Hz, 1H), 8.46 (s, 1H), 7.96 (dd, J 8.2, 2.5 Hz, 1H), 7.59-7.27 (m, 5H), 7.20 (d, J 8.0 Hz, 1H), 7.15-7.10 (m, 1H), 7.06-7.02 (m, 1H), 4.38 (s, 2H), 2.70 (tt, J 11.8, 3.4 Hz, 1H), 2.32 (s, 3H), 2.25 (tt, J 11.9, 3.5 Hz, 1H), 2.07-1.96 (m, 2H), 1.96-1.87 (m, 2H), 1.58 (qd, J 12.8, 2.9 Hz, 2H), 1.47 (qd, J 12.8, 2.9 Hz, 2H). Method D HPLC-MS: MH+ m/z 492, RT 1.87 minutes.

Example 133

4-[5-(3-{[2-(Difluoromethoxy)phenyl]methyl}-2-methylimidazo[1,2-a]pyridin-6-yl)-pyridin-2-yl]cyclohex-3-ene-1-carboxylic acid Purification by preparative HPLC (Method A) of the crude mixture resulting from the reaction carried out to prepare Example 132 afforded the title compound (10 mg, 4%) as a white solid. $\delta_H$ (500 MHz, DMSO-$d_6$) 8.81 (d, J 2.3 Hz, 1H), 8.50 (s, 1H), 8.01 (dd, J 8.4, 2.5 Hz, 1H), 7.63-7.25 (m, 5H), 7.20 (d, J 8.0 Hz, 1H), 7.16-7.10 (m, 1H), 7.08-7.03 (m, 1H), 6.78 (s, 1H), 4.39 (s, 2H), 2.74-2.61 (m, 1H), 2.48-2.34 (m, 4H), 2.32 (s, 3H), 2.14-2.05 (m, 1H), 1.78-1.63 (m, 1H). Method D HPLC-MS: MH+ m/z 490, RT 2.02 minutes.

Example 134

Potassium 3-[5-(3-{[2-(difluoromethoxy)phenyl]methyl}-2-methylimidazo[1,2-a]pyridin-6-yl)pyridin-2-yl]-3-azabicyclo[3.1.0]hexane-1-carboxylate (Enantiomer A)

A mixture of Intermediate 101 (200 mg, 0.52 mmol) and Intermediate 144 (185 mg, 1.04 mmol) in pyridine (2 mL) was heated at 180° C. under microwave irradiation for 4 h. The reaction mixture was diluted with ethyl acetate (10 mL) and a solid precipitated. The solid was washed with ethyl acetate (20 mL) and purified by preparative HPLC (Method C). The resulting light brown solid was suspended in ethanol (3 mL) and heated at 70° C. for 30 minutes. Aqueous potassium hydroxide solution (1M, 0.05 mL) was added and the mixture was allowed to stir at 70° C. for 1 h. The mixture was concentrated under reduced pressure to afford the title compound (25.9 mg, 9%) as a brown solid. $\delta_H$ (500 MHz, CD$_3$OD) 8.14 (d, J 2.4 Hz, 1H), 8.07 (s, 1H), 7.69 (dd, J 8.8, 2.5 Hz, 1H), 7.52 (d, J 9.3 Hz, 1H), 7.48 (dd, J 9.3, 1.6 Hz, 1H), 7.32-7.26 (m, 1H), 7.22 (d, J 8.1 Hz, 1H), 7.14 (t, J 7.5 Hz, 1H), 7.08-6.77 (m, 2H), 6.59 (d, J 8.9 Hz, 1H), 4.39 (s, 2H), 3.85 (d, J 10.0 Hz, 1H), 3.78-3.70 (m, 2H), 3.53 (dd, J 10.2, 4.4 Hz, 1H), 2.45 (s, 3H), 2.08-2.00 (m, 1H), 1.53 (dd, J 8.1, 3.9 Hz, 1H), 0.66 (t, J 4.4 Hz, 1H). Method D HPLC-MS: MH+ m/z 491, RT 1.66 minutes.

Example 135

Potassium 1-[3-chloro-5-(3-{[2-(difluoromethoxy)phenyl]methyl}-2-methylimidazo[1,2-a]pyridin-6-yl)pyridin-2-yl]-4-methylpiperidine-4-carboxylate Intermediate 146 (56 mg, 0.08 mmol) and 2M aqueous potassium hydroxide solution (60 µL, 0.12 mmol) were dissolved in EtOH (2 mL) and water (0.5 mL) and the mixture was heated to 120° C. under microwave irradiation for 18 h. The reaction mixture was concentrated in a vacuum centrifuge to afford the title compound (41 mg, 72%) as a cream solid. $\delta_H$ (500 MHz, DMSO-$d_6$) 8.51-8.41 (m, 2H), 8.02 (d, J 2.2 Hz, 1H), 7.51 (s, 2H), 7.48-7.08 (m, 4H), 7.00 (d, J 6.5 Hz, 1H), 4.37 (s, 2H), 3.46 (d, J 12.7 Hz, 2H), 3.02 (t, J 10.5 Hz, 2H), 2.28 (s, 3H), 2.07 (d, J 12.6 Hz, 2H), 1.28-1.14 (m, 2H), 0.94 (s, 3H). Method D HPLC-MS: MH+ m/z 541, RT 2.51 minutes.

Example 136

Potassium 4-[5-(3-{[2-(difluoromethoxy)phenyl]methyl}-2-methylimidazo[1,2-a]pyridin-6-yl)pyrimidin-2-yl]-3-methylcyclohexane-1-carboxylate (unknown isomer)

Intermediate 151 (13 mg, 0.02 mmol) was dissolved in ethanol (1 mL) and 2M aqueous potassium hydroxide solution (12 µL) was added. The reaction mixture was heated at 80° C. in a sealed tube overnight for 2 nights. Further aqueous potassium hydroxide solution (5 µL) was added and the reaction mixture was heated at 80° C. in a sealed tube overnight. Further aqueous potassium hydroxide solution (5 µL) was added and the reaction mixture was heated at 80° C. in a sealed tube overnight. The reaction mixture was concentrated by evaporation, to afford the title compound (12.7 mg, 87%) as a yellow solid. $\delta_H$ (500 MHz, DMSO-$d_6$) 9.02 (s, 2H), 8.67 (s, 1H), 7.67-7.53 (m, 2H), 7.46-7.10 (m, 4H), 7.05 (d, J 7.6 Hz, 1H), 4.40 (s, 2H), 3.16 (d, J 3.8 Hz, 1H), 2.30 (s, 3H), 2.00 (q, J 12.4, 11.9 Hz, 2H), 1.89 (d, J 4.2 Hz, 1H), 1.82-1.63 (m, 3H), 1.56 (d, J 12.5 Hz, 1H), 1.50 (d, J 11.8 Hz, 1H), 0.81 (d, J 6.9 Hz, 3H). Method D HPLC-MS: MH+ m/z 507, RT 2.17 minutes.

Example 137

Potassium 4-{[5-(3-{[2-(difluoromethoxy)phenyl]methyl}-2-methylimidazo[1,2-a]-pyridin-6-yl)pyrimidin-2-yl]methyl}cyclohexane-1-carboxylic acid Intermediate 153 (21 mg, 0.03 mmol) was dissolved in EtOH (1 mL), then 2M aqueous potassium hydroxide solution (0.02 mL) was added. The mixture was stirred at room temperature overnight, then heated at 80° C. for a total of 11 h. Further 2M aqueous potassium hydroxide solution (5 µL) was added. The mixture was heated at 80° C. overnight, then for a further 2.5 h. The mixture was concentrated under vacuum to afford the title compound (21 mg, 97% yield at 90% purity) as a brown solid. $\delta_H$ (500 MHz, CD$_3$OD) 8.91 (s, 2H), 8.41 (s, 1H), 7.65-7.57 (m, 2H), 7.32-7.27 (m, 1H), 7.20 (d, J 8.1 Hz, 1H), 7.14 (t, J 7.4 Hz, 1H), 7.10 (d, J 7.6 Hz, 1H), 6.92 (t, J 74.0 Hz, 1H), 4.43 (s, 2H), 2.85 (d, J 7.1 Hz, 2H), 2.44 (s, 3H), 2.09 (tt, J 12.0, 3.3 Hz, 1H), 1.93 (d, J 11.2 Hz, 2H), 1.73 (d, J 10.8 Hz, 2H), 1.57 (dt, J 9.1, 4.5 Hz, 1H), 1.52 (dt, J 8.3, 4.5 Hz, 1H), 1.43 (qd, J 13.1, 3.1 Hz, 2H), 1.12 (qd, J 13.2, 3.3 Hz, 1H). Method D HPLC-MS: MH+ m/z 492, RT 2.01-2.07 minutes.

Example 138

4-[5-(3-{[2-(Difluoromethoxy)phenyl]methyl}-7-fluoro-2-methylimidazo[1,2-a]pyridin-6-yl)pyrimidin-2-yl]bicyclo[4.1.0]heptane-1-carboxylic acid Intermediate 162 (13 mg, 0.022 mmol) was suspended in THF (0.5 mL), then water (0.5 mL) and 2M aqueous potassium hydroxide solution (65 µL) was added. The reaction mixture was stirred at room temperature for 22 h. The THF was removed in vacuo and the aqueous layer was extracted with EtOAc (3×1 mL). The aqueous layer was acidified to pH 2 with 1N HCl and extracted with DCM (3×2 mL) followed by 1:1 isopropanol/chloroform (3×2 mL). The combined organic layers were dried over sodium sulfate and concentrated. The residue was triturated in hot heptane, and dried, to afford the title compound (7.0 mg, 55%) as a light orange oil. $\delta_H$ (500 MHz, CD$_3$OD) (peaks for major isomer) 8.89 (d, J 6.1 Hz, 2H), 8.80 (s, 1H), 7.83 (d, J 9.0 Hz, 1H), 7.36 (t, J 7.8 Hz, 2H), 7.21 (t, J 8.0 Hz, 2H), 6.92 (t, J 73.9 Hz, 1H), 4.50 (s, 2H), 2.97-2.79 (m, 1H), 2.48 (s, 3H), 2.39 (ddt, J 20.2, 14.8, 6.5 Hz, 1H), 2.25 (dd, J 8.2, 3.4 Hz, 1H), 1.89 (ddd, J 14.0, 8.3, 4.7 Hz, 2H), 1.67-1.57 (m, 1H), 1.49 (dq, J 8.7, 4.4 Hz, 1H), 1.37-1.26 (m, 2H), 0.84 (ddd, J 24.4, 6.5, 4.2 Hz, 1H). Method D HPLC-MS: MH+ m/z 523, RT 2.11-2.13 minutes.

Example 139

Potassium 6-[5-(3-{[2-(difluoromethoxy)phenyl]methyl}-2-methylimidazo[1,2-a]pyridin-6-yl)pyrimidin-2-yl]bicyclo[4.1.0]heptane-3-carboxylate Intermediate 163 (38.3 mg, 0.074 mmol) was suspended in methanol (1 mL), 2M aqueous potassium hydroxide solution (0.04 mL) was added and the reaction mixture was stirred at room temperature for 1 h. The mixture was heated at 55° C. overnight and for a further 2 h, then heated at 80° C. overnight. Further 2M aqueous potassium hydroxide solution (8 µL) was added and the mixture was heated at 80° C. for a total of 29 h. The mixture was cooled to room temperature, diluted with water (2 mL), acidified to pH 5 using 1N HCl, and extracted with EtOAc (3×2 mL). The organic extracts were combined, dried over sodium sulfate and concentrated. The resulting off-white solid was dissolved in ethanol (2 mL) and 2M aqueous potassium hydroxide solution (1 eq) was added. The mixture was stirred at room temperature for 1 h, then concentrated under vacuum, to afford the title compound (17 mg, 40%) as an off-white solid. $\delta_H$ (500 MHz, DMSO-$d_6$) 8.93-8.92 (s, 2H), 8.56 (s, 1H), 7.57 (q, J 9.3 Hz, 2H), 7.45-7.01 (m, 5H), 4.37 (s, 2H), 2.31 (s, 3H), 2.12 (td, J 11.2, 9.9, 6.2 Hz, 1H), 1.97-1.33 (m, 7H), 1.13 (ddt, J 15.9, 10.7, 5.4 Hz, 1H), 0.83 (td, J 8.2, 6.5, 4.4 Hz, 1H). Method D HPLC-MS: MH+ m/z 505, RT 2.14-2.22 minutes.

Example 140

Potassium (1r,4r)-4-[5-(3-{[2-(difluoromethoxy)phenyl]methyl}-2-methylimidazo[1,2-a]pyridin-6-yl)pyrazin-2-yl]cyclohexane-1-carboxylate Intermediate 166 (25 mg, 0.05 mmol) was dissolved in ethanol (2 mL) and 2M aqueous potassium hydroxide solution (0.07 mL) was added. The reaction mixture was heated at 80° C. in a sealed tube for 4 h. The cooled reaction mixture was acidified with 2M hydrochloric acid to pH 2, then partitioned between 10% isopropanol/chloroform (5 mL) and water (3 mL). The aqueous layer was separated and further extracted with 10% isopropanol/chloroform (2×5 mL). The combined organic extracts were washed with brine (5 mL), dried over sodium sulfate and evaporated. To the resulting pale yellow solid were added isopropanol (1 mL), water (0.2 mL) and 1M aqueous potassium hydroxide solution (36 µL). The mixture was brought into solution with a heat gun, then stirred at room temperature for 1 h. The reaction mixture was concentrated by evaporation to afford the title compound (19 mg, 72%) as an off-white solid. $\delta_H$ (500 MHz, DMSO-$d_6$) 9.10 (d, J 1.3 Hz, 1H), 8.84 (s, 1H), 8.60 (d, J 1.3 Hz, 1H), 7.88 (dd, J 9.4, 1.6 Hz, 1H), 7.59 (d, J 9.4 Hz, 1H), 7.51-7.18 (m, 3H), 7.16-7.11 (m, 1H), 7.02 (d, J 7.6 Hz, 1H), 4.39 (s, 2H), 2.78 (ddd, J 12.0, 8.5, 3.4 Hz, 1H), 2.32 (s, 3H), 2.25 (ddt, J 11.9, 6.8, 3.5 Hz, 1H), 2.02 (d, J 10.6 Hz, 2H), 1.93 (d, J 10.7 Hz, 2H), 1.60 (qd, J 12.8, 2.8 Hz, 2H), 1.48 (qd, J 12.9, 2.9 Hz, 2H). Method D HPLC-MS: MH+ m/z 493, RT 2.10 minutes.

Example 141

Ammonium 3-[5-(3-{[2-(difluoromethoxy)phenyl]methyl}-2-methylimidazo[1,2-a]-pyridin-6-yl)pyrimidin-2-yl]cyclopentane-1-carboxylate Intermediate 171 (90%, 43 mg, 0.08 mmol) was suspended in ethanol (2 mL), then 1M aqueous potassium hydroxide solution (0.08 mL) was added and the mixture was allowed to stir at 70° C. for 1 h. The reaction mixture was concentrated under reduced pressure. The residue was purified by preparative HPLC (Method C) to afford the title compound (30 mg, 70%) as an orange-yellow solid. $\delta_H$ (500 MHz, CD$_3$OD) 8.87 (d, J 1.6 Hz, 2H), 8.37 (s, 1H), 7.61-7.54 (m, 2H), 7.32-7.26 (m, 1H), 7.20 (d, J 8.1 Hz, 1H), 7.14 (t, J 7.5 Hz, 1H), 7.09 (d, J 7.5 Hz, 1H), 6.91 (t, J 74.0 Hz, 1H), 4.42 (s, 2H), 3.64-3.37

(m, 1H), 2.98-2.78 (m, 1H), 2.43 (s, 3H), 2.40-2.31 (m, 1H), 2.26-1.92 (m, 5H). Method D HPLC-MS: MH+ m/z 481, RT 1.89 minutes.

Example 142

Ethyl 4-[5-(3-{[2-(difluoromethoxy)phenyl]methyl}-7-fluoro-2-methylimidazo[1,2-a]-pyridin-6-yl)pyrimidin-2-yl]-2-methylcyclohexane-1-carboxylate Intermediate 175 (541 mg, 0.98 mmol) was dissolved in methanol (50 mL), then activated charcoal (500 mg) was added and the mixture was heated at 60° C. for 15 minutes. The mixture was cooled to room temperature, filtered through Celite, and concentrated. The resulting clear oil (427 mg) was dissolved in ethyl acetate (20 mL). Palladium on carbon (10%, 82.69 mg, 0.08 mmol) and triethylamine (0.108 mL, 0.78 mmol) were added. The suspension was degassed using vacuum/$N_2$/$H_2$, and the reaction mixture was stirred under hydrogen at room temperature and atmospheric pressure for 4 h. The mixture was filtered through celite and re-treated with palladium on carbon (10%, 6.01 mg, 0.01 mmol) and triethylamine (7.87 μL, 0.06 mmol), then stirred under hydrogen for another 14 h. This process was repeated again and the mixture was stirred for another 5 h. The mixture was filtered through celite, then concentrated under reduced pressure, to provide the title compound (390 mg, 90%) as a sticky solid. $\delta_H$ (500 MHz, $CDCl_3$) 8.70 (d, J 1.4 Hz, 2H), 7.81-7.71 (m, 1H), 7.40 (d, J 10.4 Hz, 1H), 7.29 (d, J 7.4 Hz, 1H), 7.17 (d, J 8.1 Hz, 1H), 7.11 (t, J 7.5 Hz, 1H), 6.89 (d, J 7.6 Hz, 1H), 6.62 (t, J 73.6 Hz, 1H), 4.29 (s, 2H), 4.15 (qd, J 7.1, 1.7 Hz, 2H), 2.99 (tt, J 11.9, 3.5 Hz, 1H), 2.69 (s, 1H), 2.52 (s, 3H), 2.20-2.00 (m, 3H), 1.99-1.81 (m, 3H), 1.81-1.69 (m, 1H), 1.30-1.25 (m, 3H), 1.07 (d, J 6.8 Hz, 3H).

Example 143

Potassium (1s,4s)-4-[5-(3-{[2-(difluoromethoxy)phenyl]methyl}-2-methylimidazo[1,2-a]pyridin-6-yl)pyrazin-2-yl]cyclohexane-1-carboxylate Intermediate 167 (30 mg, 0.06 mmol) was dissolved in ethanol (2 mL) and 2M aqueous potassium hydroxide solution (0.09 mL) was added. The reaction mixture was heated at 80° C. in a sealed tube for 4 h. The cooled reaction mixture was acidified with 2M hydrochloric acid to pH 2, then partitioned between 10% isopropanol in chloroform (5 mL) and water (3 mL). The aqueous layer was separated and further extracted into 10% isopropanol in chloroform (2×5 mL). The combined organic extracts were washed with brine (5 mL), dried over sodium sulfate and evaporated. The resulting pale yellow foam was purified by preparative HPLC (Method D). The resulting off-white solid (14 mg (48%) of the free acid) was dissolved in a 5:1 mixture of isopropanol:water (1.2 mL). 1M aqueous potassium hydroxide solution (29 μL) was added and the mixture was stirred at room temperature for 1 h. The reaction mixture was evaporated to afford the title compound (14 mg, 92%) as a pale yellow solid. $\delta_H$ (500 MHz, DMSO-$d_6$) 9.07 (d, J 1.2 Hz, 1H), 8.83 (s, 1H), 8.52 (d, J 1.2 Hz, 1H), 7.87 (dd, J 9.4, 1.6 Hz, 1H), 7.57 (d, J 9.4 Hz, 1H), 7.50-6.99 (m, 5H), 4.39 (s, 2H), 2.73 (td, J 11.0, 9.3, 5.5 Hz, 1H), 2.33 (s, 3H), 2.12 (dd, J 8.4, 4.0 Hz, 2H), 2.04 (m, 1H), 1.89-1.77 (m, 2H), 1.66-1.54 (m, 2H), 1.38 (td, J 12.2, 10.4, 4.1 Hz, 2H). Method D HPLC-MS: MH+ m/z 493, RT 2.21 minutes.

Example 144

(1r,4r)-4-[5-(3-{[2-(Difluoromethoxy)phenyl]methyl}-2,7-dimethylimidazo[1,2-a]-pyridin-6-yl)pyrimidin-2-yl]cyclohexane-1-carboxylic acid Sodium methoxide solution in methanol (2M) was prepared by dissolving sodium metal (11.5 mg) in dry methanol (0.25 mL). Intermediate 177 (45 mg, 0.086 mmol) in dry methanol (3 mL) was added and the mixture was heated at 65° C. overnight under nitrogen. The reaction mixture was adjusted to pH 3 using 6M HCl and saturated aqueous sodium carbonate solution. The mixture was extracted with 1:1 isopropanol: chloroform (25 mL), dried with sodium sulfate and concentrated under vacuum. The residue was purified by preparative HPLC (Method C) to afford the title compound (4 mg, 10%) as a brown solid. $\delta_H$ (500 MHz, DMSO-$d_6$) 12.05 (br s, 1H), 8.78 (s, 2H), 8.31 (s, 1H), 7.53 (s, 1H), 7.43-6.90 (m, 5H), 4.33 (s, 2H), 2.91-2.81 (m, 1H), 2.32-2.21 (m, 7H), 2.12-1.98 (m, 4H), 1.69-1.56 (m, 2H), 1.55-1.42 (m, 2H). Method B HPLC-MS: MH+m/z 507, RT 1.97 minutes.

Example 145

Potassium 2-{4-[5-(3-{[2-(difluoromethoxy)phenyl]methyl}-7-fluoro-2-methylimidazo-[1,2-a]pyridin-6-yl)pyrimidin-2-yl]cyclohexyl}acetate Intermediate 180 (107 mg, 0.2 mmol) was suspended in ethanol (3 mL), 1M aqueous potassium hydroxide solution (0.2 mL) was added and the mixture was allowed to stir at 70° C. for 18 h. Additional 1M aqueous potassium hydroxide solution (0.02 mL) was added and the mixture was allowed to stir at 70° C. for 4 h. The mixture was concentrated under reduced pressure to afford the title compound (97 mg, 83%) as a brown gum. $\delta_H$ (500 MHz, DMSO-$d_6$) 8.80 (d, J 1.3 Hz, 2H), 8.30 (d, J 7.1 Hz, 1H), 7.33 (d, J 10.8 Hz, 1H), 7.31-7.25 (m, 1H), 7.20-7.08 (m, 3H), 6.89 (t, J 74.0 Hz, 1H), 4.38 (s, 2H), 3.08-2.81 (m, 1H), 2.39 (s, 3H), 2.24-1.64 (m, 9H). Method D HPLC-MS: MH+ m/z 525, RT 2.15 minutes.

Example 146

Potassium 3-[5-(3-{[2-(difluoromethoxy)phenyl]methyl}-7-fluoro-2-methylimidazo[1,2-a]pyridin-6-yl)pyrimidin-2-yl]cyclopentane-1-carboxylate Intermediate 181 (84 mg, 0.16 mmol) was suspended in ethanol (3 mL), then a 1M aqueous potassium hydroxide solution (0.16 mL) was added and the mixture was allowed to stir at 70° C. for 18 h. Additional 1M aqueous potassium hydroxide solution (0.02 mL) was added and the mixture was allowed to stir at 70° C. for 4 h. The mixture was concentrated under reduced pressure to afford the title compound (74 mg, 85%) as a light brown solid. $\delta_H$ (500 MHz, $CD_3OD$) 8.79 (d, J 1.3 Hz, 2H), 8.30 (d, J 7.1 Hz, 1H), 7.34 (d, J 10.8 Hz, 1H), 7.31-7.25 (m, 1H), 7.14 (ddd, J 22.2, 15.5, 7.9 Hz, 3H), 6.89 (t, J 74.0 Hz, 1H), 4.39 (s, 2H), 3.65-3.37 (m, 1H), 2.96-2.77 (m, 1H), 2.40 (s, 4H), 2.28-1.93 (m, 5H). Method D HPLC-MS: MH+ m/z 497, RT 1.98 minutes.

Example 147

6-[2-(4-Carboxy-3-methylcyclohexyl)pyrimidin-5-yl]-3-{[2-(difluoromethoxy)phenyl]-methyl}-7-ethoxy-2-methylimidazo[1,2-a]pyridin-1-ium formate Example 142 (63 mg, 0.11 mmol) was dissolved in ethanol (3 mL) and 2M aqueous potassium hydroxide solution (171 μL) was added. The reaction mixture was heated at 70° C. for 27 h, then additional 2M aqueous potassium hydroxide solution (171 μL) was added and the mixture was heated for 5 h. The mixture was concentrated under reduced pressure, diluted with water (30 mL) and extracted with a 1:1 isopropanol:chloroform mixture (2×25 mL), then dried over magnesium sulfate, filtrated and concentrated under reduced pressure. The residue was purified by preparative HPLC (Method A) to afford the title compound (5 mg, 7%) as an off-white solid, as a mixture of isomers. $\delta_H$ (500 MHz, CDCl$_3$) 8.70 (d, J 1.4 Hz, 2H), 7.81-7.71 (m, 1H), 7.40 (d, J 10.4 Hz, 1H), 7.29 (d, J 7.4 Hz, 1H), 7.17 (d, J 8.1 Hz, 1H), 7.11 (t, J 7.5 Hz, 1H), 6.89 (d, J 7.6 Hz, 1H), 6.62 (t, J 73.6 Hz, 1H), 4.29 (s, 2H), 4.15 (qd, J 7.1, 1.7 Hz, 2H), 2.99 (tt, J 11.9, 3.5 Hz, 1H), 2.69 (s, 1H), 2.52 (s, 3H), 2.20-2.00 (m, 3H), 1.99-1.81 (m, 3H), 1.81-1.69 (m, 1H), 1.30-1.25 (m, 3H), 1.07 (d, J 6.8 Hz, 3H). Method D HPLC-MS: MH+ m/z 551, RT 2.20, 2.23 minutes.

Example 148

Ammonium 5-[5-(3-{[2-(difluoromethoxy)phenyl]methyl}-7-fluoro-2-methylimidazo-[1,2-a]pyridin-6-yl)pyrimidin-2-yl]bicyclo[2.2.2]octane-2-carboxylate Intermediate 184 (69 mg, 0.13 mmol) was dissolved in methanol (1.5 mL), and 1M aqueous potassium hydroxide solution (150 μL) was added. The reaction mixture was heated at 70° C. until the reaction was complete. The reaction mixture was acidified to pH 1 using 6M HCl solution, then the aqueous phase was extracted with 1:1 isopropanol/chloroform (2×15 mL). The aqueous phase was adjusted to pH 3 using saturated aqueous sodium carbonate solution, then extracted with 1:1 isopropanol/chloroform (20 mL). The organic extract was dried over sodium sulfate and concentrated under vacuum. The resulting crude gum was purified by preparative HPLC (Method C) to afford the title compound (68 mg, 49%) as a white solid. $\delta_H$ (250 MHz, DMSO-d$_6$) 9.00-8.83 (m, 2H), 8.60 (d, J 7.2 Hz, 1H), 7.53 (d, J 11.2 Hz, 1H), 7.36-6.90 (m, 5H), 4.34 (s, 2H), 3.12 (s, 1H), 2.23 (d, J 8.3 Hz, 5H), 2.12-1.14 (m, 9H). Method D HPLC-MS: MH+ m/z 507, RT 2.35 minutes.

Example 149

Potassium 4-[5-(3-{[2-(difluoromethoxy)phenyl]methyl}-2-methylimidazo[1,2-a]pyridin-6-yl)pyrimidin-2-yl]-3-methylcyclohexane-1-carboxylate Intermediate 189 (70 mg, 0.13 mmol) was dissolved in ethanol (3 mL) and 1M aqueous potassium hydroxide solution (0.39 mL) was added. The reaction mixture was heated at 80° C. in a sealed tube for 3 h. Further 1M aqueous potassium hydroxide solution (0.13 mL) was added and the reaction mixture was heated at 80° C. in a sealed tube for 1 h. The cooled reaction mixture was acidified with 2M hydrochloric acid to pH 2, then partitioned between 10% isopropanol:chloroform (5 mL) and water (3 mL). The aqueous layer was separated and further extracted into 10% isopropanol:chloroform (5 mL). The combined organic extracts were washed with brine (5 mL), dried over sodium sulfate and evaporated. The resulting pale yellow oil (carboxylic acid intermediate, 37 mg, 0.07 mmol) was dissolved in a 5:1 mixture of isopropanol:water (1.2 mL) and 1M aqueous potassium hydroxide solution (73 μL). The mixture was brought into solution with a heat gun, then stirred at room temperature for 1 h. The reaction mixture was evaporated to afford the title compound (34 mg, 85%) as a pale yellow solid. $\delta_H$ (250 MHz, DMSO-d$_6$) 9.03 (s, 2H), 8.65 (s, 1H), 7.64-7.55 (m, 2H), 7.35-6.94 (m, 5H), 4.39 (s, 2H), 2.30 (s, 3H), 2.25 (m, 1H), 2.02-1.79 (m, 4H), 1.60 (d, J 12.9 Hz, 1H), 1.39 (d, J 13.1 Hz, 1H), 1.26-1.06 (m, 1H), 0.66 (d, J 6.2 Hz, 3H). One proton partially obscured under DMSO peak. Method A HPLC-MS: MH+ m/z 507, RT 3.04 minutes.

Example 150

Ethyl (1R,5S,6r)-3-[5-(3-{[2-(difluoromethoxy)phenyl]methyl}-7-fluoro-2-methyl-imidazo[1,2-a]pyridin-6-yl)pyrimidin-2-yl]bicyclo[3.1.0]hexane-6-carboxylate Intermediate 190 (280 mg, 0.52 mmol) was dissolved in ethanol (5 mL) and ethyl acetate (5 mL). Triethylamine (90 μL, 0.65 mmol) was added, followed by palladium hydroxide on carbon (10%, 70 mg, 0.07 mmol). The reaction mixture was flushed with nitrogen (3 times) and hydrogen (3 times). The mixture was stirred under hydrogen overnight. The mixture was filtered through Kieselguhr and washed through with ethyl acetate, then the filtrate was concentrated. The crude residue was purified by column chromatography (0 to 4% methanol in dichloromethane) to afford the title compound (269 mg, 96%). Method D HPLC-MS: MH+ m/z 538, RT 2.59 minutes.

Example 151

Potassium (1R,5S,6r)-3-[5-(3-{[2-(difluoromethoxy)phenyl]methyl}-7-fluoro-2-methyl-imidazo[1,2-a]pyridin-6-yl)pyrimidin-2-yl]bicyclo[3.1.0]hexane-6-carboxylate Example 150 (269 mg, 0.5 mmol) was stirred in tetrahydrofuran (5 mL) and 2M aqueous potassium hydroxide solution (5 mL) at 60° C. for 25 h. 1,4-Dioxane (5 mL) was added and the reaction mixture was stirred at 60° C. for a further 18 h. The reaction mixture was allowed to cool, then ethyl acetate (10 mL) and 2M aqueous potassium hydroxide solution (10 mL) were added. The layers were separated. The aqueous phase was washed with ethyl acetate (10 mL) and adjusted to pH 4-5 using 6M hydrogen chloride solution. The resulting solid was collected by filtration, washed with diethyl ether and dried, then dissolved in dimethylsulfoxide (5 mL) and water (2 mL) with heating. Aqueous potassium hydroxide solution (1M, 267 μL) was added and the solution was heated at 60° C. for 30 minutes. The reaction mixture was concentrated in a genevac for 24 h. Water (2 mL) was added to the resulting oil, then the mixture was dried in a genevac for 2 h. Diethyl ether was added to the resulting brown oily solid. The mixture was sonicated, then triturated with a spatula. The resulting grey/light brown solid was collected by filtration, and dried in a vacuum oven at 60° C. for 2 h, to afford the title compound (139 mg, 95%) as a grey/light brown solid. $\delta_H$ (500 MHz, DMSO-d$_6$) 8.86 (d, J 1.4 Hz, 2H), 8.55 (d, J 7.4 Hz, 1H), 7.52 (d, J 11.3 Hz, 1H), 7.42-7.09 (m, 4H), 7.02 (dd, J 7.6, 1.3 Hz, 1H), 4.34 (s, 2H), 3.08-2.96 (m, 1H), 2.27 (s, 3H), 2.16-2.02 (m, 4H), 1.55-1.49 (m, 2H), 1.26-1.20 (m, 1H). Method D HPLC-MS: MH+ m/z 509, RT 1.97 minutes.

Example 152

(1R,4R)-4-[5-(3-{[2-(Difluoromethoxy)phenyl]methyl}-7-fluoro-2-methylimidazo[1,2-a]pyridin-6-yl)pyrimidin-2-yl]-1-methylcyclohexane-1-carboxylic acid Intermediate 192 (100 mg, 0.19 mmol) was suspended in ethanol (2 mL) and water (0.6 mL). Aqueous sodium hydroxide solution (0.5M, 385 µL) was added, followed by palladium on carbon (10%, 10 mg, 0.01 mmol). The flask was cycled thrice between vacuum and nitrogen, then filled with hydrogen and stirred for 3 h under a hydrogen atmosphere. The reaction mixture was filtered through celite. The solid was washed with methanol/water (1:1, ~25 mL) and the filtrate was concentrated to dryness. The residue was purified by preparative HPLC to afford the title compound (8 mg, 9%) of as a white solid. $\delta_H$ (500 MHz, DMSO-$d_6$) 9.04 (s, 2H), 8.62 (s, 1H), 7.66-7.54 (m, 2H), 7.48-7.08 (m, 4H), 7.04 (d, J 6.9 Hz, 1H), 4.39 (s, 2H), 2.92-2.80 (m, 1H), 2.31 (s, 3H), 1.96-1.71 (m, 6H), 1.64 (d, J 13.0 Hz, 2H), 1.17 (s, 3H). Method D HPLC-MS: MH+ m/z 507, RT 2.09 minutes.

Alternative Preparation

A solution of Example 262 (20 mg, 0.046 mmol) in THF (2 mL) and water (2 mL) was treated with conc. HCl (1.5 mL) and heated at 70° C. for 7 h. The reaction mixture was cooled to r.t. and applied to a SCX-2 cartridge, eluting with methanol followed by ammonia (3M in MeOH). The fractions obtained were concentrated in vacuo to give the title compound (11 mg, 45%) as a white solid. LCMS (pH 10) m/z 525.8 [M+H]+, RT 1.62 minutes.

Example 153

Potassium 3-[5-(3-{[2-(Difluoromethoxy)phenyl]methyl}-7-fluoro-2-methylimidazo[1,2-a]pyridin-6-yl)pyrimidin-2-yl]bicyclo[4.1.0]heptane-7-carboxylate Intermediate 201 (12.4 mg, 23 µmol) was dissolved in 1,4-dioxane (0.5 mL) and water (0.5 mL), then 2M aqueous potassium hydroxide solution (11 µL) was added and the reaction mixture was heated at 85° C. in a sealed tube for 20 h. Additional 2M aqueous potassium hydroxide solution (11 µL) was added and the reaction mixture was heated at 85° C. in a sealed tube for 6 h. The reaction mixture was concentrated to dryness in a genevac to afford the title compound (13 mg, 96%) (mixture of isomers containing one equivalent of potassium hydroxide) as a yellow solid. $\delta_H$ (500 MHz, DMSO-$d_6$) 8.92-8.84 (m, 2H), 8.57 (d, J 7.3 Hz, 1H), 7.53 (d, J 11.3 Hz, 1H), 7.45-7.09 (m, 4H), 7.01 (d, J 7.5 Hz, 1H), 4.35 (s, 2H), 2.66 (dd, J 14.9, 2.6 Hz, 1H), 2.27 (s, 4H), 2.19-1.40 (m, 5H), 1.37-1.09 (m, 3H), 1.04-0.92 (m, 1H). Method D HPLC-MS: MH+ m/z 523, RT 2.08 minutes.

Examples 154 & 155

4-[5-(3-{[2-(Difluoromethoxy)phenyl]methyl}-7-fluoro-2-methylimidazo[1,2-a]pyridin-6-yl)pyrimidin-2-yl]-2-methylcyclohexane-1-carboxylic acid (Isomers A & B)

Example 142 (300 mg) was subjected to chiral SFC (carbon dioxide/ethanol+0.1% triethylamine) to afford purified material (84.7 mg, one isomer, unknown stereochemistry). This material (78 mg, 0.14 mmol) was dissolved in 1,4-dioxane (1 mL) and 1M aqueous potassium hydroxide solution (0.71 mL) was added. The reaction mixture was heated at 80° C. in a sealed tube for 3 h, then at 90° C. overnight. The cooled reaction mixture was acidified with 2M hydrochloric acid to pH 2, then partitioned between a 10% solution of isopropanol in chloroform (5 mL) and water (3 mL). The aqueous layer was separated and further extracted into a 10% solution of isopropanol in chloroform (2×5 mL). The combined organic extracts were washed with brine (5 mL), dried over sodium sulfate and evaporated. The resulting yellow solid (80 mg) was purified by preparative HPLC (low pH method).

Example 154 (Isomer A) (3.6 mg, 4%) was obtained as an off-white solid. $\delta_H$ (500 MHz, DMSO-$d_6$) 8.89 (d, J 1.3 Hz, 2H), 8.56 (d, J 7.4 Hz, 1H), 7.53 (d, J 11.3 Hz, 1H), 7.45-7.10 (m, 4H), 7.02 (d, J 7.6 Hz, 1H), 4.35 (s, 2H), 3.06 (dd, J 11.2, 4.5 Hz, 1H), 2.49-2.43 (m, 2H), 2.28 (s, 3H), 2.00 (dd, J 12.6, 3.0 Hz, 1H), 1.88 (dd, J 9.6, 3.7 Hz, 2H), 1.79-1.51 (m, 3H), 0.98 (d, J 7.1 Hz, 3H). Method D HPLC-MS: MH+ m/z 525, RT 2.10 minutes.

Example 155 (Isomer B) (13.5 mg, 18%) was obtained as an off-white solid. $\delta_H$ (500 MHz, DMSO-$d_6$) 8.89 (d, J 1.3 Hz, 2H), 8.56 (d, J 7.4 Hz, 1H), 7.53 (d, J 11.3 Hz, 1H), 7.43-7.09 (m, 4H), 7.02 (d, J 6.4 Hz, 1H), 4.35 (s, 2H), 2.93 (ddd, J 12.0, 8.3, 3.7 Hz, 1H), 2.55 (d, J 13.5 Hz, 1H), 2.27 (s, 3H), 2.11-1.97 (m, 2H), 1.95-1.87 (m, 1H), 1.86-1.77 (m, 2H), 1.71 (dt, J 13.4, 6.8 Hz, 2H), 1.02 (d, J 6.9 Hz, 3H). Method D HPLC-MS: MH+ m/z 525, RT 2.27 minutes.

Examples 156 & 157

4-[5-(3-{[2-(Difluoromethoxy)phenyl]methyl}-7-fluoro-2-methylimidazo[1,2-a]pyridin-6-yl)pyrimidin-2-yl]-2-methylcyclohexane-1-carboxylic acid (Isomers C & D)

Example 142 (300 mg) was subjected to chiral SFC (carbon dioxide/ethanol+0.1% triethylamine) to afford purified material (78.9 mg, one isomer, unknown stereochemistry). This material (72 mg, 0.13 mmol) was dissolved in 1,4-dioxane (1 mL) and 1M aqueous potassium hydroxide solution (0.65 mL) was added. The reaction mixture was heated at 80° C. in a sealed tube for 3 h, then at 90° C. overnight. The cooled reaction mixture was acidified with 2M hydrochloric acid to pH 2, then partitioned between a 10% solution of isopropanol in chloroform (5 mL) and water (3 mL). The aqueous layer was separated and further extracted into a 10% solution of isopropanol in chloroform (2×5 mL). The combined organic extracts were washed with brine (5 mL), dried over sodium sulfate and evaporated. The resulting yellow solid was purified by preparative HPLC (low pH method).

Example 156 (Isomer C) (7.0 mg, 10%) was obtained as an off-white solid. $\delta_H$ (500 MHz, DMSO-$d_6$) 8.89 (d, J 1.4 Hz, 2H), 8.55 (d, J 7.4 Hz, 1H), 7.53 (d, J 11.3 Hz, 1H), 7.44-7.09 (m, 4H), 7.01 (d, J 7.6 Hz, 1H), 4.35 (s, 2H), 3.11-3.02 (m, 1H), 2.48-2.39 (m, 2H), 2.27 (s, 3H), 1.99 (dd, J 12.7, 3.2 Hz, 1H), 1.87 (dd, J 9.7, 3.8 Hz, 2H), 1.71 (tt, J 15.2, 8.2 Hz, 2H), 1.67-1.52 (m, 1H), 0.97 (d, J 7.1 Hz, 3H). Method D HPLC-MS: MH+ m/z 525, RT 2.10 minutes.

Example 157 (Isomer D) (10.3 mg, 15%) was obtained as an off-white solid. $\delta_H$ (500 MHz, DMSO-$d_6$) 8.88 (d, J 1.3 Hz, 2H), 8.55 (d, J 7.4 Hz, 1H), 7.52 (d, J 11.3 Hz, 1H), 7.43-7.09 (m, 4H), 7.01 (d, J 6.5 Hz, 1H), 4.34 (s, 2H), 2.92 (ddd, J 12.0, 8.4, 3.6 Hz, 1H), 2.56 (m, 1H), 2.27 (s, 3H), 2.10-1.86 (m, 3H), 1.85-1.76 (m, 2H), 1.70 (dt, J 13.4, 6.8 Hz, 2H), 1.01 (d, J 6.9 Hz, 3H). Method D HPLC-MS: MH+ m/z 525, RT 2.27 minutes (98%).

Example 158

Potassium (1R,5S,6S)-3-[5-(3-{[2-(difluoromethoxy)phenyl]methyl}-7-fluoro-2-methyl-imidazo[1,2-a]pyridin-6-yl)pyridin-2-yl]bicyclo[3.1.0]hexane-6-carboxylate Intermediate 204 (75.3 mg, 0.14 mmol) was dissolved in 1,4-dioxane (3 mL) and water (0.5 mL), then 2M aqueous potassium hydroxide solution (85 µL) was added and the reaction mixture was heated at 70° C. overnight. Additional 2M aqueous potassium hydroxide solution (0.35 mL) was added and the reaction mixture was stirred at 70° C. for 3.5 h. The reaction mixture was cooled to room temperature and a 3:1 mixture of ethyl acetate:water (10 mL) was added. The organic phase was separated, concentrated and diluted in a 1:1 isopropanol:chloroform mixture (10 mL). The aqueous phase was adjusted to pH 2/3 using 1M hydrogen chloride solution and a saturated aqueous solution of sodium carbonate, then extracted with a 1:1 isopropanol:chloroform mixture (20 mL). The aqueous phase was further adjusted to pH 3 using a saturated aqueous solution of sodium carbonate, then re-extracted with 1:1 isopropanol:chloroform mixture (10 mL). The organic phases were combined, dried over sodium sulphate, and concentrated under vacuum. The resulting gum was dissolved in 1,4-dioxane (1 mL), then water (0.1 mL) and 2M aqueous potassium hydroxide solution (70 µL) were added. The reaction mixture was stirred at room temperature for 1.5 h, then concentrated under vacuum. The residue was triturated in diethyl ether to afford the title compound (46 mg, 56%) as a yellow solid. $\delta_H$ (500 MHz, DMSO-d$_6$) 11.89 (s, 1H), 8.81 (d, J 6.6 Hz, 1H), 8.66 (d, J 15.8 Hz, 1H), 7.90 (t, J 9.4 Hz, 2H), 7.48-7.05 (m, 6H), 4.45 (s, 2H), 3.77-3.65 (m, 1H), 2.43 (t, J 10.1 Hz, 2H), 2.34 (s, 3H), 2.25 (dd, J 13.7, 3.7 Hz, 2H), 1.83 (s, 2H), 1.52 (t, J 2.8 Hz, 1H). Method D HPLC-MS: MH+ m/z 507, RT 2.02, 2.11 minutes.

Example 159

(4s)-1-[5-(3-{[2-(Difluoromethoxy)phenyl]methyl}-7-fluoro-2-methylimidazo[1,2-a]pyridin-6-yl)pyrimidin-2-yl]-6-hydroxy-4-methyl-2-oxabicyclo[2.2.2]octan-3-one Intermediate 192 (50 mg, 0.03 mmol) was dissolved in ethanol (1 mL). Iodine (53.4 mg, 0.21 mmol) was added, followed by potassium iodide (104.8 mg, 0.63 mmol). The reaction mixture was stirred at 80° C. for 3.5 h, at room temperature for 2 days, then at 80° C. for 1.5 h. The reaction mixture was cooled to room temperature, diluted with ethyl acetate (10 mL) and washed with brine (10 mL), then dried over sodium sulfate and concentrated under vacuum to dryness. The resulting gum was purified by preparative HPLC (Method C) to afford the title compound (6.8 mg, 13%) as a yellow solid/gum. $\delta_H$ (500 MHz, DMSO-d$_6$) 9.21-9.03 (m, 2H), 8.99 (d, J 6.7 Hz, 1H), 7.99 (d, J 10.0 Hz, 1H), 7.45-7.02 (m, 5H), 5.27-4.99 (m, 1H), 4.45 (s, 2H), 2.99-2.86 (m, 1H), 2.35 (d, J 3.6 Hz, 3H), 2.16 (dd, J 12.2, 6.6 Hz, 1H), 1.71 (dt, J 13.5, 10.2 Hz, 1H), 1.63-1.54 (m, 2H), 1.38 (d, J 12.2 Hz, 1H), 1.19 (d, J 43.3 Hz, 1H), 1.05 (s, 3H). Method A HPLC-MS: MH+ m/z 539, RT 3.10 minutes.

Example 160

Potassium 7-[5-(3-{[2-(difluoromethoxy)phenyl]methyl}-7-fluoro-2-methylimidazo[1,2-a]pyridin-6-yl)pyrimidin-2-yl]-3-oxa-7-azabicyclo[3.3.1]nonane-9-carboxylate Intermediate 209 (85 mg, 0.15 mmol) was suspended in ethanol (3 mL), then 1M aqueous potassium hydroxide solution (0.15 mL) was added and the reaction mixture was allowed to stir at 70° C. for 18 h. The mixture was concentrated under reduced pressure to afford the title compound (60 mg, 68%) as a light orange solid. $\delta_H$ (250 MHz, CD$_3$OD) 8.35 (dd, J 13.7, 1.2 Hz, 2H), 8.07 (d, J 7.1 Hz, 1H), 7.32-7.24 (m, 2H), 7.19 (d, J 8.2 Hz, 1H), 7.14 (t, J 7.5 Hz, 1H), 7.08-6.74 (m, 2H), 4.99 (d, J 12.8 Hz, 1H), 4.69 (d, J 13.4 Hz, 1H), 4.37 (s, 2H), 4.03 (d, J 11.0 Hz, 1H), 3.98 (d, J 11.4 Hz, 1H), 3.79-3.71 (m, 2H), 3.53 (d, J 13.4 Hz, 1H), 3.28 (s, 1H), 2.57 (s, 1H), 2.40 (s, 3H), 2.27 (s, 2H). Method D HPLC-MS: MH+ m/z 554, RT 1.97 minutes.

Example 161

Potassium 5-[5-(3-{[2-(difluoromethoxy)phenyl]methyl}-7-fluoro-2-methylimidazo[1,2-a]pyridin-6-yl)pyrimidin-2-yl]piperidine-2-carboxylate Intermediate 215 (40 mg, 0.08 mmol) was dissolved in 1,4-dioxane (1 mL), then water (0.2 mL) and 1M aqueous potassium hydroxide solution (76 µL) was added. The reaction mixture was heated at 80° C. overnight in a sealed tube. The reaction mixture was evaporated to dryness in a genevac. The resulting yellow solid was re-dissolved in 1,4-dioxane (1 mL) and water (0.2 mL), then 1M aqueous potassium hydroxide solution (15 µL) was added. The reaction mixture was heated at 80° C. overnight in a sealed tube. The reaction mixture was evaporated to dryness in a genevac to afford the title compound (42 mg, 100%) (mixture of isomers) as a pale yellow solid. $\delta_H$ (500 MHz, CD$_3$OD) 8.95-8.73 (m, 2H), 8.39-8.24 (m, 1H), 7.40-7.35 (m, 1H), 7.34-7.28 (m, 1H), 7.22-7.08 (m, 3H), 6.92 (t, J 74.0 Hz, 1H), 4.41 (s, 2H), 3.68 (s, 2H), 3.53-3.37 (m, 1H), 3.30-3.01 (m, 2H), 2.42 (s, 3H), 2.37-2.06 (m, 2H), 2.00-1.83 (m, 1H), 1.82-1.57 (m, 1H). Method D HPLC-MS: MH+ m/z 512, RT 1.33 minutes.

Example 162

8-[5-(3-{[2-(Difluoromethoxy)phenyl]methyl}-7-fluoro-2-methylimidazo[1,2-a]pyridin-6-yl)pyrimidin-2-yl]-2-methyl-2,4,8-triazaspiro[4.5]decane-1,3-dione Prepared from Intermediate 152 (100 mg, 0.24 mmol) and 2-methyl-2,4,8-triazaspiro[4.5]decane-1,3-dione (50 mg, 0.27 mmol) according to General Method B. The crude residue was purified by preparative HPLC to give the title compound (90 mg, 67%) as a white solid. $\delta_H$ (300 MHz, DMSO-d$_6$) 8.90 (s, 1H), 8.53 (d, J 1.6 Hz, 2H), 8.38 (d, J 7.5 Hz, 1H), 7.47 (d, J 11.3 Hz, 1H), 7.30 (m, 1H), 7.26 (t, J 74.1 Hz, 1H), 7.19 (m, 1H), 7.13 (td, J 7.5, 1.2 Hz, 1H), 7.02 (dd, J 7.6, 1.6 Hz, 1H), 4.49 (dt, J 13.8, 3.9 Hz, 2H), 4.34 (s, 2H), 3.49 (m, 2H), 2.85 (s, 3H), 2.27 (s, 3H), 1.81 (m, 2H), 1.63 (m, 2H). LC-MS (pH 3): MH+ m/z 566.8, RT 1.69 minutes. LC-MS (pH 10): MH+ m/z 566.8, RT 2.23 minutes.

Example 163

Ethyl 4-[5-(3-{[2-(difluoromethoxy)phenyl]methyl}-7-fluoro-2-methylimidazo[1,2-a]-pyridin-6-yl)pyrimidin-2-yl]cyclohex-3-ene-1-carboxylate Prepared from Intermediate 68 (1.00 g, 2.60 mmol) and Intermediate 220 (1.12 g, 3.13 mmol) according to General Method A. The crude material was purified by flash column chromatography (Biotage SNAP 50 g, Isolera), eluting with 0-6% EtOH/DCM. The orange solid thus obtained was triturated with ether to give the title compound (750 mg, 54%) as an off-white powder. $\delta_H$ (300 MHz, DMSO-$d_6$) 8.93 (d, J 1.6 Hz, 2H), 8.55 (d, J 7.4 Hz, 1H), 7.53 (d, J 11.5 Hz, 1H), 7.29 (m, 2H), 7.26 (1H, t, J 74.1 Hz, 1H), 7.18 (m, 1H), 7.13 (td, J 7.5, 1.1 Hz, 1H), 7.04 (dd, J 7.6, 1.5 Hz, 1H), 4.36 (s, 2H), 4.11 (qd, J 7.2, 1.3 Hz, 2H), 2.68 (m, 3H), 2.50 (m, 2H), 2.28 (s, 3H), 2.11 (m, 1H), 1.74 (m, 1H), 1.21 (t, J 7.1 Hz, 3H). LC-MS (pH 3): MH+ m/z 537.8, RT 2.63 minutes. LC-MS (pH 10): MH+ m/z 537.8, RT 2.93 minutes.

Example 164

Ethyl 4-[5-(3-{[2-(difluoromethoxy)phenyl]methyl}-7-fluoro-2-methylimidazo[1,2-a]-pyridin-6-yl)pyrimidin-2-yl]cyclohexanecarboxylate A solution of Example 163 (~0.05M, 545 mg, 1.01 mmol) in ethanol was hydrogenated using an H-Cube® (ThalesNano) at a flow rate of 0.5 mL/minute, in full $H_2$ mode (1 bar) at 50° C. Removal of the ethanol under vacuum gave the title compound (545 mg, 89%) as a pale brown foam consisting of a pair diastereoisomers in a 3:1 ratio. $\delta_H$ (300 MHz, $CD_3OD$) 8.76 (s, 2H), 8.24 (d, J 7.4 Hz, 1H), 7.25 (m, 2H), 7.07 (m, 3H), 6.81 (t, J 74.1 Hz, 1H), 4.32 (s, 2H), 4.09 (2H, qd, J 7.3, 1.2 Hz), 2.97 (m, 1H), 2.64 (m, 1H), 2.33 (m, 1H), 1.83 (m, 8H), 1.21 (t, J 7.1 Hz, 3H). LC-MS (pH 3): MH+ m/z 539.8, RT 2.46 minutes; 539.8, RT 2.51 minutes. LC-MS (pH 10): MH+ m/z 539.8, RT 2.47 minutes; 539.8, RT 2.51 minutes.

Examples 165 & 166

4-[5-(3-{[2-(Difluoromethoxy)phenyl]methyl}-7-fluoro-2-methylimidazo[1,2-a]pyridin -6-yl)pyrimidin-2-yl]cyclohexanecarboxylic acid (cis & trans isomers)

Example 164 (500 mg, 0.81 mmol) was dissolved in THF (6 mL) and water (6 mL). Lithium hydroxide monohydrate (170 mg, 4.04 mmol) was added and the reaction mixture was stirred at room temperature for 12 h. The solution was adjusted to pH 3 with aqueous 1M HCl solution, then extracted with ethyl acetate. The combined organic phase was dried, filtered and concentrated under vacuum. Trituration of the resulting orange foam with acetonitrile yielded the title compound (250 mg, 60%) as a pale yellow solid, consisting of a pair of diastereoisomers in a 3:1 ratio. The constituent diastereoisomers were then separated by preparative HPLC.

Example 165 (trans isomer) (41 mg, 10%): $\delta_H$ (300 MHz, DMSO-$d_6$) 9.02 (d, J 6.6 Hz, 1H), 8.96 (d, J 1.4 Hz, 2H), 8.06 (d, J 9.8 Hz, 1H), 7.35 (m, 1H), 7.25 (t, J 74.1 Hz, 1H), 7.20 (m, 3H), 4.46 (s, 2H), 2.89 (m, 1H), 2.36 (s, 3H), 2.26 (m, 1H), 2.04 (m, 4H), 1.57 (m, 4H). LC-MS (pH 3): MH+ m/z 511.8, RT 1.69 minutes. LC-MS (pH 10): MH+ m/z 511.8, RT 1.50 minutes.

Example 166 (cis isomer) (96 mg, 23%): $\delta_H$ (300 MHz, DMSO-$d_6$) 9.07 (d, J 6.5 Hz, 1H), 8.96 (d, J 1.4 Hz, 2H), 8.11 (d, J 9.7 Hz, 1H), 7.35 (m, 1H), 7.24 (t, J 73.9 Hz, 1H), 7.20 (m, 3H), 4.47 (s, 2H), 3.02 (m, 1H), 2.59 (m, 1H), 2.36 (s, 3H), 1.96 (m, 4H), 1.80 (m, 2H), 1.65 (m, 2H). LC-MS (pH 3): MH+ m/z 511.8, RT 1.82 minutes. LC-MS (pH 10): MH+ m/z 511.8, RT 1.94 minutes.

Example 167

1-[5-(3-{[2-(Difluoromethoxy)phenyl]methyl}-2-methylimidazo[1,2-a]pyridin-6-yl)-4-(trifluoromethyl)pyrimidin-2-yl]-1,4-diazepan-5-one Prepared from Intermediate 222 (70 mg, 0.21 mmol) and Intermediate 31 (80 mg, 0.24 mmol) in accordance with General Method A. The crude material was purified by preparative HPLC, yielding the title compound (17 mg) as a white solid. $\delta_H$ (300 MHz, DMSO-$d_6$) 8.56 (s, 1H), 8.14 (s, 1H), 7.71 (t, J 5.3 Hz, 1H), 7.54 (d, J 9.2 Hz, 1H), 7.30 (t, J 7.9 Hz, 1H), 7.25 (t, J 74.2 Hz, 1H), 7.18 (d, J 8.1 Hz, 1H), 7.12 (m, 2H), 6.95 (dd, J 7.4, 0.8 Hz, 1H), 4.29 (s, 2H), 3.98 (m, 4H), 3.26 (m, 2H), 2.56 (m, 2H), 2.34 (s, 3H). LC-MS (pH 3): MH+ m/z 547.7, RT 1.99 minutes. LC-MS (pH 10): MH+ m/z 547.7, RT 2.05 minutes.

Example 168

(3S)-{4-[5-(3-{[2-(Difluoromethoxy)phenyl]methyl}-7-fluoro-2-methylimidazo[1,2-a]-pyridin-6-yl)pyrimidin-2-yl]morpholin-3-yl}methanol Prepared from Intermediate 152 (235 mg, 0.56 mmol) and [(3S)-morpholin-3-yl]methanol (68 mg, 0.58 mmol) according to General Method B. Purification of the crude material by preparative HPLC gave the title compound (93 mg, 33%) as a white solid. $\delta_H$ (400 MHz, DMSO-$d_6$) 8.52 (s, 2H), 8.35 (d, J 7.4 Hz, 1H), 7.47 (d, J 11.3 Hz, 1H), 7.30 (t, J 7.4 Hz, 1H), 7.27 (t, J 74.1 Hz, 1H), 7.19 (d, J 8.1 Hz, 1H), 7.14 (t, J 7.4 Hz, 1H), 7.02 (d, J 7.1 Hz, 1H), 4.89 (t, J 5.5 Hz, 1H), 4.50 (m, 1H), 4.35 (m, 3H), 4.08 (d, J 11.5 Hz, 1H), 3.91 (dd, J 11.3, 3.1 Hz, 1H), 3.76 (m, 1H), 3.44 (m, 3H), 3.14 (td, J 13.0, 3.8 Hz, 1H), 2.29 (s, 3H). LC-MS (pH 3): MH+ m/z 500.8, RT 1.55 minutes. LC-MS (pH 10): MH+ m/z 500.8, RT 1.95 minutes.

Example 169

(3R)-{4-[5-[3-[[2-(Difluoromethoxy)phenyl]methyl]-7-fluoro-2-methylimidazo[1,2-a]pyridin-6-yl] pyrimidin-2-yl]morpholin-3-yl}methanol Prepared from Intermediate 152 (230 mg, 0.55 mmol) and [(3R)-morpholin-3-yl]methanol (65 mg, 0.55 mmol) according to General Method B. Purification of the crude material by preparative HPLC gave the title compound (86 mg, 31%) as a white solid. $\delta_H$ (400 MHz, DMSO-$d_6$) 8.52 (s, 2H), 8.35 (d, J 7.4 Hz, 1H), 7.47 (d, J 11.3 Hz, 1H), 7.30 (t, J 7.4 Hz, 1H), 7.27 (t, J 74.1 Hz, 1H), 7.19 (d, J 8.1 Hz, 1H), 7.14 (t, J 7.4 Hz, 1H), 7.02 (d, J 7.1 Hz, 1H), 4.89 (t, J 5.5 Hz, 1H), 4.50 (m, 1H), 4.35 (m, 3H), 4.08 (d, J 11.5 Hz, 1H), 3.91 (dd, J 11.3, 3.1 Hz, 1H), 3.76 (m, 1H), 3.44 (m, 3H), 3.14 (td, J 13.0, 3.8 Hz, 1H), 2.29 (s, 3H). LC-MS (pH 3): MH+ m/z 500.8, RT 1.73 minutes. LC-MS (pH 10): MH+ m/z 500.8, RT 1.93 minutes.

Example 170

(3R)-4-[5-(3-{[2-(Difluoromethoxy)phenyl]methyl}-7-fluoro-2-methylimidazo[1,2-a]-pyridin-6-yl)pyrimidin-2-yl]morpholine-3-carboxylic acid Example 168 (150 mg, 0.30 mmol) and 4-methylmorpholine N-oxide (355 mg, 3.03 mmol) were dissolved in MeCN (1 mL). Tetrapropylammonium perruthenate (12 mg, 0.034 mmol) was added and the reaction mixture was stirred at room temperature for 12 h. The reaction was quenched with an excess of isopropanol and the solvent removed under vacuum. The residue was re-dissolved in water and extracted with ethyl acetate. The combined organic phase was then extracted with 10% NaOH and the organic layer was discarded. The combined aqueous phase was adjusted to pH 4 with acetic acid and extracted with ethyl acetate. The combined organic phase was dried, filtered and concentrated under vacuum. The resulting pale yellow oil was purified by preparative HPLC to give the title compound (45 mg, 33%) as a white solid. $\delta_H$ (400 MHz, DMSO-$d_6$) 8.55 (s, 2H), 8.40 (d, J 7.4 Hz, 1H), 7.47 (d, J 11.3 Hz, 1H), 7.30 (m, 1H), 7.26 (t, J 74.3 Hz, 1H), 7.19 (d, J 8.1 Hz, 1H), 7.14 (t, J 7.5 Hz, 1H), 7.03 (d, J 7.3 Hz, 1H), 4.99 (s, 1H); 4.34 (m, 3H), 4.28 (d, J 12.8 Hz, 1H), 3.95 (dd, J 11.4, 3.4 Hz, 1H), 3.69 (dd, J 11.7, 4.0 Hz, 1H), 3.50 (m, 1H), 2.50 (m, 1H), 3.30 (m, 1H), 2.28 (s, 3H). LC-MS (pH 3): MH+ m/z 514.8, RT 1.77 minutes. LC-MS (pH 10): MH+ m/z 514.7, RT 1.42 minutes.

Example 171

(3S)-4-[5-(3-{[2-(Difluoromethoxy)phenyl]methyl}-7-fluoro-2-methylimidazo[1,2-a]-pyridin-6-yl)pyrimidin-2-yl]morpholine-3-carboxylic acid Prepared from Example 169 (120 mg, 0.240 mmol) by the method of Example 170. The crude material was purified by preparative HPLC to give the title compound (16 mg, 12%) as a white solid. $\delta_H$ (400 MHz, DMSO-$d_6$) 8.55 (s, 2H), 8.40 (d, J 7.4 Hz, 1H), 7.47 (d, J 11.3 Hz, 1H), 7.30 (m, 1H), 7.26 (t, J 74.3 Hz, 1H), 7.19 (d, J 8.1 Hz, 1H), 7.14 (t, J 7.5 Hz, 1H), 7.03 (d, J 7.3 Hz, 1H), 4.99 (s, 1H), 4.34 (m, 3H), 4.28 (d, J 12.8 Hz, 1H), 3.95 (dd, J 11.4, 3.4 Hz, 1H), 3.69 (dd, J 11.7, 4.0 Hz, 1H), 3.50 (m, 1H), 2.50 (m, 1H), 3.30 (m, 1H), 2.28 (s, 3H). LC-MS (pH 3): MH+ m/z 514.6, RT 1.74 minutes. LC-MS (pH 10): MH+ m/z 514.6, RT 1.42 minutes.

Example 172

4-(3-{[2-(Difluoromethoxy)phenyl]methyl}-7-fluoro-2-methylimidazo[1,2-a]pyridin-6-yl)-3,5-dimethylisoxazole Prepared from 3,5-dimethylisoxazole-4-boronic acid (109 mg, 0.77 mmol) and Intermediate 68 (258 mg, 0.67 mmol) in accordance with General Method A. The material was purified by preparative HPLC to yield the title compound (128 mg, 48%) as a pale pink solid. $\delta_H$ (400 MHz, DMSO-$d_6$) 8.21 (d, J 7.2 Hz, 1H), 7.48 (d, J 11.0 Hz, 1H), 7.30 (t, J 7.8 Hz, 1H), 7.24 (t, J 74.1 Hz, 1H), 7.18 (m, 1H), 7.14 (m, 1H), 7.08 (m, 1H), 4.31 (s, 2H), 2.32 (s, 3H), 2.25 (s, 3H), 2.07 (s, 3H). LC-MS (pH 3): MH+ m/z 402.6, RT 1.62 minutes. LC-MS (pH 10): MH+ m/z 402.6, RT 1.78 minutes.

Example 173

2-[5-(3-{[2-(Difluoromethoxy)phenyl]methyl}-7-fluoro-2-methylimidazo[1,2-a]pyridin-6-yl)pyrimidin-2-yl]propan-2-ol A mixture of Intermediate 68 (0.5 g, 1.543 mmol), 2-[5-(4,4,5,5-tetramethyl-1,3,2-dioxaborolan-2-yl)pyrimidin-2-yl]propan-2-ol (0.5 g, 1.89 mmol), Pd(dppf)Cl$_2$ (32 mg, 0.039 mmol) and 2M aqueous sodium carbonate solution (3 mL) in 1,4-dioxane (12 mL) was degassed and stirred at 110° C. for 2 h. The mixture was partitioned between EtOAc and brine, then the organic layer was dried (MgSO$_4$) and concentrated. The crude residue was purified by column chromatography using EtOAc-hexane (2:1, then 3:2). The resulting material was crystallised from diethyl ether/hexane, then filtered. The residue was washed with diethyl ether and hexane, then dried, to give the title compound (0.5 g, 90%) as an off-white solid. $\delta_H$ (400 MHz, DMSO-$d_6$) 8.97 (d, J 1.4 Hz, 2H), 8.60 (d, J 7.4 Hz, 1H), 7.55 (d, J 11.4 Hz, 1H), 7.30 (m, 1H), 7.26 (t, J 74 Hz, 1H), 7.19 (d, J 7.9 Hz, 1H), 7.14 (m, 1H), 7.03 (dd, J 7.6, 1.2 Hz, 1H), 5.14 (s, 1H), 4.37 (s, 2H), 2.29 (s, 3H), 1.54 (s, 6H). LCMS (pH 10): MH+ 443, RT 1.89 minutes.

Example 174

Ethyl 1-[5-(3-{[2-(difluoromethoxy)phenyl]methyl}-7-fluoro-2-methylimidazo[1,2-a]-pyridin-6-yl)pyrimidin-2-yl]-4-(hydroxymethyl)piperidine-4-carboxylate A mixture of Intermediate 68 (120 mg, 0.31 mmol), Intermediate 223 (135 mg, 0.437 mmol), Pd(dppf)Cl$_2$ (6.5 mg, 0.008 mmol) and 2M aqueous sodium carbonate solution (2 mL) in 1,4-dioxane (5 mL) was degassed and stirred at 110° C. for 5 h. Additional boronic acid and catalyst were added, then the mixture was degassed and stirred at 110° C. for a further 2 h. The reaction mixture was diluted with EtOAc and washed with brine. The organic extract was dried (MgSO$_4$) and the solvent was removed by rotary evaporation. The crude residue was purified by column chromatography, using 4:1 EtOAc-hexane, then EtOAc, to give the title compound (100 mg, 60%) as a colourless gum. LCMS (pH 10): MH+ 570, RT 1.50 minutes.

Example 175

Sodium 1-[5-[3-[[2-(difluoromethoxy)phenyl]methyl]-7-fluoro-2-methylimidazo[1,2-a]-pyridin-6-yl]pyrimidin-2-yl]-4-(hydroxymethyl)piperidine-4-carboxylate Sodium hydroxide (7 mg, 0.175 mmol) was added to a solution of Example 174 (0.1 g, 0.176 mmol) in THF-MeOH-water, 1:1:1 (4 mL). The mixture was stirred at 70° C. for 2 h. The mixture was concentrated and diluted with water, then washed with EtOAc. The aqueous layer was freeze-dried. The resulting material (95 mg) was purified by HPLC to give the title compound (30 mg, 30%) as a white lyophilised solid. $\delta_H$ (400 MHz, DMSO-$d_6$) 8.48 (m, 2H), 8.34 (d, J 7.5 Hz, 1H), 7.46 (m, 1H), 7.30 (m, 1H), 7.26 (t, J 72 Hz, 1H), 7.19 (m, 1H), 7.14 (td, J 7.5, 1.1 Hz, 1H), 7.02 (m, 1H), 4.39 (m, 2H), 4.34 (s, 2H), 3.43 (s, 2H), 3.23 (m, 2H), 2.28 (s, 3H), 1.98 (m, 2H), 1.40 (m, 2H). LCMS (pH 10): MH+ 542, RT 1.44 minutes.

Example 176

1-[5-(3-{[2-(Difluoromethoxy)phenyl]methyl}-7-fluoro-2-methylimidazo[1,2-a]pyridin-6-yl)pyrimidin-2-yl]-4-(methoxycarbonyl)piperidine-4-carboxylic acid A mixture Intermediate 68 (0.2 g, 0.52 mmol), dimethyl 1-[5-(4,4,5,5-tetramethyl-1,3,2-dioxaborolan-2-yl)pyrimidin-2-yl]piperidine-4,4-dicarboxylate (0.29 g, 0.73 mmol), Pd(dppf)Cl$_2$ (0.0108 g, 0.0130 mmol) and 2M aqueous sodium carbonate solution (2.5 mL) in 1,4-dioxane (6 mL)

was degassed and stirred at 110° C. for 5 h. The mixture was cooled to room temperature, then partitioned between EtOAc and water. The aqueous layer was neutralised using acetic acid, then extracted with EtOAc, dried (MgSO$_4$) and filtered. The solvent was removed by rotary evaporation. The crude residue was purified by HPLC to give the title compound (34 mg, 11%) as a white lyophilised solid. $\delta_H$ (400 MHz, DMSO-d$_6$) 8.50 (d, J 1.5 Hz, 2H), 8.36 (d, J 7.5 Hz, 1H), 7.46 (m, 1H), 7.30 (m, 1H), 7.26 (t, J 72 Hz, 1H), 7.20 (m, 1H), 7.14 (m, 1H), 7.02 (m, 1H), 4.34 (s, 2H), 3.97 (m, 2H), 3.67 (s, 3H), 3.65 (m, 1H), 2.50 (m, 1H), 2.28 (s, 3H), 1.98 (m, 4H). LCMS (pH 10): MH+ 570, RT 1.61 minutes.

Example 177

Ethyl 3-[5-(3-{[2-(difluoromethoxy)phenyl]methyl}-7-fluoro-2-methylimidazo[1,2-a]-pyridin-6-yl)pyrimidin-2-yl]-3-azabicyclo[4.1.0]heptane-1-carboxylate A mixture of Intermediate 68 (0.16 g, 0.42 mmol), Intermediate 224 (0.181 g, 0.62 mmol), Pd(dppf)Cl$_2$ (0.00865 g, 0.0104 mmol) and 2M aqueous sodium carbonate solution (2 mL) in 1,4-dioxane (8 mL) was degassed and stirred at 110° C. for 4 h. The cooled reaction mixture was diluted with EtOAc and washed once with brine. The organic extract was dried (MgSO$_4$) and the solvent was removed under reduced pressure. The crude residue was purified by column chromatography using 2:1 EtOAc-hexane. The resulting material was crystallised from diethyl ether, then filtered. The residue was washed with diethyl ether and hexane, then dried, to give the title compound (0.104 g, 45%) as an off-white solid. $\delta_H$ (400 MHz, DMSO-d$_6$) 8.50 (d, J 1.5 Hz, 2H), 8.35 (d, J 7.5 Hz, 1H), 7.46 (m, 1H), 7.31 (m, 1H), 7.26 (t, J 72, 76 Hz, 1H), 7.19 (m, 1H), 7.14 (m, 1H), 7.01 (dd, J 7.6, 1.4 Hz, 1H), 4.40 (m, 1H), 4.34 (s, 2H), 4.23 (m, 1H), 4.08 (m, 2H), 3.69 (m, 1H), 3.41 (m, 1H), 2.29 (s, 3H), 2.12 (m, 1H), 1.76 (m, 2H), 1.29 (dd, J 9.2, 4.4 Hz, 1H), 1.18 (t, J 7.1 Hz, 3H), 0.84 (dd, J 6.4, 4.6 Hz, 1H). LCMS (pH 10): MH+ 552, RT 1.63 minutes.

Example 178

Sodium 3-[5-(3-{[2-(difluoromethoxy)phenyl]methyl}-7-fluoro-2-methylimidazo[1,2-a]-pyridin-6-yl)pyrimidin-2-yl]-3-azabicyclo[4.1.0]heptane-1-carboxylate Sodium hydroxide (7.5 mg, 0.188 mmol) was added to a solution of Example 177 (0.104 g, 0.188 mmol) in THF-MeOH-water, 1:1:1 (4 mL). The mixture was stirred at 70° C. for 3 h. The reaction mixture was concentrated, diluted with water and washed with diethyl ether, then the aqueous layer was freeze-dried, to give the title compound (100 mg, 100%) as a white lyophilised solid. $\delta_H$ (400 MHz, DMSO-d$_6$) 8.21 (d, J 1.3 Hz, 2H), 8.12 (d, J 7.5 Hz, 1H), 7.22 (m, 1H), 7.08 (m, 1H), 7.05 (t, J 72, 76 Hz, 1H), 6.97 (m, 1H), 6.92 (m, 1H), 6.81 (dd, J 7.5, 1.1 Hz, 1H), 4.12 (s, 2H), 4.04 (m, 1H), 3.96 (m, 1H), 3.43 (m, 1H), 3.07 (m, 1H), 2.07 (s, 3H), 1.76 (m, 1H), 1.50 (m, 1H), 1.15 (m, 1H), 0.72 (dd, J 8.7, 2.9 Hz, 1H), 0.00 (dd, J 5.4, 3.2 Hz, 1H). LCMS (pH 10): MH+ 524, RT 1.56 minutes.

Example 179

Ethyl 1-[5-(3-{[2-(difluoromethoxy)phenyl]methyl}-2-methylimidazo[1,2-a]pyridin-6-yl)pyrimidin-2-yl]-4-(hydroxymethyl)piperidine-4-carboxylate A mixture of Intermediate 7, Intermediate 223 (0.6 g, 1.94 mmol), Pd(dppf)Cl$_2$ dichloromethane complex (0.03 g, 0.04 mmol) and 2M aqueous sodium carbonate solution (3 mL) in 1,4-dioxane (8 mL) was degassed and stirred at 100° C. for 5 h. The reaction mixture was diluted with EtOAc and washed with brine. The organic extract was dried (MgSO$_4$) and concentrated. Column chromatography, using EtOAc, then 30:1 EtOAc-MeOH, gave the title compound (0.22 g, 30%) as a pale yellow gum. $\delta_H$ (400 MHz, DMSO-d$_6$) 8.65 (s, 2H), 8.38 (s, 1H), 7.53 (m, 2H), 7.30 (m, 2H), 7.21 (m, 1H), 7.13 (m, 1H), 7.04 (m, 1H), 4.92 (t, J 5.5 Hz, 1H, OH), 4.37 (m, 4H), 4.14 (m, 2H), 4.04 (m, 1H), 3.48 (d, J 5.5 Hz, 2H), 3.17 (m, 2H), 2.32 (s, 3H), 2.03 (m, 1H), 1.45 (m, 2H), 1.20 (m, 3H). LCMS (pH 10): MH+ 552, RT 1.55 minutes.

Example 180

Sodium 1-[5-(3-{[2-(difluoromethoxy)phenyl]methyl}-2-methylimidazo[1,2-a]pyridin-6-yl)pyrimidin-2-yl]-4-(hydroxymethyl)piperidine-4-carboxylate Example 179 (0.22 g, 0.4 mmol) was dissolved in THF-MeOH-water, 1:1:1 (4 mL). Sodium hydroxide (16 mg, 0.4 mmol) was added and the mixture was stirred at 70° C. for 6 h. The reaction mixture was concentrated, diluted with water (~5 mL) and washed with diethyl ether. The ether washing was discarded and the aqueous layer was filtered through a plug of celite to remove turbidity. The clear solution was freeze-dried to give the title compound (175 mg, 80%) as an off-white solid. $\delta_H$ (400 MHz, DMSO-d$_6$) 8.59 (s, 2H), 8.36 (s, 1H), 7.53 (m, 1H), 7.46 (m, 1H), 7.30 (m, 1H), 7.29 (t, J 72, 76 Hz, 1H), 7.21 (m, 1H), 7.14 (m, 1H), 7.05 (m, 1H), 6.15 (m, 1H, OH), 4.36 (s, 2H), 4.14 (m, 2H), 3.51 (m, 2H), 3.24 (s, 2H), 2.32 (s, 3H), 1.93 (m, 2H), 1.20 (m, 2H). LCMS (pH 10): MH+ 524, RT 1.60 minutes.

Example 181

Ethyl 1-[5-(3-{[2-(difluoromethoxy)phenyl]methyl}-2-methylimidazo[1,2-a]pyridin-6-yl)pyrimidin-2-yl]-4-(trifluoromethyl)piperidine-4-carboxylate A mixture of Intermediate 7 (0.34 g, 0.93 mmol), Intermediate 225 (0.45 g, 1.3 mmol), Pd(dppf)Cl$_2$ (0.019 g, 0.023 mmol) and 2M aqueous sodium carbonate solution (3.5 mL) in 1,4-dioxane (mL) was de-gassed and stirred at 110° C. under nitrogen for 5 h. The reaction mixture was partitioned between EtOAc and brine, then the organic layer was dried (MgSO$_4$), filtered and concentrated under vacuum. The crude residue was subjected to column chromatography with 4:1 EtOAc-hexane, to give the title compound (0.41 g, 75%). $\delta_H$ (400 MHz, DMSO-d$_6$) 8.69 (s, 2H), 8.41 (s, 1H), 7.55 (m, 1H), 7.48 (m, 1H), 7.30 (m, 1H), 7.29 (t, J 72, 76 Hz, 1H), 7.20 (m, 1H), 7.13 (m, 1H), 7.04 (m, 1H), 4.76 (d, J 13.9 Hz, 2H), 4.37 (s, 2H), 4.32 (m, 2H), 2.96 (t, J 12.4 Hz, 2H), 2.32 (m, 5H), 1.74 (td, J 13.1, 4.4 Hz, 2H), 1.27 (t, J 7.1 Hz, 3H). LCMS (pH 10): MH+ 590, RT 1.74 minutes.

Example 182

1-[5-(3-{[2-(Difluoromethoxy)phenyl]methyl}-2-methylimidazo[1,2-a]pyridin-6-yl)-pyrimidin-2-yl]-4-(trifluoromethyl)piperidine-4-carboxylic acid Example 181 (0.41 g, 0.70 mmol) was dissolved in THF: MeOH:water, 1:1:1 (6 mL), then lithium hydroxide hydrate (0.058 g, 1.4 mmol) was added and the mixture was stirred at 60° C. overnight. The reaction mixture was concentrated. The residue was diluted with water (3 mL) and washed twice with diethyl ether. The aqueous layer was neutralised using acetic acid. The resulting white solid was filtered, washed several times with cold water and dried by suction. The solid was dissolved in hot methanol, then filtered and dried under vacuum, to give the title compound (0.17 g, 43%) as a white solid. $\delta_H$ (400 MHz, DMSO-$d_6$) 8.69 (s, 2H), 8.42 (s, 1H), 7.56 (m, 1H), 7.49 (m, 1H), 7.30 (m, 1H), 7.29 (t, J 72, 76 Hz, 1H), 7.21 (m, 1H), 7.14 (m, 1H), 7.05 (m, 1H), 4.74 (m, 2H), 4.37 (m, 2H), 2.98 (m, 2H), 2.32 (s, 3H), 2.29 (m, 1H), 1.68 (m, 2H), 1.07 (m, 1H). LCMS (pH 10): MH+ 562, RT 1.93 minutes.

Example 183

Ethyl 1-[5-(3-{[2-(difluoromethoxy)phenyl]methyl}-7-fluoro-2-methylimidazo[1,2-a]-pyridin-6-yl)pyrimidin-2-yl]-4-fluoropiperidine-4-carboxylate A mixture of Intermediate 68, Intermediate 226 (0.35 g, 1.18 mmol), Pd(dppf)Cl$_2$ dichloromethane complex (20 mg, 0.025 mmol) and 2M aqueous sodium carbonate solution (2.5 mL) in 1,4-dioxane (8 mL) was degassed and stirred under nitrogen at 110° C. for 1 h. The reaction mixture was partitioned between EtOAc and brine, then the organic layer was dried (MgSO$_4$), filtered and concentrated under vacuum. The crude residue was purified by column chromatography (ethyl acetate in hexanes). The resulting material was crystallised from diethyl ether, then filtered. The residue was washed with diethyl ether and hexane, then dried, to give the title compound (0.21 g, 50%) as an off-white solid. $\delta_H$ (400 MHz, DMSO-$d_6$) 8.55 (s, 2H), 8.38 (d, J 7.5 Hz, 1H), 7.47 (m, 1H), 7.30 (m, 1H), 7.27 (t, J 72, 76 Hz, 1H), 7.20 (m, 1H), 7.14 (t, J 7.6 Hz, 1H), 7.02 (d, J 7.2 Hz, 1H), 4.59 (m, 2H), 4.35 (s, 2H), 4.20 (q, J 7.1 Hz, 2H), 3.29 (m, 2H), 2.29 (s, 3H), 1.98 (m, 4H), 1.23 (t, J 7.1 Hz, 3H). LCMS (pH 10): MH+ 558, RT 1.60 minutes.

Example 184

Sodium 1-[5-(3-{[2-(difluoromethoxy)phenyl]methyl}-7-fluoro-2-methylimidazo[1,2-a]-pyridin-6-yl]pyrimidin-2-yl]-4-fluoropiperidine-4-carboxylate Example 183 (0.21 g, 0.377 mmol) was dissolved in THF:MeOH:water, 1:1:1 (5 mL). Sodium hydroxide (15 mg, 0.38 mmol) was added and the mixture was stirred at 70° C. for 1.5 h. The reaction mixture was concentrated to remove the organic solvents. The residue was diluted with water, and freeze-dried, to give the title compound (205 mg, 98%) as a white lyophilised solid. $\delta_H$ (400 MHz, DMSO-$d_6$) 8.49 (m, 2H), 8.38 (m, 1H), 7.45 (m, 1H), 7.31 (m, 1H), 7.26 (t, J 72, 76 Hz, 1H), 7.20 (m, 1H), 7.15 (m, 1H), 7.04 (m, 1H), 4.44 (m, 2H), 4.34 (m, 2H), 3.27 (m, 1H), 2.28 (s, 3H), 1.97 (m, 2H), 1.70 (m, 2H). LCMS (pH 10): MH+ 530, RT 1.46 minutes.

Example 185

Methyl 1-[5-(3-{[2-(difluoromethoxy)phenyl]methyl}-2-methylimidazo[1,2-a]pyridin-6-yl)pyrimidin-2-yl]-4-methoxypiperidine-4-carboxylate A mixture of Intermediate 7 (0.3 g, 0.8 mmol), Intermediate 227 (0.4 g, 1 mmol), Pd(dppf)Cl$_2$ (0.02 g, 0.02 mmol) and 2M aqueous sodium carbonate solution (3 mL) in 1,4-dioxane (6 mL) was de-gassed and stirred under nitrogen at 110° C. for 2.5 h. The reaction mixture was partitioned between EtOAc and brine, then the organic layer was dried (MgSO$_4$), filtered and concentrated. The crude residue was purified by column chromatography (30:1 EtOAc-MeOH), and crystallised from diethyl ether. The solid was filtered, then washed with diethyl ether and dried, to give the title compound (0.25 g, 60%) as a white solid. $\delta_H$ (400 MHz, DMSO-$d_6$) 8.67 (s, 2H), 8.40 (s, 1H), 7.55 (m, 1H), 7.47 (m, 1H), 7.30 (m, 1H), 7.29 (t, J 76 Hz, 1H), 7.21 (m, 1H), 7.13 (m, 1H), 7.04 (d, J 7.5 Hz, 1H), 4.37 (s, 2H), 4.30 (dt, J 13.1, 3.6 Hz, 2H), 3.70 (s, 3H), 3.38 (m, 2H), 3.22 (s, 3H), 2.32 (s, 3H), 1.87 (m, 4H). LCMS (pH 10): MH+ 538, RT 1.51 minutes.

Example 186

Sodium 1-[5-(3-{[2-(difluoromethoxy)phenyl]methyl}-2-methylimidazo[1,2-a]pyridin-6-yl)pyrimidin-2-yl]-4-methoxypiperidine-4-carboxylate Example 185 (0.25 g, 0.466 mmol) was dissolved in THF:MeOH:water, 1:1:1 (3 mL). Sodium hydroxide (18.5 mg, 0.46 mmol) was added and the mixture was stirred at 70° C. for 5 h. The reaction mixture was concentrated to remove organic solvents, then the residue was diluted with water and washed with diethyl ether. The aqueous layer was freeze-dried to give the title compound (245 mg, 97%) as a white lyophilised solid. $\delta_H$ (400 MHz, DMSO-$d_6$) 8.61 (s, 2H), 8.37 (s, 1H), 7.53 (m, 1H), 7.46 (m, 1H), 7.30 (m, 1H), 7.29 (t, J 76 Hz, 1H), 7.20 (m, 1H), 7.14 (m, 1H), 7.05 (m, 1H), 4.36 (s, 2H), 4.04 (m, 2H), 3.50 (m, 2H), 3.15 (s, 3H), 2.32 (s, 3H), 1.87 (m, 2H), 1.60 (m, 2H). LCMS (pH 10): MH+ 524, RT 1.64 minutes.

Example 187

1-[5-(3-{[2-(Difluoromethoxy)phenyl]methyl}-2-methylimidazo[1,2-a]pyridin-6-yl)pyrimidin-2-yl]-4-fluoropiperidine-4-carboxylic acid A mixture of Intermediate 7 (0.5 g, 1.36 mmol), Intermediate 226 (0.6 g, 2.02 mmol), Pd(dppf)Cl$_2$ (30 mg, 0.037 mmol) and 2M aqueous sodium carbonate solution (4 mL) in 1,4-dioxane (15 mL) was degassed and stirred at 110° C. for 2 h. Lithium hydroxide (100 mg, 2.38 mmol) was added and the reaction mixture was stirred at 60° C. for 6 h. The reaction mixture was concentrated to remove most of the 1,4-dioxane, then diluted with water and neutralised using acetic acid. The solid was filtered, washed several times with cold water and dried by suction, to give crude material (0.7 g, free acid). A portion of this material (200 mg) was purified by HPLC to give the title compound (98 mg, 49%) as a white lyophilised solid. $\delta_H$ (300 MHz, DMSO-$d_6$) 8.67 (s, 2H), 8.41 (s, 1H), 7.55 (m, 1H), 7.47 (m, 1H), 7.29 (m, 2H), 7.19 (m, 1H), 7.13 (td, J 7.6, 1.1 Hz, 1H), 7.03 (m, 1H), 4.52 (m, 2H), 4.36 (s, 2H), 3.25 (m, 2H), 2.31 (s, 3H), 2.00 (m, 1H), 1.85 (m, 3H). LCMS (pH 10): MH+ 512, RT 1.32 minutes.

Example 188

Methyl 1-[5-(3-{[2-(difluoromethoxy)phenyl]methyl}-2-methylimidazo[1,2-a]pyridin-6-yl)pyrimidin-2-yl]-4-ethylpiperidine-4-carboxylate A mixture of Intermediate 7 (0.5 g, 1.36 mmol), Intermediate 228 (0.6 g, 2 mmol), Pd(dppf)Cl$_2$ (30 mg, 0.037 mmol), and 2M aqueous sodium carbonate solution (2 mL) in 1,4-dioxane (15 mL) was degassed and stirred at 110° C. for 5 h. The reaction mixture was partitioned between EtOAc and brine. The organic layer was dried (MgSO$_4$), filtered and concentrated. The crude material was purified by column chromatography (eluting with 4:1 EtOAc-hexane, then EtOAc), then crystallised from diethyl ether. The solid was filtered, washed with diethyl ether and hexane, then dried, to give the title compound (0.24 g, 30%) as an off-white solid. $\delta_H$ (400 MHz, DMSO-d$_6$) 8.65 (s, 2H), 8.38 (s, 1H), 7.53 (m, 1H), 7.47 (m, 1H), 7.30 (m, 1H), 7.29 (t, J 72, 76 Hz, 1H), 7.21 (m, 1H), 7.13 (m, 1H), 7.04 (m, 1H), 4.42 (m, 2H), 4.36 (m, 2H), 3.69 (s, 3H), 3.12 (m, 2H), 2.32 (s, 3H), 2.08 (d, J 13.4 Hz, 2H), 1.56 (m, 2H), 1.39 (m, 2H), 0.77 (m, 3H). LCMS (pH 10): MH+ 536, RT 2.37 minutes.

Example 189

1-[5-(3-{[2-(Difluoromethoxy)phenyl]methyl}-2-methylimidazo[1,2-a]pyridin-6-yl)-pyrimidin-2-yl]-4-ethylpiperidine-4-carboxylic acid Example 188 (0.22 g, 0.41 mmol) and lithium hydroxide (35 mg, 0.83 mmol) in THF (5 mL) and water (1 mL) were stirred at 80° C. for 2 days. The reaction mixture was diluted with water and extracted with EtOAc. The aqueous layer was neutralised using acetic acid and extracted thrice with EtOAc. The combined organic extracts were dried (MgSO$_4$) and filtered, then the solvent was removed under reduced pressure. The material was triturated with ether, filtered, washed with ether and hexane, then dried, to give the title compound (15 mg, 7%) as a pale yellow solid. $\delta_H$ (400 MHz, DMSO-d$_6$) 8.60 (m, 2H), 8.36 (m, 1H), 7.53 (m, 1H), 7.45 (m, 1H), 7.29 (m, 2H), 7.22 (m, 1H), 7.13 (m, 1H), 7.04 (m, 1H), 4.42 (m, 2H), 4.36 (s, 2H), 3.14 (m, 2H), 2.31 (m, 3H), 2.08 (m, 2H), 1.41 (m, 2H), 1.18 (m, 2H), 0.79 (m, 3H). LCMS (pH 10): MH+ 522, RT 2.05 minutes.

Example 190

Methyl (1R,5S)-3-[5-(3-{[2-(difluoromethoxy)phenyl]methyl}-7-fluoro-2-methylimidazo-[1,2-a]pyridin-6-yl)pyrimidin-2-yl]-3-azabicyclo[3.2.1]octane-8-carboxylate Intermediate 68 (305 mg, 0.80 mmol), Intermediate 229 (475 mg, 1.1 mmol) and 2M aqueous K$_3$PO$_4$ solution (2.0 mL) were suspended in 1,4-dioxane (10 mL). The mixture was degassed three times (evacuated and refilled with nitrogen). Bis[3-(diphenylphosphanyl)cyclopenta-2,4-dien-1-yl] iron dichloropalladium (29 mg, 0.04 mmol) was added and the mixture was again degassed, then heated at 100° C. for 18 h. The mixture was cooled to room temperature, diluted with water (50 mL) and extracted with ethyl acetate (3×50 mL). The combined organic layers were washed with water (20 mL), dried over Na$_2$SO$_4$ and purified by silica gel chromatography, eluting with 40-100% ethyl acetate in isohexane, to afford the title compound (125 mg, 28%) (1:1 mixture of diastereoisomers) as a brown oil. $\delta_H$ (400 MHz, DMSO-d$_6$) 8.49 (2H, s), 8.36 (1H, dd, J 7.4, 3.4 Hz), 7.46 (1H, d, J 11.2 Hz), 7.30 (1H, t, J 7.4 Hz), 7.26 (1H, t, J 74.2 Hz), 7.20 (1H, d, J 8.0 Hz), 7.14 (1H, t, J 7.4 Hz), 7.02 (1H, d, J 7.5 Hz), 4.47-4.43 (1H, m), 4.34 (2H, s), 4.28-4.24 (1H, m), 3.68 (1.5H, s), 3.64 (1.5H, s), 3.24-3.19 (1H, m), 3.05 (1H, d, J 12.6 Hz), 2.81-2.78 (1H, m), 2.63 (2H, br s), 2.28 (3H, s), 1.78-1.67 (2H, m), 1.50-1.39 (2H, m). HPLC-MS (pH 10): MH+ m/z 552, RT 2.50 minutes. HPLC-MS (pH 3): MH+ m/z 552, RT 2.13 minutes.

Example 191

Methyl (1R,5S)-3-[5-(3-{[2-(difluoromethoxy)phenyl]methyl}-7-fluoro-2-(methoxy-methyl)imidazo[1,2-a]pyridin-6-yl)pyrimidin-2-yl]-3-azabicyclo[3.2.1]octane-8-carboxylate Intermediate 55 (305 mg, 0.74 mmol), Intermediate 229 (475 mg, 1.1 mmol) and 2M aqueous K$_3$PO$_4$ solution (2.0 mL) were suspended in 1,4-dioxane (10 mL). The mixture was degassed three times (evacuated and refilled with nitrogen). Bis[3-(diphenylphosphanyl)cyclopenta-2,4-dien-1-yl] iron dichloropalladium (58 mg, 0.08 mmol) was added and the mixture was again degassed, then heated at 100° C. for 18 h. The mixture was cooled to room temperature, diluted with water (50 mL) and extracted with ethyl acetate (3×50 mL). The combined organic layers were washed with water (20 mL), dried over Na$_2$SO$_4$ and purified by silica gel chromatography, eluting with 40-100% ethyl acetate in isohexane, to afford the title compound (110 mg, 19%) (1:1 mixture of diastereoisomers) as a brown oil. $\delta_H$ (400 MHz, DMSO-d$_6$) 8.48 (1H, s), 8.47 (1H, s), 8.37-8.34 (1H, m), 7.55 (1H, d, J 11.3 Hz), 7.32-7.26 (1H, m), 7.25 (1H, t, J 74.1 Hz), 7.20-7.17 (1H, m), 7.11 (1H, td, J 7.5, 1.2 Hz), 6.97-6.93 (1H, m), 4.47 (2H, s), 4.47-4.45 (1H, m), 4.41 (2H, s), 4.27-4.22 (1H, m), 3.67 (1.5H, s), 3.63 (1.5H, s), 3.21 (3H, s), 3.21-3.17 (1H, m), 3.04 (1H, dd, J 12.3, 0.5 Hz), 2.80-2.77 (1H, m), 2.62 (1H, br s), 2.53 (1H, br s), 1.78-1.66 (2H, m), 1.47-1.38 (2H, m). HPLC-MS (pH 10): MH+ m/z 582, RT 2.64, 2.66 minutes. HPLC-MS (pH 3): MH+ m/z 582, RT 2.37 minutes.

Example 192

(1R,5S)-3-[5-(3-{[2-(Difluoromethoxy)phenyl]methyl}-7-fluoro-2-methylimidazo[1,2-a]-pyridin-6-yl)pyrimidin-2-yl]-3-azabicyclo[3.2.1]octane-8-carboxylic acid Example 190 (85 mg, 0.14 mmol) was dissolved in THF (2 mL) and water (1 mL). Lithium hydroxide monohydrate (36 mg, 0.61 mmol) was added, and the mixture was stirred at r.t. for 18 h. The mixture was distributed between water (50 mL) and ethyl acetate (50 mL) and the phases were separated. The aqueous layer was acidified to pH 3-4 with 2M HCl, then extracted with EtOAc (3×50 mL). The combined organic layers were washed with brine, dried over Na$_2$SO$_4$ and concentrated in vacuo, to afford the title compound (55 mg, 72%) (1:1 mixture of diastereoisomers) as an off-white solid. $\delta_H$ (300 MHz, DMSO-d$_6$) 12.30 (1H, br s), 8.48 (1H, s), 8.47 (1H, s), 8.35 (1H, dd, J 7.4, 1.2 Hz), 7.45 (1H, d, J 11.2 Hz), 7.32-7.26 (1H, m), 7.25 (1H, t, J 74.1 Hz), 7.19-7.16 (1H, m), 7.15-7.10 (1H, m), 7.02-6.98 (1H, m), 4.46-4.41 (1H, m), 4.33 (2H, s), 4.27-4.22 (1H, m), 3.28-3.22 (1H, m), 3.02 (1H, d, J 13.0 Hz), 2.68 (1H, br s), 2.59 (2H, br s), 2.27 (3H, s), 1.77-1.66 (2H, m), 1.47-1.35 (2H, m). HPLC-MS (pH 10): MH+ m/z 538, RT 1.48, 1.54 minutes. HPLC-MS (pH 3): MH+ m/z 538, RT 1.87, 1.99 minutes.

Example 193

Methyl (1R,5S,8s)-3-[5-(3-{[2-(difluoromethoxy)phenyl]methyl}-7-fluoro-2-methyl-imidazo[1,2-a]pyridin-6-yl)pyrimidin-2-yl]-3-azabicyclo[3.2.1]octane-8-carboxylate Intermediate 68 (350 mg, 0.91 mmol), Intermediate 230 (400 mg, 1.4 mmol) and 2M aqueous K$_3$PO$_4$ solution (1.0 mL) were suspended in 1,4-dioxane (10 mL). The mixture was degassed (evacuated and re-filled with nitrogen 3 times). Bis[3-(diphenyl-phosphanyl)cyclopenta-2,4-dien-1-yl]iron dichloropalladium dichloromethane complex (37 mg, 0.05 mmol) was added. The mixture was again degassed, then heated at 100° C. for 18 h. The mixture was cooled to room temperature, diluted with water (50 mL) and extracted with ethyl acetate (3×50 mL). The combined organic layers were washed with water (20 mL), dried over $Na_2SO_4$ and purified by silica gel chromatography, eluting with 35-100% ethyl acetate in isohexane, to afford the title compound (209 mg, 42%) as a brown oil. HPLC-MS (pH 10): MH+ m/z 552, RT 2.49 minutes.

Example 194

(1R,5S,8s)-3-[5-(3-{[2-(Difluoromethoxy)phenyl] methyl}-7-fluoro-2-methylimidazo[1,2-a]pyridin-6-yl)pyrimidin-2-yl]-3-azabicyclo[3.2.1]octane-8-carboxylic acid Example 193 (209 mg, 0.38 mmol) was dissolved in THF (6 mL) and water (3 mL). Lithium hydroxide monohydrate (64 mg, 0.61 mmol) was added and the mixture was stirred at r.t. for 18 h. The mixture was distributed between water (50 mL) and ethyl acetate (50 mL) and the phases were separated. The aqueous layer was acidified to pH 3-4 with 2M HCl, then extracted with EtOAc (3×50 mL). The combined organic layers were washed with brine, dried over $Na_2SO_4$ and concentrated in vacuo, to afford the title compound (146 mg, 72%) as an off-white solid. $\delta_H$ (300 MHz, DMSO-$d_6$) 12.2 (1H, br s), 8.48 (2H, d, J 1.6 Hz), 8.35 (1H, d, J 7.4 Hz), 7.45 (1H, d, J 11.3 Hz), 7.32-7.26 (1H, m), 7.26 (1H, t, J 74.1 Hz), 7.20-7.10 (2H, m), 7.02-6.99 (1H, m), 4.43 (2H, dd, J 13.4, 3.9 Hz), 4.33 (2H, s), 3.02 (2H, d, J 12.2 Hz), 2.68 (1H, br s), 2.59 (2H, br s), 2.27 (3H, s), 1.71-1.67 (2H, m), 1.42-1.37 (2H, m). HPLC-MS (pH 10): MH+ m/z 538, RT 1.52 minutes. HPLC-MS (pH 3): MH+ m/z 538, RT 1.90 minutes.

Example 195

(1R,5S,8e)-3-[5-(3-{[2-(Difluoromethoxy)phenyl] methyl}-7-fluoro-2-methylimidazo[1,2-a]pyridin-6-yl)pyrimidin-2-yl]-3-azabicyclo[3.2.1]octane-8-carboxylic acid Example 192 (14 mg) was purified by preparative HPLC to afford the title compound (1.6 mg) (single diastereomer) as a white solid. $\delta_H$ (300 MHz, DMSO-$d_6$) 8.47 (2H, m), 8.36 (1H, d, J 7.5 Hz), 7.47 (1H, d, J 11.2 Hz), 7.30 (1H, td, J 8.2, 1.6 Hz), 7.27 (1H, t, J 74.0 Hz), 7.19 (1H, d, J 8.0 Hz), 7.14 (1H, td, J 7.6, 1.0 Hz), 7.01 (1H, dd, J 7.7, 1.3 Hz), 4.33 (2H, s), 4.22 (2H, dd, J 12.8, 2.6 Hz), 3.31 (2H, d, J 12.4 Hz), 2.63-2.60 (1H, m), 2.45 (2H, br s), 2.28 (3H, s), 1.74-1.72 (2H, m), 1.46-1.42 (2H, m). HPLC-MS (pH 10): MH+ m/z 538, RT 1.58 minutes. HPLC-MS (pH 3): MH+ m/z 538, RT 2.06 minutes.

Example 196

Methyl (1R,6S or 1S,6R)-3-[5-(3-{[2-(difluoromethoxy)phenyl]methyl}-7-fluoro-2-methylimidazo[1,2-a]pyridin-6-yl)pyrimidin-2-yl]-3-azabicyclo[4.1.0]heptane-6-carboxylate To a stirred solution of Intermediate 68 (161 mg, 0.42 mmol) and Intermediate 231 (142 mg, 0.51 mmol) in 1,4-dioxane (9 mL) was added 2M aqueous sodium carbonate solution (2 mL), followed by tetrakis(triphenylphosphine) palladium (0) (15 mg, 0.013 mmol). The reaction mixture was degassed (3×vacuum/$N_2$) and stirred at 100° C. for 3 h. The reaction mixture was cooled to room temperature, diluted with ethyl acetate (100 mL), and washed with water (100 mL) and brine (50 mL), then dried ($MgSO_4$), filtered and concentrated in vacuo, to give the title compound (276 mg, quantitative) as a yellow oily solid. $\delta_H$ (DMSO-$d_6$) 8.49 (d, 2H, J 1.6 Hz), 8.35 (d, 1H, J 7.5 Hz), 7.45 (d, 1H, J 11.3 Hz), 7.25-7.33 (m, 1H), 7.26 (t, 1H, J 74.1 Hz), 7.09-7.22 (m, 2H), 6.96-7.01 (m, 1H), 4.33 (s, 2H), 4.24 (dd, 1H, J 13.9, 2.3 Hz), 3.91 (dd, 1H, J 13.7, 4.7 Hz), 3.70-3.81 (m, 1H), 3.61 (s, 3H), 3.33-3.46 (m, 2H), 2.28 (s, 3H), 1.72-1.84 (m, 2H), 1.32 (dd, 1H, J 9.2, 4.5 Hz), 0.82 (dd, 1H, J 6.4, 4.7 Hz). LCMS (ES+) 538 (M+H)+, RT 2.40 minutes.

Example 197

(1R,6S or 1S,6R)-3-[5-(3-{[2-(Difluoromethoxy) phenyl]methyl}-7-fluoro-2-methyl-imidazo[1,2-a] pyridin-6-yl)pyrimidin-2-yl]-3-azabicyclo[4.1.0] heptane-6-carboxylic acid To a stirred solution of Example 196 (223 mg, 0.42 mmol) in THF (10 mL) was added lithium hydroxide monohydrate (72 mg, 1.72 mmol) in water (2 mL). The mixture was stirred at 60° C. over the weekend. The reaction mixture was cooled to room temperature, acidified with acetic acid, diluted with water (20 mL) and extracted with EtOAc (4×50 mL). The combined organic layers were dried ($Na_2SO_4$), filtered and concentrated in vacuo. The residue was purified by preparative HPLC to obtain the title compound (16 mg, 7%) as a white solid. $\delta_H$ (DMSO-$d_6$) 8.48 (d, 2H, J 1.6 Hz), 8.35 (d, 1H, J 7.5 Hz), 7.45 (d, 1H, J 11.4 Hz), 7.25-7.33 (m, 1H), 7.26 (t, 1H, J 74.1 Hz), 7.16-7.21 (m, 1H), 7.13 (td, 1H, J 7.5, 1.2 Hz), 6.98-7.03 (m, 1H), 4.33 (s, 2H), 4.21 (dd, 1H, J 13.6, 2.3 Hz), 3.89 (dd, 1H, J 13.7, 4.8 Hz), 3.70-3.80 (m, 1H), 3.30-3.42 (m, 2H), 2.28 (s, 3H), 1.66-1.84 (m, 2H), 1.24 (dd, 1H, J 9.1, 4.2 Hz), 0.64-0.70 (m, 1H). LCMS (ES+) 524 (M+H)+, RT 1.83 minutes.

Example 198

Methyl (1S,5S or 1R,5R)-3-[5-(3-{[2-(difluoromethoxy)phenyl]methyl}-7-fluoro-2-methylimidazo[1,2-a]pyridin-6-yl)pyrimidin-2-yl]-3-azabicyclo[3.1.0]hexane-1-carboxylate To a stirred solution of Intermediate 68 (163 mg, 0.42 mmol) and Intermediate 232 (164 mg, 0.62 mmol) in 1,4-dioxane (8 mL) and 2M aqueous sodium carbonate solution (2 mL) was added tetrakis(triphenylphosphine)palladium(0) (11 mg, 0.013 mmol). The reaction mixture was degassed (3×vacuum/$N_2$) and stirred at 110° C. for 5 h. The reaction mixture was then cooled to room temperature and concentrated in vacuo. The residue was diluted with water (30 mL) and extracted with ethyl acetate (3×30 mL). The combined organic layers were dried ($MgSO_4$), filtered and concentrated in vacuo. The crude material was purified by column chromatography ($SiO_2$, 15-100% EtOAc in hexane), and the resulting material was freeze-dried from acetonitrile/water, to give the title compound (68 mg, 38%) as an off-white solid. $\delta_H$ (DMSO-$d_6$) 8.49 (d, 2H, J 1.6 Hz), 8.32 (d, 1H, J 7.4 Hz), 7.46 (d, 1H, J 11.3 Hz), 7.26-7.33 (m, 1H), 7.26 (t, 1H, J 74.1 Hz), 7.16-7.21 (m, 1H), 7.13 (td, 1H, J 7.5, 1.1 Hz), 7.01 (dd, 1H, J 7.5, 1.5 Hz), 4.33 (s, 2H), 3.93-3.99 (m, 1H), 3.83-3.90

(m, 2H), 3.67 (s, 3H), 3.58-3.65 (m, 1H), 2.28 (s, 3H), 2.22-2.28 (m, 1H), 1.52-1.59 (m, 1H), 0.95 (t, 1H, J 4.9 Hz). LCMS (ES+) 524 (M+H)$^+$, RT 2.49 minutes.

Example 199

(1S,5S or 1R,5R)-3-[5-(3-{[2-(Difluoromethoxy)phenyl]methyl}-7-fluoro-2-methyl-imidazo[1,2-a]pyridin-6-yl)pyrimidin-2-yl]-3-azabicyclo[3.1.0]hexane-1-carboxylic acid To a stirred solution of Example 198 (65 mg, 0.124 mmol) in THF (5 mL) was added lithium hydroxide monohydrate (24 mg, 0.57 mmol) in water (2 mL) and the reaction mixture was stirred at 60° C. overnight The reaction mixture was cooled to room temperature and acidified with acetic acid, then diluted with water (10 mL) and extracted with EtOAc (3×20 mL). The combined organic layers were dried (MgSO$_4$), filtered and concentrated in vacuo. The crude material was purified by column chromatography (SiO$_2$, 0-20% MeOH in DCM), and the resulting material was freeze-dried from acetonitrile/water, to give title compound (34 mg, 54%) as an off-white solid. $\delta_H$ (DMSO-d$_6$) 8.47 (d, 2H, J 1.5 Hz), 8.32 (d, 1H, J 7.5 Hz), 7.45 (d, 1H, J 11.3 Hz), 7.25-7.33 (m, 1H), 7.26 (t, 1H, J 74.1 Hz), 7.16-7.21 (m, 1H), 7.13 (td, 1H, J 7.6, 1.1 Hz), 6.98-7.04 (m, 1H), 4.33 (s, 2H), 3.80-3.87 (m, 3H), 3.55-3.63 (m, 1H), 2.28 (s, 3H), 2.01-2.10 (m, 1H), 1.42-1.52 (m, 1H), 0.68-0.82 (m, 1H). LCMS (ES+) 510 (M+H)$^+$, RT 1.82 minutes.

Example 200

Methyl (1R or 1S)-3-[5-(3-{[2-(difluoromethoxy)phenyl]methyl}-7-fluoro-2-methyl-imidazo[1,2-a]pyridin-6-yl)pyrimidin-2-yl]-3-azabicyclo[3.1.0]hexane-1-carboxylate To a stirred solution of Intermediate 152 (250 mg, 0.60 mmol) and Intermediate 233 (127.5 mg, 0.72 mmol) in ethanol (7 mL) was added triethylamine (0.1 mL, 0.7 mmol) and the mixture was heated at 80° C. for 4.5 h, after which time the reaction mixture was cooled to room temperature and concentrated in vacuo. The residue was partitioned between EtOAc (30 mL) and water (10 mL) basified with 10% aqueous NaOH solution (10 mL). The layers were separated and the aqueous layer was back extracted with EtOAc (2×30 mL). The combined organic layers were dried (Na$_2$SO$_4$), filtered and concentrated in vacuo. The crude material was purified by column chromatography (SiO$_2$, 25-85% EtOAc in hexane), and the resulting material was freeze-dried from acetonitrile/water, to give the title compound (237 mg, 76%) as an off-white solid. $\delta_H$ (DMSO-d$_6$) 8.49 (d, 2H, J 1.6 Hz), 8.32 (d, 1H, J 7.5 Hz), 7.46 (d, 1H, J 11.3 Hz), 7.26-7.33 (m, 1H), 7.26 (t, 1H, J 74.1 Hz), 7.16-7.21 (m, 1H), 7.13 (td, 1H, J 7.5, 1.3 Hz), 7.01 (dd, 1H, J 7.6, 1.9 Hz), 4.33 (s, 2H), 3.93-3.99 (m, 1H), 3.82-3.91 (m, 2H), 3.67 (s, 3H), 3.61 (dd, 1H, J 11.3, 4.3 Hz), 2.22-2.30 (m, 4H), 1.52-1.59 (m, 1H), 0.95 (t, 1H, J 5.1 Hz). LCMS (ES+) 524 (M+H)$^+$, RT 2.24 minutes.

Example 201

(1R,5R or 1S,5S)-3-[5-(3-{[2-(Difluoromethoxy)phenyl]methyl}-7-fluoro-2-methyl-imidazo[1,2-a]pyridin-6-yl)pyrimidin-2-yl]-3-azabicyclo[3.1.0]hexane-5-carboxylic acid To a stirred solution of Example 200 (237 mg, 0.45 mmol) in THF (5 mL) was added lithium hydroxide monohydrate (78 mg, 1.86 mmol) in water (2.2 mL) and the reaction mixture was heated at 60° C. for 3.5 h. The reaction mixture was cooled to room temperature and acidified with acetic acid, then diluted with water (25 mL) and extracted with EtOAc (4×40 mL). The combined organic layers were dried (Na$_2$SO$_4$), filtered and concentrated in vacuo. The crude material was purified by column chromatography (SiO$_2$, 0-45% MeOH in DCM), and the resulting material was further purified by preparative HPLC, to obtain the title compound (120 mg, 52%) as a white solid. $\delta_H$ 8.48 (d, 2H, J 1.5 Hz), 8.33 (d, 1H, J 7.5 Hz), 7.46 (d, 1H, J 11.3 Hz), 7.25-7.33 (m, 1H), 7.27 (t, 1H, J 74.1 Hz), 7.16-7.21 (m, 1H), 7.12 (td, 1H, J 7.5, 1.2 Hz), 6.98-7.02 (m, 1H), 4.33 (s, 2H), 3.80-3.92 (m, 3H), 3.60 (dd, 1H, J 11.2, 4.4 Hz), 2.28 (s, 3H), 2.08-2.17 (m, 1H), 1.46-1.53 (m, 1H), 0.81 (t, 1H, J 4.8 Hz). LCMS (ES+) 510 (M+H)$^+$, RT 1.74 minutes.

Example 202

Methyl (1S,6R or 1R,6S)-3-[5-(3-{[2-(difluoromethoxy)phenyl]methyl}-7-fluoro-2-methylimidazo[1,2-a]pyridin-6-yl)pyrimidin-2-yl]-3-azabicyclo[4.1.0]heptane-6-carboxylate (Enantiomer B)

To a stirred solution of Intermediate 68 (163 mg, 0.42 mmol) and Intermediate 234 (170 mg, 0.63 mmol) in 1,4-dioxane (8 mL) and 2M aqueous sodium carbonate solution (2 mL) was added tetrakis(triphenylphosphine)palladium(0) (11 mg, 0.013 mmol). The reaction mixture was degassed (3×vacuum/N$_2$) and stirred at 110° C. for 5 h. The reaction mixture was cooled to room temperature and concentrated in vacuo. The residue was partitioned between EtOAc (30 mL) and water (30 mL), then the layers were separated and the aqueous layer was back extracted with EtOAc (3×30 mL). The combined organic layers were dried (MgSO$_4$), filtered and concentrated in vacuo. The crude material was purified by column chromatography (SiO$_2$, 20-100% EtOAc in hexane), and the resulting material was freeze-dried from acetonitrile/water, to give the title compound (115 mg, 50%) as an off-white solid. $\delta_H$ (DMSO-d$_6$) 8.49 (d, 2H, J 1.6 Hz), 8.35 (d, 1H, J 7.4 Hz), 7.45 (d, 1H, J 11.3 Hz), 7.26-7.33 (m, 1H), 7.26 (t, 1H, J 74.1 Hz), 7.16-7.21 (m, 1H), 7.13 (td, 1H, J 7.5, 1.2 Hz), 6.98-7.03 (m, 1H), 4.33 (s, 2H), 4.24 (dd, 1H, J 13.9, 2.4 Hz), 3.91 (dd, 1H, J 13.8, 4.7 Hz), 3.70-3.80 (m, 1H), 3.61 (s, 3H), 3.35-3.46 (m, 1H), 2.55 (m, 1H), 2.28 (s, 3H), 1.75-1.92 (m, 2H), 1.32 (dd, 1H, J 9.1, 4.3 Hz), 0.79-0.85 (m, 1H). LCMS (ES+) 538 (M+H)$^+$, RT 2.63 minutes.

Example 203

(1S,6R or 1R,6S)-3-[5-(3-{[2-(Difluoromethoxy)phenyl]methyl}-7-fluoro-2-methyl-imidazo[1,2-a]pyridin-6-yl)pyrimidin-2-yl]-3-azabicyclo[4.1.0]heptane-6-carboxylic acid (Enantiomer B)

To a stirred solution of Example 202 (107 mg, 0.210 mmol) in THF (5 mL) was added lithium hydroxide monohydrate (36 mg, 0.85 mmol) in water (2 mL) and the reaction mixture was heated at 60° C. for 5 h. The reaction mixture was cooled to room temperature and acidified with acetic acid, then diluted with water (10 mL) and extracted with EtOAc (3×20 mL). The combined organic layers were dried (MgSO$_4$), filtered and concentrated in vacuo, then freeze-dried from acetonitrile/water, to give the title compound (89 mg, 85%) as an off-white solid. $\delta_H$ (DMSO-d$_6$) 8.48 (d, 2H, J 1.5 Hz), 8.35 (d, 1H, J 7.5 Hz), 7.45 (d, 1H, J 11.3 Hz), 7.27-7.33 (m, 1H), 7.26 (t, 1H, J 74.3 Hz), 7.17-7.21 (m, 1H), 7.13 (td, 1H, J 7.5, 1.0 Hz), 6.99-7.03 (m, 1H), 4.34 (s, 2H), 4.19-4.24 (m, 1H), 3.90 (dd, 1H, J 13.7, 4.7 Hz), 3.72-3.79 (m, 1H), 3.34-3.42 (m, 1H) (peak is partially under D$_2$O peak), 2.51-2.55 (m, 1H) (peak is partially under DMSO peak), 2.28 (s, 3H), 1.66-1.83 (m, 2H), 1.22-1.27 (m, 1H), 0.63-0.71 (m, 1H). LCMS (ES+) 524 (M+H)$^+$, RT 1.39 minutes.

Example 204

(1R,6S or 1S,6R)-3-[5-(3-{[2-(Difluoromethoxy) phenyl]methyl}-7-fluoro-2-methyl-imidazo[1,2-a] pyridin-6-yl)pyrimidin-2-yl]-3-azabicyclo[4.1.0] heptane-1-carboxylic acid To a stirred solution of Intermediate 68 (153 mg, 0.40 mmol) and Intermediate 235 (192 mg, 0.65 mmol) in 1,4-dioxane (8 mL) and 2M aqueous potassium phosphate solution (3 mL) was added tetrakis(triphenylphosphine)palladium(0) (17 mg, 0.02 mmol). The reaction mixture was stirred at 90° C. for 18 h. The reaction mixture was cooled to room temperature and filtered through celite, then washed with EtOAc and concentrated in vacuo. The crude residue was then dissolved in THF (8 mL) and lithium hydroxide monohydrate (130 mg, 3.12 mmol) in water (3 mL) was added. The reaction mixture was stirred and heated at 60° C. for 18 h. The reaction mixture was cooled to room temperature and concentrated in vacuo. The crude material was purified by column chromatography (SiO$_2$, 0-100% MeOH in EtOAc), and the resulting material was further purified by preparative HPLC, to obtain the title compound (30 mg, 15%) as a white solid. δ$_H$(DMSO-d$_6$) 8.48 (d, 2H, J 1.6 Hz), 8.35 (d, 1H, J 7.5 Hz), 7.45 (d, 1H, J 11.3 Hz), 7.26-7.33 (m, 1H), 7.26 (t, 1H, J 74.1 Hz), 7.16-7.21 (m, 1H), 7.13 (td, 1H, J 7.6, 1.0 Hz), 6.98-7.03 (m, 1H), 4.38 (d, 1H, J 13.8 Hz), 4.33 (s, 2H), 4.14 (d, 1H, J 13.8 Hz), 3.60-3.71 (m, 1H), 3.37-3.48 (m, 1H), 2.28 (s, 3H), 2.03-2.16 (m, 1H), 1.59-1.83 (m, 2H), 1.22 (dd, 1H, J 9.1, 4.0 Hz), 0.69-0.77 (m, 1H). LCMS (ES+) 524 (M+H)$^+$, RT 1.53 minutes.

Examples 205 & 206

Ethyl (1S,3R and 1R,3S)-3-[5-(3-{[2-(difluoromethoxy)phenyl]methyl}-2-methyl-imidazo-[1,2-a]pyridin-6-yl)pyrimidin-2-yl]cyclohexanecarboxylate (racemic cis and trans isomers)

Intermediate 239 (250 mg) was separated by preparative HPLC to yield the racemic cis and trans isomers.

Example 205 (racemic cis isomer) (33.3 mg) was obtained as a white solid. δ$_H$ (CD$_3$OD) 8.94 (s, 2H), 8.41 (s, 1H), 7.59-7.66 (m, 2H), 7.29-7.35 (m, 1H), 7.20-7.24 (m, 1H), 7.10-7.19 (m, 2H), 6.94 (t, 1H, J 74.0 Hz), 4.45 (s, 2H), 4.15 (q, J 7.2 Hz, 2H), 2.96-3.06 (m, 1H), 2.50-2.60 (m, 1H), 2.46 (s, 3H), 2.23-2.31 (m, 1H), 1.98-2.11 (m, 3H), 1.83 (q, J 12.6 Hz, 1H), 1.41-1.69 (m, 3H), 1.27 (t, J 7.1 Hz, 3H). LCMS (ES+) 521 (M+H)$^+$, RT 2.38 minutes.

Example 206 (racemic trans isomer) (28.4 mg) was obtained as a brown solid. δ$_H$ (CD$_3$OD) 8.94 (s, 2H), 8.41 (s, 1H), 7.59-7.66 (m, 2H), 7.29-7.35 (m, 1H), 7.21-7.25 (m, 1H), 7.10-7.20 (m, 2H), 6.94 (t, 1H, J 74.0 Hz), 4.45 (s, 2H), 4.20 (q, J 7.1 Hz, 2H), 3.21-3.29 (m, 1H), 2.86-2.93 (m, 1H), 2.46 (s, 3H), 2.25-2.32 (m, 1H), 2.13-2.21 (m, 1H), 1.93-2.09 (m, 2H), 1.81-1.92 (m, 1H), 1.60-1.76 (m, 3H), 1.30 (t, J 7.1 Hz, 3H). LCMS (ES+) 521 (M+H)$^+$, RT 2.68 minutes.

Example 207

3-[5-(3-{[2-(Difluoromethoxy)phenyl]methyl}-2-methylimidazo[1,2-a]pyridin-6-yl)-pyrimidin-2-yl] cyclohexanecarboxylic acid To a stirred solution of Intermediate 239 (49.9 mg, 0.096 mmol) in THF (5 mL) was added lithium hydroxide monohydrate (27.3 mg, 0.65 mmol) and the reaction mixture was stirred at 60° C. for 36 h. The reaction mixture was cooled to room temperature, diluted with water (8 mL) and extracted with EtOAc (15 mL). The aqueous layer was neutralised using acetic acid and extracted with EtOAc (3×20 mL). The combined organic layers were dried (Na$_2$SO$_4$), filtered and concentrated in vacuo, then freeze-dried from acetonitrile/water, to give the title compound (34 mg, 72%) (mixture of diastereoisomers) as an off-white solid. δ$_H$ (CD$_3$OD) 8.83-8.85 (m, 2H), 8.34-8.37 (m, 1H), 7.56 (d, 2H, J 1.2 Hz), 7.18-7.25 (m, 1H), 7.02-7.14 (m, 3H), 6.84 (t, 1H, J 74.1 Hz), 4.35 (s, 2H), 2.72-2.97 (m, 1H), 2.36 (s, 3H), 2.12-2.23 (m, 2H), 1.85-2.03 (m, 3H), 1.40-1.64 (m, 4H). LCMS (ES+) 493 (M+H)$^+$, RT 1.57, 1.60 minutes.

Example 208

3-[5-(3-{[2-(Difluoromethoxy)phenyl]methyl}-2-methylimidazo[1,2-a]pyridin-6-yl)-pyrimidin-2-yl] cyclohexanecarboxylic acid (racemic trans diastereomer)

To a stirred solution of Example 206 (20.4 mg, 0.039 mmol) in THF (5 mL) was added lithium hydroxide monohydrate (20.4 mg, 0.49 mmol) in water (3 mL) and the reaction mixture was stirred at 60° C. for 31 h. The reaction mixture was cooled to room temperature and concentrated in vacuo to remove THF. The residue was diluted with water (10 mL) and extracted with EtOAc (20 mL). The aqueous layer was neutralised using acetic acid, then diluted with water (10 mL) and extracted with EtOAc (4×30 mL). The combined organic layers were dried (Na$_2$SO$_4$), filtered and concentrated in vacuo, and freeze-dried from acetonitrile/water, to give the title compound (8.9 mg, 46%) as a white solid. δ$_H$ (CD$_3$OD) 8.82 (s, 2H), 8.29-8.31 (m, 1H), 7.50-7.53 (m, 2H), 7.17-7.24 (m, 1H), 7.09-7.13 (m, 1H), 6.98-7.09 (m, 2H), 6.82 (t, 1H, J 73.9 Hz), 4.34 (s, 2H), 2.70-2.78 (m, 1H), 2.35 (s, 3H), 2.13-2.23 (m, 1H), 2.03-2.11 (m, 1H), 1.69-2.02 (m, 4H), 1.54-1.63 (m, 3H). LCMS (ES+) 493 (M+H)$^+$, RT 1.40 minutes.

Example 209

3-[5-(3-{[2-(Difluoromethoxy)phenyl]methyl}-2-methylimidazo[1,2-a]pyridin-6-yl)-pyrimidin-2-yl] cyclohexanecarboxylic acid (racemic cis diastereomer)

To a stirred solution of Example 205 (21.6 mg, 0.042 mmol) in THF (5 mL) was added lithium hydroxide monohydrate (20.2 mg, 0.48 mmol) in water (3 mL) and the reaction mixture was stirred at 60° C. for 18 h. The reaction mixture was cooled to room temperature and concentrated in vacuo to remove THF. The residue was diluted with water (10 mL) and extracted with EtOAc (20 mL). The aqueous layer was neutralised using acetic acid and extracted with EtOAc (4×20 mL). The combined organic layers were dried (Na$_2$SO$_4$), filtered and concentrated in vacuo, then freeze-dried from acetonitrile/water, to give the title compound (19.6 mg, 96%) as an off white solid. δ$_H$ (CD$_3$OD) 8.82 (s, 2H), 8.28-8.32 (m, 1H), 7.47-7.55 (m, 2H), 7.17-7.24 (m, 1H), 6.98-7.13 (m, 3H), 6.82 (t, 1H, J 73.9 Hz), 4.34 (s, 2H), 2.82-2.95 (m, 1H), 2.29-2.44 (m, 4H), 2.11-2.22 (m, 1H), 1.86-2.03 (m, 3H), 1.64-1.79 (m, 1H), 1.27-1.55 (m, 3H). LCMS (ES+) 493 (M+H)$^+$, RT 170 minutes.

Example 210

Ethyl 1-[5-(3-{[2-(difluoromethoxy)phenyl]methyl}-7-fluoro-2-methylimidazo[1,2-a]-pyridin-6-yl)pyrimidin-2-yl]-3-methylpiperidine-3-carboxylate To Intermediate 152 (353 mg, 0.23 mmol) were added ethanol (5 mL), ethyl 3-methylpiperidine-3-carboxylate (91.9 mg, 0.44 mmol) and triethylamine (1.1 mL, 7.8 mmol). The mixture was heated at 80° C. for 1 h, then cooled to room temperature and stirred for 1 h. The solvent was removed in vacuo. The resulting brown oil was purified by flash column chromatography on silica. Gradient elution with 35% ethyl acetate/isohexane to 80% ethyl acetate/isohexane afforded a pale brown oil (144 mg, 0.26 mmol). A portion of the crude material (48.1 mg) was purified by preparative HPLC, and freeze-dried from acetonitrile/water, to afford the title compound (25.3 mg, 0.046 mmol) as an off-white solid. $\delta_H$ (300 MHz, DMSO-d$_6$) 8.47 (d, J 1.7 Hz, 2H), 8.33 (d, J 7.6 Hz, 1H), 7.45 (d, J 11.4 Hz, 1H), 7.34-7.25 (m, 1H), 7.26 (t, J 74.3 Hz, 1H), 7.21-7.16 (m, 1H), 7.13 (td, J 7.6, 1.2 Hz, 1H), 7.05-7.00 (m, 1H), 4.43 (d, J 13.0 Hz, 1H), 4.33 (s, 2H), 4.10-3.95 (m, 3H), 3.55-3.39 (m, 2H), 2.28 (s, 3H), 2.10-2.01 (m, 1H), 1.70-1.47 (m, 3H), 1.13 (s, 3H), 1.06 (t, J 7.1 Hz, 3H). LCMS (pH 3): MH+ m/z 555, RT 2.37 minutes. LCMS (pH 10): MH+ m/z 555, RT 2.43 minutes.

Example 211

1-[5-(3-{[2-(Difluoromethoxy)phenyl]methyl}-7-fluoro-2-methylimidazo[1,2-a]pyridin-6-yl)pyrimidin-2-yl]-3-methylpiperidine-3-carboxylic acid To Example 210 (96.2 mg, 0.17 mmol) dissolved in tetrahydrofuran (4 mL) and water (1 mL, 55.5 mmol) was added lithium hydroxide monohydrate (39.0 mg, 0.93 mmol) and the reaction mixture was stirred at room temperature for 60 h. The reaction mixture was heated at 80° C. for 3 h, then at 70° C. overnight. Methanol (1 mL) was added and the reaction mixture was heated for 3 h before cooling to room temperature and acidifying to pH 3 with 2M aqueous hydrochloric acid. The mixture was partitioned between water (20 mL) and ethyl acetate (20 mL). The aqueous layer was removed and the organic layer was washed with water (20 mL). The organic layer was separated, dried (Na$_2$SO$_4$) and filtered under reduced pressure. The solvent was removed in vacuo. The resulting crude material was purified by preparative HPLC, and freeze-dried from acetonitrile/water, to afford the title compound (24 mg, 26% yield) as a white solid. $\delta_H$ (300 MHz, DMSO-d$_6$) 8.46 (d, J 1.7 Hz, 2H), 8.35 (d, J 7.5 Hz, 1H), 7.45 (d, J 11.3 Hz, 1H), 7.33-7.25 (m, 1H), 7.26 (t, J 74.1 Hz, 1H), 7.18 (d, J 7.6 Hz, 1H), 7.13 (td, J 7.5, 1.2 Hz, 1H), 7.04-6.98 (m, 1H), 4.33 (s, 2H), 4.21-4.07 (m, 1H), 3.90-3.55 (m, 3H), 2.28 (s, 3H), 2.06-1.92 (m, 1H), 1.70-1.43 (m, 3H), 1.09 (s, 3H). LCMS (pH 3): MH+ m/z 527, RT 2.07 minutes. LCMS (pH 10): MH+ m/z 527, RT 2.05 minutes.

Example 212

Ethyl 1-[5-(3-{[2-(difluoromethoxy)phenyl](hydroxy)methyl}-2-methylimidazo[1,2-a]-pyridin-6-yl]pyrimidin-2-yl]-4-methylpiperidine-4-carboxylate To Intermediate 6 (260 mg, 0.68 mmol) was added [1,1'-bis(diphenylphosphino)-ferrocene]dichloropalladium(II) (49.1 mg, 0.067 mmol) in a microwave vial and the reaction mixture was degassed under three cycles of vacuum and nitrogen. To the dry reaction materials were added 2M aqueous potassium carbonate solution (0.63 mL, 1.26 mmol) and Intermediate 58 (269 mg, 0.68 mmol) dissolved in tetrahydrofuran (4 mL). The reaction mixture was degassed under three cycles of vacuum and nitrogen, and was heated under microwave irradiation at 100° C. for 3 h before cooling to room temperature. The reaction mixture was partitioned between water (5 mL) and dichloromethane, and was filtered through a phase separation cartridge, then the solution was concentrated in vacuo. The crude product was purified by flash column chromatography on silica. Gradient elution, with 50% ethyl acetate/isohexane to 100% ethyl acetate, afforded the title compound (202 mg, 54%) as a brown solid. $\delta_H$ (300 MHz, DMSO-d$_6$) 8.59 (s, 2H), 8.53 (br s, 1H), 8.01 (dd, J 5.6, 3.5 Hz, 1H), 7.52 (dd, J 9.7, 0.9 Hz, 1H), 7.46 (dd, J 9.3, 1.7 Hz, 1H), 7.41-7.34 (m, 2H), 7.16-7.08 (m, 1H), 7.11 (t, J 72.8 Hz, 1H), 6.43 (d, J 4.4 Hz, 1H), 6.18 (d, J 4.4 Hz, 1H), 4.33-4.22 (m, 2H), 4.14 (q, J 6.9 Hz, 2H), 3.37-3.25 (m, 2H, under water peak), 2.16 (s, 3H), 2.08-1.98 (m, 2H), 1.49-1.37 (m, 2H), 1.25-1.15 (m, 6H). LCMS (pH 3): MH+ m/z 553, RT 2.28 minutes. LCMS (pH 10): MH+ m/z 553, RT 2.52 minutes.

Example 213

1-[5-(3-{[2-(Difluoromethoxy)phenyl](hydroxy)methyl}-2-methylimidazo[1,2-a]pyridin-6-yl)pyrimidin-2-yl]-4-methylpiperidine-4-carboxylic acid To Example 212 (202 mg) were added tetrahydrofuran (4 mL), water (1 mL, 55.51 mmol) and lithium hydroxide monohydrate (76.0 mg, 1.81 mmol). The mixture was stirred at room temperature for 60 h. The reaction mixture was diluted with methanol (2 mL) and heated at 70° C. overnight. The reaction mixture was cooled to room temperature, then acidified to pH 3 with 2M aqueous hydrochloric acid. Ethyl acetate (10 mL) was added and the mixture was stirred for 30 minutes. The mixture was partitioned between ethyl acetate (20 mL) and water (20 mL). The aqueous layer was discarded and the organic layer was washed with water (20 mL). The aqueous layer was discarded and the organic layer was washed with further water (20 mL). The organic layer was separated, dried (Na$_2$SO$_4$), and filtered under reduced pressure. The solvent was removed in vacuo to yield brown oils/foams. The organic layer was separated, dried (Na$_2$SO$_4$), and filtered under reduced pressure, then the solvent was removed in vacuo. The resulting brown oil was purified by preparative HPLC, and freeze-dried from acetonitrile/water, to afford the title compound (62.4 mg, 47%) as an off-white solid. $\delta_H$ (300 MHz, DMSO-d$_6$) 8.63-8.52 (m, 3H), 8.07-7.96 (m, 1H), 7.48 (q, J 9.3 Hz, 2H), 7.42-7.33 (m, 2H), 7.17-7.07 (m, 1H), 7.10 (m, 1H), 6.44 (s, 1H), 4.35-4.22 (m, 2H), 3.38-3.23 (m, 2H), 2.16 (s, 3H), 2.10-1.97 (m, 2H), 1.39-1.23 (m, 2H), 1.14 (s, 3H). LCMS (pH 3): MH+ m/z 525, RT 1.58 minutes. LCMS (pH 10): MH+ m/z 525, RT 1.21 minutes.

Example 214

Sodium 4-amino-1-[5-(3-{[2-(difluoromethoxy)phenyl]methyl}-7-fluoro-2-methyl-imidazo[1,2-a]pyridin-6-yl)pyrimidin-2-yl]piperidine-4-carboxylate Intermediate 242 (105 mg, 0.194 mmol) was dissolved in tetrahydrofuran (5 mL) and water (2 mL). Sodium hydroxide (7.70 mg, 0.194 mmol) was added and the mixture was heated to reflux for 48 h. The mixture was concentrated in vacuo, then azeotroped from toluene to give a solid. The residue was treated with diethyl ether (5 mL) and scratched. The resulting free-flowing powder was transferred to a vial, and dried under high vacuum, to afford the title compound (75 mg, 70%) as a white solid. $\delta_H$ (DMSO-d$_6$) 8.43 (s, 2H), 8.35 (d, 1H, J 7.4 Hz), 7.43 (d, 1H, J 7.4 Hz), 7.29-7.01 (m, 5H), 4.32 (s, 2H), 4.16-4.08 (m, 2H), 3.57-3.50 (m, 2H), 2.27 (s, 3H), 1.91-1.83 (m, 2H), 1.23-1.11 (m, 2H). LCMS (pH 10): MH$^+$ (527.8), RT 1.63 minutes.

Example 215

8-[5-[3-[[2-(Difluoromethoxy)phenyl]methyl]-7-fluoro-2-methylimidazo[1,2-a]pyridin-6-yl]pyrimidin-2-yl]-8-azabicyclo[3.2.1]octan-3-one Intermediate 68 (2.20 g, 5.71 mmol) and Intermediate 243 (1.91 g, 7.73 mmol) were dissolved in 1,4-dioxane (40 mL), then tetrakis(triphenylphosphine)palladium(0) (198 mg, 0.171 mmol) and 2M aqueous sodium carbonate solution (8 mL, 16 mmol) were added and the mixture was heated to 100° C. for 4 h. The mixture was diluted with ethyl acetate (100 mL), and washed with water (100 mL) and brine (50 mL), then dried ($Na_2SO_4$) and concentrated in vacuo. The residue was purified by chromatography (silica 100 g, gradient 0 to 5% MeOH in DCM over 15 CVs). The product fractions were concentrated in vacuo. The resulting pale orange oil (2.60 g) was purified by further chromatography (silica 50 g, 50% DCM, 50% EtOAc, isocratic elution) to give the title compound (1.10 g) as a white solid. $\delta_H$ (DMSO-$d_6$) 8.61 (d, 2H, J 1.6 Hz), 8.38 (d, 1H, J 7.4 Hz), 7.49 (d, 1H, J 11.4 Hz), 7.31-6.96 (m, 4H), 7.27 (t, 1H, J 74.1 Hz), 4.90 (br m, 2H), 4.34 (s, 2H), 2.68-2.60 (m, 2H), 2.30-2.20 (m, 2H), 2.28 (s, 3H), 2.16-2.10 (m, 2H), 1.75-1.70 (m, 2H). LCMS (pH 3), MH$^+$ (508.8), RT 1.76 minutes.

Example 216

Ethyl 2-{8-[5-(3-{[2-(difluoromethoxy)phenyl]methyl}-7-fluoro-2-methylimidazo[1,2-a]-pyridin-6-yl)pyrimidin-2-yl]-8-azabicyclo[3.2.1]octan-3-ylidene}acetate Triethyl phosphonoacetate (88 µL, 0.434 mmol) was dissolved in dry tetrahydrofuran (10 mL). The mixture was cooled in an ice bath and sodium hydride (19 mg, 0.473 mmol, 60% dispersion in oil) was added. The mixture was stirred for 10 minutes and Example 215 (200 mg, 0.394 mmol) was added, then the mixture was heated to reflux for 18 h. The mixture was concentrated in vacuo and purified by chromatography (silica, 50:50 EtOAc/DCM). The resulting colourless gum was freeze-dried to give the title compound (110 mg, 48%) as a white solid. $\delta_H$ (DMSO-$d_6$) 8.56 (d, 2H, J 1.6 Hz), 8.37 (d, 1H, J 7.5 Hz), 7.47 (d, 1H, J 10.4 Hz), 7.32-7.27 (m, 1H), 7.26 (t, 1H, J 74.1 Hz), 7.20-7.10 (m, 2H), 7.01-6.98 (m, 1H), 5.85 (s, 1H), 4.79 (br s, 2H), 4.33 (s, 2H), 4.05 (q, 2H, J 7.1 Hz), 3.65-3.60 (m, 2H), 2.60-2.50 (m, 1H, partially obscured by DMSO signal), 2.30-2.25 (m, 2H), 2.27 (s, 3H), 2.03-1.95 (m, 2H), 1.72-1.55 (m, 2H), 1.20 (t, 3H, J 7.1 Hz). LCMS (pH10): MH$^+$ (578.8), RT 2.96 minutes.

Example 217

2-(Morpholin-4-yl)ethyl 1-[5-(3-{[2-(difluoromethoxy)phenyl]methyl}-2-methylimidazo-[1,2-a]pyridin-6-yl)pyrimidin-2-yl]-4-methylpiperidine-4-carboxylate The sodium salt of Example 44 (200 mg, 0.378 mmol) was suspended in dichloromethane (25 mL). A drop of DMF was added, followed by oxalyl chloride (50 mg, 0.39 mmol). The mixture was stirred at room temperature for 2 h, then 2-(morpholin-4-yl)ethanol (99 mg, 0.75 mmol) was added and the mixture was stirred at room temperature overnight. The reaction mixture was washed with aqueous sodium bicarbonate solution and the organic layer was concentrated in vacuo. Chromatography (silica, 0 to 10% MeOH in DCM), followed by freeze-drying, gave the title compound (35 mg, 15%) as an off-white solid. $\delta_H$ (DMSO-$d_6$) 8.64 (s, 2H), 8.37 (s, 1H), 7.55-7.43 (m, 2H), 7.31-7.10 (m, 4H), 7.04-7.01 (m, 1H), 4.35 (s, 2H), 4.34-4.28 (m, 2H), 4.25-4.21 (m, 2H), 3.52-3.48 (m, 4H), 3.36-3.25 (m, 2H), 2.60-2.54 (m, 2H), 2.42-2.38 (m, 4H), 2.32 (s, 3H), 2.10-2.04 (m, 2H), 1.45-1.35 (m, 2H), 1.19 (s, 3H). LCMS (pH10): MH$^+$ (621.8), RT 2.01 minutes.

Example 218

(3-{[2-(Difluoromethoxy)phenyl]methyl}-7-fluoro-6-[2-(morpholin-4-yl)pyrimidin-5-yl]-imidazo[1,2-a]pyridin-2-yl)methanol Prepared from Intermediate 54 (200 mg, 0.50 mmol) and Intermediate 38 (125 mg, 0.60 mmol) in accordance with General Method A. Purification by preparative HPLC yielded the title compound (20 mg, 8%). $\delta_H$ (300 MHz, DMSO-$d_6$) 8.52 (d, J 1.6 Hz, 2H), 8.44 (br s, 1H), 8.29 (d, J 7.4 Hz, 1H), 7.54 (d, J 11.2 Hz, 1H), 7.28 (t, J 73.9 Hz, 1H), 7.27 (m, 1H), 7.18 (m, 1H), 7.09 (td, J 7.5, 1.2 Hz, 1H), 6.94 (dd, J 7.8, 1.5 Hz, 1H), 4.58 (s, 2H), 4.44 (s, 2H), 3.75 (m, 4H), 3.67 (m, 4H). LC-MS (pH 3): MH+ m/z 486.8, RT 1.69 minutes. LC-MS (pH 10): MH+ m/z 486.8, RT 2.00 minutes.

Example 219

4-[5-(3-{[2-(Difluoromethoxy)phenyl](hydroxy)methyl}-2-methylimidazo[1,2-a]pyridin-6-yl)pyrimidin-2-yl]piperazin-2-one Prepared from Intermediate 6 (1.02 g, 2.66 mmol) and Intermediate 71 (695 mg, 3.13 mmol) in accordance with General Method A. Trituration of the crude product in diethyl ether yielded the title compound (1.10 g, 86%). $\delta_H$ (300 MHz, DMSO-$d_6$) 8.67 (s, 2H), 8.58 (br s, 1H), 8.16 (br s, 1H), 8.01 (dd, J 5.6, 3.7 Hz, 1H), 7.51 (m, 2H), 7.38 (m, 2H), 7.12 (m, 1H), 7.11 (t, J 73.9 Hz, 1H), 6.45 (s, 1H), 6.24 (br s, 1H), 4.24 (s, 2H), 3.96 (m, 2H), 3.32 (m, 2H), 2.15 (s, 3H). LC-MS (pH 3): MH+ m/z 481.6, RT 1.34 minutes. LC-MS (pH 10): MH+ m/z 481.8, RT 1.57 minutes.

Example 220

4-[5-(3-{(S or R)-[2-(Difluoromethoxy)phenyl](hydroxy)methyl}-2-methylimidazo[1,2-a]pyridin-6-yl)pyrimidin-2-yl]piperazin-2-one (Enantiomer A)

Separation of Example 219 (700 mg, 1.46 mmol) into its constituent enantiomers by chiral preparative HPLC gave the title compound (283 mg, 40%). $\delta_H$ (300 MHz, DMSO-$d_6$) 8.67 (s, 2H), 8.57 (br s, 1H), 8.13 (br s, 1H), 8.01 (dd, J 5.7, 3.7 Hz, 1H), 7.50 (m, 2H), 7.38 (m, 2H), 7.12 (m, 1H), 7.10 (t, J 73.9 Hz, 1H), 6.45 (d, J 3.9 Hz, 1H), 6.17 (d, J 4.3 Hz, 1H), 4.24 (s, 2H), 3.97 (m, 2H), 3.32 (m, 2H), 2.16 (s, 3H). LC-MS (pH 3): MH+ m/z 481.8, RT 1.37 minutes. LC-MS (pH 10): MH+ m/z 481.8, RT 1.60 minutes.

Example 221

4-[5-(3-{(R or S)-[2-(Difluoromethoxy)phenyl](hydroxy)methyl}-2-methylimidazo[1,2-a]pyridin-6-yl)pyrimidin-2-yl]piperazin-2-one (Enantiomer B)

Separation of Example 219 (700 mg, 1.46 mmol) into its constituent enantiomers by chiral preparative HPLC gave the title compound (315 mg, 45%). $\delta_H$ (300 MHz, DMSO-$d_6$)

8.67 (s, 2H), 8.56 (br s, 1H), 8.13 (br s, 1H), 8.01 (dd, J 5.7, 3.7 Hz, 1H), 7.50 (m, 2H), 7.38 (m, 2H), 7.12 (m, 1H), 7.11 (t, J 73.9 Hz, 1H), 6.45 (d, J 3.9 Hz, 1H), 6.18 (d, J 4.3 Hz, 1H), 4.24 (s, 2H), 3.97 (m, 2H), 3.33 (m, 2H), 2.15 (s, 3H). LC-MS (pH 3): MH+ m/z 481.6, RT 1.37 minutes. LC-MS (pH 10) MH+ m/z 481.8, RT 1.56 minutes.

Example 222

1-[5-(3-{[2-(Difluoromethoxy)phenyl]methyl}-2-methylimidazo[1,2-a]pyridin-6-yl)-4-methoxypyrimidin-2-yl]-1,4-diazepan-5-one Prepared from Intermediate 7 (200 mg, 0.542 mmol) and [4-methoxy-2-(5-oxo-1,4-diazepan-1-yl)pyrimidin-5-yl]boronic acid (345 mg, 1.30 mmol) according to General Method A. Purification by preparative HPLC yielded the title compound (95 mg, 34%). $\delta_H$ (300 MHz, DMSO-$d_6$) 8.23 (s, 1H), 8.17 (br s, 1H), 7.66 (t, J 4.8 Hz, 1H), 7.47 (dd, J 9.3, 0.6 Hz, 1H), 7.31 (m, 1H), 7.29 (t, J 74.1 Hz, 1H), 7.22 (m, 1H), 7.15 (td, J 7.5, 1.2 Hz, 1H), 6.99 (dd, J 7.6, 1.5 Hz, 1H), 4.20 (s, 2H), 3.94 (m, 4H), 3.83 (s, 3H), 3.22 (m, 2H), 2.51 (m, 2H), 2.36 (s, 3H). LC-MS (pH 3): MH+ m/z 509.7, RT 1.70 minutes. LC-MS (pH 10): MH+ m/z 509.8, RT 2.01 minutes.

Example 223

Methyl 1-[5-(3-{[2-(difluoromethoxy)phenyl]methyl}-2-methylimidazo[1,2-a]pyridin-6-yl)-4-methoxypyrimidin-2-yl]piperidine-4-carboxylate Prepared from {4-methoxy-2-[4-(methoxycarbonyl)piperidin-1-yl]pyrimidin-5-yl}boronic acid (380 mg, 1.12 mmol) and Intermediate 7 (304 mg, 0.83 mmol) according to General Method A. The crude material was purified by flash column chromatography on silica (Biotage SNAP 25 g, Isolera), eluting with 0-8% EtOH/DCM. Concentration in vacuo gave the title compound (380 mg, 85%). $\delta_H$ (300 MHz, DMSO-$d_6$) 8.19 (s, 1H), 8.16 (m, 1H), 7.47 (dd, J 9.3, 0.7 Hz, 1H), 7.31 (m, 2H), 7.29 (t, J 74.1 Hz, 1H), 7.21 (m, 1H), 7.15 (td, J 7.5, 1.3 Hz, 1H), 7.00 (dd, J 7.6, 1.5 Hz, 1H), 4.55 (m, 2H), 4.30 (s, 2H), 3.82 (s, 3H), 3.62 (s, 3H), 3.07 (m, 2H), 2.36 (s, 3H), 1.90 (dd, J 13.1, 3.1 Hz, 2H), 1.49 (m, 2H). LC-MS (pH 3): MH+ m/z 538.8, RT 2.00 minutes. LC-MS (pH 10): MH+ m/z 538.8, RT 2.28 minutes.

Example 224

1-[5-(3-{[2-(Difluoromethoxy)phenyl]methyl}-2-methylimidazo[1,2-a]pyridin-6-yl)-4-methoxypyrimidin-2-yl]piperidine-4-carboxylic acid Example 223 (330 mg, 0.61 mmol) was dissolved in THF (4 mL) and water (4 mL). Lithium hydroxide monohydrate (104 mg, 2.48 mmol) was added and the reaction mixture was stirred at room temperature for 4 h. The solution was adjusted to pH 3 using aqueous 1M HCl solution and extracted with ethyl acetate. The combined organic phase was dried, filtered and reduced under vacuum, to give the title compound (220 mg, 69%). $\delta_H$ (300 MHz, DMSO-$d_6$) 12.27 (br s, 1H), 8.19 (s, 1H), 8.17 (s, 1H), 7.48 (d, J 9.4 Hz, 1H), 7.32 (m, 2H), 7.29 (t, J 73.9 Hz, 1H), 7.21 (m, 1H), 7.15 (td, J 7.5, 1.2 Hz, 1H), 7.01 (dd, J 7.6, 1.3 Hz, 1H), 4.54 (m, 2H), 4.30 (s, 2H), 3.82 (s, 3H), 3.07 (m, 2H), 2.36 (s, 3H), 1.90 (m, 2H), 1.49 (m, 2H). LC-MS (pH 3): MH+ m/z 524.8, RT 1.76 minutes. LC-MS (pH 10): MH+ m/z 524.8, RT 1.88 minutes.

Example 225

4-(3-{[2-(Difluoromethoxy)phenyl]methyl}-2-methylimidazo[1,2-a]pyridin-6-yl)-3,5-dimethylisoxazole Prepared from (3,5-dimethylisoxazol-4-yl)boronic acid (310 mg, 2.20 mmol) and Intermediate 7 (254 mg, 0.692 mmol) according to General Method A. The crude material was purified by flash column chromatography on silica (Biotage SNAP 10 g, Isolera), eluting with 0-20% EtOH/DCM. Concentration in vacuo gave the title compound (160 mg, 60%). $\delta_H$ (300 MHz, DMSO-$d_6$) 8.05 (d, J 0.3 Hz, 1H), 7.55 (dd, J 9.2, 0.7 Hz, 1H), 7.30 (m, 1H), 7.27 (t, J 74.1 Hz, 1H), 7.19 (dd, J 9.1, 1.5 Hz, 2H), 7.14 (td, J 7.6, 1.2 Hz, 1H), 7.06 (dd, J 7.7, 1.6 Hz, 1H), 4.32 (s, 2H), 2.37 (s, 3H), 2.28 (s, 3H), 2.12 (s, 3H). LC-MS (pH 3): MH+ m/z 384.8, RT 1.45 minutes. LC-MS (pH 10): MH+ m/z 384.8, RT 1.58 minutes.

Example 226

(3-{[2-(Difluoromethoxy)phenyl]methyl}-7-fluoro-6-[4-(methylsulfonyl)phenyl]imidazo-[1,2-a]pyridin-2-yl]methanol Intermediate 54 (250 mg, 0.6231 mmol), 4-(methylsulfonyl)phenylboronic acid (262 mg, 1.246 mmol) and Pd(PPh$_3$)$_4$ (72 mg, 0.06231 mmol) were dissolved in 1,4-dioxane (10 mL), and saturated aqueous sodium carbonate solution (4 mL) was added. The reaction mixture was degassed and heated to 90° C. for 30 minutes. The reaction mixture was partitioned between DCM and water, then the organic layer was separated, dried, and evaporated onto silica. Purification by column chromatography (5% to 15% MeOH in DCM), followed by trituration from MeOH/DCM into hexane, gave the title compound (0.19 g, 64%) as a pure grey solid. $\delta_H$ (300 MHz, DMSO-$d_6$) 8.41 (d, 1H, J 7.4 Hz), 8.03 (d, 2H, J 8.6 Hz), 8.03 (d, 1H, J 8.6 Hz), 7.79 (dd, 2H, J 8.5, 1.7 Hz), 7.56 (m, 2H), 7.28 (m, 2H), 7.18 (m, 1H), 7.10 (td, 1H, J 7.6, 1.3 Hz), 6.98 (m, 2H), 5.12 (t, 1H, J 5.6 Hz), 4.60 (d, 2H, J 5.6 Hz), 4.47 (s, 2H), 3.27 (s, 4H). LCMS (pH 3): (M+H)+ 477.6, RT 1.55 minutes. LCMS (pH 10): (M+H)+ 477.6, RT 1.93 minutes.

Example 227

3-{[2-(Difluoromethoxy)phenyl]methyl}-7-fluoro-6-[4-(methylsulfonyl)phenyl]-2-{[4-(methylsulfonyl)phenyl]methyl}imidazo[1,2-a]pyridine Intermediate 244 (60 mg, 0.111 mmol, 100 mass %), 4-(methylsulfonyl)phenylboronic acid, (44 mg, 0.222 mmol) and Pd(PPh$_3$)$_4$ (12.7 mg, 0.011 mmol) were dissolved in 1,4-dioxane (3 mL) and saturated aqueous sodium carbonate solution (1 mL) was added. The mixture was degassed and heated to 100° C., whereupon the solution turned black. Reaction was complete after 3 h by LCMS. Water was added and the mixture was extracted with EtOAc and dried with Na$_2$SO$_4$, then evaporated onto silica and purified by column chromatography. Trituration of the resulting yellow oil with diethyl ether gave the title compound (40 mg) as an off white solid. $\delta_H$ (300 MHz, DMSO-$d_6$) 8.60 (m, 1H), 8.49 (d, 1H, J 7.4 Hz), 8.04 (m, 2H), 7.92 (m, 1H), 7.86 (m, 1H), 7.80 (dd, 2H, J 8.5, 1.6 Hz), 7.59 (d, 1H, J 11.6 Hz), 7.28 (m, 1H), 7.24 (t, 1H, J 74.1 Hz), 7.17 (m, 1H), 7.08 (td, 1H, J 7.5, 1.2 Hz), 6.94 (dd, 1H, J 7.6, 1.4 Hz), 4.51 (s, 2H), 4.20 (s, 2H), 3.27 (s, 3H), 3.23 (s, 3H). LCMS (pH 3): (M+H)+ 616.6, RT 2.15 minutes. LCMS (pH 10): (M+H)+ 616.6, RT 2.20 minutes.

Example 228

3-{[2-(Difluoromethoxy)phenyl]methyl}-7-fluoro-6-[4-(methylsulfonyl)phenyl]-2-{[6-(methylsulfonyl)pyridin-3-yl]methyl}imidazo[1,2-a]pyridine The title compound was synthesised from Intermediate 244 and [6-(methylsulfonyl)pyridin-3-yl]boronic acid in accordance with the method of Example 227. $\delta_H$ (300 MHz, DMSO-d$_6$) 8.60 (d, 1H, J 1.0 Hz), 8.49 (d, 1H, J 7.4 Hz), 8.04 (m, 2H), 7.91 (m, 1H), 7.86 (m, 1H), 7.80 (dd, 2H, J 8.5, 1.6 Hz), 7.59 (d, 1H, J 11.6 Hz), 7.28 (m, 1H), 7.24 (t, 1H, J 74.1 Hz), 7.17 (m, 1H), 7.08 (td, 1H, J 7.5, 1.2 Hz), 6.94 (dd, 1H, J 7.6, 1.4 Hz), 4.51 (s, 2H), 4.20 (s, 2H), 3.27 (s, 3H), 3.23 (s, 3H). LCMS (pH 3): (M+H)+ 616.1, RT 2.07 minutes. LCMS (pH 10): (M+H)+ 616.1, RT 2.24 minutes.

Example 229

3-{[2-(Difluoromethoxy)phenyl]methyl}-7-fluoro-6-[4-(methylsulfonyl)phenyl]-2-{[2-(methylsulfonyl)pyridin-4-yl]methyl}imidazo[1,2-a]pyridine The title compound was synthesised from Intermediate 244 and [2-(methylsulfonyl)pyridin-4-yl]boronic acid in accordance with the method of Example 227. $\delta_H$ (300 MHz, DMSO-d$_6$) 8.62 (dd, 1H, J 4.9, 0.6 Hz), 8.48 (d, 1H, J 7.4 Hz), 8.04 (m, 2H), 7.81 (m, 2H), 7.62 (d, 1H, J 11.6 Hz), 7.52 (dd, 1H, J 4.9, 1.6 Hz), 7.25 (m, 2H), 7.22 (t, 1H, J 73.9 Hz), 7.14 (m, 1H), 7.05 (td, 1H, J 7.6, 1.2 Hz), 6.85 (dd, 1H, J 7.6, 1.5 Hz), 4.50 (s, 2H), 4.24 (s, 2H), 3.31 (s, 6H). LCMS (pH 3): (M+H)+ 616.60, RT 2.12 minutes. LCMS (pH 10): (M+H)+ 616.60, RT 2.18 minutes.

Example 230

3-{[2-(Difluoromethoxy)phenyl]methyl}-2-methyl-6-[4-(methylsulfonyl)phenyl]imidazo-[1,2-a]pyridine Prepared from Intermediate 7 (100 mg, 0.272 mmol) and 4-(methylsulfonyl)-phenylboronic acid in accordance with General Method A to give the title compound (50 mg) as a yellow solid. $\delta_H$ (300 MHz, DMSO-d$_6$) 8.56 (d, 1H, J 0.8 Hz), 7.97 (m, 4H), 7.60 (d, 2H, J 1.2 Hz), 7.29 (t, 1H, J 74.1 Hz), 7.28 (m, 1H), 7.20 (m, 1H), 7.12 (dd, 1H, J 7.1, 1.1 Hz), 7.05 (m, 1H), 4.42 (s, 2H), 3.21 (s, 3H), 2.33 (s, 3H). LCMS (pH 3): (M+H)+ 443.60, RT 1.81 minutes. LCMS (pH 10): (M+H)+ 443.60, RT 2.20 minutes.

Example 231

3-{3-[(3-{[2-(Difluoromethoxy)phenyl]methyl}-7-fluoro-6-(1-methylpyrazol-4-yl) -imidazo[1,2-a]pyridin-2-yl)methoxy]phenyl}oxazolidin-2-one Intermediate 246 (200 mg, 0.356 mmol, 100 mass %), 1-methyl-4-(4,4,5,5-tetramethyl-1,3,2-dioxaborolan-2-yl)-1H-pyrazole (115 mg, 0.5335 mmol) and Pd(PPh$_3$)$_4$ (41 mg, 0.035 mmol) were dissolved in 1,4-dioxane (7 mL) and saturated aqueous sodium carbonate solution (3 mL). The reaction mixture was degassed and heated at 90° C. for 6 h. The reaction mixture was partitioned between DCM and water. The organic layer was separated, dried over sodium sulphate, filtered and evaporated. The resulting crude yellow oil was purified by column chromatography, eluting with EtOAc in hexanes (30% to 100%), and crystallised from pure EtOAc, to afford the title compound (106 mg) as white crystals. $\delta_H$ (300 MHz, DMSO-d$_6$) 8.47 (d, 1H, J 7.2 Hz), 8.08 (d, 1H, J 2.6 Hz), 7.81 (s, 1H), 7.55 (m, 2H), 7.26 (m, 3H), 7.17 (m, 3H), 7.06 (m, 3H), 6.77 (ddd, 1H, J 8.2, 2.3, 0.7 Hz), 4.43 (m, 4H), 4.01 (m, 2H), 3.89 (s, 3H). LCMS (pH 3): (M+H)+ 564.7, RT 1.96 minutes. LCMS (pH 10): (M+H)+ 564.8, RT 2.21 minutes.

Example 232

Methyl 1-[5-(3-{[2-(difluoromethoxy)phenyl]methyl}-7-fluoro-2-(methoxymethyl) -imidazo[1,2-a]pyridin-6-yl)pyrimidin-2-yl]-4-methylpiperidine-4-carboxylate A mixture of Intermediate 55 (0.4 g, 1 mmol), Intermediate 57 (0.4 g, 1 mmol), Pd(dppf)Cl$_2$ (0.02 g, 0.02 mmol), and 2M aqueous sodium carbonate solution (2 mL) in 1,4-dioxane (8 mL) was degassed and stirred under nitrogen at 110° C. for 2 h. The cooled reaction mixture was partitioned between EtOAc and brine, then the organic layer was dried over MgSO$_4$, filtered and concentrated in vacuo. The crude residue was purified by column chromatography on silica gel, eluting with 2:1 EtOAc-hexane, to give the title compound (0.21 g, 40%) as a colourless gum. $\delta_H$ (400 MHz, DMSO-d$_6$) 8.49 (m, 2H), 8.36 (m, 1H), 7.56 (m, 1H), 7.32 (m, 1H), 7.26 (t, J 72, 76 Hz, 1H), 7.21 (m, 1H), 7.13 (m, 1H), 6.97 (m, 1H), 4.49 (s, 2H), 4.43 (s, 2H), 4.25 (m, 2H), 3.68 (s, 3H), 3.35 (m, 2H), 3.24 (s, 3H), 2.03 (m, 2H), 1.43 (m, 2H), 1.22 (s, 3H). LCMS (pH 10): MH+ 570, RT 1.62 minutes.

Example 233

1-[5-(3-{[2-(Difluoromethoxy)phenyl]methyl}-7-fluoro-2-(methoxymethyl)imidazo[1,2-a]pyridin-6-yl)pyrimidin-2-yl]-4-methylpiperidine-4-carboxylic acid Example 232 (0.2 g, 0.35 mmol) was dissolved in THF (6 mL), then water (2 mL) and lithium hydroxide hydrate (30 mg, 0.71 mmol) were added and the mixture was stirred for two days. Further lithium hydroxide (10 mg, 24 mmol) was added and the mixture was stirred for 4 days. The reaction mixture was diluted with water (~6 mL) and washed with EtOAc. The aqueous layer was carefully neutralised using a few drops of acetic acid, then extracted using EtOAc. The organic extract was washed with water, dried over MgSO$_4$, filtered and concentrated in vacuo. The syrupy material was triturated in diethyl ether. The resulting solid was filtered, washed with diethyl ether and hexane, then dried, to give the title compound (70 mg, 40%) as a light brown solid. $\delta_H$ (400 MHz, DMSO-d$_6$) 12.40 (br s, 1H), 8.49 (d, J 1.5 Hz, 2H), 8.35 (d, J 7.4 Hz, 1H), 7.55 (d, J 11.2 Hz, 1H), 7.30 (m, 1H), 7.26 (t, J 72, 76 Hz, 1H), 7.20 (m, 1H), 7.12 (m, 1H), 6.97 (dd, J 7.5, 1.2 Hz, 1H), 4.48 (s, 2H), 4.43 (s, 2H), 4.27 (m, 2H), 3.35 (m, 2H), 3.24 (m, 3H), 2.01 (m, 2H), 1.38 (m, 2H), 1.19 (s, 3H). LCMS (pH 10): MH+ 556, RT 2.00 minutes.

Example 234

Methyl 1-[5-(3-{[2-(difluoromethoxy)phenyl]methyl}-2-methylimidazo[1,2-a]pyridin-6-yl)pyrimidin-2-yl]-4-isopropylpiperidine-4-carboxylate Prepared from Intermediate 7 and Intermediate 248 in accordance with General Method A to give the title compound (20% yield) as a white crystalline solid. $\delta_H$ (400 MHz, DMSO-d$_6$) 8.66 (m, 2H), 8.38 (s, 1H), 7.55 (m, 1H), 7.47 (m, 1H), 7.30 (m, 1H), 7.29 (t, J 72, 76 Hz, 1H), 7.21 (m, 1H), 7.14 (m, 1H), 7.05 (m, 1H), 4.64 (m, 2H), 4.37 (m, 2H), 3.72 (s, 3H), 2.87 (m, 2H), 2.32 (s, 3H), 2.11 (m, 2H), 1.72 (m, 1H), 1.39 (m, 2H), 0.82 (d, J 4 Hz, 6H). LCMS (pH 10): MH+ 550, RT 2.52 minutes.

Example 235

Methyl 1-[5-(3-{1-[2-(difluoromethoxy)phenyl]ethyl}-2-methylimidazo[1,2-a]pyridin-6-yl)pyrimidin-2-yl]-4-methylpiperidine-4-carboxylate A solution of Example 43 (1 g, 1.97 mmol) and methyl iodide (0.25 mL, 4.1 mmol) in THF (10 mL) was cooled under nitrogen to −78° C. and 1M lithium hexamethyldisilazane solution (8.0 mL, 8 mmol) was added dropwise. The mixture was left stirring overnight, allowing the temperature to rise slowly to ambient temperature. The reaction mixture was partitioned between EtOAc and brine. The organic layer was washed once with brine, dried over $MgSO_4$, filtered and concentrated in vacuo, then purified by column chromatography on $SiO_2$, eluting with EtOAc-hexane (4:1 v/v). The residue was crystallised from diethyl ether/hexane, filtered, and washed with diethyl ether/hexane, then dried, to give the title compound (0.26 g, 25%) as a white solid. $\delta_H$ (400 MHz, DMSO-$d_6$) 8.63 (m, 2H), 8.35 (m, 1H), 7.56 (dd, J 7.6, 1.5 Hz, 1H), 7.50 (m, 1H), 7.43 (m, 1H), 7.34 (m, 1H), 7.28 (m, 1H), 7.16 (d, J 7.9 Hz, 1H), 7.12 (t, J 72, 76 Hz, 1H), 4.96 (m, 1H), 4.25 (m, 2H), 3.66 (s, 3H), 3.34 (m, 2H), 2.27 (s, 3H), 2.03 (m, 2H), 1.72 (d, J 7.3 Hz, 3H), 1.44 (m, 2H), 1.23 (m, 3H). LCMS (pH 10): MH+ 536, RT 2.31 minutes.

Example 236

1-[5-(3-{[2-(Difluoromethoxy)phenyl]methyl}-2-methylimidazo[1,2-a]pyridin-6-yl)-pyrimidin-2-yl]-4-hydroxypiperidine-4-carboxylic acid Prepared from Intermediate 7 and Intermediate 250 to give the title compound as a white lyophilised solid. $\delta_H$ (400 MHz, DMSO-$d_6$) 8.63 (m, 2H), 8.38 (m, 1H), 7.53 (m, 1H), 7.47 (m, 1H), 7.29 (t, J 72, 76 Hz, 1H), 7.28 (m, 1H), 7.20 (m, 1H), 7.14 (m, 1H), 7.05 (m, 1H), 4.43 (m, 4H), 3.34 (m, 2H), 2.30 (s, 3H), 1.81 (m, 2H), 1.56 (m, 2H) (OH proton exchanged). LCMS (pH 10): MH+ 510, RT 1.56 minutes.

Examples 237 to 242

The following compounds were synthesised from Intermediate 255 and the appropriate boronic acid in accordance with General Method A.

Examples 237 and 242 were prepared from (4-sulfamoylphenyl)boronic acid and (6-methoxy-3-pyridyl)boronic acid respectively.

Examples 238-241 were prepared from Intermediates 71, 38, 256 and 37 respectively.

Example 243

3-[2-(Difluoromethoxy)benzyl]-7-fluoro-2-(methoxymethyl)-6-{2-[4-(methylsulfonyl)-piperazin-1-yl]pyrimidin-5-yl}imidazo[1,2-a]pyridine To a solution of Intermediate 55 (151 mg, 0.37 mmol) and Intermediate 256 (126 mg, 0.44 mmol) in 1,4-dioxane (9 mL) and 2N aqueous potassium phosphate solution (3 mL) was added [1,1'-bis(diphenylphosphino)ferrocene]dichloropalladium(II) (16 mg, 0.020 mmol). The reaction mixture was heated to 100° C. for 4 h, then cooled to room temperature. The reaction mixture was partitioned between water (10 mL) and ethyl acetate (10 mL). The layers separated, and the aqueous layer was extracted further with ethyl acetate (3×10 mL). The combined organic layers were dried ($MgSO_4$), filtered and concentrated in vacuo. The crude material was purified by column chromatography ($SiO_2$, 50-100% EtOAc in hexane), and the residue was freeze-dried from acetonitrile/water, to give the title compound (87 mg, 41%) as an off-white solid. $\delta_H$ (400 MHz, DMSO-$d_6$) 8.56 (d, 2H, J 1.5 Hz), 8.37 (d, 1H, J 7.4 Hz), 7.57 (d, 1H, J 11.2 Hz), 7.27-7.33 (m, 1H), 7.26 (t, 1H, J 74.0 Hz), 7.18-7.22 (m, 1H), 7.12 (td, 1H, J 7.6, 1.0 Hz), 6.97 (dd, 1H, J 7.7, 1.3 Hz), 4.49 (s, 2H), 4.43 (s, 2H), 3.93 (t, 4H, J 4.9 Hz), 3.23 (s, 3H), 3.19-3.23 (m, 4H), 2.90 (s, 3H). LCMS (ES+) 577 (M+H)+, RT 2.18 minutes.

Example 244

3-[(2,5-Dimethylphenyl)methyl]-2-(pyridin-4-ylmethoxymethyl)imidazo[1,2-a]pyridine Intermediate 258 was dissolved in THF (5 mL) and DMF (5 mL) and cooled on an ice bath. To the solution was added 4-(bromomethyl)pyridine hydrobromide (1 eq), followed by sodium hydride (3 eq). The mixture was stirred at ambient temperature overnight, then quenched with methanol (2 mL). The reaction mixture was poured into DCM/water. The organic phases were washed four times with water, dried over magnesium sulphate, and filtered, then the solvent was removed in vacuo. The residue was purified by gradient silica column chromatography, eluting with 0-20% methanol in DCM, followed by preparative chromatography (pH 10), to afford the title compound (200 mg, 22%) as an off-white solid. $\delta_H$ (400 MHz, $CDCl_3$) 8.48 (d, J 6.0 Hz, 2H), 7.63 (d, J

| Example | Name | LCMS RT (minutes) | Mass Ion |
|---|---|---|---|
| 237 | 4-(7-Chloro-3-{[2-(difluoromethoxy)phenyl]methyl}-2-methylimidazo[1,2-a]pyridin-6-yl)benzenesulfonamide | 2.20 | 478 |
| 238 | 4-[5-(7-Chloro-3-{[2-(difluoromethoxy)phenyl]methyl}-2-methylimidazo[1,2-a]pyridin-6-yl)-pyrimidin-2-yl]piperazin-2-one | 2.15 | 499 |
| 239 | 4-[5-(7-Chloro-3-{[2-(difluoromethoxy)phenyl]methyl}-2-methylimidazo[1,2-a]pyridin-6-yl)-pyrimidin-2-yl]morpholine | 2.48 | 486 |
| 240 | 7-Chloro-3-{[2-(difluoromethoxy)phenyl]methyl}-2-methyl-6-{2-[4-(methylsulfonyl)piperazin-1-yl]pyrimidin-5-yl}imidazo[1,2-a]pyridine | 2.49 | 563 |
| 241 | 1-[5-(7-Chloro-3-{[2-(difluoromethoxy)phenyl]methyl}-2-methylimidazo[1,2-a]pyridin-6-yl)-pyrimidin-2-yl]piperidine-4-carboxylic acid | 1.79 | 528 |
| 242 | 7-Chloro-3-{[2-(difluoromethoxy)phenyl]methyl}-6-(6-methoxypyridin-3-yl)-2-methylimidazo[1,2-a]pyridine | 2.62 | 430 |

8.50 Hz, 2H), 7.05-7.22 (m, 4H), 6.94 (d, J 7.5 Hz, 1H), 6.71 (t, J 6.6 Hz, 1H), 6.44 (s, 1H), 4.77 (s, 2H), 4.61 (s, 2H), 4.22 (s, 2H), 2.35 (s, 3H), 1.86 (s, 3H). LCMS (ES+) (M+H)+ 358, RT 2.30 minutes.

Example 245

3-{3-[(3-{[2-(Difluoromethoxy)phenyl]methyl}-7-fluoro-6-(6-methoxypyridin-3-yl)-imidazo[1,2-a]pyridin-2-yl)methoxy]phenyl}oxazolidin-2-one The title compound was prepared from Intermediate 246 and 2-methoxy-5-pyridineboronic acid in accordance with General Method A. $\delta_H$ (DMSO-$d_6$) 8.39 (d, 1H, J 7.5 Hz), 8.28-8.31 (m, 1H), 7.88 (dt, 1H, J 8.6, 2.0 Hz), 7.62 (d, 1H, J 11.2 Hz), 7.31-6.94 (m, 5H), 6.80-6.74 (m, 1H), 5.18 (s, 2H), 4.50-4.38 (m, 4H), 4.04-3.98 (m, 2H), 3.89 (s, 3H). LCMS m/z 592 (M+H)+, RT 2.55 minutes.

Example 246

3-{3-[(3-{[2-(Difluoromethoxy)phenyl]methyl}-7-fluoro-6-(6-oxo-1H-pyridin-3-yl)-imidazo[1,2-a]pyridin-2-yl)methoxy]phenyl}oxazolidin-2-one Example 245 (273 mg, 0.4622 mmol) was mixed with pyridine hydrochloride (0.21 g, 1.85 mmol) and placed on a prewarmed heating block at 160° C. The reaction mixture was heated for 5 minutes, then allowed to cool to room temperature. The solution was adsorbed onto silica, then purified by column chromatography with 5% DCM/MeOH to 10% DCM/MeOH. The resulting solid was washed with water, and dried, to afford the title compound (95 mg, 35%) as a pale solid. LCMS m/z 577.6 (M+H)+, RT 1.81 minutes.

Example 247

5-(3-[2-(Difluoromethoxy)benzyl]-7-fluoro-2-{[3-(2-oxo-1,3-oxazolidin-3-yl)phenoxy]-methyl}imidazo[1,2-a]pyridin-6-yl)pyridine-2-carboxylic acid The title compound was prepared from Intermediate 246 and 2-carboxypyridine-5-boronic acid in accordance with General Method A. LCMS m/z 561.7 (M–H)−, RT 1.87 minutes.

Example 248

2-(3-{[2-(Difluoromethoxy)phenyl]methyl}-7-fluoro-6-[2-(morpholin-4-yl)pyrimidin-5-yl]imidazo[1,2-a]pyridin-2-yl)acetonitrile Intermediate 245 (387 mg) was dissolved in dimethylsulfoxide (2 mL) and treated with sodium cyanide (0.045 g, 0.92 mmol), then the reaction mixture was stirred at r.t. for 18 h. The solution was diluted into ethyl acetate (50 mL), then washed with water (3×50 mL). The organic layer was separated, dried with sodium sulphate, and filtered, then the solvent was removed under reduced pressure. The resulting clear oil was purified using silica gel chromatography to afford a pale solid (235 mg, 62%). The title compound was then prepared by reacting the material thus obtained with Intermediate 38 in accordance with General Method A. LCMS m/z 495.6 (M+H)+, RT 2.19 minutes.

Example 249

{1-[5-(3-{[2-(Difluoromethoxy)phenyl]methyl}-7-fluoro-2-methylimidazo[1,2-a]pyridin-6-yl)pyrimidin-2-yl]-4-methypiperidin-4-yl}methanol Intermediate 68 (0.75 g, 1.95 mmol), Intermediate 259 (0.700 g, 2.79 mmol) and Pd(PPh$_3$)$_4$ (0.113 g, 0.098 mmol) were placed in a 100 mL round-bottomed flask. 1,4-Dioxane (30 mL) and 2M aqueous sodium carbonate solution (12 mL, 24 mmol) were added, then the flask was flushed with nitrogen and heated at 100° C. under nitrogen overnight. The reaction mixture was cooled and water (20 mL) was added. The mixture was extracted with EtOAc (3×50 mL), dried over sodium sulphate, filtered and concentrated in vacuo. The resulting crude yellow semi solid was purified by NP flash chromatography (SiO$_2$, EtOAc/hexanes, 10-100%) to afford the title compound (690 mg, 69%) as an off-white solid. $\delta_H$ (300 MHz, DMSO-$d_6$) 8.46 (s, 2H), 8.33 (d, J 7.5 Hz, 1H), 7.47 (d, J 11.3 Hz, 1H), 7.29-7.19 (m, 1H), 7.26 (t, J 74.1 Hz, 1H), 7.15-7.10 (m, 2H), 7.00 (m, 1H), 4.56 (m, 1H), 4.32 (s, 2H), 4.14 (m, 2H), 3.46 (m, 2H), 3.20 (m, 2H), 2.27 (s, 3H), 1.50 (m, 2H), 1.33 (m, 2H), 0.95 (s, 3H). HPLC-MS: MH+ m/z 512.8, RT 2.14 minutes.

Example 250

1-[5-(3-{[2-(Difluoromethoxy)phenyl]methyl}-7-fluoro-2-methylimidazo[1,2-a]pyridin-6-yl)pyrimidin-2-yl]-4-methylpiperidine-4-carbaldehyde Example 249 (0.62 g, 1.212 mmol) in DCM (5 mL) was treated with Dess-Martin Periodinane (0.6360 g, 1.455 mmol) and the reaction mixture was stirred at r.t. for 18 h. Aqueous sodium thiosulphate solution (5 mL) and saturated aqueous NaHCO$_3$ solution (5 mL) were added and the reaction mixture was stirred for a further 30 minutes. The reaction mixture was then extracted with DCM (2×50 mL) and the combined organic layers were concentrated in vacuo. The resulting crude orange solid was purified by NP flash chromatography (SiO$_2$, EtOAc/hexanes, 5-100%) to give the title compound (570 mg, 92%) as a clear orange solid. $\delta_H$ (300 MHz, DMSO-$d_6$) 9.52 (s, 1H), 8.49 (d, J 1.6 Hz, 2H), 8.34 (d, J 7.5 Hz, 1H), 7.46 (d, J 11.3 Hz, 1H), 7.32-7.26 (m, 1H), 7.26 (t, J 74.1 Hz, 1H), 7.16 (m, 2H), 7.02 (s, 1H), 4.33 (s, 2H), 4.06 (m, 2H), 3.50 (m, 2H), 2.28 (s, 3H), 1.92 (m, 2H), 1.42 (m, 2H), 1.07 (s, 3H). HPLC-MS: MH+ m/z 510.8, RT 2.18 minutes.

Example 251

1-[5-(3-{[2-(Difluoromethoxy)phenyl]methyl}-7-fluoro-2-methylimidazo[1,2-a]pyridin-6-yl)pyrimidin-2-yl]piperidine-4-sulfonamide Prepared from Intermediate 68 (0.2 g, 0.519 mmol) and Intermediate 260 (0.23 g, 0.804 mmol) by the method of Example 249. The resulting off-white solid was triturated with EtOAc and diethyl ether. The resulting off-white solid (250 mg) was further purified by NP flash column chromatography (SiO$_2$, EtOAc/hexanes, 75-100%) to afford the title compound (160 mg, 56%) as a white solid. $\delta_H$ (300 MHz, DMSO-$d_6$) 8.43 (d, J 1.6 Hz, 2H), 8.11 (d, J 7.2 Hz, 1H), 7.33-7.27 (m, 2H), 7.21-7.08 (m, 3H), 6.90 (t, J 74.1 Hz, 1H), 4.98 (m, 2H), 4.38 (s, 2H), 3.35 (m, 1H), 3.00 (m, 2H), 2.43 (s, 3H), 2.36 (m, 2H), 1.70 (m, 2H). HPLC-MS: MH+ m/z 547.7, RT 2.05 minutes.

Example 252

3-{[2-(Difluoromethoxy)phenyl]methyl}-7-fluoro-2-methyl-6-{2-[4-(methylsulfonyl)-piperidin-1-yl]pyrimidin-5-yl}imidazo[1,2-a]pyridine Prepared from Intermediate 68 (0.2 g, 0.519 mmol) and Intermediate 261 (0.23 g, 0.804 mmol) by the method of Example 249. The resulting crude off white solid was purified by NP flash column chromatography (SiO$_2$, EtOAc/hexanes, 75-100%) to afford the title compound (168 mg) as a white solid. $\delta_H$ (300 MHz, DMSO-d$_6$) 8.59 (d, J 1.6 Hz, 2H), 8.43 (d, J 7.4 Hz, 1H), 7.32 (m, 4H), 7.26-7.16 (m, 1H), 7.09-7.06 (m, 1H), 4.90 (m, 2H), 4.40 (s, 2H), 3.55 (m, 1H), 3.02 (m, 5H), 2.34 (s, 3H), 2.17 (m, 2H), 1.60 (m, 2H).
HPLC-MS: m/z MH+ 546.6, RT 1.78 minutes.

Example 253

N-({1-[5-(3-{[2-(Difluoromethoxy)phenyl]methyl}-7-fluoro-2-methylimidazo[1,2-a]-pyridin-6-yl)pyrimidin-2-yl]piperidin-4-yl}sulfonyl)acetamide Example 251 (0.14 g, 0.256 mmol) and acetic anhydride (0.0404 g, 0.384 mmol were suspended in DCM (3 mL) and zinc chloride (0.0011 g, 0.0077 mmol) was added. The reaction mixture was stirred at r.t. for 1 h, then heated to reflux for 1 h. THF (1 mL) was added and heating was increased to 60° C. for 1 h. Acetyl chloride (0.100 mL) and a pinch of DMAP were added. Further zinc chloride (0.0011 g, 0.0077 mmol) was added and heating at 60° C. was continued for 48 h. Water (20 mL) was added and the mixture was extracted with DCM (3×50 mL). The combined organic layer was concentrated in vacuo and purified by NP flash column chromatography (SiO$_2$, MeOH/EtOAc, 0-5%) to afford the title compound (34 mg, 23%) as a white solid. $\delta_H$ (300 MHz, DMSO-d$_6$) 11.62 (m, 1H), 8.52 (m, 2H), 8.38 (d, J 7.5 Hz, 1H), 7.47 (d, J 11.3 Hz, 1H), 7.29 (m, 1H), 7.26 (t, J 74.1 Hz, 1H), 7.15 (m, 2H), 7.02 (m, 1H), 4.80 (m, 2H), 4.33 (s, 2H), 3.74 (m, 1H), 3.04 (m, 2H), 2.28 (s, 3H), 2.05 (m, 2H), 2.00 (s, 3H), 1.59 (m, 2H).
HPLC-MS: m/z MH+ 589.7, RT 1.53 minutes.

Example 254

5-{1-[5-(3-{[2-(Difluoromethoxy)phenyl]methyl}-7-fluoro-2-methylimidazo[1,2-a]-pyridin-6-yl]pyrimidin-2-yl]piperidin-4-yl}-1,3,4-oxadiazol-2-ol Prepared from Intermediate 68 (0.2 g, 0.519 mmol) and Intermediate 262 (0.23 g, 0.804 mmol) by the method of Example 249 to afford the title compound (45 mg) as a white solid after freeze-drying. $\delta_H$ (300 MHz, DMSO-d$_6$) 12.05 (m, 1H), 8.45 (m, 2H), 8.30 (d, J 7.4 Hz, 1H), 7.41 (d, J 11.3 Hz, 1H), 7.25 (m, 1H), 7.19 (t, J 74.1 Hz, 1H), 7.08 (m, 2H), 6.94 (m, 1H), 4.53 (m, 2H), 4.28 (s, 2H), 3.13 (m, 2H), 2.95 (m, 1H), 2.21 (s, 3H), 1.91 (m, 2H), 1.50 (m, 2H). HPLC-MS: m/z MH+ 552.8, RT 1.85 minutes.

Example 255

{1-[5-(3-{1-[2-(Difluoromethoxy)phenyl]ethyl}-7-fluoro-2-methylimidazo[1,2-a]pyridin-6-yl)pyrimidin-2-yl]-4-methylpiperidin-4-yl}methanol Prepared from Intermediate 263 (0.5 g, 1.25 mmol) and Intermediate 259 (0.32 g, 1.25 mmol) by the method of Example 249 to afford the title compound (630 mg) as an off-white solid. $\delta_H$ (300 MHz, DMSO-d$_6$) 8.54 (m, 1H), 8.48 (m, 2H), 7.60 (m, 3H), 7.32 (m, 2H), 7.16 (m, 1H), 4.98 (m, 1H), 4.55 (m, 1H), 4.16 (m, 2H), 3.49 (m, 2H), 3.21 (s, 2H), 2.19 (m, 3H), 1.71 (m, 3H), 1.48 (m, 2H), 1.24 (m, 2H), 0.97 (s, 3H). HPLC-MS: m/z MH+ 526.8, RT 1.99 minutes.

Example 256

1-{3-[(6-Bromo-3-{[2-(difluoromethoxy)phenyl]methyl}-7-fluoroimidazo[1,2-a]pyridin-2-yl)methylamino]phenyl}pyrrolidin-2-one To a solution of 1-(3-aminophenyl)pyrrolidin-2-one (105 mg, 0.60 mmol) and Intermediate 264 (200 mg, 0.50 mmol) in THF (5 mL), cooled in an ice bath, was added sodium borohydride (23 mg, 0.60 mmol) in one portion. After 1 h the reaction mixture had turned orange and was allowed to warm to room temperature. The reaction mixture was separated between aqueous sodium bicarbonate solution and EtOAc. The organic layer was dried (phase separator) and evaporated in vacuo. The resulting crude residue was purified by preparative HPLC to afford the title compound (75 mg, 27%) as a white powder. $\delta_H$ (300 MHz, DMSO-d$_6$) 8.58 (d, 1H, J 6.7 Hz), 7.66 (d, 1H, J 9.6 Hz), 7.25 (m, 3H), 7.07 (td, 1H, J 7.5, 1.1 Hz), 6.98 (m, 1H), 6.90 (m, 2H), 6.82 (m, 1H), 6.38 (m, 1H), 6.02 (t, 1H, J 5.6 Hz), 4.42 (s, 2H), 4.27 (d, 2H, J 5.6 Hz), 3.70 (t, 2H, J 6.9 Hz), 2.43 (t, 2H, J 7.8 Hz), 2.00 (m, 2H). LCMS (ES+) 560 (M+H)$^+$, RT 2.4 minutes.

Example 257 tert-Butyl 4-[5-(3-{[2-(difluoromethoxy)phenyl]methyl}-7-fluoro-2-{[3-(2-oxooxazolidin-3-yl)phenoxy]methyl}imidazo[1,2-a]pyridin-6-yl)pyrimidin-2-yl]piperazine-1-carboxylate A mixture of Intermediate 246 (0.2 g, 0.36 mmol), tert-butyl 4-[5-(4,4,5,5-tetramethyl-1,3,2-dioxaborolan-2-yl)pyrimidin-2-yl]piperazine-1-carboxylate (170 mg, 0.43 mmol), tetrakis(triphenylphosphine)palladium(0) (41 mg, 0.036 mmol) and potassium carbonate (0.099 g, 0.71 mmol) in 1,4-dioxane (2M) was heated under microwave irradiation for 2 h at 110° C. The reaction mixture was partitioned between aqueous sodium bicarbonate solution and EtOAc. The organic layer was separated, dried over anhydrous sodium sulphate, filtered and concentrated in vacuo. The residue was purified by column chromatography (SiO$_2$, 1-10% MeOH in DCM) to give the title compound (75 mg, 28%). LCMS (ES+) 747 (M+H)$^+$, RT 3.0 minutes.

Example 258

3-{3-[(3-{[2-(Difluoromethoxy)phenyl]methyl}-7-fluoro-6-[2-(piperazin-1-yl)pyrimidin-5-yl]imidazo[1,2-a]pyridin-2-yl)methoxy]phenyl}oxazolidin-2-one hydrochloride To a solution of Example 257 (50 mg, 0.067 mmol) in 1,4-dioxane (5 mL) was added 4M HCl in 1,4-dioxane (5 mL, 20 mmol), and the reaction mixture was stirred for 3 h. The solvent was removed in vacuo, and the residue was freeze-dried, to afford the title compound (25 mg, 58%). $\delta_H$ (300 MHz, DMSO-d$_6$) 9.23 (m, 2H), 8.68 (m, 1H), 8.63 (d, 2H, J 1.4 Hz), 7.86 (d, 1H, J 10.2 Hz), 7.29 (m, 4H), 7.19 (m, 1H), 7.12 (dd, 1H, J 7.8, 1.5 Hz), 7.08 (m, 2H), 6.77 (dd, 1H, J 8.0, 2.0 Hz), 5.25 (s, 2H), 4.56 (s, 2H), 4.43 (m, 2H), 4.02 (m, 6H), 3.19 (m, 4H). LCMS (ES+) 647 (M+H)$^+$, RT 1.90 minutes.

Example 259

3-{1-[2-(Difluoromethoxy)phenyl]ethyl}-7-fluoro-2-methyl-6-(1-methyl-1H-pyrazol-4-yl)imidazo[1,2-a]pyridine A mixture of Intermediate 263 (0.50 g, 1.25 mmol), (1-methylpyrazol-4-yl)-boronic acid pinacol ester (313 mg, 1.503 mmol) and sodium carbonate (398 mg, 3.76 mmol) in 1,2-dimethoxyethane (5 mL) and water (2.5 mL) was degassed with argon. trans-Bis(triphenylphosphine)palladium(II) chloride (88 mg, 0.125 mmol) was added and the mixture was stirred at 95° C. for 1 h. After concentration of the mixture, the solid was taken up in EtOAc (25 mL), and washed with water and brine, then dried over sodium sulfate and concentrated in vacuo. The crude residue was purified by flash column chromatography on silica gel (eluting with 1% to 10% methanol in DCM). The resulting crude material was purified by C18-reversed phase column (12 g, eluent: 5% water to 100% acetonitrile+0.1% formic acid). The collected fractions were lyophilised to give the title compound (312 mg, 62%) as an off-white foam. $\delta_H$ (400 MHz, DMSO-d$_6$) 8.42 (d, J 7.3 Hz, 1H), 8.06 (d, J 2.6 Hz, 1H), 7.80 (s, 1H), 7.57-7.55 (m, 1H), 7.40-7.24 (m, 4H), 7.14 (d, J 7.8 Hz, 1H), 7.10 (t, J 74.0 Hz, 1H), 4.94 (q, J 7.2 Hz, 1H), 3.90 (s, 3H), 2.19 (s, 3H), 1.70 (d, J 7.3 Hz, 3H). LCMS (pH 10): [M+H]$^+$ 401, RT 3.503 minutes.

Example 260

Butyl 1-[5-(3-{[2-(difluoromethoxy)phenyl]methyl}-7-fluoro-2-methylimidazo[1,2-a]-pyridin-6-yl)pyrimidin-2-yl]-4-methylpiperidine-4-carboxylate A suspension of the sodium salt of Example 46 (207 mg, 0.38 mmol) and tetra-n-butylammonium chloride (42 mg, 1.5 mmol) in DMSO (2.5 mL) was heated under microwave irradiation, in a sealed tube, to 180° C. for 10 minutes. The reaction mixture was diluted with EtOAc (30 mL), and washed with HCl (1M, 20 mL), water (2×20 mL) and brine (20 mL), then the organic layers were dried over MgSO$_4$ and the solvent was removed. The resulting crude yellow gum (270 mg) was purified by uv-directed preparative HPLC (pH 10 method eluting with 50-65% solvent B) to give the title compound (90 mg, 41%) as a colourless gum. $\delta_H$ (400 MHz, CD$_3$OD) 8.39 (s 2H), 8.10 (d, 1H, J 7.3 Hz), 7.32-7.26 (m 2H), 7.21 (m, 1H), 7.16 (t, 1H, J 7.7 Hz), 7.10-7.08 (m, 1H), 6.92 (t, 1H, J 74 Hz), 4.42 (t, 2H, J 4.0 Hz), 4.38 (s, 2H), 4.18 (t, 2H, J 6.4 Hz), 3.40-3.37 (m, 2H), 2.42 (s, 3H), 2.17 (d, 2H, J 13.6 Hz), 1.69 (m, 2H), 1.51-1.42 (m, 4H), 1.26 (s, 3H), 0.99 (t, 3H, J 7.3 Hz). HPLC-MS (pH 10): MH+ m/z 582.8, RT 3.04 minutes.

Examples 261 & 262

Methyl 4-[5-[3-[[2-(difluoromethoxy)phenyl]methyl]-7-fluoro-2-methylimidazo[1,2-a]pyridin-6-yl]pyrimidin-2-yl]-1-methylcyclohexanecarboxylate (cis and trans isomers)

To a suspension of Intermediate 274 (300 mg, 0.56 mmol) in EtOH (25 mL), MeOH (5 mL) and EtOAc (5 mL) was added palladium on carbon (30 mg) and the reaction mixture was heated at 50° C. under H$_2$ (1 atm) for 12 h. The reaction mixture was filtered and concentrated in vacuo, then the residue was purified by preparative HPLC.

Example 261 (cis isomer) (92 mg, 31%) was obtained as a white solid. LCMS (pH 10) m/z 539.8 [M+H]$^+$, RT 2.69 minutes.

Example 262 (trans isomer) (20 mg, 7%) was obtained as a white solid. LCMS (pH 10) m/z 539.8 [M+H]$^+$, RT 2.63 minutes.

Example 263 cis-4-[5-(3-{[2-(Difluoromethoxy)phenyl]methyl}-7-fluoro-2-methylimidazo[1,2-a]-pyridin-6-yl)pyrimidin-2-yl]-1-methylcyclohexanecarboxylic acid The title compound was synthesised from Example 261 in accordance with the method of Example 152. HPLC-MS (pH 10): MH+ m/z 525.8 [M+H]$^+$, RT 1.55 minutes.

Example 264

(8-anti)-3-(5-{3-[2-(Difluoromethoxy)benzyl]-7-fluoro-2-(hydroxymethyl)imidazo[1,2-a]pyridin-6-yl}pyrimidin-2-yl)-3-azabicyclo[3.2.1]octane-8-carboxylic acid meglumine salt A suspension of Intermediate 275 (200 mg, 0.35 mmol) in THF (5 mL) was treated with water (1 mL) and 10% aqueous NaOH solution (210 µL) and heated at 70° C. for 10 h. The reaction mixture was acidified by addition of acetic acid (2 mL) and partitioned between water (30 mL) and EtOAc (30 mL). The aqueous layer was extracted with 2-methyltetrahydrofuran (2×30 mL). The combined organic extracts were washed with water (30 mL) and brine (30 mL), then dried over MgSO$_4$ and concentrated in vacuo. The resulting crude solid was triturated in diisopropyl ether to give the carboxylic acid (117 mg) as an off-white solid. $\delta_H$ (300 MHz, DMSO-d$_6$) 12.20 (br s, 1H), 8.47 (d, 1H, J 1.7 Hz), 8.32 (d, 1H, J 7.3 Hz), 7.69 (d, 1H, J 6.3 Hz), 7.54 (d, 1H, J 11.2 Hz), 7.31-7.25 (m, 2H), 7.26 (t, 1H, J 74 Hz), 7.19 (m, 1H), 7.10 (m, 1H), 5.11 (br s, 1H), 4.58 (s, 2H), 4.45-4.38 (m, 4H), 3.02 (d, 2H, J 12 Hz), 2.68 (s, 1H), 2.59 (s, 2H), 1.71-1.65 (m, 2H), 1.40-1.35 (m, 2H), 1.04 (d, 2H, J 6 Hz). This material was dissolved in methanol (20 mL) and MeCN (10 mL) and treated with methylglucamine (42 mg, 211 mmol, added in methanol/water, 3 mL). The mixture was filtered and concentrated in vacuo to give the title compound (110 mg) as a pale, fluffy solid. LCMS (pH 10): m/z 554.8 [M+H]$^+$, RT 1.24 minutes.

Example 265

(3-{[2-(Difluoromethoxy)phenyl]methyl}-7-fluoro-6-[6-(methylsulfonyl)pyridin-3-yl]-imidazo[1,2-a]pyridin-2-yl)methanol Prepared from Intermediate 54 and 2-(methylsulfonyl)pyridine-5-boronic acid in accordance with General Method A. The title compound (38 mg, 16%) was obtained as a beige powder. $\delta_H$ (300 MHz, DMSO-d$_6$) 8.93 (s, 1H), 8.53 (d, 1H, J 8.0 Hz), 8.33 (dt, 1H, J 8.5, 1.9 Hz), 8.16 (dd, 1H, J 8.3, 0.6 Hz), 7.63 (d, 1H, J 13.5 Hz), 7.26 (t, 1H, J 74 Hz), 7.25-7.31 (m, 2H), 7.09 (m, 1H), 5.12 (t, 1H, J 5.5 Hz), 4.58 (d, 2H, J 5.5 Hz), 4.48 (s, 2H), 3.29 (s, 3H). LCMS (pH 10): m/z 460.6 [M−OH]$^+$, RT 1.74 minutes.

Example 266

2-{1-[7-Fluoro-2-methyl-6-(1-methyl-1H-pyrazol-4-yl)imidazo[1,2-a]pyridin-3-yl]ethyl}phenyl methanesulfonate A solution of Intermediate 270 (90 mg, 0.26 mmol) in pyridine (1 mL) was cooled to 0° C. and treated with methanesulfonyl chloride (59 mg, 0.51 mmol, 0.04 mL). The mixture was allowed to warm to room temperature and stirred for 3 h. Additional methanesulfonyl chloride (22.1 mg, 0.193 mmol) was added. After stirring for 90 minutes, the reaction mixture was concentrated in vacuo and EtOAc was added. The mixture was washed with water and brine, dried over $Na_2SO_4$ and concentrated in vacuo. The resulting crude product was purified by flash column chromatography on silica gel (eluting with 0.5% to 6% methanol in DCM). The isolated yellowish oil was lyophilised from acetonitrile and water to give the title compound (37.5 mg, 43%) as a white foam. LCMS (pH 10): $[M+H]^+$ 429, RT 3.351 minutes.

Example 267

2-{(1S or 1R)-1-[7-Fluoro-2-methyl-6-(1-methyl-1H-pyrazol-4-yl)imidazo[1,2-a]pyridin-3-yl]ethyl}phenyl methanesulfonate Purification of racemic Example 266 by SFC preparative HPLC using a Chiracel OD column (50×266 mm) at 25° C., eluting with 20% 2-propanol in $CO_2$ at 360 mL/minute, gave the title compound (10.1 mg, 39%) as a white solid. Chrial HPLC (Chiralcel OJ-H, EtOH 30%, n-heptane 70%, diethylamine 0.1%, 30° C., 1 mL/minute, 5 μm particle size): RT 7.35 minutes. Optical rotation +71.7°. LCMS (pH 10): m/z 429.6 [M+H]+. RT 1.98 minutes.

Example 268

3-[2-(Difluoromethoxy)benzyl]-2-methyl-6-[2-(methylsulfanyl)pyrimidin-5-yl]imidazo-[1,2-a]pyridine Prepared from Intermediate 7 and 2-(methylsulfanyl)-5-(4,4,5,5-tetramethyl-1,3,2-dioxaborolan-2-yl)pyrimidine (0.69 g, 4.1 mmol) in accordance with General Method A. The title compound (900 mg, 80%) was obtained as a pink solid. HPLC-MS (pH 10): m/z 413.6 $[M+H]^+$, RT 1.96 minutes.

Example 269

3-[2-(Difluoromethoxy)benzyl]-2-methyl-6-[2-(methylsulfonyl)pyrimidin-5-yl]imidazo-[1,2-a]pyridine A solution of Example 268 (4 g, 9.697 mmol) in MeOH (150 mL) and acetone (20 mL) at 0° C. was treated with Oxone® (potassium peroxymonosulfate; 11.92 g, 19.39 mmol) in water (100 mL). The resulting suspension was allowed to warm to r.t. and stirred for 18 h. The reaction mixture was treated with water and extracted with DCM (4×300 mL). The combined organic layers were concentrated in vacuo. A portion of the resulting crude yellow solid (4.4 g, 100%) was further purified by preparative HPLC to give the title compound (56 mg was obtained from 130 mg of crude material) as a white solid. HPLC-MS (pH 10): MH+ m/z 445.6 $[M+H]^+$, RT 1.54 minutes.

Example 270

1-(5-{3-[2-(Difluoromethoxy)benzyl]-7-fluoro-2-methylimidazo[1,2-a]pyridin-6-yl}-pyrimidin-2-yl)-4-methylpiperidine-4-carbonitrile Prepared from Intermediate 68 and Intermediate 265 in accordance with General Method A. The title compound (380 mg, 39%) was obtained as a white solid. HPLC-MS (pH 10): MH+ m/z 507.8 $[M+H]^+$, RT 2.38 minutes.

Example 271

5-(5-{3-[2-(Difluoromethoxy)benzyl]-2-methylimidazo[1,2-a]pyridin-6-yl}pyrimidin-2-yl)tetrahydro-2H-[1,2,5]thiadiazolo[2,3-a]pyrazin-3(3 aH)-one 1,1-dioxide Prepared from Intermediate 7 and Intermediate 266 in accordance with General Method A. The title compound (20 mg, 7%) was obtained as a white solid. HPLC-MS (pH 10): MH+ m/z 556.2 $[M+H]^+$, RT 0.70 minutes.

Example 272

1-(5-{3-[2-(Difluoromethoxy)benzyl]-2-methylimidazo[1,2-a]pyridin-6-yl}pyrimidin-2-yl)-N-methoxypiperidine-4-carboxamide A solution of Example 23 (0.108 g, 0.22 mmol), O-methylhydroxylamine hydrochloride (0.022 g, 0.26 mmol), 1-ethyl-3-(3-dimethylaminopropyl)carbodiimide hydrochloride (0.053 g, 0.26 mmol) and DIPEA (0.057 g, 0.44 mmol) in DMF (5 mL) was stirred at r.t. for 18 h. Further O-methylhydroxylamine hydrochloride (0.10 g, 1.2 mmol) and DIPEA (300 μL) were added and the reaction mixture was heated at 50° C. for 2 days. The reaction mixture was cooled to r.t., treated with water (10 mL) and extracted with DCM (3×50 mL). The combined organic layers were concentrated in vacuo, and the resulting orange oil was purified by FCC (eluting with 3-10% MeOH in DCM), to give the title compound (4 mg, 3%) as an orange solid. HPLC-MS (pH 10): MH+ m/z 523.8 $[M+H]^+$, RT 1.82 minutes.

Example 273

1-(5-{3-[2-(Difluoromethoxy)benzyl]-2-methylimidazo[1,2-a]pyridin-6-yl}pyrimidin-2-yl)-2-methyl-1,4-diazepan-5-one Prepared from Intermediate 267 and Intermediate 7 in accordance with General Method A. The title compound (47 mg, 18%) was obtained as a white solid. HPLC-MS (pH 10): MH+ m/z 493.8 $[M+H]^+$, RT 1.78 minutes.

Example 274

1-(5-{3-[2-(Difluoromethoxy)benzyl]-2-methylimidazo[1,2-a]pyridin-6-yl}pyrimidin-2-yl)-7-methyl-1,4-diazepan-5-one Prepared from Intermediate 268 and Intermediate 7 in accordance with General Method A. The title compound (46 mg, 17%) was obtained as a white solid. HPLC-MS (pH 10): MH+ m/z 493.8 [M+H]⁺, RT 1.81 minutes.

Example 275

1-(5-{3-[2-(Difluoromethoxy)benzyl]-2-methylimidazo[1,2-a]pyridin-6-yl}pyrimidin-2-yl)-N-(methylsulfonyl)piperidine-4-carboxamide A solution of Example 23 (0.138 g, 0.28 mmol) in DCM (6 mL) was treated with methanesulphonamide (0.1 g, 1.0 mmol 1), 1-ethyl-3-(3-dimethylaminopropyl)-carbodiimide hydrochloride (0.2 g, 1.0 mmol) and 4-(dimethylamino)pyridine (0.033 g, 0.28 mmol) and the mixture was heated to reflux for 3 days. The reaction mixture was concentrated in vacuo and the crude residue was partitioned between DCM (20 mL) and water (10 mL). The organic layer was concentrated in vacuo, and the crude residue purified by FCC on silica gel (eluting with 0-10% MeOH/DCM), to give the title compound (38 mg, 24%) as a white solid. HPLC-MS (pH 10): MH+ m/z 571.7 [M+H]⁺, RT 1.49 minutes.

Example 276

3-[2-(Difluoromethoxy)benzyl]-7-fluoro-2-(methoxymethyl)-6-{2-[4-(2H-tetrazol-5-yl)-piperidin-1-yl]pyrimidin-5-yl}imidazo[1,2-a]pyridine, sodium salt Prepared from Intermediate 55 and Intermediate 269 in accordance with General Method A. The title compound (120 mg, 60%) was obtained as a white solid. HPLC-MS (pH 10): m/z 566.8 [M+H]⁺, RT 1.73 minutes.

Example 277

3-[2-(Difluoromethoxy)benzyl]-2-methyl-6-{2-[(1R,5S)-3-oxa-8-azabicyclo[3.2.1]oct-8-yl]pyrimidin-5-yl}imidazo[1,2-a]pyridine A mixture of Intermediate 29 (0.25 g, 0.56 mmol), 3-oxa-8-azabicyclo[3.2.1]-octane hydrochloride (0.126 g, 0.84 mmol) and triethylamine (0.12 g, 1.13 mmol) was dissolved in THF (15 mL) and water (5 mL) and heated at 140° C. for 4 h under microwave irradiation. The reaction mixture was diluted with water and extracted with DCM (2×50 mL). The combined organic layers were concentrated in vacuo, and purified by FCC on silica gel (eluting with 0-2% MeOH in EtOAc), to give the title compound (23 mg, 9%) as a white solid. HPLC-MS (pH 10): m/z 478.8 [M+H]⁺, RT 2.29 minutes.

Example 278

3-[2-(Difluoromethoxy)benzyl]-2-methyl-6-{2-[4-(2H-tetrazol-5-yl)piperidin-1-yl]-pyrimidin-5-yl}imidazo[1,2-a]pyridine Prepared from Intermediate 7 and Intermediate 269 in accordance with General Method A. The title compound (32 mg, 11%) was obtained as a white solid. HPLC-MS (pH 10): m/z 518.8 [M+H]⁺, RT 1.73 minutes.

Example 279

3-[2-(Difluoromethoxy)benzyl]-6-{2-[(2R,6S)-2,6-dimethylmorpholin-4-yl]pyrimidin-5-yl}-2-methylimidazo[1,2-a]pyridine A solution of Intermediate 29 (0.2 g, 0.45 mmol), (2S,6R)-2,6-dimethyl-morpholine (0.067 g, 0.59 mmol) and triethylamine (0.092 g, 0.90 mmol) in THF (15 mL) and water (5 mL) was heated at 80° C. for 18 h. The reaction mixture was diluted with water (10 mL) and extracted with DCM (2×50 mL). The combined organic layers were concentrated in vacuo and purified by FCC on silica gel, eluting with 0-10% MeOH in EtOAc, to give the title compound (30 mg, 14%) as a white solid. HPLC-MS (pH10): m/z 480.8 [M+H]⁺, RT 2.13 minutes.

Example 280

Ethyl 1-(5-{3-[2-(difluoromethoxy)benzyl]-2-methylimidazo[1,2-a]pyridin-6-yl}-pyrimidin-2-yl)pyrrolidine-3-carboxylate Prepared from Example 7 and ethyl pyrrolidine-3-carboxylate hydrochloride in accordance with General Method B. The title compound (31 mg, 11%) was obtained as a white solid. HPLC-MS (pH 10): m/z 508.80 [M+H]⁺, RT 2.47 minutes.

Example 281

1-(5-{3-[2-(Difluoromethoxy)benzyl]-2-methylimidazo[1,2-a]pyridin-6-yl}pyrimidin-2-yl)pyrrolidine-3-carboxylic acid To a solution of Example 280 (0.11 g, 0.22 mmol) in THF (12 mL) and water (4 mL) was added 1M aqueous NaOH solution (0.22 mL). The resulting mixture was stirred for 18 h at r.t. and concentrated in vacuo. The crude residue was purified by preparative HPLC to afford the title compound (18 mg, 17%) as a white solid. HPLC-MS (pH 10): m/z 480.8 [M+H]⁺, RT 1.37 minutes.

Example 282

1-(5-{3-[2-(Difluoromethoxy)benzyl]-2-methylimidazo[1,2-a]pyridin-6-yl}pyrimidin-2-yl)azetidine-3-carboxylic acid Prepared from Intermediate 29 and azetidine-3-carboxylic acid in accordance with General Method B. The title compound (62 mg, 30%) was obtained as a white solid. HPLC-MS (pH 10): MH+ m/z 466.0 [M+H]⁺, RT 1.24 minutes.

Example 283

Ethyl 1-[5-(3-{1-[2-(difluoromethoxy)phenyl]ethyl}-7-fluoro-2-methylimidazo[1,2-a]-pyridin-6-yl)pyrimidin-2-yl]-4-methylpiperidine-4-carboxylate Intermediate 263 (500 mg, 1.25 mmol) and Intermediate 58 (514 mg, 1.75 mmol) were dissolved in 1,4-dioxane (40 mL), then tetrakis(triphenylphosphine)palladium(0) (72 mg, 0.0626 mmol) and 2.0M aqueous sodium carbonate solution (8 mL, 16 mmol) were added. The mixture was heated at 90° C. under nitrogen for 2 h, then partitioned between EtOAc (100 mL) and water (50 mL). The organic layer was washed with brine (50 mL), dried (Na$_2$SO$_4$), filtered and concentrated in vacuo. Purification by column chromatography (silica, 40 to 80% gradient EtOAc in isohexanes) gave the title compound (470 mg, 66%) as a foamy white solid. δ$_H$ (300 MHz, DMSO-d$_6$) 8.48 (d, 2H, J 1.6 Hz), 8.35 (d, 1H, J 7.5 Hz), 7.54 (dd, 1H, J 7.5, 1.6 Hz), 7.41 (d, 1H, J 11.3 Hz), 7.29 (m, 2H), 7.13 (d, 1H, J 7.5 Hz), 7.09 (t, 1H, J$_{H-F}$ 73.9 Hz), 4.92 (m, 1H), 4.28 (m, 2H), 4.14 (q, 2H, J 7.1 Hz), 3.29 (m, 2H), 2.19 (s, 3H), 2.03 (m, 2H), 1.69 (d, 3H, J 7.3 Hz), 1.43 (m, 2H), 1.21 (m, 6H). LCMS (pH 10) MH$^+$ (568.8), RT 2.99 minutes.

Example 284

1-[5-(3-{1-[2-(Difluoromethoxy)phenyl]ethyl}-7-fluoro-2-methylimidazo[1,2-a]pyridin-6-yl)pyrimidin-2-yl]-4-methylpiperidine-4-carboxylic acid Example 283 (75 mg, 0.18 mmol) was dissolved in THF (1 mL) and water (0.5 mL) was added, followed by LiOH.H$_2$O (30 mg, 0.72 mmol). The reaction mixture was heated at 40° C. for 3 h, then methanol (4 mL) was added and the mixture was heated at reflux overnight. The mixture was concentrated in vacuo and freeze-dried. The resultant solid was treated with acetic acid (100 µL) in DMSO (1 mL) and water (1 mL). The mixture was treated with silica, then freeze-dried to remove solvent. The residue was purified by chromatography (5 to 15% MeOH in CH$_2$Cl$_2$), then freeze-dried from MeCN/water overnight, to give the title compound (36 mg, 51%) as a white solid. δ$_H$ (300 MHz, DMSO-d$_6$) 12.30 (br s, 1H), 8.40 (d, 2H, J 1.6 Hz), 8.27 (d, 1H, J 7.5 Hz), 7.47 (dd, 1H, J 7.5, 1.7 Hz), 7.26 (m, 3H), 7.06 (m, 1H), 7.02 (t, 1H, J 74.0 Hz), 4.86 (m, 1H), 4.21 (dt, 2H, J 13.4, 4.1 Hz), 3.27 (m, 2H), 2.13 (s, 3H), 1.94 (m, 2H), 1.62 (d, 3H, J 7.3 Hz), 1.32 (m, 2H), 1.12 (s, 3H). LCMS (pH 10): MH$^+$ (540.8), RT 1.97 minutes.

Example 285

1-[5-(3-{[2-(Difluoromethoxy)phenyl]methyl}-7-fluoro-2-methylimidazo[1,2-a]pyridin-6-yl)pyrimidin-2-yl]piperidin-4-one Intermediate 68 (1.00 g, 2.60 mmol), 1-[5-(4,4,5,5-tetramethyl-1,3,2-dioxaborolan-2-yl)pyrimidin-2-yl]piperidin-4-one (0.945 g, 3.12 mmol) and tetrakis-(triphenylphosphine) palladium(0) (0.150 g, 0.130 mmol) were dissolved in 1,4-dioxane (40 mL) and 2.0M aqueous sodium carbonate solution (8 mL, 16 mmol) was added. The mixture was heated to 100° C. for 4 h. The reaction mixture was cooled and diluted with ethyl acetate (150 mL), and washed with water (150 mL) and brine (50 mL), then dried over Na$_2$SO$_4$ and concentrated in vacuo. The residual solid was recrystalised from EtOAc:isohexanes (1:2, 30 mL) to give the title compound (1.05 g, 2.18 mmol) as an off-white solid. δ$_H$ (300 MHz, DMSO-d$_6$) 8.58 (d, 2H, J 1.6 Hz), 8.37 (d, 1H, J 7.5 Hz), 7.50 (m, 1H), 7.30 (m, 2H), 7.15 (m, 2H), 7.00 (m, 1H), 4.34 (s, 2H), 4.10 (t, 4H, J 6.1 Hz), 2.44 (t, 4H, J 6.2 Hz), 2.28 (s, 3H). LCMS (pH 10): MH$^+$ (482.8), RT 2.08 minutes.

Example 286

1-[5-(3-{[2-(Difluoromethoxy)phenyl]methyl}-7-fluoro-2-methylimidazo[1,2-a]pyridin-6-yl)pyrimidin-2-yl]-4-methylpiperidin-4-ol Example 285 (150 mg, 0.31 mmol) was dissolved in dry tetrahydrofuran (10 mL) and cooled to −78° C. under nitrogen. Methylmagnesium bromide (114 µL, 0.34 mmol, 3.00M) was added, and the stirred mixture was allowed to warm to room temperature over 3 h. The reaction mixture was quenched with water (50 mL) and extracted with EtOAc (50 mL), then dried (Na$_2$SO$_4$), filtered and concentrated in vacuo. The residue was subjected to column chromatography (silica, 50 to 80% EtOAc in isohexanes). The product fractions were concentrated in vacuo and triturated with diethyl ether. The resulting white solid was dried under vacuum to give the title product (35 mg, 23%) as a white solid. δ$_H$ (300 MHz, DMSO-d$_6$) 8.46 (d, 2H, J 1.6 Hz), 8.34 (d, 1H, J 7.5 Hz), 7.46 (d, 1H, J 11.3 Hz), 7.30 (m, 2H), 7.15 (m, 2H), 7.00 (m, 1H), 4.42 (s, 1H), 4.33 (s, 2H), 4.22 (m, 2H), 3.45 (m, 2H), 2.28 (s, 3H), 1.47 (m, 4H), 1.15 (s, 3H). LCMS (pH 10): MH$^+$ (498.8), RT 2.21 minutes.

Example 287

1-[5-(3-{[2-(Difluoromethoxy)phenyl]methyl}-7-fluoro-2-methylimidazo[1,2-a]pyridin-6-yl)pyrimidin-2-yl]-4-(trifluoromethyl)piperidin-4-ol Example 285 (150 mg, 0.31 mmol) was dissolved in dry tetrahydrofuran (10 mL and (trifluoromethyl)trimethylsilane (51 µL, 0.35 mmol) was added, followed by cesium fluoride (52 mg, 0.34 mmol). The mixture was stirred at room temperature for 4 h. 2M HCl solution (1 mL) was added and the mixture was stirred at room temperature for 10 minutes. The mixture was basified with saturated sodium carbonate solution (3 mL), then extracted with EtOAc (75 mL) and water (50 mL). The organic layer was dried (Na$_2$SO$_4$), filtered and concentrated in vacuo. The residue was purified by column chromatography to give the title compound (45 mg, 26%) as an off-white solid. δ$_H$ (300 MHz, DMSO-d$_6$) 8.31 (d, 2H, J 1.5 Hz), 8.16 (d, 1H, J 7.4 Hz), 7.27 (d, 1H, J 11.3 Hz), 7.09 (m, 1H), 7.06 (t, 1H, J 73.9 Hz), 6.94 (m, 2H), 6.80 (m, 1H), 5.95 (s, 1H), 4.48 (m, 2H), 4.13 (s, 2H), 2.98 (m, 2H), 2.08 (s, 3H), 1.56 (m, 2H), 1.42 (m, 2H). LCMS (pH 10): MH$^+$ (552.7), RT 2.48 minutes.

Example 288

(3R)-1-[5-(3-{[2-(Difluoromethoxy)phenyl]methyl}-2-methylimidazo[1,2-a]pyridin-6-yl)pyrimidin-2-yl]piperidine-3-carboxylic acid Prepared from Intermediate 7 (500 mg, 1.36 mmol) and Intermediate 276 (470 mg, 1.63 mmol) in accordance with General Method A to give the title compound (178 mg, 27%) as a white solid. δ$_H$ (300 MHz, DMSO-d$_6$) 8.62 (s, 2H), 8.37 (s, 1H), 7.53 (m, 1H), 7.45 (m, 1H), 7.29 (m, 1H), 7.28 (t, 1H, J 74.0 Hz) 7.16 (m, 2H), 7.04 (m, 1H), 4.74 (m, 1H), 4.54 (m, 1H), 4.35 (s, 2H), 2.95 (m, 2H), 2.31 (s, 3H), 2.18 (m, 1H), 1.99 (m, 1H), 1.69 (m, 1H), 1.57 (m, 1H), 1.39 (m, 1H). LCMS (pH 10): MH$^+$ (494.8), RT 1.55 minutes.

Example 289

3 (S)-1-[5-(3-{[2-(Difluoromethoxy)phenyl]methyl}-2-methylimidazo[1,2-a]pyridin-6-yl)pyrimidin-2-yl]piperidine-3-carboxylic acid Prepared from Intermediate 7 (500 mg, 1.36 mmol) and Intermediate 277 (470 mg, 1.63 mmol) in accordance with General Method A to give the title compound (128 mg, 19%) as a white solid. δ$_H$ (300 MHz, DMSO-d$_6$) 8.62 (s, 2H), 8.37 (s, 1H), 7.53 (m, 1H), 7.45 (m, 1H), 7.29 (m, 1H), 7.28 (t, 1H, J 74.0 Hz) 7.16 (m, 2H), 7.04 (m, 1H), 4.74 (m, 1H), 4.54 (m, 1H), 4.35 (s, 2H), 2.95 (m, 2H), 2.31 (s, 3H), 2.18 (m, 1H), 1.99 (m, 1H), 1.69 (m, 1H), 1.57 (m, 1H), 1.39 (m, 1H). LCMS (pH 10): MH$^+$ (494.8), RT 1.55 minutes.

Example 290

Methyl 1-[5-(3-{[2-(difluoromethoxy)phenyl]methyl}-7-fluoro-2-methylimidazo[1,2-a]-pyridin-6-yl)pyrimidin-2-yl]piperidine-4-carboxylate Intermediate 68 (1.50 g, 3.89 mmol), [2-(4-(methoxycarbonyl)piperidin-1-yl)-pyrimidin-5-yl]boronic acid (synthesised in an analogous method to Intermediate 37; 1.55 g, 5.84 mmol) and tetrakis(triphenylphosphine)palladium(0) (225 mg, 0.194 mmol) were dissolved in 1,4-dioxane (40 mL) and 2.0M aqueous sodium carbonate solution (8 mL, 16 mmol) was added. The mixture was heated to 100° C. for 4 h. The mixture was cooled, diluted with ethyl acetate (150 mL), washed with water (150 mL) and brine (50 mL), then dried over anhydrous sodium sulphate, filtered and concentrated in vacuo. The crude material was purified by chromatography (silica, 60% to 90% EtOAc in isohexane) to give the title compound (1.35 g, 66.0%) as an off-white solid. $\delta_H$ (300 MHz, DMSO-d$_6$) 8.49 (d, 2H, J 1.6 Hz), 8.35 (d, 1H, J 7.4 Hz), 7.45 (d, 1H, J 11.4 Hz), 7.30 (m, 1H), 7.26 (t, 1H, J 74.1 Hz), 7.15 (m, 2H), 7.01 (m, 1H), 4.56 (dt, 2H, J 13.2, 3.3 Hz), 4.33 (s, 2H), 3.62 (s, 3H), 3.12 (m, 2H), 2.69 (m, 1H), 2.28 (s, 3H), 1.91 (dd, 2H, J 13.3, 3.4 Hz), 1.51 (m, 2H). LCMS (pH 10): MH$^+$ (526.8), RT 2.35 minutes.

Example 291

Sodium 1-[5-(3-{[2-(difluoromethoxy)phenyl]methyl}-7-fluoro-2-methylimidazo[1,2-a]-pyridin-6-yl)pyrimidin-2-yl]piperidine-4-carboxylate Example 290 (650 mg, 1.24 mmol) was dissolved in tetrahydrofuran (10 mL). Water (5 mL) and lithium hydroxide monohydrate (104 mg, 2.47 mmol) were added, and the mixture was stirred at room temperature for 6 h. The solution was concentrated in vacuo to remove the THF, then treated with acetic acid (150 μL, 2.5 mmol) to neutralise the base. The resultant solids were filtered off and washed with water, then freeze-dried to give a white solid (545 mg, 1.07 mmol). A batch (350 mg, 0.68 mmol) was dissolved in hot ethanol (20 mL), then NaOH (27.2 mg, 0.68 mmol) dissolved in ethanol/water (1:1, 1 mL) was added. The mixture was heated to dissolve all material, then allowed to crystallize for three days. The solid was filtered off, and dried under high vacuum, to give the title compound (215 mg) as a white solid. $\delta_H$ (300 MHz, DMSO-d$_6$) 8.45 (d, 2H, J 1.6 Hz), 8.35 (d, 1H, J 7.4 Hz), 7.45 (d, 1H, J 11.3 Hz), 7.32 (m, 1H), 7.27 (t, 1H, J$_{H-F}$ 74.1 Hz), 7.15 (m, 2H), 7.02 (m, 1H), 4.41 (m, 2H), 4.33 (s, 2H), 3.10 (m, 2H), 2.28 (s, 3H), 2.05 (m, 1H), 1.75 (m, 2H), 1.46 (m, 2H). LCMS (pH 10): MH$^+$ (512.8), RT 1.77 minutes.

Example 292

(2R)-4-[5-(3-{[2-(Difluoromethoxy)phenyl]methyl}-7-fluoro-2-(methoxymethyl)imidazo-[1,2-a]pyridin-6-yl)pyrimidin-2-yl]morpholine-2-carboxylic acid Intermediate 279 (343 mg, 0.650 mmol) and Intermediate 55 (189 mg, 0.433 mmol) were dissolved in dry 1,4-dioxane (15 mL), then 2M aqueous sodium carbonate solution (1.5 mL, 3.0 mmol) and tetrakis(triphenylphosphine)palladium (0) (25.1 mg, 0.0217 mmol) were added and the mixture was heated to 100° C. under nitrogen for 18 h. The mixture was diluted with water (75 mL), acidified to pH 4.5 with acetic acid (~2 mL) and extracted with ethyl acetate. The organic layers were dried (Na$_2$SO$_4$), filtered and concentrated in vacuo. The residue was purified by chromatography (silica, 12 g, eluent: DCM:MeOH:H$_2$O:AcOH 187:10:1:2), then freeze-dried overnight, to give the title compound (49 mg, 21%) as an off-white solid. $\delta_H$ (300 MHz, DMSO-d$_6$) 8.53 (d, 2H, J 1.6 Hz), 8.37 (d, 1H, J 7.3 Hz), 7.55 (d, 1H, J 11.2 Hz), 7.21 (m, 4H), 6.98 (m, 1H), 4.50 (m, 1H), 4.49 (s, 2H), 4.42 (s, 2H), 4.20 (m, 1H), 3.97 (m, 2H), 3.53 (m, 1H), 3.30 (m, 2H), 3.22 (s, 3H). LCMS (pH 10): MH$^+$ (544.8), RT 1.54 minutes.

Example 293

2(S)-4-[5-(3-{[2-(difluoromethoxy)phenyl]methyl}-7-fluoro-2-(methoxymethyl)imidazo-[1,2-a]pyridin-6-yl)pyrimidin-2-yl]morpholine-2-carboxylic acid Prepared from Intermediate 278 and Intermediate 55 in an analogous manner to Example 292 to yield the title compound (35 mg) as a white solid. $\delta_H$ (300 MHz, DMSO-d$_6$) 8.53 (d, 2H, J 1.6 Hz), 8.37 (d, 1H, J 7.3 Hz), 7.55 (d, 1H, J 11.2 Hz), 7.21 (m, 4H), 6.98 (m, 1H), 4.50 (m, 1H), 4.49 (s, 2H), 4.42 (s, 2H), 4.20 (m, 1H), 3.97 (m, 2H), 3.53 (m, 1H), 3.30 (m, 2H), 3.22 (s, 3H). LCMS (pH 10): MH$^+$ (544.8), RT 1.54 minutes.

Example 294

(1R,5S)-3-[5-(3-{[2-(Difluoromethoxy)phenyl]methyl}-2-methylimidazo[1,2-a]pyridin-6-yl)pyrimidin-2-yl]-3-azabicyclo[3.1.0]hexane-6-carboxylic acid Intermediate 29 (250 mg, 0.563 mmol) was dissolved in 1,4-dioxane (10 mL), and ethyl (1S,5R)-3-azabicyclo[3.1.0]hexane-6-carboxylate hydrochloride (105 mg, 0.59 mmol) and triethylamine (0.121 g, 1.18 mmol) were added. The mixture was heated at 100° C. for 18 h. The mixture was concentrated in vacuo, then partitioned between water and EtOAc. The organic layer was concentrated in vacuo. The crude residue was dissolved in THF (10 mL) and water (5 mL), and 1M aqueous NaOH solution (0.6 mL, 0.6 mmol) was added. The mixture was stirred for 16 h before being concentrated in vacuo. Purification by preparative HPLC at pH 3 gave the title compound (7.0 mg, 2.5%) as a white solid. $\delta_H$ (300 MHz, DMSO-d$_6$) 8.63 (s, 2H), 8.37 (s, 1H), 7.54 (m, 1H), 7.45 (m, 1H), 7.29 (m, 1H), 7.28 (t, 1H, J 74 Hz), 7.15 (m, 2H), 7.03 (m, 1H), 4.35 (s, 2H), 3.87 (d, 2H, J 11.5 Hz), 3.56 (m, 2H), 2.31 (s, 3H), 2.11 (s, 2H), 1.32 (t, 1H, J 3.0 Hz). LCMS (pH 10): MH$^+$ (492.7), RT 1.34 minutes.

Example 295

1-[5-(3-{[2-(Difluoromethoxy)phenyl](hydroxy)methyl}-2-methylimidazo[1,2-a]pyridin-6-yl)pyrimidin-2-yl]piperidine-4-carboxylic acid Prepared from Intermediate 6 (250 mg, 0.652 mmol) and Intermediate 37 (197 mg, 0.783 mmol) in accordance with General Method A to afford the title compound (53 mg, 16%) as a white solid. $\delta_H$ (300 MHz, DMSO-d$_6$) 12.26 (s, 1H), 8.60 (s, 2H), 8.54 (s, 1H), 8.01 (dd, 1H, J 5.7, 3.5 Hz), 7.50 (m, 2H), 7.38 (m, 2H), 7.11 (m, 1H), 7.11 (t, 1H, J 74.0 Hz), 6.44 (d, 1H, J 4.3 Hz), 6.18 (d, 1H, J 4.3 Hz), 4.57 (m, 2H), 3.12 (m, 2H), 2.59 (m, 1H), 2.17 (s, 3H), 1.91 (m, 2H), 1.50 (m, 2H). LCMS (pH10): MH+ (510.8), RT 1.17 minutes.

Example 296

3-{[2-(Difluoromethoxy)phenyl]methyl-}6-(2,3-dimethyl-3H-imidazol-4-yl)-2-methylimidazo[1,2-a]pyridine Prepared from Intermediate 7 (250 mg, 0.681 mmol) and 1,2-dimethyl-5-(4,4,5,5-tetramethyl-1,3,2-dioxaborolan-2-yl)-1H-imidazole (185 mg, 0.817 mmol) in accordance with General Method A to afford the title compound (40 mg, 15%) as a pale brown solid. $\delta_H$ (300 MHz, DMSO-$d_6$) 8.08 (m, 1H), 7.54 (m, 1H), 7.22 (m, 5H), 7.04 (m, 1H), 6.83 (s, 1H), 4.32 (s, 2H), 3.40 (s, 3H), 2.35 (s, 3H), 2.33 (s, 3H). LCMS (pH 10): MH+ (383.8), RT 1.84 minutes.

Example 297

Ethyl 1-[5-(7-chloro-3-{[2-(difluoromethoxy)phenyl]methyl}-2-methylimidazo[1,2-a]-pyridin-6-yl)pyrimidin-2-yl]-4-methylpiperidine-4-carboxylate Prepared from Intermediate 255 (0.5 g, 1.245 mmol) and Intermediate 58 in accordance with General Method A to afford the title compound (0.395 g, 56%) as a white solid. $\delta_H$ (400 MHz, DMSO-$d_6$) 8.41 (s, 2H), 8.31 (s, 1H), 7.77 (s, 1H), 7.30 (m, 1H), 7.25 (t, 1H, J 78 Hz), 7.25 (s, 1H), 7.16 (m, 2H), 7.00 (d, 1H, J 7.4 Hz), 4.33 (s, 2H), 4.27 (m, 3H), 4.15 (q, 2H, J 7.1 Hz), 2.30 (s, 4H), 2.03 (m, 2H), 1.43 (m, 2H), 1.20 (m, 5H). LCMS (pH 10): MH+ 570.2, RT 1.73 minutes.

Example 298

Sodium 1-[5-(7-chloro-3-{[2-(difluoromethoxy)phenyl]methyl}-2-methylimidazo[1,2-a]-pyridin-6-yl)pyrimidin-2-yl]-4-methylpiperidine-4-carboxylate To a suspension of Example 297 (0.40 g, 0.71 mmol) in THF (4 mL) and methanol (4 mL) was added 1M aqueous sodium hydroxide solution (0.67 mL, 0.68 mmol), and the mixture was heated at 55° C. The mixture was stirred at room temperature overnight. The mixture was concentrated in vacuo to remove the organic solvents and the residue was treated with diethyl ether (50 mL). The ether was decanted and the aqueous layer was diluted with water, then freeze dried, to give the title compound (0.39 g, 97%) as an off-white solid. $\delta_H$ 1.07 (s, 3H), 1.22 (m, 2H), 2.02 (m, 2H), 2.28 (m, 2H), 2.35 (s, 3H), 4.29 (m, 4H), 6.99 (m, 1H), 7.14 (m, 2H), 7.24 (s, 1H), 7.30 (m, 2H), 7.49 (s, 1H), 7.75 (d, J 0.2 Hz, 1H), 8.30 (s, 1H), 8.36 (s, 2H). LCMS (pH 3): MH+ 540.0, RT 2.02 minutes. LCMS (pH 10): MH+ 540.0, RT 1.69 minutes.

Example 299

1-[5-(3-{[2-(Difluoromethoxy)phenyl]methyl}-7-fluoro-2-methylimidazo[1,2-a]pyridin-6-yl)pyrimidin-2-yl]-4-(nitromethyl)piperidin-4-ol To a suspension of Example 285 (0.3 g, 0.62 mmol) in THF (4.45 g, 61.7 mmol, 5.01 mL) was added triethylamine (1.5 mL, 11 mmol, 1.5 mL), followed by nitromethane (0.75 mL, 14 mmol, 0.75 mL). The mixture was stirred at room temperature for 2 days. To the reaction mixture was added diethyl ether (5 mL), and the suspension was filtered and washed on a sinter with diethyl ether, to give the title compound (0.228 g, 67%) as a white solid. $\delta_H$ (400 MHz, DMSO-$d_6$) 8.51 (d, 2H, J 1.5 Hz), 8.51 (d, J 1.5 Hz), 8.34 (d, 1H, J 7.5 Hz), 8.34 (d, J 7.5 Hz), 7.46 (m, 1H), 7.30 (m, 1H), 7.20 (m, 1H), 7.14 (td, 1H, J 7.6, 0.9 Hz), 7.01 (dd, 1H, J 7.6, 1.2 Hz), 4.58 (s, 2H), 4.43 (m, 2H), 4.34 (s, 2H), 3.35 (m, 4H), 2.56 (s, 5H), 2.29 (s, 3H), 1.67 (m, 4H). LCMS (pH 3): MH+ 543.2, RT 1.73 minutes.

Example 300

Ethyl 1-[5-(3-{(amino) [2-(difluoromethoxy)phenyl]methyl}-2-methylimidazo[1,2-a]-pyridin-6-yl)pyrimidin-2-yl]-4-methylpiperidine-4-carboxylate Prepared from Intermediate 281 (0.40 g, 1.05 mmol) and Intermediate 58 (0.37 g, 1.27 mmol) in accordance with General Method A to give the title compound (0.165 g, 28%) as a white solid. $\delta_H$ (400 MHz, DMSO-$d_6$) 8.64 (s, 1H), 8.61 (s, 2H), 8.03 (m, 1H), 7.46 (m, 2H), 7.35 (m, 2H), 7.11 (m, 2H), 5.87 (s), 5.87 (s, 1H), 4.28 (m, 2H), 4.15 (q, 2H, J 7.0 Hz), 3.33 (m), 2.19 (s, 3H), 2.04 (d, 2H, J 13.5 Hz), 1.44 (m, 2H), 1.22 (m, 6H). LCMS (pH 10): MH+ 551.2, RT 1.53 minutes.

Example 301

Sodium 1-[5-(3-{(amino)[2-(difluoromethoxy)phenyl]methyl}-2-methylimidazo[1,2-a]-pyridin-6-yl)pyrimidin-2-yl]-4-methylpiperidine-4-carboxylate To a suspension of Example 300 (0.155 g, 0.2815 mmol) in THF (1 mL) and methanol (1 mL) was added 1.0M aqueous sodium hydroxide solution (0.27 mL, 0.28 mmol) and the mixture was heated at 60° C. for a total of 18 h. The mixture was concentrated in vacuo and re-dissolved in water (10 mL), then frozen and freeze-dried, to afford the title compound (0.138 g, 90%) as an off white solid. $\delta_H$ (400 MHz, DMSO-$d_6$) 8.62 (d, 1H, J 0.2 Hz), 8.54 (s, 2H), 8.04 (m, 1H), 7.42 (m, 3H), 7.11 (m, 1H), 5.87 (m, 1H), 4.32 (m, 2H), 3.25 (m, 2H), 2.42 (d, 2H, J 5.6 Hz), 2.20 (s, 3H), 2.08 (m, 2H), 1.10 (m, 2H), 0.99 (s, 3H). LCMS (pH 3): MH+ 523.8, RT 1.48 minutes.

Example 302

1-[5-(3-{(Amino) [2-(difluoromethoxy)phenyl]methyl}-2-methylimidazo[1,2-a]pyridin-6-yl)pyrimidin-2-yl]-1,4-diazepan-5-one Prepared from Intermediate 281 (0.4 g, 1.047 mmol) and Intermediate 72 (0.27 g, 1.15 mmol) in accordance with General Method A to give the title compound (0.380 g, 74%) as an off-white solid. $\delta_H$ (400 MHz, DMSO-$d_6$) 8.66 (m, 3H), 8.03 (m, 1H), 7.69 (m, 1H), 7.47 (m, 2H), 7.36 (m, 2H), 7.10 (m, 2H), 5.88 (s, 1H), 3.98 (m, 4H), 3.24 (m, 2H), 2.19 (s, 3H). LCMS (pH 10): MH+ 494.8, RT 1.59 minutes.

Example 303

N-([2-(Difluoromethoxy)phenyl]{2-methyl-6-[2-(morpholin-4-yl)pyrimidin-5-yl]imidazo-[1,2-a]pyridin-3-yl}methyl)acetamide Prepared from Intermediate 280 (0.25 g, 0.59 mmol) and Intermediate 38 (0.136 g, 0.65 mmol) in accordance with General Method A to provide the title compound (0.074 g, 25%) as a pale grey powder. $\delta_H$ (400 MHz, DMSO-$d_6$) 9.00 (d, 1H, J 8.2 Hz), 8.64 (s, 1H), 8.30 (m, 1H), 7.63 (m, 1H), 7.57 (m, 2H), 7.46 (m, 2H), 7.33 (m, 2H), 7.20 (m, 1H), 7.12 (s, 1H), 7.09 (s, 1H), 6.92 (d, 1H, J 14.2 Hz), 6.83 (d, 1H, J 8.3 Hz), 6.73 (d, 1H, J 8.1 Hz), 3.73 (m, 7H), 2.03 (d, 3H, J 14.9 Hz), 1.96 (s, 3H). LCMS (pH 10): MH+ 509.8, RT 1.755 minutes.

Example 304

2-([2-(Difluoromethoxy)phenyl]{2-methyl-6-[2-(morpholin-4-yl)pyrimidin-5-yl]imidazo-[1,2-a]pyridin-3-yl}methoxy)acetic acid To a solution of Intermediate 283 (0.1 g, 0.172 mmol) in DCM (5 mL) at room temperature was added trifluoroacetic acid (0.7 g, 6 mmol, 0.5 mL) and the mixture was stirred overnight. The mixture was placed under vacuum to remove TFA. The residue was triturated in diethyl ether to give the title compound (0.079 g, 87%) as a white solid. $\delta_H$ (400 MHz, DMSO-d$_6$) 9.25 (s, 1H), 8.81 (s, 2H), 8.17 (d, 1H, J 9.0 Hz), 7.93 (m, 2H), 7.49 (m, 2H), 7.26 (d, 1H, J 8.0 Hz), 7.17 (s, 1H), 6.56 (s, 1H), 4.23 (m, 3H), 3.75 (m, 10H), 2.11 (s, 3H). LCMS (pH 3): MH+ 526.8, RT 1.56 minutes.

Example 305

6-Bromo-3-{(1R or 1S)-1-[2-(difluoromethoxy)phenyl]ethyl}-2-methylimidazo[1,2-a]-pyridine (Enantiomer A)

A portion of Intermediate 284 was separated by chiral HPLC to yield the title compound. $\delta_H$ (400 MHz, CDCl$_3$) 7.88 (d, 1H, J 1.3 Hz), 7.32 (d, 1H, J 9.4 Hz), 7.20 (m, 3H), 7.10 (m, 1H), 7.05 (m, 2H), 6.37 (t, 1H, J 73.8 Hz), 4.68 (q, 1H, J 7.4 Hz), 2.40 (s, 3H), 1.70 (d, 3H, J 7.4 Hz). LCMS (pH 3): MH+ 381, 383, RT 1.67 minutes.

Example 306

6-Bromo-3-{(1R or 1S)-1-[2-(difluoromethoxy)phenyl]ethyl}-2-methylimidazo[1,2-a]-pyridine (Enantiomer B)

A portion of Intermediate 284 was separated by chiral HPLC to yield the title compound. $\delta_H$ (400 MHz, CDCl$_3$) 7.88 (d, 1H, J 1.3 Hz), 7.32 (d, 1H, J 9.4 Hz), 7.20 (m, 3H), 7.10 (m, 1H), 7.05 (m, 2H), 6.37 (t, 1H, J 73.8 Hz), 4.68 (q, 1H, J 7.4 Hz), 2.40 (m, 3H), 1.70 (d, 3H, J 7.4 Hz). LCMS (pH 3): MH+ 381, 383, RT 1.67 minutes.

Example 307

1-[5-(3-{1-[2-(Difluoromethoxy)phenyl]ethyl}-2-methylimidazo[1,2-a]pyridin-6-yl)-pyrimidin-2-yl]-1,4-diazepan-5-one Prepared from Intermediate 284 (0.2 g, 0.52 mmol) and Intermediate 72 (0.136 g, 0.57 mmol) in accordance with General Method A to give the title compound (118 mg, 46%) as a white solid. $\delta_H$ (400 MHz, DMSO-d$_6$) 8.67 (s, 2H), 8.38 (s, 1H), 7.69 (m, 1H), 7.54 (m, 1H), 7.53 (m), 7.44 (m, 1H), 7.31 (m, 2H), 7.14 (m, 2H), 5.76 (s), 4.97 (m, 1H), 3.98 (m, 4H), 3.23 (m, 2H), 2.26 (s, 3H), 1.73 (m, 3H). LCMS (pH 3): MH+ 493.8, RT 1.65 minutes.

Example 308

Methyl 1-[5-(3-{1-[2-(difluoromethoxy)phenyl]ethyl}-2-methylimidazo[1,2-a]pyridin-6-yl)pyrimidin-2-yl]piperidine-4-carboxylate Prepared from Intermediate 284 (0.36 g, 0.94 mmol) and {2-[4-(methoxycarbonyl)piperidin-1-yl]pyrimidin-5-yl}boronic acid (synthesised in an analogous manner to Intermediate 61; 0.30 g, 1.13 mmol) in accordance with General Method A to give the title compound (0.32 g, 65%) as a white foam. $\delta_H$ (400 MHz, DMSO-d$_6$) 8.63 (s, 2H), 8.36 (s, 1H), 7.56 (dd, 1H, J 7.6, 1.5 Hz), 7.47 (m, 2H), 7.33 (m, 1H), 7.27 (m, 1H), 7.15 (d, 1H, J 7.8 Hz), 4.96 (m, 1H), 4.58 (m, 2H), 3.63 (m, 3H), 3.13 (m, 2H), 2.71 (m, 1H), 2.26 (s, 3H), 1.93 (m, 2H), 1.92 (m), 1.73 (d, 3H, J 7.3 Hz), 1.53 (m, 2H). LCMS (pH 3): MH+ 522.8, RT 2.20 minutes.

Example 309

1-[5-(3-{1-[2-(Difluoromethoxy)phenyl]ethyl}-2-methylimidazo[1,2-a]pyridin-6-yl)-pyrimidin-2-yl]piperidine-4-carboxylic acid To a solution of Example 308 (0.28 g, 0.54 mmol) in THF (4 mL) at room temperature was added lithium hydroxide monohydrate (0.04 g, 0.81 mmol) in water (1 mL). The mixture was stirred for 2 h. The solution was adjusted to pH 6 by dropwise addition of acetic acid. The volatiles were removed in vacuo and the residue was treated with acetone (2 mL), causing a thick solid precipitate to form. The mixture was filtered and washed on the sinter with water and acetone, then dried in vacuo, to give the title compound (0.216 g, 79%) as a white solid. $\delta_H$ (400 MHz, DMSO-d$_6$) 8.59 (s, 2H), 8.59 (s), 8.33 (s, 1H), 8.33 (s), 7.56 (dd, 1H, J 7.5, 1.3 Hz), 7.45 (m, 2H), 7.33 (m, 1H), 7.27 (m, 1H), 7.16 (d, 1H, J 8.1 Hz), 7.13 (t, 1H, J 78 Hz), 4.96 (m, 1H), 4.47 (m, 2H), 3.10 (m, 2H), 2.18 (m, 1H), 1.80 (m, 2H), 1.72 (m, 9H), 1.49 (m, 2H). LCMS (pH 3): MH+ 508.8, RT 1.77 minutes.

Example 310

4-[5-(3-{[2-(Difluoromethoxy)phenyl](methoxy)methyl}-2-methylimidazo[1,2-a]pyridin-6-yl)pyrimidin-2-yl]morpholine Prepared from Intermediate 285 (0.2 g, 0.55 mmol) and Intermediate 38 (0.12 g, 0.55 mmol) in accordance with General Method A to give the title compound (0.05 g, 20%) as a white solid. $\delta_H$ (300 MHz, DMSO-d$_6$) 8.66 (s, 2H), 8.56 (t, 1H, J 1.1 Hz), 7.84 (dd, 1H, J 7.3, 2.0 Hz), 7.53 (m, 2H), 7.38 (m, 2H), 7.16 (m, 2H), 6.17 (s, 1H), 3.72 (m, 8H), 3.33 (s, 3H), 2.20 (s, 3H). LCMS (pH 3): MH+ 482.8, RT 1.88 minutes.

Example 311

Benzyl 2-[2-(difluoromethoxy)phenyl]-2-{2-methyl-6-[2-(5-oxo-1,4-diazepan-1-yl)-pyrimidin-5-yl]imidazo[1,2-a]pyridin-3-yl}acetate Prepared from Intermediate 286 (0.4 g, 0.8 mmol) and Intermediate 72 (0.226 g, 0.96 mmol) in accordance with General Method A to give the title compound (0.254 g, 50%) as a pale solid. $\delta_H$ (400 MHz, DMSO-d$_6$) 8.61 (s, 2H), 8.39 (s, 1H), 7.68 (m, 1H), 7.55 (m, 3H), 7.41 (m, 1H), 7.26 (m, 6H), 7.18 (t, 1H, J 7.6 Hz), 6.97 (d, 1H, J 7.3 Hz), 6.02 (s, 1H), 5.23

Example 312

2-[2-(Difluoromethoxy)phenyl]-2-{2-methyl-6-[2-(5-oxo-1,4-diazepan-1-yl)pyrimidin-5-yl]imidazo[1,2-a]pyridin-3-yl}acetic acid To a solution of Example 311 (0.219 g, 0.358 mmol) in THF (4 mL) was added lithium hydroxide monohydrate (0.03 g, 0.716 mmol) and the mixture was stirred at room temperature for 4 h. The pH of the mixture was adjusted to ~6 by the dropwise addition of a 10% aqueous solution of citric acid. The material was concentrated in vacuo, and the residue was washed with acetone, to furnish the title compound (0.135 g, 72%). $\delta_H$ (300 MHz, DMSO-d$_6$) 8.57 (m, 3H), 7.66 (m, 1H), 7.51 (m, OH), 7.41 (dd, OH, J 9.3, 1.5 Hz), 7.23 (m, 1H), 7.09 (m, 2H), 6.99 (m, OH), 5.31 (m, OH), 3.95 (d, 4H, J 3.9 Hz), 3.20 (m, 2H), 2.25 (s, 3H). LCMS (pH 10): MH+ 523.2, RT 1.05 minutes.

Example 313

1-[2-(Difluoromethoxy)phenyl]-1-{2-methyl-6-[6-(piperazin-1-yl)pyridin-3-yl]imidazo-[1,2-a]pyridin-3-yl}ethanol To a solution of Intermediate 288 (0.145 g, 0.2502 mmol) in DCM (5 mL) at 0-5° C. was added trifluoroacetic acid (0.7 g, 6 mmol, 0.5 mL). The mixture was warmed to room temperature. After a further 1.5 h the reaction mixture was quenched by addition of saturated aqueous NaHCO$_3$ solution (3 mL) and DCM (5 mL). The organic layers were separated and washed with brine (2 mL), then dried (Na$_2$SO$_4$), filtered and concentrated in vacuo. The resulting crude residue was purified by preparative mass-directed HPLC to give the title compound (46 mg, 38%) as a white solid. $\delta_H$ (300 MHz, DMSO-d$_6$) 8.21 (dd, 1H, J 1.6, 0.9 Hz), 8.14 (m, 1H), 8.04 (d, 1H, J 2.4 Hz), 7.45 (m, 1H), 7.42 (d, OH, J 0.7 Hz), 7.36 (m, 3H), 7.02 (m, 1H), 7.11 (t, 1H, J 78 Hz), 6.85 (d, 1H, J 8.9 Hz), 6.27 (s, 1H), 3.43 (m, 5H), 2.77 (m, 4H), 2.56 (s, 3H), 2.05 (s, 3H). LCMS (pH 10): MH+ 480.8, RT 1.34 minutes.

Example 314

[2-(Difluoromethoxy)phenyl]{2-methyl-6-[6-(piperazin-1-yl)pyridin-3-yl]imidazo[1,2-a]-pyridin-3-yl}methanol To a suspension of Intermediate 289 (0.1 g, 0.176 mmol) in DCM (5 mL) was added trifluoroacetic acid (0.5 mL, 6 mmol). The mixture was stirred at room temperature for 1 h. The mixture was concentrated in vacuo and the residue was treated with saturated aqueous NaHCO$_3$ solution (~5 mL), then filtered and sucked dry on a sinter overnight, to give the title compound (0.072 g, 87%) as a pale grey powder. $\delta_H$ (400 MHz, DMSO-d$_6$) 8.48 (s, 1H), 8.34 (d, 1H, J 2.4 Hz), 8.00 (dd, 1H, J 5.8, 3.8 Hz), 7.75 (dd, 1H, J 8.9, 2.6 Hz), 7.48 (m, 2H), 7.39 (dd, 2H, J 5.9, 3.5 Hz), 7.14 (m, 1H), 7.13 (t, 1H, J 78 Hz), 6.94 (d, 1H, J 3.1 Hz), 6.43 (d, 1H, J 4.3 Hz), 6.18 (d, 1H, J 4.4 Hz), 3.50 (m, 4H), 2.84 (m, 4H), 2.19 (s, 3H). LCMS (pH 3): MH+ 467.2, RT 1.10 minutes.

Example 315

4-[5-[3-[1-[2-(Difluoromethoxy)phenyl]ethyl]-2-methylimidazo[1,2-a]pyridin-6-yl]pyrimidin-2-yl]morpholine Can be prepared from Intermediate 284 and Intermediate 38 in accordance with General Method A to give the title compound as a pale solid. $\delta_H$ (400 MHz, DMSO-d$_6$) 8.48 (s, 2H), 7.91 (s, 1H), 7.59 (m, 1H), 7.50 (m, 3H), 7.37 (td, 1H, J 7.5, 1.0 Hz), 7.19 (d, 1H, J 8.1 Hz), 6.94 (t, 1H, J 74.0 Hz), 5.85 (d, 2H, J 23.5 Hz), 3.70 (m, 9H), 2.25 (s, 3H). LCMS (pH 10): MH+ 466.8, RT 1.91 minutes.

Example 316

2-[5-(3-{[2-(Difluoromethoxy)phenyl](hydroxy)methyl}-7-fluoro-2-methylimidazo[1,2-a]pyridin-6-yl)pyrimidin-2-yl]propan-2-ol Can be prepared from Intermediate 67 and 2-[5-(4,4,5,5-tetramethyl-1,3,2-dioxaborolan-2-yl)pyrimidin-2-yl]propan-2-ol in accordance with General Method A to give the title compound as a white solid. $\delta_H$ (400 MHz, DMSO-d$_6$) 8.94 (d, 2H, J 1.4 Hz), 8.73 (d, 1H, J 7.4 Hz), 7.98 (dd, 1H, J 7.1, 1.8 Hz), 7.54 (d, 1H, J 11.3 Hz), 7.38 (m, 2H), 7.12 (m, 2H), 6.46 (d, 1H, J 4.5 Hz), 6.20 (d, 1H, J 4.5 Hz), 5.17 (s, 1H), 2.11 (s, 3H), 1.56 (s, 6H). LCMS (pH 10): m/z 459 (M+H)$^+$, RT 1.80 minutes.

Alternative Method

To a suspension of Intermediate 311 (200 mg, 1 eq) in 2-propanol (10 mL) was added sodium borohydride (1 eq) in one portion and the reaction mixture was stirred at ambient temperature for 1 h. The reaction mixture was quenched by the addition of saturated aqueous ammonium chloride solution (50 mL), then extracted with ethyl acetate (3×100 mL). The combined organic layers were washed with brine (200 mL), dried over sodium sulphate and filtered, then the solvents were removed in vacuo. The resultant crude residue was purified by column chromatography on silica (eluent: 0 to 30% isopropanol in DCM), followed by freeze-drying from isopropanol/acetonitrile/water mixture, to give the title compound (82 mg) as an off white solid.

Example 317

2-[5-(3-{[2-(Difluoromethoxy)phenyl]methyl}-2-methylimidazo[1,2-a]pyridin-6-yl)-pyridin-2-yl]propan-2-ol Intermediate 292 (90 mg, 0.30 mmol) and Intermediate 31 (124 mg, 0.36 mmol) were dissolved in 1,4-dioxane (5 mL) and 2M aqueous potassium carbonate solution (0.46 mL) was added. The mixture was degassed thoroughly under nitrogen. Pd(dppf)Cl$_2$ complex with dichloromethane (11 mg, 0.015 mmol) was added. The mixture was heated at 105° C. in a sealed tube for 2 h. The reaction mixture was then cooled to room temperature. Ethyl acetate (10 mL) was added and the mixture was filtered through plug of Celite. After further washings with ethyl acetate (3×10 mL), the combined organic layers were washed with brine (15 mL), dried over sodium sulphate and filtered, then the solvent was removed in vacuo. The dark brown oil was purified by chromatography on silica (Biotage, 10 g cartridge), eluting with 0 to 100% ethyl acetate in heptanes, to afford an orange-brown oil (68 mg, 44%). To the foregoing material (112 mg, 0.217 mmol), dissolved in ethyl acetate (5 mL), was added 1M TBAF solution in THF (1 mL), and the reaction mixture was stirred for 1 h at room temperature. The reaction mixture was quenched with water (5 mL) and extracted with ethyl acetate (2×5 mL). The combined organic layers were washed successively with water and brine, dried over sodium sulfate, filtered and concentrated under reduced pressure. The resulting crude brown solid product (123 mg) was dissolved in ethyl acetate and a minimum amount of heptanes was added. The sample was heated until dissolved, then cooled to afford a beige-white precipitate. Slow evaporation of solvents with nitrogen, followed by filtering of the solid and drying in a vacuum oven, afforded the title compound (85 mg, 93%) as a beige solid. $\delta_H$ (500 MHz, DMSO-$d_6$) 8.76 (d, J 2.3 Hz, 1H), 8.49 (s, 1H), 8.04 (dd, J 8.3, 2.4 Hz, 1H), 7.73 (d, J 8.3 Hz, 1H), 7.59 (d, J 9.2 Hz, 1H), 7.55 (dd, J 9.3, 1.6 Hz, 1H), 7.30 (t, J 74.1 Hz, 1H), 7.31-7.27 (m, 1H), 7.21 (d, J 8.1 Hz, 1H), 7.17-7.11 (m, 1H), 7.07-7.03 (m, 1H), 5.27 (s, 1H), 4.40 (s, 2H), 2.33 (s, 3H), 1.47 (s, 6H). Method D HPLC-MS: MH+ m/z 424, RT 1.77 minutes.

Example 318

4-[5-(3-{[2-(Difluoromethoxy)phenyl]methyl}-2-methylimidazo[1,2-a]pyridin-6-yl)-pyridin-2-yl]oxan-4-ol Prepared from Intermediate 310 (50 mg, 0.19 mmol) and Intermediate 31 (65 mg, 0.18 mmol) in accordance with General Method A to give the title compound as an off-white solid. $\delta_H$ (500 MHz, DMSO-$d_6$) 8.81 (d, J 2.3 Hz, 1H), 8.51 (s, 1H), 8.07 (dd, J 8.3, 2.4 Hz, 1H), 7.75 (d, J 8.3 Hz, 1H), 7.59 (d, J 9.2 Hz, 1H), 7.55 (dd, J 9.3, 1.6 Hz, 1H), 7.31-7.28 (m, 1H), 7.30 (t, J 74.1 Hz, 1H), 7.20 (d, J 8.1 Hz, 1H), 7.16-7.11 (m, 1H), 7.06-7.02 (m, 1H), 5.33 (s, 1H), 4.40 (s, 2H), 3.81-3.72 (m, 4H), 2.33 (s, 3H), 2.21 (td, J 12.9, 5.5 Hz, 2H), 1.48 (d, J 12.3 Hz, 2H). Method D HPLC-MS: MH+ m/z 466, RT 1.78 minutes.

Example 319

4-[5-(3-{[2-(Difluoromethoxy)phenyl]methyl}-7-fluoro-2-methylimidazo[1,2-a]pyridin-6-yl)pyrimidin-2-yl]oxan-4-ol Intermediate 303 (57 mg, 0.15 mmol) and Intermediate 68 (58 mg, 0.15 mmol) were dissolved in a mixture of 2M aqueous $K_2CO_3$ solution (0.23 mL) and 1,4-dioxane (1 mL). The solution was degassed for 10 minutes under a stream of nitrogen, then Pd(dppf)Cl$_2$ complex with DCM (12 mg, 15 µmol) was added. The reaction mixture was heated under microwave irradiation at 110° C. for 1 h. TBAF in THF (1M, 0.45 mL) was added and the reaction mixture was stirred for 1 h. Additional 1M TBAF in THF (0.45 mL) was added and the reaction mixture was stirred at room temperature overnight. The solvent was removed under reduced pressure, and the crude brown oil was purified by chromatography on silica (Biotage, 10 g cartridge), eluting with 20-100% EtOAc in heptanes. The resulting crude material was purified by preparative HPLC (Method D) to afford the title compound (9 mg, 12%) as a brown oil. $\delta_H$ (500 MHz, CDCl$_3$) 8.87 (d, J 1.2 Hz, 2H), 7.58 (d, J 10.7 Hz, 1H), 7.38-7.31 (m, 1H), 7.19 (dd, J 10.6, 7.3 Hz, 2H), 7.12 (t, J 7.6 Hz, 1H), 6.68 (m, 2H), 5.42 (s, 2H), 4.02-3.92 (m, 4H), 2.63 (s, 3H), 2.44 (td, J 12.8, 6.1 Hz, 2H), 1.57 (d, J 11.9 Hz, 2H). Method D HPLC-MS: MH+ m/z 485, RT 1.83 minutes.

Example 320 tert-Butyl 3-[5-(3-{[2-(difluoromethoxy)phenyl]methyl}-7-fluoro-2-methylimidazo[1,2-a]pyridin-6-yl)pyrimidin-2-yl]-3-hydroxyazetidine-1-carboxylate Intermediate 295 (700 mg, 1.56 mmol) and Intermediate 68 (500 mg, 1.30 mmol) were dissolved in 1,4-dioxane (20 mL) and 2M aqueous potassium carbonate solution (2 mL) was added. The mixture was degassed with nitrogen for 5 minutes. PdCl$_2$(dppf) complex with DCM (55 mg, 0.067 mmol) was added. The mixture was stirred at 100° C. under nitrogen for 17 h. The reaction mixture was allowed to cool, then treated with 1M TBAF in THF (4 mL) and stirred at room temperature for 1 h. The reaction mixture was partitioned between ethyl acetate (30 mL) and water (50 mL). The aqueous layer was separated and extracted with further ethyl acetate (30 mL). The combined organic phases were dried over sodium sulfate and concentrated under vacuum. The resulting dark oil (884 mg) was loaded onto a 25 g KP-silica cartridge, eluting with a 0-100% ethyl acetate in heptanes gradient, followed by a 0-5% methanol in ethyl acetate gradient, to afford the title compound (346 mg, 44%) as a light brown coloured solid. $\delta_H$ (500 MHz, CDCl$_3$) 8.83 (s, 2H), 7.85 (d, J 6.9 Hz, 1H), 7.43 (d, J 10.4 Hz, 1H), 7.29 (td, J 8.3, 1.5 Hz, 1H), 7.17 (d, J 7.9 Hz, 1H), 7.12 (td, J 7.6, 0.9 Hz, 1H), 6.96-6.90 (m, 1H), 6.63 (t, J 73.6 Hz, 1H), 5.15 (s, 1H), 4.41 (d, J 9.0 Hz, 2H), 4.30 (s, 2H), 4.25 (d, J 9.1 Hz, 2H), 2.54 (s, 3H), 1.49 (s, 9H). Method D HPLC-MS: MH+ m/z 556, RT 2.37 minutes.

Example 321

2-[5-(3-{[2-(Difluoromethoxy)phenyl]methyl}-7-fluoro-2-methylimidazo[1,2-a]pyridin-6-yl)pyridin-2-yl]propan-2-ol Intermediate 292 (250 mg, 0.83 mmol) and Intermediate 290 (493.3 mg, 0.92 mmol) were dissolved in 1,4-dioxane (8 mL) and 2M aqueous potassium carbonate solution (1.27 mL) was added. The mixture was degassed thoroughly under nitrogen. Pd(dppf)Cl$_2$ complex with dichloromethane (31 mg, 0.042 mmol) was added. The mixture was heated at 105° C. in a sealed tube for 2 h. The reaction mixture was then cooled to room temperature. Ethyl acetate (10 mL) was added and the mixture was filtered through plug of Celite. After further washings with ethyl acetate (3×10 mL), the combined organic layers were washed with brine (15 mL), dried over sodium sulphate and filtered, then the solvent was removed in vacuo. The crude dark brown oil was purified by chromatography on silica (Biotage 10 g cartridge), eluting with 0 to 100% ethyl acetate in heptane, to afford a yellow oil (372 mg, 47%). To a solution of the foregoing material (372 mg, 0.5 mmol) in ethyl acetate (15 mL) was added a 1M solution of TBAF in THF (2.5 mL) and the reaction mixture was stirred for 1 h at room temperature. The reaction mixture was quenched with water (5 mL) and extracted with ethyl acetate (2×5 mL). The combined organic layers were washed successively with water (3×5 mL) and brine, dried over sodium sulfate, filtered and concentrated under reduced pressure. The resulting crude brown oil was purified by preparative HPLC (Method C), followed by trituration from water, to afford the title compound (68 mg, 31%) as a beige solid. $\delta_H$ (500 MHz, CDCl$_3$) 8.54 (s, 1H), 7.80 (ddd, J 6.5, 4.4, 2.2 Hz, 2H), 7.49 (d, J 8.2 Hz, 1H), 7.38 (d, J 10.5 Hz, 1H), 7.34-7.29 (m, 1H), 7.19 (d, J 8.0 Hz, 1H), 7.13 (t, J 7.5 Hz, 1H), 6.92 (d, J 7.7 Hz, 1H), 6.64 (t, J 73.6 Hz, 1H), 4.75 (br s, 1H), 4.31 (s, 2H), 2.53 (s, 3H), 1.60 (s, 6H). Method D HPLC-MS: MH+ m/z 442, RT 1.86 minutes.

Example 322

3-[5-(3-{[2-(Difluoromethoxy)phenyl]methyl}-7-fluoro-2-methylimidazo[1,2-a]pyridin-6-yl)pyrimidin-2-yl]oxetan-3-ol Intermediate 299 (379 mg, 0.49 mmol) was dissolved in anhydrous THF (15 mL), then a 1M TBAF solution in THF (2.50 mL, 2.50 mmol) was added. The reaction mixture was stirred at room temperature for 1 h. The mixture was quenched with water (5 mL) and the aqueous phase was extracted with ethyl acetate (2×10 mL). The combined organic layers were washed with water (10 mL) and brine (10 mL). The organic phase was dried over sodium sulphate, filtered and concentrated in vacuo. The crude brown oil was purified by chromatography on silica (Biotage, 25 g cartridge), eluting with 0 to 3% methanol in dichloromethane, followed by preparative HPLC (Method C), to afford the title compound (73.2 mg, 32%) as a white solid. $\delta_H$ (500 MHz, DMSO-$d_6$) 9.06 (d, J 1.3 Hz, 2H), 8.61 (d, J 7.3 Hz, 1H), 7.56 (d, J 11.4 Hz, 1H), 7.43-7.13 (m, 3H), 7.12 (d, J 8.7 Hz, 1H), 7.06-7.01 (m, 1H), 6.44 (s, 1H), 5.01 (d, J 6.6 Hz, 2H), 4.72 (d, J 6.6 Hz, 2H), 4.37 (s, 2H), 2.28 (s, 3H). Method D HPLC-MS: MH+ m/z 457, RT 1.64 minutes. Melting point: 143-144° C.

Example 323

[4-(3-{[2-(Difluoromethoxy)phenyl]methyl}-7-fluoro-2-methylimidazo[1,2-a]pyridin-6-yl)phenyl]methanamine formate salt Prepared from Intermediate 68 (0.25 g, 0.65 mmol) and [4-(aminomethyl)phenyl]-boronic acid (0.11 g, 0.71 mmol) in accordance with General Method A to give the title compound (75 mg, 26%) as a colourless solid. $\delta_H$ (500 MHz, DMSO-$d_6$) 8.23 (d, J 7.4 Hz, 1H), 7.52 (s, 3H), 7.45 (d, J 11.4 Hz, 1H), 7.28 (dd, J 16.5, 8.5 Hz, 1H), 7.25 (t, J 74 Hz, 1H), 7.18 (d, J 8.1 Hz, 1H), 7.13 (t, J 7.5 Hz, 1H), 7.03 (d, J 7.3 Hz, 1H), 4.35 (s, 2H), 3.98 (s, 2H), 2.30 (s, 3H). Method D HPLC-MS: MH+ m/z 412, RT 1.26 minutes.

Example 324

4-[5-(3-{[2-(Difluoromethoxy)phenyl]methyl}-7-fluoro-2-methylimidazo[1,2-a]pyridin-6-yl)pyrimidin-2-yl]-1-methylpiperidin-4-ol Intermediate 290 (444 mg, 1.03 mmol), Intermediate 304 (254 mg, 0.93 mmol) and 2M aqueous sodium bicarbonate solution (1.8 mL) were combined in 1,4-dioxane (5 mL) and the mixture was degassed thoroughly under nitrogen. $PdCl_2$ (dppf) complex with DCM (50 mg, 0.06 mmol) was added and the mixture was heated at 80° C. in a sealed tube for 1.5 h. The reaction mixture was cooled to room temperature and diluted using saturated sodium bicarbonate solution (1 mL). The mixture was extracted using ethyl acetate (3×10 mL). The combined organic phase was washed using brine (5 mL), dried over magnesium sulphate, filtered and concentrated under vacuum. The crude brown residue was purified by chromatography on silica (Biotage, 10 g cartridge), eluting with 0 to 10% 7N methanolic ammonia in DCM. Product fractions were combined and concentrated under vacuum, then purified using preparative HPLC (Method D), to afford the title compound (22 mg, 4.7%) as a pale brown coloured solid. $\delta_H$ (250 MHz, $CDCl_3$) 8.76 (d, J 1.6 Hz, 2H), 7.78 (d, J 7.0 Hz, 1H), 7.33 (d, J 10.8 Hz, 1H), 7.26 (m, 1H), 7.20-7.02 (m, 2H), 6.88 (dd, J 7.6, 1.5 Hz, 1H), 6.62 (t, J 73.6 Hz, 1H), 4.41 (s, 1H), 4.28 (s, 2H), 2.81 (d, J 9.9 Hz, 2H), 2.63-2.43 (m, 6H), 2.38 (d, J 7.4 Hz, 4H), 1.67 (d, J 11.4 Hz, 2H). Method D HPLC-MS: MH+ m/z 498, RT 1.12 minutes.

Example 325

3-[5-(3-{[2-(Difluoromethoxy)phenyl]methyl}-7-fluoro-2-methylimidazo[1,2-a]pyridin-6-yl)pyrimidin-2-yl]azetidin-3-ol formic acid salt A solution of Example 320 (92%, 346 mg, 0.573 mmol) in 1,4-dioxane (3 mL) was treated with 4M hydrogen chloride in 1,4-dioxane (2.8 mL). The mixture was placed in a sonic bath for 15 minutes, then stirred at room temperature for 2 h to give a suspension. The reaction mixture was concentrated under vacuum, and purified by preparative HPLC (Method A), to afford the title compound (36 mg, 12.5%) as a colourless solid. $\delta_H$ (500 MHz, $CD_3OD$) 9.05 (d, J 1.4 Hz, 2H), 8.38 (d, J 7.1 Hz, 1H), 8.23 (s, 1H), 7.41 (d, J 10.8 Hz, 1H), 7.33-7.27 (m, 1H), 7.18 (d, J 8.0 Hz, 1H), 7.16-7.12 (m, 1H), 7.11 (dd, J 7.7, 1.8 Hz, 1H), 6.91 (t, J 74.0 Hz, 1H), 4.64 (d, J 11.8 Hz, 2H), 4.42 (s, 2H), 4.33 (d, J 11.8 Hz, 2H), 2.42 (s, 3H). Method D HPLC-MS: MH+ m/z 456, RT 0.98 minutes.

Example 326

3-[5-(3-{[2-(Difluoromethoxy)phenyl]methyl}-7-fluoro-2-methylimidazo[1,2-a]pyridin-6-yl)pyrimidin-2-yl]-1-methylazetidin-3-ol formic acid salt To a suspension of Example 325 (81%, 195 mg, 0.3 mmol) in ethanol (4 mL) was added 37% aqueous formaldehyde solution (0.1 mL, 1.33 mmol) and the resulting solution was stirred at room temperature for 20 minutes. Sodium triacetoxyborohydride (160 mg, 0.76 mmol) was added in one portion, followed by acetic acid (0.1 mL), and the whole mixture was stirred at room temperature under nitrogen for 2 h. The reaction mixture was diluted and neutralised with saturated sodium bicarbonate solution (15 mL). The crude material was then extracted into dichloromethane (2×20 mL). The combined organic extracts were dried over sodium sulphate, filtered and concentrated under vacuum. The resulting brown oil (140 mg) was purified by preparative HPLC (Method A) to afford the title compound (27 mg, 17%) as a colourless solid. $\delta_H$ (500 MHz, $CD_3OD$) 9.05 (d, J 1.4 Hz, 2H), 8.38-8.35 (m, 2H), 7.41 (d, J 10.9 Hz, 1H), 7.33-7.27 (m, 1H), 7.18 (d, J 7.9 Hz, 1H), 7.14 (td, J 7.6, 0.9 Hz, 1H), 7.10 (dd, J 7.6, 1.7 Hz, 1H), 6.91 (t, J 74.0 Hz, 1H), 4.72 (d, J 11.3 Hz, 2H), 4.42 (s, 2H), 4.35 (d, J 11.4 Hz, 2H), 3.08 (s, 3H), 2.42 (s, 3H). Method D HPLC-MS: MH+ m/z 470, RT 1.09 minutes.

Example 327

2-[5-(3-{[2-(Difluoromethoxy)phenyl]methyl}-7-fluoro-2-methylimidazo[1,2-a]pyridin-6-yl)-1,3-thiazol-2-yl]propan-2-ol A suspension of Intermediate 68 (49 mg, 0.13 mmol), 2-[5-(tributylstannyl)-1,3-thiazol-2-yl]propan-2-ol (50 mg, 0.12 mmol) and potassium acetate (34 mg, 0.35 mmol) was degassed for 15 minutes under a stream of $N_2$ gas. Pd(dppf)

Cl₂ complex with dichloromethane (9 mg, 0.01 mmol) was added and the suspension was degassed for a further 5 minutes. The reaction mixture was heated under microwave irradiation for 1 h at 100° C. with stirring. The reaction mixture was next heated at 110° C. for 4 h, then concentrated and redissolved in EtOAc (3 mL). The organic solution was washed with water (3 mL), then the organic phase was dried over MgSO₄, filtered and concentrated under reduced pressure. The crude residue was purified by preparative HPLC (Method D) to afford the title compound (22 mg, 42%) as an off white solid. $\delta_H$ (500 MHz, CD₃OD) 8.32 (d, J 6.9 Hz, 1H), 7.87 (d, J 1.0 Hz, 1H), 7.35 (d, J 10.9 Hz, 1H), 7.31 (td, J 7.7, 6.8, 2.3 Hz, 1H), 7.21 (d, J 8.1 Hz, 1H), 7.19-7.12 (m, 2H), 6.92 (t, J 74.0 Hz, 1H), 4.39 (s, 2H), 2.42 (s, 3H), 1.63 (s, 6H). Method D HPLC-MS: MH+ m/z 448, RT 1.99 minutes.

Example 328

1-[5-(3-{[2-(Difluoromethoxy)phenyl]methyl}-7-fluoro-2-methylimidazo[1,2-a]pyridin-6-yl)pyrimidin-2-yl]cyclobutan-1-ol Intermediate 68 (350 mg, 0.91 mmol) and Intermediate 309 (73%, 500 mg, 1.05 mmol) were dissolved in dry 1,4-dioxane (6 mL) and 2M aqueous K₂CO₃ solution (1.4 mL) was added. The resulting mixture was degassed with nitrogen for 10 minutes, then PdCl₂(dppf) complex with DCM (50 mg, 0.06 mmol) was added. The reaction mixture was heated at 80° C. for 1 h in a sealed tube. TBAF solution in THF (1M, 5 mL) was added and the reaction mixture was allowed to stir for 1 h at r.t. The reaction mixture was concentrated under vacuum, diluted with EtOAc (25 mL), and washed with aqueous NaHCO₃ solution (15 mL), water (20 mL) and brine (15 mL), then dried over sodium sulfate, filtered and concentrated under vacuum. The residue was purified by chromatography on silica (Biotage, 10 g cartridge), eluting with 0-10% methanol in DCM, to afford the title compound (65 mg, 15%) as a light brown solid. $\delta_H$ (500 MHz, CDCl₃) 8.78 (s, 2H), 7.82 (d, J 6.9 Hz, 1H), 7.45 (d, J 10.5 Hz, 1H), 7.31-7.26 (m, 1H), 7.17 (d, J 8.0 Hz, 1H), 7.14-7.08 (m, 1H), 6.94-6.88 (m, 1H), 6.63 (t, J 73.6 Hz, 1H), 4.29 (s, 2H), 2.66 (ddt, J 13.3, 9.0, 3.7 Hz, 2H), 2.56-2.47 (m, 5H), 2.17-1.99 (m, 2H). Method D (uPLC)-MS: MH+ m/z 456, RT 2.01 minutes.

Example 329

4-[5-(3-{[2-(Difluoromethoxy)phenyl]methyl}-7-fluoro-2-methylimidazo[1,2-a]pyridin-6-yl)pyrimidin-2-yl]-4-hydroxycyclohexane-1-carboxylic acid A solution of Intermediate 306 (0.1 g, 0.18 mmol) in THF (0.5 mL) and 2M aqueous LiOH solution (0.27 mL) was heated at 40° C. under microwave irradiation with stirring. Aqueous NaOH solution (5N, 0.25 mL) was added and the reaction mixture was heated at 60° C. for a total of 5 h under microwave irradiation. The reaction mixture was acidified to pH 1 with 6M HCl, then extracted with EtOAc. The organic layer was separated and the volatiles were removed under reduced pressure. The crude residue was purified using preparative HPLC (Method A), to afford the title compound (28 mg, 29%) as a pale brown solid. $\delta_H$ (500 MHz, DMSO-d₆) 12.06 (s, 1H), 8.97 (s, 2H), 8.60 (d, J 7.3 Hz, 1H), 7.55 (d, J 11.3 Hz, 1H), 7.29 (t, J 7.5 Hz, 2H), 7.25 (t, J 74 Hz, 1H), 7.18 (d, J 8.1 Hz, 1H), 7.12 (t, J 8.0 Hz, 1H), 7.02 (d, J 7.3 Hz, 1H), 5.01 (s, 1H), 4.35 (s, 2H), 2.30-2.23 (m, 4H), 2.00-1.72 (m, 8H). Method D HPLC-MS: MH+ m/z 527, RT 1.88 minutes.

Examples 330 & 331

2-(5-{3-[(1R or 1S)-1-[2-(Difluoromethoxy)phenyl]ethyl]-2-methylimidazo[1,2-a]-pyridin-6-yl}pyrimidin-2-yl)propan-2-ol (Enantiomers A and B)

A suspension of Intermediate 284 (0.32 g, 0.84 mmol), 2-[5-(4,4,5,5-tetramethyl-1,3,2-dioxaborolan-2-yl)pyrimidin-2-yl]propan-2-ol (0.23 g, 0.88 mmol) and Pd(dppf)Cl₂ complex with dichloromethane (0.07 g, 0.08 mmol) in 1,4-dioxane (10 mL) and 2M aqueous K₂CO₃ solution (1.2 mL) was degassed under a stream of N₂ for 15 minutes. The reaction vessel was sealed and heated at 90° C. for 1 h. The reaction mixture was cooled and diluted with EtOAc (20 mL), then washed with water (20 mL). The organic layer was dried over MgSO₄, filtered and concentrated under reduced pressure. The resulting crude material was purified by chromatography on silica (Biotage, 10 g cartridge), eluting with 40-100% EtOAc in heptanes, to afford a brown oil (275 mg) (racemic mixture of enantiomers). A sample (100 mg) of the enantiomer mixture was separated on a 25 cm OD-H column, eluting with 90% heptane:10% ethanol, to afford Enantiomer A (23 mg, 6%; RT 19.9 minutes) and Enantiomer B (22 mg, 6%; RT 37.3 minutes).

Example 330 (Enantiomer A): $\delta_H$ (500 MHz, CDCl₃) 8.78 (s, 2H), 8.02 (s, 1H), 7.65 (d, J 9.2 Hz, 1H), 7.32-7.24 (m, 3H), 7.23-7.16 (m, 1H), 7.13 (d, J 8.1 Hz, 1H), 6.48 (t, J 73.9 Hz, 1H), 4.87 (q, J 7.3 Hz, 1H), 4.60 (s, 1H), 2.56 (s, 3H), 1.82 (d, J 7.4 Hz, 3H), 1.63 (s, 6H). Method D HPLC-MS: MH+ m/z 439, RT 1.91 minutes.

Example 331 (Enantiomer B): $\delta_H$ (500 MHz, CDCl₃) 8.78 (s, 2H), 8.02 (s, 1H), 7.65 (d, J 9.2 Hz, 1H), 7.26 (m, 3H), 7.23-7.17 (m, 1H), 7.13 (d, J 8.1 Hz, 1H), 6.48 (t, J 73.9 Hz, 1H), 4.87 (q, J 7.4 Hz, 1H), 4.60 (s, 1H), 2.56 (s, 3H), 1.82 (d, J 7.4 Hz, 3H), 1.63 (s, 6H). Method D HPLC-MS: MH+ m/z 439, RT 1.91 minutes.

Example 332

2-[5-(3-{[2-(Difluoromethoxy)phenyl]methyl}-7-fluoro-2-methylimidazo[1,2-a]pyridin-6-yl)pyrazin-2-yl]propan-2-ol Intermediate 290 (50%, 300 mg, 0.35 mmol), Intermediate 301 (95%, 94.58 mg, 0.52 mmol) and 2M aqueous sodium bicarbonate solution (0.52 mL) were combined in 1,4-dioxane (3 mL) and the mixture was degassed thoroughly under nitrogen. (1E,4E)-1,5-diphenylpenta-1,4-dien-3-one-palladium (3:2) (8 mg, 0.01 mmol) and dicyclohexyl-[2',4',6'-tri(propan-2-yl)biphenyl-2-yl]phosphane (8 mg, 0.02 mmol) were added, and the mixture was heated at 110° C. in a sealed tube for 90 minutes. The reaction mixture was cooled to room temperature and diluted with DCM (20 mL). The mixture was washed using saturated aqueous sodium bicarbonate solution (1×15 mL). The aqueous layer was re-extracted with DCM (15 mL), and the organic layers were combined. The organic phase was dried over sodium sulphate, filtered and concentrated in vacuo. The crude orange oil was purified by chromatography on silica (Biotage, 10 g cartridge), eluting with 0 to 100% ethyl acetate in heptane, to afford the title compound (15 mg, 10%) as an off-white solid. $\delta_H$ (500 MHz, DMSO-d₆) 8.98 (d, J 1.5 Hz, 1H), 8.89-8.83 (m, 1H), 8.66 (d, J 7.3 Hz, 1H), 7.54 (d, J 11.9 Hz, 1H), 7.34-7.26 (m, 1H), 7.29 (t, J 74.0 Hz, 1H), 7.21 (d, J 8.0 Hz, 1H), 7.14 (td, J 7.5, 0.9 Hz, 1H), 7.02 (dd, J 7.7, 1.3 Hz, 1H), 5.54 (s, 1H), 4.36 (s, 2H), 2.33 (s, 3H), 1.50 (s, 6H). Method D HPLC-MS: MH+ m/z 433, RT 1.99 minutes.

Example 333

5-(3-{[2-(Difluoromethoxy)phenyl]methyl}-7-fluoro-2-methylimidazo[1,2-a]pyridin-6-yl)-2-(2-fluoropropan-2-yl)pyrimidine DAST (0.04 mL, 0.34 mmol) was added to a solution of Example 173 (0.1 g, 0.23 mmol) in anhydrous tetrahydrofuran (2 mL) at room temperature under $N_2$ gas. The mixture was stirred at room temperature for 2 h, quenched with water (5 mL) and poured onto saturated aqueous $NaHCO_3$ solution (10 mL). The crude residue was extracted with EtOAc (3×10 mL), dried ($MgSO_4$) and concentrated in vacuo. The resulting light yellow glass was purified by chromatography on silica (Biotage, 10 g cartridge), eluting with 0 to 100% EtOAc in heptanes. The resulting crude off white gum was further purified by preparative HPLC (preparative method C, neutral) to give the title compound (0.031 g, 31%) as a pale orange glass. $\delta_H$ (500 MHz, $CDCl_3$) 8.80 (d, J 1.4 Hz, 2H), 7.79 (d, J 7.0 Hz, 1H), 7.37 (d, J 10.6 Hz, 1H), 7.30-7.27 (m, 1H), 7.17 (d, J 7.9 Hz, 1H), 7.11 (t, J 7.5 Hz, 1H), 6.90 (dd, J 7.7, 1.2 Hz, 1H), 6.62 (t, J 73.6 Hz, 1H), 4.29 (s, 2H), 2.52 (s, 3H), 1.83 (d, J 21.7 Hz, 6H). Method D HPLC-MS: MH+ m/z 445, RT 2.24 minutes.

Example 334

2-[4-(3-{[2-(Difluoromethoxy)phenyl]methyl}-7-fluoro-2-methylimidazo[1,2-a]pyridin-6-yl)phenyl]propan-2-amine formate salt Intermediate 290 (0.2 g, 0.29 mmol), 2-(4-bromophenyl)propan-2-aminium chloride (0.09 g, 0.34 mol), $PdCl_2$(dppf) complex with DCM (0.02 g, 0.03 mmol) and 2M aqueous $K_2CO_3$ solution (0.43 mL) in 1,4-dioxane (5 mL) was degassed under a stream of nitrogen for 15 minutes, then heated at 105° C. for 1 h in a sealed tube. The mixture was cooled to room temperature, diluted with EtOAc (15 mL) and poured onto water (40 mL). The mixture was extracted with EtOAc (3×50 mL) and the combined organic phases were washed with brine (40 mL), dried over $MgSO_4$ and concentrated in vacuo. The resulting crude brown gum was purified by preparative HPLC (Method A) to give the title compound (14 mg, 10%) as a yellow glass. $\delta_H$ (500 MHz, $CD_3OD$) 10.00 (s, 1H), 9.65 (d, J 7.1 Hz, 1H), 9.22-9.16 (m, 2H), 9.17-9.11 (m, 2H), 8.90-8.82 (m, 2H), 8.75 (d, J 8.0 Hz, 1H), 8.70 (td, J 7.6, 1.0 Hz, 1H), 8.64 (dd, J 7.7, 1.5 Hz, 1H), 8.46 (t, J 74.0 Hz, 1H), 5.94 (s, 2H), 4.00 (s, 3H), 3.34 (s, 6H). Method D HPLC-MS: MH+ m/z 440.1, RT 1.41 minutes.

Example 335

5-(3-{[2-(Difluoromethoxy)phenyl]methyl}-7-fluoro-2-methylimidazo[1,2-a]pyridin-6-yl)-2-[1-(fluoromethyl)cyclopropyl]pyrimidine Example 328 (130 mg, 0.29 mmol) was dissolved in DCM (5 mL) under nitrogen. BAST (95%, 100 mg, 0.43 mmol) was added dropwise and the reaction mixture was allowed to stir for 45 minutes at r.t. The reaction mixture neutralised with saturated aqueous $NaHCO_3$ solution (10 mL), then diluted with water (20 mL) and extracted with DCM (3×25 mL). The organic extracts were dried over sodium sulfate, filtered and concentrated under vacuum. The resulting yellow oil was purified by chromatography on silica (Biotage, 10 g cartridge), eluting with 0-100% ethyl acetate in heptanes. The residue was further purified by preparative HPLC (Method C) to afford the title compound (20 mg, 15%) as a peach solid. $\delta_H$ (500 MHz, $CDCl_3$) 8.65 (s, 2H), 7.71 (d, J 7.0 Hz, 1H), 7.32 (d, J 10.6 Hz, 1H), 7.26 (d, J 2.5 Hz, 2H), 7.16 (d, J 8.1 Hz, 1H), 7.09 (t, J 7.5 Hz, 1H), 6.86 (d, J 7.5 Hz, 1H), 6.62 (t, J 73.6 Hz, 1H), 4.90 (d, J 48.3 Hz, 2H), 4.27 (s, 2H), 2.49 (s, 3H), 1.60-1.50 (m, 2H), 1.27-1.21 (m, 2H). Method D (uPLC)-MS: MH+ m/z 457, RT 2.38 minutes.

Example 336

2-[5-(3-{[2-(Difluoromethoxy)phenyl]methyl}-7-fluoro-2-methylimidazo[1,2-a]pyridin-6-yl)pyrimidin-2-yl]propan-2-yl acetate Example 173 (0.05 g, 0.11 mmol) was dissolved in acetonitrile (0.5 mL) and treated with acetic acid (0.09 mL, 1.6 mmol). The mixture was cooled to 0° C. and treated with concentrated $H_2SO_4$ (0.084 mL, 1.6 mmol). The mixture was then warmed to 55° C. for 3 h. The reaction mixture was cooled to room temperature and poured onto ice/water (10 mL). The pH was adjusted to ~12 using 5M aqueous NaOH solution, and the crude residue was extracted with EtOAc (3×20 mL). The combined organic phase was washed with brine (20 mL), dried over $MgSO_4$ and concentrated in vacuo. The resulting crude off-white glass was purified by chromatography on silica (Biotage, 10 g cartridge), eluting with 0 to 100% EtOAc in heptanes, to afford a colourless gum, which was triturated with water, to give the title compound (37 mg, 66%) as an off-white solid. $\delta_H$ (500 MHz, $CDCl_3$) 8.72 (d, J 1.5 Hz, 2H), 7.76 (d, J 7.0 Hz, 1H), 7.36 (d, J 10.6 Hz, 1H), 7.30-7.27 (m, 1H), 7.16 (d, J 7.7 Hz, 1H), 7.09 (td, J 7.6, 1.0 Hz, 1H), 6.84 (dd, J 7.7, 1.3 Hz, 1H), 6.63 (t, J 73.6 Hz, 1H), 4.28 (s, 2H), 2.50 (s, 3H), 2.09 (s, 3H), 1.81 (s, 6H). Method D HPLC-MS: MH+ m/z 485.0, RT 2.28 minutes.

Example 337

5-(3-{[2-(Difluoromethoxy)phenyl]methyl}-7-fluoro-2-methylimidazo[1,2-a]pyridin-6-yl)-2-(3-fluorooxetan-3-yl)pyrimidine Example 322 (40 mg, 0.09 mmol) was dissolved in DCM (3 mL) under nitrogen and the solution was cooled to 0° C. using an ice/water bath. BAST (41 mg, 0.17 mmol) was added to the solution, and the cooling bath was removed after the addition was complete. The reaction mixture was allowed to warm to room temperature and was stirred for 1 h before additional BAST (41 mg, 0.17 mmol) was added. After a further 15 minutes of stirring at room temperature, the reaction mixture was quenched with water (5 mL), then basified to pH 8 using saturated aqueous sodium bicarbonate solution with continual stirring. The reaction mixture was partitioned and the aqueous phase was further extracted with DCM (3×5 mL). The combined organic layers were washed with brine (10 mL), then dried over sodium sulfate. The reaction mixture was filtered and concentrated under vacuum. The crude yellow oil was purified by chromatography on silica (Biotage, 10 g catridge), eluting with 0 to 100% ethyl acetate in heptanes, to afford the title compound (11.4 mg, 28%) as an off-white solid. $\delta_H$ (250 MHz, $CDCl_3$) 8.88 (d, J 1.5 Hz, 2H), 7.84 (d, J 7.0 Hz, 1H), 7.41 (d, J 10.7 Hz, 1H), 7.35-7.27 (m, 1H), 7.22-7.07 (m, 2H), 6.98-6.28 (m, 2H), 5.29-5.04 (m, 4H), 4.30 (s, 2H), 2.53 (s, 3H). Method D HPLC-MS: MH+ m/z 459, RT 1.96 minutes.

Examples 338 & 339

2-[5-[3-[1-[2-(Difluoromethoxy)phenyl]ethyl]-7-fluoro-2-methylimidazo[1,2-a]pyridin-6-yl]pyrimidin-2-yl]propan-2-ol (Enantiomers A and B)

A suspension of Intermediate 263 (0.32 g, 0.8 mmol), 2-[5-(4,4,5,5-tetramethyl-1,3,2-dioxaborolan-2-yl)pyrimidin-2-yl]propan-2-ol (0.23 g, 0.88 mmol) and PdCl$_2$(dppf) complex with DCM (0.07 g, 0.08 mmol) in 1,4-dioxane (10 mL) and 2M aqueous K$_2$CO$_3$ solution (1.2 mL) was degassed under a stream of nitrogen for 15 minutes. The reaction vessel was sealed and heated at 90° C. for 1 h. The reaction mixture was diluted with EtOAc (20 mL) and washed with water (20 mL). The organic layer was dried over MgSO$_4$ and concentrated under reduced pressure. The resulting crude material was purified by chromatography on silica (Biotage, 10 g silica), eluting with 1-1.5% MeOH in DCM, to afford a brown oil (280 mg) (mixture of enantiomers). A sample (100 mg) of the enantiomer mixture was separated on chiral SFC (10% isopropanol:90% CO$_2$) on a Chiralcel OD-H 25 cm column to afford Enantiomer A (37 mg; RT 5.72 minutes) and Enantiomer B (32 mg; RT 7.70 minutes).

Example 338 (Enantiomer A): $\delta_H$ (500 MHz, CDCl$_3$) 8.76 (d, J 1.2 Hz, 2H), 8.24 (s, 1H), 7.94 (d, J 6.8 Hz, 1H), 7.59 (d, J 10.2 Hz, 1H), 7.35-7.28 (m, 2H), 7.25-7.19 (m, 1H), 7.13 (d, J 8.0 Hz, 1H), 6.50 (t, J 73.7 Hz, 1H), 4.81 (q, J 7.3 Hz, 1H), 2.52 (s, 3H), 1.80 (d, J 7.4 Hz, 3H), 1.65 (s, 6H). Method D HPLC-MS: MH+ m/z 458, RT 1.97 minutes.

Example 339 (Enantiomer B): $\delta_H$ (500 MHz, CDCl$_3$) 8.75 (d, J 1.4 Hz, 2H), 7.87 (d, J 7.0 Hz, 1H), 7.26 (s, 3H), 7.23-7.17 (m, 1H), 7.12 (d, J 8.1 Hz, 1H), 6.47 (t, J 73.9 Hz, 1H), 4.81 (q, J 7.3 Hz, 1H), 4.58 (s, 1H), 2.52 (s, 3H), 1.80 (d, J 7.4 Hz, 3H), 1.64 (s, 6H). Method D HPLC-MS: MH+ m/z 458, RT 1.96 minutes.

Example 340

N-({1-[5-(3-{[2-(Difluoromethoxy)phenyl]methyl}-7-fluoro-2-methylimidazo[1,2-a]pyridin-6-yl)pyrimidin-2-yl]cyclopropyl}methyl)acetamide Intermediate 290 (50%, 400 mg, 0.46 mmol) and Intermediate 312 were dissolved in 1,4-dioxane (6 mL) and 2M aqueous Na$_2$CO$_3$ solution (0.7 mL) was added. The resulting mixture was degassed with nitrogen for 10 minutes, then PdCl$_2$(dppf) complex with DCM (40 mg, 0.05 mmol) was added and the reaction mixture was heated at 80° C. for 1 h in a sealed tube. The reaction mixture was diluted with EtOAc (30 mL), and washed with saturated aqueous NaHCO$_3$ solution (20 mL), water (2×20 mL) and brine (15 mL), then dried over sodium sulfate and concentrated under vacuum. The resulting brown oil was purified by chromatography on silica (Biotage 10 g cartridge), eluting with a gradient of 50-100% ethyl acetate in heptanes, then 0-10% methanol in DCM. The residue was triturated with diethyl ether (2×25 mL) to afford the title compound (31 mg, 13%) as a light brown solid. $\delta_H$ (500 MHz, CDCl$_3$) 8.63 (d, J 1.2 Hz, 2H), 7.75 (d, J 7.0 Hz, 1H), 7.33 (d, J 10.7 Hz, 1H), 7.29-7.26 (m, 1H), 7.16 (d, J 8.0 Hz, 1H), 7.10 (t, J 7.5 Hz, 1H), 6.89 (d, J 7.1 Hz, 1H), 6.63 (t, J 73.6 Hz, 2H), 4.28 (s, 2H), 3.70 (d, J 6.2 Hz, 2H), 2.50 (s, 3H), 1.98 (s, 3H), 1.41 (q, J 3.9 Hz, 2H), 1.23 (q, J 4.0 Hz, 2H). Method D (uPLC)-MS: MH+ m/z 497, RT 1.95 minutes.

Example 341

2-[5-(3-{[2-(Difluoromethoxy)-5-fluorophenyl]methyl}-7-fluoro-2-methylimidazo[1,2-a]pyridin-6-yl)pyrimidin-2-yl]propan-2-ol Intermediate 317 (231 mg, 0.57 mmol), 2-[5-(4,4,5,5-tetramethyl-1,3,2-dioxaborolan-2-yl)pyrimidin-2-yl]propan-2-ol (166 mg, 0.63 mmol) and 2M aqueous sodium carbonate solution (0.86 mL) were dissolved in 1,4-dioxane (6 mL) and the mixture was degassed with nitrogen for 15 minutes. PdCl$_2$(dppf) complex with DCM (23 mg, 0.03 mmol) was added to this mixture. The mixture was stirred at 100° C. for 1.5 h. The reaction mixture was cooled to room temperature, diluted with ethyl acetate (20 mL) and filtered, then the filtrate was evaporated under reduced pressure. The crude residue was purified by chromatography on silica (Biotage, 25 g cartridge), eluting with 40-100% ethyl acetate in heptanes, then 0 to 5% MeOH in DCM, to afford the title compound (132 mg, 50%) as a white solid. $\delta_H$ (500 MHz, DMSO-d$_6$) 8.97 (d, J 1.3 Hz, 2H), 8.63 (d, J 7.3 Hz, 1H), 7.55 (d, J 11.3 Hz, 1H), 7.23 (dd, J 9.0, 4.7 Hz, 1H), 7.21 (t, J 75 Hz 1H), 7.15 (td, J 8.5, 3.1 Hz, 1H), 6.87 (dd, J 9.2, 3.1 Hz, 1H), 5.15 (s, 1H), 4.35 (s, 2H), 2.27 (s, 3H), 1.53 (s, 6H). Method D HPLC-MS: MH+ m/z 461, RT 1.96 minutes.

Example 342

5-(3-{[2-(Difluoromethoxy)phenyl]methyl}-7-fluoro-2-methylimidazo[1,2-a]pyridin-6-yl)-2-(4-fluorooxan-4-yl)pyrimidine Example 319 (250 mg, 0.495 mmol) was dissolved in DCM (20 mL) under nitrogen and cooled to 0° C. using an ice/water bath. BAST (95%, 231 mg, 0.991 mmol) was added dropwise and the cooling bath was removed. The reaction mixture was allowed to stir for 1 h at room temperature. The reaction mixture was re-treated with a further 5 equal portions of BAST (231 mg, 0.991 mmol) at 1 h intervals. The reaction mixture was quenched with water (5 mL), then basified with continual stirring to pH 8 using saturated aqueous NaHCO$_3$.solution. The reaction mixture was partitioned and the aqueous layer further extracted with DCM (3×5 mL). The combined organic extracts were washed using brine (10 mL), then dried over sodium sulfate. The reaction mixture was filtered and concentrated under vacuum. The crude yellow-brown oil was purified using preparative mass-directed HPLC (Method C) to afford the title compound (63 mg, 25%) as a beige solid. $\delta_H$ (500 MHz, DMSO-d$_6$) 9.09 (s, 2H), 8.65 (d, J 7.3 Hz, 1H), 7.58 (d, J 11.4 Hz, 1H), 7.33-7.28 (m, 1H), 7.27 (t, J 74.2 Hz, 1H), 7.19 (d, J 8.1 Hz, 1H), 7.16-7.11 (m, 1H), 7.03-6.99 (m, 1H), 4.37 (s, 2H), 3.86-3.80 (m, 2H), 3.79-3.72 (m, 2H), 2.40-2.30 (m, 2H), 2.28 (s, 3H), 2.14 (t, J 11.8 Hz, 2H). Method D HPLC-MS: MH+ m/z 487, RT 2.11 minutes.

Example 343

3-[5-(3-{[2-(Difluoromethoxy)phenyl]methyl}-7-fluoro-2-methylimidazo[1,2-a]pyridin-6-yl)pyrazin-2-yl]oxetan-3-ol Intermediate 290 (40%, 400 mg, 0.37 mmol), Intermediate 318 (95%, 135 mg, 0.56 mmol) and 2M aqueous sodium bicarbonate solution (0.55 mL) were combined in 1,4-dioxane (3 mL) and the mixture was degassed thoroughly under nitrogen. PdCl$_2$(dppf) complex with DCM (30 mg, 0.04 mmol) was added and the mixture was heated at 110° C. in a sealed tube for 90 minutes. The reaction mixture was cooled to room temperature and diluted with DCM (20 mL). The mixture was washed with saturated aqueous sodium bicarbonate solution (15 mL), then the organic phase was dried over sodium sulphate, filtered and concentrated in vacuo. The crude orange oil was purified by chromatography on silica (Biotage, 10 g cartridge), eluting with 0 to 100% ethyl acetate in heptanes, followed by preparative HPLC (Method A), to afford the title compound (13 mg, 7%) as a grey solid. δ$_H$ (500 MHz, DMSO-d$_6$) 9.02 (s, 1H), 8.90 (d, J 1.4 Hz, 1H), 8.68 (d, J 7.3 Hz, 1H), 7.55 (d, J 11.9 Hz, 1H), 7.33-7.26 (m, 1H), 7.29 (t, J 74.0 Hz, 1H), 7.20 (d, J 8.1 Hz, 1H), 7.13 (t, J 7.5 Hz, 1H), 7.04-6.99 (m, 1H), 6.88 (s, 1H), 4.94 (d, J 6.4 Hz, 2H), 4.72 (d, J 6.4 Hz, 2H), 4.36 (s, 2H), 2.33 (s, 3H). Method D HPLC-MS: MH+ m/z 457, RT 1.77 minutes.

Example 344

3-[5-(3-{[2-(Difluoromethoxy)phenyl]methyl}-7-fluoro-2-methylimidazo[1,2-a]pyridin-6-yl)pyrimidin-2-yl]oxolan-3-ol Intermediate 319 (86%, 500 mg, 1.75 mmol), Intermediate 290 (50%, 1.37 g, 1.58 mmol) and 2M aqueous potassium carbonate solution (2.6 mL) were combined in 1,4-dioxane (7 mL) and the mixture was degassed for 10 minutes under a stream of nitrogen. Pd(dppf)Cl$_2$ complex with DCM (143 mg, 0.17 mmol) was added, and the mixture was heated in a sealed tube at 90° C. for 2 h. The reaction mixture was cooled to room temperature, then diluted with ethyl acetate (10 mL) and filtered through a plug of Celite. The mixture was washed using water (10 mL), then the aqueous phase was re-extracted using ethyl acetate (2×10 mL) and the combined organic layers were washed with brine (15 mL). The organic phase was dried over sodium sulphate, filtered and concentrated in vacuo. The resulting crude dark brown oil was purified by chromatography on silica (Biotage, 25 g cartridge), eluting with 0 to 3% methanol in DCM, followed by preparative mass-directed HPLC (Method C), to afford the title compound (40 mg, 4.8%) as a white solid. δ$_H$ (500 MHz, DMSO-d$_6$) 9.00 (d, J 1.3 Hz, 2H), 8.59 (d, J 7.3 Hz, 1H), 7.55 (d, J 11.3 Hz, 1H), 7.44-6.99 (m, 5H), 5.67 (s, 1H), 4.36 (s, 2H), 4.08 (d, J 8.9 Hz, 1H), 4.06-3.95 (m, 2H), 3.90 (d, J 8.9 Hz, 1H), 2.57-2.51 (m, 1H), 2.28 (s, 3H), 2.18 (ddd, J 12.4, 6.3, 3.4 Hz, 1H). Method D HPLC-MS: MH+ m/z 471.5, RT 1.74 minutes.

Example 345

3-[2-(Difluoromethoxy)benzyl]-6-[2-(4,4-difluoropiperidin-1-yl)pyrimidin-5-yl]-2-methylimidazo[1,2-a]pyridine Prepared from Intermediate 29 and 4,4-difluoropiperidine hydrochloride in accordance with General Method B to give the title compound (52 mg, 37%) as an off-white solid. HPLC-MS (pH 10): MH+ m/z 486.8 [M+H]$^+$, RT 2.70 minutes.

Example 346

4-(5-{3-[2-(Difluoromethoxy)benzyl]-2-methylimidazo[1,2-a]pyridin-6-yl}pyrimidin-2-yl)piperazine-2-carboxylic acid A solution of Intermediate 271 (80 mg, 0.14 mmol) in DCM (5 mL) was treated with trifluoroacetic acid (0.5 mL) and stirred at r.t. for 18 h. The reaction mixture was concentrated in vacuo, and the residue was taken up in aqueous MeCN and freeze-dried, to give the title compound tris(trifluoroacetate) salt (47 mg, 40%) as a brown solid. HPLC-MS (pH 10): MH+ m/z 495.8 [M+H]$^+$, RT 1.40 minutes.

Example 347

1-(5-{3-[2-(Difluoromethoxy)benzyl]-2,7-dimethylimidazo[1,2-a]pyridin-6-yl}pyrimidin-2-yl)-4-hydroxypiperidine-4-carboxylic acid Intermediate 47 (100 mg, 0.241 mmol), methyl 4-hydroxypiperidine-4-carboxylate (62 mg, 0.384 mmol), DIPEA (0.125 mL, 0.723 mmol) and NMP (2 mL) were charged to a sealed tube under nitrogen. The reaction mixture was stirred at 80° C. for 2 h. The reaction mixture was partitioned between DCM (15 mL) and water (15 mL). The organic phase was washed with brine (10 mL), then dried over sodium sulfate, filtered and concentrated. The residue was diluted with water (0.5 mL) and purified by preparative mass-directed HPLC (Method D). The resulting mixture was stirred in water (5 mL) and concentrated HCl (0.5 mL) for 5 h, then concentrated in vacuo, to afford the title compound bis(HCl) salt (58 mg, 40%) as a white solid. δ$_H$ (250 MHz, D$_2$O) 8.40 (s, 2H), 8.20 (s, 1H), 7.73 (s, 1H), 7.18 (m, J 23.3, 11.0, 5.2 Hz, 4H), 7.09-6.48 (t, J 73.7 Hz, 1H), 4.29 (m, J 19.2 Hz, 4H), 3.51 (t, J 11.4 Hz, 2H), 2.43 (s, 3H), 2.36 (s, 3H), 2.16-1.98 (m, 2H), 1.86 (d, J 13.9 Hz, 2H). Method A HPLC-MS: MH+ m/z 524.3, RT 2.94 minutes.

Example 348

1-[5-(3-{(1S or 1R)-1-[2-(Difluoromethoxy)phenyl]ethyl}-2-methylimidazo[1,2-a]-pyridin-6-yl)pyrimidin-2-yl]-1,4-diazepan-5-one (Enantiomer A)

A portion of Example 307 was purified by chiral HPLC (on a Chiracel OD column, with particle size 10 μm, in polar organic mode eluting with 0.1% diethylamine in MeOH at 9 mL/minute at 40° C.). The enantiomer which eluted at 14.4 minutes was collected and concentrated in vacuo to give the title compound as a colourless gum.

Example 349

1-[5-(3-{(1R or 1S)-1-[2-(Difluoromethoxy)phenyl]ethyl}-2-methylimidazo[1,2-a]-pyridin-6-yl)pyrimidin-2-yl]-1,4-diazepan-5-one (Enantiomer B)

A portion of Example 307 was purified by chiral HPLC (on a Chiracel OD column, with particle size 10 μm, in polar organic mode eluting with 0.1% diethylamine in MeOH at 9 mL/minute at 40° C.). The enantiomer which eluted at 15.9 minutes was collected and concentrated in vacuo to give the title compound as a colourless gum.

Example 350

Methyl 3-[5-(3-{[2-(difluoromethoxy)phenyl]methyl}-2-methylimidazo[1,2-a]pyridin-6-yl)pyrimidin-2-yl]-3-azabicyclo[3.1.0]hexane-1-carboxylate (Enantiomer A)

Intermediate 29 (80%, 200 mg, 0.4 mmol) was dissolved in NMP (2 mL) and Intermediate 144 (110 mg, 0.62 mmol) was added, followed by triethylamine (125 μL, 0.9 mmol). The reaction mixture was heated at 120° C. under microwave irradiation for 45 minutes. The reaction mixture was re-treated with Intermediate 144 (30 mg, 0.17 mmol) and triethylamine (50 μL, 0.36 mmol), then heated at 120° C. under microwave irradiation for 30 minutes. The reaction mixture was diluted with EtOAc (3 mL), and washed with water (2 mL) and brine (2 mL), then dried ($Na_2SO_4$) and concentrated to dryness. The residue was purified by chromatography (Biotage, 10 g silica), eluting with 30-100% EtOAc in heptanes, to afford the title compound (128 mg, 63.4%) as a white solid. $\delta_H$ (500 MHz, $CD_3OD$) 8.50 (s, 2H), 8.16 (s, 1H), 7.56 (d, J 9.3 Hz, 1H), 7.47 (dd, J 9.2, 1.7 Hz, 1H), 7.35-7.25 (m, 1H), 7.22 (d, J 8.2 Hz, 1H), 7.19-7.12 (m, 1H), 7.10-6.76 (m, 2H), 4.41 (s, 2H), 4.04 (d, J 11.1 Hz, 1H), 3.97 (dd, J 11.2, 3.1 Hz, 2H), 3.75 (s, 3H), 3.65 (dd, J 11.1, 4.4 Hz, 1H), 2.45 (s, 3H), 2.32-2.25 (m, 1H), 1.67 (dd, J 8.4, 4.6 Hz, 1H), 0.94 (t, J 5.0 Hz, 1H). Method D HPLC-MS: MH+ m/z 506, RT 2.35.

Example 351

Methyl 3-[5-(3-{[2-(difluoromethoxy)phenyl]methyl}-2-methylimidazo[1,2-a]pyridin-6-yl)pyrimidin-2-yl]-3-azabicyclo[3.1.0]hexane-1-carboxylate (Enantiomer B)

Intermediate 29 (80%, 200 mg, 0.4 mmol) was dissolved in NMP (2 mL) and Intermediate 233 (110 mg, 0.62 mmol) was added, followed by triethylamine (125 μL, 0.9 mmol). The reaction mixture was heated at 120° C. under microwave irradiation for 45 minutes. The reaction mixture was re-treated with Intermediate 233 (30 mg, 0.17 mmol) and triethylamine (50 μL, 0.36 mmol), then heated at 120° C. under microwave irradiation for 30 minutes. The reaction mixture was diluted with EtOAc (3 mL), and washed with water (2 mL) and brine (2 mL), then dried over $Na_2SO_4$ and concentrated to dryness. The residue was purified by chromatography (Biotage, 10 g silica), eluting with 50-100% EtOAc in heptanes, to afford the title compound (115 mg, 57%) as a white solid. $\delta_H$ (500 MHz, $CD_3OD$) 8.50 (s, 2H), 8.16 (s, 1H), 7.56 (d, J 9.3 Hz, 1H), 7.47 (dd, J 9.2, 1.8 Hz, 1H), 7.34-7.27 (m, 1H), 7.22 (d, J 7.9 Hz, 1H), 7.15 (td, J 7.6, 1.0 Hz, 1H), 7.11-6.77 (m, 2H), 4.41 (s, 2H), 4.03 (d, J 11.1 Hz, 1H), 3.96 (dd, J 11.2, 3.1 Hz, 2H), 3.75 (s, 3H), 3.65 (dd, J 11.1, 4.3 Hz, 1H), 2.45 (s, 3H), 2.33-2.23 (m, 1H), 1.67 (dd, J 8.5, 4.7 Hz, 1H), 0.94 (t, J 5.0 Hz, 1H). Method D HPLC-MS: MH+ m/z 506, RT 2.35.

Example 352

3-[5-(3-{[2-(Difluoromethoxy)phenyl]methyl}-2-methylimidazo[1,2-a]pyridin-6-yl)-pyrimidin-2-yl]-3-azabicyclo[3.1.0]hexane-1-carboxylic acid (Enantiomer A)

Example 350 (110 mg, 0.22 mmol) was dissolved in ethanol (5 mL) and 2M aqueous potassium hydroxide solution (110 μL) was added. The reaction mixture was heated at 80° C. for 17 h. The reaction mixture was concentrated to dryness to yield the title compound potassium salt (131 mg) as a yellow solid. $\delta_H$ (500 MHz, $CD_3OD$) 8.45 (s, 2H), 8.13 (s, 1H), 7.54 (d, J 9.3 Hz, 1H), 7.45 (dd, J 9.3 Hz, 1H), 7.34-7.25 (m, 1H), 7.20 (d, J 7.9 Hz, 1H), 7.14 (t, J 7.5 Hz, 1H), 7.10-6.74 (m, 2H), 4.39 (s, 2H), 3.98 (s, 2H), 3.88 (d, J 11.1 Hz, 1H), 3.66-3.58 (m, 1H), 2.43 (s, 3H), 2.06-1.99 (m, 1H), 1.53 (dd, J 8.2, 4.0 Hz, 1H), 0.60 (t, J 4.5 Hz, 1H). Method D HPLC-MS: MH+ m/z 492, RT 2.01 minutes.

Example 353

3-[5-(3-{[2-(Difluoromethoxy)phenyl]methyl}-2-methylimidazo[1,2-a]pyridin-6-yl)-pyrimidin-2-yl]-3-azabicyclo[3.1.0]hexane-1-carboxylic acid (Enantiomer B)

Example 351 (100 mg, 0.2 mmol) was dissolved in ethanol (5 mL) and 2M aqueous potassium hydroxide solution (100 μL) was added. The reaction mixture was heated at 80° C. for 17 h. The reaction mixture was concentrated to dryness to yield the title compound potassium salt (123 mg) as a yellow solid. $\delta_H$ (500 MHz, $CD_3OD$) 8.45 (s, 2H), 8.14 (s, 1H), 7.54 (d, J 9.3 Hz, 1H), 7.45 (dd, J 9.3, 1.5 Hz, 1H), 7.33-7.25 (m, 1H), 7.21 (d, J 8.1 Hz, 1H), 7.14 (t, J 7.5 Hz, 1H), 7.11-6.73 (m, 2H), 4.39 (s, 2H), 3.98 (s, 2H), 3.88 (d, J 11.0 Hz, 1H), 3.67-3.55 (m, 1H), 2.44 (s, 3H), 2.07-1.97 (m, 1H), 1.53 (dd, J 8.2, 4.0 Hz, 1H), 0.60 (t, J 4.5 Hz, 1H). Method D HPLC-MS: MH+ m/z 492, RT 1.99 minutes.

Examples 354 & 355

1-[5-(3-{[2-(Difluoromethoxy)phenyl]methyl}-2-methylimidazo[1,2-a]pyridin-6-yl)-pyrimidin-2-yl]-3-methylpiperidine-3-carboxylic acid (Enantiomers A and B)

Example 38 (105 mg, 0.207 mmol) was subjected to chiral preparative HPLC (15% methanol:85% $CO_2$ with Lux Cellulose-3), to afford the title compounds. of Example 354 (Enantiomer A) and (11%) of Example 355 (Enantiomer B) as a pale yellow solid.
Example 354 (Enantiomer A) (19.2 mg, 13%) was obtained as a pale yellow solid. $\delta_H$ (500 MHz, $CD_3OD$) 8.47 (s, 2H), 8.16 (s, 1H), 7.55 (d, J 9.2 Hz, 1H), 7.49 (dd, J 9.3, 1.5 Hz, 1H), 7.34-7.26 (m, 1H), 7.21 (d, J 8.0 Hz, 1H), 7.15 (t, J 7.5 Hz, 1H), 7.11-7.04 (m, 1H), 6.84 (d, J 74.0 Hz, 1H), 4.44-4.33 (m, 3H), 4.07-3.89 (m, 1H), 3.69-3.59 (m, 1H), 3.54 (d, J 13.2 Hz, 1H), 2.44 (s, 3H), 2.14 (dd, J 11.9, 5.2 Hz, 1H), 1.77-1.55 (m, 3H), 1.21 (s, 3H). Method (Chiral SFCMS analysis): MH+ m/z 508, RT 6.34 minutes.
Example 355 (Enantiomer B) (14.5 mg, 11%) was obtained as a pale yellow solid. $\delta_H$ (500 MHz, $CD_3OD$) 8.46 (s, 2H), 8.15 (s, 1H), 7.55 (d, J 9.3 Hz, 1H), 7.48 (dd, J 9.3, 1.5 Hz, 1H), 7.33-7.25 (m, 1H), 7.20 (d, J 7.9 Hz, 1H), 7.14 (t, J 7.5 Hz, 1H), 7.10-7.05 (m, 1H), 6.84 (d, J 74.0 Hz, 1H), 4.42-4.33 (m, 3H), 4.04-3.93 (m, 1H), 3.63 (ddd, J 12.6, 7.8, 4.3 Hz, 1H), 3.54 (d, J 13.0 Hz, 1H), 2.43 (s, 3H), 2.20-2.07 (m, 1H), 1.78-1.51 (m, 3H), 1.20 (s, 3H). Method (Chiral SFCMS analysis): MH+ m/z 508, RT 8.75 minutes.

Example 356 cis-1-[5-(3-{[2-(Difluoromethoxy)phenyl]methyl}-2-methylimidazo[1,2-a]pyridin-6-yl)-pyrimidin-2-yl]-3-methylpiperidine-4-carboxylic acid (Racemic)

Intermediate 323 (102 mg, 0.2 mmol) was dissolved in methanol (5 mL) and 2M aqueous potassium hydroxide solution (100 μL) was added. The reaction mixture was heated at 50° C. for 2.5 h. The reaction mixture was left to stand over 2 days, then additional 2M aqueous potassium hydroxide solution (65 μL) was added. The reaction mixture was heated at 50° C. for a further 6.5 h, then left to stand at room temperature overnight. The reaction mixture was concentrated to dryness, diluted with water (3 mL) and extracted with ethyl acetate (3 mL). The aqueous layer was neutralised to pH 6 with 1M aqueous hydrogen chloride solution. The resulting precipitate was collected by filtration to afford the title compound (73 mg, 73%) (containing 12% of the trans isomer) as a white solid. $\delta_H$ (500 MHz, DMSO-$d_6$) 8.62 (s, 2H), 8.38 (s, 1H), 7.53 (d, J 9.3 Hz, 1H), 7.46 (dd, J 9.3, 1.6 Hz, 1H), 7.44-7.10 (m, 4H), 7.02 (d, J 6.6 Hz, 1H), 4.53 (dt, J 11.9, 3.6 Hz, 1H), 4.42 (dd, J 13.3, 4.0 Hz, 1H), 4.35 (s, 2H), 3.13 (ddd, J 13.5, 9.8, 4.4 Hz, 1H), 2.71-2.63 (m, 2H), 2.31 (s, 3H), 2.29-2.22 (m, 1H), 1.74-1.64 (m, 2H), 0.82 (d, J 6.9 Hz, 3H). Method D HPLC-MS: MH+ m/z 508, RT 2.14 minutes.

Example 357 trans-1-[5-(3-{[2-(Difluoromethoxy)phenyl]methyl}-2-methylimidazo[1,2-a]pyridin-6-yl)pyrimidin-2-yl]-3-methylpiperidine-4-carboxylic acid (Racemic)

Intermediate 324 (65 mg, 0.12 mmol) was dissolved in methanol (4 mL) and 2M aqueous potassium hydroxide solution (65 μL) was added. The reaction mixture was heated at 50° C. for 2.5 h. The reaction mixture was left to stand over two days, then additional 2M aqueous potassium hydroxide solution (100 μL) was added and the reaction mixture was heated at 50° C. for a further 6.5 h. The reaction mixture was left to stand overnight, then was heated at 50° C. for 6.5 h. The reaction mixture was concentrated to dryness, diluted with water (3 mL) and extracted with ethyl acetate (3 mL). The aqueous layer was neutralised to pH 6 with 1M aqueous hydrogen chloride solution. The resulting precipitate was collected by filtration to afford the title compound (32 mg, 51%) (containing 7% of the cis isomer) as a white solid. $\delta_H$ (500 MHz, DMSO-$d_6$) 8.65 (s, 2H), 8.39 (s, 1H), 7.54 (d, J 9.5 Hz, 1H), 7.46 (dd, J 9.3, 1.6 Hz, 1H), 7.44-7.11 (m, 4H), 7.04 (d, J 6.6 Hz, 1H), 4.75-4.66 (m, 1H), 4.66-4.58 (m, 1H), 4.36 (s, 2H), 2.93 (td, J 12.9, 2.4 Hz, 1H), 2.66-2.57 (m, 1H), 2.31 (s, 3H), 2.18 (td, J 11.4, 3.7 Hz, 1H), 1.93-1.84 (m, 1H), 1.75-1.60 (m, 1H), 1.48 (qd, J 12.5, 4.3 Hz, 1H), 0.91 (d, J 6.6 Hz, 3H). Method D HPLC-MS: MH+ m/z 508, RT 2.18 minutes.

Example 358

Methyl (2S)-5-(3-{[2-(difluoromethoxy)phenyl]methyl}-2-methylimidazo[1,2-a]pyridin-6-yl)-1-methylpyrrolidine-2-carboxylate Intermediate 328 (150 mg, 0.36 mmol) and formaldehyde (37% in water; 0.04 mL, 0.53 mmol) were dissolved in DMF (1 mL) and sodium triacetoxyborohydride (153 mg, 0.72 mmol) was added. The mixture was stirred at room temperature for 16 h. The mixture was diluted with ethyl acetate (10 mL), then washed with water (2 mL) followed by brine (2×2 mL). The organic layer was dried over sodium sulphate, filtered and concentrated under vacuum. The residue was purified by flash chromatography, eluting with a gradient of 0-5% MeOH in DCM, to afford the title compound (87 mg, 56%) as a yellow gum. $\delta_H$ (500 MHz, CD$_3$OD) 8.06-7.90 (s, 1H), 7.43 (d, J 9.3 Hz, 1H), 7.34-7.25 (m, 2H), 7.19 (t, J 7.7 Hz, 1H), 7.13-6.76 (m, 3H), 4.33-4.32 (s, 2H), 3.98-3.76 (m, 1H), 3.75-3.70 (s, 3H), 3.41-3.22 (m, 1H), 2.42-2.41 (s, 3H), 2.18-2.15 (m, 1H), 2.13 (s, 3H), 2.02-1.85 (m, 2H), 1.74 (m, 1H).

Example 359

N-{[4-(3-{[2-(Difluoromethoxy)phenyl]methyl}-2-methylimidazo[1,2-a]pyridin-6-yl)phenyl]methyl}acetamide Prepared from Intermediate 7 and (4-acetamidomethylphenyl)boronic acid by a method analogous to General Method A, giving the title compound (111 mg, 53%) as a yellow solid. MS: m/z 436.3 [M+H]$^+$. HPLC-MS (Method F): RT 1.38 minutes.

The invention claimed is:
1. A compound represented by formula (IIB) or a pharmaceutically acceptable salt thereof:

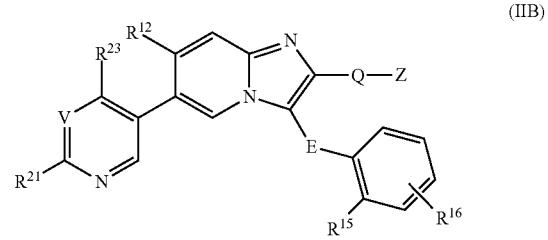

(IIB)

wherein
E represents —N(R$^5$), —CH$_2$—, —CH(OH)—, —CH(OCH$_3$)—, —CH(OCH$_2$CO$_2$H)—, —CH(NH$_2$)—, —CH(NHCOCH$_3$)—, —CH(CO$_2$H)—, —CH(CO$_2$benzyl)—, —CH(CH$_3$)— or -C(CH$_3$)(OH)—;
Q represents a covalent bond; or Q represents —CH$_2$—, —CH(CN)—, —CH(OH)—, —CH(OCH$_3$)—, —CH$_2$O—, —CH$_2$N(R$^6$)— or —H$_2$OCH$_2$—;
Z represents hydrogen, halogen or trifluoromethyl; or Z represents C$_{1-6}$ alkyl, C$_{3-7}$ cycloalkyl, aryl, C$_{3-7}$ heterocycloalkyl, C$_{3-7}$ heterocycloalkenyl or heteroaryl, any of which groups is optionally substituted by one or more substituents; or Z represents —Z$^1$—Z$^2$ or —Z$^1$—C(O)—Z$^2$, either of which moieties is optionally substituted by one or more halogen, cyano, nitro, C$_{1-6}$ alkyl, trifluoromethyl, oxo, hydroxy, hydroxy(C$_{1-6}$)alkyl, C$_{1-6}$ alkoxy, difluoromethoxy, trifluoromethoxy, C$_{1-3}$ alkylenedioxy, C$_{1-6}$ alkylsulfonyl, amino, di(C$_{1-6}$)alkylamino, di(C$_{1-6}$)alkylamino(C$_{1-6}$)alkyl, C$_{2-6}$ alkylcarbonylamino, C$_{1-6}$ alkyl-sulfonylamino, formyl, carboxy, C$_{2-6}$ alkoxycarbonyl, aminocarbonyl, C$_{1-6}$ alkylaminocarbonyl, di(C$_{1-6}$)alkylaminocarbonyl, aminocarbonylamino, and hydrazinocarbonyl;
Z$^1$ represents a divalent radical derived from an aryl, C$_{3-7}$ heterocycloalkyl or heteroaryl group;
Z$^2$ represents aryl, C$_{3-7}$ heterocycloalkyl, C$_{3-7}$ heterocycloalkenyl or heteroaryl;
V represents C—R$^{22}$ or N;
R$^5$ and R$^6$ independently represent hydrogen or C$_{1-6}$ alkyl;
R$^{12}$ represents hydrogen, halogen, trifluoromethyl or C$_{1-6}$ alkyl optionally substituted with C$_{2-6}$ alkoxycarbonyl;
R$^{15}$ and R$^{16}$ independently represent hydrogen, halogen, cyano, nitro, C$_{1-6}$ alkyl, trifluoromethyl, hydroxy, C$_{1-6}$ alkoxy, difluoromethoxy, trifluoromethoxy, C$_{1-6}$ alkylthio, C$_{1-6}$ alkylsulfinyl, C$_{1-6}$ alkylsulfonyl, amino, C$_{1-6}$ alkylamino, di(C$_{1-6}$)alkylamino, arylamino, C$_{2-6}$ alkylcarbonylamino, C$_{1-6}$ alkylsulfonylamino, formyl, C$_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$alkylaminosufonyl;

$R^{21}$ represents hydrogen, halogen, halo($C_{1-6}$)alkyl, cyano, $C_{1-6}$ alkyl, trifluoro-methyl, $C_{2-6}$ alkenyl, $C_{2-6}$ alkynyl, hydroxy, hydroxy($C_{1-6}$)alkyl, $C_{1-6}$ alkoxy,($C_{1-6}$)alkoxy-($C_{1-6}$)alkyl, difluoromethoxy, trifluoromethoxy, trifluoroethoxy, carboxy($C_{3-7}$)cycloalkyloxy, $C_{1-6}$ alkylthio, $C_{1-6}$ alkylsulphonyl, ($C_{1-6}$)alkylsulphonyl($C_{1-6}$)alkyl, amino, amino-($C_{1-6}$)alkyl, $C_{1-6}$ alkylamino, di($C_{1-6}$)alkylamino, ($C_{1-6}$)alkoxy($C_{1-6}$)alkylamino, N-[($C_{1-6}$) -alkyl]-N-[hydroxy($C_{1-6}$)alkyl]amino, $C_{2-6}$ alkylcarbonylamino, ($C_{2-6}$)alkylcarbonylamino-($C_{1-6}$)alkyl, $C_{2-6}$ alkoxycarbonylamino, N-[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, $C_{1-6}$ alkyl-sulphonylamino, $C_{1-6}$ alkylsulphonylamino($C_{1-6}$)alkyl, formyl, $C_{2-6}$ alkylcarbonyl, ($C_{2-6}$)alkylcarbonyloxy($C_{1-6}$)alkyl, carboxy, carboxy($C_{1-6}$)alkyl, $C_{2-6}$ alkoxycarbonyl, morpholinyl($C_{1-6}$)alkoxycarbonyl, $C_{2-6}$ alkoxycarbonyl($C_{1-6}$)alkyl, $C_{2-6}$ alkoxycarbonyl-methylidenyl, aminocarbonyl, $C_{1-6}$ alkylaminocarbonyl, di($C_{1-6}$)alkylaminocarbonyl, aminosulphonyl, $C_{1-6}$ alkylaminosulphonyl or di($C_{1-6}$)alkylaminosulphonyl; or $R^{21}$ represents ($C_{3-7}$)cycloalkyl, ($C_{3-7}$)cycloalkyl($C_{1-6}$)alkyl, ($C_{4-7}$)cycloalkenyl, ($C_{4-9}$)bicycloalkyl, ($C_{3-7}$)heterocycloalkyl, ($C_{3-7}$)heterocycloalkenyl, ($C_{4-9}$)heterobicycloalkyl or ($C_{4-9}$)spiroheterocycloalkyl, any of which groups is optionally substituted by one, two or three substituents independently selected from $C_{1-6}$ alkyl, oxo, carboxy, carboxy($C_{1-6}$)alkyl, $C_{2-6}$ alkoxycarbonyl, tetrazolyl, tetrazolyl($C_{1-6}$)alkyl, halogen, halo($C_{1-6}$)alkyl, cyano, nitro($C_{1-6}$)alkyl, trifluoromethyl, hydroxy, hydroxy($C_{1-6}$)alkyl, $C_{1-6}$ alkoxy, $C_{1-6}$ alkylsulphonyl, amino, ($C_{2-6}$)alkylcarbonylamino ($C_{1-6}$)alkyl, formyl, morpholinyl($C_{1-6}$)alkoxycarbonyl, $C_{2-6}$ alkoxycarbonylmethylidenyl, hydroxyoxadiazolyl, $C_{1-6}$ alkoxyaminocarbonyl, $C_{1-6}$ alkylsulphonylaminocarbonyl, aminosulphonyl and $C_{2-6}$ alkylcarbonylaminosulphonyl;

$R^{22}$ represents hydrogen, halogen or $C_{1-6}$ alkyl; and $R^{23}$ represents hydrogen, $C_{1-6}$ alkyl, trifluoromethyl or $C_{1-6}$ alkoxy.

2. The compound as claimed in claim 1 or a pharmaceutically acceptable salt thereof wherein $R^{21}$ represents hydroxy ($C_{1-6}$)alkyl.

3. The compound as claimed in claim 1 represented by formula (IIC), (IID), (IIE), (IIF), (IIG), (IIH), (IIJ), (IIK) or (IIL) or a pharmaceutically acceptable salt thereof:

(IIC)

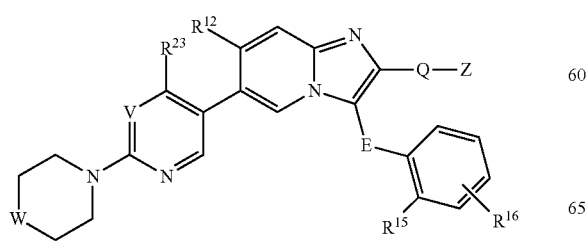

(IID)

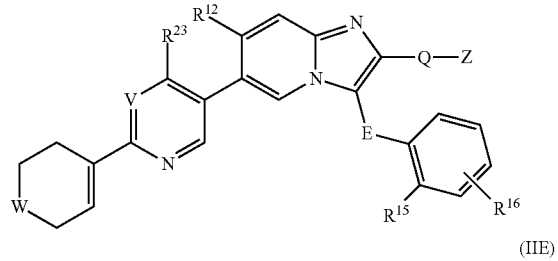

(IIE)

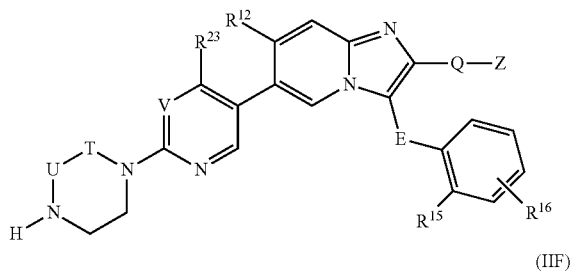

(IIF)

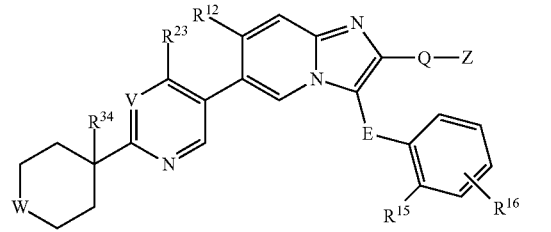

(IIG)

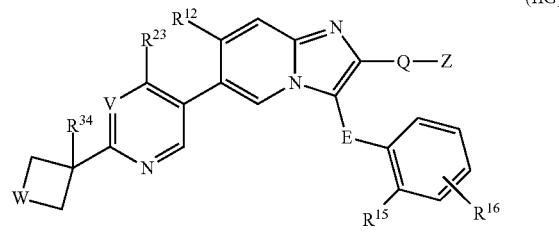

(IIH)

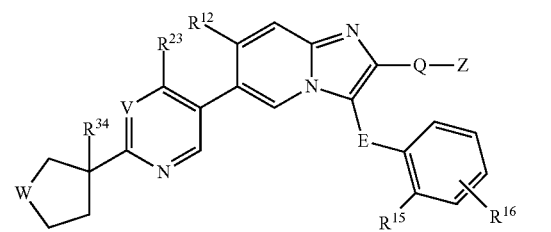

(IIJ)

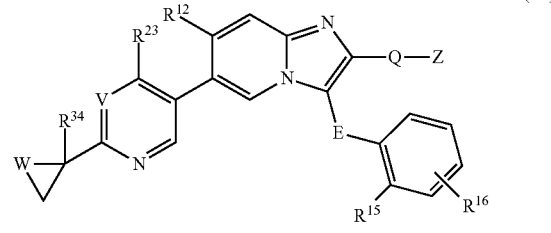

-continued

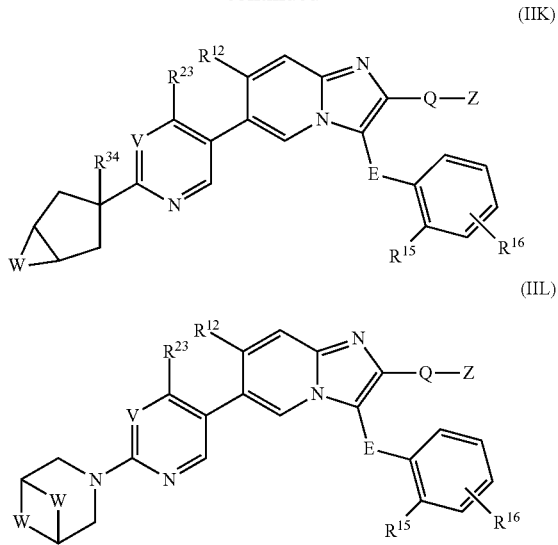

(IIK)

(IIL)

wherein
T represents —CH$_2$— or —CH$_2$CH$_2$—;
U represents C(O) or S(O)$_2$;
W represents O, S, S(O), S(O)$_2$, N(R$^{31}$) or C(R$^{32}$)(R$^{33}$);
-M-represents —CH$_2$— or —CH$_2$CH$_2$—;
R$^{31}$ represents hydrogen, cyano(C$_{1-6}$)alkyl, C$_{1-6}$ alkyl, trifluoromethyl, trifluoroethyl, C$_{1-6}$ alkylsulphonyl, (C$_{1-6}$) alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, aminocarbonyl, C$_{1-6}$ alkylamino-carbonyl, di(C$_{1-6}$)alkylaminocarbonyl, aminosulphonyl, (C$_{1-6}$)alkylaminosulphonyl, di(C$_{1-6}$)alkyalaminosulphonyl or tetrazolyl(C$_{1-6}$)alkyl;
R$^{32}$ represents hydrogen, halogen, cyano, hydroxy, hydroxy(C$_{1-6}$)alkyl, C$_{1-6}$ alkylsulphonyl, formyl, carboxy, carboxy (C$_{1-6}$)alkyl, C$_{2-6\ alkylcarbonyl}$, C$_{2-6}$ alkoxycarbonyl, (C$_{1-6}$ )alkyl, aminosulphonyl, (C$_{1-6}$) alkoxyaminocarbonyl,(C$_{1-6}$)alkyl-sulphonylaminocarbonyl, (C$_{2-6}$) alkylcarbonlaminosulphonyl, hydroxyoxadiazolyl or tetrazolyl;
R$^{33}$ represents hydrogen, halogen, C$_{1-6}$ alkyl, trifluoromethyl, hydroxy, hydroxy-(C$_{1-6}$)alkyl, C$_{1-6}$ alkoxy, amino or carboxy;
R$^{34}$ represents hydrogen, halogen, halo(C$_{1-6}$)alkyl, hydroxy, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino, di(C$_{1-6}$)alkylamino, (C$_{2-6}$)alkylcarbonylamino, (C$_{2-6}$) alkylcarbonylamino(C$_{1-6}$)alkyl, (C$_{1-6}$)alkylsulphonylamino, or (C$_{1-6}$)alkylsulphonylamino(C$_{1-6}$)alkyl.

4. The compound as claimed in claim 3 or a pharmaceutically acceptable salt thereof, wherein R$^{34}$ represents hydrogen or hydroxy.

5. The compound as claimed in claim 1 or a pharmaceutically acceptable salt thereof, wherein R$^{15}$ represents difluoromethoxy.

6. A compound according to claim 1 that is,
N-(2,5-Dichlorophenyl)-6-(6-methoxypyridin-3-yl)-2-methylimidazo[1,2-a]pyridin-3-amine,
3-[2-(Difluoromethoxy)benzyl]-6-(6-methoxy-5-methylpyridin-3-yl)-2-methyl -imidazo[1,2-a]pyridine,
5-{3-[2-(Difluoromethoxy)benzyl]-2-methylimidazo[1,2-a]pyridin-6-yl}-3-methyl-pyridin-2(1H)-one,
3-[2-(Difluoromethoxy)benzyl]-2-methyl-6-[6-(piperazin-1-yl)pyridin-3-yl]imidazo[1,2-a]pyridine,
3-[2-(Difluoromethoxy)benzyl]-6-(6-methoxypyridin-3-yl)-2-methylimidazo[1,2-a]-pyridine,
{3-[2-(Difluoromethoxy)benzyl]-6-(6-methoxypyridin-3-yl)imidazo[1,2-a]pyridin-2-yl}-methanol,
3-[2-(Difluoromethoxy)benzyl]-2-methyl-6-[2-(piperazin-1-yl)pyrimidin-5-yl]-imidazo[1,2-a]pyridine,
4-(5-{3-[2-(Difluoromethoxy)benzyl]-2-methylimidazo[1,2-a]pyridin-6-yl}pyrimidin-2-yl)piperazin-2-one,
3-[2-(Difluoromethoxy)benzyl]-6-[2-(1,1-dioxidothiomorpholin-4-yl)pyrimidin -5-yl]-2-methylimidazo[1,2-a]pyridine,
5-{3-[2-(Difluoromethoxy)benzyl]-2-methylimidazo[1,2-a]pyridin-6-yl}pyridin-2(1H)-one,
4-(5-{3-[2-(Difluoromethoxy)benzyl]-2-methylimidazo[1,2-a]pyridin-6-yl}pyridin-2-yl)-morpholine,
5-{3-[2(Difluoromethoxy)benzyl]-2-methylimidazo[1,2-a]pyridin-6-yl}-2-methoxy-4-methylpyridine,
5{3[2-(Difluoromethoxy)benzyl]-2-methylimidazo[1,2-a]pyridin 6-yl}-4-methyl-pyridin-2(1H)-one,
1-(5-{3-[2-(Difluoromethoxy)benzyl]-2-methylimidazo[1,2-a]pyridin-6-yl}pyrimidin-2-yl)piperidine-4-carboxylic acid,
4-(5-{3-[2-(Difluoromethoxy)benzyl]-2-methylimidazo[1,2-a]pyridin-6-yl}pyrimidin-2-yl)morpholine,
1-(5-{3-[2-(Difluoromethoxy)benzyl]-2-methylimidazo[1,2-a]pyridin-6-yl}pyrimidin-2-yl)-1,4-diazepan-5-one,
5-(5{3-[2-(Difluoromethoxy)benzyl]-2-methylimidazo[1,2-a]pyridin-6-yl}pyrimidin-2-yl)-1,2,5-thiadiazepan-1,1-dioxide,
4-(5-{3-[2-(Difluoromethoxy)benzyl]-2-methyl-7-(trifluoromethyl)imidazo[1,2-a]-pyridin-6-yl}pyrimidin-2-yl)piperazin-2-one,
4-(5-{3-[2-(Difluoromethoxy)benzyl]-2-methyl-7-(trifluoromethyl)imidazo[1,2-a]-pyridin-6-yl}pyrimidin-2-yl)morpholine,
5-{3-[2(Difluoromethoxy)benzyl]-2-methyl-7-(trifluoromethyl)imidazo[1,2-a]pyridin-6-yl}-2-(piperazin-1yl),pyrimidine,
1-(5-{3-[2-(Difluoromethoxy)benzyl]-2-methyl-7-(trifluoromethyl)imidazo[1,2-a]-pyridin-6-yl}pyridin-2-yl)piperazine,
4-(5-{3-[2-(Difluoromethoxy)benzyl]-2,7-dimethylimidazo[1,2-a]pyridin-6-yl}pyrimidin-2-yl)piperazin-2-one,
4-(5-{3-[2-(Difluoromethoxy)benzyl]-2,7-dimethylimidazo[1,2-a]pyridin-6-yl}pyrimidin-2-yl)morpholine,
1-(5-{3-[2-(Difluoromethoxy)benzyl]-2,7-dimethylimidazo[1,2-a]pyridin-6-yl}pyridin-2-yl)piperazine,
1-(5-{3-[2-(Difluoromethoxy)benzyl]-7-fluoro-2-(methoxymethyl)imidazo[1,2-a]pyridin-6-yl}pyrimidin-2-yl)piperidine-4-carboxylic acid,
5-{3-[2-(Difluoromethoxy)benzyl]-2-methylimidazo[1,2-a]pyridin-6-yl}pyrimidin-2-yl)-2-oxa-5-azabicyclo[2.2.1]heptane,
Ethyl 1-[5-(3-{[2-(difluoromethoxy)phenyl]methyl}-2-methylimidazo[1,2-a]pyridin-6-yl)pyrimidin-2-yl]-3-methylpiperidine-3-carboxylate,
1-[5-(3-{[2-(Difluoromethoxy)phenyl]methyl}-2-methylimidazo [1,2-a]pyridin-6-yl)-pyrimidin-2-yl]-3-methylpiperidine-3-carboxylic acid hydrochloride,
Ethyl 4-[5-(3-{[2-(difluoromethoxy)phenyl]methyl}-2-methylimidazo[1,2-a]pyridin-6-yl)pyrimidin-2-yl]cyclohex-3-ene-1-carboxylate, 4-[5-(3-{[2-(Difluoromethoxy)phenyl]methyl}-2-methylimidazo [1,2-a]pyridin-6-yl)-pyrimidin-2-yl]cyclohex-3-ene-1-carboxylic acid, trans-4-[5-(3-{[2-(Difluoromethoxy)phenyl]methyl}-2-methylimidazo[1,2-]pyridin-6-yl)pyrimidin-2-yl]cyclohexane-1-carboxylic acid, cis-4-[5-(3-{[2-(Difluoromethoxy)phenyl]methyl}-2-methylimidazo[1,2-a]pyridin-6-yl)-pyrimidin-2-yl]cyclohexane-1-carboxylic acid, Methyl 1-[5-(3-{[2-(difluoromethoxy)phenyl]methyl}-2-methylimidazo[1,2-a]pyridin-6-yl)pyrimidin-2-yl]-4-methylpiperidine-4-carboxylate, 1-[5-(3-{[2-(Difluoromethoxy)phenyl]methyl}-2-methylimidazo [1,2-a]pyridin-6-yl)-pyrimidin-2-yl]-4-methylpiperidine-4-carboxylic acid, Ethyl 1-[5-(3-{[2-(difluoromethoxy)phenyl]methyl}-7-fluoro-2-methylimidazo[1,2-a]-pyridin-6-yl)pyrimidin-2-yl]-4-methylpiperidine-4-carboxylate, 1-[5-(3-{[2-(Difluoromethoxy)phenyl]methyl}-7-fluoro-2-methylimidazo [1,2-a]pyridin-6-yl)pyrimidin-2-yl]-4-methylpiperidine-4-carboxylic acid, Ethyl 3-[5-(3-{[2-(difluoromethoxy)phenyl]methyl}-2,7-dimethylimidazo[1,2-a]pyridin-6-yl)pyrimidin-2-yl]-3-azabicyclo [3.1.0]hexane -6-carboxylate, 3-[5-(3-{[2-(Difluoromethoxy)phenyl]methyl }-2,7-dimethylimidazo [1,2-]pyridin-6-yl)-pyrimidin-2-yl]-3-azabicyclo [3.1.0 ]hexane-6-carboxylic acid, Ethyl 1-[5-(3-{[2-(difluoromethoxy)phenyl]methyl}-2,7-dimethylimidazo[1,2-a]pyridin-6-yl)pyrimidin-2-yl]piperidine-4-carboxylate, 1-[5-(3-{[2-(Difluoromethoxy)phenyl]methyl }-2,7-dimethylimidazo [1,2-a]pyridin-6-yl)-pyrimidin-2-yl]piperidine-4-carboxylic acid, 2-[5-(3-{[2-(Difluoromethoxy)phenyl]methyl }-2,7-dimethylimidazo [1,2-a]pyridin-6-yl)-pyrimidin-2-yl]-2-azaspiro [3.3 ]heptane -6-carboxylic acid, 5-(3-{[2-(Difluoromethoxy)phenyl]methyl }-2,7-dimethylimidazo[1,2-a]pyridin-6-yl)-2-[4-(1H-tetrazol-5-yl-methyl)piperazin-1-yl]pyrimidine formate, 5-(3-{[2-(Difluoromethoxy)phenyl]methyl }-2,7-dimethylimidazo[1,2-a]pyridin-6-yl)-2-[4-(1H-tetrazol-5-yl)piperidin-1-yl]pyrimidine, (3R)-1-[5-(3-{[2-(Difluoromethoxy)phenyl]methyl }-2,7-dimethylimidazo [1,2-a]pyridin-6-yl)pyrimidin-2-yl]pyrrolidine-3-carboxylic acid, 2-{4-[5-(3-{[2-(Difluoromethoxy)phenyl]methyl }-2,7-dimethylimidazo[1,2-a]pyridin-6-yl)pyrimidin-2-yl]piperazin-1-yl}propanoic acid, (3S)-1-[5-(3-{[2-(Difluoromethoxy)phenyl]methyl }-2,7-dimethylimidazo [1,2-a]pyridin-6-yl)pyrimidin-2-yl]pyrrolidine-3-carboxylic acid, (1R,2S)-2-{[5-(3-{[2-(Difluoromethoxy)phenyl]methyl }-2,7-dimethylimidazo[1,2-a]-pyridin-6-yl)pyrimidin-2-yl]amino}cyclopentane-1-carboxylic acid, Ethyl 1-[5-(3-{[2-(difluoromethoxy)phenyl]methyl}-2,7-dimethylimidazo[1,2-a]pyridin-6-yl)pyrimidin-2-yl]-4-methylpiperidine-4-carboxylate, 4-[5-(3-{[2-(Difluoromethoxy)phenyl]methyl }-2,7-dimethylimidazo [1,2-a]pyridin-6-yl)-pyrimidin-2-yl]morpholine-2-carboxylic acid, (3S)-1-[5-(3-{[2-(Difluoromethoxy)phenyl]methyl}-2,7-dimethylimidazo [1,2-a]pyridin-6-yl)pyrimidin-2-yl]piperidine-3-carboxylic acid, 1-[5-(3-{[2-(Difluoromethoxy)phenyl]methyl}-2,7-dimethylimidazo[1,2-a]pyridin-6-yl)-pyrimidin-2-yl]-4-methylpiperidine-4-carboxylic acid, (1R,3S)-3-{[5-(3-{[2-(Difluoromethoxy)phenyl]methyl}-2,7-dimethylimidazo [1,2-a]-pyridin-6-yl)pyrimidin-2-yl]amino}cyclopentane-1-carboxylic acid, Ammonium (3R)-1-[5-(3-{[2-(difluoromethoxy)phenyl]methyl}-2,7-dimethylimidazo-[1,2-a]pyridin-6-yl)pyrimidin-2-yl]piperidine-3-carboxylate, Ammonium 1-({[5-(3-{[2-(difluoromethoxy)phenyl]methyl}-2,7-dimethylimidazo [1,2-a]pyridin-6-yl)pyrimidin-2-yl]amino}methyl)cyclopropane-1-carboxylate, Ethyl 2-[5-(3-{[2-(difluoromethoxy)phenyl]methyl}-2,7-dimethylimidazo[1,2-a]pyridin-6-yl)pyrimidin-2-yl]propanoate, Ammonium (2S)-1-[5-(3-{[2-(difluoromethoxy)phenyl]methyl}-2,7-dimethylimidazo-[1,2---a]pyridin-6-yl)pyrimidin-2-yl]piperidine-2-carboxylate, (2S)-2-{N-[5-(3-{[2-(Difluoromethoxy)phenyl]methyl}-2,7-dimethylimidazo [1,2-a]-pyridin-6-yl)pyrimidin-2-yl]-N-(methyl)amino}propanoic acid, 1-[5-(3-{[2-(Difluoromethoxy)phenyl]methyl}-2,7-dimethylimidazo[1,2-a]pyridin-6-yl)-pyrimidin-2-yl]azetidine-3-carboxylic acid, (1S,3R)-3-{[5-(3-{[2-(Difluoromethoxy)phenyl]methyl}-2,7-dimethylimidazo [1,2-a ]-pyridin-6-yl)pyrimidin-2-yl]amino}cyclopentane-1-carboxylic acid, Ammonium (2R)-1-[5-(3-{[2-(difluoromethoxy)phenyl]methyl}-2,7-dimethylimidazo-[1,2-a ]pyridin-6-yl)pyrimidin-2-yl]piperidine-2-carboxylate, (2S)-4-[5-(3-{[2-(Difluoromethoxy)phenyl]methyl}-2-methylimidazo[1,2-a]pyridin-6-yl)pyrimidin-2-yl]morpholine-2-carboxylic acid, 3-{[5-(3-{[2-(Difluoromethoxy)phenyl]methyl }-2-methylimidazo [1,2-a]pyridin-6-yl)-pyrimidin-2-yl]oxy}cyclobutane-1-carboxylic acid, Ammonium 3-[5-(3-{[2-(difluoromethoxy)phenyl]methyl}-2,7-dimethylimidazo[1,2-a ]pyridin-6-yl)pyrimidin-2-yl]-3-azabicyclo[3.1.0]hexane-1-carboxylate, Ammonium 4-[5-(3-{[2-(difluoromethoxy)phenyl]methyl}-2-methylimidazo [1,2-a]pyridin-6-yl)pyrimidin-2-yl]-1,4-oxazepane-7-carboxylate, 2-[(2R)-1-[5-(3-{[2-(Difluoromethoxy)phenyl]methyl }-2-methylimidazo [1,2-a]pyridin-6-yl)pyrimidin-2-yl]pyrrolidin-2-yl]acetic acid, 5-(3-{[2-(Difluoromethoxy)phenyl]methyl }-2-methylimidazo[1,2-a]pyridin-6-yl)-2-[3-(2H-1,2,3,4-tetrazol-5-yl)azetidin-1-yl]pyrimidine, Ammonium 3-[5-(3-{[2-(difluoromethoxy)phenyl]methyl}-2-methylimidazo [1,2-a]pyridin-6-yl)pyrimidin-2-yl]-3-azabicyclo[3.1.0]hexane-1-carboxylate, 5-[5-(3-{[2-(Difluoromethoxy)phenyl]methyl }-2-methylimidazo [1,2-a ]pyridin-6-y1)-pyrimidin-2-yl]-5-azaspiro[2.4]heptane-1-carboxylic acid, 5-[5-(3-{[2-(Difluoromethoxy)phenyl]methyl }-2-methylimidazo [1,2---a]pyridin-6-y1)-pyrimidin-2-yl]-5-azaspiro[2.3]hexane-1-carboxylic acid, Ammonium (2R)-4-[5-(3-{[2-(difluoromethoxy)phenyl]methyl}-2-methylimidazo[1,2-a]-pyridin-6-yl)pyrimidin-2-yl]morpholine-2-carboxylate, 3-[5-(3-{[2-(Difluoromethoxy)phenyl]methyl}-2-methylimidazo [1,2-a]pyridin-6-yl)-pyrimidin-2-yl]-3,6-diazabicyclo[3.2.2]nonan-7-one, Ammonium (1R,5S,6r)-3-[5-(3-{[2-(difluoromethoxy)phenyl]methyl}-2-methylimidazo-[1,2-a]pyridin-6-yl)pyridin-2-yl]-3-azabicyclo[3.1.0]hexane-6-carboxylate, 3-[5-(3-{[2-(Difluoromethoxy)phenyl]methyl}-2-methylimidazo [1,2-a]pyridin-6-yl)-pyrimidin-2-yl]-3-azabicyclo[4.1.0]heptane-6-carboxylic acid, 2-[(2S)-1-[5-(3-{[2-(Difluoromethoxy)phenyl]methyl}-2-methylimidazo [1,2-a]pyridin-6-yl)pyrimidin-2-yl]pyrrolidin-2-yl]acetic acid, N-[5-(3-{[2-(Difluoromethoxy)phenyl]methyl}-2-methylimidazo [1,2-a]pyridin-6-yl)-pyridin-2-yl]methanesulfonamide, Ammonium 1-[5-(3-{[2-(difluoromethoxy)phenyl]methyl}-2-methylimidazo[1,2-a]-pyridin-6-yl)pyrimidin-2-yl]-3-methylpyrrolidine-3-carboxylic, 2-[(2R)-1-[5-(3-{[2-(Difluoromethoxy)phenyl]methyl}-2-methylimidazo [1,2-a]-pyridin-6-yl)-pyrimidin-2-yl]-piperidin-2-yl]acetic acid, 5-[5-(3-{[2-(Difluoromethoxy)phenyl]methyl}-2-methylimidazo[1,2-a]pyridin-6-yl)-pyrimidin-2-yl]2-oxa-5-azabicyclo[2.2.1]heptane-1carboxtlic acid, Ammonium 3-[5-(3-{[2-(difluoromethoxy)phenyl]methyl}-2-methylimidazo [1,2-a]-pyridin-6-yl)pyrimidin-2-yl]-3-azabicyclo [4.1.0]heptane-1-carboxylate, 3-[5-(3-{[2-(Difluoromethoxy)phenyl]methyl}-2-methylimidazo[1,2-a]pyridin-6-yl)-pyrimidin-2-yl]-3-azabicyclo[3.1.1]heptane-6-carboxylic acid, 2-[(2S)-1-[5-(3-{[2-(Difluoromethoxy)phenyl]methyl}-2-methylimidazo[1,2-a]pyridin-6-yl)pyrimidin-2-yl]piperidin-2-yl]acetic acid, Potassium 5-[5-(3-{[2-(difluoromethoxy)phenyl]methyl}-2-methylimidazo [1,2-a]pyridin-6-yl)pyrimidin-2-yl]-1-methyl-5-azaspiro[2.3]hexane-1-carboxylate, Potassium 1-[5-(3-{[2-(difluoromethoxy)phenyl]methyl}-2-methylimidazo [1,2-a]pyridin-6-yl)pyrimidin-2-yl]-4-methylpiperidine-4-carboxylate, (1R,5S,6r)-3-[5-(3-{1-[2-(Difluoromethoxy)phenyl]ethyl}-2,7-dimethylimidazo[1,2-a]-pyridin-6-yl)pyrimidin-2-yl]-3-azabicyclo[3.1.0]hexane-6-carboxylic acid, Ethyl 2-{1-[5-(3-{[2-(difluoromethoxy)phenyl]methyl}-2-methylimidazo [1,2-a]pyridin-6-yl)pyrimidin-2-yl]piperidin-4-yl}acetate, Potassium 3-[5-(3-{[2-(difluoromethoxy)phenyl]methyl}-2-methylimidazo [1,2-a]pyridin-6-yl)pyrimidin-2-yl]-5-methyl-3-azabicyclo[3.1.0]hexane-1-carboxylate, Potassium 2-{1-[5-(3-{[2-(difluoromethoxy)phenyl]methyl}-2-methylimidazo [1,2-a]-pyridin-6-yl)pyrimidin-2-yl]piperidin-4-yl}acetate, Potassium 3-[5-(3-{[2-(difluoromethoxy)phenyl]methyl}-2,7-dimethylimidazo[1,2-a]-pyridin-6-yl)pyrimidin-2-yl]-3-azabicyclo[4.1.0]heptane-6-carboxylate (Enantiomer A), Potassium 3-[5-(3-{[2-(difluoromethoxy)phenyl]methyl}-2,7-dimethylimidazo[1,2-a]-pyridin-6-yl)pyrimidin-2-yl]-3-azabicyclo[4.1.0]heptane-6-carboxylate (Enantiomer B), Potassium 3-[5-(3-{[2-(difluoromethoxy)phenyl]methyl}-2,7-dimethylimidazo[1,2-a]-pyridin-6-yl)pyrimidin-2-yl]-3-azabicyclo[4.1.0]heptane-1-carboxylate (Enantiomer A), Potassium 3-[5-(3-{[2-(difluoromethoxy)phenyl]methyl}-2,7-dimethylimidazo [1,2-a]-pyridin-6-yl)pyrimidin-2-yl]-3-azabicyclo [4.1.0]heptane-1-carboxylate (Enantiomer B), Potassium 2-{4-[5-(3-{[2-(difluoromethoxy)phenyl]methyl}-2-methylimidazo [1,2-a]-pyridin-6-yl)pyrimidin-2-yl]morpholin-3-yl}acetate, Potassium 3-[5-(3-{[2-(difluoromethoxy)phenyl]methyl}-2-methylimidazo [1,2-a]pyridin-6-yl)pyrimidin-2-yl]-3-azabicyclo [4.1.0]heptane-6-carboxylate (Enantiomer A), Potassium 3-[5-(3-{[2-(difluoromethoxy)phenyl]methyl}-2-methylimidazo [1,2-a]pyridin-6-yl)pyridin-2-yl]-3-azabicyclo [4.1.0]heptane-6-carboxylate (Enantiomer B), Potassium 3-[5-(3-{[2-(difluoromethoxy)phenyl]methyl}-2-methylimidazo [1,2-a]pyridin-6-yl)pyridin-2-yl]-3-azabicyclo [4.1.0]heptane-1-carboxylate (Enantiomer A), Potassium 3-[5-(3-{[2-(difluoromethoxy)phenyl]methyl}-2-methylimidazo [1,2-a]pyridin-6-yl)pyridin-2-yl]-3-azabicyclo [4.1.0]heptane-1-carboxylate (Enantiomer B), Potassium 1-[5-(3-{[2-(difluoromethoxy)phenyl]methyl}-2-methylimidazo [1,2-a]pyridin-6-yl)pyrimidin-2-yl]azepane-4-carboxylate, 5-(3-{[2-(Difluoromethoxy)phenyl]methyl}-2-methylimidazo[1,2-a]pyridin-6-yl)-2-(piperidin-1-yl)pyridine, 1-[5-(3-{[2-(Difluoromethoxy)phenyl]methyl}-2-methylimidazo [1,2-a]pyridin-6-yl)-3-fluoropyridin-2-yl]-4-methylpiperidine-4-carboxylic acid, 2-{4-[5-(3-{[2-(Difluoromethoxy)phenyl]methyl}-2-methylimidazo [1,2-a]pyridin-6-yl)-pyrimidin-2-yl]piperidin-1-yl}acetic acid, Ethyl (1R,5S,6r)-3-[5-(3-{[2-(difluoromethoxy)phenyl]methyl}-2-methylimidazo [1,2-a]-pyridin-6-yl)pyrimidin-2-yl]bicyclo [3.1.0]hexane-6-carboxylate, Ammonium (1R,5S,6r)-3-[5-(3-{[2-(difluoromethoxy)phenyl]methyl}-2-methylimidazo-[1,2-a]pyridin-6-yl)pyrimidin-2-yl]bicyclo [3.1.0]hexane-6-carboxylate, Potassium 4-[5-(3-{[2-(difluoromethoxy)phenyl]methyl}-2-methylimidazo [1,2-a]pyridin-6-yl)pyrimidin-2-yl]-2-methylmorpholine-2-carboxylate, (1R,4R)-4-[5-(3-{[2-(Difluoromethoxy)phenyl]methyl}-2-methylimidazo[1,2-a]pyridin-6-yl)pyridin-2-yl]cyclohexane-1-carboxylic acid, 4-[5-(3-{[2-(Difluoromethoxy)phenyl]methyl}-2-methylimidazo [1,2-a]pyridin-6-yl)-pyridin-2-yl]cyclohex-3-ene-1-carboxylic acid, Potassium 3-[5-(3-{[2-(difluoromethoxy)phenyl]methyl}-2-methylimidazo[1,2-a]pyridin-6-yl)pyridin-2-yl]-3-azabicyclo[3.1.0]hexane-1-carboxylate (Enantiomer A), Potassium 1-[3-chloro-5-(3-{[2-(difluoromethoxy)phenyl]methyl}-2-methylimidazo[1,2-a]pyridin-6-yl)pyridin-2-yl]-4-methylpiperidine-4-carboxylate, Potassium 4-[5-(3-{[2-(difluoromethoxy)phenyl]methyl}-2-methylimidazo[1,2-a]pyridin-2-yl]-3-methylcyclohexane-1-carboxylate (unknown isomer), Potassium 4-{[5-(3-{[2-(difluoromethoxy)phenyl]methyl}-2-methylimidazo[1,2-a]-pyridin-6-yl)pyrimidin-2-yl]methyl}cyclohexane-1-carboxylic acid, 4-[5-(3-{[2-(Difluoromethoxy)phenyl]methyl}-7-fluoro-2-methylimidazo [1,2-a]pyridin-6-yl)pyrimidin-2-yl]bicyclo[4.1.0]heptane-1-carboxylic acid, Potassium 6-[5-(3-{[2-(difluoromethoxy)phenyl]methyl}-2-methylimidazo[1,2-a]pyridin-2-yl]bicyclo[4.1.0]heptane-3-carboxylate, Ammonium 3-[5-(3-{[2-(difluoromethoxy)phenyl]methyl}-2-methylimidazo[1,2-a]-pyridin-6-yl)pyrimidin-2-yl]cyclopentane-1-carboxylate, Ethyl 4-[5-(3-{[2-(difluoromethoxy)phenyl]methyl}-7-fluoro-2-methylimidazo[1,2-a]-pyridin-6-yl)pyrimidin-2-yl]-2-methylcyclohexane-1-carboxylate, (1r,4r)-4-[5-(3-{[2-(Difluoromethoxy)phenyl]methyl}-2,7-dimethylimidazo[1,2-a]-pyridin-6-yl)pyrimidin-2-yl]cyclohexane-1-carboxylic acid,
Potassium 2-{4-[5-(3-{[2-(difluoromethoxy)phenyl]methyl}-7-fluoro-2-methylimidazo-[1,2-a]pyridin-6-yl) pyrimidin-2-yl]cyclohexyl}acetate,
Potassium 3-[5-(3-{[2-(difluoromethoxy)phenyl]methyl}-7-fluoro-2-methylimidazo[1,2-a]pyridin-6-yl)pyrimidin-2-yl]cyclopentane-1-carboxylate,
6-[2-(4-Carboxy-3-methylcyclohexyl)pyrimidin-5-yl]-3-{[2-(difluoromethoxy)phenyl]-methyl}-7-ethoxy-2-methylimidazo[1,2-a]pyridin-1-ium formate,
Ammonium 5-[5-(3-{[2-(difluoromethoxy)phenyl]methyl}-7-fluoro-2-methylimidazo-[1,2-a]pyridin-6-yl)pyrimidin-2-yl]bicyclo[2.2.2]octane-2-carboxylate,
Potassium 4-[5-(3-{[2-(difluoromethoxy)phenyl]methyl}-2-methylimidazo [1,2-a]pyridin-6-yl)pyrimidin-2-yl]-3-methylcyclohexane-1-carboxylate,
Ethyl (1R,5S,6r)-3-[5-(3-{[2-(difluoromethoxy)phenyl]methyl}-7-fluoro-2-methyl-imidazo [1,2-a]pyridin-6-yl)pyrimidin-2-yl]bicyclo[3.1.0]hexane-6-carboxylate,
Potassium (1R,5S,6r)-3-[5-(3-{[2-(difluoromethoxy)phenyl]methyl}-7-fluoro-2-methyl-imidazo [1,2-a]pyridin-6-yl)pyrimidin-2-yl]bicyclo[3.1.0]hexane-6-carboxylate,
(1R,4R)-4-[5-(3-{[2-(Difluoromethoxy)phenyl]methyl}-7-fluoro-2-methylimidazo[1,2-a]pyridin-6-yl)pyrimidin-2-yl]-1-methylcyclohexane-1-carboxylic acid,
Potassium 3-[5-(3-{[2-(Difluoromethoxy)phenyl]methyl}-7-fluoro-2-methylimidazo[1,2-a]pyridin-6-yl)pyrimidin-2-yl]bicyclo [4.1.0]heptane-7-carboxylate,
4-[5-(3-{[2-(Difluoromethoxy)phenyl]methyl}-7-fluoro-2-methylimidazo [1,2-a]pyridin-6-yl)pyrimidin-2-yl]-2-methylcyclohexane-1-carboxylic acid (Isomers A),
4-[5-(3-{[2-(Difluoromethoxy)phenyl]methyl}-7-fluoro-2-methylimidazo[1,2-a]pyridin-6-yl)pyrimidin-2-yl]-2-methylcyclohexane-1-carboxylic acid (Isomers B),
4-[5-(3-{[2-(Difluoromethoxy)phenyl]methyl}-7-fluoro-2-methylimidazo[1,2-a]pyridin-6-yl)pyrimidin-2-yl]-2-methylcyclohexane-1-carboxylic acid (Isomers C),
4-[5-(3-{[2-(Difluoromethoxy)phenyl]methyl}-7-fluoro-2-methylimidazo [1,2-a]pyridin-6-yl)pyrimidin-2-yl]-2-methylcyclohexane-1-carboxylic acid (Isomers D),
Potassium (1R,5S,6S)-3-[5-(3-{[2-(difluoromethoxy)phenyl]methyl}-7-fluoro-2-methyl-imidazo [1,2-a]pyridin-6-yl)pyrimidin-2-yl]bicyclo[3.1.0]hexane-6-carboxylate,
(4s)-1-[5-(3-{[2-(Difluoromethoxy)phenyl]methyl}-7-fluoro-2-methylimidazo[1,2-a]pyridin-6-yl)pyrimidin-2-yl]-6-hydroxy-4-methyl-2-oxabicyclo[2.2.2]octan-3-one,
Potassium 7-[5-(3-{[2-(difluoromethoxy)phenyl]methyl}-7-fluoro-2-methylimidazo[1,2-a]pyridin-6-yl)pyrimidin-2-yl]-3-oxa-7-azabicyclo[3.3.1]nonane-9-carboxylate,
Potassium 5-[5-(3-{[2-(difluoromethoxy)phenyl]methyl}-7-fluoro-2-methylimidazo[1,2-a]pyridin-6-yl)pyrimidin-2-yl]piperidine-2-carboxylate,
8-[5-(3-{[2-(Difluoromethoxy)phenyl]methyl}-7-fluoro-2-methylimidazo[1,2-a]pyridin-6-yl)pyrimidin-2-yl]-2-methyl-2,4,8-triazaspiro[4.5]decane-1,3-dione,
Ethyl 4-[5-(3-{[2-(difluoromethoxy)phenyl]methyl}-7-fluoro-2-methylimidazo[1,2-a]-pyridin-6-yl)pyrimidin-2-yl]cyclohex-3-ene-1-carboxylate,
Ethyl 4-[5-(3-{[2-(difluoromethoxy)phenyl]methyl}-7-fluoro-2-methylimidazo[1,2-a]-pyridin-6-yl)pyrimidin-2-yl]cyclohexanecarboxylate,
4-[5-(3-{[2-(Difluoromethoxy)phenyl]methyl}-7-fluoro-2-methylimidazo[1,2-a]pyridin-6-yl)pyrimidin-2-yl]cyclohexanecarboxylic acid (cis isomer),
4-[5-(3-{[2-(Difluoromethoxy)phenyl]methyl}-7-fluoro-2-methylimidazo [1,2-a]pyridin-6-yl)pyrimidin-2-yl]cyclohexanecarboxylic acid (trans isomer),
1-[5-(3-{[2-(Difluoromethoxy)phenyl]methyl}-2-methylimidazo[1,2-a]pyridin-6-yl)-4-(trifluoromethyl)pyrimidin-2-yl]-1,4-diazepan-5-one,
(3S)-{4-[5-(3-{[2-(Difluoromethoxy)phenyl]methyl}-7-fluoro-2-methylimidazo[1,2-a]-pyridin-6-yl)pyrimidin-2-yl]morpholin-3-yl}methanol,
(3R)-{445-[3-[[2-(Difluoromethoxy)phenyl]methyl]-7-fluoro-2-methylimidazo[1,2-a]pyridin-6-yl]pyrimidin-2-yl]morpholin-3-yl}methanol,
(3R)-4-[5-(3-{[2-(Difluoromethoxy)phenyl]methyl}-7-fluoro-2-methylimidazo[1,2-a]-pyridin-6-yl)pyrimidin-2-yl]morpholine-3-carboxylic acid,
(3S)-4-[5-(3-{[2-(Difluoromethoxy)phenyl]methyl}-7-fluoro-2-methylimidazo[1,2-a]-pyridin-6-yl)pyrimidin-2-yl]morpholine-3-carboxylic acid,
2-[5-(3-{[2-(Difluoromethoxy)phenyl]methyl}-7-fluoro-2-methylimidazo[1,2-a]pyridin-6-yl)pyrimidin-2-yl]propan-2-ol,
Ethyl 1-[5-(3-{[2-(difluoromethoxy)phenyl]methyl}-7-fluoro-2-methylimidazo[1,2-a]-pyridin-6-yl)pyrimidin-2-yl]-4-(hydroxymethyl)piperidine-4-carboxylate,
Sodium 1-[5-[3-[[2-(difluoromethoxy)phenyl]methyl]-7-fluoro-2-methylimidazo[1,2-a]pyridin-6-yl]pyrimidin-2-yl]-4-(hydroxymethyl)piperidine-4-carboxylate,
1-[5-(3-{[2-(Difluoromethoxy)phenyl]methyl}-7-fluoro-2-methylimidazo [1,2-a]pyridin-6-yl)pyrimidin-2-yl]-4-(methoxycarbonyl)piperidine-4-carboxylic acid,
Ethyl 3-[5-(3-{[2-(difluoromethoxy)phenyl]methyl}-7-fluoro-2-methylimidazo[1,2-a]-pyridin-6-yl)pyrimidin-2-yl]-3-azabicyclo[4.1.0]heptane-1-carboxylate,
Sodium 3-[5-(3-{[2-(difluoromethoxy)phenyl]methyl}-7-fluoro-2-methylimidazo[1,2-a]-pyridin-6-yl)pyrimidin-2-yl]-3-azabicyclo[4.1.0]heptane-1-carboxylate,
Ethyl 1-[5-(3-{[2-(difluoromethoxy)phenyl]methyl}-2-methylimidazo[1,2-a]pyridin-6-yl)pyrimidin-2-yl]-4-(hydroxymethyl)piperidine-4-carboxylate,
Sodium 1-[5-(3-{[2-(difluoromethoxy)phenyl]methyl}-2-methylimidazo[1,2-a]pyridin-6-yl)pyrimidin-2-yl]-4-(hydroxymethyl)piperidine-4-carboxylate,
Ethyl 1-[5-(3-{[2-(difluoromethoxy)phenyl]methyl}-2-methylimidazo[1,2-a]pyridin-6-yl)pyrimidin-2-yl]-4-(trifluoromethyl)piperidine-4-carboxylate,
1-[5-(3-{[2-(Difluoromethoxy)phenyl]methyl}-2-methylimidazo[1,2-a]pyridin-6-yl)-pyrimidin-2-yl]-4-(trifluoromethyl)piperidine-4-carboxylic acid,
Ethyl 1-[5-(3-{[2-(difluoromethoxy)phenyl]methyl}-7-fluoro-2-methylimidazo[1,2-a]-pyridin-6-yl)pyrimidin-2-yl]-4-fluoropiperidine-4-carboxylate,
Sodium 1-[5-(3-{[2-(difluoromethoxy)phenyl]methyl}-7-fluoro-2-methylimidazo[1,2-a]-pyridin-6-yl)pyrimidin-2-yl]-4-fluoropiperidine-4-carboxylate,
Methyl 1-[5-(3-{[2-(difluoromethoxy)phenyl]methyl}-2-methylimidazo[1,2-a]pyridin-6-yl)pyrimidin-2-yl]-4-methoxypiperidine-4-carboxylate,
Sodium 1-[5-(3-{[2-(difluoromethoxy)phenyl]methyl}-2-methylimidazo[1,2-a]pyridin-6-yl)pyrimidin-2-yl]-4-methoxypiperidine-4-carboxylate,
1-[5-(3-{[2-(Difluoromethoxy)phenyl]methyl}-2-methylimidazo[1,2-a]pyridin-6-yl)pyrimidin-2-yl]-4-fluoropiperidine-4-carboxylic acid, Methyl 1-[5-(3-{[2-(difluoromethoxy)phenyl]methyl}-2-methylimidazo[1,2-a]pyridin-6-yl)pyrimidin-2-yl]-4-ethylpiperidine-4-carboxylate, 1-[5-(3-{[2-(Difluoromethoxy)phenyl]methyl}-2-methylimidazo[1,2-a]pyridin-6-yl)-pyrimidin-2-yl]-4-ethylpiperidine-4-carboxylic acid, Methyl (1R,5S)-3-[5-(3-{[2-(difluoromethoxy)phenyl]methyl}-7-fluoro-2-methylimidazo-[1,2-a]pyridin-6-yl)pyrimidin-2-yl}-3-azabicyclo [3.2.1]octane-8-carboxylate, Methyl (1R,5S)-3-[5-(3-{[2-(difluoromethoxy)phenyl]methyl}-7-fluoro-2-(methoxy-methyl)imidazo[1,2-a]pyridin-6-yl)pyrimidin-2-yl]-3-azabicyclo[3.2.1]octane-8-carboxylate, (1R,5S)-3-[5-(3-{[2-(Difluoromethoxy)phenyl]methyl}-7-fluoro-2-methylimidazo[1,2-a]-pyridin-6-yl)pyrimidin-2-yl]-3-azabicyclo[3.2.1]octane-8-carboxylic acid, Methyl (1R,5S,8s)-3-[5-(3-{[2-(difluoromethoxy)phenyl]methyl}-7-fluoro-2-methyl-imidazo[1,2-a 9-pyridin-6-yl)pyrimidin-2-yl]-3-azabicyclo[3.2.1]octane-8-carboxylic, (1R,5S,8s)-3-[5-(3-{[2-(Difluoromethoxy)phenyl]methyl}-7-fluoro-2-methylimidazo[1,2-a]-pyridin-6-yl)pyrimidin-2-yl]-3-azabicyclo[3.2.1]octane-8-carboxylic acid, (1R,5S,8e)-3-[5-(3-{[2-(Difluoromethoxy)phenyl]methyl}-7-fluoro-2-methylimidazo[1,2-a]pyridin-6-yl)pyrimidin-2-yl]-3-azabicyclo[3.2.1]octane-8-carboxylic acid, Methyl (1R,6S or 1S, 6R)-3-[5-(3-{[2-(difluoromethoxy)phenyl]methyl}-7-fluoro-2-methylimidazo[1,2-a]pyridin-6-yl)pyrimidin-2-yl]-3-azabicyclo[4.1.0]heptane-6-carboxylate, (1R,6S or 1S, 6R)-3-[5-(3-{[2-(Difluoromethoxy)phenyl]methyl}-7-fluoro-2-methyl-imidazo[1,2-a]pyridin-6-yl)pyrimidin-2-yl]-3-azabicyclo[4.1.0]heptane-6-carboxylic acid, Methyl (1S,5S or 1R,5R)-3-[5-(3-{[2-(difluoromethoxy)phenyl]methyl}-7-fluoro-2-methylimidazo [1,2-a]pyridin-6-yl)pyrimidin-2-yl]-3-azabicyclo[3.1.0]hexane-1-carboxylate, (1S,5S or 1R,5R)-3-[5-(3-{[2-(Difluoromethoxy)phenyl]methyl}-7-fluoro-2-methyl-imidazo[1,2-a]pyridin-6-yl)pyrimidin-2-yl]-3-azabicyclo [3.1.0]hexane-1-carboxylic acid, Methyl (1R or 1S)-3-[5-(3-{[2-(difluoromethoxy)phenyl]methyl}-7-fluoro-2-methyl-imidazo[1,2-a]pyridin-6-yl)pyrimidin-2-yl]-3-azabicyclo[3.1.0]hexane-1-carboxylate, (1R,5R or 1S,5S)-3-[5-(3-{[2-(Difluoromethoxy)phenyl]methyl}-7-fluoro-2-methyl-imidazo[1,2-a]pyridin-6-yl)pyrimidin-2-yl]-3-azabicyclo[3.1.0]hexane-5-carboxylic acid, Methyl (1S,6R or 1R,6S)-3-[5-(3-{[2-(difluoromethoxy)phenyl]methyl}-7-fluoro-2-methylimidazo[1,2-a]pyridin-6-yl)pyrimidin-2-yl]-3-azabicyclo[4.1.0]heptane-6-carboxylate (Enantiomer B), (1S,6R or 1R,6S)-3-[5-(3-{[2-(Difluoromethoxy)phenyl]methyl}-7-fluoro-2-methyl-imidazo[1,2-a]pyridin-6-yl)pyrimidin-2-yl]-3-azabicyclo[4.1.0]heptane-6-carboxylic acid (Enantiomer B), (1R,6S or 1S6R)-3-[5-(3-{[2-(Difluoromethoxy)phenyl]methyl}-7-fluoro-2-methyl-imidazo[1,2-a]pyridin-6-yl)pyrimidin-2-yl]-3-azabicyclo[4.1.0]heptane-1-carboxylic acid, Ethyl (1S,3R and 1R,3S)-3-[5-(3-{[2-(difluoromethoxy)phenyl]methyl}-2-methylimidazo-[1,2-a]pyridin-6-yl)pyrimidin-2-yl]cyclohexanecarboxylate (racemic cis isomer), Ethyl (1S,3R and 1R,3S)-3-[5-(3-{[2-(difluoromethoxy)phenyl]methyl}-2-methylimidazo-[1,2-a]pyridin-6-yl)pyrimidin-2-yl]cyclohexanecarboxylate (racemic trans isomers), 3-[5-(3-{[2-(Difluoromethoxy)phenyl]methyl}-2-methylimidazo [1,2-a]pyridin-6-yl)-pyrimidin-2-yl]cyclohexanecarboxylic acid, 3-[5-(3-{[2-(Difluoromethoxy)phenyl]methyl}-2-methylimidazo[1,2-a]pyridin-6-yl) -pyrimidin-2-yl]cyclohexanecarboxylic acid (racemic trans diastereomer), 3-[5-(3-{[2-(Difluoromethoxy)phenyl]methyl}-2-methylimidazo[1,2-a]pyridin-6-yl) -pyrimidin-2-yl]cyclohexanecarboxylic acid (racemic cis diastereomer), Ethyl 1-[5-(3-{[2-(difluoromethoxy)phenyl]methyl}-7-fluoro-2-methylimidazo[1,2-a]-pyridin-6-yl)pyrimidin-2-yl]-3-methylpiperidine-3-carboxylate, 1-[5-(3-{[2-(Difluoromethoxy)phenyl]methyl}-7-fluoro-2-methylimidazo[1,2-a]pyridin-6-yl)pyrimidin-2-yl]-3-methylpiperidine-3-carboxylic acid, Ethyl 1-[5-(3-{[2-(difluoromethoxy)phenyl](hydroxy)methyl}-2-methylimidazo[1,2-a]-pyridin-6-yl)pyrimidin-2-yl]-4-methylpiperidine-4-carboxylate, 1-[5-(3-{[2-(Difluoromethoxy)phenyl](hydroxy)methyl}-2-methylimidazo[1,2-a]pyridin-6-yl)pyrimidin-2-yl]-4-methylpiperidine-4-carboxylic acid, Sodium 4-amino-1-[5-(3-{[2-(difluoromethoxy)phenyl]methyl}-7-fluoro-2-methyl-imidazo[1,2-a]pyridin-6-yl)pyrimidin-2-yl]piperidine-4-carboxylate, 8-[5-(3-[[2-(Difluoromethoxy)phenyl]methyl]-7-fluoro-2-methylimidazo[1,2-a]pyridin-6-yl)pyrimidin-2-yl]-8-azabicyclo [3.2.1]octan-3-one, Ethyl 2-{8-[5-(3-{[2-(difluoromethoxy)phenyl]methyl}-7-fluoro-2-methylimidazo[1,2-a]-pyridin-6-yl)pyrimidin-2-yl]-8-azabicyclo [3.2.1]octan-3-ylidene}acetate, 2-(Morpholin-4-yl)ethyl 1-[5-(3-{[2-(difluoromethoxy)phenyl]methyl}-2-methylimidazo-[1,2-a]pyridin-6-yl)pyrimidin-2-yl]-4-methylpiperidine-4-carboxylate, (3-{[2-(Difluoromethoxy)phenyl]methyl}-7-fluoro-6-[2-(morpholin-4-yl)pyrimidin-5-yl]-imidazo [1,2-a]pyridin-2-yl)methanol, 4-[5-(3-{[2-(Difluoromethoxy)phenyl](hydroxy)methyl}-2-methylimidazo[1,2-a]pyridin-6-yl)pyrimidin-2-yl]piperazin-2-one, 4-[5-(3-{(S or R)-[2-(Difluoromethoxy)phenyl](hydroxy)methyl}-2-methylimidazo[1,2-a]pyridin-6-yl)pyrimidin-2-yl]piperazin-2-one (Enantiomer A), 4-[5-(3-{(R or S)-[2-(Difluoromethoxy)phenyl](hydroxy)methyl}-2-methylimidazo[1,2-a]pyridin-6-yl)pyrimidin-2-yl]piperazin-2-one (Enantiomer B), 1-[5-(3-{[2-(Difluoromethoxy)phenyl]methyl}-2-methylimidazo[1,2-a]pyridin-6-yl)-4-methoxypyrimidin-2-yl]-1,4-diazepan-5-one, Methyl 1-[5-(3-{[2-(difluoromethoxy)phenyl]methyl}-2-methylimidazo[1,2-a]pyridin-6-yl)-4-methoxypyrimidin-2-yl]piperidine-4-carboxylate, 1-[5-(3-{[2-(Difluoromethoxy)phenyl]methyl}-2-methylimidazo[1,2-a]pyridin-6-yl)-4-methoxypyrimidin-2-yl]piperidine-4-carboxylic acid, Methyl 1-[5-(3-{[2-(difluoromethoxy)phenyl]methyl}-7-fluoro-2-(methoxymethyl)-imidazo[1,2-a]pyridin-6-yl)pyrimidin-2-yl]-4-methylpiperidine-4-carboxylate, 1-[5-(3-{[2-(Difluoromethoxy)phenyl]methyl}-7-fluoro-2-(methoxymethyl)imidazo[1,2-a]pyridin-6-yl)pyrimidin-2-yl]-4-methylpiperidine-4-carboxylic acid, Methyl 1-[5-(3-{[2-(difluoromethoxy)phenyl]methyl}-2-methylimidazo[1,2-a]pyridin-6-yl)pyrimidin-2-yl]-4-isopropylpiperidine-4-carboxylate, Methyl 1-[5-(3-{1-[2-(difluoromethoxy)phenyl]ethyl}-2-methylimidazo[1,2-a]pyridin-6-yl)pyrimidin-2-yl]-4-methylpiperidine-4-carboxylate, 1-[5-(3-{[2-(Difluoromethoxy)phenyl]methyl}-2-methylimidazo[1,2-a]pyridin-6-yl)-pyrimidin-2-yl]-4-hydroxypiperidine-4-carboxylic acid, 4-[5-(7-Chloro-3-{[2-(difluoromethoxy)phenyl]-methyl}-2-methylimidazo[1,2-a]pyridin-6-yl)-pyrimidin-2-yl]piperazin-2-one, 4-[5-(7-Chloro-3-{[2-(difluoromethoxy)phenyl]-methyl}-2-methylimidazo[1,2-a]pyridin-6-yl)-pyrimidin-2-yl]morpholine, 7-Chloro-3-{[2-(difluoromethoxy)phenyl]methyl}-2-methyl-6-{2-[4-(methylsulfonyl)piperazin-1-yl]-pyrimidin-5-yl}imidazo[1,2-a]pyridine, 1-[5-(7-Chloro-3-{[2-(difluoromethoxy)phenyl]-methyl}-2-methylimidazo[1,2-a]pyridin-6-yl)-pyrimidin-2-yl]piperidine-4-carboxylic acid, 7-Chloro-3-{[2-(difluoromethoxy)phenyl]methyl}-6-(6-methoxypyridin-3-yl)-2-methylimidazo[1,2-a]-pyridine, 3-[2-(Difluoromethoxy)benzyl]-7-fluoro-2-(methoxymethyl)-6-{2-[4-(methylsulfonyl)-piperazin-1-yl]pyrimidin-5-yl}imidazo[1,2-a]pyridine, 3-{3-[(3-{[2-(Difluoromethoxy)phenyl]methyl}-7-fluoro-6-(6-methoxypyridin-3-yl)-imidazo[1,2-a]pyridin-2-yl)methoxy]phenyl}oxazolidin-2-one, 3-{3-[(3-{[2-(Difluoromethoxy)phenyl]methyl}-7-fluoro-6-(6-oxo-1H-pyridin-3-yl)-imidazo[1,2-a]pyridin-2-yl)methoxy]phenyl}oxazolidin-2-one, 5-(3-[2-(Difluoromethoxy)benzyl]-7-fluoro-2-{[3-(2-oxo-1,3-oxazolidin-3-yl)phenoxy]-methyl}imidazo[1,2-a]pyridin-6-yl)pyridine-2-carboxylic acid, 2-(3-{[2-(Difluoromethoxy)phenyl]methyl}-7-fluoro-6-[2-(morpholin-4-yl)pyrimidin-5-yl]imidazo[1,2-a]pyridin-2-yl)acetonitrile, {1-[5-(3-{[2-(Difluoromethoxy)phenyl]methyl}-7-fluoro-2-methylimidazo[1,2-a]pyridin-6-yl)pyrimidin-2-yl]-4-methypiperidin-4-yl}methanol, 1-[5-(3-{[2-(Difluoromethoxy)phenyl]methyl}-7-fluoro-2-methylimidazo[1,2-a]pyridin-6-yl)pyrimidin-2-yl]-4-methylpiperidine-4-carbaldehyde, 1-[5-(3-{[2-(Difluoromethoxy)phenyl]methyl}-7-fluoro-2-methylimidazo[1,2-a]pyridin-6-yl)pyrimidin-2-yl]piperidine-4-sulfonamide, 3-{[2-(Difluoromethoxy)phenyl]methyl}-7-fluoro-2-methyl-6-{2-[4-(methylsulfonyl)-piperidin-1-yl]pyrimidin-5-yl}imidazo [1,2-a]pyridine, N-({1-[5-(3-{[2-(Difluoromethoxy)phenyl]methyl}-7-fluoro-2-methylimidazo[1,2-a]pyridin-6-yl)pyrimidin-2-yl]piperidin-4-yl}sulfonyl)acetamide, 5-{1-[5-(3-{[2-(Difluoromethoxy)phenyl]methyl}-7-fluoro-2-methylimidazo[1,2-a]pyridin-6-yl]pyrimidin-2-yl]piperidin-4-yl}-1,3,4-oxadiazol-2-ol, {1-[5-(3-{1-[2-(Difluoromethoxy)phenyl]ethyl}-7-fluoro-2-methylimidazo[1,2-a]pyridin-6-yl)pyrimidin-2-yl]-4-methylpiperidin-4-yl}methanol, tert-Butyl 4-[5-(3-{[2-(difluoromethoxy)phenyl]methyl}-7-fluoro-2-{[3-(2-oxo-oxazolidin-3-yl)phenoxy]methyl}imidazo[1,2-a ]pyridin-6-yl)pyrimidin-2-yl]piperazine-1-carboxylate, 3-{3-[(3-{[2-(Difluoromethoxy)phenyl]methyl}-7-fluoro-6-[2-(piperazin-1-yl)pyrimidin-5-yl]imidazo[1,2-a ]pyridin-2-yl)methoxy]phenyl}oxazolidin-2-one hydrochloride, Butyl 1-[5-(3-{[2-(difluoromethoxy)phenyl]methyl}-7-fluoro-2-methylimidazo[1,2-a]-pyridin-6-yl)pyrimidin-2-yl]-4-methylpiperidine-4-carboxylate, Methyl 4-[5-[3-[[2-(difluoromethoxy)phenyl]methyl]-7-fluoro-2-methylimidazo[1,2-a]pyridin-6-yl]pyrimidin-2-yl]-1-methylcyclohexanecarboxylate (cis isomer), Methyl 4-[5-[5[3-[[2-(difluoromethoxy)phenyl]methyl]-7-fluoro-2-methylimidazo[1,2- ]pyridin-6-yl]pyrimidin-2-yl]-1-methylcyclohexanecarboxylate (trans isomer), cis-4-[5-(3-{[2-(Difluoromethoxy)phenyl]methyl}-7-fluoro-2-methylimidazo[1,2-a]-pyridin-6-yl)pyrimidin-2-yl]-1-methylcyclohexanecarboxylic acid, (8-anti)-3-(5-{3-[2-(Difluoromethoxy)benzyl]-7-fluoro-2-(hydroxymethyl)imidazo[1,2-a]pyridin-6-yl}pyrimidin-2-yl)-3-azabicyclo[3.2.1]octane-8-carboxylic acid meglumine salt, (3-{[2-(Difluoromethoxy)phenyl]methyl}-7-fluoro-6-[6-(methylsulfonyl)pyridin-3-yl]-imidazo[1,2-a]pyridin-2-yl)methanol, 3-[2-(Difluoromethoxy)benzyl]-2-methyl-6-[2-(methylsulfanyl)pyrimidin-5-yl]imidazo-[1,2-a]pyridine, 3-[2-(Difluoromethoxy)benzyl]-2-methyl-6-[2-(methylsulfonyl)pyrimidin-5-yl]imidazo-[1,2-a]pyridine, 1-(5-{3-[2-(Difluoromethoxy)benzyl]-7-fluoro-2-methylimidazo[1,2-a]pyridin-6-yl}-pyrimidin-2-yl)-4-methylpiperidine-4-carbonitrile, 5-(5-{3-[2-(Difluoromethoxy)benzyl]-2-methylimidazo[1,2-a]pyridin-6-yl}pyrimidin-2-yl)tetrahydro-2H-[1,2,5]thiadiazolo[2,3-a]pyrazin-3(3aH)-one 1,1-dioxide, 1-(5-{3-[2-(Difluoromethoxy)benzyl]-2-methylimidazo[1,2-a]pyridin-6-yl}pyrimidin-2-yl)-N-methoxypiperidine-4-carboxamide, 1-(5-{3-[2-(Difluoromethoxy)benzyl]-2-methylimidazo[1,2-a]pyridin-6-yl}pyrimidin-2-yl)-2-methyl-1,4-diazepan-5-one, 1-(5-{3-[2-(Difluoromethoxy)benzyl]-2-methylimidazo[1,2-a]pyridin-6-yl}pyrimidin-2-yl)-7-methyl-1,4-diazepan-5-one, 1-(5-{3-[2-(Difluoromethoxy)benzyl]-2-methylimidazo[1,2-a]pyridin-6-yl}pyrimidin-2-yl)-N-(methylsulfonyl)piperidine-4-carboxamide, 3-[2-(Difluoromethoxy)benzyl]-7-fluoro-2-(methoxymethyl)-6-{2-[4-(2H-tetrazol-5-yl)-piperidin-1-yl]pyrimidin-5-yl}imidazo[1,2-a]pyridine, sodium salt, 3-[2-(Difluoromethoxy)benzyl]-2-methyl-6-{2-[(1R,5S)-3-oxa-8-azabicyclo[3.2.1 ]oct-8-yl]pyrimidin-5-yl}imidazo[1,2-a]pyridine, 3-[2-(Difluoromethoxy)benzyl]-2-methyl-6-{2-[4-(2H-tetrazol-5-yl)piperidin-1-yl]-pyrimidin-5-yl}imidazo[1,2-a]pyridine, 3-[2-(Difluoromethoxy)benzyl]-6-{2-[(2R,6S)-2,6-dimethylmorpholin-4-yl]pyrimidin-5-yl}-2-methylimidazo[1,2-a]pyridine, Ethyl 1-(5-{3-[2-(difluoromethoxy)benzyl]-methylimidazo[1,2-a]pyridin-6-yl}-pyrimidin-2-yl)pyrrolidine-3-carboxylate, 1-(5-{3-[2-(Difluoromethoxy)benzyl]-2-methylimidazo[1,2-a]pyridin-6-yl}pyrimidin-2-yl)pyrrolidine-3-carboxylic acid, 1-(5-{3-[2-(Difluoromethoxy)benzyl]-2-methylimidazo[1,2-a]pyridin-6-yl}pyrimidin-2-yl)azetidine-3-carboxylic acid, Ethyl 1-[5-(3-{1-[2-(difluoromethoxy)phenyl]ethyl}-7-fluoro-2-methylimidazo[1,2-a]-pyridin-6-yl)pyrimidin-2-yl]-4-methylpiperidine-4-carboxylate, 1-[5-(3-{1-[2-(Difluoromethoxy)phenyl]ethyl}-7-fluoro-2-methylimidazo[1,2-a]pyridin-6-yl)pyrimidin-2-yl]-4-methylpiperidine-4-carboxylic acid, 1-[5-(3-{[2-(Difluoromethoxy)phenyl]methyl}-7-fluoro-2-methylimidazo[1,2-a]pyridin-6-yl)pyrimidin-2-yl]piperidin-4-one, 1-[5-(3-{[2-(Difluoromethoxy)phenyl]methyl}-7-fluoro-2-methylimidazo[1,2-a]pyridin-6-yl)pyrimidin-2-yl]-4-methylpiperidin-4-ol, 1-[5-(3-{[2-(Difluoromethoxy)phenyl]methyl}-7-fluoro-2-methylimidazo[1,2-a]pyridin-6-yl)pyrimidin-2-yl]-4-(trifluoromethyl)piperidin-4-ol, (3R)-1-[5-(3-{[2-(Difluoromethoxy)phenyl]methyl}-2-methylimidazo[1,2-a]pyridin-6-yl)pyrimidin-2-yl]piperidine-3-carboxylic acid, 3(S)-1-[5-(3-{[2-(Difluoromethoxy)phenyl]methyl}-2-methylimidazo[1,2-a]pyridin-6-yl)pyrimidin-2-yl]piperidine-3-carboxylic acid, Methyl 1-[5-(3-{[2-(difluoromethoxy)phenyl]methyl}-7-fluoro-2-methylimidazo[1,2-a]-pyridin-6-yl)pyrimidin-2-yl]piperidine-4-carboxylate, Sodium 1-[5-(3-{[2-(difluoromethoxy)phenyl]methyl}-7-fluoro-2-methylimidazo[1,2-a]-pyridin-6-yl)pyrimidin-2-yl]piperidine-4-carboxylate, (2R)-4-[5-(3-{[2-(Difluoromethoxy)phenyl]methyl}-7-fluoro-2-(methoxymethyl)imidazo-[1,2-a]pyridin-6-yl)pyrimidin-2-yl]morpholine-2-carboxylic acid, 2(S)-4-[5-(3-{[2-(difluoromethoxy)phenyl]methyl}7-fluoro-2-(methoxymethyl) imidazo-[1,2-a]pyridin-6-yl)pyrimidin-2-yl]morpholine-2-carboxylic acid, (1R,5S)-3-[5-(3-{[2-(Difluoromethoxy)phenyl]methyl}-2-methylimidazo[1,2-a]pyridin-6-yl)pyrimidin-2-yl]-3-azabicyclo[3.1.0]hexane -6-carboxylic acid, 1-[5-(3-{[2-(Difluoromethoxy)phenyl](hydroxy)methyl}-2-methylimidazo[1,2-a]pyridin-6-yl)pyrimidin-2-yl]piperidine-4-carboxylic acid, Ethyl 1-[5-(7-chloro-3-{[2-(difluoromethoxy)phenyl]methyl}-2-methylimidazo[1,2-a]-pyridin-6-yl)pyrimidin-2-yl]-4-methylpiperidine -4-carboxylate, Sodium 1-[5-(7-chloro-3-{[2-(difluoromethoxy)phenyl]methyl}-2-methylimidazo[1,2-a]-pyridin-6-yl)pyrimidin-2-yl]-4-methylpiperidine -4-carboxylate, 1-[5-(3-{[2-(Difluoromethoxy)phenyl]methyl}-7-fluoro-2-methylimidazo[1,2-a]pyridin-6-yl)pyrimidin-2-yl]-4-(nitromethyl)piperidin-4-ol, Ethyl 1-[5-(3-{(amino)[2-(difluoromethoxy)phenyl]methyl}-2-methylimidazo[1,2-a]-pyridin-6-yl)pyrimidin-2-yl]-4-methylpiperidine-4-carboxylate, Sodium 1-[5-(3-{(amino)[2-(difluoromethoxy)phenyl]methyl}-2-methylimidazo[1,2-a]pyridin-6-yl)pyrimidin-2-yl]-4-methylpiperidine-4-carboxylate, 1-[5-(3-{(Amino)[2-(difluoromethoxy)phenyl]methyl}-2-methylimidazo[1,2-a]pyridin-6-yl)pyrimidin-2-yl]-1,4-diazepan-5-one, N-([2-(Difluoromethoxy)phenyl]{2-methyl-6-[2-(morpholin-4-yl)pyrimidin-5-yl]imidazo-[1,2-a]pyridin-3-yl}methyl)acetamide, 2-([2-(Difluoromethoxy)phenyl]{2-methyl-6-[2-(morpholin-4-yl)pyrimidin-5-yl]imidazo-[1,2-a]pyridin-3-yl}methoxy)acetic acid, 1-[5-(3-{1[2-(Difluoromethoxy)phenyl]ethyl}-2-methylimidazo[1,2-a]pyridin-6-yl)-pyrimidin-2-yl]-1,4-diazepan-5-one, Methyl 1-[5-(3-{1-[2-(difluoromethoxy)phenyl]ethyl}-2-methylimidazo[1,2-a]pyridin-6-yl)pyrimidin-2-yl]piperidine-4-carboxylate, 1-[5-(3-{1-[2-(Difluoromethoxy)phenyl]ethyl}-2-methylimidazo[1,2-a]pyridin-6-yl)-pyrimidin-2-yl]piperidine-4-carboxylic acid, 4-[5-(3-{[2-(Difluoromethoxy)phenyl](methoxy)methyl}-2-methylimidazo[1,2-a]pyridin-6-yl)pyrimidin-2-yl]morpholine, Benzyl 2-[2-(difluoromethoxy)phenyl]-2-{2-methyl-6-[2-(5-oxo-1,4-diazepan-1-yl)-pyrimidin-5-yl]imidazo[1,2-a]pyridin-3-yl}acetate, 2-[2-(Difluoromethoxy)phenyl]-2-{2-methyl-6-[2-(5-oxo-1,4-diazepan-1-yl)pyrimidin-5-yl]imidazo[1,2-a]pyridin-3-yl}acetic acid, 1[2-(Difluoromethoxy)phenyl]-1-{2-methyl-6[6-(piperazin-1-yl)pyridin-3-yl]imidazo-[1,2-a]pyridin-3-yl}ethanol, 2-(Difluoromethoxy)phenyl]{2-methyl-6-[6-(piperazin-1-yl)pyridin-3-yl]imidazo[1,2-a]-pyridin-3-yl}methanol, 4-[5-(3-[1-[2-(Difluoromethoxy)phenyl]ethyl]-2-methylimidazo[1,2-a]pyridin-6-yl]pyrimidin-2-yl]morpholine, 2-[5-(3-{[2-(Difluoromethoxy)phenyl](hydroxy)methyl}-7-fluoro-2-methylimidazo[1,2-a]pyridin-6-yl)pyrimidin-2-yl]propan-2-ol, 2-[5-(3-{[2-(Difluoromethoxy)phenyl]methyl}-2-methylimidazo[1,2-a]pyridin-6-yl)-pyridin-2-yl]propan-2-ol, 4-[5-(3-{[2-(Difluoromethoxy)phenyl]methyl}-2-methylimidazo[1,2-a]pyridin-6-yl)-pyridin-2-yl]oxan-4-ol, 4-[5-(3-{[2-(Difluoromethoxy)phenyl]methyl}-7-fluoro-2-methylimidazo[1,2-a]pyridin-6-yl)pyrimidin-2-yl]oxan-4-ol, tert-Butyl 3-[5-(3-{[2-(difluoromethoxy)phenyl]methyl}-7-fluoro-2-methylimidazo[1,2-a]pyridin-6-yl)pyrimidin-2-yl]-3-hydroxyazetidine-1-carboxylate, 2-[5-(3-{[2-(Difluoromethoxy)phenyl]methyl}7-fluoro-2-methylimidazo[1,2-a]pyridin-6-yl)pyridin-2-yl]propan-2-ol, 3-[5-(3-{[2-(Difluoromethoxy)phenyl]methyl}7-fluoro-2-methylimidazo[1,2-a]pyridin-6-yl)pyrimidin-2-yl]oxetan-3-ol, 4-[5-(3-{[2-(Difluoromethoxy)phenyl]methyl}7-fluoro-2-methylimidazo[1,2-a]pyridin-6-yl)pyrimidin-2-yl]-1-methylpiperidin-4-ol, 3-[5-(3-{[2-(Difluoromethoxy)phenyl]methyl}7-fluoro-2-methylimidazo[1,2-a]pyridin-6-yl)pyrimidin-2-yl]azetidin-3-ol formic acid salt, 3-[5-(3-{[2-(Difluoromethoxy)phenyl]methyl}7-fluoro-2-methylimidazo[1,2-a]pyridin-6-yl)pyrimidin-2-yl]-1-methylazetidin-3-ol formic acid salt, 1-[5-(3-{[2-(Difluoromethoxy)phenyl]methyl}7-fluoro-2-methylimidazo[1,2-a]pyridin-6-yl)pyrimidin-2-yl]cyclobutan-1-ol, 4-[5-(3-{[2-(Difluoromethoxy)phenyl]methyl}7-fluoro-2-methylimidazo[1,2-a]pyridin-6-yl)pyrimidin-2-yl]-4-hydroxycyclohexane-1-carboxylic acid, 2-(5-{3-[(1R or 1S)-1-[2-(Difluoromethoxy)phenyl]ethyl]-2-methylimidazo[1,2-a]-pyridin-6-yl}pyrimidin-2-yl)propan-2-ol (Enantiomers A), 2-(5-{3-[(1R or 1S)-1-[2-(Difluoromethoxy)phenyl]ethyl]-2-methylimidazo[1,2a]-pyridin-6-yl}pyrimidin-2-yl)propan-2-ol (Enantiomers B), 5-(3-{[2-(Difluoromethoxy)phenyl]methyl}7-fluoro-2-methylimidazo[1,2-a]pyridin-6-yl)-2-(2-fluoropropan-2-yl)pyrimidine, 5-(3-{[2-(Difluoromethoxy)phenyl]methyl}7-fluoro-2-methylimidazo[1,2-a]pyridin-6-yl)-2 [1-(fluoromethyl) cyclopropyl]pyrimidine, 2-[5-(3-{[2-(Difluoromethoxy)phenyl]methyl}-7-fluoro-2-methylimidazo[1,2-a]pyridin-6-yl)pyrimidin-2-yl] propan-2-yl acetate, 5-(3-{[2-(Difluoromethoxy)phenyl]methyl}-7-fluoro-2-methylimidazo[1,2-a]pyridin-6-yl)-2-(3-fluorooxetan-3-yl)pyrimidine, 2-[5-[3-[1-[2-(Difluoromethoxy)phenyl]ethyl]-7-fluoro-2-methylimidazo[1,2-a]pyridin-6-yl]pyrimidin-2-yl] propan-2-ol (Enantiomers A), 2-[5-[3-[1-[2-(Difluoromethoxy)phenyl]ethyl]-7-fluoro-2-methylimidazo[1,2-a]pyridin-6-yl]pyrimidin-2-yl] propan-2-ol (Enantiomers B), N-({1-[5-(3-{[2-(Difluoromethoxy)phenyl]methyl}-7-fluoro-2-methylimidazo[1,2-a]pyridin-6-yl)pyrimidin-2-yl]cyclopropyl}methyl)acetamide, 2-[5-(3-{[2-(Difluoromethoxy)-5-fluorophenyl]methyl}-7-fluoro-2-methylimidazo[1,2-a]pyridin-6-yl)pyrimidin-2-yl]propan-2-ol, 5-(3-{[2-(Difluoromethoxy)phenyl]methyl}-7-fluoro-2-methylimidazo[1,2-a]pyridin-6-yl)-2-(4-fluorooxan-4-yl)pyrimidine 3-[5(3-{[2-(Difluoromethoxy)phenyl]methyl}-7-fluoro-2-methylimidazo[1,2-a]pyridin-6yl)pyrimidin-2-yl]oxolan-3-ol, 3-[2-(Difluoromethoxy)benzyl]-6-[2-(4,4-difluoropiperidin-1yl)pyrimidin-5-yl]-2-methylimidazol]1,2-a]pyridine, 4-(5-{3-[2-(Difluoromethoxy)benzyl]-2-methylimidazo [1,2-a]pyridin-6-yl}pyrimidin-2-yl)piperazine-2-carboxylic acid, 1-(5-{3-[2-(Difluoromethoxy)benzyl]-2,7-dimethylimidazo[1,2-a]pyridin-6-yl}pyrimidin-2-yl)-4-hydroxypiperidine-4-carboxylic acid, 1-[5-(3-{(1S or 1R)-1-[2-(Difluoromethoxy)phenyl] ethyl}-2-methylimidazo[1,2-a]-pyridin-6-yl)pyrimidin-2-yl]-1,4-diazepan-5-one (Enantiomer A), 1-[5-(3-{(1R or 1S)-1-[2-(Difluoromethoxy)phenyl] ethyl}-2-methylimidazo[1,2-a]-pyridin-6-yl)pyrimidin-2-yl]-1,4-diazepan-5-one (Enantiomer B), Methyl 3-[5-(3-{[2-(difluoromethoxy)phenyl]methyl}-2-methylimidazo[1,2-a]pyridin-6-yl)pyrimidin-2-yl]-3-azabicyclo[3.1.0]hexane-1-carboxylate (Enantiomer A), Methyl 3-[5-(3-{[2-(difluoromethoxy)phenyl]methyl}-2-methylimidazo[1,2-a]pyridin-6-yl)pyrimidin-2-yl]-3-azabicyclo[3.1.0]hexane-1-carboxylate (Enantiomer B), 3-[5-(3-{[2-(Difluoromethoxy)phenyl]methyl}-2-methylimidazo[1,2-a]pyridin-6-yl)-pyrimidin-2-yl]-3-azabicyclo[3.1.0]hexane-1-carboxylic acid (Enantiomer A), 3-[5-(3-{[2-(Difluoromethoxy)phenyl]methyl}-2-methylimidazo[1,2-a]pyridin-6-yl)-pyrimidin-2-yl]-3-azabicyclo[3.1.0]hexane-1-carboxylic acid (Enantiomer B), 1-[5-(3-{[2-(Difluoromethoxy)phenyl]methyl}-2-methylimidazo[1,2-a]pyridin-6-yl)-pyrimidin-2-yl]-3-methylpiperidine-3-carboxylic acid (Enantiomer A), 1-[5-(3-{[2-(Difluoromethoxy)phenyl]methyl}-2-methylimidazo[1,2-a]pyridin-6-yl)-pyrimidin-2-yl]-3-methylpiperidine-3-carboxylic acid (Enantiomer B), cis-1-[5-(3-{[2-(Difluoromethoxy)phenyl]methyl}-2-methylimidazo[1,2-a]pyridin-6-yl)-pyrimidin-2-yl]-3-methylpiperidine-4-carboxylic acid (Racemic), or trans-1-[5-(3-{[2-(Difluoromethoxy)phenyl]methyl}-2-methylimidazo[1,2-a]pyridin-6-yl)pyrimidin-2-yl]-3-methylpiperidine-4-carboxylic acid (Racemic), or a pharmaceutically acceptable salt thereof.

7. The pharmaceutical composition comprising a compound of formula (IIA) according to claim 1 or a pharmaceutically acceptable salt thereof, in association with a pharmaceutically acceptable carrier.

8. The pharmaceutical composition as claimed in claim 7 further comprising an additional pharmaceutically active ingredient.

9. The compound as claimed in claim 1 or a pharmaceurically acceptable salt thereof, wherein E represents —CH$_2$— or —CH(CH$_3$)—.

10. The compound as claimed in claim 1 or a pharmaceutically acceptable salt thereof, wherein R$^{12}$ represents hydrogen or fluoro.

11. The compound as claimed in claim 2 wherein R$^{21}$ is 2-hydroxyprop-2-yl.

\* \* \* \* \*